(12) United States Patent
Kawakami et al.

(10) Patent No.: US 7,737,166 B2
(45) Date of Patent: Jun. 15, 2010

(54) ANTIFUNGAL BICYCLIC HETERO RING COMPOUNDS

(75) Inventors: Katsuhiro Kawakami, Tokyo (JP); Kazuo Kanai, Tokyo (JP); Takao Horiuchi, Tokyo (JP); Hiroshi Takeshita, Tokyo (JP); Syozo Kobayashi, Tokyo (JP); Yuichi Sugimoto, Tokyo (JP); Issei Achiwa, Tokyo (JP); Junichi Kuroyanagi, Tokyo (JP)

(73) Assignee: Daiichi Sankyo Company, Limited, Tokyo (JP)

(*) Notice: Subject to any disclaimer, the term of this patent is extended or adjusted under 35 U.S.C. 154(b) by 25 days.

(21) Appl. No.: 12/063,981

(22) PCT Filed: Aug. 16, 2006

(86) PCT No.: PCT/JP2006/316085

§ 371 (c)(1),
(2), (4) Date: Feb. 15, 2008

(87) PCT Pub. No.: WO2007/020936

PCT Pub. Date: Feb. 22, 2007

(65) Prior Publication Data

US 2009/0143353 A1   Jun. 4, 2009

(30) Foreign Application Priority Data

Aug. 17, 2005 (JP) .............................. 2005-236837
Aug. 24, 2005 (JP) .............................. 2005-242786

(51) Int. Cl.
| C07D 417/04 | (2006.01) |
| C07D 417/14 | (2006.01) |
| C07D 413/14 | (2006.01) |
| C07D 413/04 | (2006.01) |
| C07D 413/06 | (2006.01) |
| C07D 413/12 | (2006.01) |
| C07D 403/04 | (2006.01) |
| C07D 405/04 | (2006.01) |
| C07D 263/56 | (2006.01) |
| C07D 263/58 | (2006.01) |
| A61K 31/496 | (2006.01) |
| A61K 31/4439 | (2006.01) |
| A61K 31/427 | (2006.01) |
| A61K 31/428 | (2006.01) |
| A61K 31/423 | (2006.01) |
| A61K 31/454 | (2006.01) |
| A61K 31/5377 | (2006.01) |

(52) U.S. Cl. .................. 514/375; 548/217; 548/306.1; 548/466; 548/178; 548/525; 548/203; 548/222; 514/367; 514/414; 514/422; 514/394; 514/210.21; 514/321; 514/365; 514/338; 514/233.8; 514/254.02; 514/255.05; 546/198; 546/271.7; 544/137; 544/368; 544/405

(58) Field of Classification Search ................. 548/222, 548/224

See application file for complete search history.

(56) References Cited

U.S. PATENT DOCUMENTS

| 6,376,449 B2 | 4/2002 | Olsen |
| 6,376,491 B1 | 4/2002 | Aoki et al. |
| 6,555,569 B2 | 4/2003 | Sutcliffe et al. |
| 7,037,932 B2 | 5/2006 | Gallagher et al. |
| 2001/0046985 A1 | 11/2001 | Sutcliffe et al. |
| 2004/0018192 A1 | 1/2004 | Wakabayashi et al. |
| 2004/0176435 A1 | 9/2004 | Gallagher et al. |
| 2005/0176712 A1 | 8/2005 | Wakabayashi et al. |

FOREIGN PATENT DOCUMENTS

| WO | 03022850 A1 | 3/2003 |
| WO | 03064422 A1 | 8/2003 |
| WO | 2004098494 A2 | 11/2004 |
| WO | WO 2004098494 A2 * | 11/2004 |

OTHER PUBLICATIONS

Jordan, V. C. Nature Reviews: Drug Discovery, 2, 2003, pp. 205-213.*

Vippagunta et al. Advanced Drug Delivery Reviews, 48 (2001), pp. 3-26.*

(Continued)

Primary Examiner—Rebecca L Anderson
Assistant Examiner—Matthew P Coughlin
(74) Attorney, Agent, or Firm—Sughrue Mion, PLLC

(57) ABSTRACT

A 1,6-β-glucan synthetase inhibitor is provided, having potent growth inhibition and having excellent safety. A compound is provided, capable of expressing in a wide spectral range and specifically or selectively, an antifungal effect based on its functional mechanism of 1,6-β-glucan synthesis inhibition. Also provided is a drug, a salt or hydrate thereof, especially an antifungal that contains the compound. Concretely, provided is a compound of the following formula (I), its salt or hydrate, and a drug or antifungal containing, as the active ingredient, the compound, its salt or hydrate:

[Formula 1]

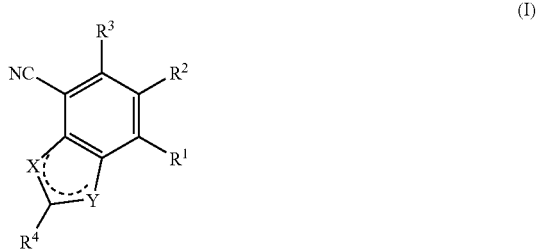

(I)

6 Claims, No Drawings

OTHER PUBLICATIONS

Souillac, et al., Characterization of Delivery Systems, Differential Scanning Calorimetry, pp. 217-218 (in Encyclopedia of Controlled Drug Delivery, 1999, John Wiley & Sons, pp. 212-227).*

Dörwald, F. Zaragoza. Side Reactions in Organic Synthesis: A Guide to Successful Synthesis Design, Weinheim: Wiley-VCH Verlag GmbH & Co. KGaA, 2005, Preface.*

Gunter Rommele et al., "Papulacandins—The Relationship between Chemical structure and effect on Glucan Synthesis in Yeast", The Journal of Antibiotics, Pharmaceutical Research Laboratories, Ciba-Geigy Limited, Basel, Switzerland, vol. XXXVI, No. 11 pp. 1539-1542, 1983.

Manuel Debono et al., "Semisynthetic Chemical Modification of the Antifungal Lipopeptide Echinocandin B (ECB): Structure- Activity Studies of the Lipophilic and Geometric Parameters of Polyarylated Acyl Analogs of ECB", J. Med. Chem., 1995, vol. 38, pp. 3271-3281, American Chemical Society.

Otto D. Hensens et al., "Pneumocandins from *Zalerion arboricola*", the Journal of Antibiotics, vol. 45, No. 12, pp. 1875-1885, Dept. of Natural Products Chemistry, Merck Research Laboratories, USA, 1992.

Hideo Takeshima et al., "A Deacylation Enzyme for Aculeacin A, a Neutral Lipopeptide Antibiotic from *Actinoplanes utahensis*: Purification and Characterization", Journal of Biochemistry, vol. 105, No. 4, 1989, pp. 606-610.

F. Aileen Bouffard et al., "Synthesis and Antifungal Activity of Novel Cationic Pneumocandin B0 Derivatives", Journal of Medicinal Chemistry, vol. 37, pp. 222-225, 1994, American Chemical Society.

Masaki Tomishima et al., "FK463, a Novel Water- soluble Echinocandin Lipopeptide: Synthesis and Antifungal Activity", The Journal of Antibiotics, vol., 52, No. 7, Jul. 1999, pp. 674-676.

Ganapathi R. Revankar et al., "Synthesis and Antimicrobial Activity of Certain Imidazo [1,2 -a] pyrimidines", Journal of Medicinal Chemistry, vol. 18, No. 12, pp. 1253-1255, 1975.

* cited by examiner

ANTIFUNGAL BICYCLIC HETERO RING COMPOUNDS

TECHNICAL FIELD

The present invention relates to compounds, their salts or their solvates exhibiting an antifungal effect to pathogenic fungi. It also relates to an antifungal agent containing them.

BACKGROUND ART

Fungi are known to infect humans, animals, plants and others to cause various diseases. For example, they cause superficial mycosis in various human tissues such as epidermic corneal layers of skins, keratinous tissues such as nails and hairs, and mucosal epitherlia in oral cavities, and cause deep skin mycosis even in deep skin tissues existing in the depth from the body surfaces, for example, causing profound mycosis even in deep tissues in esophagi, internal organs and brains. Typical pathogenic fungi known to infect humans to cause profound mycosis are those of the genera *Candida, Cryptococcus* and *Aspergillus*; and typical pathogenic fungi to cause superficial mycosis will be those of the genus *Candida* that infect skins, oral cavities and vaginas, and those of the genus *Trichophyton* that infect the skins of hands and feet. Apart from these, there will be many other various fungi to infect animals and plants.

With the rapid progress in studies and developments relating to antibiotics and drugs for chemical therapy and with wide popularization thereof since 1950s, a lot of drugs for curing bacterial infections have been developed. Similarly, much effort has been paid to development of antifungal drugs. However, as compared with the development of antibacterial agents for chemical therapy, there are not so many compounds that are at present put in clinical use. On the other band, compromised hosts with immunity depression are increasing owing to frequent use of antibacterial drugs (antibiotics, chemical therapy agents) in actual clinical sites or caused by malignant tumors, leukemia, organ or bone marrow transplantation, and AIDS (acquired immunodeficiency syndrome), and, as a result, cases with profound mycosis are increasing in these days, and are now problematic.

Typical antifungals that are now used in the actual clinical sites are polyenemacrolides, phloropyrimidines, azoles, etc. They are essentially for external applications for treatment for superficial mycosis, including, for example, various azole-based drugs, and polyenemacrolide-type nystatin, griseofulvin, terbinafine hydrochloride, butenafine hydrochloride and amorolfine chloride. On the other hand, for treatment for profound mycosis that is significantly increasing these days, azole-based fluconazole and itraconazole are much used because of their safety as compared with any other drugs, but these are problematic in that their antifungal spectrum is narrow. Amphotericin B, a type of polyenemacrolide drugs has a broad antifungal spectrum and is highly effective, but it is problematic in point of its toxicity (side effect). Flucytosine, a type of phloropyrimidine drugs is not toxic, but it readily causes fungal tolerance to drugs. Accordingly, at present, only a few drugs that are at present used for treatment for profound mycosis could be on a satisfactory level for medical treatment in point of the antifungal spectrum, the potency and the safety thereof. In addition, fluconazole that is at present the most popular drug for profound mycosis is poorly susceptible to some pathogenic fungi such as *Candida glabrata, Candida tropicalis, Candida krusei*, and there are appearing some fungi resistant to it. In the clinical sites, therefore, novel antifungal drugs that overcome these problems are much desired.

On the other hand, a test method of scientifically evaluating the usefulness of substances has been established for development of recent antifungal therapies and novel antifungals. The method is with the progress of the studies of the functions and mechanisms of antifungal drugs, and it is desired to develop more effective and safer drugs. From the point of the overcoming the problem with drug-resistant fungi, it is much desired to develop antifungals having a novel function and mechanism.

Further, from the point of safety, fungi are, differing from bacterial (prokaryotic cells), eukaryotic cells like human cells, and therefore, it is necessary to develop compounds that attack and injure specifically (selectively) fungal cells.

Given that situation, a chemical capable of inhibiting the synthesis of essential cell wall constitutive components of fungi, a so-called cell wall polysaccharide synthesis inhibitor, or that is, an antifungal which targets molecules of cell wall polysaccharide synthetase specifically existing in fungi is expected from the viewpoint of the novelty of the function and the mechanism thereof and from the selective toxicity thereof. For polysaccharides that constitute the cell wall of fungi, known are β-glucan, chitin, chitosan and mannan of which β-glucan is an essential constitutive component of the cell wall of fungi, and this is grouped into 1,3-β-glucan and 1,6-β-glucan.

For 1,3-β-glucan synthetase inhibitor, heretofore reported are papracandins (Non-Patent Reference 1), echinocandins (Non-Patent Reference 2), pneumocandins (Non-Patent Reference 3), aculeacins (Non-Patent Reference 4), etc. Recently, caspofungin (Non-Patent Reference 5) and micafungin (Non-Patent Reference 6) have been developed and put on the market. However, these are all only for injections, and a novel antifungal effective in oral administration is desired.

As a 1,6-β-glucan synthetase inhibitor, reported are tricyclic imidazo[1,2-a]pyridine derivatives (Patent Reference 1); but it is necessary to develop a 1,6-β-glucan synthetase inhibitor that exhibits more potent growth inhibition and has a broad spectrum to objective pathogenic fungi.

On the other hand, it is known that imidazopyridine, triazolopyridine, pyrazolopyridine and their derivatives that are bicyclic skeleton-having pyridine derivatives have a pharmacological activity in an extremely broad range; and there are known reports saying that imidazopyrimidine and pyrazolopyrimidine derivatives exhibit an antifungal effect to fungi that causes plant diseases (Patent Reference 2, Non-Patent Reference 7).

Patent Reference 1: Japanese Patent Application No. 2002-022767 (International Patent Application No. PCT/JP03/00912)

Patent Reference 2: WO03/022850

Non-Patent Reference 1: Journal of Antibiotics, Vol. 36, p. 1539 (1983)

Non-Patent Reference 2: Journal of Medicinal Chemistry, Vol. 38, p. 3271 (1995)

Non-Patent Reference 3: Journal of Antibiotics, Vol. 45, p. 1875 (1992)

Non-Patent Reference 4: Journal of Biochemistry, Vol. 105, p. 606 (1959)

Non-Patent Reference 5: Journal of Medicinal Chemistry, Vol. 37, p. 222 (1994)

Non-Patent Reference 6: Journal of Antibiotics, Vol. 52, p. 647 (1999)

Non-Patent Reference 7: Journal of Medicinal Chemistry, Vol. 18, p. 1253 (1975)

DISCLOSURE OF THE INVENTION

Problems that the Invention is to Solve

An object of the invention is to provide a compound capable of specifically or selectively expressing an antifungal effect based on its functional mechanism of 1,6-β-glucan synthesis inhibition, to pathogenic fungi such as those of the genus *Candida*, and to provide an antifungal agent for oral administration that contains the compound, its salt or their hydrate.

Means for Solving the Problems

The present inventors have searched for compounds for the purpose of getting those having an antifungal activity of inhibiting 1,6-β-glucan synthetase, and have found out compounds having an effect of inhibiting 1,6-β-glucan synthesis through biopolymer synthesis inhibition experiments based on a [$^{14}$C]-glucose uptake index. In addition, we have further investigated as to whether any other compounds similar to the compounds in point of the structure are also antifungal to pathogenic fungi. As a result, we have found that imidazopyridine, triazolopyridine and pyrazolopyridine derivatives having, as the substituent therein, a basic substituent and represented by a formula (I), their salts and their solvates have a broad and potent antifungal effect with a functional mechanism of 1,6-β-glucan synthesis inhibition, and have an especially excellent antifungal effect to fungi of causing profound mycosis, especially those of the genus *Candida*, and have completed the invention.

Specifically, the invention includes the following aspects:

1. A compound of the following formula (I), its salt or their hydrate:

[Formula 1]

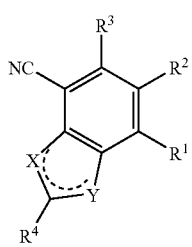

(I)

[In the formula, $R^1$ means a group selected from the following [a] to [c], having, as a basic substituent, 1) an amino group, 2) an alkylamino group having an alkyl group having from 1 to 6 carbon atoms, 3) a dialkylamino group having alkyl groups having from 1 to 6 carbons that may be the same or different, 4) an aminomethyl group, 5) an alkylaminomethyl group having an alkyl group having from 1 to 6 carbon atoms, or 6) a dialkylaminomethyl group having alkyl groups having from 1 to 6 carbon atoms that may be the same or different,

[a]: a saturated or partially-saturated heterocyclic group containing 1 or 2 hetero atoms selected, optionally duplicatively, from hetero atoms of a group consisting of a nitrogen atom, an oxygen atom and a sulfur atom,

[b]: a 5-membered or 6-membered cyclic hydrocarbon group optionally containing a double bond,

[c]: a group of the following formula:

—$X^1$-(alkyl group having from 1 to 6 carbon atoms), (wherein $X^1$ means an oxygen atom, a sulfur atom, —$CH_2$—, or a structure of a formula:

—N(—$R^{11}$)—, $R^{11}$ on the nitrogen atom means a hydrogen atom, an alkyl group having from 1 to 6 carbon atoms, a cycloalkyl group having 3 to 6 carbon atoms, or an aralkyl group having from 7 to 9 carbon, atoms), in this, the heterocyclic group and the cyclic hydrocarbon group in [a] and [b] may have one or more groups selected, optionally duplicatively, from [substituent group 1], [substituent group 1]:

a halogen atom, a hydroxyl group, a carboxyl group, an alkyl group having from 1 to 6 carbon atoms, an alkoxy group having from 1 to 6 carbon atoms, an alkylthio group having from 1 to 6 carbon atoms, an acyl group having from 2 to 7 carbon atoms, an alkoxycarbonyl group having from 2 to 7 carbon atoms, a cycloalkyl group having from 3 to 6 carbon atoms, an aralkyloxy group having from 7 to 9 carbon atoms, an aralkyloxycarbonyl group having from 8 to 10 carbon atoms, and a group of the following formula:

—C(═O)—N(—$R^{12}$)$R^{13}$ (wherein $R^{12}$ and $R^{13}$ on the nitrogen atom each independently represent a hydrogen atom, an alkyl group having from 1 to 6 carbon atoms, or an aryl group having from 6 to 10 carbon atoms);

$R^2$ means a halogen atom, a hydroxymethyl group, a formyl group, a dialkylamino group having alkyl groups having from 1 to 6 carbon atoms that may be the same or different, an alkyl group having from 1 to 8 carbon atoms, an alkenyl group having from 2 to 8 carbon atoms, an alkynyl group having from 2 to 8 carbon atoms, an alkoxycarbonyl group having from 2 to 8 carbon atoms, a cycloalkyl group having from 3 to 6 carbon atoms, a cycloalkenyl group having from 5 to 6 carbon atoms, a monocyclic or bicyclic aryl group, a monocyclic or bicyclic heteroaryl group (containing from 1 to 4 hetero atoms selected, optionally duplicatively, from a group consisting of a nitrogen atom, an oxygen atom and a sulfur atom), or a group of the following formula:

$$-X^2-R^{21}$$

[wherein $X^2$ means $-C(=O)-$, $-(CH_2)_n-$, $-C(=O)-N(-R^{22})-$ or $-N(-R^{23})-C(=O)-$, n means any of an integer of from 1 to 3, $R^{21}$ is a monocyclic or bicyclic aryl group, or a monocyclic or bicyclic heteroaryl group (containing from 1 to 4 hetero atoms selected, optionally duplicatively, from a group consisting of a nitrogen atom, an oxygen atom and a sulfur atom), $R^{22}$ and $R^{23}$ each independently mean a hydrogen atom or an alkyl group having from 1 to 6 carbon atoms], and these alkyl group, alkenyl group, alkynyl group, cycloalkyl group, cycloalkenyl group, aryl group and heteroaryl group may have one or more groups selected, optionally duplicatively, from [substituent group 2];

[substituent group 2]:

a halogen atom, an amino group, a hydroxyl group, a carboxy group, a nitrile group, a halogenomethyl group, a hydroxymethyl group, an alkyl group having from 1 to 6 carbon atoms, an alkoxy group having from 1 to 6 carbon atoms, an alkylthio group having from 1 to 6 carbon atoms, an acyl group having from 2 to 7 carbon atoms, an alkoxycarbonyl group having from 2 to 7 carbon atoms, a cycloalkyl group having from 3 to 6 carbon atoms, and a group of the following formula:

$$-C(=O)-N(-R^{24})R^{25}$$

(wherein $R^{24}$ and $R^{25}$ on the nitrogen atom each independently represent a hydrogen atom, an alkyl group having from 1 to 6 carbon atoms, or an aryl group having from 6 to 10 carbon atoms);

in this, the amino group in the [substituent group 2] may have 1 or 2 substituents selected from a group consisting of an alkyl group having from 1 to 6 carbon atoms, an acyl group having from 2 to 7 carbon atoms, a cycloalkyl group having from 3 to 6 carbon atoms, an aryl group having from 6 to 10 carbon atoms, an aralkyl group having from 7 to 12 carbon atoms, an aromatic heterocyclic group, an alkylsulfonyl group having from 1 to 6 carbon atoms, and an arylsulfonyl group having from 6 to 10 carbon atoms, and when the amino group has two substituents, then they may bond to each other to form a cyclic structure;

$R^3$ means a hydrogen atom, a linear-chain or branched-chain alkyl group having from 1 to 4 carbon atoms, a cyclic alkyl group having 3 or 4 carbon atoms, an alkoxy group having from 1 to 4 carbon atoms, a dialkylamino group having the same or different alkyl chains and having from 2 to 4 carbon atoms in total, a halogenomethyl group, or an alkoxymethyl group having an alkoxy group having from 1 to 3 carbon atoms;

$R^4$ means a group selected from the following groups [i] to [vi]:

[i]:

a linear-chain or branched-chain alkyl group having from 1 to 6 carbon atoms, and a cycloalkyl group having from 3 to 6 carbon atoms, these may have one or more groups selected, optionally duplicatively, from the following [substituent group 4] (but for the alkyl group, an alkyl group is excluded from the [substituent group 4]);

[ii]:

an aromatic hydrocarbon group, and a 5-membered or 6-membered aromatic heterocyclic group containing from 1 to 4 hetero atoms selected, optionally duplicatively, from a nitrogen atom, an oxygen atom and a sulfur atom, these may have one or more groups selected, optionally duplicatively, from the following [substituent group 4];

[iii]:

an aromatic hetero ring-substituted alkyl group composed of a 5-membered or 6-membered aromatic heterocyclic group containing from 1 to 4 hetero atoms selected, optionally duplicatively, from a nitrogen atom, an oxygen atom and a sulfur atom, and a divalent hydrocarbon group having from 1 to 3 carbon atoms, and an aralkyl group composed of an aromatic hydrocarbon group and a divalent hydrocarbon group having from 1 to 3 carbon atoms, these aromatic heterocyclic group and aromatic hydrocarbon group may have one or more groups selected, optionally duplicatively, from the [substituent group 4];

[iv]:

an amino group, an alkylamino group having an alkyl group having front 1 to 6 carbon atoms, a dialkylamino group having alkyl groups having from 1 to 6 carbon atoms that may be the same or different, a 4-membered to 6-membered, saturated, nitrogen-containing heterocyclic group having a bonding site at the nitrogen atom, and a disubstituted amino group in which one substituent is a 4-membered to 6-membered, saturated, nitrogen-containing heterocyclic group having a bonding site at the carbon atom and the other is an alkyl group having from 1 to 6 carbon atoms, these alkyl moieties may have one or more groups selected, optionally duplicatively, from the [substituent group 4] (in this case, an alkyl group is excluded from the [substituent group 4]), and the nitrogen-containing heterocyclic group may have one or more groups selected, optionally duplicatively, from the [substituent group 4];

[v]:

a group of the following formula:

—C(=O)—R$^{41}$ (wherein R$^{41}$ on the carbon atom means an alkylamino group having an alkyl group having from 1 to 6 carbon atoms, a dialkylamino group having alkyl groups having from 1 to 6 carbon atoms that may be the same or different, an alkoxy group having from 1 to 6 carbon atoms, an alkyl(alkoxy)amino group having an alkyl group having from 1 to 6 carbon atoms and an alkoxy group having from 1 to 6 carbon atoms, a 5-membered or 6-membered, saturated cyclic, nitrogen-containing heterocyclic group containing 1 or 2 hetero atoms selected, optionally duplicatively, from a group consisting of a nitrogen atom, an oxygen atom and a sulfur atom and bonding to the carbonyl at the nitrogen atom, a disubstituted amino group having a 5-membered or 6-membered aromatic heterocyclic group containing from 1 to 4 hetero atoms selected, optionally duplicatively, from a group consisting of a nitrogen atom, an oxygen atom and a sulfur atom, and an alkyl group having from 1 to 6 carbon atoms, an aromatic hetero ring-substituted alkyl group composed of a 5-membered or 6-membered aromatic heterocyclic group containing from 1 to 4 hetero atoms selected, optionally duplicatively, from a group consisting of a nitrogen atom, an oxygen atom and a sulfur atom, and an alkylene group having from 1 to 3 carbon atoms, or a substituted dialkylamino group having alkyl groups having from 1 to 6 carbon atoms),

[vi]:

a group of the following formula:

—N(—R$^{42}$)—C(=O)R$^{43}$ (wherein R$^{42}$ and R$^{43}$ each independently mean a hydrogen atom or an alkyl group having from 1 to 6 carbon atoms, or they may combine together to be a polymethylene chain to form a cyclic structure);

the alkyl moiety of the group in the above [v] and [vi] and the alkyl moiety of the alkoxy group therein may have one or more groups selected, optionally duplicatively, from the groups of the [substituent group 4] (in this case, an alkyl group is excluded from the [substituent group 4]), and the aromatic or saturated heterocyclic group may have one or more groups selected, optionally duplicatively, from the [substituent group 4];

[substituent group 4]:

a halogen atom, an amino group, a hydroxyl group, a carboxy group, an alkoxy group having from 1 to 6 carbon atoms, an alkylthio group having from 1 to 6 carbon atoms, an acyl group having from 2 to 7 carbon, atoms, an alkoxycarbonyl group having from 2 to 7 carbon atoms, an alkyl group having from 1 to 6 carbon atoms, a cycloalkyl group having from 3 to 6 carbon atoms, an aralkyloxy group having from 7 to 9 carbon atoms, an aralkyloxycarbonyl group having from 8 to 10 carbon atoms, and a group of the following formula:

—C(=O)—N(—R$^{44}$)R$^{45}$ (wherein R$^{44}$ and R$^{45}$ on the nitrogen atom each independently represent a hydrogen atom, an alkyl group having from 1 to 6 carbon atoms, or an aryl group having from 6 to 10 carbon atoms);

in this, the amino group in the [substituent group 4] may have 1 or 2 substituents selected from a group consisting of an alkyl group having from 1 to 6 carbon atoms, an acyl group having from 2 to 7 carbon atoms, a cycloalkyl group having from 3 to 6 carbon atoms, an aryl group having from 6 to 10 carbon atoms, an aralkyl group having from 7 to 12 carbon atoms, an aromatic heterocyclic group, an alkylsulfonyl group having from 1 to 6 carbon atoms, and an arylsulfonyl group having from 6 to 10 carbon atoms, and when the amino group has two substituents, then they may bond to each other to form a cyclic structure;

X and Y each independently mean a nitrogen atom, an oxygen atom, a sulfur atom, N—R$^5$ or C—R$^6$, R$^5$ and R$^6$ each independently mean a hydrogen atom or an alkyl group having from 1 to 6 carbon atoms, and the ring containing X and Y may be an aromatic ring].

2. The compound, its salt or their hydrate described in 1, wherein the ring containing X and Y is an aromatic ring, and X and Y are any one of the following combinations:

(1) X is a nitrogen atom and Y is an oxygen atom, (2) X is a nitrogen atom and Y is N—R$^5$, (3) X is an oxygen atom and Y is a nitrogen atom, (4) X is an oxygen atom and Y is C—R$^6$, (5) X is N—R$^5$ and Y is C—R$^6$, (6) X is a nitrogen atom and Y is a sulfur atom, (7) X is a sulfur atom and Y is a nitrogen atom.

3. A drug comprising the compound, the salt or the hydrate described in the above 1 or 2.

4. A remedy for infections, comprising the compound, the salt or the hydrate described in the above 1 or 2.

5. An antifungal comprising the compound, the salt or the hydrate described in the above 1 or 2.

6. A method for treating infection, using the compound, the salt or the hydrate described in the above 1 or 2.

7. Use of the compound, the salt or the hydrate described in the above 1 or 2 for treating infection.

8. Use of the compound, the salt or the hydrate described in the above 1 or 2 for production of a remedy for infection.

EFFECT OF THE INVENTION

The invention provides a compound capable of specifically or selectively expressing an antifungal effect with a broad spectrum based on its functional mechanism of 1,6-β-glucan synthesis inhibition, and provides an antifungal that contains such a compound, its salt or their hydrate.

BEST MODE FOR CARRYING OUT THE INVENTION

The definitions of the terms used in this description are shown below. The terms may be suitably selected from those, depending on the definition of each substituent of $R^1$ to $R^4$.

"Alkyl group" and the alkyl moiety in an alkyl moiety-containing substituent (e.g., alkoxy group) may be a linear-chain or branched-chain one. Concretely, the alkyl group includes a methyl group, an ethyl group, a normal propyl group, a normal butyl group, a normal pentyl group, a normal hexyl group, a normal heptyl group, a normal octyl group, a normal nonyl group, a normal undecyl group, a normal dodecyl group, a normal tridecyl group, a normal tetradecyl group, a normal pentadecyl group, a normal hexadecyl group, a normal heptadecyl group, a normal octadecyl group, an isopropyl group, an isobutyl group, a secondary butyl group, a tertiary butyl group, an isopentyl group, a neopentyl group, a tertiary pentyl group, an isohexyl group, a 1,1-dimethylpropyl group, an n-heptyl group, an n-octyl group.

"Cycloalkyl group" means a monocyclic or bicyclic cycloalkyl group, including, for example, a cyclopropyl group, a cyclobutyl group, a cyclopentyl group, a cyclohexyl group, a bicyclo[3.2.1]oct-2-yl group.

"Alkenyl group" may be a linear-chain or branched-chain one, and has one or more carbon-carbon double bonds. Concretely, it includes a vinyl group, a propenyl group, a buten-1-yl group, an isobutenyl group, a penten-1-yl group, a 2-methylbuten-1-yl group, a 3-methylbuten-1-yl group, a hexen-1-yl group, a hepten-1-yl group, an octen-1-yl group.

"Cycloalkenyl group" means a monocyclic or bicyclic cycloalkenyl group, including, for example, a 2-cyclopenten-1-yl group, a 2,4-cyclopentadien-1-yl group, a 5-norbornen-2-yl group.

"Alkynyl group" may be a linear-chain or branched-chain one, and has one or more carbon-carbon triple bonds. Concretely, it includes an ethynyl group, a propynyl group.

"Halogen atom" means a fluorine atom, a chlorine atom, a bromine atom, or an iodine atom.

"Aryl group" means a monovalent group derived from an aromatic ring of an aromatic hydrocarbon by removing one hydrogen atom from the ring. The aromatic ring to constitute the aryl group may be a monocyclic ring or a fused ring. For example, it includes a phenyl group, a naphthyl group, an anthryl group, an azulenyl group.

"Aralkyl group" means a group formed by substituting the hydrogen atom(s) of an alkyl group with one or more aryl groups such as those mentioned above. For example, it includes a benzyl group, a benzhydryl group, a trityl group.

"Heterocyclic group" means a group derived from a saturated, partially-saturated or unsaturated heterocyclic compound, and may be monocyclic, bicyclic or spirocyclic. The heterocyclic compound to give the heterocyclic group includes, for example, aziridine, azetidine, pyrrole, furan, thiophene, pyrrolidine, tetrahydrofuran, tetrahydrothiophene, imidazole, pyrazole, imidazolidine, pyrazolidine, oxazole, isoxazole, thiazole, isothiazole, pyridine, dihydropyridine, tetrahydropyran, piperidine, pyridazine, pyrimidine, triazine, pyrazine, piperazine, pyrrolidone, dioxane, pyran, morpholine, benzofuran, indolidine, benzothiophene, indole, naphthyridine, quinoxaline, quinazoline, chroman. In addition, the following are further exemplified.

[Formula 2]

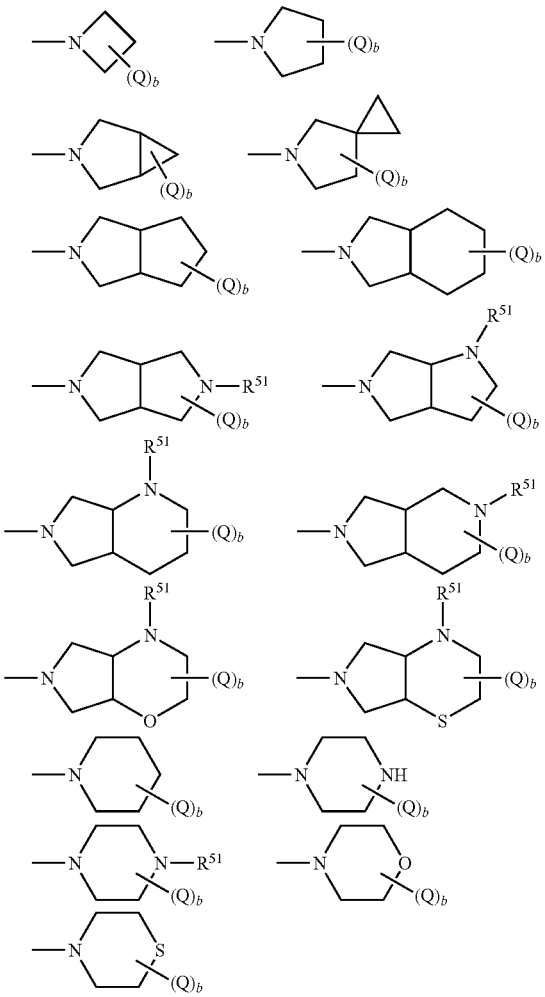

(In the formulae, $R^{51}$ means a hydrogen atom, an alkyl group having from 1 to 6 carbon atoms, a halogenoalkyl group having from 1 to 6 carbon atoms, or a cycloalkyl group having from 3 to 6 carbon atoms; the substituent Q means a substituent represented by the following formula:

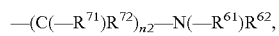

b means an integer of 0, 1 or 2, n2 means an integer of 0, 1 or 2, $R^{61}$ and $R^{62}$ each independently mean a hydrogen atom, an alkyl group having from 1 to 6 carbon atoms, a halogenoalkyl group having from 1 to 6 carbon atoms, an amino acid, a dipeptide, or a polypeptide comprising from 3 to 5 amino acids;

$R^{71}$ and $R^{72}$ each independently mean a hydrogen atom, an alkyl group having from 1 to 6 carbon atoms, a halogenoalkyl group having from 1 to 6 carbon atoms, a hydroxyalkyl group having from 1 to 6 carbon atoms, an aminoalkyl group having from 1 to 6 carbon atoms, an alkoxyalkyl group having from 2 to 12 carbon atoms, a cycloalkyl group having from 3 to 6 carbon atoms, a phenyl group optionally having a substituent, or a heteroaryl group having from 3 to 10 carbon atoms and optionally having a substituent.)

$R^{51}$ is preferably a hydrogen atom or an alkyl group. The alkyl group is preferably a methyl group, an ethyl group, a normal propyl group or an isopropyl group.

$R^{61}$ and $R^{62}$ each are preferably a hydrogen atom or an alkyl group. The alkyl group is preferably a methyl group, an ethyl group, a normal propyl group or an isopropyl group.

Preferably $R^{71}$ and $R^{72}$ are each independently a hydrogen atom, an alkyl group, a halogenoalkyl group, an alkoxyalkyl group, a cycloalkyl group, or a phenyl group. Of those, more preferred are a hydrogen atom, a methyl group, an ethyl group, a fluoromethyl group, a trifluoromethyl group, a 2-fluoromethyl group, a methoxymethyl group, a cyclopropyl group, a cyclobutyl group, and a phenyl group.

$R^{71}$ and $R^{72}$ may combine together to form a polymethylene chain, and, including the carbon atom to which they bond, they may form a cyclic structure having from 3 to 6 carbon atoms. Further, the ring may contain a nitrogen atom as a ring-constituting atom. Preferred cyclic structures are cyclopropyl, cyclobutyl, and cyclopentyl.

"Heteroaryl group" specifically means an aromatic group of the above-mentioned heterocyclic groups, and means a group referred to as "aromatic heterocycle". For example, it includes a 5-membered or 6-membered monocyclic, benzo-fused bicyclic group, or a hetero ring/hetero ring-fused 5-6 ring or 6-6 ring group. For example, it includes a pyrrolyl group, a furyl group, a thienyl group, an imidazolyl group, a pyrazolyl group, an oxazolyl group, an isoxazolyl group, a thiazolyl group, an isothiazolyl group, a tetrazolyl group, a pyridyl group, a pyridazinyl group, a pyrimidinyl group, a triazinyl group, a pyrazinyl group, a benzofuryl group, an indolyl group, a naphthyridinyl group, a quinoxalinyl group, a quinazolinyl group.

"Aromatic heterocyclic group" as referred to in this description specifically means, of the above-mentioned heteroaryl group, a monocyclic 5-membered or 6-membered ring that contains from 1 to 4 atoms of at least one type of hetero atoms selected from a group consisting of a nitrogen atom, an oxygen atom and a sulfur atom. For example, it includes a pyrrolyl group, a furyl group, a thienyl group, a imidazolyl group, a pyrazolyl group, an oxazolyl group, an isoxazolyl group, a thiazolyl group, an isothiazolyl group, a pyridyl group, a pyridazinyl group, a pyrimidinyl group, a triazinyl group, a pyrazinyl group.

This description says that an amino group, a hydroxyl group, a mercapto group and others "may be protected with a protective group", in which the "protective group" is not specifically defined and may be any one generally used in this technical field. For example, it includes alkoxycarbonyl groups such as tertiary butoxycarbonyl group, 2,2,2-trichloroethoxycarbonyl group; aralkyloxycarbonyl groups group such as benzyloxycarbonyl group, paramethoxybenzyloxycarbonyl group, paranitrobenzyloxycarbonyl group; acyl groups such as acetyl group, methoxyacetyl group, trifluoroacetyl group, chloroacetyl group, pivaloyl group, formyl group, benzoyl group; alkyl groups or aralkyl groups such as tertiary butyl group, benzyl group, paranitrobenzyl group, paramethoxybenzyl group, triphenylmethyl group; ethers such as methoxymethyl group, tertiary butoxymethyl group, tetrahydropyranyl group, 2,2,2-trichloroethoxymethyl group; (alkyl and/or aralkyl)-substituted silyl groups such as trimethylsilyl group, isopropyldimethylsilyl group, tertiary-butyldimethylsilyl group, tribenzylsilyl group, tertiary-butyl-diphenylsilyl group. An amino group may be protected as phthalimide.

"A group derived from an amino acid, a dipeptide, or a polypeptide comprising from 3 to 5 amino acids", or "an amino acid bonding to an amino group, a dipeptide or a polypeptide comprising from 3 to 5 amino acids" includes, for example, amino acids, dipeptides, and tripeptides, or substituted carbonyl groups derived from these. Specifically, there are mentioned amino acids such as glycine, alanine, aspartic acid; dipeptides such as glycine-glycine, glycine-alanine, alanine-alanine; tripeptides such as glycine-glycine-alanine, glycine-alanine-alanine; and substituted carbonyl groups derived from these.

The partial structures and the substituents of the compound of formula (I) of the invention are described.

The compound of the following formula (I):

[Formula 3]

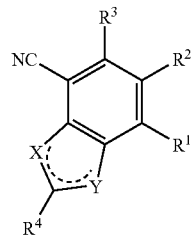

(I)

has a structure that has substituents of $R^1$ to $R^4$ and a cyano group in the bicyclic mother nucleus thereof.

$R^1$ is a basic group. Specifically, it may be a group that is so constituted that the basal group thereof shown as the following groups [a] to [c] is substituted with a basic substituent. The basic substituent to constitute the basic group is described. Specifically, it includes the following:

1) an amino group, 2) an alkylamino group having an alkyl group having from 1 to 6 carbon atoms, 3) a dialkylamino group having alkyl groups having from 1 to 6 carbons that may be the same or different, 4) an aminomethyl group, 5) an alkylaminomethyl group having an alkyl group having from 1 to 6 carbon atoms, or 6) a dialkylaminomethyl group having alkyl groups having from 1 to 6 carbon atoms that may be the same or different.

Examples of 2) are a methylamino group, an ethylamino group, a propylamino group, an isopropylamino group, a butylamino group, an isobutylamino group, a sec-butylamino group. The alkyl group with which the amino group is substituted may be a linear-chain or branched-chain one.

Examples of 3) may be those derived from the alkylamino group of 2) by further substituting the nitrogen atom with an alkyl group having from 1 to 6 carbon atoms; and the secondary alkyl group of the type includes a methyl group, an ethyl group, a propyl group, an isopropyl group, a butyl group, an isobutyl group, a sec-butyl group. The two alkyl groups may be the same or different.

The aminomethyl group and the dialkylaminomethyl group of 5) and 6) may be composed of an alkylamino group or a dialkylamino group described in the above 2) and 3) and a methylene group (—$CH_2$—).

The basic substituent is preferably an alkylamino group or a dialkylamino group. Concretely, it is preferably a methylamino group, an ethylamino group, a dimethylamino group.

The basal group that constitutes the basic group is a group selected from the following groups [a] to [c]. These groups are substituted with a basic substituent to constitute basic groups.

[a]: A saturated or partially-saturated heterocyclic group obtaining 1 or 2 hetero atoms selected, optionally duplicatively, from hetero atoms of a group consisting of a nitrogen atom, an oxygen atom and a sulfur atom,

[b]: a 5-membered or 6-membered cyclic hydrocarbon group optionally containing a double bond,

[c]: a group of the following formula:

—X$^1$-(alkyl group having from 1 to 6 carbon atoms), (wherein X$^1$ means an oxygen atom, a sulfur torn, —CH$_2$—, or a structure of a formula:

—N(—R$^{11}$)—,

R$^{11}$ on the nitrogen atom means a hydrogen atom, an alkyl group having from 1 to 6 carbon atoms, a cycloalkyl group having from 3 to 6 carbon atoms, or an aralkyl group having from 7 to 9 carbon atoms), in this, the heterocyclic group and the cyclic hydrocarbon group in [a] and [b] may have one or more groups selected, optionally duplicatively, from [substituent group 1];

[substituent group 1]:

a halogen atom, a hydroxyl group, a carboxyl group, an alkyl group having from 1 to 6 carbon atoms, an alkoxy group having from 1 to 6 carbon atoms, an alkylthio group having from 1 to 6 carbon atoms, an acyl group having from 2 to 7 carbon atoms, an alkoxycarbonyl group having from 2 to 7 carbon atoms, a cycloalkyl group having from 3 to 6 carbon atoms, an aralkyloxy group haying from 7 to 9 carbon atoms, an aralkyloxycarbonyl group having from 8 to 10 carbon atoms, or a group of the following formula:

—C(=O)—N(—R$^{12}$)R$^{13}$ (wherein R$^{12}$ and R$^{13}$ on the nitrogen atom each independently represent a hydrogen atom, an alkyl group having from 1 to 6 carbon atoms, or an aryl group having from 6 to 10 carbon atoms).

The saturated or partially-saturated heterocyclic group in [a] may be selected from the above-mentioned heterocyclic group so as to be the following:

1. It contains 1 or 2 hetero atoms selected, optionally duplicatively, from hetero atoms of a group consisting of a nitrogen atom, an oxygen atom and a sulfur atom, 2. it is saturated or partially saturated, and 3. it is a monocyclic, 4- to 6-membered heterocyclic group.

For example, it includes an azetidinyl group, a pyrrolidinyl group, a piperidinyl group; further including a heterocyclic group derived from the pyrrolidinyl group or the piperidinyl group of those additionally haying a sulfur atom or an oxygen atom as the second hetero atom.

Of those, preferred is a 4-membered or 5-membered heterocyclic group of a saturated ring having a nitrogen atom as the hetero atom. Further, the heterocyclic group preferably bonds to the bicyclic mother nucleus at the nitrogen atom.

The cyclic hydrocarbon group of [b] preferably has one double bond, and is preferably a cyclopentenyl group or a cyclohexenyl group. Regarding the position of the double bond, it is desirable that the carbon atom bonding to the bicyclic mother nucleus is one carbon atom of the double bond and is positioned to be conjugated with the bicyclic mother nucleus.

Preferably, the substituting position of the basic substituent relative to the group of [a] and [b] is a 2- or 3-position (the substituting position of [a] and [b] to the bicyclic mother nucleus is 1). The group of [a] or [b] having the basic substituent is preferably a 4-membered or 5-membered, saturated heterocyclic group or a hydrocarbon group having one double bond, which has an alkylamino group, a dialkylamino group, an alkylaminomethyl group, or a dialkylaminomethyl group. More concretely, preferred is a 1-pyrrolidinyl group or a 1-cyclopentenyl group having a methylamino group or a dimethylamino group at the 3-position thereof; or a 1-pyrrolidinyl group or a 1-azetidinyl group having a methylaminomethyl group or a dimethylaminomethyl group at the 2-position thereof.

The carbon atom to which the basic substituent bonds may further have a substituent. The substituent is preferably an alkyl group having from 1 to 6 carbon atoms, more preferably a methyl group or an ethyl group, even more preferably a methyl group. The basic group constituted as above is shown below:

[Formula 4]

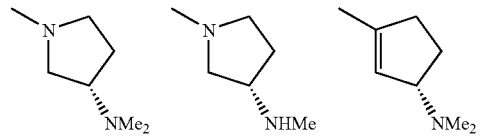

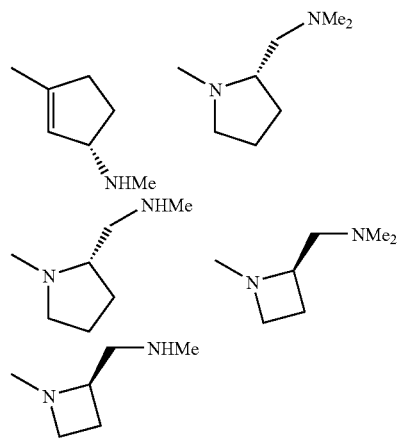

Of those, the following are more preferred.

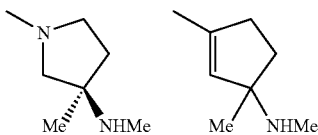

The group of [c] is an alkyl group having $X^1$ (nitrogen atom, oxygen atom, methylene, or sulfur atom) as a linker to the bicyclic mother nucleus. The alkyl moiety has from 1 to 6 carbon atoms, and may be a linear-chain or branched-chain one. The position of the basic substituent on the alkyl may be any position, but preferably, it is at the terminal of the alkyl chain.

The linker is preferably a nitrogen atom, more preferably the nitrogen atom has an alkyl group as a substituent. The chain length containing the linker moiety is preferably a chain length corresponding to 3 or 4 atoms.

More preferably, the basic group for $R^1$ has a cyclic structure. Specifically, it is preferably a structure having a basic substituent on the group of [a] or [b], and concretely it includes the above-mentioned structures.

$R^2$ means a halogen atom, a hydroxymethyl group, a formyl group, a dialkylamino group having alkyl groups having from 1 to 6 carbon atoms that may be the same or different, an alkyl group having from 1 to 8 carbon atoms, an alkenyl group having from 2 to 8 carbon atoms, an alkynyl group having from 2 to 8 carbon atoms, an alkoxycarbonyl group having from 2 to 8 carbon atoms, a cycloalkyl group having from 3 to 6 carbon atoms, a cycloalkenyl group having from 5 to 6 carbon atoms, a monocyclic or bicyclic aryl group, a monocyclic or bicyclic heteroaryl group (containing from 1 to 4 hetero atoms selected, optionally duplicatively, from a group consisting of a nitrogen atom, an oxygen atom and a sulfur atom), or a group of the following formula:

—$X^2$—$R^{21}$

[wherein $X^2$ means —C(═O)—, —(CH$_2$)$_n$—, —C(═O)—N(—$R^{22}$)— or —N(—$R^{23}$)—C(═O)—, n means any of an integer of from 1 to 3, $R^{21}$ is a monocyclic or bicyclic aryl group, or a monocyclic or bicyclic heteroaryl group (containing from 1 to 4 hetero atoms selected, optionally duplicatively, from a group consisting of a nitrogen atom, an oxygen atom and a sulfur atom), $R^{22}$ and $R^{23}$ each independently mean a hydrogen atom or an alkyl group having from 1 to 6 carbon atoms], and these alkyl group, alkenyl group, alkynyl group, cycloalkyl group, cycloalkenyl group, aryl group and heteroaryl group may have one or more groups selected, optionally duplicatively, from [substituent group 2];

[substituent group 2]:

a halogen atom, an amino group, a hydroxyl group, a carboxy group, a nitrile group, a halogenomethyl group, a hydroxymethyl group, an alkyl group having from 1 to 6 carbon atoms, an alkoxy group having from 1 to 6 carbon atoms, an alkylthio group having from 1 to 6 carbon atoms, an acyl group having from 2 to 7 carbon atoms, an alkoxycarbonyl group having from 2 to 7 carbon atoms, a cycloalkyl group having from 3 to 6 carbon atoms, and a group of the following formula:

—C(═O)—N(—$R^{24}$)$R^{25}$ (wherein $R^{24}$ and $R^{25}$ on the nitrogen atom each independently represent a hydrogen atom, an alkyl group having from 1 to 6 carbon atoms, or an aryl group having from 6 to 10 carbon atoms);

in this, the amino group in the [substituent group 2] may have 1 or 2 substituents selected from a group consisting of an alkyl group having from 1 to 6 carbon atoms, an acyl group having from 2 to 7 carbon atoms, a cycloalkyl group having from 3 to 6 carbon atoms, an aryl group having from 6 to 10 carbon atoms, an aralkyl group having from 7 to 12 carbon atoms, an aromatic heterocyclic group, an alkylsulfonyl group having from 1 to 6 carbon atoms, and an arylsulfonyl group having from 6 to 10 carbon atoms, and when the amino group has two substituents, then they may bond to each other to form a cyclic structure.

Of those, preferred is a monocyclic or bicyclic aryl group, or a monocyclic or bicyclic heteroaryl group (containing from 1 to 4 hetero atoms selected, optionally duplicatively, from a group consisting of a nitrogen atom, an oxygen atom and a sulfur atom).

The aryl group is preferably monocyclic, and is preferably a phenyl group. The phenyl group may have a substituent, and may be substituted with one or more of a hydroxyl group, an amino group, a halogen atom, a nitrile group and an alkyl group having from 1 to 3 carbon atoms. Preferably, the position at which the group is substituted with these substituents is an ortho-position or a meta-position, more preferably a meta-position. These are shown below.

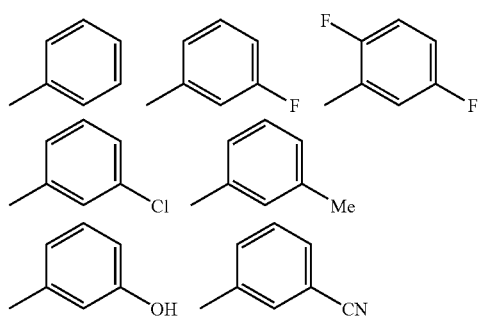

The heteroaryl group is preferably a monocyclic 5- or 6-membered heteroaryl group. The 5- or 6-membered heteroaryl group contains one or two hetero atoms selected, optionally duplicatively, from a nitrogen atom, an oxygen atom and a sulfur atom. For example, it includes a furyl group, a thiazolyl group, a pyridyl group, a pyrimidyl group, a pyridazyl group.

Of those, preferred is a 5-membered heteroaryl group, and its examples are a 4-thiazolyl group, a 2-furyl group, a 3-furyl group, a 2-thiophene group, a 3-thiophene group, a 1-pyrrole group. These are shown below.

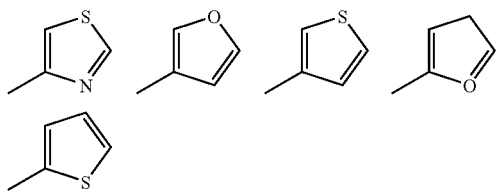

The heteroaryl group may have a substituent, and may be substituted with an alkyl group having from 1 to 6 carbon atoms. The alkyl group is preferably a methyl group. Its examples are a 2-methyl-4-thiazolyl group, a 3-methyl-4-thiophene group.

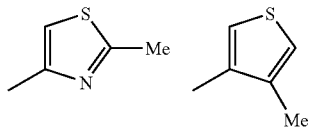

$R^2$ is more preferably a phenyl group, a 2-fluorophenyl group, a 2-methyl-4-thiazolyl group.

Except for an aryl group and a heteroaryl group, $R^2$ is preferably a halogen atom, more preferably a bromine atom.

$R^3$ means a hydrogen atom, a linear-chain or bunched-chain alkyl group having from 1 to 4 carbon atoms, a cyclic alkyl group having 3 or 4 carbon atoms, an alkoxy group having from 1 to 4 carbon atoms, a dialkylamino group having the same or different alkyl chains and having from 2 to 4 carbon atoms in total, a halogenomethyl group, or an alkoxymethyl group having an alkoxy group having from 1 to 3 carbon atoms.

$R^3$ is preferably a group having a bulkiness of from 1 to 4 carbon atoms or so. For example, it includes a methyl group, an ethyl group, an isopropyl group, a cyclopropyl group, a cyclobutyl group, a dimethylamino group, an ethylmethylamino group, a diethylamino group, a trifluoromethyl group, a methoxymethyl group, an ethoxymethyl group, a methoxyethyl group.

Of those, $R^3$ is preferably an alkyl group, concretely, it is preferably a methyl group.

$R^4$ means a group selected from the following groups [i] to [vi]:

[i]:

a linear-chain or branched-chain alkyl group having from 1 to 6 carbon atoms, and a cycloalkyl group having from 3 to 6 carbon atoms, these may have one or more groups selected, optionally duplicatively, from the following [substituent group 4] (but for the alkyl group, an alkyl group is excluded from the [substituent group 4]);

[ii]:

an aromatic hydrocarbon group, and a 5-membered or 6-membered aromatic heterocyclic group containing from 1 to 4 hetero atoms selected, optionally duplicatively, from a nitrogen atom, an oxygen atom and a sulfur atom, these may have one or more groups selected, optionally duplicatively, from the following [substituent group 4];

[iii]:

an aromatic hetero ring-substituted alkyl group composed of a 5-membered or 6-membered aromatic heterocyclic group containing from 1 to 4 hetero atoms selected, optionally duplicatively, from a group consisting of a nitrogen atom, an oxygen atom and a sulfur atom, and a divalent hydrocarbon group having from 1 to 3 carbon atoms, and an aralkyl group composed of an aromatic hydrocarbon group and a divalent hydrocarbon group having from 1 to 3 carbon atoms, these aromatic heterocyclic group and aromatic hydrocarbon group may have one or more groups selected, optionally duplicatively, from a group consisting of the [substituent group 4] and an alkyl group having from 1 to 6 carbon, atoms added thereto;

[iv]:

an amino group, an alkylamino group having an alkyl group haying from 1 to 6 carbon atoms, a dialkylamino group having alkyl groups having from 1 to 6 carbon atoms that may be the same or different, a 4-membered to 6-membered saturated nitrogen-containing heterocyclic group having a bonding site at the nitrogen atom, and a disubstituted amino group in which one substituent is a 4-membered to 6-membered, saturated, nitrogen-containing heterocyclic group having a bonding site at the carbon atom and the other is an alkyl group having from 1 to 6 carbon atoms, these alkyl moieties may have one or more groups selected, optionally duplicatively, from the [substituent group 4] (in this case, an alkyl group is excluded from the [substituent group 4], and the nitrogen-containing heterocyclic group may have one or more groups selected, optionally duplicatively, from a group consisting of the [substituent group 4] and an alkyl group having from 1 to 6 carbon atoms added thereto;

[v]:

a group of the following formula:

—C(=O)—R$^{41}$ (wherein R$^{41}$ on the carbon atom means an alkylamino group having an alkyl group having from 1 to 6 carbon atoms, a dialkylamino group having alkyl groups having from 1 to 6 carbon atoms that may be the same or different, an alkoxy group having from 1 to 6 carbon atoms, an alkyl(alkoxy)amino group having an alkyl group having from 1 to 6 carbon atoms and an alkoxy group having from 1 to 6 carbon atoms, a 5-membered or 6-membered, saturated cyclic, nitrogen-containing heterocyclic group containing 1 or 2 hetero atoms selected, optionally duplicatively, from a group consisting of a nitrogen atom, an oxygen atom and a sulfur atom and bonding to the carbonyl at the nitrogen atom, a disubstituted amino group having a 5-membered or 6-membered aromatic heterocyclic group containing from 1 to 4 hetero atoms selected, optionally duplicatively, from a group consisting of a nitrogen atom, an oxygen atom and a sulfur atom, and an alkyl group having from 1 to 6 carbon atoms, an aromatic hetero ring-substituted alkyl group composed of a 5-membered or 6-membered aromatic heterocyclic group containing from 1 to 4 hetero atoms selected, optionally duplicatively, from a group consisting of a nitrogen atom, an oxygen atom and a sulfur atom, and an alkylene group having from 1 to 3 carbon atoms, or a substituted dialkylamino group having alkyl groups having from 1 to 6 carbon atoms),

[vi]:

a group of the following formula:

—N(—R$^{42}$)—C(=O)R$^{43}$ (wherein R$^{42}$ and R$^{43}$ each independently mean a hydrogen atom or an alkyl group having from 1 to 6 carbon atoms, or they may combine together to be a polymethylene chain to form a cyclic structure);

the alkyl moiety of the group in the above [v] and [vi] and the alkyl moiety of the alkoxy group therein may have one or more groups selected, optionally duplicatively, from the groups of the [substituent group 4] (in this ease, an alkyl group is excluded from the [substituent group 4]), and the aromatic or saturated heterocyclic group may have one or more groups selected, optionally duplicatively, from a group consisting of the [substituent group 4] and an alkyl group having from 1 to 6 carbon atoms added thereto;

[substituent group 4]:

a halogen atom, an amino group, a hydroxyl group, a carboxy group, an alkoxy group having from 1 to 6 carbon atoms, an alkylthio group having from 1 to 6 carbon atoms, an acyl group having from 2 to 7 carbon atoms, an alkoxycarbonyl group having from 2 to 7 carbon atoms, an alkyl group having from 1 to 6 carbon atoms, a cycloalkyl group having from 3 to 6 carbon atoms, an aralkyloxy group having from 7 to 9 carbon atoms, an aralkyloxycarbonyl group having from 8 to 10 carbon atoms, and a group of the following formula:

—C(=O)—N(—R$^{44}$)R$^{45}$ (wherein R$^{44}$ and R$^{43}$ on the nitrogen atom each independently represent a hydrogen atom, an alkyl group having from 1 to 6 carbon atoms, or an aryl group having from 6 to 10 carbon atoms);

in this, the amino group in the [substituent group 4] may have 1 or 2 substituents selected from a group consisting of an alkyl group having from 1 to 6 carbon atoms, an acyl group having from 2 to 7 carbon atoms, a cycloalkyl group having from 3 to 6 carbon atoms, an aryl group having from 6 to 10 carbon atoms, an aralkyl group having from 7 to 12 carbon atoms, an aromatic heterocyclic group, an alkylsulfonyl group having from 1 to 6 carbon atoms, and an arylsulfonyl group having from 6 to 10 carbon atoms, and when the amino group has two substituents, then they may bond to each other to form a cyclic structure.

The group of [1] includes alkyl groups, preferably having 2 or 3 carbon atoms or so. For example, preferred are an ethyl group, an isopropyl group, a tertiary butyl group, a cyclopropyl group. These may have a substituent, and may be substituted with a hydroxyl group, an alkoxy group having from 1 to 6 carbon atoms, and further an aralkyloxy group having from 2 to 9 carbon atoms.

The alkoxy group as the substituent is preferably a methoxy group; and the aralkyloxy group is preferably a benzyloxy group.

The group of [ii] includes aromatic substituents. These may be aromatic substituents containing a hetero atom.

The aromatic hydrocarbon group is preferably monocyclic, and is preferably a phenyl group. The aromatic heterocyclic group is a 5-membered or 6-membered aromatic heterocyclic group containing from 1 to 4 hetero atoms selected, optionally duplicatively, from a nitrogen atom, an oxygen atom and a sulfur atom. Of those, preferred is an aromatic heterocyclic group. The aromatic heterocyclic group is preferably a thiazolyl group, a furyl group, a pyrrolyl group, a pyridyl group, a pyrazolyl group. More preferably, it is a 2-thiazolyl group, a 2-furyl group, a 2-pyrrolyl group, a 2-pyridyl group, a 4-imidazolyl group. These may further have a substituent, and the substituent is preferably an alkyl group having from 1 to 6 carbon atoms. The alkyl group is preferably a methyl group.

The group of [iii] is a group having a (hetero)aralkyl group structure in which an alkylene chain having from 1 to 3 carbon atoms is bonded to the above-mentioned aromatic substituent. The aromatic substituent is preferably a monocyclic heteroaryl group; examples of the 6-membered ring are a pyridine ring, a pyrimidine ring, a pyrazine ring; and examples of the 5-membered ring are a furan ring, a triazole ring, an imidazole ring, a thiophene ring, a pyrrole ring. The alkylene chain is preferably a methylene group (—CH$_2$—); and as combined with the above-mentioned monocyclic heteroaryl group, there are the following substituents:

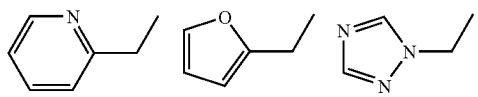

The group of [iv] includes amine-type substituents. These may have a chain structure or a cyclic structure.

The chain structure includes an alkylamine-type structure and a dialkylamine-type structure; and any of which is employable herein. It also includes a simple amino group not having an alkyl group. The alkyl group on the nitrogen atom includes a methyl group, an ethyl group, a propyl group, an isopropyl group, a butyl group, an isobutyl group, a sec-butyl group. The alkyl group may be a linear-chain or branched-chain one. These alkyl groups may have a substituent, and may have a hydroxyl group, a carboxy group, a (substituted) carboxamide group. Preferred are an amino group, a methylamino group, a dimethylamino group, a diethylamino group, a methylethylamino group, a methylisopropylamino group, a methyl-tert-butylamino group. Those having a hydroxyl group include a 2-hydroxyethylmethylamino group, a 2-(dimethylamino carbonyl)ethylmethylamino group, a 3-(dimethylaminocarbonyl)propylmethylamino group.

The cyclic structure is preferably a saturated, 4- to 6-membered nitrogen-containing heterocyclic substituent, in which the nitrogen atom is its bonding site to the bicyclic mother nucleus. It includes an azetidinyl group, a pyrrolidinyl group, a piperazinyl group, a morpholinyl group, a piperazinyl group. Like the chain structures, these may also have a substituent, and may have a hydroxyl group, a carboxy group. These include a 3-hydroxyazetidinyl group, a 3-carboxyazetidinyl group.

The group of [v] is a substituent in which the carbonyl group is its bonding site, and is an ester or amide-structure substituent. Of those, preferred is an amide-structure substituent.

In the ester structure, the group bonding to the carbonyl group may be an alkoxy group having from 1 to 6 carbon atoms, in which the alkyl moiety may be a linear-chain or branched-chain one. The alkoxy group includes a methoxy group, an ethoxy group, a propoxy group, an isopropoxy group. The alkoxy group in this part is preferably a methoxy group or an ethoxy group.

In the amide structure-having substituent, the substituted amino group may bond to the carbonyl group, and the substituted amino group may have a chain structure or a cyclic structure. Containing a nitrogen atom bonding to the carbonyl group, the cyclic structure is a structure to form a cyclic structure. For example, the alkyl group to form alkylamino groups may be a linear-chain or branched-chain one having from 1 to 6 carbon atoms. For example, it includes a methyl group, an ethyl group, a propyl group, an isopropyl group, a butyl group, an isobutyl group, a sec-butyl group. The alkylamino groups include a methylamino group, a dimethylamino group, a diethylamino group, a methylethylamino group. The alkyl group may further have a substituent, and may have a halogen atom, a hydroxyl group, an alkoxy group, a (substituted)aminocarbonyl group. For example, mentioned are a 2-fluoroethylmethylamino group, a 2-hydroxyethylmethylamino group, a 2-methoxyethylmethylamino group, a (dimethylaminocarbonylmethyl)methylamino group.

It may also be an alkoxyalkylamino group in which the alkylamino group is further substituted with an alkoxy group at the nitrogen atom. For example, it includes a methyl-methoxyamino group.

In the cyclic structure-having amino group, the nitrogen atom of the 5-membered or 6-membered saturated nitrogen-containing heterocyclic substituent is the bonding site to the carbonyl group. Concretely mentioned are a pyrrolidinyl group and a piperazinyl group, in which the ring may contain at least one hetero atoms of a nitrogen atom, an oxygen atom and a sulfur atom. When the second hetero atom is a nitrogen atom, then it may have a substituent, and may have ah alkyl group having from 1 to 6 carbon atoms, an acyl group having from 2 to 7 carbon atoms. The cyclic alkyl group includes an azetidinyl group, a pyrrolidinyl group, a piperazinyl group, a morpholinyl group, a piperidinyl group; and the group having a substituent includes a 4-acetylpiperazinyl group.

The group of [vi] is a substituted amide group having a bonding site at the nitrogen atom. The substituent at file carbonyl group and that at the nitrogen atom may be a hydrogen atom or an alkyl group, but preferably they are both an alkyl group, more preferably a methyl group.

It is also desirable that the alkyl group at the carbonyl group and that at the nitrogen atom combine together to from a polymethylene chain to give a cyclic structure, thereby forming a lactam structure.

X and Y each independently mean a nitrogen atom, an oxygen atom, a sulfur atom, N—$R^5$ or C—$R^5$; $R^5$ and $R^6$ each independently mean a hydrogen atom or an alkyl group having from 1 to 6 carbon atoms; and the ring containing X and Y may be an aromatic ring.

X and Y include the following combinations:

(1) X is a nitrogen atom and Y is an oxygen atom, (2) X is a nitrogen atom and Y is N—$R^5$, (3) X is an oxygen atom and Y is a nitrogen atom, (4) X is an oxygen atom and Y is C—$R^6$, (5) X is N—$R^5$ and Y is C—$R^6$, (6) X is a nitrogen atom and Y is a sulfur atom, (7) X is a sulfur atom and Y is a nitrogen atom.

$R^5$ and $R^6$ each are a hydrogen atom or an alkyl group; and the alkyl group is preferably a methyl group. The ring containing X and Y may be a saturated ring, but may also be an aromatic ring. More preferably, it is an aromatic ring.

Examples of the compound of the invention having a bicyclic mother nuclei are compounds having the following structure.

[Formula 5]

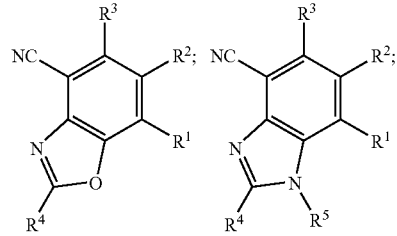

-continued

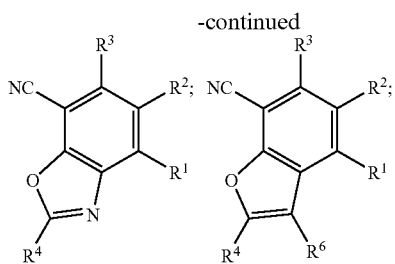

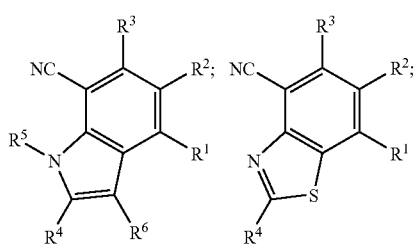

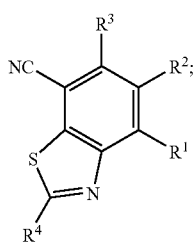

Of those, preferred are the compounds having the following structure.

[Formula 6]

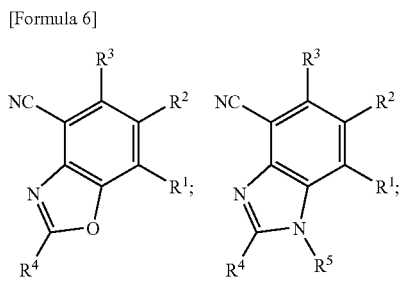

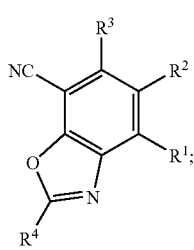

More preferred are the compounds having the following structure.

[Formula 7]

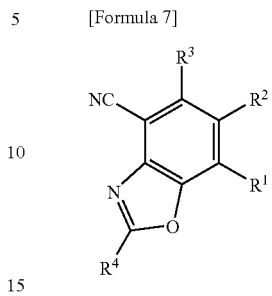

When the compound of formula (I) is constituted to have enantiomers, then each enantiomer thereof, a 1/1 racemic mixture of the enantiomers, and other enantiomer mixtures comprising the enantiomers in any desired ratio and having an optical purity of smaller than 100% are all within the scope of the compound of the invention. When the compound of formula (I) is constituted to have diastereomers, then the single diastereomers and diastereomer mixtures are within the scope of the compound of the invention.

When the compound of formula (I) includes enantiomers, then it is desirable that a single enantiomer thereof is administered to humans and animals. The "single enantiomer" should be so understood that it does not contain the other enantiomer at all or it may contain the other enantiomer to such a degree that it is chemically pure. In other words, it should be so understood that the single enantiomer may contain the other enantiomer so far as the other enantiomer added thereto does not have any influence on the physical constant and the physiological activity of the single enantiomer.

When the compound of formula (I) includes diastereomers, then it is also desirable that a single diastereomer thereof is administered to humans and animals. The "single diastereomer" should be so understood that it does not contain the other diastereomer at all or it may contain the other diastereomer to such a degree that it is chemically pure. In other words, it should be so understood that the single diastereomer may contain the other diastereomer so far as the other diastereomer added thereto does not have any influence on the physical constant and the physiological activity of the single diastereomer.

The wording "stereochemically single" means as follows: When a compound contains an asymmetric carbon and therefore the compound includes isomers, then one of the isomers, or that is, the single isomer is a stereochemically single compound. Also in this case, the wording "single" should be interpreted as in the above.

When the compound of formula (I) is an acid derivative having a phenolic hydroxyl group, a carboxyl group (carboxylic acid derivative) or a sulfo group (sulfonic acid derivative) in any desired substituent moiety, then the acid derivative may be a free acid thereof, or may be formed into a salt thereof at the phenolic hydroxyl group, the carboxyl group or the sulfo group.

The salt may be any of inorganic salts or organic salts, including, for example, alkali metal salts such as lithium salts, sodium salts, potassium salts; alkaline earth metal salts such as magnesium salts, calcium salts; ammonium salts; and triethylamine salts, N-methylglutamine salts, tris-(hydroxymethyl)aminomethane salts. These free acid derivatives and their salts may form hydrates.

On the other hand, when the compound of formula (I) is a basic derivative having an amino group or an amine structure in any desired substituent moiety thereof, then the basic derivative may be a free base thereof, or may form an acid-addition salt thereof.

Examples of the acid-addition salt include inorganic acid salts such as hydrochlorides, sulfates, nitrate, hydrobromides, hydroiodides, phosphates; and organic acid salts such as methanesulfonates, benzenesulfonates, paratoluene-sulfonates (sulfonates), acetates, citrates, maleates, fumarates, lactates, tartrates (carboxylates). These free base derivatives and their sails may form hydrates.

When the compound of formula (I) is a carboxylic acid compound and when it forms an ester thereof at the carboxylic acid moiety, then the derivative is useful as an intermediate for synthesis or as a prodrug. For example, alkyl esters, benzyl esters, alkoxyalkyl esters, phenylalkyl esters and phenyl esters are useful as intermediates for synthesis.

When the carboxylic acid compound of the invention is used for antifungal purpose and when its ester is used as a prodrug, then the ester is readily cleaved in living bodies to give its free carboxylic acid. For example, it includes acetoxymethyl esters, pivaloyloxymethyl esters, ethoxycarbonyl esters, choline esters, dimethylaminoethyl esters, 5-indanyl esters and phthalazinyl esters, as well as oxoalkyl esters such as 5-alkyl-2-oxo-1,3-dioxol-4-ylmethyl esters and 3-acetoxy-2-oxobutyl esters.

When the compound of formula (I) is an amino group-having basic compound and when an amino acid, dipeptide or tripeptide bonds to the amino group, then the derivative is useful as a prodrug.

The amino acid, dipeptide and tripeptide for the prodrug are such that the peptide bond to be formed by the carboxyl group therein and the amino group in the compound of formula (I) of the invention is readily cleaved in living bodies to give a free amine. For example, they include amino acids such as glycine, alanine, aspartic acid; dipeptides such as glycine-glycine, glycine-alanine, alanine-alanine; and tripeptides such as glycine-glycine-alanine, glycine-alanine-alanine.

The compound of formula (I) may be produced in various methods. Some preferred and typical examples of the production methods are mentioned below, to which, however, the invention should not be limited. Regarding reaction, the substituents may be optionally protected with a protective group, and the order of converting the substituents (functional groups) is not specifically defined.

Production Method 1:

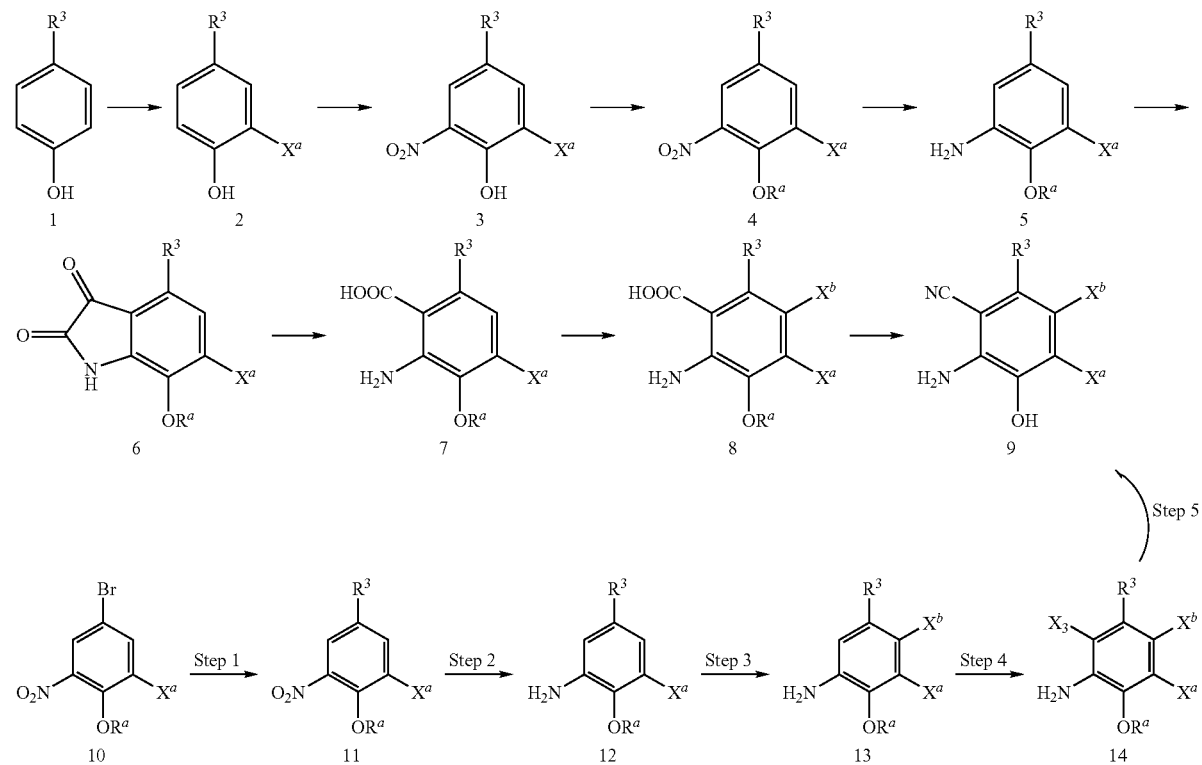

[Formula 8]

(In the formula, $R^3$ has the same definition as that of the substituent in formula (I); $R^a$ represents a protective group for hydroxyl group; $X^a$, $X^b$ and $X^c$ each represents a halogen atom or a leaving group, $OR^b$ (e.g., OTf, OMs).)

The production method 1 is a method for producing a substituted benzonitrile (9) that can be used as an intermediate in synthesis of producing the compound of formula (I).

Specifically, the compound (9) can be produced as follows; A compound (4) is produced from a compound (1) according to the method described in Chem. Pharm. Bull, Vol. 18, p. 2208, 1970; then the nitro group is selectively reduced to give a compound (5); a compound (8) is produced from the compound (5) according to the method described in Eur. J. Med. Chem., Vol. 34, p. 729, 1999; and the carboxyl group is converted into a nitrile group. The compound (9) may also be produced from a compound (10) (commercial product, $X^a$=F, $R^a$=Me) through the step 1 (introduction of $R^3$ by Suzuki coupling with a boronic acid or a boronate in the presence of a catalyst such as palladium), the step 2 (reduction of nitro group), the step 3 (halogenation: $X^b$), the step 4 (halogenation: $X^a$) and the step 5 (introduction of nitrile group: $X^c$→CN).

Production Method 2;

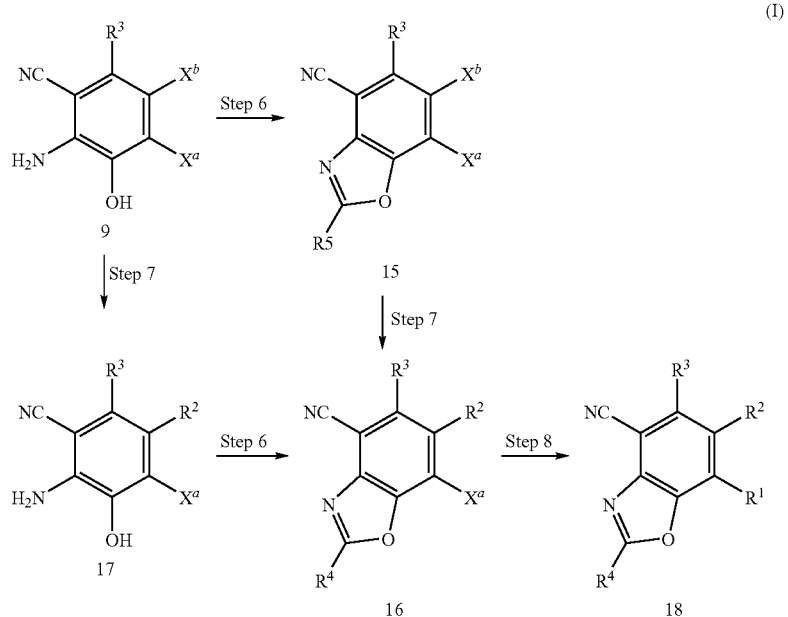

[Formula 9]

(In the formula, $X^a$ and $X^b$ each represents a halogen atom or a leaving group, $OR^b$ (e.g., OTf, OMs); and $R^1$, $R^2$, $R^3$ and $R^4$ have the same definitions as those of the substituents in (I).)

The production method 2 is a method for producing the intended compound of formula (I) from the benzonitrile (9) obtained in the production method 1.

The step 6 is a step of reacting the compound (9) with an acid chloride or an ortho ester to acylate the amino group (hydroxyl group depending on the condition), optionally followed by dehydration to form an oxazole ring.

The step 7 is a step of introducing a substituent corresponding to $R^2$ or a substituent to be its precursor into the substituent $X^b$ on the benzene ring in the presence of a palladium catalyst, or under a (Suzuki coupling) condition for reaction with a boronic acid or a boronate, or under a (Stille coupling) condition for reaction with a tin compound.

The step 8 is a step of producing the compound of the invention by reacting the substituent $X^a$ on the benzene ring with an amine derivative. In this case, when $R^1$ is an aryl group, a heteroaryl group, a cycloalkenyl group or an alkyl group, the compound may be derived from the product obtained under the above-mentioned Suzuki coupling condition or Stille coupling condition.

The order of the steps 6, 7 and 8 may be suitably changed, depending on the substituent (functional group) to be introduced and on the chemical properties of the product; and the introduced substituent may be suitably subjected to functional group protection, protective group removal and functional group conversion, if desired.

The intended compounds thus obtained may be purified, if desired, in an ordinary method, for example, through recrystallization, reprecipitation, chromatography or the like.

The compound of the invention specifically (selectively) exhibits an antifungal activity, not exhibiting an antibacterial activity or an anticancer activity, and is active to a broad range of fungi that cause various fungal infections. Therefore, the compound may be used for treating, preventing or lightening the diseases caused by such pathogens.

Examples of fungi to which the compound of the invention is effective include those of the genus *Candida* such as *Candida albicans, Candida glabrata, Candida krusei, Candida tropicalis*; the genus *Cryptococcus* such as *Chryptococcus neoformans*; the genus *Aspergillus* such as *Aspergillus fumigatus, Aspergillus flavus; Pneumocystis carinii*; the genus *Rhisopus*; the genus *Absidia*; the genus *Histoplasma* such as *Histoplasma capsulatum*; the genus *Coccidioides* such as *Coccidioides immitis*; the genus *Blastomyces*; the genus *Paracoccidioides* such as *Paracoccidioides brasiliensis*; the genus *Penicilium*, the genus *Pseudallescheria*; the genus *Sporothrix*; the genus *Dematiaceous*; the genus *Tricophiton*; the genus *Microsporum*; the genus *Epidermophyton*; the genus *Malassezia*; the genus *Foncecaea*; the genus *Fusarium*; the genus *Paecilomyces*; the genus *Trichosporon* such as *Trichosporon cutaneum*; the genus *Hyalohora*; and the genus *Cladosporium*. In addition, further mentioned are *Saccharomyces cerevisiae, Candida albicans, Candida glabrata, Candida krusei, Candida tropicalis, Chryptococcus neoformans, Trichosporon cutaneum*, and *Aspergillus fumigatus*.

The diseases to be caused by these pathogens include internal organ mycosis (deep seated mycosis) such as candidosis, cryptococosis, aspergillosis, actinomycosis, nocardiosis, mucormycosis, geotrichosis, histoplasmosis, coccidiosis, paracoccidiosis, blastomicosis and peniciliosis, concretely hematomyelia, respiratory system mycosis, digestive system mycosis, urinary tract mycosis, mycotic meningitis; deep skin mycosis such as sporotricosis, chromomycosis, mycetoma; and superficial mycosis such as conventional trichophytosis, profound trichophytosis, intractable trichophytosis, nail trichophotosis, tinea versicolor, skin candidosis, oral cavity candidosis.

The method of administering the drug of the invention, the dose thereof and the frequency of administration are not specifically defined, and may be suitably determined depending on various conditions including the type of pathogenic fungi, the age, the body weight and the condition of patients. In ordinary oral or parenteral (injection, drip) administration to adults, the dose may be from 0.1 to 100 mg/kg/day, and it may be administered all at once or in multiple times after divided.

In addition, the compound of the invention is effective also to various fungi that cause fungal infections in animals.

Based on the antifungal effect to pathogenic fungi thereof, the compound of the invention, its salt and their solvate are applicable to drugs, remedies for infections and antifungals, and to animal drugs, marine drugs and antifungal preservatives.

The compound of the invention, its salt and their solvate may be used for producing drugs, remedies for infections and antifungals that contain it. For example, the compound of the invention, its salt and their solvate may be used for producing injections that are provided in the form of solutions and for producing liquid preparations. Optionally combined with suitable additives added thereto, the compound of the invention, its salt and their solvate may be formulated into drugs, remedies for infections or antifungals in an ordinary method of producing pharmaceutical preparations.

Regarding the form of the antifungals that contain the compound of the invention, its salt or their solvate, for example, there are mentioned oral preparations such as tablets, powders, granules, capsules, solutions, syrups, elixirs, oily or aqueous suspensions.

Injections may contain a stabilizer, a preservative or a dissolution aid, and the solution that contains the auxiliary additives may be put in containers and then freeze-dried into solid preparations, which may be re-formulated into actual preparations before use.

Examples of external applications include solutions, suspensions, emulsions, ointments, gels, creams, lotions, and sprays.

Solid preparations may contain, along with the compound of the invention, its salt or their solvate, any pharmaceutically acceptable additive. For example, the additive includes fillers, vehicles, binders, disintegrators, dissolution promoters, moisturizers, lubricants. These may be suitably selected and mixed with the active ingredient in formulating the preparations.

Liquid preparations include solutions, suspensions and emulsions, to which an additive of a suspending agent and an emulsifier may be added.

For administrating the compound of the invention, its salt or their solvate to animals, for example, it may be orally administered thereto directly or after mixed in feed; or after the compound or the like has been formed into a solution thereof, it may be directly administered or may be added to drinking water or feed for oral administration; or the solution may be administered through injection.

The preparations mat contain the compound of the invention, its salt or their solvate for administration to animals may be produced according to an ordinary technique known in the art, for example, as powders, granules, soluble powders, syrups, solutions or injections.

EXAMPLES

The invention is described with reference to Examples and Reference Examples, to which, however, the invention should not be limited.

Reference Example 1

N-(3-Bromo-2-methoxy-5-methylphenyl)-2-hydroxyiminoacetamide (I-1)

Produced according to the method described in literature (Eur. J. Med. Chem., 34, 729 (1999)).

An N,N-dimethylformamide (5 ml) solution of 3-bromo-2-methoxy-5-methylaniline (467 mg, 2.16 mmol), concentrated hydrochloric acid (268 µl) were added to an aqueous (11 ml) solution of trichloroacetaldehyde monohydrate (715 mg, 4.32 mmol), anhydrous sodium sulfate (2.46 g, 17.3 mmol), followed by stirring at 90° C. for 25 minutes. Hydroxylamine hydrochloride (901 mg, 13.0 mmol) was added to it, followed by stirring overnight at 90° C.

After cooling, water (50 ml) was added, and the product was extracted with ethyl acetate (100 ml×2), the organic layer was washed with saturated brine (50 ml), dried over anhydrous magnesium sulfate, concentrated under reduced pressure. The residue was purified by silica gel column chromatography (n-hexane:ethyl acetate=3:1) to obtain the entitled compound (278 mg, 45%) as a yellow white solid.

MS (FAB) m/z: 287 (M+1 for $^{79}$Br)$^+$, 289 (M+1 for $^{81}$Br)$^+$.
$^1$H-NMR (DMSO-d$_6$) δ: 2.26 (3H, s), 3.75 (3H, s), 7.21 (1H, d, J=1.5 Hz), 7.92 (1H, d, J=1.5 Hz), 9.35 (1H, brs), 12.4 (1H, brs).

Reference Example 2

6-Bromo-7-methoxy-4-methyl-1H-indole-2,3-dione (I-2)

Produced according to the method described in literature (Eur. J. Med. Chem., 34, 729 (1999)).

Polyphosphoric acid (2.97 g) was added to N-(3-bromo-2-methoxy-5-methylphenyl)-2-hydroxyiminoacetamide (I-1) (260 mg, 906 µmol), followed by stirring at 80° C. for 3 hours. Ice (about 10 g) was put into the reaction liquid, then water (30 ml) was added and the product was extracted with ethyl acetate (70 ml×2). The organic layer was washed with saturated brine (50 ml×2), then dried over anhydrous magnesium sulfate, concentrated under reduced pressure. The residue was purified by silica gel column chromatography (n-hexane: ethyl acetate=3:1→3:2) to obtain the entitled compound (103 mg, 42%) as an orange solid.

MS (FAB) m/z: 270 (M+1 for $^{79}$Br)$^+$, 272 (M+1 for $^{81}$Br)$^+$.
$^1$H-NMR (DMSO-d$_6$) δ: 2.38 (3H, s), 3.73 (3H, s), 7.16 (1H, s), 11.41 (1H, brs).

Reference Example 3

2-Amino-4-bromo-3-methoxy-6-methylbenzoic acid (I-3)

Produced according to the method described in literature (Eur. J. Med. Chem., 34, 729 (1999)).

6-Bromo-7-methoxy-4-methyl-1H-indole-2,3-dione (I-2) (92.3 mg, 342 µmol) was dissolved in 1,4-dioxane (1.5 ml), at 0° C., aqueous hydrogen peroxide (175 µl, 30%, d=1.11, 1.71 mmol), aqueous 0.67 N sodium hydroxide solution (6.38 ml, 4.27 mmol) were added, followed by stirring for 3 hours with gradually heating. Acetic acid was added to the reaction liquid for controlling at pH of 4 to 5, saturated brine (50 ml) was added, the product was extracted with ethyl acetate (50 ml×2). The organic layer was washed with saturated brine (50 ml), then dried over anhydrous magnesium sulfate, concentrated under reduced pressure, the residue was purified by silica gel column chromatography (chloroform:methanol=50:1) to obtain the entitled compound (72 mg, 80%) as a yellow solid.

MS (FAB) m/z: 260 (M+1 for $^{79}$Br)$^+$, 262 (M+1 for $^{81}$Br)$^+$.
$^1$H-NMR (MeOH-d$_4$) δ: 2.37 (3H, s), 3.76 (3H, s), 6.64 (1H, s).

Reference Example 4

2-Amino-4-bromo-5-iodo-3-methoxy-6-methylbenzoic acid (I-4)

N-Iodosuccinimide (104 mg, 461 µmol) was put into an N,N-dimethylformamide (2.0 ml) solution of 2-amino-4-bromo-3-methoxy-6-methylbenzoic acid (I-3) (100 mg, 384 µmol), followed by stirring at room temperature for 40 minutes. The reaction liquid was put into water (30 ml), followed by controlling at pH of 4 with aqueous 2 N sodium hydroxide solution, then saturated brine (30 ml) was added, the product was extracted with ethyl acetate (50 ml×2). The organic layer was dried over anhydrous magnesium sulfate, concentrated under reduced pressure, the residue was purified by silica gel column chromatography (chloroform:methanol=1:0→100:3) to obtain the entitled compound (84.9 mg, 57%) as a yellow white solid.

MS (FAB) m/z; 386 (M+1 for $^{79}$Br)$^+$, 388 (M+1 for $^{81}$Br)$^+$.
$^1$H-NMR (DMSO-d$_6$) δ: 2.44 (3H, s), 3.65 (3H, s).

Reference Example 5

4-Bromo-2-(2,2-dimethylpropionylamino)-5-iodo-3-methoxy-6-methylbenzamide (I-5)

A benzene (1.0 ml) suspension of 2-amino-4-bromo-5-iodo-3-methoxy-6-methylbenzoic acid (I-4) (77 mg, 199 µmol) was cooled at 0° C., pivaloyl chloride (61.4 µl, 499 µmol), pyridine (40.3 µl, 499 µmol) were put thereinto, followed by stirring at room temperature for 1 hour. Ethyl acetate (30 ml) was added to the reaction liquid, the organic layer was washed with 1 N hydrochloric acid (30 ml×2), saturated brine (30 ml×2), then dried over anhydrous magnesium sulfate, concentrated under reduced pressure. To the residue, added were toluene (2.0 ml), 4-dimethylaminopyridine (25.6 mg, 209 µmol), followed by stirring at room temperature for 15 minutes and then stirring at 50° C. for 1.15 hours, further followed by refluxing for 30 minutes. After cooling, ethyl acetate (30 ml) was added, the organic layer was washed with 1 N hydrochloric acid (30 ml×2), saturated brine (30 ml×2), then dried over anhydrous magnesium sulfate, then concentrated under reduced pressure to obtain 7-bromo-2-tert-butyl-6-iodo-8-methoxy-5-methylbenzo[d][1,3]oxazin-4-one (87.5 mg, 97%) as a yellow ocher solid. A tetrahydrofuran (1.0 ml) solution of a part of it (65 mg, 144 µmol) was cooled at 0° C., followed by adding aqueous 28% ammonia (97.1 µl, 1.44 mmol) and stirring overnight with gradually heating up to room temperature. On the next day, this was further cooled at 0° C., followed by adding aqueous 28% ammonia (97.1 µl, 1.44 mmol) and stirring for 2 hours with gradually heating up to room temperature. Aqueous saturated ammonium chloride solution (30 ml) was added to the reaction liquid, the product was extracted with ethyl acetate (30 ml×2). The organic layer was dried over anhydrous magnesium sulfate, concentrated under reduced pressure, the residue was purified by silica gel column chromatography (chloroform:ethyl acetate=4:1→chloroform:methanol=20:1) to obtain the entitled compound (35.8 mg, 53%) as a colorless solid.

MS (FAB) m/z: 469 (M+1 for $^{79}$Br)$^+$, 471 (M+1 for $^{81}$Br)$^+$.
$^1$H-NMR (MeOH-d$_4$) δ: 1.29 (9H, s), 2.57 (3H, s), 3.75 (3H, s).

Reference Example 6

N-(3-Bromo-6-cyano-4-iodo-2-methoxy-5-methylphenyl)-2,2-dimethylpropionamide (I-6)

4-Dimethylaminopyridine (54.2 mg, 443 µmol) was added to a pyridine (40 ml) suspension of 4-bromo-2-(2,2-dimethylpropionylamino)-5-iodo-3-methoxy-6-methylbenzamide (I-5) (2.08 g, 4.43 mmol), followed by cooling at 0° C. To this, trifluoromethanesulfonic acid anhydride (2.25 ml, 13.3 mmol) was dropwise added, followed by stirring at room temperature for 2.5 hours, the reaction liquid was put into 1 N hydrochloric acid (200 ml), followed by extraction with ethyl acetate (200 ml×2). The organic layer was washed successively with 1 N hydrochloric acid (200 ml×2), saturated sodium bicarbonate water (50 ml), saturated brine (50 ml), then dried over anhydrous magnesium sulfate, concentrated under reduced pressure, the residue was purified twice by silica gel column chromatography (n-hexane:ethyl acetate=4:1) to obtain the entitled compound (1.86 g, quant.) as a pale yellow solid.

MS (FAB) m/z: 451 (M+1 for $^{79}$Br)$^+$, 453 (M+1 for $^{81}$Br)$^+$.
$^1$H-NMR (CDCl$_3$) δ: 1.39 (9H, s), 2.81 (3H, s), 3.76 (3H, s), 7.39 (1H, brs).

Reference Example 7

N-(3-Bromo-6-cyano)-2-hydroxy-4-iodo-5-methylphenyl)-2,2-dimethylpropionamide (I-7)

A dichloromethane (15 ml) solution of N-(3-bromo-6-cyano-4-iodo-2-methoxy-5-methylphenyl)-2,2-dimethylpropionamide (I-6) (300 mg, 665 µmol) was cooled at −78° C., a dichloromethane solution of 1 N tribromoborane (2.33 ml, 2.33 mmol) was dropwise added thereto, followed by stirring at −78° C. for 40 minutes. Afterwards, this was heated up to −12° C. and stirred for 3.5 hours. During the course, the starting material appeared to precipitate out, and dichloromethane (7.5 ml) was further added but could not bring about complete dissolution. The reaction liquid was heated up to room temperature, taking 15 minutes, then put into cold water (100 ml), saturated brine (100 ml) was added, the product was extracted with ethyl acetate (100 ml×2). The organic layer was washed with saturated brine (50 ml×2), then dried over anhydrous magnesium sulfate, concentrated under reduced pressure to obtain the entitled compound (282 mg, 97%) as a yellow solid.
MS (FAB) m/z: 437 (M+1 for $^{79}$Br)$^+$, 439 (M+1 for $^{81}$Br)$^+$.
$^1$H-NMR (CDCl$_3$) δ: 1.41 (9H, s), 2.75 (3H, s), 7.98 (1H, brs), 10.15 (1H, s).

Reference Example 8

7-Bromo-2-tert-butyl-6-iodo-5-methyl-1,3-benzoxazole-4-carbonitrile (I-8)

Toluene (25 ml), p-toluenesulfonic acid monohydrate (10.9 mg, 57.2 μmol) were added to N-(3-bromo-6-cyano-2-hydroxy-4-iodo-5-methylphenyl)-2,2-dimethylpropionamide (I-7) (250 mg, 572 μmol), followed by refluxing with a Dean-Stark condenser for 3 hours. After cooling, saturated sodium bicarbonate water (30 ml) was added to the reaction liquid, the product was extracted with ethyl acetate (50 ml×2). The organic layer was washed with saturated brine (50 ml), dried over anhydrous magnesium sulfate, concentrated under reduced pressure, the residue was purified by silica gel column chromatography (n-hexane:ethyl acetate=6:1) to obtain the entitled compound (225 mg, 94%) as a pale yellow solid.
MS (FAB) m/z: 419 (M+1 for $^{79}$Br)$^+$, 421 (M+1 for $^{81}$Br)$^+$.
$^1$H-NMR (CDCl$_3$) δ: 1.52 (9H, s), 2.92 (3H, s).

Reference Example 9

7-Bromo-2-tert-butyl-5-methyl-6-phenyl-1,3-benzoxazole-4-carbonitrile (I-9)

Tetrakis(triphenylphosphine)palladium(0) (300 mg, 0.26 mmol) was added to an N,N-dimethylformamide (60 ml) suspension of 7-bromo-2-tert-butyl-6-iodo-5-methyl-1,3-benzoxazole-4-carbonitrile (I-8) (545 mg, 1.30 mmol), 2-phenyl-1,3,2-dioxaborinane (205 μl, 1.37 mmol), anhydrous potassium phosphate (552 mg, 2.60 mmol), followed by stirring at 100° C. for 1 hour. After cooling, 1 N hydrochloric acid (100 ml) was added, the product was extracted with ethyl acetate (100 ml×2), the organic layer was washed with saturated brine (50 ml×2), then dried over anhydrous magnesium sulfate, concentrated under reduced pressure. The residue was purified by silica gel column chromatography (n-hexane:ethyl acetate=8:1→6:1) to obtain the entitled compound (210 mg, 44%) as a colorless solid.
MS (FAB) m/z: 369 (M+1 for $^{79}$Br)$^+$, 371 (M+1 for $^{81}$Br)$^+$.
$^1$H-NMR (CDCl$_3$) δ: 1.54 (9H, s), 2.37 (3H, s), 7.10-7.17 (2H, m), 7.42-7.55 (3H, m).

Example 1

2-tert-Butyl-7-[(3S)-3-(dimethylamino)pyrrolidin-1-yl]-5-methyl-6-phenyl-1,3-benzoxazole-4-carbonitrile hydrochloride (#1)

(S)-(−)-2,2'-Bis(diphenylphosphino)-1,1'-binaphthyl (463 mg, 743 μmol) was dissolved in toluene (18 ml) under heat, cooled to room temperature, then palladium(II) acetate (111 mg, 496 μmol) was added, followed by stirring for 1 minute. 7-Bromo-2-tert-butyl-5-methyl-6-phenyl-1,3-benzoxazole-4-carbonitrile (I-9) (1.83 g, 4.96 mmol), (3S)-3-(dimethylamino)pyrrolidine (755 μl, 5.95 mmol), sodium tert-butoxide (667 mg, 6.94 mmol), toluene (18 ml) were successively put into it followed by stirring at 80° C. for 15 hours. After cooling, saturated sodium bicarbonate water (100 ml) was added to the reaction liquid, the product was extracted with chloroform (150 ml×2). The organic layer was washed with saturated brine (50 ml×2), then dried over anhydrous magnesium sulfate, concentrated under reduced pressure. The residue was purified twice by silica gel column chromatography (chloroform:methanol=1:0→100:1) to obtain a non-salt form of the entitled compound (365 mg, 18%) as a yellow ocher semi-solid. This was dissolved in diethyl ether (100 ml), 4 N hydrogen chloride/1,4-dioxane solution (238 μl, 952 μmol) was dropwise added, followed by stirring for 3 minutes. The precipitated matter was collected by filtration, dried to obtain the entitled compound (375 mg, salting yield 94%) as a pale yellow ocher solid.
mp: 198-201° C. (dec.).
MS (FAB) m/z: 403 (M+1-HCl)$^+$.
$^1$H-NMR (CDCl$_3$) δ: 1.51 (9H, s), 2.15-2.30 (2H, m), 2.22 (3H, s), 2.56 (6H, brs), 3.18-3.28 (1H, m), 3.35-3.44 (1H, m), 3.46-3.72 (3H, m), 7.15-7.22 (2H, m), 7.37-7.52 (3H, m).
IR (diffuse reflectance spectroscopy): 2968, 2581, 2464, 2209, 1609, 1474, 1368 cm$^{-1}$. Anal. Calcd for C$_{25}$H$_{30}$N$_4$O.HCl.H$_2$O: C, 65.70; H, 7.28; N, 12.26; Cl, 7.76. Found: C, 65.85; H, 7.31; N, 12.14; Cl, 7.72.

Example 2

2-tert-Butyl-5-methyl-7-[(3S)-3-(methylamino)pyrrolidin-1-yl]-6-phenyl-1,3-benzoxazole-4-carbonitrile hydrochloride (#2)

(S)-(−)-2,2-bis(diphenylphosphino)-1,1'-binaphthyl (288 mg, 463 μmol) was dissolved in toluene (11 ml) under heat, cooled to room temperature, then palladium(II) acetate (69.3 mg, 309 μmol) was added, followed by stirring for 1 minute, 7-Bromo-2-tert-butyl-5-methyl-6-phenyl-1,3-benzoxazole-4-carbonitrile (I-9) (1.14 g, 3.09 mmol), (3S)-3-methylaminopyrrolidine (395 μl, 3.70 mmol) sodium tert-butoxide (415 mg, 4.32 mmol), toluene (11 ml) were successively put into it, followed by stirring at 80° C. for 17 hours. After cooling, saturated sodium bicarbonate water (100 ml) was added to the reaction liquid, the product was extracted with chloroform (100 ml×2). The organic layer was washed with saturated brine (50 ml×2), then dried over anhydrous magnesium sulfate, concentrated under reduced pressure. The residue was purified twice by silica gel column chromatography (chloroform:methanol=1:0→100:1) to obtain a non-salt form of the entitled compound (144 mg, 12%) as a yellow ocher solid. This was dissolved in diethyl ether (50 ml), 4 N hydrogen chloride/1,4-dioxane solution (97.3 μl, 389 μmol) was dropwise added, followed by stirring for 3 minutes. The precipitated matter was collected by filtration, dried to obtain the entitled compound (140 mg, salting yield 89%) as a yellow white solid.
mp: 237-240° C. (dec.).
MS (FAB) m/z: 389 (M+1-HCl)$^+$.
$^1$H-NMR (CDCl$_3$) δ: 1.50 (9H, s), 1.50-1.62 (1H, m), 2.06-2.22 (2H, m), 2.20 (3H, s), 2.41 (3H, s), 3.19-3.29 (1H, m), 3.42-3.56 (4H, m), 7.17-7.24 (2H, m), 7.34-7.48 (3H, m).
IR (diffuse reflectance spectroscopy): 2972, 2873, 2728, 2208, 1608, 1560, 1472, 1368 cm$^{-1}$.
Anal. Calcd for C$_{24}$H$_{28}$N$_4$O.HCl.0.75H$_2$O: C, 65.74; H, 7.01; N, 12.78; Cl, 8.09. Found: C, 65.91; H, 6.99; N, 12.36; Cl, 8.00.

Example 3

2-tert-Butyl-7-[3-(dimethylamino)cyclopent-1-en-1-yl]-5-methyl-6-phenyl-1,3-benzoxazole-4-carbonitrile (#3)

A 1,4-dioxane (20 ml) solution of 7-bromo-2-tert-butyl-5-methyl-6-phenyl-1,3-benzoxazole-4-carbonitrile (I-9) (414 mg, 1.12 mmol), 1-(N-tert-butoxycarbonylamino)-3-tri-n-butylstannyl-2-cyclopentene (530 mg, 1.12 mmol), bis(triphenylphosphine)palladium(II) chloride (39.3 mg, 56.1 µmol), 2,6-di-tert-butyl-p-cresol (28 mg, 127 µmol) was refluxed overnight. After cooling, the reaction liquid was concentrated under reduced pressure, the residue was purified by silica gel column chromatography (n-hexane:ethyl acetate=10:1→8:1) to obtain tert-butyl [3-(2-tert-butyl-4-cyano-5-methyl-6-phenyl-1,3-benzoxazol-7-yl)-2-cyclopentenyl]carbamate (322 mg, 61%) as a yellow white solid. A part of it (270 mg) was stirred in hydrochloric acid/1,4-dioxane solution, followed by purifying by silica gel column chromatography to obtain 7-(3-amino-cyclopent-1-enyl)-2-tert-butyl-5-methyl-6-phenyl-1,3-benzoxazole-4-carbonitrile (157 mg). This was dissolved in methanol (4 ml), aqueous formalin solution (324 µl, 46-38%, 4.23 mmol), sodium cyanoborohydride (80 mg, 1.27 mmol) and acetic acid (87 µl, 1.52 mmol) were successively added, followed by stirring at room temperature for 2.5 hours. The reaction liquid was concentrated under reduced pressure, aqueous 10% sodium carbonate solution was added to the residue, the organic matter was extracted with chloroform. The organic layer was washed with saturated brine, then dried over anhydrous magnesium sulfate, the solvent was concentrated under reduced pressure. The resulting residue was purified by silica gel column chromatography (chloroform:methanol=40:1) to obtain the entitled compound (84.8 mg, 50%) as a yellow solid.

mp: 114-116° C.

MS (FAB) m/z: 400 (M+1)$^+$.

$^1$H-NMR (CDCl$_3$) δ: 1.51 (9H, s), 1.60-1.90 (4H, m), 2.11 (6H, s), 2.33 (3H, s), 3.75-3.84 (1H, m), 5.81-5.85 (1H, m), 7.04-7.16 (2H, m), 7.33-7.45 (3H, m).

IR (diffuse reflectance spectroscopy): 2969, 2934, 2771, 2222, 1549, 1456 cm$^{-1}$.

Anal. Calcd for C$_{26}$H$_{29}$N$_3$O.0.5H$_2$O: C, 76.44; H, 7.40; N, 10.29. Found: C, 76.42; H, 7.17; N, 10.34.

Reference Example 10

7-Bromo-2-tert-butyl-6-(2-furyl)-5-methyl-1,3-benzoxazole-4-carbonitrile (I-10)

Bis(triphenylphosphine)palladium(II) chloride (0.5 mg, 0.72 µmol) was added to a benzene (1.0 ml) solution of 7-bromo-2-tert-butyl-6-iodo-5-methyl-1,3-benzoxazole-4-carbonitrile (I-8) (30 mg, 71.6 µmol), (2-tri-n-butylstannyl)furan (23.7 µl, 75.2 µmol), followed by refluxing overnight. After cooling, water (30 ml) was added, the product was extracted with ethyl acetate (30 ml×2), the organic layer was washed with saturated brine (30 ml), then dried over anhydrous magnesium sulfate, concentrated under reduced pressure. The residue was purified by silica gel column chromatography (h-hexane:ethyl acetate=8:1) to obtain the entitled compound (19 mg) as a colorless solid.

MS (FAB) m/z: 359 (M+1 for $^{79}$Br)$^+$, 361 (M+1 for $^{81}$Br)$^+$.

$^1$H-NMR (CDCl$_3$) δ: 1.54 (9H, s), 2.49 (3H, s), 6.48 (1H, dd, J=0.6, 3.3 Hz), 6.57 (1H, dd, J=2.1, 3.3 Hz), 7.58-7.60 (1H, m).

Example 4

2-tert-Butyl-7-[(3S)-3-(dimethylamino)pyrrolidin-1-yl]-6-(2-furyl)-5-methyl-1,3-benzoxazole-4-Carbonitrile (#4)

(R)-(+)-2,2'-Bis(diphenylphosphino)-1,1'-binaphthyl (10.4 mg, 16.7 µmol) was dissolved in toluene (0.5 ml) under heat, cooled to room temperature, palladium(II) acetate (2.5 mg, 11.1 µmol) was added, followed by stirring for 1 minute. This was put into a toluene (0.5 ml) suspension of 7-bromo-2-tert-butyl-6-(2-furyl)-5-methyl-1,3-benzoxazole-4-carbonitrile (I-10) (40 mg, 111 µmol), (3S)-3-(dimethylamino)pyrrolidine (16.9 µl, 134 µmol), sodium tert-butoxide (15.0 mg, 156 µmol), followed by stirring at 80° C. for 17 hours. After cooling, brine (30 ml) was added to the reaction liquid, the product was extracted with chloroform (30 ml×3). The organic layer was washed with saturated brine (30 ml), then dried over anhydrous magnesium sulfate, concentrated under reduced pressure. The residue was purified by silica gel column chromatography (chloroform:methanol=1:0→100:1) to obtain the entitled compound (5.9 mg, 13%) as a yellow solid.

MS (FAB) m/z: 393 (M+1)$^+$.

$^1$H-NMR (CDCl$_3$) δ: 1.48 (9H, s), 1.60-1.78 (1H, m), 2.00-2.12 (1H, m), 2.22 (6H, s), 2.23 (3H, s), 2.52-2.64 (1H, m), 3.12 (1H, t, J=9.4 Hz), 3.42-3.63 (3H, m), 6.23 (1H, dd, J=0.9, 3.3 Hz), 6.48 (1H, dd, J=1.8, 3.3 Hz), 7.52-7.54 (1H, m). Anal. Calcd for C$_{23}$H$_{28}$N$_4$O$_2$.HCl.1.5H$_2$O: C, 60.58; H, 7.07; N, 12.29; Cl, 7.77. Found: C, 60.27; H, 7.24; N, 32.12; Cl, 8.31.

Reference Example 11

N-(3-Bromo-6-cyano-2-methoxy-5-methyl-4-styrylphenyl)-2,2-dimethylpropionamide (I-11)

Tetrakis(triphenylphosphine)palladium(0) (6.4 mg, 5.5 µmol) was added to an N,N-dimethylformamide (1.0 ml) suspension of N-(3-bromo-6-cyano-4-iodo-2-methoxy-5-methylphenyl)-2,2-dimethylpropionamide (I-6) (50 mg, 111 µmol), trans-β-styreneboronic acid (17.2 mg, 116 µmol), potassium phosphate n-hydrate (74-78%, 64 mg, 222 µmol), followed by stirred overnight at 95° C. The reaction liquid was cooled, then ethyl acetate (30 ml) was added, followed by washing with saturated brine (30 ml×2), drying over anhydrous magnesium sulfate, concentrating under reduced pressure.

The residue was purified by silica gel column chromatography (n-hexane:ethyl acetate=6:1) to obtain the entitled compound (38 mg, 80%) as a colorless solid.

MS (FAB) m/z: 427 (M+1 for $^{79}$Br)$^+$, 429 (M+1 for $^{81}$Br)$^+$.

$^1$H-NMR (CDCl$_3$) δ: 1.40 (9H, s), 2.62 (3H, s), 3.80 (3H, s), 6.63 (1H, d, J=16.5 Hz), 6.98 (1H, d, J=16.5 Hz), 7.30-7.45 (4H, m), 7.50-7.55 (2H, m).

Reference Example 12

N-(2-Bromo-5-cyano-3-methoxy-6-methyl-3'-nitrobiphenyl-4-yl)-2,2-dimethylpropionamide (I-12)

N-(3-Bromo-6-cyano-4-iodo-2-methoxy-5-methylphenyl)-2,2-dimethylpropionamide (I-6) (965 mg, 2.14 mmol), 3-nitrophenylboronic acid (375 mg, 2.25 mmol), tripotassium phosphate (74-85%, 1.23 g, 4.28 mmol) and tetrakis(triphenylphosphine)palladium(0) (247 mg, 0.214 mmol) were added to a 50-ml eggplant-type flask, followed by purging with nitrogen. N,N-Dimethylformamide (20 ml) was injected into it with a syringe, followed by stirring at 95° C. for 4 hours. After cooling, the reaction liquid was diluted with ethyl acetate, successively washed with saturated brine (×3), 1 N hydrochloric acid, saturated brine, an aqueous saturated sodium hydrogencarbonate solution and saturated brine, dried on anhydrous magnesium sulfate, then the solvent was concentrated under reduced pressure to obtain a pale brown residue. The resulting residue was purified by silica gel column chromatography (n-hexane:ethyl acetate=6:1→4:1) to obtain the entitled compound (645 mg, 68%) as a pale yellow solid.

MS (FAB) m/z: 446 (M+1 for $^{79}$Br)$^+$, 448 (M+1 for $^{81}$Br)$^+$.
$^1$H-NMR (CDCl$_3$) δ: 1.43 (9H, s), 2.27 (3H, s), 3.83 (3H, s), 7.46-7.53 (2H, m), 7.67-7.73 (1H, m), 8.02-8.05 (1H, m), 8.29-8.34 (1H, m).

Reference Example 13

N-(3'-Benzyloxy-2-bromo-5-cyano-3-methoxy-6-methylbiphenyl-4-yl)-2,2-dimethylpropionamide (I-13)

N-(3-Bromo-6-cyano-4-iodo-2-methoxy-5-methylphenyl)-2,2-dimethylpropionamide (I-6) (1.02 g, 2.26 mmol), 3-benzyloxybenzeneboronic acid (541 mg, 2.37 mmol), tripotassium phosphate (74-85%, 1.30 g, 4.52 mmol) and tetrakis(triphenylphosphine)palladium(0) (261 mg, 0.226 mmol) were added to a 50-ml eggplant-type flask, followed by purging with nitrogen. N,N-Dimethylformamide (20 ml) was injected into it with a syringe, followed by stirring at 95° C. for 4 hours. After cooling, the reaction liquid was diluted with ethyl acetate, successively washed with saturated brine (×3), 1 N hydrochloric acid, saturated brine, an aqueous saturated sodium hydrogencarbonate solution and saturated brine, dried on anhydrous magnesium sulfate, then the solvent was concentrated under reduced pressure to obtain a pale brown residue. The resulting residue was purified by silica gel column chromatography (n-hexane:ethyl acetate=6:1) to obtain the entitled compound (630 mg, 55%) as a pale brown solid.

MS (FAB) m/z: 507 (M+1 for $^{79}$Br)$^+$, 509 (M+1 for $^{81}$Br)$^+$.
$^1$H-NMR (CDCl$_3$) δ: 1.41 (9H, s), 2.23 (3H, s), 3.80 (3H, s), 5.09 (2H, s), 6.67-6.72 (2H, m), 7.02-7.07 (1H, m), 7.30-7.47 (7H, m).

Reference Example 14

N-(3-Bromo-6-cyano-2-hydroxy-5-methyl-4-styrylphenyl)-2,2-dimethylpropionamide (I-14)

A dichloromethane (1.0 ml) solution of N-(3-bromo-6-cyano-2-methoxy-5-methyl-4-styrylphenyl)-2,2-dimethylpropionamide (I-11) (34 mg, 79.6 μmol) was cooled at −78° C., a dichloromethane solution of 1 N tribromoborane (239 μl, 239 μmol) was dropwise added, followed by stirring at −78° C. for 70 minutes. Afterwards, this was heated up to −12° C. and stirred for 1 hour. The reaction liquid was put into cold water (50 ml), saturated brine (50 ml) was added, the intended product was extracted with ethyl acetate (50 ml×2). The organic layer was dried over anhydrous magnesium sulfate, concentrated under reduced pressure to obtain the entitled compound (32 mg, 96%) as a yellow white semi-solid.

MS (FAB) m/z: 413 (M+1 for $^{79}$Br)$^+$, 415 (M+1 for $^{81}$Br)$^+$.
$^1$H-NMR (CDCl$_3$) δ: 1.35 (9H, s), 2.51 (3H, s), 6.54 (1H, d, J=16.8 Hz), 6.94 (1H, d, J=16.8 Hz), 7.23-7.36 (3H, m), 7.44-7.47 (2H, m), 7.94 (1H, brs), 9.79 (1H, brs).

Reference Example 15

N-(2-Bromo-5-cyano-3-hydroxy-6-methyl-3'-nitrobiphenyl-4-yl)-2,2-dimethylpropionamide (I-15)

N-(2-Bromo-5-cyano-3-methoxy-6-methyl-3'-nitrobiphenyl-4-yl)-2,2-dimethylpropionamide (I-12) (630 mg, 1.41 mmol) was dissolved in dichloromethane (dewatered, 20 ml) under nitrogen atmosphere, cooled at −70° C. in a dry ice-methanol bath. 1 M tribromoborane (dichloromethane solution) (4.23 ml) was dropwise added to it at −70° C. to −68° C., followed by stirring for 2 hours with heating up to 0° C. The reaction liquid was diluted with cold water, followed by pH control at 6 to 7 by addition of aqueous 10% sodium carbonate solution. The organic matter was extracted with ethyl acetate, washed with saturated brine, dried on anhydrous magnesium sulfate, the solvent was evaporated away under reduced pressure. The resulting residue was purified by silica gel column chromatography (n-hexane:ethyl acetate=3:1→3:2) to obtain the entitled compound (503 mg, 82%) as a pale yellow solid.

MS (FAB) m/z: 432 (M+1 for $^{79}$Br)$^+$, 434 (M+1 for $^{81}$Br)$^+$.
$^1$H-NMR (CDCl$_3$) δ: 1.45 (9H, s), 2.23 (3H, s), 7.44-7.48 (1H, m), 7.69 (1H, t, J=7.9 Hz), 8.02 (1H, t, J=1.8 Hz), 8.07 (1H, brs), 8.28-8.33 (1H, m), 10.05 (1H, s).

Reference Example 16

N-(2-Bromo-5-cyano-3,3'-dihydroxy-6-methylbiphenyl-4-yl)-2,2-dimethylpropionamide (I-16)

A dichloromethane (18 ml) solution of N-(3'-benzyloxy-2-bromo-5-cyano-3-methoxy-6-methylbiphenyl-4-yl)-2,2-dimethylpropionamide (I-13) (620 mg, 1.22 mmol) was cooled at −78° C., a dichloromethane solution of 1 N tribromoborane (3.67 ml, 3.67 mmol) was dropwise added, followed by stirring at −78° C. for 20 minutes. Afterwards, this was heated up to −12° C. and stirred for 1 hour, then heated up to 0° C. and stirred for 30 minutes. The reaction liquid was put into cold water (50 ml), saturated brine (50 ml) was added, the intended product was extracted with ethyl acetate (70 ml×2). The organic layer was dried over anhydrous magnesium sulfate, concentrated under reduced pressure, the residue was purified by silica gel column chromatography (n-hexane:ethyl acetate=3:1) to obtain the entitled compound (457 mg, 96%) as a yellow white semi-solid.

MS (FAB) m/z: 403 (M+1 for $^{79}$Br)$^+$, 405 (M+1 for $^{81}$Br)$^+$.
$^1$H-NMR (CDCl$_3$) δ: 1.43 (9H, s), 2.23 (3H, s), 4.99 (1H, s), 6.57 (1H, dd, J=1.5, 2.4 Hz), 6.66 (1H, dt, J=1.2, 7.8 Hz), 6.88 (1H, ddd, J=0.9, 2.4, 7.8 Hz), 7.34 (1H, t, J=7.8 Hz), 8.01 (1H, brs), 9.80 (1H, s).

Reference Example 17

7-Bromo-2-tert-butyl-5-methyl-6-styryl-1,3-benzoxazole-4-carbonitrile (I-17)

Toluene (3 ml), p-toluenesulfonic acid monohydrate (1.4 mg, 7.5 μmol) were added to N-(3-bromo-6-cyano-2-hydroxy-5-methyl-4-styrylphenyl)-2,2-dimethylpropionamide (I-14) (31 mg, 75 μmol), followed by refluxing with a Dean-Stark condenser for 2.5 hours. After cooling, saturated sodium bicarbonate water (30 ml) was added to the reaction liquid, the product was extracted with ethyl acetate (30 ml×2). The organic layer was washed with saturated brine (30 ml), dried over anhydrous magnesium sulfate, concentrated under reduced pressure, the residue was purified by silica gel column chromatography (n-hexane:ethyl acetate=8:1) to obtain the entitled compound (25 mg, 84%) as a colorless solid.

MS (FAB) m/z: 395 (M+1 for $^{79}$Br)$^+$, 397 (M+1 for $^{81}$Br)$^+$.

$^1$H-NMR (CDCl$_3$) δ: 1.54 (9H, s), 2.72 (3H, s), 6.75 (1H, d, J=16.5 Hz), 7.05 (1H, d, J=16.5 Hz), 7.33-7.45 (3H, m), 7.53-7.58 (2H, m).

Reference Example 18

7-Bromo-2-tert-butyl-5-methyl-6-(3-nitrophenyl)-1,3-benzoxazole-4-carbonitrile (I-18)

A mixture of N-(2-bromo-5-cyano-3-hydroxy-6-methyl-3'-nitrobiphenyl-4-yl)-2,2-dimethylpropionamide (I-15) (490 mg, 1.13 mmol), p-toluenesulfonic acid monohydrate (22 mg, 4.23 mmol) and toluene (50 ml) was heated under reflux for 3 hours. After cooling, the reaction liquid was diluted with ethyl acetate, successively washed with an aqueous saturated sodium hydrogencarbonate solution and saturated brine, dried on anhydrous magnesium sulfate, the solvent was evaporated away under reduced pressure to obtain a pale brown residue. The resulting residue was purified by silica gel column chromatography (n-hexane:ethyl acetate=5:1) to obtain the entitled compound (433 mg, 93%) as a pale yellow solid.

MS (FAB) m/z: molecular ion peak not detected.

$^1$H-NMR (CDCl$_3$) δ: 1.55 (9H, s), 2.39 (3H, s), 7.49-7.55 (1H, m), 7.72 (1H, t, J=7.9 Hz), 8.08 (1H, t, J=1.9 Hz), 8.32-8.37 (1H, m).

Reference Example 19

7-Bromo-2-tert-butyl-6-(3-hydroxyphenyl)-5-methyl-1,3-benzoxazole-4-carbonitrile (I-19)

Toluene (45 ml), p-toluenesulfonic acid monohydrate (21.0 mg, 111 μmol) were added to N-(2-bromo-5-cyano-3,3'-dihydroxy-6-methylbiphenyl-4-yl)-2,2-dimethylpropionamide (I-16) (446 mg, 1.11 mmol), followed by refluxing with a Dean-Stark condenser for 3 hours. After cooling, water (50 ml) was added to the reaction liquid, the product was extracted with ethyl acetate (50 ml×2). The organic layer was washed with saturated brine (50 ml), dried over anhydrous magnesium sulfate, concentrated under reduced pressure, the residue was purified by silica gel column chromatography (n-hexane:ethyl acetate=3:1) to obtain the entitled compound (404 mg, 95%) as a colorless solid.

MS (FAB) m/z: 385 (M+1 for $^{79}$Br)$^+$, 387 (M+1 for $^{81}$Br)$^+$.

$^1$H-NMR (CDCl$_3$) δ: 1.54 (9H, s), 2.39 (3H, s), 5.17 (1H, s), 6.63 (1H, dd, J=1.5, 2.4 Hz), 6.70 (1H, dt, J=1.5, 7.8 Hz), 6.93 (1H, ddd, J=0.9, 2.7, 7.8 Hz), 7.37 (1H, t, J=7.8 Hz).

Reference Example 20

7-Bromo-2-tert-butyl-4-cyano-6-(3-methoxyphenyl)-5-methyl-1,3-benzoxazole-4-carbonitrile (I-20)

7-Bromo-2-tert-butyl-6-(3-hydroxyphenyl)-5-methyl-1,3-benzoxazole-4-carbonitrile (I-19) (169 mg, 439 μmol) was dissolved in tetrahydrofuran (5.0 ml), at −12° C., sodium hydride (19.3 mg, 60%, 483 μmol) was added followed by stirring for 5 minutes. Iodomethane (1372.19 mmol) was added to it, followed by stirring at room temperature for 1.5 hours, heating up to 50° C. and stirring for 1 hour. Water (50 ml), sodium thiosulfate (1 g) were added to the reaction liquid, the intended product was extracted with ethyl acetate (50 ml×2). The organic layer was washed with saturated brine (50 ml), dried over anhydrous magnesium sulfate, concentrated under reduced pressure, the residue was purified by silica gel column chromatography (n-hexane:ethyl acetate=6:1) to obtain the entitled compound (160 mg, 91%) as a pale yellow solid.

MS (FAB) m/z: 399 (M+1 for $^{79}$Br)$^+$, 401 (M+1 for $^{81}$Br)$^+$.

$^1$H-NMR (CDCl$_3$) δ: 1.54 (9H, s), 2.39 (3H, s), 3.84 (3H, s), 6.68 (1H, dd, J=1.5, 2.4 Hz), 6.72 (1H, dt, J=1.5, 8.4 Hz), 6.99 (1H, ddd, J=0.9, 2.7, 8.4 Hz), 7.41 (1H, t, J=8.4 Hz).

Reference Example 21

2-(tert-Butyl)-7-[(3S)-3-(dimethylamino)pyrrolidin-1-yl]-5-methyl-6-styryl-1,3-benzoxazole-4-carbonitrile hydrochloride (I-21)

(R)-(+)-2,2'-Bis(diphenylphosphino)-1,1'-binaphthyl (117 mg, 188 μmol) was dissolved in toluene (5.0 ml) under heat, cooled to room temperature, then palladium(II) acetate (28.1 mg, 125 μmol) was added followed by stirring for 1 minute. 7-Bromo-2-tert-butyl-5-methyl-6-styryl-1,3-benzoxazole-4-carbonitrile (I-17) (495 mg, 1.25 mmol), (3S)-3-(dimethylamino)pyrrolidine (191 μl, 1.50 mmol), sodium tert-butoxide (168 mg, 1.75 mmol), toluene (5.0 ml) were successively put into it, followed by stirring overnight at 80° C. Saturated brine (30 ml) and saturated sodium bicarbonate water (30 ml) were added to the reaction liquid, the product was extracted with chloroform (50 ml×2), ethyl acetate (50 ml). The organic layer was dried over anhydrous magnesium sulfate, concentrated under reduced pressure, the residue was purified twice by silica gel column chromatography (chloroform:methanol=100:1), (chloroform:methanol=1:0→100:1) to obtain a non-salt form of the entitled compound (330 mg) as a yellow ocher semi-solid. This was dissolved in diethyl ether (20 ml), 4 N hydrogen chloride/1,4-dioxane solution (193 μl, 772 μmol) was dropwise added, followed by stirring for 3 minutes. The precipitated matter was collected by filtration, dried to obtain the entitled compound (299 mg, 51%) as a pale yellow ocher solid.

mp: 173-175° C. MS (FAB) m/z: 429 (M+1-HCl)$^+$.

$^1$H-NMR (CDCl$_3$) δ: 1.51 (9H, s), 2.33-2.51 (2H, m), 2.58 (3H, s), 2.74 (6H, brs), 3.60-3.97 (4H, m), 4.22 (1H, dd, J=5.7, 10.8 Hz), 6.58 (1H, d, J=16.5 Hz), 7.06 (1H, d, J=16.5 Hz), 7.29-7.45 (3H, m), 7.49-7.55 (2H, m).

IR (diffuse reflectance spectroscopy): 2968, 2590, 2458, 2212, 1608, 1473, 1367 cm$^{-1}$. Anal. Calcd for C$_{27}$H$_{32}$N$_4$O.HCl.H$_2$O: C, 67.13; H, 7.30; N, 11.60; Cl, 7.34. Found: C, 66.87; H, 7.26; N, 11.23; Cl, 7.50.

Example 5

2-(tert-Butyl)-7-[(3S)-3-dimethylamino)pyrrolidin-1-yl]-5-methyl-6-(2-phenethyl)-1,3-benzoxazole-4-carbonitrile (#5)

Under nitrogen atmosphere, 2-(tert-butyl)-7-[(3S)-3-(dimethylamino)pyrrolidin-1-yl]-5-methyl-6-styryl-1,3-benzoxazole-4-carbonitrile hydrochloride (I-21) (50 mg, 0.11 mmol) was dissolved in ethanol (1 ml), 1 N hydrochloric acid-ethanol solution (108 μl, 0.11 mmol) was added, a carbon-held palladium catalyst (Kawaken M) (5 mg, 10 wt. %) were suspended, the system was purged with hydrogen, followed by stirring a room temperature under normal pressure for 5 hours. Since the reaction did not goon, this was stirred under a middle pressure (3 atm) for 2 hours. The reaction liquid was purged with nitrogen, the catalyst was removed by Celite filtration, the filtrate was concentrated under reduced pressure. The resulting residue was dissolved in methylene chloride, washed with water and saturated brine. The obtained organic layer was dried over anhydrous sodium sulfate, the solvent was evaporated away under reduced pressure. The resulting residue was subjected to preparative thin-layer silica gel column chromatography, followed by elution with a mixed solvent of chloroform-methanol (20:1, v/v) to obtain the entitled compound (7.8 mg, 17%) as a pale yellow oily substance.

MS (FAB) m/z: 431 (M+1)$^+$.

$^1$H-NMR (CDCl$_3$) δ: 1.50 (9H, s), 1.88-1.99 (1H, m), 2.19-2.26 (1H, m), 2.32 (6H, s), 2.59 (3H, s), 2.73-2.84 (2H, m), 2.89-2.97 (1H, m), 3.09 (1H, t, J=8.2 Hz), 3.42-3.47 (3H, m), 3.57 (1H, td, J=7.2, 8.8 Hz), 7.15-7.31 (5H, m).

Reference Example 22

2-tert-Butyl-7-[(3S)-3-(dimethylamino)pyrrolidin-1-yl]-5-methyl-6-(3-nitrophenyl)-1,3-benzoxazole-4-carbonitrile (I-22)

(S)-(−)-2,2'-Bis(diphenylphosphino)-1,1'-binaphthyl (180 mg, 0.29 mmol) was dissolved in toluene (8 ml) under heat, cooled to room temperature, then palladium(II) acetate (43 mg, 0.193 mmol) was added, followed by stirring for 5 minutes. 7-Bromo-2-tert-butyl-5-methyl-6-(3-nitrophenyl)-1,3-benzoxazole-4-carbonitrile (I-18) (400 mg, 0.966 mmol), (3S)-3-(dimethylamino)pyrrolidine (306 μl, 2.42 mmol), sodium tert-butoxide (260 mg, 2.71 mmol), toluene (5 ml) were successively put into it, followed by stirring at 80° C. for 13 hours. After cooling, brine (10 ml), saturated sodium bicarbonate water (25 ml) were added to the reaction liquid, the product was extracted with chloroform (25 ml×2). The organic layer was washed with saturated brine (10 ml×2), then dried over anhydrous magnesium sulfate, concentrated under reduced pressure. The residue was purified twice by silica gel column chromatography (chloroform:methanol=100:1) to obtain a fraction containing the entitled compound (35.1 mg) as a dark brown solid. Not further purified, this was used in the next reaction.

MS (FAB) m/z: 448 (M+1)$^+$.

Example 6

6-(3-Aminophenyl)-2-tert-butyl-7-[(3S)-3-(dimethylamino)pyrrolidin-1-yl]-5-methyl-1,3-benzoxazole-4-carbonitrile (#6)

2-tert-Butyl-7-[(3S)-3-(dimethylamino)pyrrolidin-1-yl]-5-methyl-6-(3-nitrophenyl)-1,3-benzoxazole-4-carbonitrile (I-22) (30.7 mg, 68.6 μmol) was dissolved in 4 N hydrogen chloride (ethyl acetate solution, 2 ml) and the solvent was concentrated under reduced pressure. The residue was dissolved in methanol (8 ml), followed by catalytic hydrogenation at room temperature under normal pressure for 3 hours in the presence of 5% palladium-carbon (50% wet, 30 mg). The catalyst was separated by filtration, the filtrate was concentrated under reduced pressure, aqueous 10% sodium carbonate solution and ethyl acetate were added to the residue followed by stirring. The organic layer was collected by liquid-liquid separation, concentrated and purified by preparative TLC (developing solvent, chloroform:methanol=10:1) to obtain the entitled compound (4.9 mg) as a brown solid.

MS (FAB) m/z: 491 (M+1)$^+$.

$^1$H-NMR (CDCl$_3$) δ: 1.48 (9H, s), 1.56-2.05 (3H, m), 2.17 and 2.18 (6H, s each), 2.21 and 2.22 (3H, s each), 2.55 (1H, brs), 3.10-3.55 (4H, m), 3.71 (1H, brs), 6.40-6.44 (1H, m), 6.48-6.53 (1H, m), 6.54-6.56 (1H, m), 6.60-6.95 (1H, m).

Reference Example 23

2-tert-Butyl-7-[(3S)-3-(dimethylamino)pyrrolidin-1-yl]-6-(3-methoxyphenyl)-5-methyl-1,3-benzoxazole-4-carbonitrile (I-23)

(R)-(+)-2,2'-Bis(diphenylphosphino)-1,1'-binaphthyl (70.2 mg, 113 μmol) was dissolved in toluene (2.7 ml) under heat, cooled to room temperature, then palladium(II) acetate (16.9 mg, 75.1 μmol) was added followed by stirring for 1 minute. 7-Bromo-2-tert-butyl-6-(3-methoxyphenyl)-5-methyl-1,3-benzoxazole-4-carbonitrile (I-20) (300 mg, 751 μmol), (3S)-3-(dimethylamino)pyrrolidine (114 μl, 902 μmol), sodium tert-butoxide (101 mg, 1.05 mmol), toluene (2.7 ml) were successively put into it, followed by stirring at 80° C. for 16 hours. After cooling, saturated sodium bicarbonate water (50 ml) was added to the reaction liquid, the product was extracted with chloroform (50 ml×2). The organic layer was washed with saturated brine (50 ml), dried over anhydrous magnesium sulfate, concentrated under reduced pressure. The residue was purified by silica gel column chromatography (chloroform:methanol=100:1), then further purified by silica gel thin-layer partitioning (chloroform:methanol:acetic acid=80:10:5) to obtain the entitled compound (7.3 mg, 2.2%) as a yellow semi-solid.

MS (FAB) m/z: 433 (M+1)$^+$.

$^1$H-NMR (CDCl$_3$) δ: 1.49 (9H, s), 1.96-2.10 (1H, m), 2.21 and 2.22 (3H, s each), 2.28 (6H, brs), 2.75-2.90 (1H, m), 3.10 (1H, q, J=7.3 Hz), 3.18-3.54 (4H, m), 3.81 and 3.82 (3H, s each), 6.65-6.93 (3H, m), 7.32 (1H, dt, J=3.9, 8.1 Hz).

Example 7

2-tert-Butyl-7-[(3S)-3-(dimethylamino)pyrrolidin-1-yl]-6-(3-hydroxyphenyl)-5-methyl-1,3-benzoxazole-4-carbonitrile (#7)

2-tert-Butyl-7-[(3S)-3-(dimethylamino)pyrrolidin-1-yl]-6-(3-methoxyphenyl)-5-methyl-1,3-benzoxazole-4-carbonitrile (I-23) (10 mg, 23.1 μmol) was dissolved (partially suspended) in benzene (2.0 ml), and dropwise added to a benzene (2.0 ml) suspension reflux liquid of aluminium chloride (9.2 mg, 69.0 μmol). The benzene wash (8.0 ml) of the eggplant-type flask with the starting material adhering thereto was also added, followed by refluxing for 0.5 hours. After cooling, aluminium chloride (61.7 mg, 462 μmol) was further added, followed by further stirring under reflux for 15 minutes. After cooling, saturated sodium bicarbonate water (50 ml) was added to the reaction liquid, the product was extracted with chloroform (50 ml×2), ethyl acetate (50 ml).

The organic layer was dried over anhydrous magnesium sulfate, concentrated under reduced pressure, the residue was purified by silica gel column chromatography (chloroform:methanol=10:0→10:1), then further purified by silica gel thin-layer partitioning (chloroform:methanol=10:1) to obtain the entitled compound (3.9 mg, 40%) as a yellow ocher solid.

MS (FAB) m/z: 419 (M+1)$^+$.

$^1$H-NMR (CDCl$_3$) δ: 1.49 (9H, s), 1.60-1.85 (1H, m), 1.91-2.10 (1H, m), 2.19 (3H, s), 2.20 and 2.22 (6H, s each), 2.61-2.79 (1H, m), 3.20-3.60 (4H, m), 3.35 (1H, brs), 6.58-6.82 (3H, m), 7.23 (1H, t, J=7.8 Hz).

Reference Example 24

2-Fluoro-4-methyl-6-nitrophenol (I-24)

70% Nitric acid (d=1.42) (5.5 ml, 87.4 mmol) was dropwise added to an acetic acid (105 ml) solution of 2-fluoro-4-methyl-phenol (10.5 g, 83.2 mmol), taking 20 minutes, followed by stirring at room temperature for 30 minutes. Water was added to the reaction liquid, followed by extraction three times with diethyl ether, the organic layer was washed with saturated brine, dried over anhydrous magnesium sulfate. After filtration and concentration under reduced pressure, the resulting residue was subjected to column chromatography, and the eluate with n-hexane:ethyl acetate (10:1) was concentrated under reduced pressure to obtain the entitled compound (5.47 g, 31%) as a yellow solid.

MS (FAB) m/z: Molecular ion peak not detected.

$^1$H-NMR (CDCl$_3$) δ: 2.35 (3H, s), 7.26 (1H, dd, J=2.4, 10.8 Hz), 7.70-7.72 (1H, m), 10.29 (1H, s).

Reference Example 25

1-Fluoro-2-methoxy-5-methyl-3-nitrobenzene (I-25)

Sodium carbonate (11.0 g, 103.5 mmol) and dimethyl sulfate (9.0 ml, 95 mmol) were added to a toluene (35 ml) solution of 2-fluoro-4-methyl-6-nitrophenol (I-24) (5.9 g, 34.5 mmol), followed by stirring at 80° C. for 15 hours, then dimethyl sulfate (90 ml, 95 mmol) was further added, followed by stirring with heating under reflux for 2.5 hours. After cooling to room temperature, aqueous 10% sodium carbonate solution was added to the reaction liquid, followed by extraction three times with ethyl acetate, the organic layer was washed with aqueous 10% sodium carbonate solution, water, saturated brine in that order, then dried over anhydrous magnesium sulfate. After filtration and concentration under reduced pressure, the resulting residue was subjected to column chromatography, and the eluate with n-hexane:ethyl acetate (5:1) was concentrated under reduced pressure to obtain the entitled compound (6.42 g, quant.) as an orange oily substance.

MS (FAB) m/z: Molecular ion peak not detected.

$^1$H-NMR (CDCl$_3$) δ: 2.37 (3H, s), 4.02 (3H, d, J=1.5 Hz), 7.13-7.17 (1H, m), 7.37-7.39 (1H, m).

(Alternative Method)

Under nitrogen atmosphere, potassium carbonate (218 mg, 1.58 mmol), tetrakistriphenylphosphine palladium(0) (58 mg, 50 μmol), trimethylboroxine (77 μl, 0.55 mmol) were added to a 1,4-dioxane (5 ml) solution of 4-bromo-2-fluoro-6-nitroanisole (125 mg, 0.5 mmol), followed by stirring with heating under reflux for 1 hour and a half. After cooling to room temperature, saturated sodium bicarbonate water was added to the reaction liquid, followed by extraction three times with ethyl acetate, the organic layer was washed with saturated brine, then dried over anhydrous magnesium sulfate. After filtration and concentration under reduced pressure, the resulting residue was subjected to column chromatography, and the eluate with n-hexane:ethyl acetate (20:1) was concentrated under reduced pressure to obtain the entitled compound (68 mg, 70%) as an orange oily substance.

Reference Example 26

3-Fluoro-2-methoxy-5-methylaniline (I-26)

5% Palladium-carbon (wet, 100 mg) was added to a methanol (5 ml) solution of 1-fluoro-2-methoxy-5-methyl-3-nitrobenzene (I-25) (250 mg, 1.35 mmol), followed by stirring under hydrogen atmosphere for 30 minutes. After filtration and concentration under reduced pressure, the resulting residue was subjected to column chromatography, and the eluate with n-hexane:ethyl acetate (9:1) was concentrated under reduced pressure to obtain the entitled compound (170 mg, 81%) as a yellow oily substance.

MS (FAB) m/z: 156 (M+1)$^+$.

$^1$H-NMR (CDCl$_3$) δ: 2.19 (3H, s), 3.86 (3H, d, J=1.2 Hz), 6.26-6.31 (1H, m), 6.31 (1H, d, J=1.2 Hz).

Reference Example 27

(3-Fluoro-2-methoxy-5-methylphenyl)-2-hydroxy-imino-acetamide (I-27)

A N,N-dimethylformamide (30 ml) solution of 3-fluoro-2-methoxy-5-methylaniline (I-26) (4.31 g, 27.8 mmol) and concentrated hydrochloric acid (3.5 ml, 33.4 mmol) were added to a water (60 ml) suspension of trichloroacetaldehyde monohydrate (9.2 g, 55.6 mmol) and anhydrous magnesium sulfate (31.6 g, 222.4 mmol), followed by stirring at 90° C. for 30 minutes, then hydroxylamine hydrochloride (116 g, 166.8 mmol) was added, followed by stirring at the same temperature for 13 hours and a half. After cooling to room temperature, the reaction liquid was filtered through Celite, the filtrate was extracted three times with ethyl acetate, then the organic layer was washed twice with saturated brine, dried over anhydrous magnesium sulfate. After filtration and concentration under reduced pressure, the resulting residue was subjected to column chromatography, and the eluate with chloroform was concentrated under reduced pressure to obtain the entitled compound (596 mg, 10%) as a pale brown solid.

MS (FAB) m/z: 227 (M+1)$^+$.

$^1$H-NMR (CDCl$_3$) δ: 2.31 (3H, s), 3.95 (3H, d, J=1.8 Hz), 6.64-6.69 (1H, m), 7.59 (1H, s), 8.00 (1H, s), 8.33 (1H, brs), 8.90 (1H, brs).

Reference Example 28

6-Fluoro-7-methoxy-4-methyl-1H-indole-2,3-dione (I-28)

With cooling with ice, concentrated sulfuric acid (81 ml) was added to water (9 ml) and fully cooled, then (3-fluoro-2-methoxy-5-methylphenyl)-2-hydroxyimino-acetamide (I-27) (5.13 g) was added at the same temperature, followed by stirring at the same temperature for 40 minutes and stirring at 85° C. for 40 minutes. After cooling to room temperature, the reaction mixture was poured into ice (300 g), extracted three times with ethyl acetate, the organic layer was washed with saturated brine, then dried over anhydrous magnesium sulfate. After filtration and concentration under reduced pressure, the resulting residue was subjected to column chromatography, and the eluate with chloroform was concentrated under reduced pressure to obtain a crude product of the entitled compound (2.57 g) as an orange solid.

MS (FAB) m/z: 210 (M+1)$^+$.

Reference Example 29

2-Amino-4-fluoro-3-methoxy-6-methylbenzoic acid (I-29)

With cooling with ice, a solution of 30% aqueous hydrogen peroxide (6.3 ml, 61.5 mmol) diluted with water (8.2 ml) was added to a dioxane (50 ml) solution of 6-fluoro-7-methoxy-4-methyl-1H-indole-2,3-dione (I-28) (2.57 g), at the same temperature, a water (230 ml) solution of sodium hydroxide (6.15 g, 153.8 mmol) was dropwise added, taking 1 hour, followed by stirring for 4 hours with gradually heating up to room temperature. The reaction liquid was washed twice with chloroform, acetic acid was added to the aqueous layer followed by controlling at pH of 3 to 4 and extraction three times with ethyl acetate, the organic layer was washed twice with saturated brine, then dried over anhydrous magnesium sulfate. After filtration and concentration under reduced pressure, the resulting residue was subjected to column chromatography, and the eluate with chloroform alone was concentrated under reduced pressure to obtain the entitled compound (1.54 g, 28% from I-30) as a yellow solid.

MS (FAB) m/z: 200 (M+1)$^+$.
$^1$H-NMR (CDCl$_3$) δ: 2.51 (3H, s), 3.90 (3H, d, J=1.2 Hz), 6.27 (1H, dd, J=0.6, 12.0 Hz).

Reference Example 30

2-Amino-4-fluoro-5-iodo-3-methoxy-6-methylbenzoic acid (I-30)

An N,N-dimethylformamide (14 ml) solution of N-iodosuccinimide (1.89 g, 8.4 mmol) was dropwise added to an N,N-dimethylformamide (14 ml) solution of 2-amino-4-fluoro-3-methoxy-6-methylbenzoic acid (I-29) (1.4 g), followed by stirring at room temperature for 2 hours and a half. Water was added to the reaction liquid, followed by extraction three times with ethyl acetate, the organic layer was washed with aqueous saturated sodium thiosulfate solution and saturated brine, then dried over anhydrous magnesium sulfate. After filtration and concentration under reduced pressure, the resulting residue was subjected to column chromatography, and the eluate with n-hexane:ethyl acetate (2:1) was concentrated under reduced pressure to obtain the entitled compound (1.77 g, 78%) as a brown solid.

MS (FAB) m/z: 326 (M+1)$^+$.
$^1$H-NMR (CDCl$_3$) δ: 2.67 (3H, s), 3.91 (3H, d, J=1.2 Hz).

Reference Example 31

7-Fluoro-6-iodo-8-methoxy-5-methyl-1H-benzo[d][1,3]oxazine-2,4-dione (I-31)

Under nitrogen atmosphere, triphosgene (1.5 g, 5.04 mmol) was added to a tetrahydrofuran (200 ml) solution of 2-amino-4-fluoro-5-iodo-3-methoxy-6-methylbenzoic acid (I-30) (4.1 g, 12.6 mmol), followed by stirring at 40° C. for 16 hours.

The reaction liquid was concentrated under reduced pressure, the residue was suspended in diisopropyl ether, followed by filtering and drying to obtain the entitled compound (4.27 g, 97%) as a pale yellow solid.

MS (FAB) m/z: 352 (M+1)$^+$.
$^1$H-NMR (DMSO-d$_6$) δ: 2.78 (3H, s), 3.82 (3H, s), 11.53 (1H, s).

Reference Example 32

7-Bromo-6-iodo-8-methoxy-5-methyl-1H-benzo[d][1,3]oxazine-2,4-dione (I-32)

According to the same method as in Reference Example 31, 2-amino-4-bromo-5-iodo-3-methoxy-6-methylbenzoic acid (I-4) (3.42 g, 8.86 mmol) and bis(trichloromethyl) carbamate (893 mg, 3.01 mmol) were dissolved in dewatered tetrahydrofuran (70 ml) under nitrogen atmosphere, followed by stirring at 40° C. for 1 hour. The reaction liquid was concentrated under reduced pressure to obtain the entitled compound (3.89 g, quant.) as a pale brown solid. Not further purified, this was used in the next reaction.

MS (FAB) m/z: 412 (M+1 for $^{79}$Br)$^+$, 414 (M+1 for $^{81}$Br)$^+$.

Reference Example 33

2-Amino-4-fluoro-5-iodo-3-methoxy-6-methylbenzamide (I-33)

Under nitrogen atmosphere, ammonium acetate (4.62 g, 60.0 mmol) was added to an N,N-dimethylformamide (120 ml) solution of 7-fluoro-6-iodo-8-methoxy-5-methyl-1H-benzo[d][1,3]oxazine-2,4-dione (I-31) (4.2 g, 12.0 mmol), followed by stirring at room temperature for 16 hours. The reaction liquid was concentrated under reduced pressure, the residue was dissolved in ethyl acetate, washed three times with saturated brine, then dried over anhydrous magnesium sulfate. After filtration and concentration under reduced pressure, the resulting residue was suspended in diisopropyl ether, followed by filtration and drying to obtain the entitled compound (3.74 g, 96%) as a white solid.

MS (FAB) m/z: 325 (M+1)$^+$.
$^1$H-NMR (CDCl$_3$) δ: 2.48 (3H, s), 3.89 (3H, s), 4.55 (2H, brs), 5.68 (1H, brs), 5.85 (1H, brs).

Reference Example 34

2-Amino-4-bromo-5-iodo-3-methoxy-6-methylbenzamide (I-34)

Under nitrogen atmosphere, 7-bromo-6-iodo-5-methoxy-5-methyl-1H-benzo[d][1,3]oxazine-2,4-dione (I-32) (3.68 g, 8.93 mmol) and ammonium acetate (3.44 g, 44.7 mmol) were added to dewatered N,N-dimethylformamide (80 ml), followed by stirring at room temperature for 2 hours. The reaction liquid was concentrated under reduced pressure, ethyl acetate and water were added to the residue, the precipitated insoluble matter was separated by filtration. The organic layer was collected by liquid-liquid separation, washed with aqueous saturated sodium chloride solution and dried on anhydrous magnesium sulfate, the solvent was evaporated away under reduced pressure to obtain the entitled compound (1.73 g, 50%) as a brown solid. Not further purified, this was used in the next reaction.

MS (FAB) m/z: 385 (M+1 for $^{79}$Br)$^+$, 387 (M+1 for $^{81}$Br)$^+$.

Reference Example 35

N-(2-Cyano-5-fluoro-4-iodo-6-methoxy-3-methylphenyl)-2,2,2-trifluoroacetamide (I-35)

Under nitrogen atmosphere, triethylamine (7.0 ml, 50.2 mmol) was added to a tetrahydrofuran (90 ml) solution of 2-amino-4-fluoro-5-iodo-3-methoxy-6-methylbenzamide (I-33) (3.7 g, 11.4 mmol), with cooling in a salt ice water bath, a tetrahydrofuran (30 ml) solution of trifluoroacetic acid anhydride (4.2 ml, 29.6 mmol) was dropwise added, taking 15 minutes, followed by stirring for 16 hours and a half with gradually heating up to room temperature. The reaction liquid was diluted with ethyl acetate, washed with saturated brine, 1 N hydrochloric acid, saturated brine in that order, then dried over anhydrous magnesium sulfate. After filtration and concentration under reduced pressure, the resulting residue was subjected to column chromatography, and the eluate with n-hexane:ethyl acetate (10:1) was concentrated under reduced pressure, the residue was suspended in hexane, filtered followed by drying to obtain the entitled compound (2.73 g, 60%) as a white solid.

MS (FAB) m/z: 403 (M+1)$^+$.
$^1$H-NMR (CDCl$_3$) δ: 2.72 (3H, s), 4.01 (3H, d, J=2.7 Hz), 7.88 (1H, brs).

Reference Example 36

N-(3-Bromo-6-cyano-4-iodo-2-methoxy-5-methylphenyl)-2,2,2-trifluoroacetamide (I-36)

Under nitrogen atmosphere, 2-amino-4-bromo-5-iodo-3-methoxy-6-methylbenzamide (I-34) (100 mg, 0.26 mmol) was dissolved in dewatered tetrahydrofuran (1 ml), triethylamine (160 μl, 1.14 mmol) was added, followed by cooling in a water-ice hath. A dewatered tetrahydrofuran (0.25 ml) solution of trifluoroacetic anhydride (95 μl, 0.676 mmol) was dropwise added to it with a syringe, followed by stirring at 0° C. for 1 hour. Ice was added to the reaction liquid, the organic matter was extracted with diethyl ether. The organic layer was washed with aqueous saturated sodium chloride solution, dried on anhydrous magnesium sulfate, then the solvent was evaporated away under reduced pressure. The resulting residue was purified by silica gel column chromatography (n-hexane:ethyl acetate=6:1) to obtain the entitled compound (85 mg, 70%) as a colorless, solid.

MS (FAB) m/z: 463 (M+1 for $^{79}$Br)$^+$, 465 (M+1 for $^{81}$Br)$^+$.
$^1$H-NMR (CDCl$_3$) δ: 2.85 (3H, s), 3.82 (3H, s), 7.97 (1H, brs).
IR (diffuse reflectance spectroscopy): 3214, 2937, 2227, 1730, 1571, 1526 cm$^{-1}$.

Reference Example 37

N-(5-Cyano-2-fluoro-3-methoxy-6-methylbiphenyl-4-yl)-2,2,2-trifluoroacetamide (I-37)

Under nitrogen atmosphere, tetrakistriphenylphosphine palladium(0) (288 mg, 0.25 mmol) was added to an N,N-dimethylformamide (15 ml) suspension of N-(2-cyano-5-fluoro-4-iodo-6-methoxy-3-methylphenyl)-2,2,2-trifluoroacetamide (I-35) (500 mg, 1.24 mmol), phenylboronic acid (228 mg, 1.87 mmol), potassium phosphate n-hydrate (890 mg, 3.1 mmol), followed by stirring with heating under reflux for 15 hours and a half. After cooling to room temperature, water and saturated brine were added to the reaction liquid, followed by extraction three times with ethyl acetate, the organic layer was washed with saturated ammonium chloride water, then dried over anhydrous magnesium sulfate. After filtration and concentration under reduced pressure, the resulting residue was subjected to column chromatography, and the eluate with n-hexane:ethyl acetate (5:1) was concentrated under reduced pressure to obtain the entitled compound (427 mg, 98%) as a white solid.

MS (FAB) m/z: 353 (M+1)$^+$.
$^1$H-NMR (CDCl$_3$) δ: 2.32 (3H, s), 4.00 (3H, d, J=2.4 Hz), 7.21-7.24 (2H, m), 7.45-7.53 (3H, m), 7.98 (1H, brs).

Reference Example 38

N-(2-Bromo-5-cyano-3-methoxy-6-methylbiphenyl-4-yl)2,2,2-trifluoroacetamide (I-38)

N-(3-Bromo-6-cyano-4-iodo-2-methoxy-5-methylphenyl)-2,2,2-trifluoroacetamide (I-36) (1.29 g, 2.79 mmol), 2-phenyl-1,3,2-dioxaborinane (474 mg, 2.93 mmol), tripotassium phosphate (74-85%, 1.48 g, 5.58 mmol) and tetrakis(triphenylphosphine)palladium(0) (406 mg, 0.352 mmol) were added to a 30-ml eggplant-type flask, followed by purging with nitrogen, N,N-dimethylformamide (50 ml) was injected into it with a syringe, followed by stirring overnight at 95° C. After cooling, the reaction liquid was diluted with ethyl acetate, successively washed with saturated brine (×3), 1 N hydrochloric acid, saturated brine, an aqueous saturated sodium hydrogencarbonate solution and saturated brine. The organic layer was dried on anhydrous magnesium sulfate, then the solvent was concentrated under reduced pressure to obtain a brown residue. The resulting residue was purified by silica gel column chromatography (n-hexane:ethyl acetate=6:1) to obtain the entitled compound (968 mg, 84%) as a brown solid.

MS (FAB) m/z: 413 (M+1 for $^{79}$Br)$^+$, 415 (M+1 for $^{81}$Br)$^+$.
$^1$H-NMR (CDCl$_3$) δ: 2.28 (3H, s), 3.86 (3H, s), 7.08-7.14 (2H, m), 7.45-7.55 (3H, m), 8.06 (1H, brs).

Reference Example 39

4-Amino-3-cyano-6-fluoro-5-methoxy-2-methylbiphenyl (I-39)

Aqueous 20% (w/v) potassium carbonate solution (9.0 ml, 13.0 mmol) was added to a methanol (9 ml) suspension of N-(5-cyano-2-fluoro-3-methoxy-6-methylbiphenyl-4-yl)-2,2,2-trifluoroacetamide (I-37) (400 mg, 1.14 mmol), followed by stirring at 70° C. for 16 hours. The reaction liquid became uniform with temperature elevation. The reaction liquid was cooled to room temperature, methanol was evaporated away under reduced pressure, water was added to the residue, followed by extraction twice with ethyl acetate, the organic layer was washed with saturated brine, then dried over anhydrous magnesium sulfate. After nitration and concentration under reduced pressure, the entitled compound (266 mg, 91%) was obtained as a white solid.

MS (FAB) m/z: 257 (M+1)$^+$.
$^1$H-NMR (CDCl$_3$) δ: 2.22 (3H, s), 3.92 (3H, d, J=1.5 Hz), 4.69 (2H, brs), 7.18-7.22 (2H, m), 7.38-7.47 (3H, m).

Reference Example 40

4-Amino-6-bromo-5-methoxy-2-methylbiphenyl-3-carbonitrile (I-40)

Aqueous potassium carbonate solution (1.25 ml) [potassium carbonate (15 g) was dissolved in water (100 ml)] and methanol (1.25 ml) were added to N-(2-bromo-5-cyano-3-methoxy-6-methylbiphenyl-4-yl)2,2,2-trifluoroacetamide (I-38) (133 mg, 0.322 mmol), followed by stirring overnight at 70° C. After cooling, methanol was evaporated away under reduced pressure, followed by extraction with ethyl acetate, washing with saturated brine and drying on anhydrous magnesium sulfate, the solvent was concentrated under reduced pressure to obtain a pale brown residue. The resulting residue was purified by silica gel column chromatography (n-hexane:ethyl acetate=6:1) to obtain the entitled compound (95 mg, 94%) as a colorless solid.

MS (FAB) m/z: 317 (M+1 for $^{79}$Br)$^+$, 319 (M+1 for $^{81}$Br)$^+$.

$^1$H-NMR (CDCl$_3$) δ: 2.16 (3H, s), 3.85 (3H, s), 4.67 (2H, brs), 7.08-7.13 (2H, m), 7.34-7.46 (3H, m).

Reference Example 41

4-Amino-3-cyano-6-fluoro-5-hydroxy-2-methylbiphenyl (I-41)

Under nitrogen atmosphere, at −78° C., 1 M borane trifluoride/methylene chloride solution (3.0 ml, 3.0 mmol) was dropwise added to a methylene chloride (10 ml) solution of 4-amino-3-cyano-6-fluoro-5-methoxy-2-methylbiphenyl (I-39) (250 mg, 1.0 mmol), taking 10 minutes, followed by stirring for 4 hours and a half with gradually heating up to 0° C. Water with ice was added to the reaction liquid, followed by neutralization at pH of 7 with aqueous 10% sodium carbonate solution and extraction three times with chloroform, the organic layer was washed with saturated brine, then dried over anhydrous magnesium sulfate. After filtration and concentration under reduced pressure, the resulting residue gave the entitled compound (225 mg, 93%) as a white solid.

MS (FAB) m/z: 243 (M+1)$^+$.

$^1$H-NMR (CDCl$_3$) δ: 2.22 (3H, s), 4.62 (2H, brs), 5.23 (1H, brs), 7.19-7.22 (2H, m), 7.36-7.47 (3H, m).

Reference Example 42

4-Amino-6-bromo-5-hydroxy-2-methylbiphenyl-3-carbonitrile (I-42)

4-Amino-6-bromo-5-methoxy-2-methylbiphenyl-3-carbonitrile (I-40) (44.5 mg, 0.14 mmol) was dissolved in dichloromethane (dewatered, 1.4 ml) under nitrogen atmosphere, and cooled in a dry ice-methanol bath at −70° C. 1 M Tribromoborane (dichloromethane solution, 0.42 ml) was dropwise added to it at −70 to −68° C., followed by stirring for 1.5 hours with heating up to 0° C. The reaction liquid was diluted with cold water, and controlled to have a pH of 6 to 7 with aqueous 10% sodium carbonate solution added thereto. The organic matter was extracted with ethyl acetate, washed with saturated brine, then dried on anhydrous magnesium sulfate, the solvent was evaporated away under reduced pressure to obtain the entitled compound (42.4 mg, quant.) as a pale brown solid.

MS (FAB) m/z: 303 (M+1 for $^{79}$Br)$^+$, 305 (M+1 for $^{81}$Br)$^+$.

$^1$H-NMR (CDCl$_3$) δ: 2.15 (3H, s), 4.66 (2H, brs), 5.59 (1H, brs), 7.08-7.14 (2H, m), 7.36-7.48 (3H, m).

Reference Example 43

4-Bromo-3-fluoro-2-methoxy-5-methylaniline (I-43)

With cooling with ice, an N,N-dimethylformamide (10 ml) solution of N-bromosuccinimide (1.84 g, 10.2 mmol) was dropwise added to an N,N-dimethylformamide (20 ml) solution of 3-fluoro-2-methoxy-5-methylaniline (I-26) (1.55 g, 10.0 mmol), taking 25 minutes, followed by stirring for 18 hours with gradually heating up to room temperature. Saturated brine was added to the reaction liquid, followed by extraction twice with ethyl acetate, the organic layer was washed with saturated brine, dried over anhydrous magnesium sulfate. After filtration and concentration under reduced pressure, the resulting residue was subjected to column chromatography, and the eluate with n-hexane:ethyl acetate (4:1) was concentrated under reduced pressure to obtain the entitled compound (1.91 g, 81%) as a brown oily substance.

MS (FAB) m/z: Molecular ion peak not detected.

$^1$H-NMR (CDCl$_3$) δ: 2.27 (3H, s), 3.86 (2H, brs), 3.88 (3H, d, J=1.5 Hz), 6.43-6.44 (1H, m).

Reference Example 44

4-Bromo-3-fluoro-6-iodo-2-methoxy-5-methylphenylamine (I-44)

N-iodosuccinimide (1.91 g, 8.5 mmol) was added to an acetic acid (40 ml) solution of 4-bromo-3-fluoro-2-methoxy-5-methylaniline (I-43) (1.90 g, 8.1 mmol), followed by stirring at room temperature for 67 hours. Saturated brine was added to the reaction liquid, followed by extraction twice with ethyl acetate, the organic layer was washed three times with saturated brine, dried over anhydrous magnesium sulfate.

After filtration and concentration under reduced pressure, the resulting residue was subjected to column chromatography, and the eluate with n-hexane:ethyl acetate (20:1) was concentrated wider reduced pressure to obtain the entitled compound (2.86 g, 98%) as a pale brown solid.

MS (FAB) m/z: 360 (M+1 for $^{79}$Br)$^+$, 362 (M+1 for $^{81}$Br)$^+$.

$^1$H-NMR (CDCl$_3$) δ: 2.62 (3H, s), 3.91 (3H, d, J=1.5 Hz), 4.50 (2H, brs).

Reference Example 45

2-Amino-5-bromo-4-fluoro-3-methoxy-6-methylbenzonitrile (I-45)

Under nitrogen atmosphere, water (0.1 ml), zinc cyanide (59 mg, 0.5 mmol), 1,1'-bis(diphenylphosphino)ferrocene (67 mg, 0.12 mmol), bis(dibenzylideneacetone)palladium(0) (58 mg, 0.1 mmol) were added to an N,N-dimethylformamide (10 ml) solution of 4-bromo-3-fluoro-6-iodo-2-methoxy-5-methylphenylamine (I-44) (359 mg, 1.0 mmol), followed by stirring at 120 to 130° C. for 3 hours. After cooling to room temperature, saturated brine was added to the reaction liquid, followed by extraction twice with ethyl acetate, the organic layer was washed with saturated brine, then dried over anhydrous magnesium sulfate. After filtration and concentration under reduced pressure, the resulting residue was subjected to column chromatography, and the eluate with n-hexane:ethyl acetate (10:1) was concentrated under reduced pressure to obtain the entitled compound (208 mg, 80%) as a white solid.

MS (FAB) m/z: 258 (M for $^{79}$Br)$^+$, 260 (M for $^{81}$Br)$^+$.

$^1$H-NMR (CDCl$_3$) δ: 2.51 (3H, s), 3.93 (3H, d, J=1.8 Hz), 4.70 (2H, brs).

Reference Example 39-a

Alternative Method from Reference Example 45

4-Amino-3-cyano-6-fluoro-5-methoxy-2-methylbiphenyl (I-39)

Under nitrogen atmosphere, 2-amino-5-bromo-4-fluoro-3-methoxy-6-methylbenzonitrile (I-45) (20.0 g, 77.20 mmol), phenylboronic acid (11.3 g, 92.64 mmol), potassium phosphate (34.4 g, 162.11 mmol) were dissolved in a mixed liquid of 1,4-dioxane (400 ml) and water (20 ml), tetrakis(triphenylphosphine)palladium (2.6 g, 2.32 mmol) was added, followed by stirring at 110° C. for 15 hours. After cooling, the insoluble matter was separated by filtration through Celite, the reaction solvent was evaporated away under reduced pressure. The resulting residue was dissolved in ethyl acetate, washed with water and saturated brine, the organic layer was dried over anhydrous sodium sulfate, then the solvent was evaporated away under reduced pressure. The resulting residue was subjected to silica gel column chromatography, eluted wrath a mixed solvent of n-hexane/ethyl acetate (3:1, v/v) to obtain the entitled compound (20.12 g, quant) as a yellow white solid.

Reference Example 46

7-Bromo-2-cyclopropyl-5-methyl-6-phenyl-1,3-benzoxazole-4-carbonitrile (I-46)

Under nitrogen atmosphere, 4-amino-6-bromo-5-hydroxy-2-methylbiphenyl-3-carbonitrile (I-42) (150 mg, 0.495 mmol) was dissolved in ethyl acetate (6 ml), diisopropylethylamine (431 μl, 2.48 mmol) was added, followed by cooling in an ice-water bath. Cyclopropanecarbonyl chloride (112 μl, 1.24 mmol) was dropwise added to it, followed by stirring overnight with restoring to room temperature. The reaction liquid was diluted with ethyl acetate, washed with saturated brine, then dried over anhydrous magnesium sulfate, concentrated under reduced pressure. The residue was purified by silica gel column chromatography (n-hexane:ethyl acetate=5:1) to obtain 2-bromo-5-cyano-4-(cyclopropanecarbonylamino)-6-methylbiphenyl-3-yl cyclopropanecarboxylate (87 mg) and a mixture of (2-bromo-5-cyano-3-hydroxy-6-methylbiphenyl-4-yl)cyclopropanecarboxamide and 4-amino-2-bromo-5-cyano-6-methylbiphenyl-4-yl cyclopropanecarboxylate (110 mg). Subsequently, 2-bromo-5-cyano-4-(cyclopropanecarbonylamino)-6-methylbiphenyl-3-yl cyclopropanecarboxylate was dissolved in ethanol (30 ml), aqueous 0.1 N sodium hydroxide solution (5.94 ml) was added, followed by stirring overnight at room temperature. Ethanol was evaporated away under reduced pressure, then the residue was dissolved in ethyl acetate, followed by successively washing with 1 N hydrochloric acid, saturated brine, dried on anhydrous magnesium sulfate, concentrated under reduced pressure to obtain (2-bromo-5-cyano-3-hydroxy-6-methylbiphenyl-4-yl)cyclopropanecarboxamide (56 mg) as a colorless oil.

Next, a mixture of (2-bromo-5-cyano-3-hydroxy-6-methylbiphenyl-4-yl)cyclopropanecarboxamide/4-amino-2-bromo-5-cyano-6-methylbiphenyl-4-yl cyclopropanecarboxylate mixture (160 mg, 0.426 mmol), p-toluenesulfonic acid monohydrate (24 mg, 0.128 mmol) and toluene (13 ml) was heated under reflux for 1.5 hours. After cooling, the reaction liquid was diluted with ethyl acetate, successively washed with an aqueous saturated sodium hydrogencarbonate solution and saturated brine, dried on anhydrous magnesium sulfate, then the solvent was evaporated away under reduced pressure to obtain a pale brown residue. The resulting residue was purified by silica gel column chromatography (n-hexane:ethyl acetate=5:1) to obtain the entitled compound (129 mg) as a colorless solid.

MS (FAB) m/z: 353 (M+1 for $^{79}$Br)$^+$, 355 (M+1 for $^{81}$Br)$^+$.

$^1$H-NMR (CDCl$_3$) δ: 1.24-1.32 (2H, m), 1.37-1.45 (2H, m), 2.25-2.42 (4H, m), 7.32-7.36 (2H, m), 7.42-7.54 (3H, m).

Reference Example 47 tert-Butyl [3-(4-cyano-2-cyclopropyl-5-methyl-6-phenyl-1,3-benzoxazol-7-yl)cyclopent-2-enyl]carbamate (I-47)

A 1,4-dioxane (6 ml) solution of 7-bromo-2-cyclopropyl-5-methyl-6-phenyl-1,3-benzoxazole-4-carbonitrile (I-46) (89 mg, 0.252 mmol), 1-(N-tert-butoxycarbonylamino)-3-tri-n-butylstannyl-2-cyclopentene (143 mg, 0.302 mmol), bis(triphenylphosphine)palladium(II) chloride (8.8 mg, 0.0126 mmol), 2,6-di-tert-butyl-p-cresol (5.6 mg, 0.0252 mmol) was refluxed overnight. After cooling, the reaction liquid was concentrated under reduced pressure, the residue was purified by silica gel column chromatography (n-hexane:ethyl acetate=10:1→8:1→5:1) to obtain the entitled compound (87 mg, 75%) as a pale brown solid.

MS (FAB) m/z: 456 (M+1)$^+$.

$^1$H-NMR (CDCl$_3$) δ: 1.18-1.70 (13H, m), 2.12-2.36 (8H, m), 4.15-4.22 (1H, m), 4.65 (1H, brs), 5.59 (1H, brs), 7.03-7.12 (2H, m), 7.35-7.45 (3H, m).

Example 8

2-Cyclopropyl-7-(3-dimethylaminocyclopent-1-en-1-yl)-5-methyl-6-phenyl-1,3-benzoxazole-4-carbonitrile (#8)

tert-Butyl [3-(4-cyano-2-cyclopropyl-5-methyl-6-phenyl-1,3-benzoxazol-7-yl)cyclopent-2-enyl]carbamate (I-47) (68 mg, 0.149 mmol) was dissolved in 1,4-dioxane (1 ml), and cooled in an ice-water bath. 4 N hydrogen chloride (1,4-dioxane solution, 1 ml) was added to it, followed by stirring at room temperature for 3.5 hours, then 4 N hydrogen chloride (1,4-dioxane solution, 1 ml) was further added to it, followed by stirring at room temperature for 1.5 hours. The reaction liquid was concentrated under reduced pressure, ethyl acetate and an aqueous saturated sodium hydrogencarbonate solution were added to the resulting residue for liquid-liquid separation of the organic layer. The aqueous layer was washed with ethyl acetate, the organic layer and the wash liquid were combined, washed with saturated brine, dried on anhydrous magnesium sulfate.

The solvent was evaporated away under reduced pressure, the resulting residue (brown oil) was dissolved in methanol (1.4 ml), aqueous formalin solution (88 μl, 36-38%, 1.49 mmol), sodium cyanoborohydride (28 mg, 0.447 mmol) and acetic acid (31 μl, 0.536 mmol) were added successively, followed by stirring overnight at room temperature. The reaction liquid was concentrated under reduced pressure, aqueous 10% sodium carbonate solution was added to the residue, the organic matter was extracted with chloroform. The organic layer was washed with saturated brine, dried on anhydrous magnesium sulfate, the solvent was evaporated away under reduced pressure. The resulting residue was purified by silica gel column chromatography (chloroform:methanol=40:1) to obtain the entitled compound (25 mg, 44%) as a pale yellow solid.

mp: 144-146° C. MS (FAB) m/z: 384 (M+1)$^+$.

$^1$H-NMR (CDCl$_3$) δ: 1.18-1.38 (4, m), 1.51-1.73 (1H, m), 1.73-1.91 (1H, m), 2.03-2.19 (8H, m), 2.22-2.38 (4H, m), 3.72-3.84 (1H, m), 5.75-5.80 (1H, m), 7.04-7.18 (2H, m), 7.30-7.43 (3H, m) IR (diffuse reflectance spectroscopy): 2941, 2857, 2818, 2774, 2223, 1610, 1590, 1454 cm$^{-1}$.

Anal. Calcd for C$_{25}$H$_{25}$N$_3$O.0.25H$_2$O: C, 77.39; H, 6.62; N, 10.83. Found: C, 77.65; H, 6.62; N, 10.76.

Reference Example 48

4-Fluoro-3-iodo-6-isobutyrylamino-5-methoxy-2-methylbenzamide (I-48)

A benzene (10 ml) suspension of 2-amino-4-fluoro-5-iodo-3-methoxy-6-methylbenzoic acid (I-33) (500 mg, 1.54 mmol) was cooled at 0° C., isobutyryl chloride (403 μl, 3.85 mmol), pyridine (311 μl, 3.85 mmol) were put into it, followed by stirring at room temperature for 3 hours. Ethyl acetate (50 ml) was added to the reaction liquid, the organic layer was washed with 1 N hydrochloric acid (50 ml×2), saturated brine (50 ml), then dried over anhydrous magnesium sulfate, concentrated under reduced pressure. N,N-Dimethylformamide (5.0 ml), ammonium acetate (593 mg, 7.69 mmol) were added to the residue, followed by stirring at room temperature for 10 minutes, then stirring at 50° C. for 45 minutes. Ethyl acetate (100 ml) was added to the reaction liquid, the organic layer was washed with saturated brine (50 ml×3), dried over anhydrous magnesium sulfate, then concentrated under reduced pressure. The residue was purified twice by silica gel column chromatography (chloroform:methanol=100:1→100:7), (n-hexane:ethyl acetate=3:2→chloroform:methanol=50:1) to obtain the entitled compound (178 mg, 29%) as a colorless solid.

MS (FAB) m/z: 395 (M+1)$^+$.

$^1$H-NMR (DMSO-d$_6$) δ: 1.07 (6H, d, J=6.9 Hz), 2.34 (3H, s), 2.52-2.65 (1H, m), 3.72 (3H, s), 7.34 (1H, brs), 7.57 (1H, brs), 9.21 (1H, brs).

Reference Example 49

N-(2-Cyano-5-fluoro-4-iodo-6-methoxy-3-methylphenyl)isobutylamide (I-49)

4-Dimethylaminopyridine (5.3 mg, 43.1 μmol) was added to a pyridine (7.0 ml) solution of 4-fluoro-3-iodo-6-isobutyrylamino-5-methylbenzamide (I-48) (170 mg, 431 μmol), followed by cooling at 0° C. Trifluoromethanesulfonic acid anhydride (219 μl, 1.29 mmol) was dropwise added to it, followed by stirring at room temperature for 40 minutes. Ethyl acetate (50 ml) was put into the reaction liquid, followed by successively washing with 1 N hydrochloric acid (30 ml×3), saturated brine (30 ml×2), then drying over anhydrous magnesium sulfate, concentration under reduced pressure. The residue was purified by silica gel column chromatography (n-hexane:ethyl acetate=3:1) to obtain the entitled compound (149 mg, 92%) as a pale yellow solid.

MS (FAB) m/z: 377 (M+1)$^+$.

$^1$H-NMR (CDCl$_3$) δ: 1.31 (6H, d, J=6.6 Hz), 2.61-2.71 (1H, m), 2.69 (3H, s), 3.94 (3H, s), 7.19 (1H, brs).

Reference Example 50

N-(5-Cyano-2-fluoro-3-methoxy-6-methylbiphenyl-4-yl)isobutylamide (I-50)

Tetrakis(triphenylphosphine)palladium(0) (87.2 mg, 75.5 μmol) was added to an N,N-dimethylformamide (3.0 ml) suspension of N-(2-cyano-5-fluoro-4-iodo-6-methoxy-3-methylphenyl)isobutylamide (I-49) (142 mg, 377 μmol), phenylboronic acid (69.0 mg, 566 μmol), potassium phosphate n-hydrate (74-78%, 217 mg, 755 μmol), followed by stirring at 95° C. for 1.5 hours. The reaction liquid was cooled, then ethyl acetate (50 ml) was added, followed by washing with saturated brine (50 ml×3), drying over anhydrous magnesium sulfate, concentration under reduced pressure. The residue was purified by silica gel column chromatography (n-hexane:ethyl acetate=4:1) to obtain the entitled compound (117 mg, 95%) as an orange brown solid.

MS (FAB) m/z; 327 (M+1)$^+$.

$^1$H-NMR (CDCl$_3$) δ: 1.35 (6H, d, J=6.9 Hz), 2.30 (3H, s), 2.62-2.76 (1H, m), 3.94 (3H, s), 7.16-7.24 (3H, m), 7.38-7.52 (3H, m).

Reference Example 51

N-(5-Cyano-2-fluoro-3-hydroxy-6-methylbiphenyl-4-yl)-isobutylamide (I-51)

A dichloromethane (3.5 ml) solution of N-(5-cyano-2-fluoro-3-methoxy-6-methylbiphenyl-4-yl)isobutylamide (I-50) (117 mg, 358 μmol) was cooled at −78° C., a dichloromethane solution of 1 N tribromoborane (1.08 ml, 1.08 mmol) was dropwise added, followed by stirring at −78° C. for 30 minutes. Afterwards, this was heated up to −12° C. and stirred for 10 minutes. The reaction liquid was put into cold water (50 ml), saturated brine (50 ml) was added, the intended product was extracted with ethyl acetate (50 ml×2). The organic layer was dried over anhydrous magnesium sulfate, concentrated under reduced pressure, the residue was purified by silica gel column chromatography (n-hexane:ethyl acetate=3:1) to obtain the entitled compound (91 mg, 81%) as a pale yellow solid.

MS (FAB) m/z: 313 (M+1)$^+$.

$^1$H-NMR (CDCl$_3$) δ: 1.38 (6H, d, J=6.9 Hz), 2.28 (3H, s), 2.74-2.88 (1H, m), 7.18-7.24 (2H, m), 7.38-7.52 (3H, m), 7.86 (1H, brs), 9.39 (1H, s).

Reference Example 52

7-Fluoro-2-isopropyl-5-methyl-6-phenyl-1,3-benzoxazole-4-carbonitrile (I-52)

Toluene (10 ml), p-toluenesulfonic acid monohydrate (5.3 mg, 28 μmol) were added to N-(5-cyano-2-fluoro-3-hydroxy-6-methylbiphenyl-4-yl)isobutylamide (I-51) (87 mg, 279 μmol), followed by refluxing with a Dean-Stark condenser for 3.5 hours. During the course, p-toluenesulfonic acid monohydrate (5.3 mg, 28 μmol) was added. Alter cooled, ethyl acetate (50 ml) was added to the reaction liquid, the organic layer was successively washed with saturated sodium bicarbonate water (30 ml), saturated brine (30 ml×2), then dried over anhydrous magnesium sulfate, concentrated under reduced pressure. The residue was purified by silica gel column chromatography (n-hexane:ethyl acetate=4:1) to obtain the entitled compound (82 mg, quant.) as a colorless solid.

MS (FAB) m/z: 295 (M+H)$^+$.

$^1$H-NMR (CDCl$_3$) δ: 1.50 (6H, d, J=7.2 Hz), 2.42 (3H, s), 3.28-3.42 (1H, m), 7.22-7.30 (2H, m), 7.42-7.54 (3H, m).

Example 9

7-[(3S)-3-(Dimethylamino)pyrrolidin-1-yl]-2-isopropyl-5-methyl-6-phenyl-1,3-benzoxazole-4-carbonitrile hydrochloride (#9)

Triethylamine (76.7 μl, 550 μmol), (3S)-3-(dimethylamino)pyrrolidine (45.4 μl, 358 μmol) were added to a dimethylsulfoxide (1.6 ml) suspension of 7-fluoro-2-isopropyl-5-methyl-6-phenyl-1,3-benzoxazole-4-carbonitrile (I-52) (81 mg, 275 μmol), followed by stirring at 90° C. for 3 hours, then (3S)-3-(dimethylamino)pyrrolidine (45.4 μl, 358 μmol) was further added, followed by stirring for 1.5 hours. After cooling, saturated sodium bicarbonate water (30 ml) was added to the reaction liquid, the product was extracted with chloroform (30 ml×3), the organic layer was washed with saturated brine (30 ml), then dried over anhydrous magnesium sulfate, concentrated under reduced pressure. The residue was purified by silica gel column chromatography (chloroform:methanol=100:1) to obtain a non-salt form of the entitled compound (92.8 mg, 87%) as a yellow ocher semisolid. This was dissolved in diethyl ether (10 ml), 4N hydrogen chloride/1,4-dioxane solution (60 μl, 241 μmol) was dropwise added, followed by stirring for 3 minutes. The precipitated matter was collected by filtration, dried to obtain the entitled compound (85 mg, salting yield 84%) as a colorless solid.

mp: 168-170° C. (dec).

MS (FAB) m/z: 389 (M+1-HCl)$^+$.

$^1$H-NMR (DMSO-d$_6$) δ: 1.40 (6H, d, J=6.9 Hz), 1.85-2.02 (1H, m), 2.05-2.20 (1H, m), 2.11 (3H, s), 2.56 (3H, brs), 2.62 (3H, brs), 2.98-3.08 (1H, m), 3.12-3.80 (5H, m), 7.17-7.25 (1H, m), 7.25-7.32 (1H, m), 7.37-7.51 (3H, m), 10.7 (1H, brs).

IR (diffuse reflectance spectroscopy): 2963, 2878, 2204, 1605, 1560, 1474 cm$^{-1}$.

Anal. Calcd for C$_{25}$H$_{25}$N$_3$O.HCl.0.75H$_2$O: C, 65.74; H, 7.01; N, 12.78; Cl, 8.09. Found: C, 66.03; H, 6.87; N, 12.82; Cl, 8.09.

Reference Example 53

N-(3'-Benzyloxy-5-cyano-2-fluoro-3-methoxy-6-methylbiphenyl-4-yl)-2,2,2-trifluoroacetamide (I-53)

Tetrakis(triphenylphosphine)palladium(0) (287 mg, 249 μmol) was added to an N,N-dimethylformamide (16.5 ml) suspension of N-(2-cyano-5-fluoro-4-iodo-6-methoxy-3-methylphenyl)-2,2,2-trifluoroacetamide (I-35) (500 mg, 1.24 mmol), 3-benzyloxyphenylboronic acid (425 mg, 1.87 mmol), potassium phosphate n-hydrate (74-78%, 713 mg, 2.49 mmol), followed by stirring at 95° C. for 5.5 hours. The reaction liquid was cooled, then ethyl acetate (100 ml) was added, followed by washing with saturated brine (50 ml×3), drying over anhydrous magnesium sulfate, concentration under reduced pressure. The residue was purified twice by silica gel column chromatography (n-hexane:ethyl acetate=4: 1), (n-hexane:ethyl acetate=6:1) to obtain the entitled compound (415 mg, 73%) as a yellow solid.

MS (FAB) m/z: 459 (M+1)$^+$.

$^1$H-NMR (CDCl$_3$) δ: 2.28 (3H, s), 4.00 (3H, d, J=2.4 Hz), 5.10 (2H, s), 6.78-6.84 (2H, m), 7.04-7.10 (1H, m), 7.26-7.47 (7H, m).

Reference Example 54

4-Amino-3'-benzyloxy-3-cyano-6-fluoro-5-methoxy-2-methylbiphenyl (I-54)

Aqueous potassium carbonate solution (20% w/v, 6.07 ml), methanol (12.1 ml) were added to N-(3'-benzyloxy-5-cyano-2-fluoro-3-methoxy-6-methylbiphenyl-4-yl)-2,2,2-trifluoroacetamide (I-53) (400 mg, 873 μmol), followed by stirring overnight at 70° C. After cooling, methanol was evaporated away under reduced pressure, saturated brine (50 ml) was added, the product was extracted with ethyl acetate (50 ml×2). The organic layer was dried over anhydrous magnesium sulfate, concentrated under reduced pressure. The residue was purified by silica gel column chromatography (n-hexane:ethyl acetate=4:1) to obtain the entitled compound (276 mg, 87%) as a colorless solid.

MS (FAB) m/z: 363 (M+1)$^+$.

$^1$H-NMR (CDCl$_3$) δ: 2.19 (3H, s), 3.91 (3H, d, J=1.2 Hz), 4.69 (2H, brs), 5.08 (2H, s), 6.77-6.87 (2H, m), 6.97-7.03 (1H, m), 7.29-7.47 (6H, m).

Reference Example 55

N-(3'-Benzyloxy-5-cyano-2-fluoro-3-methoxy-6-methylbiphenyl-4-yl)isobutylamide (I-55)

A benzene (5.5 ml) solution of 4-amino-3'-benzyloxy-3-cyano-6-fluoro-5-methoxy-2-methylbiphenyl (I-54) (275 mg, 759 μmol) was cooled at 0° C., isobutyryl chloride (159 μl, 1.52 mmol), pyridine (123 μl, 1.52 mmol) were put into it, followed by stirring overnight at room temperature. Ethyl acetate (50 ml) was added to the reaction liquid, the organic layer was washed with 1 N hydrochloric acid (50 ml), saturated brine (50 ml), then dried over anhydrous sodium sulfate, then concentrated under reduced pressure. The residue was purified by silica gel column chromatography (n-hexane:ethyl acetate=4:1→3:1) to obtain the entitled compound (280 mg, 85%) as a pale yellow solid.

MS (FAB) m/z: 433 (M+1)$^+$.

$^1$H-NMR (CDCl$_3$) δ: 1.34 (6H, d, J=6.9 Hz), 2.25 (3H, s), 2.62-2.76 (1H, m), 3.92 (3H, d, J=1.8 Hz), 5.08 (2H, s), 6.77-6.84 (2H, m), 7.02-7.08 (1H, m), 7.26-7.47 (7H, m).

Reference Example 56

N-(5-Cyano-2-fluoro-3,3'-dihydroxy-6-methylbiphenyl-4-yl)isobutylamide (I-56)

Under nitrogen atmosphere, N-(3'-benzyloxy-5-cyano-2-fluoro-3-methoxy-6-methylbiphenyl-4-yl)isobutylamide (I-55) (280 mg, 0.647 mmol) was dissolved in dichloromethane (dewatered, 6.5 ml), and cooled in a dry ice-methanol bath at −70° C. 1 M Tribromoborane (dichloromethane solution, 1.94 ml) was dropwise added to it at −70 to −68° C., followed by stirring for 1.5 hours with heating up to 0° C. The reaction liquid was diluted with cold water, the precipitated crystal was separated by filtration, from the filtrate, the organic matter was extracted with chloroform, washed with saturated brine, then dried on anhydrous magnesium sulfate, the solvent was evaporated away under reduced pressure. The resulting residue was purified by silica gel column chromatography (n-hexane:ethyl acetate=3:1→1:1→1:2) to obtain the entitled compound (62 mg, 29%) as a colorless solid.

MS (FAB) m/z: 329 (M+1)⁺.

¹H-NMR (CDCl₃) δ: 1.35 (6H, d, J=6.9 Hz), 2.28 (3H, s), 2.27-2.87 (1H, m), 6.65-6.72 (2H, m), 6.86-6.92 (1H, m), 7.26-7.33 (m, overlapped with CDCl₃ peak).

Reference Example 57

7-Fluoro-6-(3-hydroxyphenyl)-2-isopropyl-5-methyl-1,3-benzoxazole-4-carbonitrile (I-57)

A mixture of N-(5-cyano-2-fluoro-3,3'-dihydroxy-6-methylbiphenyl-4-yl)isobutylamide (I-56) (60 mg, 0.183 mmol), p-toluenesulfonic acid monohydrate (10.4 mg, 0.0548 mmol) and toluene (5 ml) was heated under reflux for 2.5 hours. After cooling, this was diluted with ethyl acetate, successively washed with 1 N hydrochloric acid and saturated brine, dried on anhydrous magnesium sulfate, the solvent was evaporated away under reduced pressure to obtain a pale brown residue. The resulting residue was purified by silica gel column chromatography (n-hexane:ethyl acetate=4:1) to obtain the entitled compound (30.9 mg, 54%) as a pale yellow solid.

MS (FAB) m/z: 311 (M+1)⁺.

¹H-NMR (CDCl₃) δ: 1.50 (6H, d, J=6.0 Hz), 2.43 (3H, s), 3.30-3.40 (1H, m), 5.03 (1H, s), 6.72-6.74 (1H, m), 6.78-6.83 (1H, m), 6.91-6.95 (1H, m), 7.37 (1H, t, J=7.8 Hz).

Example 10

7-[(3S)-3-(Dimethylamino)pyrrolidin-1-yl]-6-(3-hydroxyphenyl)-2-isopropyl-5-methyl-1,3-benzoxazole-4-carbonitrile (#10)

Triethylamine (27 μl, 193 μmol), (3S)-(dimethylamino)pyrrolidine (18.4 μl, 145 μmol) were added to a dimethyl sulfoxide (0.65 ml) solution of 7-fluoro-6-(3-hydroxyphenyl)-2-isopropyl-5-methyl-1,3-benzoxazole-4-carbonitrile (I-57) (30 mg, 96.7 μmol), followed by stirring overnight at 90° C. After cooling, the reaction liquid was diluted with ethyl acetate, washed three times with saturated brine, then dried over anhydrous magnesium sulfate, concentrated under reduced pressure. The resulting residue was purified by silica gel column chromatography (chloroform:methanol=15:1) to obtain the entitled compound (33.3 mg, 85%) as a pale yellow semi-solid.

MS (FAB) m/z: 405 (M+1)⁺.

¹H-NMR (CDCl₃) δ: 1.45 (6H, d, J=6.9 Hz), 1.50-1.85 (1H, m), 1.85-2.10 (1H, m), 2.15 (3H, s), 2.18 (3H, s), 2.21 (1.5H, s), 2.23 (1.5H, s), 2.50-2.66 (1H, m), 2.81 (0.6H, m), 3.06 (0.4H, m), 3.18-3.75 (4H, m), 6.58-6.83 (3H, m), 7.20-7.30 (m, overlapped with CHCl₃ peak).

Reference Example 58

4-Amino-5-cyano-2-fluoro-6-methylbiphenyl-3-yl methoxyacetate (I-58)

Diisopropylethylamine (0.64 ml, 3.7 mmol) was added to an ethyl acetate (8 ml) solution of 4-amino-3-cyano-6-fluoro-5-hydroxy-2-methylbiphenyl (I-41) (180 mg, 0.74 mmol), then with cooling with ice, methoxyacetyl chloride (0.17 ml, 1.85 mmol) was added, followed by stirring for 16 hours with gradually heating up to room temperature. Aqueous saturated ammonium chloride solution was added to the reaction liquid, followed by extraction three times with ethyl acetate, the organic layer was washed with saturated sodium bicarbonate water and saturated brine, then dried over anhydrous magnesium sulfate. After filtration and concentration under reduced pressure, the resulting residue was subjected to column chromatography, and the eluate with n-hexane:ethyl acetate (1:1) was concentrated under reduced pressure to obtain the entitled compound (229 mg, 99%) as a yellow solid.

MS (FAB) m/z: 3.15 (M+1)⁺.

¹H-NMR (CDCl₃) δ: 2.29 (3H, s), 3.53 (3H, s), 4.36 (2H, s), 4.55 (2H, brs), 7.21-7.23 (2H, m), 7.35-7.47 (3H, m).

Reference Example 59

7-Fluoro-2-(methoxymethyl)-5-methyl-6-phenyl-1,3-benzoxazole-4-carbonitrile (I-59)

p-Toluenesulfonic acid monohydrate (38 mg, 0.2 mmol) was added to a toluene (30 ml) solution of 4-amino-5-cyano-2-fluoro-6-methylbiphenyl-3-yl methoxyacetate (I-58) (214 mg, 0.68 mmol), followed by stirring for 3 hours and a half with heating under reflux. After cooling to room temperature, the reaction liquid was diluted with ethyl acetate, washed with saturated sodium bicarbonate water and saturated brine, then dried over anhydrous magnesium sulfate. After filtration and concentration under reduced pressure, the resulting residue was subjected to column chromatography, and the eluate with n-hexane:ethyl acetate (4:1) was concentrated under reduced pressure to obtain the entitled compound (160 mg, 79%) as a pale yellow solid.

MS (FAB) m/z: 297 (M+1)⁺.

¹H-NMR (CDCl₃) δ: 2.44 (3H, s), 3.57 (3H, s), 4.80 (2H, s), 7.24-7.26 (2H, m), 7.44-7.55 (3H, m).

Example 11

7-[(3S)-3-(Dimethylamino)pyrrolidin-1-yl]-2-(methoxymethyl)-5-methyl-6-phenyl-1,3-benzoxazole-4-carbonitrile (#11)

(3S)-3-(Dimethylamino)pyrrolidine (65 μl, 0.51 mmol) and triethylamine (0.13 ml, 0.98 mmol) were added to a dimethyl sulfoxide (4 ml) solution of 7-fluoro-2-(methoxymethyl)-5-methyl-6-phenyl)-1,3-benzoxazole-4-carbonitrile (I-59) (115 mg, 0.39 mmol), followed by stirring at 90° C. for 17 hours. After cooling to room temperature, saturated sodium bicarbonate water was added to the reaction liquid, followed by extraction three times with ethyl acetate, the organic layer was washed with saturated brine, then dried over anhydrous magnesium sulfate. After filtration and concentration under reduced pressure, the resulting residue was subjected to column chromatography, and the eluate with chloroform:methanol (50:1) was concentrated under reduced pressure, the residue was dissolved in diethyl ether, 4 N hydrochloric acid/ethyl acetate was added followed by concentration under reduced pressure to obtain a brown oily substance.

(3S)-3-(Dimethylamino)pyrrolidine (76 μl, 0.60 mmol) was added to a dimethyl sulfoxide (4 ml) solution of 7-fluoro-2-(methoxymethyl)-5-methyl-6-phenyl-1,3-benzoxazole-4-carbonitrile (I-59) (58 mg, 0.20 mmol), followed by stirring at 90° C. for 1 hour. After cooling to room temperature, the above brown oily substance and saturated sodium bicarbonate water were added, followed by extraction three times with ethyl acetate, the organic layer was washed with saturated brine, then dried over anhydrous magnesium sulfate. After filtration and concentration under reduced pressure, the resulting residue was subjected to column chromatography, and the eluate with chloroform:methanol (50:1) was concentrated under reduced pressure, the residue was dissolved in ethyl acetate, washed twice with saturated brine, then dried over anhydrous magnesium sulfate. After filtration and concentration tinder reduced pressure, the entitled compound (39 mg, 17%) was obtained as a brown oily substance.

MS (FAB) m/z: 391 (M+1)$^+$.

$^1$H-NMR (CDCl$_3$) δ: 1.59-1.73 (1H, m), 1.93-2.03 (1H, m), 2.16 (6H, s), 2.21 (3H, s), 2.55-2.65 (1H, m), 2.95 (1H, dd, J=8.7, 9.6 Hz), 3.31 (1H, dd, J=6.9, 9.6 Hz), 3.39-3.47 (2H, m), 3.52 (3H, s), 4.72 (2H, s), 7.10-7.14 (1H, m), 7.23-7.27 (1H, m), 7.33-7.53 (3H, m).

IR (diffuse reflectance spectroscopy): 2946, 2211, 1587, 1473, 1400, 1366 cm$^{-1}$.

Reference Example 60

Benzyl tert-butyl 2,2-dimethylmalonate (I-60)

Benzyl tert-butyl malonate (1.0 g, 4.0 mmol) was dissolved in tetrahydrofuran (dewatered, 20 ml) under nitrogen atmosphere and cooled in an ice-water bath. 60% sodium hydride (351 mg, 8.78 mmol) was added to it, followed by stirring with cooling for 15 minutes and at room temperature for 30 minutes. The reaction liquid was again cooled in an ice-water bath, a tetrahydrofuran (1.5 ml) solution of methyl iodide (547 µl, 8.78 mmol) was dropwise added, followed by stirring overnight at room temperature. The reaction liquid was concentrated under reduced pressure, ethyl acetate and water were added to the residue to collect the organic layer by liquid-liquid separation. The organic layer was washed with saturated brine, dried on anhydrous magnesium sulfate, the solvent was evaporated away under reduced pressure. The resulting residue was purified by silica gel column chromatography (n-hexane:ethyl acetate=20:1) to obtain the entitled compound (1.05 g, 94%) as a colorless oil.

MS (FAB) m/z: 279 (M+1)$^+$.

$^1$H-NMR (CDCl$_3$) δ: 1.33 (9H, s), 1.41 (6H, s), 5.15 (2H, s), 7.23-7.40 (5H, m).

Reference Example 61

Monobenzyl 2,2-dimethylmalonate (I-61)

Aqueous 95% trifluoroacetic acid solution (2.5 ml) cooled with ice-water was added to benzyl tert-butyl 2,2-dimethylmalonate (I-60) (100 mg, 0.4 mmol), followed by stirring at room temperature for 2.5 hours. The reaction liquid was concentrated under reduced pressure, the resulting residue was dissolved in water, followed by controlling at pH of 3 with aqueous sodium hydrogencarbonate solution added thereto. The organic matter was extracted with diethyl ether, washed with saturated brine, then the solvent was concentrated under reduced pressure to obtain the entitled compound (76.7 mg, 86%) as a pale brown solid.

MS (FAB) m/z: 0.223 (M+1)$^+$.

$^1$H-NMR (CDCl$_3$) δ: 1.50 (6H, s), 5.19 (2H, s), 7.27-7.40 (5H, m).

Reference Example 62

3-Benzyloxy-2,2-dimethylpropionic acid (I-62)

3-Benzyloxy-2,2-dimethylpropionitrile (2.0 g, 10.6 mmol), potassium hydroxide (31.2 g, 86%, 479 mmol) and potassium carbonate (1.13 g, 82 mmol) were dissolved in methanol (340 ml), concentrated under reduced pressure. The resulting residue was heated at 140° C. (bath temperature) under nitrogen atmosphere, and stirred for 22 hours. The reaction mixture was dissolved in water, cooled in an ice-water bath, followed by controlling at pH of 1 with hydrochloric acid (36%) added thereto. The organic matter was extracted with diethyl ether, washed with saturated brine, dried on anhydrous magnesium sulfate, the solvent was evaporated away under reduced pressure to obtain the entitled compound (2.18 g, 99%) as a colorless solid.

MS (FAB) m/z: 209 (M+1)$^+$.

$^1$H-NMR (CDCl$_3$) δ: 1.24 (6H, s), 3.47 (2H, s), 4.57 (2H, s), 7.26-7.39 (5H, m).

Reference Example 63

4-Amino-5-cyano-2-fluoro-6-methylbiphenyl-3-yl-benzyl 2,2-dimethylmalonate (I-63)

Under nitrogen atmosphere, 4-amino-3-cyano-6-fluoro-5-hydroxy-2-methylbiphenyl (I-41) (298 mg, 1.23 mmol) was dissolved in ethyl acetate (12 ml), diisopropylethylamine (1.07 ml, 6.15 mmol) was added, followed by cooling in an ice-water bath. To this, dropwise added was benzyl 2-chlorocarbonyl-2-methylpropionate (741 mg, 3.08 mmol) [obtained as a pale yellow oil (741 mg, 3.08 mmol), by stirring overnight monobenzyl 2,2-dimethylmalonate (800 mg, 3.60 mmol) and thionyl chloride (1 ml, 13.7 mmol) at 50° C., followed by concentrating the reaction liquid under reduced pressure], followed by stirring for 2 hours with restoring to room temperature. The reaction liquid was diluted with ethyl acetate, washed with 1 N hydrochloric acid and saturated brine, then dried over anhydrous magnesium sulfate, concentrated under reduced pressure. The residue was purified by silica gel column chromatography (n-hexane:ethyl acetate=5:1) to obtain the entitled compound (516 mg, 94%) as a colorless oil.

MS (FAB) m/z: 447 (M+1)$^+$.

$^1$H-NMR (CDCl$_3$) δ: 1.62 (6H, s), 2.26 (3H, s), 4.61 (2H, brs), 5.25 (2H, s), 7.15-7.20 (2H, m), 7.34-7.44 (8H, m).

Reference Example 64

4-Amino-5-cyano-2-fluoro-6-methylbiphenyl-3-yl 3-benzyloxy-2,2-dimethylpropionate (I-64)

Under nitrogen atmosphere, 4-amino-3-cyano-6-fluoro-5-hydroxy-2-methylbiphenyl (I-41) (300 mg, 1.23 mmol) was dissolved in ethyl acetate (12 ml), diisopropylethylamine (1.29 ml, 7.38 mmol) was added, followed by cooling in an ice-water bath. To this was added 3-benzyloxy-2,2-dimethylpropionyl chloride (851 mg, 3.69 mmol) [obtained as a pale yellow oil (851 mg, 3.69 mmol), by stirring overnight 3-benzyloxy-2,2-dimethylpropionic acid (768 mg, 3.69 mmol) and thionyl chloride (1.15 ml, 14.8 mmol) at 50° C., followed by concentrating the reaction liquid under reduced pressure], followed by stirring for 2.5 hours with restoring to room temperature. The reaction liquid was diluted with ethyl acetate, washed with 1 N hydrochloric acid and saturated brine, then dried on anhydrous magnesium sulfate, concentrated under reduced pressure. The residue was purified by silica gel column chromatography (chloroform) to obtain the entitled compound (392 mg, 74%) as a colorless solid.

MS (FAB) m/z: 433 (M+1)$^+$.

$^1$H-NMR (CDCl$_3$) δ: 1.37 (6H, s), 2.24 (3H, s), 3.68 (2H, s), 4.59 (4H, s), 7.16-7.22 (2H, m), 7.30-7.44 (8H, m).

Reference Example 65

Benzyl 2-(4-cyano-7-fluoro-5-methyl-6-phenylbenzoxazol-2-yl)-2-methylpropionate (I-65)

A mixture of 4-amino-5-cyano-2-fluoro-6-methylbiphenyl-3-yl 2,2-dimethylmalonate (I-63) (500 mg, 1.12 mmol), p-toluenesulfonic acid monohydrate (21 mg, 0.112 mmol) and toluene (20 ml) was heated under reflux for 2 hours. After cooling, the reaction liquid was diluted with ethyl acetate, successively washed with an aqueous saturated sodium hydrogencarbonate solution and saturated brine, dried on anhydrous magnesium sulfate, then the solvent was evaporated away to obtain a pale brown residue. The resulting residue was purified by silica gel column chromatography (n-hexane:ethyl acetate=6:1) to obtain the entitled compound (411 mg, 86%) as a colorless solid.

MS (FAB) m/z: 429 (M+1)$^+$.

$^1$H-NMR (CDCl$_3$) δ: 1.82 (6H, s), 2.42 (3H, s), 5.20 (2H, s), 7.19-7.60 (10H, m).

Reference Example 66

2-(2-Benzyloxy-1,1-dimethylethyl)-7-fluoro-5-methyl-6-phenyl-1,3-benzoxazole-4-carbonitrile (I-66)

A mixture of 4-amino-5-cyano-2-fluoro-6-methylbiphenyl-3-yl 3-benzyloxy-2,2-dimethylpropionate (I-64) (390 mg, 0.902 mmol), p-toluenesulfonic acid monohydrate (17 mg, 0.09 mmol) and toluene (16 ml) was heated under reflux for 3 hours. After cooling, the reaction liquid was diluted with ethyl acetate, successively washed with an aqueous saturated sodium hydrogencarbonate solution and saturated brine, dried on anhydrous magnesium sulfate, then the solvent was evaporated away to obtain a pale brown residue. The resulting residue was purified by silica gel column chromatography (n-hexane:ethyl acetate=20:1→10:1) to obtain the entitled compound (337 mg, 90%) as a colorless oil.

MS (FAB) m/z: 415 (M+1)$^+$.

$^1$H-NMR (CDCl$_3$) δ: 1.54 (6H, s), 2.41 (3H, s), 3.74 (2H, s), 4.54 (2H, s), 7.20-7.36 (7H, m), 7.42-7.56 (3H, m).

Example 12

Benzyl 2-{4-cyano-7-[(3S)-3-(dimethylamino)pyrrolidin-1-yl]-5-methyl-6-phenyl-1,3-benzoxazol-2-yl}-2-methylpropionate hydrochloride (#12)

Triethylamine (65 μl, 0.466 mmol), (3S)-3-(dimethylamino)pyrrolidine (44.4 μl, 0.35 mmol) were added to a dimethyl sulfoxide (5 ml) solution of benzyl 2-(4-cyano-7-fluoro-5-methyl-6-phenylbenzoxazol-2-yl)-2-methylpropionate (I-65) (100 mg, 0.233 mmol), followed by stirring overnight at 90° C. Triethylamine (16.3 μl, 0.117 mmol), (3S)-3-(dimethylamino)pyrrolidine (14.8 μl, 0.117 mmol) were further added to the reaction liquid, followed by stirring at 90° C. for 4 hours. After cooling, the reaction liquid was diluted with ethyl acetate, washed three times with saturated brine, then dried over anhydrous magnesium sulfate, concentrated under reduced pressure. The resulting residue was purified by silica gel column chromatography (chloroform:methanol=100; 1) to obtain a non-salt form of the entitled compound (107 mg, 88%) as a pale brown oil. This was dissolved in diethyl ether (5 ml), a 1,4-dioxane solution of 4 N hydrogen chloride (77 μl, 0.308 mmol) was added, followed by stirring for 10 minutes. The precipitated solid was collected by filtration, washed with diethyl ether, then dried under reduced pressure to obtain the entitled compound (91 mg, 80%) as a colorless solid.

MS (FAB) m/z: 523 (M−HCl+1)$^+$.

$^1$H-NMR (CDCl$_3$) δ: 1.48-1.60 (1H, m), 1.80 (3H, s), 1.81 (3H, s), 2.06-2.20 (2H, m), 2.25 (3H, s), 2.42-2.50 (3H, s), 2.06-2.58 (3H, m), 3.04-3.13 (1H, m), 3.18-3.27 (1H, m), 3.30-3.58 (3H, m), 5.20 (2H, d, J=6.6 Hz), 7.15-7.20 (2H, m), 7.20-7.38 (m, overlapped with CDCl$_3$ peak), 7.38-7.50 (3H, m).

IR (diffuse reflectance spectroscopy): 2986, 2947, 2878, 2360, 2212, 1741, 1607, 1586, 1560, 1473 cm$^{-1}$.

Example 13

2-[2-(Benzyloxy)-1,1-dimethylethyl]-7-[(3S)-3-(dimethylamino)pyrrolidin-1-yl]-5-methyl-6-phenyl-1,3-benzoxazole-4-carbonitrile (#13)

Triethylamine (222 μl, 1.59 mmol), (3S)-3-(dimethylamino)pyrrolidine (152 μl, 1.19 mmol) were added to a dimethyl sulfoxide (16.5 ml) solution of 2-[2-(benzyloxy)-1,1-dimethylethyl]-7-fluoro-5-methyl-6-phenyl-1,3-benzoxazole-4-carbonitrile (I-66) (330 mg, 0.796 mmol), followed by stirring overnight at 90° C. After cooling, the reaction liquid was diluted with ethyl acetate, washed three times with saturated brine, then dried over anhydrous magnesium sulfate, concentrated under reduced pressure. The resulting residue was purified by silica gel column chromatography (chloroform:methanol=100:1) to obtain the entitled compound (369 mg, 91%) as a pale brown oil.

MS (FAB) m/z: 509 (M+1)$^+$.

$^1$H-NMR (CDCl$_3$) δ: 1.50 (3H, s), 1.51 (3H, s), 1.52-1.64 (1H, m), 1.84-1.96 (1H, m), 2.11 (6H, s), 2.19 (3H, s), 2.39-2.50 (1H, m), 2.92 (1H, t, J=9.0 Hz), 3.18-3.36 (3H, m), 3.71 (2H, s), 4.53 (2H, s), 7.08-7.13 (1H, m), 7.20-7.44 (m, overlapped with CDCl$_3$ peak).

IR (diffuse reflectance spectroscopy): 2973, 2867, 2773, 2212, 1605, 1583, 1557, 1470, 1401 cm$^{-1}$.

Example 14

7-[3-(Dimethylamino)pyrrolidin-1-yl]-2-(2-hydroxy-1,1-dimethylethyl)-5-methyl-6-phenyl-1,3-benzoxazole-4-carbonitrile (#14)

2-[2-(Benzyloxy)-1,1-dimethylethyl]-7-[(3S)-3-(dimethylamino)pyrrolidin-1-yl]-5-methyl-6-phenyl-1,3-benzoxazole-4-carbonitrile (#13) (150 mg, 0.295 mmol) was dissolved in diethyl ether (5 ml), a 1,4-dioxane solution of 4 N hydrogen chloride (111 μl, 0.442 mmol) was added, followed by stirring at room temperature for 10 minutes. The reaction liquid was concentrated under reduced pressure to obtain a pale pink, amorphous 2-[2-(benzyloxy)-1,1-dimethylethyl]-7-(3-dimethylamino)pyrrolidin-1-yl)-5-methyl-6-phenyl-1,3-benzoxazole-4-carbonitrile hydrochloride (129 mg). The hydrochloride (118 mg, 0.216 mmol) was dissolved in methanol (7 ml), and catalytically hydrogenated at room temperature under 5 atmospheres on 10%-palladium carbon (50% wet, 75 mg), for 30 minutes. The catalyst was separated by filtration, the filtrate was concentrated under reduced pressure, the residue was dissolved in chloroform, washed with an aqueous saturated sodium hydrogencarbonate solution. The organic layer was washed with saturated brine, dried on anhydrous magnesium sulfate, concentrated under reduced pressure. The resulting residue was purified by silica gel column chromatography (chloroform:methanol=50:1) to obtain the entitled compound (48 mg, 53%) as a colorless solid.

mp: 175-178° C. MS (FAB) m/z: 419 (M+1)$^+$.

$^1$H-NMR (CDCl$_3$) δ: 1.44 (6H, s), 1.50-1.68 (1H, m), 1.90-2.00 (1H, m), 2.13 (6H, s), 2.19 (3H, s), 2.42-2.57 (1H, m), 2.98 (1H, t, J=9.2 Hz), 3.21-3.44 (4H, m), 3.83 (2H, brs), 7.06-7.12 (1H, m), 7.20-7.28 (m, overlapped with CHCl$_3$ peak), 7.32-7.7.43 (3H, m).

IR (diffuse reflectance spectroscopy): 2969, 2870, 2827, 2782, 2210, 1606, 1582, 1555, 1470, 1401 cm$^{-1}$.

Anal. Calcd for C$_{25}$H$_{30}$N$_4$O$_2$.0.25H$_2$O: C, 70.98; H, 7.27; N, 13.24. Found: C, 70.63; H, 7.23; N, 12.83.

Reference Example 67

2-tert-Butyl-7-fluoro-6-iodo-8-methoxy-5-methyl-benzo[b][1,3]oxazin-4-one (I-67)

A benzene (100 ml) suspension of 2-amino-4-fluoro-5-iodo-3-methoxy-6-methylbenzoic acid (I-30) (4.93 g, 15.2 mmol) was cooled at 0° C., pivaloyl chloride (4.67 ml, 37.9 mmol), pyridine (3.07 ml, 37.9 mmol) were put into it, followed by stirring at room temperature for 1.5 hours. Ethyl acetate (100 ml) was added to the reaction liquid, the organic layer was washed with 1 N hydrochloric acid (50 ml×3), saturated brine (50 ml), dried over anhydrous magnesium sulfate, then concentrated under reduced pressure. This was purified by silica gel column chromatography (n-hexane:ethyl acetate=4:1) to obtain the entitled compound (5.40 g, 91%) as a yellow ocher white solid.

MS (FAB) m/z: 392 (M+1)$^+$.

$^1$H-NMR (CDCl$_3$) δ: 1.41 (9H, s), 2.99 (3H, s), 4.09 (3H, s).

Reference Example 68

2-(2,2-Dimethylpropionylamino)-4-fluoro-5-iodo-3-methoxy-6-methylbenzamide (I-68)

N,N-Dimethylformamide (64 ml), ammonium acetate (4.38 g, 56.9 mmol) were added to 2-tert-butyl-7-fluoro-6-iodo-8-methoxy-5-methylbenzo[b][1,3]oxazin-4-one (I-67) (4.45 g, 11.4 mmol), followed by stirring at room temperature for 15 minutes and stirring at 50° C. for 1 hour. Ethyl acetate (600 ml) was added to the reaction liquid, the organic layer was washed with saturated brine (300 ml×3), then dried over anhydrous magnesium sulfate, concentrated under reduced pressure. This was suspended and washed in n-hexane:ethyl acetate=4:1 (100 ml) to obtain the entitled compound (4.06 g, 87%) as a colorless solid.

MS (FAB) m/z: 409 (M+1)$^+$.

$^1$H-NMR (DMSO-d$_6$) δ: 1.18 (9H, s), 2.34 (3H, s), 3.71 (3H, s), 7.21 (1H, brs), 7.61 (1H, brs), 8.80 (1H, brs).

Reference Example 69

N-(2-Cyano-5-fluoro-4-iodo-6-methoxy-3-methylphenyl)-2,2-dimethylpropionamide (I-69)

4-Dimethylaminopyridine (149 mg, 1.22 mmol) was added to a pyridine (100 ml) suspension of 2-(2,2-dimethylpropionylamino)-4-fluoro-5-iodo-3-methoxy-6-methylbenzamide (I-68) (4.97 g, 1.22 mmol), and cooled at 0° C. Trifluoromethanesulfonic acid anhydride (6.17 ml, 36.5 mmol) was dropwise added to it, followed by stirring at room temperature for 1 hour, then ethyl acetate (400 ml) was put thereinto. The organic layer was washed with 1 N hydrochloric acid (300 ml×5), saturated brine (300 ml×2), then dried over anhydrous magnesium sulfate, concentrated under reduced pressure, the residue was purified by silica gel column chromatography (n-hexane:ethyl acetate=5:1) to obtain the entitled compound (4.47 g, 94%) as a pale yellow solid.

MS (FAB) m/z: 391 (M+1)$^+$.

$^1$H-NMR (CDCl$_3$) δ: 1.37 (9H, s), 2.69 (3H, s), 3.93 (3H, d, J=2.1 Hz), 7.33 (1H, brs).

Reference Example 70

N-(5-Cyano-2-fluoro-3-methoxy-6-methylbiphenyl-4-yl)-2,2-dimethylpropionamide (I-70)

Tetrakis(triphenylphosphine)palladium(0) (1.45 g, 1.26 mmol) was added to an N,N-dimethylformamide (50 ml) suspension of N-(2-cyano-5-fluoro-4-iodo-6-methoxy-3-methylphenyl)-2,2-dimethylpropionamide (I-69) (2.45 g, 6.28 mmol), phenylboronic acid (1.15 g, 9.42 mmol), potassium phosphate n-hydrate (74-78%, 3.60 g, 12.6 mmol), followed by stirring at 95° C. for 2 hours. The reaction liquid was cooled, then ethyl acetate (200 ml) was added, followed by washing with saturated brine (50 ml×3), drying over anhydrous magnesium sulfate, concentration under reduced pressure. The residue was purified twice by silica gel column chromatography (chloroform), (n-hexane:ethyl acetate=4:1) to obtain the entitled compound (2.06 g, 96%) as a yellow solid.

MS (FAB) m/z: 341 (M+1)$^+$.

$^1$H-NMR (CDCl$_3$) δ: 1.40 (9H, s), 2.30 (3H, s), 3.92 (3H, d, J=1.8 Hz), 7.18-7.25 (2H, m), 7.38-7.52 (4H, m).

Reference Example 71

N-(5-Cyano-2-fluoro-3-hydroxy-6-methylbiphenyl-4-yl)-2,2-dimethylpropionamide (I-71)

A dichloromethane (60 ml) solution of N-(5-cyano-2-fluoro-3-methoxy-6-methylbiphenyl-4-yl)-2,2-dimethylpropionamide (I-70) (2.02 g, 5.93 mmol) was cooled at –78° C., a dichloromethane solution of 1 N tribromoborane (17.8 ml, 17.8 mmol) was dropwise added, followed by stirring at –78° C. for 15 minutes. Afterwards, this was heated up to –12° C., and stirred for 30 minutes. The reaction liquid was put into cold water (100 ml), saturated brine (50 ml) was added, the intended product was extracted with ethyl acetate (300 ml×2). The organic layer was dried over anhydrous magnesium sulfate, concentrated under reduced pressure, the residue was purified by silica gel column chromatography (n-hexane: ethyl acetate=5:1) to obtain the entitled compound (1.70 g, 88%) as a yellow solid.

MS (FAB) m/z: 327 (M+1)$^+$.

$^1$H-NMR (CDCl$_3$) δ: 1.44 (9H, s), 2.28 (3H, s), 7.17-7.24 (2H, m), 7.38-7.52 (3H, m), 8.08 (1H, brs), 9.53 (1H, s).

Reference Example 72

2-tert-Butyl-7-fluoro-5-methyl-6-phenyl-1,3-benzoxazole-4-carbonitrile (I-72)

Toluene (67 ml), p-toluenesulfonic acid monohydrate (98 mg, 515 μmol) were added to N-(5-cyano-2-fluoro-3-hydroxy-6-methylbiphenyl-4-yl)-2,2-dimethylpropionamide (I-73) (1.68 g, 5.15 mmol), followed by refluxing with a Dean-Stark condenser for 4 hours. After cooling, saturated sodium bicarbonate water (50 ml) was added to the reaction liquid, the product was extracted with ethyl acetate (200 ml).

The organic layer was washed with saturated brine (50 ml×2), then dried over anhydrous magnesium sulfate, concentrated under reduced pressure, the residue was purified by silica gel column chromatography (n-hexane:ethyl acetate=6:1) to obtain the entitled compound (1.44 g, 91%) as a colorless solid.

MS (FAB) m/z: 309 (M+1)$^+$.

$^1$H-NMR (CDCl$_3$) δ: 1.54 (9H, s), 2.41 (3H, s), 7.22-7.28 (2H, m), 7.42-7.55 (3H, m).

Reference Example 73

2-tert-Butyl-5-methyl-7-(3-methylaminoazetidin-1-yl)-6-phenyl-1,3-benzoxazole-4-carbonitrile (I-73)

Triethylamine (316 µl, 2.27 mmol) and 3-methylaminoazetidine hydrochloride trifluoroacetate (140 mg, 590 µmol) were added to a dimethyl sulfoxide (3.5 ml) solution of 2-tert-butyl-7-fluoro-5-methyl-6-phenyl-1,3-benzoxazole-4-carbonitrile (I-72) (140 mg, 454 µmol), followed by stirring overnight at 90° C., then 3-methylaminoazetidine hydrochloride trifluoroacetate (53.7 mg, 227 µmol) and triethylamine (63.3 µl, 454 µmol) were added, followed by stirring at 90° C. for 8 hours. After cooling, saturated sodium bicarbonate water and saturated brine were added to the reaction liquid, and this was extracted with ethyl acetate and chloroform. The organic layers were combined, dried over anhydrous magnesium sulfate, concentrated under reduced pressure. The resulting residue was purified by silica gel column chromatography (chloroform:methanol=100:1) to obtain the entitled compound (118 mg, 69%) as a pale yellow solid.

MS (FAB) m/z: 375 (M+1)$^+$.

$^1$H-NMR (CDCl$_3$) δ: 1.48 (10H, s), 2.16 (3H, s), 2.29 (3H, s), 3.33-3.41 (1H, m), 3.53 (2H, dd, J=4.5, 9.3 Hz), 3.90 (2H, dd, J=7.2, 9.3 Hz), 7.16-7.21 (2H, m), 7.34-7.43 (3H, m).

Example 15

2-Tert-butyl-5-methyl-7-(3-dimethylaminoazetidin-1-yl)-6-phenyl-1,3-benzoxazole-4-carbonitrile (#15)

Aqueous 36% formaldehyde solution (205 µl, 2.75 mmol) was added to a methanol (4 ml) solution of 2-tert-butyl-5-methyl-7-(3-methylaminoazetidin-1-yl)-6-phenyl-1,3-benzoxazole-4-carbonitrile (I-73) (103 mg, 275 µmol), followed by cooling at 0° C. Sodium cyanoborohydride (34.6 mg, 550 µmol) and acetic acid (40.9 µl, 715 µmol) were added, followed by stirring at room temperature for 20 minutes. Aqueous 10% sodium carbonate solution and saturated brine were added to the reaction liquid, and this was extracted with ethyl acetate and chloroform. The organic layers were combined, dried over anhydrous magnesium sulfate, concentrated under reduced pressure. The resulting residue was purified by silica gel column chromatography (chloroform:methanol=200:1), again purified by silica gel column chromatography (dichloromethane:ethyl acetate=1:1) to obtain the entitled compound (94 mg, 88%) as a colorless solid.

mp: 211-212° C. MS (FAB) m/z: 389 (M+1)$^+$.

$^1$H-NMR (CDCl$_3$) δ: 1.48 (9H, s), 2.04 (6H, s), 2.16 (3H, s), 2.82-2.91 (1H, m), 3.64-3.76 (4H, m), 7.16-7.22 (2H, m), 7.35-7.45 (3H, m).

IR (diffuse reflectance spectroscopy): 2971, 2210, 1614, 1486, 1371 cm$^{-1}$.

Anal. Calcd for C$_{23}$H$_{28}$N$_4$O.0.5H$_2$O: C, 72.52; H, 7.37; N, 14.09. Found: C, 72.78; H, 6.85; N, 13.96.

Reference Example 74

7-[(3S)-3-Benzyloxycarbonylaminopiperidin-1-yl]-2-tert-butyl-5-methyl-6-phenyl-1,3-benzoxazole-4-carbonitrile (I-74)

Triethylamine (83 µl, 598 µmol) and (3S)-3-benzyloxycarbonylaminopiperidine (70 mg, 298 µmol) were added to a dimethyl sulfoxide (3.8 ml) solution of 2-tert-butyl-7-fluoro-5-methyl-6-phenyl-1,3-benzoxazole-4-carbonitrile (I-72) (77 mg, 249 µmol), followed by stirring at 90° C. for 11 hours. After cooling, the reaction liquid was diluted with ethyl acetate, this was washed with saturated brine and 1 N hydrochloric acid. The organic layer was dried over anhydrous magnesium sulfate, concentrated under reduced pressure. The resulting residue was purified by silica gel column chromatography (n-hexane:ethyl acetate=8:1→4:1, v/v) to obtain the entitled compound (98 mg, 75%) as a colorless oil.

$^1$H-NMR (CDCl$_3$) δ: 1.14-1.38 (3H, m), 1.50 (9H, s), 2.88 (3H, s), 2.85-3.05 (3H, m), 3.22-3.35 (1H, m), 3.66-3.80 (1H, m), 4.78-4.89 (1H, m), 4.99-5.14 (2H, m), 7.07-7.19 (2H, m), 7.29-7.50 (7H, m).

Example 16

2-tert-Butyl-5-methyl-7-[(3S)-3-(dimethylamino)piperidin-1-yl]-7-phenyl-1,3-benzoxazole-4-carbonitrile (#16)

A methanol (5 ml) solution of 7-[(3S)-3-benzyloxycarbonylaminopiperidin-1-yl]-2-tert-butyl-5-methyl-6-phenyl-1,3-benzoxazole-4-carbonitrile (I-74) (90 mg, 172 µmol) was catalytically hydrogenated at room temperature under normal pressure for 1.5 hours, on 5% palladium-carbon (50% wet, 35 mg). The catalyst was separated by filtration, then the filtrate was concentrated under reduced pressure, the residue was dissolved in methanol (1.85 ml). Aqueous 36% formaldehyde solution (143 µl, 1.72 mmol), sodium cyanoborohydride (33 mg, 516 µmol) and acetic acid (35.4 µl, 619 µmol) were added to it, followed by stirring at room temperature for 4 hours. Further, aqueous 36% formaldehyde solution (286 µl, 3.44 mmol), sodium cyanoborohydride (66 mg, 1.03 mmol) and acetic acid (70 µl, 1.24 mmol) were added, followed by stirring at room temperature for 6 hours. Aqueous 10% sodium carbonate solution was added to the reaction liquid, followed by extraction with ethyl acetate. The organic layer was washed with saturated brine, dried over anhydrous magnesium sulfate, concentrated under reduced pressure. The resulting residue was purified by silica gel column chromatography (chloroform:methanol=100:1→50:1) to obtain the entitled compound (54 mg, 76%) as a pale brown oil.

MS (FAB) m/z: 417 (M+1)$^+$.

$^1$H-NMR (CDCl$_3$) δ: 1.05-1.40 (2H, m), 1.51 (9H, s), 1.71-1.94 (2H, m), 2.09 (6H, s), 2.29 (3H, s), 2.60 (1H, t, J=11 Hz), 2.75-2.90 (1H, m), 3.15-3.28 (1H, m), 3.36-3.47 (1H, m), 7.18-7.232 (2H, m), 7.32-7.38 (1H, m), 7.40-7.48 (2H, m).

IR (diffuse reflectance spectroscopy): 2974, 2933, 2220, 1610, 1588, 1560, 1464, 1399 cm$^{-1}$.

Reference Example 75

2-Amino-5-bromo-4-fluoro-3-hydroxy-6-methylbenzonitrile (I-75)

2-Amino-5-bromo-4-fluoro-3-methoxy-6-methylbenzonitrile (I-45) (8.63 g, 33.30 mmol) was dissolved in methylene chloride (270 ml), and at −20° C., boron tribromide (1 M methylene chloride solution, 100 ml, 100.00 mmol) was gradually dropwise added. With gradually heating, this was stirred at room temperature for 15 hours. After the reaction, water with ice was added, followed by neutralization to pH of 7 with an aqueous saturated sodium hydrogencarbonate solution. Adding methylene chloride for fractionation was tried, but resulted in suspension, and therefore, this was dissolved in ethyl acetate, washed with saturated brine. The obtained organic layer was dried over anhydrous sodium sulfate, the solvent was evaporated away under reduced pressure. The resulting residue was recrystallized and purified with n-hexane/methylene chloride to obtain the entitled compound (7.86 g, 96%) as a pale brown solid.

MS (ESI) m/z; 245 (M+1)$^+$.

$^1$H-NMR (CD$_3$OD) δ: 2.43 (3H, s).

Reference Example 76

2-Amino-5-bromo-3-cyano-6-fluoro-4-methylphenyl acetate (I-76)

2-Amino-5-bromo-4-fluoro-3-hydroxy-6-methylbenzonitrile (I-75) (7.86 g, 32.08 mmol) and diisopropylethylamine (19.5 ml, 112.2 mmol) were dissolved in ethyl acetate (300 ml), and at 0° C., cyclopropanecarbonyl chloride (4.4 ml, 48.12 mmol) was dropwise added, followed by stirring at room temperature for 16 hours under nitrogen atmosphere. After the reaction, ethyl acetate was added to the reaction liquid, followed by washing with water and saturated brine. The organic layer was concentrated under reduced pressure, the resulting residue was recrystallized with diisopropyl ether/ethyl acetate to obtain the entitled compound (8.96 g, 89%) as a white solid.

MS (ESI) m/z: 313, 315 (M+1)$^+$.

$^1$H-NMR (CDCl$_3$) δ: 1.11-1.16 (2H, m), 1.21-1.26 (2H, m), 1.90-1.94 (1H, m), 2.55 (3H, s), 4.55 (2H, s).

Reference Example 77

6-Bromo-2-cyclopropyl-7-fluoro-5-methyl-1,3-benzoxazole-4-carbonitrile (I-77)

2-Amino-5-bromo-3-cyano-6-fluoro-4-methylphenyl acetate (I-76) (7.95 g, 25.38 mmol) was dissolved in toluene (80 ml), p-toluenesulfonic acid monohydrate (1.60 g, 20 wt. %) was added, followed by stirring under reflux for 19 hours.

After cooling to room temperature, this was diluted with ethyl acetate, and the insoluble matter was collected by filtration. The filtrate was concentrated under reduced pressure, the resulting residue and the collected insoluble matter were recrystallized and purified with ethyl acetate to obtain the entitled compound (6.02 g, 80%) as a red white solid.

MS (ESI) m/z: 295, 297 (M+1)$^+$.

$^1$H-NMR (CDCl$_3$) δ: 1.27-1.34 (2H, m), 1.38-1.42 (2H, m), 2.25-2.32 (1H, m), 2.73 (3H, s).

Example 17

6-Bromo-2-cyclopropyl-7-[(3S)-3-(dimethylamino) pyrrolidin-1-yl]-5-methyl-1,3-benzoxazole-4-carbonitrile (#17)

(3S)-3-(Dimethylamino)pyrrolidine (157 µl, 1.24 mmol) and triethylamine (348 µl, 2.50 mmol), were added to a dimethyl sulfoxide (5 ml) solution of 6-bromo-2-cyclopropyl-7-fluoro-5-methyl-1,3-benzoxazole-4-carbonitrile (I-77) (304 mg, 1.03 mmol). The system was purged with nitrogen and then sealed up and heated at 90° C. for 2 hours. After cooling, the solvent was evaporated away under reduced pressure, then the resulting residue was dissolved in chloroform, washed with water and saturated brine. The organic layer was dried over anhydrous sodium sulfate, then the solvent was evaporated away under reduced pressure, the resulting residue was washed with a mixed solvent of isopropyl ether and ethanol. The crystal was collected by filtration to obtain the entitled compound (106 mg, 26%) as a colorless solid.

mp: 82-86° C. MS (EI) m/z: 389 (M$^+$).

$^1$H-NMR (CDCl$_3$) δ: 1.20-1.38 (4H, m), 1.90-2.03 (1H, m), 2.19-2.30 (2H, m), 2.38 (6H, s), 2.69 (3H, s), 2.88-3.02 (1H, m), 3.63-3.72 (2H, m), 3.84-3.88 (1H, m), 3.96 (1H, q, J=9.2 Hz).

IR (ATR): 2222, 1581, 1562, 1468, 1383, 1363, 1325, 1279, 1213 cm$^{-1}$.

Anal. Calcd for C$_{18}$H$_{21}$BrN$_4$O.0.5H$_2$O: C, 54.28; H, 5.57; N, 14.07. Found: C, 54.25; H, 5.44; N, 13.99.

Example 18

2-Cyclopropyl-7-[(3S)-3-(dimethylamino)pyrrolidin-1-yl]-6-(2-furyl)-5-methyl-1,3-benzoxazole-4-carbonitrile (#18)

6-Bromo-2-cyclopropyl-7-fluoro-5-methyl-1,3-benzoxazole-4-carbonitrile (I-77) (100 mg, 0.34 mmol) was dissolved in benzene (3 ml), then 2-tributylstannylfuran (117 µl, 0.37 mmol) and 2,6-di-tert-butylcresol (1 mg) and bis(triphenylphosphine)palladium(II) dichloride (3 mg, 0.003 mmol) were added, followed by hearing under reflux for 20 hours under nitrogen atmosphere. The reaction liquid was cooled, the insoluble matter was separated by filtration through Celite, the solvent was concentrated under reduced pressure. The resulting residue was fractionated with ethyl acetate and water, followed by washing with saturated brine. The obtained organic layer was dried over anhydrous sodium sulfate, the solvent was evaporated away under reduced pressure. The resulting residue was dissolved in methylene chloride, potassium fluoride (20 mg) and water (0.1 ml) were added, followed by vigorously stirring at room temperature for 30 hours. The insoluble matter was separated by filtration through Celite, followed by fractionation with methylene chloride and water and by washing with saturated brine. The obtained organic layer was dried over anhydrous sodium sulfate, the solvent was evaporated away under reduced pressure. The resulting residue was subjected to preparative silica gel column chromatography, eluted with a mixed solvent of n-hexane/ethyl acetate (3:1, v/v) to obtain 2-cyclopropyl-7-fluoro-6-(2-furyl)-5-methyl-1,3-benzoxazole-4-carbonitrile (96 mg) as a white solid. This was dissolved in dimethyl sulfoxide (2 ml), triethylamine (119 µl, 0.85 mmol) and (3S)-3-(dimethylamino)pyrrolidine (56 µl, 0.44 mmol) were added, followed by stirring at 90° C. under nitrogen atmosphere for 22 hours. After cooling to room temperature, ethyl acetate was added, followed by fractionation with water. The organic layer was washed with saturated brine, and dried over anhydrous sodium sulfate. The solvent was evaporated away, the resulting residue was subjected to preparative thin-layer silica gel column chromatography and eluted with a mixed solvent of chloroform/methanol (20:1, v/v) to obtain the entitled compound (37 mg, 29%) as a white solid.

mp: 158-159° C. MS (ESI) m/z: 377 (M+1)$^+$.

$^1$H-NMR (DMSO-d$_6$) δ: 1.12-1.26 (4H, m), 1.64-1.75 (1H, m), 2.02-2.07 (1H, m), 2.20 (6H, s), 2.22 (3H, s), 2.20-2.25 (1H, m), 2.55-2.57 (1H, m), 3.05 (1H, t, J=9.4 Hz), 3.38 (1H, dd, J=7.3, 10.3 Hz), 3.46 (1H, td, J=5.9, 10.7 Hz), 3.56 (1H, dd, J=8.8, 10.3 Hz), 6.23 (1H, d, J=3.2 Hz), 6.48 (1H, dd, J=2.0, 3.2 Hz), 7.53 (1H, s).

IR (ATR): 2208, 1606, 1583, 1473, 1149 cm$^{-1}$.

Anal. Calcd for $C_{22}H_{24}N_4O_2$: C, 70.19; H, 6.43; N, 14.88. Found: C, 69.99; H, 6.24; N, 14.28.

Example 19

2-Cyclopropyl-7-[(3S)-3-(dimethylamino)pyrrolidin-1-yl]-5-methyl-6-(1,3-thiazol-2-yl)-1,3-benzoxazole-4-carbonitrile (#19)

6-Bromo-2-cyclopropyl-7-fluoro-5-methyl-1,3-benzoxazole-4-carbonitrile (I-77) (100 mg, 0.34 mmol) was dissolved in benzene (3 ml), then 2-tributylstannylthiazole (140 μl, 0.37 mmol) and 2,6-di-tert-butylcresol (1 mg) and bis(triphenylphosphine)palladium(II) dichloride (3 mg, 0.003 mmol) were added, followed by heating under reflux for 20 hours under nitrogen atmosphere. The reaction liquid was cooled, the insoluble matter was separated by filtration through Celite, the solvent was concentrated under reduced pressure. The resulting residue was fractionated with ethyl acetate and water, followed by washing with saturated brine. The obtained organic layer was dried over anhydrous sodium sulfate, the solvent was evaporated away under reduced pressure. The resulting residue was dissolved in methylene chloride, potassium fluoride (20 mg) and water (0.1 ml) were added, followed by vigorously stirring at room temperature for 30 hours. The insoluble matter was separated by filtration through Celite, followed by fractionation with methylene chloride and water and by washing with saturated brine. The obtained organic layer was dried over anhydrous sodium sulfate, the solvent was evaporated away under reduced pressure. The resulting residue was subjected to preparative silica gel column chromatography, eluted with a mixed solvent of n-hexane/ethyl acetate (3:1, v/v) to obtain 2-cyclopropyl-7-fluoro-5-methyl-6-(1,3-thiazol-2-yl)-1,3-benzoxazole-4-carbonitrile (31 mg, 0.11 mmol, 31%) as a white solid. This was dissolved in dimethyl sulfoxide (0.7 ml), triethylamine (37 μl, 0.26 mmol) and (3S)-3-(dimethylamino)pyrrolidine (17 μl, 0.14 mmol) were added, followed by stirring at 90° C. under nitrogen atmosphere for 22 hours. After cooling to room temperature, ethyl acetate was added, followed by fractionation with water. The organic layer was washed with saturated brine, and dried over anhydrous sodium sulfate. The solvent was evaporated away, the resulting residue was subjected to preparative thin-layer silica gel column chromatography and eluted with a mixed solvent of chloroform/methanol (20:1, v/v) to obtain the entitled compound (13 mg, 32%) as a white solid.

MS (ESI) m/z: 395 (M+1)$^+$.

$^1$H-NMR (DMSO-d$_6$) δ: 1.19-1.30 (4H, m), 1.63-1.71 (1H, m), 1.98-2.04 (1H, m), 2.17 (6H, s), 2.23 (3H, d, J=2.4 Hz), 2.21-2.26 (1H, m), 2.54 (1H, brs), 2.89 (1H, t, J=9.0 Hz), 3.35-3.42 (1H, m), 3.49 (1H, dd, J=7.3, 9.3 Hz), 3.56 (1H, dd, J=8.3, 9.8 Hz), 7.52 (1H, dd, J=2.4, 3.4 Hz), 7.93 (1H, dd, J=2.4, 3.4 Hz).

IR (ATR): 2206, 1589, 1554, 1468, 1389 cm$^{-1}$.

Anal. Calcd. for $C_{21}H_{23}N_5OS$: C, 64.10; H, 5.89; N, 17.80; S, 8.15. Found: C, 63.85; H, 5.88; N, 17.74; S, 8.33.

Example 20

2-Cyclopropyl-7-[(3S)-3-(dimethylamino)pyrrolidin-1-yl]-5-methyl-6-(pyridin-2-yl)-1,3-benzoxazole-4-carbonitrile (#20)

6-Bromo-2-cyclopropyl-7-fluoro-5-methyl-1,3-benzoxazole-4-carbonitrile (I-77) (200 mg, 0.68 mmol) was dissolved in toluene (4 ml), then 2-tributylstannylpyridine (299 mg, 0.81 mmol) and 2,6-di-tert-butylcresol (2 mg) and bis(triphenylphosphine)palladium(II) dichloride (24 mg, 0.03 mmol) were added, followed by heating under reflux for 17 hours under nitrogen atmosphere. The reaction liquid was cooled, the insoluble matter was separated by filtration through Celite, the solvent was concentrated under reduced pressure. The resulting residue was subjected to silica gel column chromatography, followed by removing tin-derived side products with n-hexane and by elution with a mixed solvent of n-hexane/ethyl acetate (5:1-3:1, v/v) to obtain 2-cyclopropyl-7-fluoro-5-methyl-6-(2-pyridyl)-1,3-benzoxazole-4-carbonitrile (184 mg, 0.63 mmol, 92%) as a pale yellow transparent oily substance, A part of this (183 mg, 0.62 mmol) was dissolved in dimethyl sulfoxide (3.7 ml), triethylamine (219 μl, 1.56 mmol) and (3S)-3-(dimethylamino)pyrrolidine (103 μl, 0.81 mmol) were added, followed by stirring at 90° C. under nitrogen atmosphere for 15 hours. After cooling to room temperature, ethyl acetate was added, followed by fractionation with water. The organic layer was washed with saturated brine, and dried over anhydrous sodium sulfate. The solvent was evaporated away, the resulting residue was recrystallized and purified with a mixed solvent of diisopropyl ether/n-hexane/ethyl acetate to obtain the entitled compound (108 mg, 45%) as a pale brown solid.

mp: 150-151° C. MS (ESI) m/z: 388 (M+1)$^+$.

$^1$H-NMR (DMSO-d$_6$) δ: 1.12-1.31 (4H, m), 1.58-1.66 (1H, m), 1.95 (1H, brs), 2.12 (6H, s), 2.16 (3H, s), 2.19-2.30 (1H, m), 2.51 (1H, brs), 3.29-3.47 (3H, m), 7.27 (2H, ddd, J=0.7, 4.9, 7.3 Hz), 7.73 (1H, t, J=7.0 Hz), 8.71 (1H, d, J=4.2 Hz).

IR (ATR): 2204, 1583, 1473 cm$^{-1}$.

Anal. Calcd for $C_{23}H_{25}N_5O$: C, 71.29; H, 6.50; N, 18.07. Found: C, 71.26; H, 6.48; N, 17.98.

Example 21

2-Cyclopropyl-7-[(3S)-3-(dimethylamino)pyrrolidin-1-yl]-5-methyl-6-(pyrazin-2-yl)-1,3-benzoxazole-4-carbonitrile (#21)

6-Bromo-2-cyclopropyl-7-fluoro-5-methyl-1,3-benzoxazole-4-carbonitrile (I-77) (200 mg, 0.68 mmol) was dissolved in toluene (4 ml), then 2-tributylstannylpyrazine (300 mg, 0.81 mmol) and 2,6-di-tert-butylcresol (2 mg) and bis(triphenylphosphine)palladium(II) dichloride (24 mg, 0.03 mmol) were added, followed by heating under reflux for 15 hours under nitrogen atmosphere. The reaction liquid was cooled, the insoluble matter was separated by filtration through Celite, the solvent was concentrated under reduced pressure. The resulting residue was subjected to silica gel column chromatography, followed by removing tin-derived side products with n-hexane and by elution with a mixed solvent of n-hexane/ethyl acetate (3:1, v/v) to obtain 2-cyclopropyl-7-fluoro-5-methyl-6-(pyrazin-2-yl)-1,3-benzoxazole-4-carbonitrile (158 mg, 79%) as a yellow white solid. This was dissolved in dimethyl sulfoxide (3.2 ml), triethylamine (189 μl, 1.34 mmol) and (3S)-3-(dimethylamino)pyrrolidine (102 μl, 0.81 mmol) were added, followed by stirring at 90° C. under nitrogen atmosphere for 14 hours. After cooling to room temperature, ethyl acetate was added, followed by fractionation with water. The organic layer was washed with saturated brine, and dried over anhydrous sodium sulfate. The solvent was evaporated away, the resulting residue was subjected to silica gel column chromatography and eluted with a mixed solvent of chloroform/methanol (20:1, v/v) to obtain the entitled compound (121 mg, 58%) as a pale brown solid.

mp: 157-159° C. MS (ESI) m/z: 389 (M+1)$^+$.

$^1$H-NMR (DMSO-d$_6$) δ: 1.19-1.27 (4H, m), 1.50-1.60 (1H, m), 1.82-1.94 (1H, m), 2.01 (6H, s), 2.06 (3H, s), 2.28-2.36 (1H, m), 2.52-2.59 (1H, m), 2.69 (1H, dd, J=7.8, 9.0 Hz), 3.11-3.22 (2H, m), 3.26-3.34 (1H, m), 8.63 (2H, d, J=2.7 Hz), 8.75 (1H, dd, J=1.5, 2.4 Hz).

IR (ATR): 2206, 1606, 1591, 1469 cm$^{-1}$.

Anal. Calcd for C$_{22}$H$_{24}$N$_6$O: C, 68.02; H, 6.23; N, 21.63. Found: C, 67.74; H, 6.20; N, 21.46.

Example 22

2-Cyclopropyl-7-[(3S)-3-(dimethylamino)pyrrolidin-1-yl]-5-methyl-6-(1-methyl-1H-pyrrol-2-yl)-1,3-benzoxazole-4-carbonitrile (#22)

6-Bromo-2-cyclopropyl-7-fluoro-5-methyl-1,3-benzoxazole-4-carbonitrile (I-77) (200 mg, 0.68 mmol) was dissolved in toluene (4 ml), then 2-tributylstannyl-1-methylpyrrole (300 mg, 0.81 mmol) and 2,6-di-tert-butylcresol (2 mg) and bis(triphenylphosphine)palladium(II) dichloride (24 mg, 0.03 mmol) were added, followed by heating under reflux for 19 hours under nitrogen atmosphere. The reaction liquid was cooled, the insoluble matter was separated by filtration through Celite, the solvent was concentrated under reduced pressure. The resulting residue was subjected to silica gel column chromatography, followed by removing tin-derived side products with n-hexane and by elution with a mixed solvent of n-hexane/ethyl acetate (10:1, v/v) to obtain 2-cyclopropyl-7-fluoro-5-methyl-6-(1-methyl-1H-pyrrol-2-yl)-1,3-benzoxazole-4-carbonitrile (158 mg, 79%) as a pale yellow transparent oily substance. Apart of this (157 mg, 0.53 mmol) was dissolved in dimethyl sulfoxide (3 ml), triethylamine (187 μl, 1.33 mmol) and (3S)-3-(dimethylamino)pyrrolidine (101 μl, 0.80 mmol) were added, followed by stirring at 90° C. under nitrogen atmosphere for 13 hours. After cooling to room temperature, ethyl acetate was added, followed by fractionation with water. The organic layer was washed with saturated brine, and dried over anhydrous sodium sulfate. The solvent was evaporated away, the resulting residue was subjected to silica gel column chromatography and eluted with a mixed solvent of chloroform/methanol (20:1, v/v). The resulting residue was recrystallized and purified with a mixed solvent of diethyl ether-n to obtain the entitled compound (104 mg, 50%) as a white solid.

mp: 127-128° C. MS (ESI) m/z: 390 (M+1)$^+$.

$^1$H-NMR (DMSO-d$_6$) δ: 1.15-1.24 (4H, m), 1.53-1.62 (1H, m), 2.05 (1H, s), 2.06 (3H, s), 2.07 (3H, s), 2.12 (1H, s), 2.26-2.33 (1H, m), 2.65 (0.5H, dd, J=7.8, 10.0 Hz), 2.95 (0.5H, dd, J=7.8, 10.2 Hz), 3.07-3.12 (1H, m), 3.21 (1.5H, s), 3.28 (1.5H, s), 3.31-3.40 (1H, m), 3.49-3.56 (0.5H, m), 5.87 (0.5H, dd, J=2.0, 3.7 Hz), 5.95 (0.5H, dd, J=2.0, 3.7 Hz), 6.08 (0.5H, t, J=2.9 Hz), 6.10 (0.5H, t, J=2.9 Hz), 6.81 (0.5H, dd, J=2.2, 2.7 Hz), 6.85 (5H, t, J=1.7, 2.4 Hz).

IR (ATR): 2206, 1608, 1468 cm$^{-1}$.

Anal. Calcd for C$_{23}$H$_{27}$N$_5$O: C, 70.92; H, 6.99; N, 17.98. Found: C, 70.80; H, 7.00; N, 17.95.

Reference Example 78

2-Cyclopropyl-6-[1-(ethoxy)ethenyl]-7-fluoro-5-methyl-1,3-benzoxazole-4-carbonitrile (I-78)

6-Bromo-2-cyclopropyl-7-fluoro-5-methyl-1,3-benzoxazole-4-carbonitrile (I-77) (8.88 g, 30.08 mmol) was dissolved in toluene (130 ml), then tributyl(1-ethoxyvinyl)tin (11.2 ml, 33.09 mmol) and 2,6-di-tert-butylcresol (66 mg, 0.30 mmol) and bis(triphenylphosphine)palladium(II) dichloride (1.06 g, 1.50 mmol) were added, followed by heating under reflux for 17 hours under nitrogen atmosphere. The reaction liquid was cooled, the insoluble matter was separated by filtration through Celite, the solvent was concentrated under reduced pressure. The resulting residue was subjected to silica gel column chromatography, followed by removing tin-derived side products with n-hexane and by elution with a mixed solvent of n-hexane/ethyl acetate (7:1, v/v) to obtain the a crude product (9.34 g, quant.) as a yellow white solid.

MS (ESI) m/z: 287 (M+1)$^+$.

Reference Example 79

6-(2-Bromoacetyl)-2-cyclopropyl-7-fluoro-5-methyl-1,3-benzoxazole-4-carbonitrile (I-79)

2-Cyclopropyl-6-[1-(ethoxy)ethenyl]-7-fluoro-5-methyl-1,3-benzoxazole-4-carbonitrile (I-78) (9.34 g, 30.1 mmol) was dissolved in tetrahydrofuran (450 ml), then water (27 ml) and N-bromosuccinimide (5.73 g, 31.58 mmol) were added all at a time, followed by stirring at room temperature for 45 minutes. After the reaction, the solvent was evaporated away under reduced pressure, followed by dilution with ethyl acetate and by washing with aqueous sodium thiosulfate solution and saturated brine. The obtained organic layer was dried over anhydrous sodium sulfate, the solvent was evaporated away under reduced pressure. The resulting residue was subjected to silica gel column chromatography and eluted with a mixed solvent of n-hexane/ethyl acetate (4:1, v/v) to obtain the intended product (9.63 g, 95%) as a white solid.

MS (ESI) m/z: 337, 339 (M+1)$^+$.

$^1$H-NMR (CDCl$_3$) δ: 1.37 (2H, m), 1.40-1.46 (2H, m), 2.29-2.35 (1H, m), 2.62 (3H, s), 4.34 (2H, d, J=1.2 Hz).

Reference Example 80

2-Cyclopropyl-7-fluoro-5-methyl-6-(2-methyl-1,3-thiazol-4-yl)-1,3-benzoxazole-4-carbonitrile (I-80)

6-(2-Bromoacetyl)-2-cyclopropyl-7-fluoro-5-methyl-1,3-benzoxazole-4-carbonitrile (I-79) (39.98 g, 28.6 mmol) was dissolved in toluene (270 ml), then cesium carbonate (13.02 g, 39.90 mmol) and thioacetamide (2.58 g, 34.28 mmol) were added, followed by stirring at 100° C. for 6 hours under nitrogen atmosphere. The reaction liquid was cooled, the insoluble matter was separated by filtration through Celite, ethyl acetate was added to the filtrate, followed by washing with water and saturated brine. The obtained organic layer was dried over anhydrous sodium sulfate, the solvent was evaporated away under reduced pressure. The resulting residue was recrystallized and purified with n-hexane/ethyl acetate to obtain the entitled compound (3.96 g, 44%) as a white solid.

MS (ESI) m/z; 314 (M+1)$^+$.

$^1$H-NMR (CDCl$_3$) δ: 1.26-1.32 (2H, m), 1.38-1.43 (2H, m), 2.27-2.34 (1H, m), 2.52 (3H, s), 2.80 (3H, s), 7.20 (1H, s).

Example 23

2-Cyclopropyl-7-[(3S)-3-(dimethylamino)pyrrolidin-1-yl]-5-methyl-6-(2-methyl-1,3-thiazol-4-yl)-1,3-benzoxazole-4-carbonitrile (#23)

2-Cyclopropyl-7-fluoro-5-methyl-6-(2-methyl-1,3-thiazol-4-yl)-1,3-benzoxazole-4-carbonitrile (I-80) (3.96 g, 12.65 mmol) was dissolved in dimethyl sulfoxide (40 ml), then triethylamine (4.27 ml, 30.36 mmol) and (3S)-3-(dimethylamino)pyrrolidine (1.93 ml, 15.18 mmol) were added, followed by stirring at 90° C. for 4 hours under nitrogen atmosphere. After cooling to room temperature, water was added, the precipitated solid was collected by filtration, recrystallized and purified with a mixed solvent of diethyl ether/ethyl acetate/methanol to obtain the entitled compound (3.16 g, 61%) as a white solid.

mp: 167-168° C. MS (ESI) m/z: 40.8 (M+1)$^+$.

$^1$H-NMR (DMSO-d$_6$) δ: 1.17-1.29 (4H, m), 1.61-1.71 (1H, m), 1.98-2.05 (1H, m), 2.18 (3H, s), 2.26 (6H, s), 2.20-2.26 (1H, m), 2.53 (1H, brs), 2.77 (3H, s), 2.92 (1H, t, J=9.3 Hz), 3.37-3.45 (2H, m), 3.49-3.55 (1H, m), 6.93 (1H, s).

IR (ATR): 2206, 1587, 1444 cm$^{-1}$.

Anal. Calcd for C$_{22}$H$_{25}$N$_5$OS: C, 64.84; H, 6.18; N, 17.18; S, 7.87. Found: C, 64.49; H, 6.07; N, 17.15; S, 8.12.

Example 24

2-Cyclopropyl-7-[(3S)-3-(methylamino)pyrrolidin-1-yl]-5-methyl-6-(2-methyl-1,3-thiazol-4-yl)-1,3-benzoxazole-4-carbonitrile (#24)

2-Cyclopropyl-7-fluoro-5-methyl-6-(2-methyl-1,3-thiazol-4-yl)-1,3-benzoxazole-4-carbonitrile (I-80) (100 mg, 0.32 mmol) was dissolved in dimethyl sulfoxide (2 ml), triethylamine (112 µl, 0.80 mmol) and (3S)-3-methylaminopyrrolidine (44 µl, 0.42 mmol) were added, followed by stirring at 90° C. for 6 hours under nitrogen atmosphere. After cooling to room temperature, ethyl acetate was added, followed by fractionation with water. The organic layer was washed with saturated brine, dried over anhydrous sodium sulfate. The solvent was evaporated away and the resulting residue was subjected to preparative thin-layer silica gel column chromatography, eluted with a mixed solvent of chloroform/methanol (10:1, v/v) followed by recrystallization and purification with a mixed solvent of diethyl ether/ethyl acetate/n-hexane to obtain the entitled compound (22 mg, 17%) as a white solid.

MS (ESI) m/z: 394 (M+1)$^+$.

$^1$H-NMR (DMSO-d$_6$) δ: 1.16-1.25 (4H, m), 1.55-1.63 (1H, m), 1.80-1.88 (1H, m), 2.07 (3H, s), 2.20 (3H, s), 2.25-2.33 (1H, m), 2.70 (3H, s), 2.91-3.04 (2H, m), 3.22-3.31 (2H, m), 3.35-3.42 (1H, m), 7.29 (1H, s).

IR (ATR): 2206, 1560, 1464, 1367 cm$^{-1}$.

Anal. Calcd for C$_{21}$H$_{23}$N$_5$OS.0.25H$_2$O: C, 63.37; H, 5.95; N, 17.60; S, 8.06. Found: C, 63.13; H, 5.79; N, 17.32; S, 8.08.

Example 25

2-Cyclopropyl-7-[3-(dimethylamino)-3-methylpyrrolidin-1-yl]-5-methyl-6-(2-methyl-1,3-triazol-4-yl)-1,3-benzoxazole-4-carbonitrile (#25)

1-Benzyloxycarbonyl-3-(N-tert-butoxycarbonylamino)-3-methylpyrrolidine (0.55 g, 1.64 mmol) was dissolved in dichloromethane (7 ml), 4 N hydrochloric acid-dioxane (7 ml) was added, followed by stirring at room temperature for 30 minutes. The solvent was evaporated away under reduced pressure, the resulting residue was dissolved in dichloromethane (15 ml), 37% formalin (2 ml) was added. With cooling with ice, sodium triacetoxyborohydride (1.08 g, 5.10 mmol) was added, followed by stirring at room temperature for 19 hours. This was diluted with dichloromethane, then washed with aqueous sodium hydroxide solution. After drying over anhydrous sodium sulfate, the solvent was evaporated away under reduced pressure, the resulting residue was purified by silica gel column chromatography (dichloromethane:methanol=30:1) to obtain a pale yellow oil. This was dissolved in methanol (10 ml), 1 N hydrochloric acid (2.70 ml, 2.70 mmol) and 10% palladium-carbon (containing about 50% water, 70.0 mg) were added, followed by stirring at room temperature for 19 hours under hydrogen atmosphere. The catalyst was removed by filtration, then the solvent was evaporated away under reduced pressure. This was dissolved in dimethyl sulfoxide (7 ml), 2-cyclopropyl-7-fluoro-5-methyl-6-(2-methyl-1,3-thiazol-4-yl)-1,3-benzoxazole-4-carbonitrile (I-80) (190 mg, 0.61 mmol), triethylamine (0.51 mg, 3.68 mmol) were added, then the mixture was stirred at 90° C. for 23 hours. After dilution with ethyl acetate, this was washed with water and dried over anhydrous sodium sulfate. The solvent was evaporated away under reduced pressure, the residue was purified by silica gel column chromatography (dichloromethane:methanol=40:1), a mixed solvent of ethanol and diisopropyl ether was added, the insoluble matter was separated by filtration to obtain the intended product (75.0 mg, 30%) as a pale yellow solid.

MS (EST) m/z: 422 (M+1)$^+$.

$^1$H-NMR (DMSO-d$_6$) δ: 0.94 (3H, s), 1.15-1.30 (4H, m), 1.70-1.90 (2H, m), 2.17 (6H, s), 2.20 (3H, s), 2.20-2.30 (1H, m), 2.77 (3H, s), 3.14 (2H, s), 3.30-3.40 (1H, m), 3.40-3.50 (1H, m), 6.93 (1H, s).

Anal. Calcd for C$_{23}$H$_{27}$N$_5$OS: C, 65.53; H, 6.46; N, 16.61; S, 7.61. Found: C, 65.18; H, 6.35; N, 16.38; S, 7.70.

Reference Example 81

N-(4-Acetyl-2-cyano-5-fluoro-6-hydroxy-3-methylphenyl)cyclopropanecarboxamide (I-81)

2-Cyclopropyl-6-[1-(ethoxy)ethenyl]-7-fluoro-5-methyl-1,3-benzoxazole-4-carbonitrile (I-78) (1.0 g, 3.49 mmol) was dissolved in tetrahydrofuran (10 ml), aqueous 1 N hydrochloric acid solution (2.0 ml) was added, followed by stirring at room temperature for 19 hours. At this point in time, it was known that a mixture with an oxazole-opened compound is given, and for complete ring opening, methanol (5 ml) was added followed by stirring overnight at room temperature. The solvent was concentrated under reduced pressure, ethyl acetate was added to the resulting residue, followed by fractionation with water.

The organic layer was washed with saturated brine, and dried over anhydrous sodium sulfate. The solvent was evaporated away under reduced pressure to obtain the entitled compound (927 mg, 96%) as a yellow white solid.

MS (ESI) m/z: 277 (M+1)⁺.
¹H-NMR (CDCl₃) δ: 1.08-1.13 (2H, m), 1.23-1.28 (2H, m), 1.76-1.82 (1H, m), 2.45 (3H, s), 2.56 (3H, d, J=3.2 Hz), 8.01 (1H, s), 9.76 (1H, s).

Reference Example 82

6-Acetyl-2-cyclopropyl-7-fluoro-5-methyl-1,3-benzoxazole-4-carbonitrile (I-82)

N-(4-Acetyl-2-cyano-5-fluoro-6-hydroxy-3-methylphenyl)cyclopropanecarboxamide (I-81) (200 mg, 0.72 mmol) was dissolved in toluene (4 ml), pyridinium p-toluenesulfonate (40 mg, 0.14 mmol) was, added, followed by heating under reflux for 21 hours. After cooling to room temperature, this was diluted with ethyl acetate, washed with water and saturated brine. The obtained organic layer was dried over anhydrous sodium sulfate, the solvent was evaporated away under reduced pressure. The resulting residue was subjected to silica gel column chromatography, eluted with a mixed solvent of n-hexane/ethyl acetate (3:1, v/V) to obtain the entitled compound (133 mg, 71%) as a white solid.
MS (ESI) m/z: 259 (M+1)⁺.
¹H-NMR (CDCl₃) δ: 1.26-1.44 (4H, m), 2.26-2.35 (1H, m), 2.59 (3H, s), 2.61 (3H, d, J=2.9 Hz).

Example 26

6-Acetyl-2-cyclopropyl-7-[(3S)-3-(dimethylamino)pyrrolidin-1-yl]-5-methyl-1,3-benzoxazole-4-carbonitrile (#26)

6-Acetyl-2-cyclopropyl-7-fluoro-5-methyl-1,3-benzoxazole-4-carbonitrile (I-82) (130 mg, 0.50 mmol) was dissolved in dimethyl sulfoxide (2.6 ml), triethylamine (177 µl, 1.26 mmol) and (3S)-3-(dimethylamino)pyrrolidine (96 µl, 0.76 mmol) were added, followed by stirring at 90° C. for 6 hours under nitrogen atmosphere. After cooling to room temperature, ethyl acetate was added, followed by fractionation with water. The organic layer was washed with saturated brine, dried over anhydrous sodium sulfate. The solvent was evaporated away and the resulting residue was subjected to preparative thin-layer silica gel column chromatography, eluted with a mixed solvent of chloroform/methanol (10:1, v/v) followed by recrystallization and purification with a mixed solvent of diethyl ether/ethyl acetate/n-hexane to obtain the entitled compound (103 mg, 57%) as a red white solid.
mp: 142° C. MS (ESI) m/z: 353 (M+1)⁺.
¹H-NMR (DMSO-d₆) δ: 1.16-1.26 (4H, m), 1.75-1.34 (1H, m), 2.04-2.12 (1H, m), 2.18 (6H, s), 2.31 (3H, s), 2.27-2.34 (1H, m), 2.45 (3H, s), 2.75-2.83 (1H, m), 3.42 (1H, dd, J=7.7, 9.6 Hz), 3.60-3.68 (3H, m).
IR (ATR): 2210, 1681, 1589 cm⁻¹.
Anal. Calcd for C₂₀H₂₄N₄O₂.0.25H₂O: C, 67.30; H, 6.92; N, 15.70. Found: C, 67.56; H, 6.81; N, 15.68.

Reference Example 83

6-Bromo-2-cyclopropyl-7-methoxy-5-methyl-1,3-benzoxazole-4-carbonitrile (I-83)

6-Bromo-2-cyclopropyl-7-fluoro-5-methyl-1,3-benzoxazole-4-carbonitrile (I-77) (4.88 g, 16.5 mmol) was suspended in a mixed solvent of methanol (30 ml) and N,N-dimethylformamide (50 ml), potassium carbonate (4.57 g, 33.0 mmol) was added, followed by stirring at 60° C. for 30 minutes. With cooling with ice, water was added, followed by extraction with ethyl acetate. The organic layer was washed with saturated brine, dried over anhydrous sodium sulfate, the solvent was evaporated away. The residue was suspended in a mixed solvent of methanol (30 ml) and N,N-dimethylformamide (50 ml), potassium carbonate (4.57 g, 33.0 mmol) was added, followed by again stirring at 60° C. for 14 hours. With cooling with ice, water was added, followed by extraction with ethyl acetate. The organic layer was washed with saturated brine, dried over anhydrous sodium sulfate, the solvent was evaporated away. The precipitated solid was washed with a mixed solvent of ethyl acetate/isopropyl ether and collected by filtration to obtain the entitled compound (2.599 g, 64%) as a colorless solid.
¹H-NMR (CDCl₃) δ: 1.20-4.37 (4H, m), 2.21-2.29 (1H, m), 2.69 (3H, s), 4.37 (3H, s).

Reference Example 84

2-Cyclopropyl-6-[1-(ethoxy)ethenyl]-7-methoxy-5-methyl-1,3-benzoxazole-4-carbonitrile (I-84)

6-Bromo-2-Cyclopropyl-7-methoxy-5-methyl-1,3-benzoxazole-4-carbonitrile (I-83) (2.60 g, 8.46 mmol) was dissolved in toluene (78 ml), tributyl(1-ethoxyvinyl)tin (3.43 ml, 10.15 mmol), 2,6-di-tert-butylcresol (19 mg, 0.09 mmol) and bis(triphenylphosphine)palladium(II) dichloride (297 mg, 0.42 mmol) were added, followed by heating under reflux for 22 hours under nitrogen atmosphere. The reaction liquid was cooled, the insoluble matter was separated by filtration through Celite, the solvent was concentrated under reduced pressure. The resulting residue was subjected to silica gel column chromatography, the tin-derived side products were removed with n-hexane, followed by elution with a mixed solvent of n-hexane/ethyl:acetate (10:1→5:1, v/v) to obtain a crude product of the entitled compound (2.58 g, quant.) as a yellow white solid.
MS (ESI) m/z: 299 (M+1)⁺.

Reference Example 85

6-(2-Bromoacetyl)-2-cyclopropyl-7-methoxy-5-methyl-1,3-benzoxazole-4-carbonitrile (I-85)

2-Cyclopropyl-6-[1-(ethoxy)ethenyl]-7-methoxy-5-methyl-1,3-benzoxazole-4-carbonitrile (I-84) (2.58 g, 8.46 mmol) was dissolved in tetrahydrofuran (130 ml), water (7.7 ml) and N-bromosuccinimide (1.61 g, 8.89 mmol) were added all at a time, followed by stirring at room temperature for 1.5 hours. After the reaction, the solvent was evaporated away under reduced pressure, followed by dilution with ethyl acetate and by washing with water and saturated brine. The obtained organic layer was dried over anhydrous sodium sulfate, the solvent was evaporated away under reduced pressure. The resulting residue was subjected to silica gel column chromatography (covering) and eluted with a mixed solvent of n-hexane/ethyl acetate (2:1, v/v) to obtain the entitled compound (2.40 g, 81%) as a yellow white solid.
MS (ESI) m/z: 319, 351 (M+1)⁺.
¹H-NMR (CDCl₃) δ: 1.27-1.39 (4H, m), 2.23-2.30 (1H, m), 2.50 (3H, s), 4.30 (2H, s), 4.33 (3H, s).

Reference Example 86

2-Cyclopropyl-7-methoxy-5-methyl-6-(2-methyl-1,
3-thiazol-carbonitrile (I-86)

6-(2-Bromoacetyl)-2-cyclopropyl-7-methoxy-5-methyl-1,3-benzoxazole-4-carbonitrile (I-85) (2.40 g, 6.88 mmol, 81%) was dissolved in toluene (48 ml) under nitrogen atmosphere, cesium carbonate (3.14 g, 9.64 mmol) and thioacetamide (621 mg, 8.26 mmol) were added, followed by stirring at 100° C. for 20 hours. The reaction liquid was cooled, the insoluble matter was separated by filtration through Celite, ethyl acetate was added to the filtrate, followed by washing with water and saturated brine. The obtained organic layer was dried over anhydrous sodium sulfate, the solvent was evaporated away under reduced pressure. The precipitated solid was collected by filtration, the filtrate was concentrated under reduced pressure. The resulting residue was subjected to silica gel column chromatography, eluted with a mixed solvent of n-hexane/ethyl acetate (2:1, v/v), combined with the collected solid, recrystallized and purified with n-hexane/ethyl acetate to obtain the entitled compound (1.44 g, 64%) as a pale brown solid.

MS (ESI) m/z: 326 (M+1)$^+$.

$^1$H-NMR (CDCl$_3$) δ: 1.23-1.29 (4H, m), 1.33-1.37 (2H, m), 2.23-2.30 (1H, m), 2.36 (3H, s), 2.78 (3H, s), 4.15 (3H, s), 7.03 (1H, s).

Reference Example 87

4-Cyano-2-cyclopropyl-5-methyl-6-(2-methyl-1,3-thiazol-4-yl)-1,3-b trifluoromethanesulfonate (I-87)

2-Cyclopropyl-7-methoxy-5-methyl-6-(2-methyl-1,3-thiazol-4-yl)-1,3-benzoxazole-4-carbonitrile (I-86) (1.44 g, 4.42 mmol) and sodium acetate (25 mg, 8.84 mmol) were dissolved in dimethylacetamide (15 ml), followed by stirring at 130° C. for 43 hours under nitrogen atmosphere.

After cooling to room temperature, this was diluted with ethyl acetate, and water was added for fractionation. The organic layer was washed with saturated brine, dried over anhydrous sodium sulfate, the solvent was evaporated away under reduced pressure. The resulting residue was recrystallized and purified with a mixed solvent of ethyl acetate/n-hexane to obtain a hydroxyl form (759 mg) as a pale brown solid. The obtained hydroxyl form and 4-(dimethylamino) pyridine (15 mg, 0.12 mmol) were dissolved in pyridine (15 ml), and under nitrogen atmosphere with cooling with ice, trifluoromethanesulfonic acid anhydride (1.23 ml, 7.31 mmol) was dropwise added, followed by stirring at room temperature for 16 hours. The reaction liquid was neutralized with diluted hydrochloric acid, extracted with ethyl acetate, the organic layer was washed with saturated brine. The obtained organic layer was dried over anhydrous sodium sulfate, the solvent was evaporated away under reduced pressure. The resulting residue was subjected to silica gel column chromatography, eluted with a mixed solvent of n-hexane/ethyl acetate (2:1, v/v) to obtain the entitled compound (994 mg, 51%) as a pale yellow solid.

MS (ESI) m/z: 444 (M+1)$^+$.

$^1$H-NMR (CDCl$_3$) δ: 1.31-1.41 (4H, m), 2.29-2.36 (1H, m), 2.52 (3H, s), 2.80 (6H, s), 7.25 (1H, s).

Reference Example 88 tert-Butyl 3-[4-cyano-2-cyclopropyl-5-methyl-6-(2-methyl-1,3-thiazol-4-yl)-1,3-benzoxazol-7-yl]-2-cyclopent-1-enylcarbamate (I-88)

Lithium chloride (256 mg, 6.05 mmol), 2,6-di-tert-butylcresol (4.4 mg, 0.02 mmol), tert-butyl (3-tributylstannyl)-2-cyclopent-1-enylcarbamate (1.90 g, 4.03 mmol) and bis(triphenylphosphine)palladium(II) dichloride (142 mg, 0.20 mmol) were added to a toluene solution (18 ml) of 4-cyano-2-cyclopropyl-5-methyl-6-(2-methyl-1,3-thiazol-4-yl)-1,3-benzoxazol-7-yl trifluoromethanesulfonate (I-87) (894 mg, 2.01 mmol), followed by heating under reflux for 17 hours under nitrogen atmosphere. The reaction liquid was restored to room temperature, the insoluble matter was separated by filtration through Celite. The obtained filtrate was diluted with ethyl acetate, washed with water and saturated brine.

The organic layer was dried over anhydrous sodium sulfate, then the solvent was evaporated away under reduced pressure. The resulting residue was subjected to silica gel column chromatography and eluted with a mixed, solvent of toluene/ethyl:acetate (4:1-3:1, v/v) to obtain the entitled compound (716.9 mg, 75%) as a white solid.

MS (FAB) m/z: 477 (M+1)$^+$.

$^1$H-NMR (CDCl$_3$) δ: 1.22-1.29 (2H, m), 1.33-1.38 (2H, m), 1.46 (9H, s), 1.52-1.58 (1H, m), 2.22-2.31 (4H, m), 2.41 (3H, s), 2.79 (3H, s), 4.40 (1H, s), 4.73 (1H, s), 5.73 (1H, s), 6.93 (1H, s).

Example 27

2-Cyclopropyl-7-[3-(dimethylamino)-1-cyclopent-1-en-1-yl]-5-methyl-6-(2-methyl-1,3-thiazol-4-yl)-1,3-benzoxazole-4-carbonitrile (#27)

tert-Butyl 3-[4-cyano-2-cyclopropyl-5-methyl-6-(2-methyl-1,3-thiazol-4-yl)-1,3-benzoxazol-7-yl]-2-cyclopent-1-ethylcarbamate (I-88) (716 mg) was dissolved in tetrahydrofuran (10.5 ml), 4 N hydrochloric acid/dioxane solution (3.5 ml) was added, followed by stirring at room temperature for 6 hours. The reaction liquid was concentrated under reduced pressure, and azeotroped with toluene. The resulting residue was fractionated with n-hexane and water, the obtained aqueous layer was made basic with aqueous 1 N sodium hydroxide solution, then re-extracted with chloroform, washed with saturated brine. The obtained organic layer was dried over anhydrous sodium sulfate, then the solvent was evaporated away under reduced pressure. The resulting residue was dissolved in tetrahydrofuran (12 ml), aqueous 37% formaldehyde solution (3 ml) was added. Sodium triacetoxyborohydride (955 mg, 4.51 mmol) was added little by little, followed by stirring at room temperature for 13 hours. Aqueous 1N sodium hydroxide solution (0.12 ml) was added and the reaction solvent was concentrated under reduced pressure. The reaction solvent was concentrated under reduced pressure, the resulting residue was diluted with ethyl acetate, washed with an aqueous saturated sodium hydrogencarbonate solution and saturated brine. The obtained organic layer was dried over anhydrous sodium sulfate, the solvent was evaporated away under reduced pressure. The resulting residue was subjected to silica gel column chromatography, eluted with a mixed solvent of chloroform/methanol (50:1-20:1, v/v), recrystallized and purified with ethyl acetate/n-hexane/diisopropyl ether to obtain the entitled compound (246 mg, 41%) as a yellow white solid.

mp: 159-161° C. (dec). MS (FAB) m/z: 405 (M+1)$^+$.

$^1$H-NMR (DMSO-d$_6$) δ: 1.20-1.29 (4H, m), 1.61-1.70 (1H, m), 1.77-1.86 (1H, m), 2.06 (6H, s), 2.20 (2H, brs), 2.29 (3H, s), 2.32-2.38 (1H, m), 2.69 (3H, s), 3.70 (1H, brs), 5.82 (1H, brs), 7.34 (1H, s).

IR (ATR): 2220, 1560, 1304 cm$^{-1}$.

Anal. Calcd for C$_{23}$H$_{24}$N$_4$OS: C, 68.29; H, 5.98; N, 13.85; S, 7.93. Found: C, 67.99; H, 5.80; N, 13.67; S, 7.98.

Reference Example 89

2-(Benzyloxy)-N-(3-cyano-6-fluoro-5-hydroxy-2-methyl[1,1'-biphenyl]-4-yl)acetamide (I-89)

Under nitrogen atmosphere, benzyloxyacetyl chloride (489 μl, 3.10 mmol) was dropwise added to a tetrahydrofuran solution (10 ml) of 2-amino-5-phenyl-4-fluoro-3-hydroxy-6-methylbenzonitrile (I-41) (500 mg, 2.06 mmol) and sodium hydrogencarbonate (520 mg, 6.19 mmol) cooled with ice, followed by stirring at room temperature for 18 hours. Ethyl acetate was added to the reaction liquid, followed by washing with water and saturated brine. The obtained organic layer was dried over anhydrous sodium sulfate, the solvent was evaporated away under reduced pressure. The resulting residue was recrystallized and purified with n-hexane/ethyl acetate to obtain the entitled compound (621 mg, 1.59 mmol, 77%) as a white solid.

MS (ESI) m/z: 391 (M+1)$^+$.

$^1$H-NMR (CDCl$_3$) δ: 2.29 (3H, s), 4.24 (2H, s), 4.79 (2H, s), 7.22 (2H, dd J=1.5, 7.8 Hz), 7.37-7.49 (8H, m), 9.24 (1H, s), 9.48 (1H, s).

Reference Example 90

2-[(Benzyloxy)methyl]-7-fluoro-5-methyl-6-phenyl-1,3-benzoxazole-4-carbonitrile (I-90)

2-(Benzyloxy)-N-(3-cyano-6-fluoro-5-hydroxy-2-methyl [1,1'-biphenyl]-4-yl)acetamide (I-89) (200 mg, 0.51 mmol) was dissolved in toluene (4 ml), p-toluenesulfonic acid monohydrate (40 mg, 20 wt. %) was added, followed by heating under reflux for 12 hours.

Similarly, 2-(benzyloxy)-N-(3-cyano-6-fluoro-5-hydroxy-2-methyl[1,1'-biphenyl]-4-yl)acetamide (I-89) (418 mg, 1.07 mmol) was dissolve din toluene (8.4 ml), p-toluenesulfonic acid monohydrate (84 mg, 20 wt. %) was added, followed by heating under reflux for 18 hours.

After cooling to room temperature, the two reaction systems were combined, diluted with ethyl acetate, washed with water and saturated brine. The obtained organic layer was dried over anhydrous sodium sulfate, the solvent was evaporated away under reduced pressure. The resulting residue was subjected to silica gel column chromatography, eluted with a mixed solvent of n-hexane/ethyl acetate (4:1, v/v) to obtain the entitled compound (138 mg, 23%) as a pale red oily substance.

MS (ESI) m/z: 373 (M+1)$^+$.

$^1$H-NMR (CDCl$_3$) δ: 2.44 (3H, s), 4.75 (2H, s), 4.85 (2H, s), 7.25-7.53 (10H, m).

Example 28

2-[(Benzyloxy)methyl]-7-[(3S)-3-(dimethylamino) pyrrolidin-1-yl]-5-methyl-6-phenyl-1,3-benzoxazole-4-carbonitrile (#28)

2-[(Benzyloxy)methyl]-7-fluoro-5-methyl-6-phenyl-1,3-benzoxazole-4-carbonitrile (I-90) (70 mg, 0.19 mmol) was dissolved in dimethyl sulfoxide (1.4 ml), triethylamine (63 μl, 0.45 mmol) and (3S)-3-(dimethylamino)pyrrolidine (29 μl, 0.23 mmol) were added, followed by stirring at 90° C. for 4 hours under nitrogen atmosphere. After cooling to room temperature, ethyl acetate was added, followed by fractionation with water. The organic layer was washed with saturated brine, dried over anhydrous sodium sulfate. The solvent was evaporated away and the resulting residue was subjected to preparative, thin-layer silica gel column, chromatography, eluted with a mixed solvent of chloroform/methanol (10:1, v/v) to obtain the entitled compound (46 mg, 52%) as a yellow oily substance.

MS (EI) m/z: 466 (M)$^+$.

$^1$H-NMR (DMSO-d$_6$) δ: 1.91-1.99 (1H, m), 2.12 (6H, s), 2.21 (3H, s), 2.21 (1H, m), 2.46-2.56 (1H, m), 2.87-2.96 (1H, m), 3.27-3.47 (3H, m), 4.70 (2H, s), 4.80 (2H, s), 7.12 (1H, d, J=7.3 Hz), 7.19-7.52 (9H, m).

IR (ATR): 2924, 2210, 1587, 1469, 1398 cm$^{-1}$.

Reference Example 91

(E)-N-(3-Cyano-6-fluoro-5-hydroxy-2-methyl[1,1'-biphenyl]-4-yl)-3-phenyl-2-propenamide (I-91)

Under nitrogen atmosphere, cinnamoyl chloride (378 mg, 2.27 mmol) was dropwise added to a tetrahydrofuran solution (10 ml) of 2-amino-5-phenyl-4-fluoro-3-hydroxy-6-methyl-benzonitrile (I-41) (500 mg, 2.06 mmol) and sodium hydrogencarbonate (399 mg, 4.75 mmol) cooled with ice, followed by stirring at room temperature for 17 hours and stirring at 60° C. for 1 hour. After cooling, ethyl acetate was added to the reaction liquid, followed by washing with water and saturated brine. The obtained organic layer was dried over anhydrous sodium sulfate, the solvent was evaporated away under reduced pressure.

The resulting residue was recrystallized and purified with n-hexane/ethyl acetate to obtain the entitled compound (514 mg, 67%) as a yellow white solid.

MS (ESI) m/z: 373 (M+1)$^+$.

$^1$H-NMR (CDCl$_3$) δ: 2.31 (3H, s), 6.73 (1H, d, J=15.4 Hz), 7.24 (2H, d, J=6.8 Hz), 7.43-7.51 (6H, m), 7.62 (2H, dd, J=2.9, 6.3 Hz), 7.93 (1H, s), 7.93 (1H, d, J=15.4 Hz), 9.82 (1H, s).

Reference Example 92

7-Fluoro-5-methyl-6-phenyl-2-[(E)-2-phenylethyl]-1,3-benzoxazole-4-carbonitrile (I-92)

(E)-N-(3-Cyano-6-fluoro-5-hydroxy-2-methyl[1,1'-biphenyl]-4-yl)-3-phenyl-2-propenamide (I-91) (514 mg, 1.38 mmol) was dissolved in xylene (10 ml), pyridinium p-toluenesulfonate (87 mg, 25 wt. %) was added, followed by heating under reflux for 18 hours. After cooling to room temperature, this was diluted with ethyl acetate, washed with water and saturated brine. The obtained organic layer was dried over anhydrous sodium sulfate, the solvent was evaporated away under reduced pressure. The resulting residue was recrystallized and purified with a mixed solvent of diisopropyl ether/ethyl acetate to obtain the entitled compound (402 mg, 82%) as a yellow white solid.

MS (ESI) m/z: 355 (M+1)$^+$.

$^1$H-NMR (CDCl$_3$) δ: 2.44 (3H, s), 7.15 (1H, d, J=16.4 Hz), 7.28 (2H, dd, J=1.7, 8.3 Hz), 7.44-7.54 (6H, m), 7.62-7.65 (2H, m), 7.97 (1H, d, J=16.4 Hz).

Reference Example 93

7-[(3S)-3-(Dimethylamino)pyrrolidin-1-yl]-5-methyl-6-phenyl-2-[(E)-2-phenylethenyl]-1,3-benzoxazole-4-carbonitrile (I-93)

7-Fluoro-5-methyl-6-phenyl-2-[(E)-2-phenylethenyl]-1,3-benzoxazole-4-carbonitrile (I-92) (200 mg, 0.56 mmol) was dissolved in dimethylsulfoxide (2 ml), triethylamine (190 μl, 1.35 mmol) and (3S)-3-(dimethylamino)pyrrolidine (86 μl, 0.68 mmol) were added, followed by stirring at 90° C. for 15 hours under nitrogen atmosphere. After cooling to room temperature, ethyl acetate was added, followed by fractionation with water. The organic layer was washed with saturated brine, dried over anhydrous sodium sulfate. The solvent was evaporated away and the resulting residue was subjected to silica gel column chromatography, eluted with a mixed solvent of chloroform/methanol (50:1, v/v), recrystallized and purified with n-hexane/ethyl acetate to obtain the entitled compound (163 mg, 65%) as a yellow solid.

mp: 165-166° C. MS (ESI) m/z: 449 (M+1)$^+$.

$^1$H-NMR (CDCl$_3$) δ: 1.59-1.77 (1H, m), 1.95-2.01 (1H, m), 2.16 (6H, s), 2.22 (3H, s), 2.57 (1H, s), 3.05 (1H, t, J=8.9 Hz), 3.33-3.47 (3H, m), 7.10 (1H, d, J=16.4 Hz), 7.14 (1H, d, J=7.3 Hz), 7.24-7.27 (1H, m), 7.33-7.45 (6H, m), 7.59 (2H, dd, J=1.5, 7.8 Hz), 7.75 (1H, d, J=16.4 Hz).

IR (ATR): 2210, 1597, 1471, 1363, 962 cm$^{-1}$.

Anal. Calcd for C$_{29}$H$_{28}$N$_4$O: C, 77.65; H, 6.29; N, 12.49. Found: C, 77.35; H, 6.25; N, 12.46.

Example 29

7-[(3S)-3-(Dimethylamino)pyrrolidin-1-yl]-5-methyl-6-phenyl-2-(2-phenylethyl)-1,3-benzoxazole-4-carbonitrile (#29)

7-[(3S)-3-(Dimethylamino)pyrrolidin-1-yl]-5-methyl-6-phenyl-2-[(E)-2-phenylethenyl]-1,3-benzoxazole-4-carbonitrile (I-93) (100 mg, 0.22 mmol) and 1 N hydrochloric acid/ethanol solution (223 μl, 10.22 mmol) were dissolved in ethanol (2 ml), 10% carbon-held palladium catalyst was added, followed by stirring at room temperature under atmospheric pressure of hydrogen for 3 hours. After filtration through Celite, the solvent was concentrated under reduced pressure, ethyl acetate and an aqueous saturated sodium hydrogencarbonate solution were added to make the aqueous layer basic, followed by fractionation. The organic layer was washed with saturated brine, dried over anhydrous sodium sulfate. The solvent was evaporated away, the resulting residue was subjected to preparative thin-layer silica gel column chromatography, eluted with a mixed solvent of chloroform/methanol (20:1, v/v), recrystallized and purified with n-hexane/ethyl acetate/diisopropyl ether to obtain the entitled compound (16 mg, 16%) as a white solid.

MS (ESI) m/z: 451 (M+1)$^+$.

$^1$H-NMR (CDCl$_3$) δ: 1.60 (1H, s), 1.91 (1H, s), 2.12 (6H, s), 2.20 (3H, s), 2.51 (1H, s), 2.91 (1H, s), 3.18-3.33 (7H, m), 7.12 (1H, d, J=6.8 Hz), 7.20-7.42 (9H, m).

IR (ATR): 2210, 1587, 1466, 1363 cm$^{-1}$.

Anal. Calcd for C$_{29}$H$_{30}$N$_4$O.0.5H$_2$O: C, 75.79; H, 6.80; N, 12.19. Found: C, 75.94; H, 6.66; N, 12.15.

Reference Example 94

Ethyl 3-[(3-cyano-6-fluoro-5-hydroxy-2-methyl[1,1'-biphenyl]-4-yl)amino]-2,2-dimethyl-3-Oxopropanoate (I-94)

Diethyl dimethylmalonate (5.00 g, 26.56 mmol) was dissolved in ethanol (50 ml), an aqueous solution (25 ml) of potassium hydroxide (1.75 g, 26.56 mmol) was added, followed by stirring at room temperature for 5 hours. The reaction solvent was evaporated away under reduced pressure, water with ice was added, 1 N hydrochloric acid was added for acidification, followed by extraction with diethyl ether. The organic layer was washed with saturated brine, the obtained organic layer was dried over anhydrous sodium sulfate, the solvent was evaporated away under reduced pressure to obtain a monocarboxylic acid (4.51 g, quant.) as a colorless transparent oily substance. A part of the obtained carboxylic acid (2.00 g, 12.49 mmol) was dissolved in thionyl chloride (3.6 ml) and stirred under heat at 50° C. for 22 hours. The reaction liquid was concentrated under reduced pressure, azeotroped with toluene, and dissolved in tetrahydrofuran (7 ml). A tetrahydrofuran solution of the obtained acid chloride was dropwise added to a tetrahydrofuran solution (40 ml) of 2-amino-5-phenyl-4-fluoro-3-hydroxy-6-methylbenzonitrile (I-41) (2.52 g, 10.41 mmol) and sodium hydrogencarbonate (2.10 g, 24.97 mmol) cooled with ice, followed by stirring at room temperature for 19 hours. Ethyl acetate was added to the reaction liquid, followed by washing with aqueous 0.1 N hydrochloric acid solution and saturated brine. The obtained organic layer was dried over anhydrous sodium sulfate, the solvent was evaporated away under reduced pressure. The resulting residue was recrystallized and purified with n-hexane/ethyl acetate to obtain the entitled compound (1.15 g, 36%) as a yellow white solid.

MS (ESI) m/z: 385 (M+1)$^+$.

$^1$H-NMR (CDCl$_3$) δ: 1.35 (3H, t, J=7.1 Hz), 1.66 (6H, s), 2.29 (3H, s), 4.34 (2H, q, J=7.1 Hz), 7.21 (2H, dd, J=1.76.8 Hz), 7.41-7.49 (3H, m), 8.77 (1H, s), 9.85 (1H, s).

Reference Example 95

Ethyl 2-(4-cyano-7-fluoro-5-methyl-6-phenyl-1,3-benzoxazol-2-yl)-2-methylpropanoate (I-95)

Ethyl 3-[(3-cyano-6-fluoro-5-hydroxy-2-methyl[1,1'-biphenyl]-4-yl)amino]-2,2-dimethyl-3-oxopropanoate (I-94) (200 mg, 0.52 mmol) was dissolved in toluene (4 ml), pyridinium p-toluenesulfonate (33 mg, 0.13 mmol) was added, followed heating under reflux for 44 hours.

However, since the reaction did not finish, xylene (4 ml) was added, followed by heating under reflux at an oil bath temperature for 150° C. for 18 hours. After cooling to room temperature, this was diluted with ethyl acetate, washed with water and saturated brine. The obtained organic layer was dried over anhydrous sodium sulfate, the solvent was evaporated away under reduced pressure. The resulting residue was subjected to silica gel column chromatography, and eluted with a mixed solvent of n-hexane/ethyl acetate (4:1, v/v) to obtain the entitled compound (116 mg, 87%) as a pale red oily substance.

MS (ESI) m/z: 367 (M+1)$^+$.

$^1$H-NMR (CDCl$_3$) δ: 1.23 (3H, t, J=7.1 Hz), 1.80 (6H, s), 2.42 (3H, s), 4.21 (2H, q, J=7.1 Hz), 7.23-7.27 (2H, m), 7.45-7.53 (3H, m).

Reference Example 96

2-(4-Cyano-7-fluoro-5-methyl-6-phenyl-1,3-benzoxazol-2-yl)-2-methylpropanamide (I-96)

Ammonium chloride (73 mg, 1.36 mmol) was suspended in benzene (3.3 ml), and under nitrogen atmosphere, trimethylaluminium (1.03 M n-hexane solution) was dropwise added with keeping at 5° C. or lower, followed by stirring at room temperature for 2 hours. A benzene (1.6 ml) solution of ethyl 2-(4-cyano-7-fluoro-5-methyl-6-phenyl-1,3-benzoxazol-2-yl)-2-methylpropanoate (I-95) (166 mg, 0.45 mmol) was added, followed by stirring at 50° C. for 17 hours. Since the reaction did not finish, separately, the same amount of ammonium chloride (73 mg, 1.36 mmol) was suspended in benzene (3.3 ml), trimethylaluminium (1.03 M n-hexane solution was dropwise added with keeping at 5° C. or lower, followed by stirring at room temperature for 2 hours to prepare a solution, which was added to the original reaction solution, followed by stirring at 50° C. for 19 hours. Though the reaction did not finish, this was cooled to room temperature, fractionated with ethyl acetate and aqueous 1 N sodium hydroxide solution, and the organic layer was washed with saturated brine. The obtained organic layer was dried over anhydrous sodium sulfate, the solvent was evaporated away under reduced pressure. The resulting residue was subjected to preparative TLC, eluted with a mixed solvent of chloroform/methanol (10:1, v/v) to obtain the entitled compound (58 mg, 38%) as a yellow amorphous solid.

MS (ESI) m/z: 338 (M+1)$^+$.

$^1$H-NMR (CDCl$_3$) δ: 1.83 (6H, s), 2.44 (3H, s), 5.45 (1H, brs), 6.91 (1H, brs), 7.23-7.26 (2H, m), 7.46-7.54 (3H, m).

Example 30

2-{4-Cyano-7-[(3S)-3-(dimethylamino)pyrrolidin-1-yl]-5-methyl-6-phenyl-1,3-benzoxazol-2-yl}-2-methylpropanamide (#30)

2-(4-Cyano-7-fluoro-5-methyl-6-phenyl-1,3-benzoxazol-2-yl)-2-methylpropanamide (I-96) (58 mg, 0.17 mmol) was dissolved in dimethyl sulfoxide (1.2 ml), triethylamine (33 µl, 0.24 mmol) and (3S)-3-(dimethylamino)pyrrolidine (26 µl, 0.21 mmol) were added, followed by stirring at 90° C. for 3 hours under nitrogen atmosphere. After cooling to room temperature, ethyl acetate was added, followed by fractionation with water. The organic layer was washed with saturated brine, dried over anhydrous sodium sulfate. The solvent was evaporated away and the resulting residue was subjected to preparative silica gel column chromatography, eluted with a mixed solvent of chloroform/methanol (10:1, v/v) to obtain the entitled compound (41 mg, 0.09 mmol, 55%) as a white solid.

MS (ESI) m/z: 432 (M+1)$^+$.

$^1$H-NMR (DMSO-d$_6$) δ: 1.46-1.56 (1H, m), 1.65 (6H, s), 1.83-1.90 (1H, m), 2.01 (6H, s), 2.10 (3H, s), 2.52-2.57 (1H, m), 2.85 (1H, dd, J=8.3, 9.8 Hz), 3.21-3.37 (3H, m), 7.10 (2H, brs), 7.16 (1H, d, J=7.1 Hz), 7.26-7.49 (4H, m).

IR (ATR): 3444, 2208, 1691, 1604, 1463 cm$^{-1}$.

Anal. Calcd for C$_{25}$H$_{29}$N$_5$O$_2$S.0.25H$_2$O: C, 68.86; H, 6.82; N, 16.06. Found: C, 68.72; H, 6.78; N, 15.78.

Reference Example 97

3-(Benzyloxy)-N-(3-cyano-6-fluoro-5-hydroxy-2-methyl[1,1'-biphenyl]-4-yl)-2,2-dimethylpropanamide (I-97)

3-(Benzyloxy)-2,2-dimethylpropanoic acid (1.0 g, 4.80 mmol) was dissolved in thionyl chloride (1.2 ml), followed by stirring under heat at 50° C. for 18 hours. The reaction liquid was concentrated under reduced pressure, azeotroped with toluene, and dissolved in tetrahydrofuran (10 ml). A tetrahydrofuran solution of the obtained acid chloride was dropwise added to a tetrahydrofuran solution (20 ml) of 2-amino-5-phenyl-4-fluoro-3-hydroxy-6-methylbenzonitrile (I-41) (969 mg, 4.00 mmol) and sodium hydrogencarbonate (806 mg, 9.60 mmol) cooled with ice, followed by stirring at room temperature for 3 days. Ethyl acetate was added to the reaction liquid, followed by washing with water and saturated brine. The obtained organic layer was dried over anhydrous sodium sulfate, the solvent was evaporated away under reduced pressure. The resulting residue was subjected to silica gel column chromatography, eluted with a mixed solvent of n-hexane/ethyl acetate (4:1, v/v) to obtain the entitled compound (971.9 mg, 47%) as a brown transparent oily substance. In addition, an ester reacted on the phenolic hydroxyl group, 4-{[3-(benzyloxy)-2,2-dimethylpropanoyl]amino}-5-cyano-2-fluoro-6-methyl[1,1'-biphenyl]-3-yl 3-(benzyloxy)-2,2-dimethylpropanoate (552 mg, 21%) was obtained. This was dissolved in ethanol (5.5 ml), aqueous 1 N sodium hydroxide solution (2.5 ml, 2.50 mmol) was added, followed by stirring at 90° C. for 2 hours. After cooling, the solvent was concentrated under reduced pressure, ethyl acetate was added, followed by washing with water and saturated brine. The obtained organic layer was dried over anhydrous sodium sulfate, the solvent was evaporated away under reduced pressure to obtain the entitled compound (544 mg) as a brown transparent oily substance.

MS (ESI) m/z: 433 (M+1)$^+$.

$^1$H-NMR (CDCl$_3$) δ: 1.33 (6H, s), 2.27 (3H, s), 3.58 (2H, s), 4.78 (2H, s), 7.21 (2H, dd, J=1.5, 8.1 Hz), 7.33-7.49 (5H, m), 9.28 (1H, s), 10.06 (1H, s).

Reference Example 98

N-(3-Cyano-6-fluoro-5-hydroxy-2-methyl[1,1'-biphenyl]-4-yl)-3-hydroxy-2,2-dimethylpropanamide (I-98)

3-(Benzyloxy)-N-(3-cyano-6-fluoro-5-hydroxy-2-methyl[1,1'-biphenyl]-4-yl)-2,2-dimethylpropanamide (I-97) (540 mg, 1.25 mmol) was dissolved in ethanol (10 ml), carbon-held palladium catalyst (10% wet, 54 mg) was added followed by vigorously stirring at room temperature under atmospheric pressure of hydrogen for 20 hours. After the reaction, the insoluble matter was separated by filtration through Celite, the filtrate was concentrated under reduced pressure.

The resulting residue was subjected to silica gel column chromatography, eluted with a mixed solvent of n-hexane/ethyl:acetate (1:1, v/v) to obtain the entitled compound (184 mg, 43%) as a colorless transparent oily substance.

MS (ESI) m/z: 343 (M+1)$^+$.

$^1$H-NMR (CDCl$_3$) δ: 1.36 (6H, s), 2.27 (3H, s), 2.76 (1H, t, J=4.3 Hz), 3.84 (1H, t, J=4.3 Hz), 7.19-7.22 (2H, m), 7.39-7.49 (3H, m), 9.33 (1H, s), 10.01 (1H, s).

Reference Example 99

7-Fluoro-2-(2-hydroxy-1,1-dimethylethyl)-5-methyl-6-phenyl-1,3-benzoxazole-4-carbonitrile (I-99)

N-(3-Cyano-6-fluoro-5-hydroxy-2-methyl[1,1'-biphenyl]-4-yl)-3-hydroxy-2,2-dimethylpropanamide (I-98) (184 mg, 0.54 mmol) was dissolved in toluene (3.7 ml), pyridinium p-toluenesulfonate (34 mg, 0.13 mmol) was added, followed by stirring under heat for 15 hours. After cooling to room temperature, this was diluted with ethyl acetate, washed with aqueous sodium hydrogencarbonate solution and saturated brine. The obtained organic layer was dried over anhydrous sodium sulfate, the solvent was evaporated away under reduced pressure. The resulting residue was recrystallized and purified with diisopropyl ether/ethyl acetate to obtain the entitled compound (118.6 mg, 68%) as a white solid.

MS (ESI) m/z: 325 (M+1)$^+$.

$^1$H-NMR (CDCl$_3$) δ: 1.50 (6H, s), 2.42 (3H, s), 2.98 (1H, t, J=7.1 Hz), 3.88 (2H, d, J=6.8 Hz), 7.23-7.26 (2H, m), 7.47-7.53 (3H, m).

Reference Example 100

7-Fluoro-2-(2-methoxy-1,1-dimethylethyl)-5-methyl-6-phenyl-1,3-benzoxazole-4-carbonitrile (I-100)

7-Fluoro-2-(2-hydroxy-1,1-dimethylethyl)-5-methyl-6-phenyl-1,3-benzoxazole-4-carbonitrile (I-99) (50 mg, 0.15 mmol) was dissolved in methylene chloride (0.5 ml), aqueous 42% tetrafluoroboric acid solution (32 μl, 0.15 mmol) was added, then with cooling with ice, trimethylsilyldiazomethane (2 M hexane solution, 77 μl, 0.15 mmol) was dropwise added, followed by stirring at 0° C. for 10 minutes, further trimethylsilyldiazomethane (2 M, hexane solution, 77 μl, 0.15 mmol) was dropwise added, followed by stirring at 0° C. for 1 hour. After the reaction, water was added followed by extraction with methylene and washing with saturated brine. The obtained organic layer was dried over anhydrous sodium sulfate, the solvent was evaporated away under reduced pressure. The resulting residue was subjected to preparative thin-layer silica gel column chromatography, eluted with n-hexane/ethyl acetate (5:1, v/v) to obtain the entitled compound (41.2 mg, 79%) as a colorless transparent oily substance.

MS (ESI) m/z: 339 (M+1)$^+$.

$^1$H-NMR (CDCl$_3$) δ: 1.53 (6H, s), 2.41 (3H, s), 3.36 (3H, s), 3.67 (2H, s), 7.23-7.26 (2H, m), 7.44-7.53 (3H, m).

Example 31

7-[(3S)-3-(Dimethylamino)pyrrolidin-1-yl]-2-[2-methoxy-1,1-dimethylethyl]-5-methyl-6-phenyl-1,3-benzoxazole-4-carbonitrile (#3.1)

7-Fluoro-2-(2-methoxy-1,1-dimethylethyl)-5-methyl-6-phenyl-1,3-benzoxazole-4-carbonitrile (I-100) (40 mg, 0.12 mmol) was dissolved in dimethyl sulfoxide (0.8 ml), triethylamine (23 μl, 0.17 mmol) and (3S)-3-(dimethylamino)pyrrolidine (18 μl, 0.14 mmol) were added, followed by stirring at 90° C. for 3 hours under nitrogen atmosphere. After cooling to room temperature, ethyl acetate was added, followed by fractionation with water. The organic layer was washed with saturated brine, dried over anhydrous sodium sulfate. The solvent was evaporated away and the resulting residue was subjected to preparative thin-layer silica gel column chromatography, eluted with a mixed solvent of chloroform/methanol (10:1, v/v), and washed with n-hexane and ethyl acetate to obtain the entitled compound (18 mg, 35%) as a white solid.

MS (ESI) m/z: 433 (M+1)$^+$.

$^1$H-NMR (DMSO-d$_6$) δ: 1.26 (1H, brs), 1.55 (6H, s), 1.54-1.66 (1H, m), 1.89-1.98 (1H, m), 2.13 (6H, s), 2.18 (3H, s), 2.49-2.57 (1H, m), 3.01 (1H, t, J=9.2 Hz), 3.23-3.40 (5H, m), 3.63 (2H, s), 7.11 (1H, d, J=7.3 Hz), 7.23 (1H, d, J=7.3 Hz), 7.31-7.42 (3H, m).

IR (ATR): 2210, 1606, 1455, 1365, 1117 cm$^{-1}$.

Anal. Calcd for C$_{26}$H$_{32}$N$_4$O$_2$.0.25H$_2$O: C, 71.45; H, 7.49; N, 12.82. Found: C, 71.73; H, 7.46; N, 12.64.

Reference Example 101

6-Bromo-7-fluoro-2,5-dimethyl-1,3-benzoxazole-4-carbonitrile (I-101)

Diisopropylethylamine (22 ml, 0.126 mmol) was added to an ethyl acetate (400 ml) solution of 2-amino-5-bromo-4-fluoro-3-hydroxy-6-methylbenzonitrile (I-75) (8.85 g, 36.1 mmol), cooled with ice, then acetyl chloride (3.85 ml, 54.2 mmol) was dropwise added, followed by stirring as such for 14 hours with gradually heating up to room temperature. With cooling with ice, aqueous saturated ammonium chloride solution was added, and the organic layer was collected. This was washed with saturated brine, dried over anhydrous sodium sulfate, then the solvent was evaporated away under reduced pressure. The resulting residue was suspended in toluene (500 ml), a catalytic amount of p-toluenesulfonic acid was added, followed by heating under reflux for 3 hours with a Dean-Stark device. After cooling, the solvent was evaporated away, the resulting residue was dissolved in ethyl acetate, washed with water. After drying over anhydrous sodium sulfate, the solvent was evaporated away under reduced pressure, the precipitated crystal was washed with isopropyl ether, then collected by filtration to obtain the entitled compound (7.07 g, 73%) as a colorless solid.

MS (EI) m/z; 269 (M$^+$).

$^1$H-NMR (CDCl$_3$) δ: 2.73 (3H, s), 2.75 (3H, s).

IR (ATR): 2229, 1574, 1475, 1406, 1396, 1384, 1333, 1315, 1273, 1198, 1134 cm$^{-1}$.

Reference Example 102

7-Fluoro-2,5-dimethyl-6-phenyl-1,3-benzoxazole-4-carbonitrile (I-102)

Phenylboronic acid (1.30 g, 10.63 mmol), tetrakistriphenylphosphine palladium(0) (473 mg, 0.41 mmol) and tripotassium phosphate (4.51 g, 21.2 mmol) were added to a 1,4-dioxane (80 ml) solution of 6-bromo-7-fluoro-2,5-dimethyl-1,3-benzoxazole-4-carbonitrile (I-101) (2.2 g, 8.18 mmol), followed by heating under reflux for 3 hours under nitrogen atmosphere. After cooling, the reaction liquid was filtered, the solvent was evaporated away from the filtrate under reduced pressure. The resulting residue was subjected to silica gel column chromatography, and eluted with n-hexane/ethyl acetate (5:1, v/v→4:1, v/v) to obtain a main product. This was washed with isopropyl ether and then collected by filtration to obtain the entitled compound (985 mg, 45%) as a colorless solid.

MS (EI) m/z: 267 (M+1)$^+$.

$^1$H-NMR (CDCl$_3$) δ: 2.42 (3H, s), 2.76 (3H, s), 7.23-7.27 (2H, m), 7.40-7.53 (3H, m).

Example 32

7-[(3S)-3-(Dimethylamino)pyrrolidin-1-yl]-2,5-dimethyl-6-phenyl-4-carbonitrile (#32)

(3S)-3-(Dimethylamino)pyrrolidine (190 μl, 1.50 mmol) and triethylamine (300 μl) were added to a dimethyl sulfoxide (5 ml) solution of 7-fluoro-2,5-dimethyl-6-phenyl-1,3-benzoxazole-4-carbonitrile (I-102) (266 mg, 1.00 mmol). The system was purged with nitrogen and then sealed up, and heated at 80° C. for 14 hours. After cooling, the solvent was evaporated away under reduced pressure, then the resulting residue was dissolved in chloroform, washed with water and saturated brine. The organic layer was dried over anhydrous sodium sulfate, then the solvent was evaporated away under reduced pressure, the resulting residue was subjected to silica gel column chromatography. Eluting with a mixed solvent of chloroform/methanol (98:2, v/v→95:5, v/v) gave a main product. This was separated and purified by preparative TLC to obtain the entitled compound (110 mg, 31%) as an oil (leaving at room temperature gave a colorless solid precipitate).

MS (EI) m/z: 360 (M$^+$).

$^1$H-NMR (CDCl$_3$) δ: 1.53-1.67 (1H, m), 1.90-1.98 (1H, m), 2.19 (6H, s), 2.28 (3H, s), 2.45-2.58 (1H, m), 2.66 (3H, s), 2.90-2.98 (1H, m), 3.25-3.43 (3H, m), 7.10-7.14 (1H, m), 7.20-7.26 (1H, m), 7.32-7.50 (3H, m).

IR (ATR): 2210, 1670, 1608, 1585, 1442, 1248, 1153 cm$^{-1}$.

Anal. Calcd for C$_{22}$H$_{24}$N$_4$O.0.75H$_2$O: C, 70.66; H, 6.87; N, 14.98. Found: C, 70.73; H, 6.27; N, 14.16.

Reference Example 103

(5-Cyano-2-fluoro-3-hydroxy-2-methylbiphenyl-4-yl)-1-acetylpiperidine-4-carboxamide (I-103)

2-Amino-5-phenyl-4-fluoro-3-hydroxy-6-methylbenzonitrile (I-41) (0.10 g, 0.41 mmol) was dissolved in ethyl acetate (4 ml), then triethylamine (0.13 ml, 0.94 mmol), 1-acetylpiperidine-4-carbonyl chloride hydrochloride (0.10 g, 0.44 mmol) were added. After stirring at room temperature for 2 hours, this was heated under reflux for 3 hours. Ethyl acetate was added and the insoluble matter was collected by filtration to obtain a colorless solid (0.11 g, 68%).

$^1$H-NMR (DMSO-d$_6$) δ: 1.45-1.70 (2H, m), 1.80-2.00 (2H, m), 2.02 (3H, s), 2.16 (3H, s), 2.65-2.80 (2H, m), 3.10-3.20 (1H, m), 3.85-3.95 (1H, m), 4.30-4.45 (1H, m), 7.30-7.35 (2H, m), 7.40-7.60 (3H, m), 9.80-9.85 (1H, br), 10.15-10.30 (1H, br).

Reference Example 104

2-(1-Acetylpiperidin-4-yl)-7-fluoro-5-methyl-6-phenyl-1,3-benzoxazole-4-carbonitrile (I-104)

(5-Cyano-2-fluoro-3-hydroxy-2-methylbiphenyl-4-yl)-1-acetylpiperidine-4-carboxamide (I-103) (0.10 g, 0.25 mmol) was suspended in toluene (10 ml), a catalytic amount of p-toluenesulfonic acid monohydrate was added, followed by heating under reflux for 15 hours with removing water. After dilution with ethyl acetate, this was washed with water, dried over anhydrous sodium sulfate. The solvent was evaporated away under reduced pressure, the resulting residue was purified by preparative thin-layer chromatography (dichloromethane:methanol=20:1) to obtain a colorless oil (52 mg, 56%).

$^1$H-NMR (CDCl$_3$) δ: 1.90-2.15 (2H, m), 2.15 (3H, s), 2.20-2.30 (2H, m), 2.42 (3H, s), 2.90-3.00 (1H, m), 3.25-3.40 (2H, m), 3.90-4.00 (1H, m), 4.50-4.60 (1H, m), 7.20-7.30 (2H, m), 7.40-7.60 (3H, m).

Example 33

2-(1-Acetylpiperidin-4-yl)-7-[(3S)-3-(dimethylamino)pyrrolidin-1-yl]-5-methyl-6-phenyl-1,3-benzoxazole-4-carbonitrile (#33)

2-(1-Acetylpiperidin-4-yl)-7-fluoro-5-methyl-6-phenyl-1,3-benzoxazole-4-carbonitrile (I-104) (0.23 g, 0.61 mmol) was dissolved in dimethyl sulfoxide (7 ml), triethylamine (0.18 ml, 1.30 mmol) and (3S)-3-(dimethylamino)pyrrolidine (85.0 μl, 0.67 mmol) were added, followed by stirring an external temperature of about 90° C. for 4 hours. After dilution with ethyl acetate, this was washed with water, dried over anhydrous sodium sulfate. The solvent was evaporated away under reduced pressure and the resulting residue was purified by silica gel column chromatography (silica gel 10 g, dichloromethane:methanol=30:1) to obtain a colorless oil (73 mg, 25%). This was dissolved in dioxane and freeze-dried into solid.

$^1$H-NMR (CDCl$_3$) δ: 1.55-1.70 (1H, m), 1.80-2.10 (4H, m), 2.13 (6H, s), 2.14 (3H, s), 2.19 (3H, s), 2.10-2.30 (1H, m), 2.50-2.60 (1H, m), 2.90-3.00 (2H, m), 3.20-3.45 (5H, m), 3.90-4.00 (1H, m), 4.50-4.60 (1H, m), 7.10-7.15 (1H, m), 7.20-7.25 (1H, m), 7.30-7.45 (3H, m).

Reference Example 105

7-Fluoro-2-(furan-2-yl)-5-methyl-6-phenyl-1,3-benzoxazole-4-carbonitrile (I-105)

4-Amino-6-fluoro-5-hydroxy-2-methylbiphenyl-3-carbonitrile (I-41) (100 mg, 0.41 mmol) was dissolved in xylene (10 ml), then at room temperature, triethylamine (70 μl), 2-furoyl chloride (49 μl, 0.50 mmol), pyridinium paratoluenesulfonate (31 mg, 0.12 mmol) were added. Next, this mixture liquid was stirred at 145° C. for 108 hours, then cooled to room temperature. This reaction liquid was fractionated with ethyl acetate and an aqueous saturated sodium hydrogencarbonate solution. The aqueous layer was separated, and this was extracted twice with ethyl acetate. The organic layers were combined, this was washed with saturated brine, dried over anhydrous sodium sulfate. The insoluble matter was separated by filtration, the solvent was evaporated away, the resulting residue was purified by middle-pressure liquid chromatography (eluent, hexane:ethyl acetate=4:1), and the entitled compound (40 mg, 31%) was obtained as a white solid.

MS (ESI) m/z: 319 (M+1)$^+$.

HRMS (EI) m/z: 318.0797 (Calcd for C$_{19}$H$_{11}$FN$_2$O$_2$ 318.0805).

$^1$H-NMR (CDCl$_3$) δ: 2.45 (3H, s), 6.69 (1H, dd, J=1.7, 3.4 Hz), 7.27-7.30 (2H, m), 7.46-7.55 (4H, m), 7.75 (1H, dd, J=0.7, 1.7 Hz).

IR (ATR): 2220, 1635, 1520, 1443, 1124, 1011, 937, 756, 719 cm$^{-1}$.

Example 34

7-[(3S)-3-(Dimethylamino)pyrrolidin-1-yl]-2-(2-furyl)-5-methyl-6-phenyl-1,3-benzoxazole-4-carbonitrile (#34)

7-Fluoro-2-(2-furyl)-5-methyl-6-phenyl-1,3-benzoxazole-4-carbonitrile (I-105) (40 mg, 0.13 mmol) was dissolved in anhydrous dimethyl sulfoxide (2 ml), and at room temperature, triethylamine (26 µl, 0.19 mmol) and (3S)-3-(dimethylamino)pyrrolidine (21 µl, 0.16 mmol) were added. This mixture liquid was stirred at 90° C. for 11 hours, then cooled to room temperature. This was fractionated with ethyl acetate and saturated brine. The aqueous layer was separated, and this was extracted twice with ethyl acetate.

The organic layers were combined, this was washed with saturated brine, dried over anhydrous sodium sulfate. The insoluble matter was separated by filtration, the solvent was evaporated away, and the resulting residue was purified by preparative TLC (eluent, chloroform:methanol=9:1) to obtain the entitled compound (47 mg, 91%) as a white solid.

MS (ESI) m/z; 413 (M+1)$^+$.

HRMS (EI) m/z: 412.1890 (Calcd for $C_{25}H_{24}N_4O_2$ 412.1900).

$^1$H-NMR (CDCl$_3$) δ: 1.59-1.70 (1H, m), 1.95-2.03 (1H, m), 2.15 (6H, s), 2.20 (3H, s), 2.50-2.60 (1H, m), 2.98 (1H, t, J=9.3 Hz), 3.33-3.51 (3H, m), 6.63 (1H, dd, J=1.7, 3.4 Hz), 7.14 (1H, d, J=7.1 Hz), 7.27 (1H, d, J=7.1 Hz), 7.31 (1H, d, J=3.4 Hz), 7.33-7.45 (3H, m), 7.67 (1H, d, J=1.7 Hz).

IR (ATR): 3597, 2202, 1595, 1442, 1363, 1302, 746, 727, 705 cm$^{-1}$.

Anal. Calcd for $C_{25}H_{24}N_4O_2 \cdot 1.0H_2O$: C, 69.75; H, 6.09; N, 13.01. Found: C, 70.10; H, 5.99; N, 12.90.

Example 35

7-[(3S)-3-(Dimethylamino)pyrrolidin-1-yl]-5-methyl-6-phenyl-2-(pyridin-2-yl)-1,3-benzoxazole-4-carbonitrile (#35)

With cooling with ice, oxalyl chloride (262 µl, 3 mmol) and a catalytic amount of dimethylformamide were added to a dichloromethane (7 ml) suspension of picolinic acid (271 mg, 2.2 mmol), followed by stirring at the same temperature for 10 minutes and stirring at room temperature for 20 minutes. After again cooling with ice, a dichloromethane suspension of 4-amino-6-fluoro-5-hydroxy-2-methylbiphenyl-3-carbonitrile (I-41) (458 mg, 2.0 mmol) and diisopropylethylamine (697 µl, 4 mmol) were added, followed by stirring at room temperature for 2 hours. The reaction liquid was diluted with chloroform, then the organic layer was washed with water, dried over anhydrous sodium sulfate, and the solvent was evaporated away under reduced pressure. The resulting residue was heated under reflux for 30 minutes in toluene (20 ml) in the presence of a catalytic amount of p-tosylic acid with a Dean-Stark device. After cooling, the solvent was evaporated away, the resulting residue was dissolved in chloroform, washed with water, dried over anhydrous sodium sulfate, then the solvent was evaporated away under reduced pressure. The resulting residue was heated under reflux in xylene (20 ml) in the presence of a catalytic amount of p-tosylic acid with a Dean-Stark device. After cooling, the solvent was evaporated away, the resulting residue was dissolved in chloroform, washed with water, dried over anhydrous sodium sulfate, then the solvent was evaporated away under reduced pressure. The resulting residue was washed with a mixed solvent of ethyl acetate and isopropyl ether, the precipitated solid was collected by filtration. This was suspended in toluene (40 ml), and heated under reflux for 15 hours in the presence of a catalytic amount of pyridinium p-toluenesulfonate. Further, the solvent was changed to xylene, a catalytic amount of p-toluenesulfonic acid was added, followed by heating under reflux for 12 hours. After cooling, the solvent was evaporated away, and the resulting residue was dissolved in chloroform, washed with water, then dried over anhydrous sodium sulfate, and the solvent was evaporated away under reduced pressure. The resulting residue was subjected to silica gel column chromatography, and eluted with a mixed solvent of chloroform/methanol (100:10, v/v→98:2, v/v) to obtain a main product. This was dissolved in dimethyl sulfoxide (8 ml), and (3S)-3-(dimethylamino)pyrrolidine (129 µl, 1.02 mmol) and triethylamine (150 µl) were added.

The system was purged with nitrogen and sealed up, and heated at 100° C. for 3 hours. After cooling, the solvent was evaporated away under reduced pressure, then the resulting residue was dissolved in chloroform, washed with water. The organic layer was dried over anhydrous sodium sulfate, then the solvent was evaporated away under reduced pressure, the resulting residue was separated and purified by preparative TLC to obtain the main a main product. This was washed with a mixed solvent of isopropyl ether and ethanol, and the solid was collected by filtration to obtain the entitled compound (190 mg, 22%) as a yellow solid.

mp: 227-233° C.

MS (EI) m/z: 426 (M+1)$^+$.

$^1$H-NMR (CDCl$_3$) δ: 1.60-1.73 (1H, m), 2.02-2.10 (1H, m), 2.13 (6H, s), 2.24 (3H, s), 2.50-2.62 (1H, m), 2.85-2.93 (1H, m), 3.30 (1H, dd, J=7.2, 9.6 Hz), 3.60-3.74 (2H, m), 7.13-7.17 (1H, m), 7.26-7.30 (1H, m), 7.35-7.49 (4H, m), 7.89 (1H, dt, J=2.0, 7.6 Hz), 8.40 (1H, d, J=8.0 Hz), 8.79-8.81 (1H, m).

IR (ATR): 2206, 1604, 1581, 1458, 1435, 1367 cm$^{-1}$.

Anal. Calcd for $C_{26}H_{25}N_5O \cdot 0.75H_2O$: C, 71.46; H, 6.11; N, 16.02. Found: C, 71.70; H, 5.87; N, 15.75.

Reference Example 106

N-(4-Bromo-2-cyano-5-fluoro-6-hydroxy-3-methylphenyl)-2,2-dimethyl-3-[(phenylmethyl)oxy]propionamide (I-106)

2,2-Dimethyl-3-[(phenylmethyl)oxy]propionic acid (3.99 g, 19.16 mmol) was dissolved in thionyl chloride (4.14 ml) and stirred at 50° C. for 19 hours.

After cooling, the reaction liquid was concentrated under reduced pressure, and azeotroped with benzene. A tetrahydrofuran solution (7 ml) of the resulting residue was dropwise added to a tetrahydrofuran solution (63 ml) of 2-amino-5-bromo-4-fluoro-3-hydroxy-6-methylbenzonitrile (I-75) (3.13 g, 12.77 mmol) and sodium hydrogencarbonate (2.68 g, 31.93 mmol), followed by stirring at room temperature for 19 hours. Ethyl acetate was added to the reaction liquid, followed by washing with water and saturated brine. The organic layer was concentrated under reduced pressure, the resulting residue was dissolved in ethanol (30 ml), aqueous 1 N sodium hydroxide solution (24 ml) was added, followed by stirring at 50° C. for 23 hours. After cooling, the reaction liquid was concentrated under reduced pressure, diluted with ethyl acetate, neutralized with aqueous 1 N hydrochloric acid, washed with saturated brine. The organic layer was concentrated under reduced pressure to obtain the entitled compound (5.82 g, 70%) as a yellow white solid.
MS (ESI) m/z: 435, 437 (M+1)$^+$.
$^1$H-NMR (CDCl$_3$) δ: 1.31 (6H, s), 2.58 (3H, s), 3.55 (2H, s), 4.75 (2H, s), 7.31-7.37 (5H, m), 9.51 (1H, s), 10.07 (1H, s).

Reference Example 107

N-(4-Bromo-2-cyano-5-fluoro-6-hydroxy-3-methylphenyl)-3-hydroxy-2,2-dimethyl-1-propanamide (I-107)

N-(4-Bromo-2-cyano-5-fluoro-6-hydroxy-3-methylphenyl)-2,2-dimethyl-3-[(phenylmethyl)oxy]propionamide (I-105) (5.82 g, 13.37 mmol) was dissolved in ethyl acetate (120 ml), carbon-held palladium catalyst (5% wet, 580 mg) was added, followed by vigorously stirring at room temperature under atmospheric pressure of hydrogen for 18 hours. After the reaction, the insoluble matter was separated by filtration through Celite, the filtrate was concentrated under reduced pressure. The resulting residue was recrystallized and purified with n-hexane/ethyl acetate to obtain the entitled compound (2.32 g, 50%) as a white solid.
MS (ESI) m/z: 345, 347 (M+1)$^+$.
$^1$H-NMR (CDCl$_3$) δ: 1.34 (6H, s), 2.58 (3H, s), 2.63 (1H, t, J=3.9 Hz), 3.82 (1H, t, J=3.9 Hz), 9.57 (1H, s), 10.05 (1H, brs).

Reference Example 108

6-Bromo-7-fluoro-2-(2-hydroxy-1,1-dimethylethyl)-5-methyl-1,3-benzoxazole-4-carbonitrile (I-108)

N-(4-Bromo-2-cyano-5-fluoro-6-hydroxy-3-methylphenyl)-3-hydroxy-2,2-dimethyl-1-propanamide (I-107) (1.80 g, 5.21 mmol) was dissolved in toluene (36 ml), pyridinium p-toluenesulfonate (262 mg, 1.04 mmol) was added, followed by heating under reflux for 28 hours. After cooling to room temperature, this was diluted with ethyl acetate, and washed with aqueous sodium hydrogencarbonate solution and saturated brine. The obtained organic layer was dried over anhydrous sodium sulfate, the solvent was evaporated away under reduced pressure. The resulting residue was recrystallized and purified with n-hexane/ethyl acetate to obtain the entitled compound (912.6 mg, 54%) as a white solid. The filtrate was concentrated under reduced pressure to obtain a crude form (514.3 mg, 30%) as a pale yellow oily substance.
MS (ESI) m/z: 327, 329 (M+1)$^+$.
$^1$H-NMR (CDCl$_3$) δ: 1.49 (6H, s), 2.76 (3H, s), 2.76-2.80 (1H, m), 3.86 (2H, d, J=7.1 Hz), 7.26 (1H, s).

Reference Example 109

6-Bromo-2-[2-methoxy-1,1-dimethylethyl]-7-fluoro-5-methyl-1,3-benzoxazole-4-carbonitrile (I-109)

6-Bromo-7-fluoro-2-(2-hydroxy-1,1-dimethylethyl)-5-methyl-1,3-benzoxazole-4-carbonitrile (I-108) (912.6 mg, 2.79 mmol) and (514 mg, 1.57 mmol) were separately dissolved in methylene chloride (9 ml and 5 ml), and aqueous 42% tetrafluoroboric acid solution (420 µl, 2.79 mmol) and (240 µl, 1.57 mmol) were individually added to each, then with cooling with ice, trimethylsilyldiazomethane (2 M hexane solution, 2.8 ml, 5.58 mmol) and (1.6 ml, 3.14 mmol) were dropwise added, followed by stirring at 0° C. for 40 minutes; but since the reaction did not finish, the same amount of aqueous 42% tetrafluoroboric acid solution and trimethylsilyldiazomethane were added, followed by stirring for 19 hours with heating up to room temperature. After the reaction, the two reaction solutions were combined, water was added, followed by extraction with ethyl acetate and washing with saturated brine. The obtained organic layer was dried over anhydrous sodium sulfate, the solvent was evaporated away under reduced pressure. The resulting residue was subjected to silica gel column chromatography, and eluted with a mixed solvent of n-hexane/ethyl acetate (10:1, v/v) to obtain the entitled compound (1.01 g, 68%) as a white solid.
MS (ESI) m/z: 341, 343 (M+1)$^+$.
$^1$H-NMR (CDCl$_3$) δ: 1.51 (6H, s), 2.75 (3H, s), 3.33 (3H, s), 3.64 (2H, s).

Reference Example 110

2-[1,1-Dimethyl-2-(methoxy)ethyl]-7-fluoro-5-methyl-6-(2-methyl-1,3-thiazol-4-yl)-1,3-benzoxazole-4-carbonitrile (I-110)

6-Bromo-2-[2-methoxy-1,1-dimethylethyl]-7-fluoro-5-methyl-1,3-benzoxazole-4-carbonitrile (I-109) (1.01 g, 2.80 mmol) was dissolved in toluene (20 m), then tributyl(1-ethoxyvinyl)tin (1.04 ml, 3.08 mmol), 2,6-di-tert-butylcresol (6 mg, 0.03 mmol) and bis(triphenylphosphine)palladium(II) dichloride (98 mg, 0.14 mmol) were added, followed by heating under reflux for 6 hours under nitrogen atmosphere. The reaction liquid was cooled, the insoluble matter was separated by filtration through Celite, the solvent was concentrated under reduced pressure. The resulting residue was subjected to silica gel column chromatography, the tin-derived side products were removed with n-hexane, followed by elution with a mixed solvent of n-hexane/ethyl acetate (10:1, v/v) to obtain an ethoxyvinyl form (1.03 g, quant.) as a brown oily substance. The obtained ethoxyvinyl form was dissolved in tetrahydrofuran (50 ml), water (3 ml) and N-bromosuccinimide (617 mg, 3.40 mmol) were added all at a time, followed by stirring at room temperature for 5 hours. After the reaction, the solvent was evaporated away under reduced pressure, followed by dilution with ethyl acetate and washing with aqueous sodium thiosulfate solution and saturated brine. The obtained organic layer was dried over anhydrous sodium sulfate, and the solvent was evaporated away under reduced pressure. The resulting residue was subjected to silica gel column chromatography, eluted with a mixed solvent of n-hexane/ethyl acetate (9:1→4:1, v/v) to obtain a bromoacetyl form (994 mg, 2.60 mmol, 84%) as a colorless transparent oily substance. The obtained bromoacetyl form was dissolved in toluene (30 ml), cesium carbonate (1.18 g, 3.63 mmol) and thioacetamide (234 mg, 3.11 mmol) were added followed by heating under reflux for 1.5 hours tinder nitrogen atmosphere. The reaction liquid was cooled, the insoluble matter was separated by filtration through Celite, ethyl acetate was added to the filtrate, followed by washing with water and saturated brine. The obtained organic layer was dried over anhydrous sodium sulfate, the solvent was evaporated away under reduced pressure. The resulting residue was subjected to silica gel column chromatography, eluted with a mixed solvent of n-hexane/ethyl acetate (4:1, v/v) to obtain the entitled compound (390 mg, 42%) as a red white solid.

MS (ESI) m/z: 360 (M+1)$^+$.

$^1$H-NMR (CDCl$_3$) δ: 1.52 (6H, s), 2.53 (3H, s), 2.80 (3H, s), 3.34 (3H, s), 3.66 (2H, s), 7.20 (1H, s).

Example 36

7-[(3S)-3-(Dimethylamino)pyrrolidin-1-yl]-2-(2-methoxy-1,1-dimethylethyl)-5-methyl-6-(2-methyl-1,3-thiazol-4-yl)-1,3-benzoxazole-4-carbonitrile hydrochloride (#36)

2-[2-methoxy-1,1-dimethylethyl]-7-fluoro-5-methyl-6-(2-methyl-1,3-thiazol-4-yl)-1,3-benzoxazole-4-carbonitrile (I-110) (390 mg, 1.09 mmol) was dissolved in dimethyl sulfoxide (8 ml), and triethylamine (366 μl, 2.61 mmol) and (3S)-3-(dimethylamino)pyrrolidine (165 μl, 1.30 mmol) were added, followed by stirring at 80° C. for 1.5 hours under nitrogen atmosphere. After cooling to room temperature, ethyl acetate was added, followed by fractionation with water. The organic layer was washed with saturated brine, and dried over anhydrous sodium sulfate. The solvent was evaporated away, and the resulting residue was subjected to NH silica gel column chromatography, eluted with a mixed solvent of n-hexane/ethyl acetate (1:2, v/v) to obtain a oily substance. At this point in time, crystallization was tried, but solidification was impossible, and therefore, this was dissolved in 1,4-dioxane (8 ml), 4N hydrochloric acid/dioxane solution (0.3 ml) was added, followed by stirring at room temperature for 6 hours. The precipitated solid was collected by filtration, washed with n-hexane and ethyl acetate to obtain the entitled compound (520 mg, 90%) as a white solid.

MS (ESI) m/z: 454 (M+1)$^+$.

$^1$H-NMR (DMSO-d$_6$) δ: 1.44 (6H, s), 2.14 (3H, s), 2.08-2.24 (2H, m), 2.64 (3H, brs), 2.69 (3H, brs), 2.73 (3H, s), 3.21-3.26 (1H, m), 3.27 (3H, s), 3.35-3.42 (1H, m), 3.53-3.66 (5H, m), 3.89 (1H, s), 7.40 (1H, s), 11.19 (1H, brs).

IR (ATR): 2214, 1608, 1471, 1446, 1103 cm$^{-1}$.

Anal. Calcd for C$_{24}$H$_{31}$N$_5$O$_2$S.1.75HCl.0.75H$_2$O: C, 54.29; H, 6.50; N, 13.19; S, 6.04; Cl, 11.69. Found: C, 54.08; H, 6.33; N, 12.59; S, 6.54; Cl, 12.32.

Reference Example 111

Ethyl-4-cyano-7-fluoro-5-methyl-6-phenyl-1,3-benzoxazole-2-carboxylate (I-111)

4-Amino-6-fluoro-5-hydroxy-2-methylbiphenyl-3-carbonitrile (I-41) (5.0 g, 20.64 mmol) and ethyl methoxyacetate (18.18 g, 82.56 mmol) were stirred at 100° C. for 23 hours under nitrogen atmosphere. The reaction liquid was cooled to room temperature, and left at the same temperature for 17 hours. At 0° C., hexane was added to the suspension, and left at the same temperature for 1 hour. With washing with hexane, the precipitated crystal was collected by filtration. The crystal was collected, dried at 50° C. under reduced pressure for 4 hours, and then at room temperature for 12 hours to obtain the entitled compound (6.39 g, 96%) as a pale brown powder.

MS (ESI) m/z: 325 (M+1)$^+$.

HRMS (EI) m/z: 324.0908 (Calcd for C$_{18}$H$_{13}$N$_2$O$_3$ 324.0911).

$^1$H-NMR (CDCl$_3$) δ: 1.52 (3H, t, J=7.1 Hz), 2.48 (3H, s), 4.60 (2H, q, J=7.1 Hz), 7.25-7.29 (2H, m), 7.48-7.56 (3H, m).

IR (ATR): 2229, 1740, 1547, 1475, 1288, 1182, 1157, 1124, 1011, 849, 779, 727, 702 cm$^{-1}$.

Example 37

Ethyl-4-cyano-7-[(3S)-3-(dimethylamino)pyrrolidin-1-yl]-5-methyl-6-phenyl-1,3-benzoxazole-2-carboxylate (#37)

Ethyl-4-cyan-7-fluoro-5-methyl-6-phenyl-1,3-benzoxazole-2-carboxylate 111 (200 mg, 0.62 mmol) was dissolved in dimethyl sulfoxide (12 ml), and at room temperature, triethylamine (112 μl, 0.80 mmol) was added. Next, the solution was heated at 150° C., and a solution of (3S)-3-(dimethylamino)pyrrolidine (94 μl, 0.74 mmol) dissolved in dimethyl sulfoxide (2 ml) was added all at a time, followed by further stirring for 1 hour. The mixture liquid was cooled to room temperature, then this was fractionated with ethyl acetate and saturated brine. The aqueous layer was separated, this was extracted twice with ethyl acetate. The organic layers were combined, washed with saturated brine, and dried over anhydrous sodium sulfate. The insoluble matter was separated by filtration, the solvent was evaporated away, and the resulting residue was purified by preparative TLC (eluent, chloroform:methanol=98:2) to obtain the entitled compound (17.5 mg, 7%) as a yellow powdery crystal.

MS (ESI) m/z: 419 (M+1)$^+$.

HRMS (EI) m/z: 418.2016 (Calcd for C$_{24}$H$_{26}$N$_4$O$_3$ 418.2005).

$^1$H-NMR (CDCl$_3$) δ: 1.48 (3H, t, J=7.1 Hz), 1.59-1.70 (1H, m), 1.97-2.05 (1H, m), 2.12 (6H, s), 2.22 (3H, s), 2.49-2.57 (1H, m), 2.91 (1H, t, J=10.0 Hz), 3.31 (1H, dd, J=7.1, 10.0 Hz), 3.50-3.58 (2H, m), 4.55 (2H, q, J=7.1 Hz), 7.11-7.15 (1H, m), 7.26-7.29 (1H, m), 0.36-7.46 (3H, m).

IR (ATR): 2208, 1739, 1603, 1471, 1392, 1369, 1304, 1261, 1174, 1149 cm$^{-1}$.

Anal. Calcd for C$_{24}$H$_{26}$N$_4$O$_3$.0.25H$_2$O: C, 68.15; H, 6.31; N, 13.25. Found: C, 68.18; H, 6.15; N, 13.02.

Reference Example 112

7-Fluoro-2-(1-hydroxy-1-methylethyl)-5-methyl-6-phenyl-1,3-benzoxazole-4-carbonitrile (I-112)

Ethyl 4-cyano-7-fluoro-5-methyl-6-phenyl-1,3-benzoxazole-2-carboxylate (I-111) (100 mg, 0.31 mmol) was dissolved in tetrahydrofuran (3 ml), and under nitrogen atmosphere at 0° C., methylmagnesium bromide (0.93 M tetrahydrofuran solution, 1.0 ml, 0.93 mmol) was gradually added. After stirring at the same temperature for 1 hour, aqueous saturated ammonium chloride solution was added to the solution. After stirring at 0° C. for 15 minutes, this was extracted three times with ethyl acetate. The organic layers were combined, washed with saturated brine, then dried over anhydrous sodium sulfate. The insoluble matter was separated by filtration, the solvent was evaporated away, and the resulting residue was purified by preparative TLC (eluent, hexane:ethyl acetate=5:1) to obtain the entitled compound (36 mg, 38%) as a colorless gel.

MS (ESI) m/z: 311 (M+1)$^+$.

HRMS (EI) m/z: 310.1127 (Calcd for C$_{18}$H$_{15}$FN$_2$O$_2$ 310.1118).

$^1$H-NMR (CDCl$_3$) δ: 1.80 (6H, s), 2.43 (3H, s), 2.80-3.50 (1H, br), 7.23-7.27 (2H, m), 7.46-7.53 (3H, m).

IR (ATR): 3431, 2227, 1560, 1473, 1406, 1321, 1178, 1115, 957, 756, 721, 700 cm$^{-1}$.

Example 38

7-[(3S)-3-(Dimethylamino)pyrrolidin-1-yl]-2-(1-hydroxy-1-methylethyl)-5-methyl-6-phenyl-1,3-benzoxazole-4-carbonitrile (#46)

7-Fluoro-2-(1-hydroxy-1-methylethyl)-5-methyl-6-phenyl-1,3-benzoxazole-4-carbonitrile (I-112) (35 mg, 0.11 mmol) was dissolved in anhydrous dimethyl sulfoxide (2 ml), and at room temperature, triethylamine (24 µl, 0.17 mmol) and (3S)-3-(dimethylamino)pyrrolidine (22 µl, 0.17 mmol) were added. This mixture liquid was stirred at 90° C. for 12 hours, then cooled to room temperature. This was fractionated with ethyl acetate and saturated brine. The aqueous layer was separated, and this was extracted twice with ethyl acetate. The organic layers were combined, this was washed with saturated brine, dried over anhydrous sodium sulfate. The insoluble matter was separated by filtration, the solvent was evaporated away, and the resulting residue was purified by preparative TLC (eluent, chloroform:methanol=9:1) to obtain the entitled compound (41.5 mg, 91%) as a white solid. This was further recrystallized from hexane/diethyl ether to obtain a cream powder (27.5 mg).

MS (ESI) m/z: 405 (M+1)$^+$.

HRMS (EI) m/z: 404.2230 (Calcd for 404.2213).

$^1$H-NMR (CDCl$_3$) δ: 1.57-1.72 (1H, m), 1.70 (6H, s), 1.95 (1H, dt, J=5.6, 6.1 Hz), 2.13 (6H, s), 2.18 (3H, s), 2.50-2.59 (1H, m), 2.99 (1H, t, J=9.0 Hz), 3.20-3.90 (1H, br), 3.25-3.44 (3H, m), 7.08-7.12 (1H, m), 7.23-7.16 (1H, m), 7.33-7.45 (3H, m).

IR (ATR): 3300, 2212, 1604, 1471, 1365, 1190, 1128 cm$^{-1}$.

Anal. Calcd for C$_{24}$H$_{28}$N$_4$O$_2$·0.25H$_2$O: C, 70.48; H, 7.02; N, 13.70. Found: C, 70.73; H, 6.98; N, 13.85.

Reference Example 113

4-Cyano-7-fluoro-N,5-dimethyl-6-phenyl-1,3-benzoxazole-2-carboxamide (I-113)

Under nitrogen atmosphere, trimethylaluminium (1.03 M n-hexane solution, 1.80 ml, 1.85 mmol) was dropwise added to a dichloromethane (2 ml) solution of methylamine hydrochloride (125 mg, 1.85 mmol) at room temperature, and stirred for 40 minutes. Subsequently, a dichloromethane (2 ml) solution of ethyl-4-cyano-7-fluoro-5-methyl-6-phenyl-1,3-benzoxazole-2-carboxylate (I-111) (200 mg, 617 µl) was dropwise added and stirred for 63 hours. After the reaction, aqueous 1 N hydrochloric acid solution was added to the reaction liquid with cooling with ice, followed by stirring at room temperature. The reaction liquid was extracted with chloroform. Next, the obtained organic layers were combined, dried over anhydrous magnesium sulfate, filtered, and the filtrate was concentrated under reduced pressure. The resulting residue was subjected to silica gel column chromatography, and the eluate with dichloromethane/methanol (100:1, v/v) gave the entitled compound (122 mg, 64%) as a pale green solid.

MS (ESI) m/z: 310 (M+1)$^+$.

$^1$H-NMR (CDCl$_3$) δ: 2.47 (3H, s), 3.12 (1.5H, s), 3.13 (1.5H, s), 7.24-7.28 (2H, m), 7.41-7.46 (1H, m), 7.46-7.55 (3H, m).

IR (ATR): 3402, 2233, 1693, 1550, 1504, 1269, 1126 cm$^{-1}$.

Example 39

4-Cyano-7-[(3S)-3-(dimethylamino)pyrrolidin-1-yl]-N,5-dimethyl-6-phenyl-1,3-benzoxazole-2-carboxamide (#39)

A dimethyl sulfoxide (1.5 ml) solution of (3S)-3-(dimethylamino)pyrrolidine (57 µl, 446 µmol) was added to a dimethyl sulfoxide (6 ml) solution of 4-cyano-7-fluoro-N,5-dimethyl-6-phenyl-1,3-benzoxazole-2-carboxamide (I-113) (115 mg, 372 µmol) and triethylamine (67 µl, 484 µmol) at 150° C., followed by stirring at the same temperature for 50 minutes under nitrogen atmosphere.

After cooling, saturated brine was added to the reaction liquid, and the reaction liquid was extracted with ethyl acetate. Next, the combined organic layer was washed with saturated brine, dried over anhydrous magnesium sulfate, filtered, and the filtrate was concentrated under reduced pressure. The resulting residue was subjected to silica gel column chromatography, and the eluate with dichloromethane/methanol (30:1, v/v) gave a crude product of the entitled compound as a solid, and the solid was suspended and washed in ethyl acetate to obtain the entitled compound (18 mg, 12%) as a yellow solid.

mp: 214-216° C. MS (ESI) m/z: 404 (M+1)$^+$.

$^1$H-NMR (CDCl$_3$) δ: 1.53-1.68 (1H, m), 1.96-2.05 (1H, m), 2.10 (6H, s), 2.21 (3H, s), 2.44-2.56 (1H, m), 2.73-2.83 (1H, m), 3.07 (1.5H, s), 3.08 (1.5H, s), 3.19-3.27 (1H, m), 3.58-3.73 (2H, m), 7.11-7.15 (1H, m), 7.23-7.27 (1H, m), 7.34-7.47 (4H, m).

IR (ATR): 2206, 1655, 1595, 1475, 1456, 1394, 1369, 1309, 1151 cm$^{-1}$.

Anal. Calcd for C$_{23}$H$_{25}$N$_5$O$_2$·0.25AcOEt: C, 67.74; H, 6.40; N, 16.46. Found: C, 67.67; H, 6.23; N, 16.52.

Reference Example 114

4-Cyano-7-fluoro-N,N,5-trimethyl-6-phenyl-1,3-benzoxazole-2-carboxamide (I-114)

Under nitrogen atmosphere, trimethylamine (1.03 M n-hexane solution, 2.25 ml, 2.31 mmol) was dropwise added at room temperature to a dichloromethane (3 ml) solution of dimethylamine hydrochloride (189 mg, 2.31 mmol), followed by stilling for 25 minutes. Subsequently, a dichloromethane (2 ml) solution of ethyl 4-cyano-7-fluoro-5-methyl-6-phenyl-1,3-benzoxazole-2-carboxylate (I-111) (250 mg, 771 µmol) was dropwise added, followed by stirring for 17 hours. After the reaction, aqueous 1N hydrochloric acid solution was added to the reaction liquid with cooling with ice, followed by stirring at room temperature, and the reaction liquid was extracted with chloroform. Next, the obtained organic layers were combined, dried oil anhydrous magnesium sulfate, filtered, and the filtrate was concentrated under reduced pressure. The resulting residue was suspended and washed in diethyl ether to obtain the entitled compound (167 mg, 67%) as a white solid.

MS (ESI) m/z: 324 (M+1)$^+$.

$^1$H-NMR (CDCl$_3$) δ: 2.47 (3H, s), 3.23 (3H, s), 3.54 (3H, s), 7.24-7.28 (2H, m), 7.46-7.55 (3H, m).

IR (ATR): 2229, 1658, 1477, 1400, 1255, 1130, 1099 cm$^{-1}$.

Example 40

4-Cyano-7-[(3S)-3-(dimethylamino)pyrrolidin-1-yl]-N,N,5-trimethyl-6-phenyl-1,3-benzoxazole-2-carboxamide (#40)

Under nitrogen atmosphere, a dimethyl sulfoxide (2 ml) solution (3S)-3-(dimethylamino)pyrrolidine (75 μl, 594 μmol) was added at 150° C. to a dimethyl sulfoxide (8 ml) solution of 4-cyano-7-fluoro-N,N,5-trimethyl-6-phenyl-1,3-benzoxazole-2-carboxamide (I-114) (160 mg, 495 μmol) and triethylamine (90 μl, 644 μmol), followed by stirring at the same temperature for 50 minutes.

After cooling, saturated brine was added to the reaction liquid, and the reaction liquid was extracted with ethyl acetate. Next, the combined organic layer was washed with saturated brine, dried over anhydrous magnesium sulfate, filtered, and the filtrate was concentrated under reduced pressure. The resulting residue was subjected to silica gel column chromatography, and the eluate with dichloromethane/methanol (20:1, v/v) gave a crude product of the entitled compound as a solid, and the solid was suspended and washed in diethyl ether to obtain the entitled compound (43 mg, 21%) as a pale dark brown solid.

mp: 139-142° C. MS (ESI) m/z: 41.8 (M+1)$^+$.

$^1$H-NMR (CDCl$_3$) δ: 1.55-1.68 (1H, m), 1.91-2.02 (1H, m), 2.09 (6H, s), 2.22 (3H, s), 2.43-2.55 (1H, m), 2.73-2.81 (1H, m), 3.16-3.26 (1H, m), 3.20 (3H, s), 3.51-3.68 (2H, m), 3.55 (3H, s), 7.10-7.15 (1H, m), 7.24-7.27 (1H, m), 7.34-7.45 (3H, m).

IR (ATR): 2206, 1651, 1603, 1473, 1441, 1396, 1365, 1112 cm$^{-1}$.

Anal. Calcd for C$_{24}$H$_{27}$N$_5$O$_2$.0.25H$_2$O: C, 68.31; H, 6.57; N, 16.60. Found: C, 68.43; H, 6.49; N, 16.37.

Example 40-1

4-Cyano-N,N,5-trimethyl-7-[(3S)-3-(methylamino)pyrrolidin-1-yl]-6-phenyl-1,3-benzoxazole-2-carboxamide (#41)

Under nitrogen atmosphere, a dimethyl sulfoxide (3 ml) solution (3S)-3-methylaminopyrrolidine (139 μl, 1.40 mmol) was added at 150° C. to a dimethyl sulfoxide (18 ml) solution of 4-cyano-7-fluoro-N,N,5-trimethyl-6-phenyl-1,3-benzoxazole-2-carboxamide (I-114) (350 mg, 1.08 mmol) and triethylamine (201 μl, 1.30 mmol), followed by stirring at the same temperature for 4 hours. After cooling, saturated brine was added to the reaction liquid, and the reaction liquid was extracted with ethyl acetate. Next, the combined organic layer was washed with saturated brine, dried over anhydrous magnesium sulfate, filtered, and the filtrate was concentrated under reduced pressure. The resulting residue was subjected to silica gel column chromatography, and the eluate with chloroform/methanol (4:1, v/v) gave a crude product of the entitled compound as a solid, and the solid was suspended and washed in diisopropyl ether to obtain the entitled compound (147 mg, 34%) as a pale yellow solid.

mp: 148-151° C. MS (ESI) m/z: 404 (M+1)$^+$.

$^1$H-NMR (CDCl$_3$) δ: 1.58-1.67 (1H, m), 1.86-1.96 (1H, m), 2.22 (3H, s), 2.31 (3H, s), 2.94-2.98 (1H, m), 3.05-3.12 (1H, m), 3.20 (3H, s), 3.28-3.33 (1H, m), 3.52-3.36 (2H, m), 3.56 (3H, s), 7.18-7.20 (2H, m), 7.35-7.44 (3H, m).

IR (ATR): 2208, 1652, 1602, 1467, 1438, 1396, 1365, 1111, 704 cm$^{-1}$.

Anal. Calcd for C$_{23}$H$_{25}$N$_5$O$_2$.0.25H$_2$O: C, 67.71; H, 6.30; N, 17.71. Found: C, 67.59; H, 6.23; N, 16.84.

Example 40-2

4-Cyano-N,N,5-trimethyl-7-[(3R)-3-(dimethylamino)pyrrolidin-1-yl]-6-phenyl-1,3-benzoxazole-2-carboxamide (#40-2)

Under nitrogen atmosphere, a dimethyl sulfoxide (2 ml) solution of (3R)-3-methylaminopyrrolidine (85 μl, 660 μmol) was added at 150° C. to a dimethyl sulfoxide (11 ml) solution of 4-cyano-7-fluoro-N,N,5-trimethyl-6-phenyl-1,3-benzoxazole-2-carboxamide (I-114) (180 mg, 557 μmol) and triethylamine (101 μl, 724 μmol), followed by stirring at the same temperature for 30 minutes. After cooling, saturated brine was added to the reaction liquid, and the reaction liquid was extracted with chloroform. Next, the combined organic layer was washed with saturated brine, dried over anhydrous magnesium sulfate, filtered, and the filtrate was concentrated under reduced pressure. The resulting residue was subjected to preparative silica gel column chromatography. The eluate with chloroform/methanol (10:1, v/v) gave the entitled compound (53 mg, 23%) as a white amorphous substance.

mp: 67-70° C. MS (ESI) m/z: 4.18 (M+1)$^+$.

$^1$H-NMR (CDCl$_3$) δ: 1.55-1.68 (1H, m), 1.91-2.02 (1H, m), 2.09 (6H, s), 2.22 (3H, s), 2.43-2.55 (1H, m), 2.73-2.81 (1H, m), 3.16-3.26 (1H, m), 3.20 (3H, s), 3.51-3.68 (2H, m), 3.55 (3H, s), 7.10-7.15 (1H, m), 7.24-7.27 (1H, m), 7.34-7.45 (3H, m).

IR (ATR): 2210, 1654, 1604, 1471, 1440, 1396, 1365, 1106 cm$^{-1}$.

Anal. Calcd for C$_{24}$H$_{27}$N$_5$O$_2$.0.5H$_2$O: C, 67.59; H, 6.62; N, 16.42. Found: C, 67.79; H, 6.59; N, 16.00.

Example 40-3

4-Cyano-N,N,5-trimethyl-7-[(3R)-3-(methylamino)pyrrolidin-1-yl]-6-phenyl-1,3-benzoxazole-2-carboxamide (#40-3)

Under nitrogen atmosphere, a dimethyl sulfoxide (3 ml) solution of (3R)-3-methylaminopyrrolidine (95 μl, 0.88 mmol) was added at 150° C. to a dimethyl sulfoxide (17 ml) solution of 4-cyano-7-fluoro-N,N,5-trimethyl-6-phenyl-1,3-benzoxazole-2-carboxamide (I-114) (271 mg, 0.838 mmol) and triethylamine (156 μl, 1.09 mmol), followed by stirring at the same temperature for 30 minutes. After cooling, saturated brine was added to the reaction liquid, and the reaction liquid was extracted with chloroform.

Next, the combined organic layer was washed with saturated brine, dried over anhydrous magnesium sulfate, filtered, and the filtrate was concentrated under reduced pressure. The resulting residue was subjected to silica gel column chromatography, and the eluate with chloroform/methanol (10:1, v/v) gave a crude product of the entitled compound as a solid, and the solid was suspended and washed in diisopropyl ether to obtain the entitled compound (52 mg, 15%) as a pale yellow solid.

mp: 145-148° C. MS (ESI) m/z: 404 (M+1)$^+$.

$^1$H-NMR (CDCl$_3$) δ: 1.58-1.67 (1H, m), 1.86-1.96 (1H, m), 2.22 (3H, s), 2.31 (3H, s), 2.94-2.98 (1H, m), 3.05-3.12 (1H, m), 3.20 (3H, s), 3.28-3.33 (1H, m), 3.52-3.36 (2H, m), 3.56 (3H, s), 7.18-7.20 (2H, m), 7.35-7.44 (3H, m).

IR (ATR): 2208, 1653, 1603, 1468, 1439, 1396, 1365, 1111, 704 cm$^{-1}$.

Anal. Calcd for $C_{23}H_{25}N_5O_2 \cdot 0.5H_2O$: C, 66.97; H, 6.35; N, 16.98. Found: C, 66.88; H, 6.23; N, 16.65.

Reference Example 115

4-Cyano-7-fluoro-N-methoxy-N,5-dimethyl-6-phenyl-1,3-benzoxazole-2-carboxamide (I-115)

N,O-dimethylhydroxylamine hydrochloride (1.81 g, 18.5 mmol) was suspended in dichloromethane (40 ml), and trimethylaluminium (1.03 hexane solution, 17.96 ml, 18.5 mmol) was added at 0° C. under nitrogen atmosphere. After stirring at room temperature for 30 minutes, a solution of ethyl 4-cyano-7-fluoro-5-triethyl-6-phenyl-1,3-benzoxazole-2-carboxylate (I-111) (2.0 g, 6.17 mmol) dissolved in dichloromethane (20 ml) was gradually added at 0° C. After stirring at room temperature for 6.5 hours, aqueous 1 M hydrochloric acid solution (60 ml) was gradually added at 0° C., followed by stirring at the same temperature for 10 minutes. The solution was extracted three times with dichloromethane. The organic layers were combined, washed with saturated brine, dried over anhydrous sodium sulfate. The insoluble matter was separated by filtration, the solvent was evaporated away under reduced pressure, the resulting residue was purified by middle-pressure liquid chromatography (eluent, hexane: ethyl acetate=3:1) to obtain the entitled compound (1.932 g, 92%) as a white solid.

MS (ESI) m/z: 340 (M+1)$^+$.

HRMS (EI) m/z: 339.1019 (Calcd for $C_{18}H_{14}FN_3O_3$ 339.1019).

$^1$H-NMR (CDCl$_3$) δ: 2.47 (3H, s), 3.44 (3H, brs), 4.00 (3H, brs), 7.26-7.29 (2H, m), 7.49-7.55 (3H, m).

IR (ATR): 2227, 1668, 1124, 983, 957, 752, 723, 700 cm$^{-1}$.

Example 43

4-Cyano-7-[(3S)-3-(dimethylamino)pyrrolidin-1-yl]-N-methoxy-N,5-dimethyl-6-phenyl-1,3-benzoxazole-2-carboxamide (#41)

4-Cyano-7-fluoro-N-methoxy-N,5-dimethyl-6-phenyl-1,3-benzoxazole-2-carboxamide (I-115) (200 mg, 0.59 mmol) was dissolved in dimethyl sulfoxide (10 ml), and at room temperature, triethylamine (99 μl, 0.71 mmol) was added. Next, the solution was heated at 150° C., and a solution of (3S)-3-(dimethylamino)pyrrolidine (90 μl, 0.71 mmol) dissolved in dimethyl sulfoxide (2 ml) was added all at a time, followed by further stirring for 1.5 hours. The mixture liquid was cooled to room temperature, then this was fractionated with ethyl acetate and saturated brine. The aqueous layer was separated, this was extracted twice with ethyl acetate. The organic layers were combined, washed with saturated brine, and dried over anhydrous sodium sulfate. The insoluble matter was separated by filtration, the solvent was evaporated away, the resulting residue was purified by preparative TLC (eluent, chloroform:methanol=94:6) to obtain the entitled compound (81 mg, 32%) as a brown amorphous substance.

MS (ESI) m/z: 434 (M+1)$^+$.

HRMS (EI) m/z: 433.2124 (Calcd for $C_{24}H_{27}N_5O_3$ 433.2114).

$^1$H-NMR (CDCl$_3$) δ: 1.62 (1H, dq, J=10.5, 10.5 Hz), 1.92-2.02 (1H, m), 2.10 (6H, s), 2.22 (3H, s), 2.48-2.57 (1H, m), 2.82 (1H, t, J=9.3 Hz), 3.26 (1H, dd, J=7.1, 10.0 Hz), 3.30-3.70 (3H, br), 3.51-3.60 (2H, m), 3.70-4.15 (3H, br), 7.13 (1H, d, J=7.8 Hz), 7.26 (1H, d, J=6.6 Hz), 7.34-7.46 (3H, m).

IR (ATR): 2212, 1664, 1603, 1471, 1439, 1394, 1367, 1304, 1155, 987, 702 cm$^{-1}$.

Anal. Calcd for $C_{24}H_{27}N_5O_3 \cdot 0.75H_2O$: C, 64.49; H, 6.43; N, 15.67. Found: C, 67.13; H, 6.14; N, 15.07.

Reference Example 116

4-Cyano-7-fluoro-N,5-dimethyl-6-phenyl-N-pyridin-1-yl-1,3-benzoxazole-2-carboxamide (I-116)

Under nitrogen atmosphere, trimethylaluminium (1.03 M n-hexane solution, 1.91 ml, 1.23 mmol) was dropwise added to a dichloromethane (2 ml) solution of 2-(methylamino) pyridine (133 mg, 1.23 mmol) at room temperature, and stirred for 1 hour. Subsequently, a dichloromethane (2 ml) solution of ethyl 4-cyano-7-fluoro-5-methyl-6-phenyl-1,3-benzoxazole-2-carboxylate (I-111) (200 mg, 617 μl) was dropwise added and stirred for 63 hours. After the reaction, aqueous 1 N hydrochloric acid solution was added to the reaction liquid with cooling with ice, followed by stirring at room temperature. The reaction liquid was extracted with chloroform. Next, the obtained organic layers were combined, dried over anhydrous magnesium sulfate, filtered, and the filtrate was concentrated under reduced pressure. The resulting residue was suspended and washed in diethyl ether to obtain the entitled compound (198 mg, 83%) as a pale green solid.

MS (ESI) mix 387 (M+1)$^+$.

$^1$H-NMR (CDCl$_3$) δ: 2.40 (3H, s), 3.67 (3H, s), 7.17-7.26 (3H, m), 7.32-7.39 (1H, m), 7.44-7.53 (3H, m), 7.77-7.82 (1H, m), 8.23 (1H, d, J=3.7 Hz).

IR (ATR): 2224, 1658, 1468, 1437, 1306, 1122 cm$^{-1}$.

Example 42

4-Cyano-7-[(3S)-3-(dimethylamino)pyrrolidin-1-yl]-N,5-dimethyl-6-phenyl-N-pyridin-2-yl-1,3-benzoxazole-2-carboxamide (#42)

Under nitrogen atmosphere, a dimethyl sulfoxide (2 ml) solution of (3R)-3-(dimethylamino)pyrrolidine (74 μl, 581 μmol) was added at 150° C. to a dimethyl sulfoxide (17 ml) solution of 4-cyano-7-fluoro-N,5-dimethyl-6-phenyl-N-pyridin-1-yl-1,3-benzoxazole-2-carboxamide (I-116) (187 mg, 484 μmmol) and triethylamine (88 μl, 629 μmol), followed by stirring at the same temperature for 3 hours. After cooling, saturated brine was added to the reaction liquid, and the reaction liquid was extracted with ethyl acetate. Next, the combined organic layer was washed with saturated brine, dried over anhydrous magnesium sulfate, filtered, and the filtrate was concentrated under reduced pressure. The resulting residue was subjected to silica gel column chromatography, and the eluate with dichloromethane/methanol (20:1, v/v) gave the entitled compound (47 mg, 20%) as an amorphous substance.

MS (ESI) m/z: 481 (M+1)$^+$.

$^1$H-NMR (CDCl$_3$) δ: 1.50-1.70 (1H, m), 1.89-1.99 (1H, m), 2.09 (6H, s), 2.16 (3H, s), 2.41-2.53 (1H, m), 2.67-2.79 (1H, m), 3.12-3.21 (1H, m), 3.40-3.50 (2H, m), 3.67 (3H, s), 7.10 (1H, d, J=7.3 Hz), 7.18-7.53 (6H, m), 7.74-7.80 (1H, m), 8.33 (1H, d, J=3.7 Hz).

IR (ATR): 2210, 1670, 1604, 1587, 1471, 1437, 1365 cm$^{-1}$.

Reference Example 117

7-Fluoro-5-methyl-6-phenyl-2-(piperidin-1-ylcarbonyl)-1,3-benzoxazole-4-carbonitrile (I-117)

Under nitrogen atmosphere, trimethylaluminium (1.03 M n-hexane solution, 898 μl, 925 μmol) was dropwise added to a dichloromethane (1 ml) solution of piperidine (92 μl, 925 μmol) at room temperature, and stirred for 15 minutes. Subsequently, a dichloromethane (2 ml) solution of ethyl 4-cyano-7-fluoro-5-methyl-6-phenyl-1,3-benzoxazole-2-carboxylate (I-111) (150 mg, 463 μl) was dropwise added and stirred for 63 hours. After the reaction, aqueous 1 N hydrochloric acid solution was added to the reaction liquid with cooling with ice, followed by stirring at room temperature. The reaction liquid was extracted with chloroform. Next, the obtained organic layers were combined, dried over anhydrous magnesium sulfate, filtered, and the filtrate was concentrated under reduced pressure. The resulting residue was subjected to silica gel column chromatography, and the eluate with n-hexane/ethyl acetate (4:1, v/v) gave the entitled compound (62 mg, 37%) as a white solid.

MS (ESI) m/z: 364 (M+1)$^+$.
$^1$H-NMR (CDCl$_3$) δ: 1.70-1.78 (6H, m), 2.47 (3H, s), 3.78-3.83 (2H, m), 3.93-3.98 (2H, m), 7.24-7.28 (2H, m), 7.45-7.55 (3H, m).

Example 43

7-[(3S)-3-(dimethylamino)pyrrolidin-1-yl]-5-methyl-6-phenyl-2-(piperidin-1-ylcarbonyl)-1,3-benzoxazole-2-carbonitrile (#43)

Under nitrogen atmosphere, a dimethyl sulfoxide (700 μl) solution of (3S)-3-(dimethylamino)pyrrolidine (24 μl, 192 μmol) was added at 150° C. to a dimethyl sulfoxide (2.5 ml) solution of 7-fluoro-5-methyl-6-phenyl-2-(piperidin-1-ylcarbonyl)-1,3-benzoxazole-4-carbonitrile (I-117) (58 mg, 160 μmol) and triethylamine (29 μl, 208 μmol), followed by stirring at the same temperature for 75 minutes. After cooling, saturated brine was added to the reaction liquid, and the reaction liquid was extracted with ethyl acetate. Next, the obtained organic layers were combined, dried over anhydrous magnesium sulfate, filtered, and the filtrate was concentrated under reduced pressure. The resulting residue was subjected to silica gel column chromatography, and the eluate with dichloromethane/methanol (20:1, v/v) gave a crude product of the entitled compound as a solid, and the solid was recrystallized from diisopropyl ether/n-hexane to obtain the entitled compound (23 mg, 31%) as a pale yellow solid.

mp: 170-173° C. MS (ESI) m/z: 458 (M+1)$^+$.
$^1$H-NMR (CDCl$_3$) δ: 1.54-1.65 (1H, m), 1.74 (6H, s), 1.92-2.02 (1H, m), 2.08 (6H, s), 2.22 (3H, s), 2.43-2.54 (1H, m), 2.71-2.81 (1H, m), 3.18-3.26 (1H, m), 3.55-3.68 (2H, m), 3.75-3.80 (2H, m), 4.00-4.05 (2H, m), 7.10-7.14 (1H, m), 7.23-7.27 (1H, m), 7.34-7.45 (3H, m).
IR (ATR): 2208, 1651, 1603, 1572, 1468, 1444 cm$^{-1}$.
Anal. Calcd for C$_{27}$H$_{31}$N$_5$O$_2$.0.25H$_2$O: C, 70.18; H, 6.87; N, 15.16. Found: C, 70.31; H, 6.91; N, 14.88.

Reference Example 118

7-Fluoro-5-methyl-2-(morpholin-4-ylcarbonyl)-6-phenyl-1,3-benzoxazole-4-carbonitrile (I-118)

Morpholine (269 μl, 3.08 mmol) was dissolved in dichloromethane (3 ml), and under nitrogen atmosphere at room temperature, trimethylaluminium (1.03 M hexane solution, 2.99 ml, 3.08 mmol) was added. After stirring at the same temperature for 15 minutes, a solution of ethyl 4-cyano-7-fluoro-5-methyl-6-phenyl-1,3-benzoxazole-2-carboxylate (I-111) (500 mg, 1.54 mmol) dissolved in dichloromethane (7 ml) was added at the same temperature. After stirring at the same temperature for 30 hours, an aqueous 1 M hydrochloric acid solution was gradually added at 0° C. The solution was extracted three times with dichloromethane. The organic layers were combined, washed with saturated brine, and dried over anhydrous sodium sulfate. The insoluble matter was separated by filtration, the solvent was evaporated away under reduced pressure, and the resulting residue was purified by middle-pressure liquid chromatography (eluent, hexane:ethyl acetate=3:2) to obtain the entitled compound (460 mg, 82%) as a white solid.

MS (ESI) m/z: 366 (M+1)$^+$.
HRMS (EI) m/z: 365.1166 (Calcd for C$_{20}$H$_{16}$FN$_3$O$_3$ 365.1192).
$^1$H-NMR (CDCl$_3$) δ: 2.47 (3H, s), 3.82-3.91 (6H, m), 4.26 (2H, t, J=4.9 Hz), 7.25-7.28 (2H, m), 7.47-7.56 (3H, m).
IR (ATR): 2229, 1655, 1437, 1273, 1113, 1026, 752, 723, 702 cm$^{-1}$.

Example 44

7-[(3S)-3-(Dimethylamino)pyrrolidin-1-yl]-5-methyl-3-(morpholin-4-ylcarbonyl)-6-phenyl-1,3-benzoxazole-4-carbonitrile (#44)

7-Fluoro-5-methyl-2-(morpholin-4-ylcarbonyl)-6-phenyl-1,3-benzoxazole-4-carbonitrile (I-118) (40 mg, 0.11 mmol) was dissolved in dimethyl sulfoxide (2 ml), and at room temperature, triethylamine (20 μl, 0.14 mmol) was added. Next, the solution was heated at 150° C., and a solution of (3S)-3-(dimethylamino)pyrrolidine (17 μl, 0.13 mmol) dissolved in dimethyl sulfoxide (0.5 ml) was added all at a time, followed by further stirring for 1 hour. The mixture liquid was cooled to room temperature, then this was fractionated with ethyl acetate and saturated brine. The organic layer was washed with saturated brine, and dried over anhydrous sodium sulfate. The insoluble matter was separated by filtration, the solvent was evaporated away, and the resulting residue was purified by preparative TLC (eluent, chloroform:methanol=9:1) to obtain the entitled compound (33.7 mg, 67%) as a yellow gel.

MS (ESI) m/z: 460 (M+1)$^+$.
HRMS (EI) m/z: 459.2291 (Calcd for C$_{26}$H$_{29}$N$_5$O$_3$ 459.2271).
$^1$H-NMR (CDCl$_3$) δ: 1.64 (1H, dq, J=10.0, 10.0 Hz), 1.93-2.02 (1H, m), 2.10 (6H, s), 2.22 (3H, s), 2.48-2.57 (1H, m), 2.81 (1H, t, J=10.0 Hz), 3.24 (1H, dd, J=7.1, 10.0 Hz), 3.58-3.63 (2H, m), 3.81-3.87 (6H, m), 4.33 (2H, dd, J=4.2, 5.6 Hz), 7.11-7.13 (1H, m), 7.25 (1H, d, J=6.8 Hz), 7.36-7.45 (3H, m).
IR (ATR): 2212, 1651, 1604, 1473, 1439, 1365, 1115, 1028, 751 cm$^{-1}$.
Anal. Calcd for C$_{26}$H$_{29}$N$_3$O$_3$.0.25H$_2$O: C, 67.30; H, 6.41; N, 15.09. Found: C, 67.52; H, 6.33; N, 14.85.

Reference Example 119

2-[4-Acetylpiperazin-1-yl)-carbonyl]-7-fluoro-5-methyl-6-phenyl-1,3-benzoxazole-4-carbonitrile (I-119)

Under nitrogen atmosphere, trimethylaluminium (1.03 M n-hexane solution, 1.50 ml, 1.54 mmol) was dropwise added to a dichloromethane (3 ml) solution of N-acetylpiperazine (198 mg, 1.54 mmol) at room temperature, and stirred for 20 minutes.

Subsequently, a dichloromethane (2 ml) solution of ethyl 4-cyano-7-fluoro-5-methyl-6-phenyl-1,3-benzoxazole-2-carboxylate (I-111) (250 mg, 771 µl) was dropwise added and stirred for 40.5 hours. After the reaction, aqueous 1 N hydrochloric acid solution was added to the reaction liquid with cooling with ice, followed by stirring at room temperature. The reaction liquid was extracted with chloroform. Next, the obtained organic layers were combined, dried over anhydrous magnesium sulfate, filtered, and the filtrate was concentrated under reduced pressure. The resulting residue was suspended and washed in diethyl ether to obtain the entitled compound (269 mg, 86%) as a pale brown solid.

MS (EST) m/z: 407 (M+1)$^+$.

$^1$H-NMR (CDCl$_3$) δ: 2.18 (3H, s), 2.48 (3H, s), 3.61-3.72 (2H, m), 3.77-3.83 (2H, m), 3.85-3.93 (2H, m), 4.15-4.21 (1H, m), 4.30-4.36 (1H, m), 7.24-7.28 (2H, m), 7.48-7.56 (3H, m).

IR (ATR): 2233, 1655, 1643, 1457, 1444, 1425, 1261, 1126 cm$^{-1}$.

Example 45

2-[(4-acetylpiperazin-1-yl)carbonyl]-7-[(3S)-3-(dimethylamino)pyrrolidin-1-yl]-5-methyl-6-phenyl-1,3-benzoxazole-2-carbonitrile (#45)

Under nitrogen atmosphere, a dimethyl sulfoxide (2 ml) solution of (3S)-3-(dimethylamino)pyrrolidine (99 µl, 782 µmol) was added at 150° C. to a dimethyl sulfoxide (11 ml) solution of 2-[(4-acetylpiperazin-1-yl)carbonyl]-7-fluoro-5-methyl-6-phenyl-1,3-benzoxazole-4-carbonitrile (I-119) (265 mg, 652 µmol) and triethylamine (118 µl, 848 µmol), followed by stirring at the same temperature for 5 hours. After cooling, saturated brine was added to the reaction liquid, and the reaction liquid was extracted with ethyl acetate. Next, the combined organic layer was washed with saturated brine, dried over anhydrous magnesium sulfate, filtered, and the filtrate was concentrated under reduced pressure. The resulting residue was subjected to silica gel column chromatography, and the eluate with dichloromethane/methanol (10:1, v/v) gave a crude product of the entitled compound as a solid, and the solid was suspended and washed in diisopropyl ether to obtain the entitled compound (72 mg, 22%) as an amorphous substance.

mp: 102-105° C.

MS (ESI) m/z: 501 (M+1)$^+$.

$^1$H-NMR (CDCl$_3$) δ: 1.53-1.66 (1H, m), 1.94-2.03 (1H, m), 2.09 (6H, s), 2.18 (3H, s), 2.23 (3H, s), 2.43-2.55 (1H, m), 2.74-2.83 (1H, m), 3.20-3.28 (1H, m), 3.57-3.70 (4H, m), 3.76-3.90 (4H, m), 4.21-4.26 (1H, m), 4.37-4.42 (1H, m), 7.10-7.35 (1H, m), 7.24-7.28 (1H, m), 7.34-7.46 (3H, m).

IR (ATR): 2210, 1647, 1604, 1469, 1435, 1365, 1252, 1155 cm$^{-1}$.

Anal. Calcd for C$_{29}$H$_{32}$N$_6$O$_3$.0.25H$_2$O.0.25iPr$_2$O: C, 66.77; H, 6.84; N, 15.84. Found: C, 66.51; H, 6.61; N, 15.89.

Reference Example 120

4-Cyano-7-fluoro-N,5-dimethyl-6-phenyl-N-(2-phenylethyl)-1,3-benzoxazole-2-carboxamide (I-120)

Under nitrogen atmosphere, trimethylaluminium (1.03 M n-hexane solution, 1.80 ml, 1.85 mmol) was dropwise added at room temperature to a dichloromethane (3 ml) solution of N-methylphenethylamine (269 µl, 1.85 mmol), and stirred for 25 minutes. Subsequently, a dichloromethane (3 ml) solution of ethyl 4-cyano-7-fluoro-5-methyl-6-phenyl-1,3-benzoxazole-2-carboxylate (I-111) (300 mg, 925 µl) was dropwise added and stirred for 14.5 hours. After the reaction, aqueous 1 N hydrochloric acid solution was added to the reaction liquid with cooling with ice, followed by stirring at room temperature, and the reaction liquid was extracted with chloroform.

Next, the obtained organic layers were combined, dried over anhydrous magnesium sulfate, filtered, and the filtrate was concentrated under reduced pressure. The resulting residue was suspended and washed in diethyl ether to obtain the entitled compound (306 mg, 80%) as a pale yellow solid.

MS (ESI) m/z: 414 (M+1)$^+$.

$^1$H-NMR (CDCl$_3$) δ: 2.47 (1H, s), 2.48 (2H, s), 3.00-3.11 (2H, m), 3.25 (2H, s), 3.42 (1H, s), 3.81-3.87 (0.7H, m), 4.16 (1.3H, t, J=7.4 Hz), 7.15-7.37 (7H, m), 7.46-7.56 (3H, m).

IR (ATR): 2225, 1653, 1477, 1454, 1404, 1340, 1252, 1124 cm$^{-1}$.

Example 46

4-Cyano-7-[(3S)-3-(dimethylamino)pyrrolidin-1-yl]-N,5-dimethyl-6-phenyl-N-(2-phenylethyl)-1,3-benzoxazole-2-carboxamide (#46)

Under nitrogen atmosphere, a dimethyl sulfoxide (3 ml) solution of (3S)-3-(dimethylamino)pyrrolidine (110 µl, 871 µmol) was added at 150° C. to a dimethyl sulfoxide (12 ml) solution of 4-cyano-7-fluoro-N,5-dimethyl-6-phenyl-N-(2-phenylethyl)-1,3-benzoxazole-2-carboxamide (I-120) (300 mg, 726 µmol) and triethylamine (132 µl, 944 µmol), followed by stirring at the same temperature for 70 minutes. After cooling, saturated brine was added to the reaction liquid, and the reaction liquid was extracted with ethyl acetate. Next, the combined organic layer was washed with saturated brine, dried over anhydrous magnesium sulfate, filtered, and the filtrate was concentrated under reduced pressure. The resulting residue was subjected to silica gel column chromatography, and the eluate with dichloromethane/methanol (20:1, v/v) gave a crude product of the entitled compound as a solid, and the solid was suspended and washed in diisopropyl ether to obtain the entitled compound (161 mg, 44%) as a pale yellow solid.

mp: 138-141° C. MS (ESI) m/z: 508 (M+1)$^+$.

$^1$H-NMR (CDCl$_3$) δ: 1.54-1.66 (1H, m), 1.93-2.01 (1H, m), 2.09 (6H, s), 2.22 (1H, s), 2.24 (2H, s), 2.43-2.53 (1H, m), 2.68-2.77 (1H, m), 3.01 (0.7H, t, J=7.6 Hz), 3.09 (1.3H, t, J=7.6 Hz), 3.18-3.25 (1H, m), 3.22 (2H, s), 3.48 (1H, s), 3.51-3.68 (2H, m), 3.77-3.83 (0.7H, m), 4.18-4.24 (1.3H, m), 7.11-7.20 (2H, m), 7.24-7.43 (5H, m).

IR (ATR): 2206, 1655, 1595, 1475, 1456, 1394, 1369, 1309, 1151 cm$^{-1}$.

Anal. Calcd for C$_{31}$H$_{33}$N$_5$O$_2$: C, 73.35; H, 6.55; N, 13.80. Found: C, 73.12; H, 6.55; N, 13.68.

Reference Example 121

4-Cyano-7-fluoro-N,5-dimethyl-6-phenyl-N-[2-(2-pyridin-1-yl)ethyl]-1,3-benzoxazole-2-carboxamide (I-121)

Under nitrogen atmosphere, trimethylaluminium (1.03 M n-hexane solution, 2.40 ml, 2.47 mmol) was dropwise added at room temperature to a toluene (6 ml) solution of 2-(2-methylaminoethyl)pyridine (171 µl, 1.23 mmol), and stirred for 40 minutes. Subsequently, a dichloromethane (2 ml) solution of ethyl 4-cyano-7-fluoro-5-methyl-6-phenyl-1,3-benzoxazole-2-carboxylate (I-111) (200 mg, 617 μmol) was dropwise added and stirred for 45 hours. After the reaction, aqueous 1 N hydrochloric acid solution was added to the reaction liquid with cooling with ice, followed by stirring at room temperature, and the reaction liquid was extracted with chloroform. Next, the obtained organic layers were combined, dried over anhydrous magnesium sulfate, filtered, and the filtrate was concentrated under reduced pressure.

The resulting residue was subjected to silica gel column chromatography, and the eluate with ethyl acetate gave the entitled compound (10.5 mg, 60%) as a milky white solid.

MS (ESI) m/z: 415 (M+1)$^+$.

$^1$H-NMR (CDCl$_3$) δ: 2.46 (1H, s), 2.48 (2H, s), 3.21 (0.67H, t, J=7.3 Hz), 3.24 (2H, s), 3.30 (1.33H, t, J=7.3 Hz), 3.44 (1H, s), 4.02 (0.67H, t, J=7.3 Hz), 4.25 (1.33H, t, J=7.3 Hz), 7.13-7.20 (1H, m), 7.25-7.29 (2H, m), 7.45-7.56 (4H, m), 7.66 (1H, ddd, J=15.5, 7.7, 1.7 Hz), 8.43-8.46 (0.67H, m), 8.56-8.59 (0.33H, m).

IR (ATR): 2225, 1653, 1475, 1429, 1396, 1126 cm$^{-1}$.

Example 47

4-Cyano-7-[(3S)-3-(dimethylamino)pyrrolidin-1-yl]-N,5-dimethyl-6-phenyl-N-[2-(2-pyridin-1-yl)ethyl]-1,3-benzoxazole-2-carboxamide (#47)

Under nitrogen atmosphere, a dimethyl sulfoxide (1 ml) solution of (3S)-3-(dimethylamino)pyrrolidine (55 μl, 434 μmol) was added at 140 to 150° C. to a dimethyl sulfoxide (6 ml) solution of 4-cyano-7-fluoro-N,5-dimethyl-6-phenyl-N-[2-(2-pyridin-1-yl)ethyl]-1,3-benzoxazole-2-carboxamide (I-121) (150 mg, 362 μmol) and triethylamine (66 μl, 471 μmol), followed by stirring at the same temperature for 2 hours. After cooling, saturated brine was added to the reaction liquid, and the reaction liquid was extracted with ethyl acetate. Next, the obtained organic layers were combined, dried over anhydrous magnesium sulfate, filtered, and the filtrate was concentrated under reduced pressure. The resulting residue was subjected to silica gel column chromatography, and the eluate with dichloromethane/methanol (10:1, v/v) gave the entitled compound (87 mg, 47%) as an amorphous substance.

MS (ESI) m/z: 509 (M+1)$^+$.

$^1$H-NMR (CDCl$_3$) δ: 1.94-2.03 (2H, m), 2.10 (6H, s), 2.22 (1H, s), 2.24 (2H, s), 2.45-2.58 (1H, m), 2.73-2.82 (1H, m), 3.17-3.27 (2H, m), 3.23 (2H, s), 3.32-3.38 (1H, m), 3.47 (1H, s), 3.55-3.67 (2H, m), 3.96-4.01 (0.67H, m), 4.22-4.28 (1.33H, m), 7.11-7.19 (2H, m), 7.23-7.30 (1H, m), 7.34-7.46 (3.33H, m), 7.61-7.73 (1.67H, m), 8.47-8.50 (0.67H, m), 8.56-8.59 (0.33H, m).

IR (ATR): 2210, 1653, 1603, 1576, 1471, 1435, 1396, 1365, 1306, 1146 cm$^{-1}$.

Anal. Calcd for C$_{30}$H$_{32}$N$_6$O$_2$.0.75H$_2$O; C, 69.01; H, 6.47; N, 16.10. Found: C, 69.50; H, 6.53; N, 15.69.

Reference Example 122

4-Cyano-7-fluoro-N-(2-(methoxyethyl)-N,5-dimethyl-6-phenyl-1,3-benzoxazole-2-carboxamide (I-122)

Under nitrogen atmosphere, triethylaluminium (1.03 M n-hexane solution, 1.19 ml, 1.23 mmol) was dropwise added at room temperature to a dichloromethane (2 ml) solution of N-(2-methoxyethyl)methylamine (110 mg, 1.23 mmol), and stirred for 20 minutes. Subsequently, a dichloromethane (2 ml) solution of ethyl 4-cyano-7-fluoro-5-methyl-6-phenyl-1,3-benzoxazole-2-carboxylate (I-111) (200 mg, 617 μmol) was dropwise added and stirred for 20 hours. After the reaction, aqueous 3 N hydrochloric acid solution was added to the reaction liquid with cooling with ice, followed by stirring at room temperature, and the reaction liquid was extracted with chloroform. Next, the obtained organic layers were combined, dried over anhydrous magnesium sulfate, filtered, and the filtrate was concentrated under reduced pressure. The resulting residue was suspended and washed with diethyl ether to obtain entitled, compound (175 mg, 77%) as a white solid.

MS (ESI) m/z: 368 (M+1)$^+$.

$^1$H-NMR (CDCl$_3$) δ: 2.46 (1.4H, s), 2.47 (1.6H, s), 3.25 (1.6H, s), 3.32 (1.6H, s), 3.40 (1.4H, s), 3.58 (1.4H, s), 3.65 (1.1H, J=5.2 Hz), 3.70 (0.9H, t, J=5.2 Hz), 3.81 (0.9H, t, J=5.2 Hz), 4.12 (1.1H, t, J=5.2 Hz), 7.24-7.28 (2H, m), 7.45-7.55 (3H, m).

IR (ATR): 2227, 1651, 1454, 1406, 1333, 1186, 1122, 1088 cm$^{-1}$.

Example 48

4-Cyano-7-[(3S)-3-(dimethylamino)pyrrolidin-1-yl]-N-(2-methoxyethyl)-N,5-dimethyl-6-phenyl-1,3-benzoxazole-2-carboxamide (#48)

Under nitrogen atmosphere, a dimethyl sulfoxide (2 ml) solution of (3S)-3-(dimethylamino)pyrrolidine (70 μl, 552 μmol) was added at 150° C. to a dimethyl sulfoxide (7 ml) solution of 4-cyano-7-fluoro-N-(2-methoxyethyl)-N,5-dimethyl-6-phenyl-1,3-benzoxazole-2-carboxamide (I-122) (169 mg, 460 μmol) and triethylamine (83 μl, 598 μmol), followed by stirring at the same temperature for 2 hours. After cooling, saturated brine was added to the reaction liquid, and the reaction liquid was extracted with ethyl acetate. Next, the combined organic layer was washed with saturated brine, dried over anhydrous magnesium sulfate, filtered, and the filtrate was concentrated under reduced pressure. The resulting residue was subjected to silica gel column chromatography, and the eluate with dichloromethane/methanol (20:1, v/v) gave the entitled compound (112 mg, 53%) as an amorphous substance.

MS (ESI) m/z: 462 (M+1)$^+$.

$^1$H-NMR (CDCl$_3$) δ: 1.54-1.68 (1H, m), 1.93-2.02 (1H, m), 2.08 (6H, s), 2.21-2.23 (3H, m), 2.43-2.55 (1H, m), 2.70-2.80 (1H, m), 3.19-3.25 (1H, m), 3.23 (1.7H, s), 3.34 (1.7H, s), 3.39 (1.3H, s), 3.56-3.72 (4H, m), 3.61 (1.3H, s), 3.76-3.81 (0.9H, m), 4.09-4.22 (1.1H, m), 7.13 (1H, d, J=7.1 Hz), 7.24-7.27 (1H, m), 7.33-7.45 (3H, m).

IR (ATR): 2210, 1653, 1471, 1396, 1365, 1099 cm$^{-1}$.

Anal. Calcd for C$_{26}$H$_{31}$N$_5$O$_3$.0.25H$_2$O: C, 67.00; H, 6.81; N, 15.03. Found: C, 66.94; H, 6.77; N, 14.99.

Reference Example 123

[2-(tert-Butyldiphenylsiloxy)ethyl]methylamine (I-123)

Under nitrogen atmosphere, an N,N-dimethylformamide (33 ml) solution of tert-butylchlorodiphenylsilane (8.78 g, 32.0 mmol) was dropwise added at room temperature to an N,N-dimethylformamide (100 ml) solution of N-methylethanolamine (2.00 g, 26.6 mmol) and imidazole (2.72 g, 39.9 mmol), and stirred for 5.5 hours. The solvent was evaporated away under reduced pressure, then the residue was dissolved in ethyl acetate, and the solution was washed with saturated sodium hydrogencarbonate water, water and saturated brine. Next, the organic layer was dried over anhydrous magnesium sulfate, filtered, and the filtrate was concentrated under reduced pressure. The resulting residue was subjected to silica gel column chromatography, and the eluate with ethyl acetate gave the entitled compound (3.21 g, 39%) as a pale yellow oil.

MS (ESI) m/z: 314 (M+1)$^+$. $^1$H-NMR (CDCl$_3$) δ: 1.05 (9H, s), 2.44 (3H, s), 2.70-2.74 (2H, m), 3.75-3.79 (2H, m), 7.35-7.45 (6H, m), 7.64-7.69 (4H, m). IR (ATR): 1471, 1427, 1105, 1086 cm$^{-1}$.

Reference Example 124

N-[2-(tert-Butyldiphenylsiloxy)ethyl]-4-cyano-7-fluoro-N,5-dimethyl-6-phenyl-1,3-benzoxazole-2-carboxamide (I-124)

Under nitrogen atmosphere, trimethylaluminium (1.03 M n-hexane solution, 1.05 ml, 1.54 mmol) was dropwise added at room temperature to a dichloromethane (3 ml) solution of [2-(tert-butyldiphenylsiloxy)ethyl]methylamine (I-123) (483 mg, 1.54 mmol), and stirred for 40 minutes. Subsequently, a dichloromethane (2 ml) solution of ethyl 4-cyano-7-fluoro-5-methyl-6-phenyl-1,3-benzoxazole-2-carboxylate (I-111) (250 mg, 771 μmol) was dropwise added and stirred for 16 hours. After the reaction, aqueous 1 N hydrochloric acid solution was added to the reaction liquid with cooling with ice, followed by stirring at room temperature, and the reaction liquid was extracted with chloroform. Next, the obtained organic layers were combined, dried over anhydrous magnesium sulfate, filtered, and the filtrate was concentrated under reduced pressure. The resulting residue was subjected to silica gel column chromatography, and the eluate with n-hexane/ethyl acetate (3:1, v/v) gave the entitled compound (304 mg, 67%) as an amorphous substance.

MS (ESI) m/z: 614 (M+23)$^+$.
$^1$H-NMR (CDCl$_3$) δ: 0.95 (5.5H, s), 1.07 (3.5H, s), 2.45 (1.8H, s), 2.48 (1.2H, s), 3.19 (1.8H, s), 3.56 (1.2H, s), 3.75-3.83 (2H, m), 3.97 (1.2H, t, J=5.4 Hz), 4.24 (0.8H, t, J=4.9 Hz), 7.20-7.70 (15H, m).
IR (ATR): 2227, 1657, 1471, 1427, 1402, 1092 cm$^{-1}$.

Example 49

4-Cyano-7-[(3S)-3-(dimethylamino)pyrrolidin-1-yl] N-(2-hydroxyethyl)-N,5-dimethyl-6-phenyl-1,3-benzoxazole-2-carboxamide (#49)

Under nitrogen atmosphere, a dimethyl sulfoxide (1 ml) solution of (3R)-3-(dimethylamino)pyrrolidine (76 μl, 598 μmol) was added at 150° C. to a dimethyl sulfoxide (9 ml) solution of N-[2-(tert-butyldiphenylsiloxy)ethyl]-4-cyano-7-fluoro-N,5-dimethyl-6-phenyl-1,3-benzoxazole-2-carboxamide (I-124) (295 mg, 499 μmol) and triethylamine (90 μl, 649 μmol), followed by stirring at the same temperature for 20 minutes. After pooling, saturated brine was added to the reaction liquid, and the reaction liquid was extracted with ethyl acetate. Next, the combined organic layer was washed with saturated brine, dried over anhydrous magnesium sulfate, filtered, and the filtrate was concentrated under reduced pressure. The resulting residue was subjected to silica gel column chromatography, and the eluate with dichloromethane/methanol (10:1, v/v) gave the entitled compound (93 mg, 42%) as an amorphous substance.

MS (ESI) m/z; 448 (M+1)$^+$.
$^1$H-NMR (CDCl$_3$) δ: 1.57-1.69 (1H, m), 1.93-2.03 (1H, m), 2.10 (6H, s), 2.21 (1.8H, s), 2.22 (1.2H, s), 2.45-2.56 (1H, m), 2.74-2.85 (1H, m), 3.21-3.28 (1H, m), 3.24 (1.8H, s), 3.57-3.65 (2H, m), 3.64 (1.2H, s), 3.78-3.82 (0.8H, m), 3.94-4.01 (2H, m), 4.02-4.09 (1.2H, m), 7.10-7.15 (1H, m), 7.24-7.30 (1H, m), 7.34-7.45 (3H, m).
IR (ATR): 3437, 2210, 1649, 1604, 1577, 1471, 1439, 1396, 1365, 1304 cm$^{-1}$.
Anal. Calcd for C$_{25}$H$_{29}$N$_5$O$_3$.0.25H$_2$O: C, 66.43; H, 6.58; N, 15.49. Found: C, 66.42; H, 6.41; N, 14.92.

Reference Example 125

4-Cyano-N-[2-(dimethylamino)-2-oxoethyl]-7-fluoro-N,5-dimethyl-6-phenyl-1,3-benzoxazole-2-carboxamide (I-125)

Under nitrogen atmosphere, trimethylaluminium (1.03 M n-hexane solution, 1.19 ml, 1.23 mmol) was dropwise added at room temperature to a dichloromethane (2 ml) solution of N,N-dimethyl-2-methylaminoacetamide (143 mg, 1.23 mmol), and stirred for 35 minutes. Subsequently, a dichloromethane (2 ml) solution of ethyl 4-cyano-7-fluoro-5-methyl-6-phenyl-1,3-benzoxazole-2-carboxylate (I-111) (200 mg, 617 μmol) was dropwise added and stirred for 66.5 hours. After the reaction, aqueous 1 N hydrochloric acid solution was added to the reaction liquid with cooling with ice, followed by stirring at room temperature, and the reaction liquid was extracted with chloroform. Next, the obtained organic layers were combined, dried over anhydrous magnesium sulfate, filtered, and the filtrate was concentrated under reduced pressure. The resulting residue was subjected to silica gel column chromatography, and the eluate with ethyl acetate gave the entitled compound (144 mg, 59%) as an amorphous substance.

MS (ESI) m/z: 395 (M+1)$^+$.
$^1$H-NMR (CDCl$_3$) δ: 2.44 (2H, s), 2.47 (1H, s), 3.02 (3H, s), 3.09 (1H, s), 3.17 (2H, s), 3.32 (2H, s), 3.64 (1H, s), 4.40 (0.7H, s), 4.92 (1.3H, s), 7.23-7.28 (2H, m), 7.45-7.55 (3H, m).
IR (ATR): 2227, 1655, 1477, 1400, 1329, 1259, 1190, 1126, 1086 cm$^{-1}$.

Example 50

4-Cyano-N-[2-(dimethylamino)-2-oxoethyl]-7-[(3S)-3-(dimethylamino)pyrrolidin-1-yl]-N,5-dimethyl-6-phenyl-1,3-benzoxazole-2-carboxamide (#50)

Under nitrogen atmosphere, a dimethyl sulfoxide (1 ml) solution of (3S)-3-(dimethylamino)pyrrolidine (52 μl, 408 μmol) was added at 150° C. to a dimethyl sulfoxide (6 ml) solution of 4-cyano-N-[2-(dimethylamino)-2-oxoethyl]-7-fluoro-N,5-dimethyl-6-phenyl-1,3-benzoxazole-2-carboxamide (I-125) (134 mg, 340 μmol) and triethylamine (62 μl, 442 μmol), followed by stirring at the same temperature for 50 minutes. After cooling, saturated brine was added to the reaction liquid, and the reaction liquid was extracted with ethyl acetate. Next, the combined organic layer was washed with saturated brine, dried over anhydrous magnesium sulfate, filtered, and the filtrate was concentrated under reduced pressure. The resulting residue was subjected to silica gel column chromatography, and the eluate with dichloromethane/methanol (20:1, v/v) gave the entitled compound (24 mg, 14%) as an amorphous substance.

MS (ESI) m/z: 489 (M+1)$^+$.

$^1$H-NMR (CDCl$_3$) δ: 1.54-1.70 (1H, m), 1.94-2.02 (1H, m), 2.08 (6H, s), 2.19 (2.2H, s), 2.22 (0.5H, s), 2.42-2.54 (1H, m), 2.66-2.76 (1H, m), 3.01 (3H, s), 3.08 (0.8H, s), 3.16-3.24 (1H, m), 3.18 (2.2H, s), 3.30 (2.2H, s), 3.59-3.76 (2H, m), 3.66 (0.8H, s), 4.31-4.43 (0.6H, m), 4.97 (1.4H, s), 7.09-7.15 (1H, m), 7.22-7.30 (1H, m), 7.33-7.45 (3H, m).

IR (ATR): 2210, 1655, 1604, 1471, 1396, 1367, 1304, 1153, 1092 cm$^{-1}$.

Reference Example 126

Ethyl 6-bromo-4-cyano-7-fluoro-5-methyl-1,3-benzoxazole-2-carboxylate (I-126)

Under nitrogen atmosphere, a mixture of 2-amino-5-bromo-4-fluoro-3-hydroxy-6-methylbenzonitrile (I-75) (6.67 g, 27.2 mmol) and ethyl triethoxyacetate (24.0 g, 54.4 mmol) was stirred at 130° C. for 15 hours. After cooling, n-hexane was added to the reaction liquid, and the precipitated solid was collected by filtration. The obtained solid was suspended and washed in diethyl ether to obtain the entitled compound (7.10 g, 80%) as a pale dark brown solid.

MS (ESI) m/z: 327, 329 (M+1)$^+$.

$^1$H-NMR (CDCl$_3$) δ: 1.51 (3H, t, J=7.3 Hz), 2.82 (3H, s), 4.59 (2H, q, J=7.3 Hz).

IR (ATR): 2231, 1738, 1547, 1471, 1331, 1300, 1244, 1132 cm$^{-1}$.

Reference Example 127

6-Bromo-4-cyano-7-fluoro-N,N,5-trimethyl-1,3-benzoxazole-2-carboxamide (I-127)

Under nitrogen atmosphere, trimethylaluminium (1.03 M n-hexane solution, 57.9 ml, 59.6 mmol) was dropwise added to a dichloromethane (100 ml) solution of dimethylamine hydrochloride (4.86 g, 59.6 mmol) with cooling in a water bath, taking 30 minutes, and stirred for 65 minutes at room temperature. Subsequently, a dichloromethane (30 ml) solution of ethyl 6-bromo-4-cyano-7-fluoro-5-methyl-1,3-benzoxazole-2-carboxylate (I-126) (6.50 g, 19.9 mmol) was dropwise added and stirred for 30 hours. After the reaction, aqueous 1 N hydrochloric acid solution was added to the reaction liquid with cooling with ice, followed by stirring at room temperature, and the reaction liquid was extracted with chloroform. Next, the obtained organic layers were combined, dried over anhydrous magnesium sulfate, filtered, and the filtrate was concentrated under reduced pressure. The resulting residue was subjected to silica gel column chromatography, and the eluate with dichloromethane/methanol (100:1, v/v) gave the entitled compound (3.10 g, 48%) as a pale yellow solid. The fraction containing impurities was recovered and purified twice in the same manner to obtain the entitled compound (362 mg, 591 mg), and 4.05 g (62%) of the entitled compound was obtained in total.

MS (ESI) m/z: 326, 328 (M+1)$^+$.

$^1$H-NMR (CDCl$_3$) δ: 2.81 (3H, s), 3.22 (3H, s), 3.51 (3H, s).

Reference Example 128

6-Bromoacetyl-4-cyano-7-fluoro-N,N,5-trimethyl-1,3-benzoxazole-2-carboxamide (I-128)

Under nitrogen atmosphere, bis(triphenylphosphine)palladium chloride (435 mg, 620 μmol) was added to a toluene (125 ml) solution of 6-bromo-4-cyano-7-fluoro-N,N,5-trimethyl-1,3-benzoxazole-2-carboxamide (I-127) (4.04 g, 12.4 mmol), tributyl(1-ethoxyvinyl)tin (5.37 g, 14.9 mmol) and 2,6-di-tert-butyl-p-cresol (about 20 grains), and heated under reflux for 20 hours. After cooling, the solvent was evaporated away under reduced pressure, then n-hexane was added to the resulting residue and stirred at room temperature for 1 hour. Next, the precipitated solid was collected by filtration and subjected to silica gel column chromatography, and the eluate with n-hexane/ethyl acetate (1:1, v/v) gave 4-cyano-6-[1-(ethoxy)ethenyl]-7-fluoro-N,N,5-trimethyl-1,3-benzoxazole-2-carboxamide (3.20 g, 81%) as a yellow solid. The fraction containing impurities was recovered and purified in the same manner, and 3.57 g (91%) of 4-cyano-6-[1-(ethoxy)ethenyl]-7-fluoro-N,N,5-trimethyl-1,3-benzoxazole-2-carboxamide was obtained in total. The analytical data are shown below.

MS (ESI) m/z: 318 (M+1)$^+$.

$^1$H-NMR (CDCl$_3$) δ: 1.37 (3H, t, J=7.1 Hz), 2.66 (3H, s), 3.22 (3H, s), 3.50 (3H, s), 3.96 (2H, q, J=7.1 Hz), 4.29 (1H, d, J=2.9 Hz), 4.64 (1H, d, J=2.9 Hz). IR (ATR): 2229, 1655, 1333, 1306, 1248, 1134, 1105, 1078, 1051 cm$^{-1}$.

Next, at room temperature, N-bromosuccinimide (2.10 g, 11.8 mmol) was added to a tetrahydrofuran/water (178 ml/11 ml) mixed solution of the obtained 4-cyano-6-[1-(ethoxy)ethenyl]-7-fluoro-N,N,5-trimethyl-1,3-benzoxazole-2-carboxamide (3.56 g, 11.2 mmol), and stirred for 20 minutes. The solvent was evaporated away under reduced pressure, and the resulting residue was dissolved in ethyl acetate, and the solution was washed with water.

Next, the aqueous layer was extracted with ethyl acetate, then the organic layers were combined, dried over anhydrous magnesium sulfate, and filtered. The obtained filtrate was concentrated under reduced pressure, and the residue was subjected to silica gel column chromatography, and the eluate with chloroform gave the entitled compound (3.80 g, 92%) as a milky white solid.

MS (ESI) m/z: 368, 370 (M+1)$^+$.

$^1$H-NMR (CDCl$_3$) δ: 2.68 (3H, s), 3.24 (3H, s), 3.52 (3H, s), 4.36 (2H, d, J=1.5 Hz).

IR (ATR): 2229, 1732, 1647, 1394, 1335, 1146 cm$^{-1}$.

Reference Example 129

4-Cyano-7-fluoro-N,N,5-trimethyl-6-(2-methyl-1,3-thiazol-4-yl)-1,3-benzoxazole-2-carboxamide (I-129)

Under nitrogen atmosphere, a toluene (100 ml) suspension of 6-bromoacetyl-4-cyano-7-fluoro-N,N,5-trimethyl-1,3-benzoxazole-2-carboxamide (I-128) (3.80 g, 10.3 mmol), thioacetamide (931 mg, 12.4 mmol) and cesium carbonate (4.36 g, 13.4 mmol) was stirred at 100° C. for 45 minutes. After cooling, the reaction liquid was filtered through Celite, the obtained filtrate was washed with water and saturated brine. Next, the organic layer was dried over anhydrous magnesium sulfate, filtered, and the filtrate was concentrated under reduced pressure. The resulting residue was subjected to silica, gel column chromatography, and the eluate with n-hexane/ethyl acetate (1:1, v/v) gave the entitled compound (2.31 g, 65%) as a yellow solid.

MS (ESI) m/z: 345 (M+1)$^+$.

$^1$H-NMR (CDCl$_3$) δ: 2.59 (3H, s), 2.81 (3H, s), 3.23 (3H, s), 3.54 (3H, s), 7.26-7.28 (1H, m).

IR (ATR): 2231, 1674, 1400, 1331, 1178, 1101 cm$^{-1}$.

Example 51

4-Cyano-7-[(3S)-3-(dimethylamino)pyrrolidin-1-yl]-N,N,5-trimethyl-6-(2-methyl-1,3-thiazol-4-yl)-1,3-benzoxazole-2-carboxamide (#51)

Under nitrogen atmosphere, a dimethyl sulfoxide (2 ml) solution of (3S)-3-(dimethylamino)pyrrolidine (442 μl, 3.48 mmol) was added at 140 to 150° C. to a dimethyl sulfoxide (56 ml) solution of 4-cyano-7-fluoro-N,N,5-trimethyl-6-(2-methyl-1,3-thiazol-4-yl)-1,3-benzoxazole-2-carboxamide (I-129) (1.00 g, 2.90 mmol) and triethylamine (525 μl, 3.77 mmol), followed by stirring at the same temperature for 10 minutes. After cooling, saturated brine was added to the reaction liquid, and the reaction liquid was extracted with ethyl acetate. Next, the combined organic layer was washed with saturated brine, dried over anhydrous magnesium sulfate, filtered, and the filtrate was concentrated under reduced pressure. The resulting residue was subjected to silica gel column chromatography, and the eluate with dichloromethane/methanol (10:1, v/v) gave a crude product of the entitled compound as a solid, and the solid was suspended and washed in diethyl ether to obtain the entitled compound (670 mg, 53%) as a yellow solid. The fraction containing impurities and the filtrate in suspension washing were recovered and purified in the same manner to obtain 145 mg of the entitled compound, 815 mg (64%) of the entitled compound was obtained in total.

mp: 153-156° C.

MS (ESI) m/z: 439 (M+1)$^+$.

$^1$H-NMR (CDCl$_3$) δ: 1.57-1.74 (1H, m), 2.00-2.09 (1H, m), 2.15 (6H, s), 2.24 (3H, s), 2.47-2.58 (1H, m), 2.77-2.85 (1H, m), 2.79 (3H, s), 3.19 (3H, s), 3.33-3.40 (1H, m), 3.55 (3H, s), 3.70-3.77 (2H, m), 6.98 (1H, s).

IR (ATR): 2214, 1655, 1604, 1450, 1390, 1109 cm$^{-1}$.

Anal. Calcd for C$_{22}$H$_{26}$N$_6$O$_2$S: C, 60.25; H, 5.98; N, 19.16. Found: C, 60.08; H, 5.96; N, 18.92.

Example 52

4-Cyano-N,N,5-trimethyl-7-[(3S)-3-methylamino)pyrrolidin-1-yl]-6-(2-methyl-1,3-thiazol-4-yl)-1,3-benzoxazole-2-carboxamide (#52)

Under nitrogen atmosphere, a dimethyl sulfoxide (1 ml) solution of (3S)-3-(dimethylamino)pyrrolidine (35 μl, 348 μmol) was added at 140 to 150° C. to a dimethyl sulfoxide (5 ml) solution of 4-cyano-7-fluoro-N,N,5-trimethyl-6-(2-methyl-1,3-thiazol-4-yl)-1,3-benzoxazole-2-carboxamide (I-129) (100 mg, 290 μl) and triethylamine (53 μl, 337 μmol), followed by stirring at the same temperature for 10 minutes. After cooling, the solvent was evaporated away under reduced pressure, and the resulting residue was dissolved in chloroform. The solution was washed with saturated brine, then the aqueous layer was extracted with ethyl acetate. Next, the combined organic layer was dried over anhydrous magnesium sulfate, filtered, and the filtrate was concentrated under reduced pressure. The resulting residue was subjected to silica gel column chromatography, and the eluate with dichloromethane/methanol (5:1, v/v) gave a crude product of the entitled compound as a solid, and the solid was suspended and washed in diisopropyl ether to obtain the entitled compound (49 mg, 40%) as a pale brown solid.

mp: 99-102° C.

MS (ESI) m/z: 425 (M+1)$^+$.

$^1$H-NMR (CDCl$_3$) δ: 1.74-1.85 (1H, m), 1.95-2.05 (1H, m), 2.24 (3H, s), 2.41 (3H, s), 2.79 (3H, s), 3.17-3.25 (2H, m), 3.19 (3H, s), 3.40-3.48 (1H, m), 3.49-3.59 (2H, m), 3.56 (3H, s), 7.02 (1H, s).

IR (ATR): 2210, 1651, 1604, 1468, 1441, 1390, 1369, 1109 cm$^{-1}$.

Anal. Calcd for C$_{21}$H$_{24}$N$_6$O$_2$S.0.75H$_2$O: C, 57.58; H, 5.87; N, 19.19. Found: C, 57.83; H, 5.79; N, 18.68.

Reference Example 130

2-Chloro-7-fluoro-5-methyl-6-phenyl-1,3-benzoxazole-4-cabonitrile (I-130)

4-Amino-6-fluoro-5-hydroxy-2-methylbiphenyl-3-carbonitrile (I-41) (0.50 g, 2.06 mmol) was dissolved in pyridine (25 ml), then potassium O-ethyl dithiocarbonate (1.00 g, 6.24 mmol) was added, followed by heating under reflux for 3 hours. The solvent was evaporated away under reduced pressure, then ethyl acetate and diluted hydrochloric acid were added for liquid-liquid separation of the organic layer. After washing with water and saturated brine and drying over anhydrous sodium sulfate, the solvent was evaporated away under reduced pressure. The resulting residue was dissolved in thionyl chloride (12 ml), then N,N-dimethylformamide (0.10 ml) was added, followed by stirring at an external temperature of about 70° C. for 1 hour. The reaction liquid was concentrated under reduced pressure, then dichloromethane and aqueous sodium hydroxide solution were added, and the organic layer was collected. After washing with brine and drying over anhydrous sodium sulfate, the solvent was evaporated away under reduced pressure, and the resulting residue was purified by silica gel column chromatography (dichloromethane) to obtain the entitled compound (0.56 g, 95%) as a yellow solid.

Reference Example 131

7-Fluoro-5-methyl-2-(methylamino)-6-phenyl-1,3-benzoxazole-4-carbonitrile (I-131)

2-Chloro-7-fluoro-5-methyl-6-phenyl-1,3-benzoxazole-4-cabonitrile (I-130) (0.20 g, 0.70 mmol) was dissolved in dichloromethane (10 ml), then N,N-diisopropylethylamine (0.15 ml, 0.88 mmol), methylamine (2 M tetrahydrofuran solution, 0.50 ml, 1.00 mmol) were added. After stirring in a sealed tube at an external temperature of about 60° C. for 3 hours, this was diluted with dichloromethane.

After washing with water and drying over anhydrous sodium sulfate, the solvent was evaporated away under reduced pressure, and the resulting residue was purified by silica gel column chromatography (silica gel 10 g, dichloromethane:methanol=50:1) to obtain a pale yellow solid (0.17 g, 86%).

MS (ESI) m/z: 282 (M+1)$^+$.

$^1$H-NMR (CDCl$_3$) δ: 2.36 (3H, s), 3.27 (3H, d, J=4.9 Hz), 7.20-7.30 (2H, m), 7.40-7.50 (3H, m).

Example 53

7-[(3S)-3-(Dimethylamino)pyrrolidin-1-yl]-5-methyl-2-(methylamino)-6-phenyl-1,3-benzoxazole-4-carbonitrile (#53)

7-Fluoro-5-methyl-2-(methylamino)-6-phenyl-1,3-benzoxazole-4-carbonitrile (I-131) (0.17 g, 0.60 mmol) was dissolved in dimethyl sulfoxide (5 ml), then triethylamine (0.17 ml, 1.23 mmol) and (3S)-3-methylaminopyrrolidine (0.16 ml, 1.26 mmol) were added, followed by stirring in a sealed tube at an external temperature of about 150° C. for 4 hours. This was diluted with dichloromethane, washed with water and brine, and dried over anhydrous sodium sulfate. The solvent was evaporated away under reduced pressure, and the resulting residue was purified by silica gel column chromatography (dichloromethane:methanol=20:1 to 10:1), then diisopropyl ether was added, and the insoluble matter was collected by filtration to obtain a beige solid (68.3 mg, 27%).

MS (ESI) m/z: 376 (M+1)$^+$.
$^1$H-NMR (CDCl$_3$) δ: 1.50-1.65 (1H, m), 1.85-2.00 (1H, m), 2.13 (6H, s), 2.16 (3H, s), 2.50-2.60 (1H, m), 2.90-3.00 (1H, m), 3.15-3.25 (4H, m), 3.25-3.35 (2H, m), 7.12 (1H, d, J=7.3 Hz), 7.20-7.25 (1H, m), 7.30-7.45 (4H, m).
Anal. Calcd for C$_{22}$H$_{25}$N$_5$O: C, 70.38; H, 6.71; N, 18.65. Found: C, 69.98; H, 6.73; N, 18.39.

Example 54

N-{4-Cyano-7-[(3S)-3-(dimethylamino)pyrrolidin-1-yl]-5-methyl-6-phenyl-1,3-benzoxazol-2-yl}-N-methylacetamide (#54)

7-[(3S)-3-(Dimethylamino)pyrrolidin-1-yl]-5-methyl-2-(methylamino)-6-phenyl-1,3-benzoxazole-4-carbonitrile (#53) (60 mg, 0.16 mmol) was dissolved in tetrahydrofuran (1.2 ml), and with cooling with ice, acetyl chloride (14 μl, 0.19 mmol) and diisopropylethylamine (38 μl, 0.22 mmol) were added, followed by stirring at room temperature for 2 hours. Further, acetyl chloride (14 μl, 0.19 mmol) was added, followed by heating under reflux for 1.5 hours. Since the reaction did not go on, pyridine (1.2 ml) was added, followed by stirring at 90° C. for 15 hours. After cooling followed by fractionation with water and ethyl acetate, the organic layer was washed with saturated brine. The obtained organic layer was dried over anhydrous sodium sulfate, and the solvent was evaporated away under reduced pressure. The resulting residue was subjected to preparative silica gel column chromatography. Elution with a mixed solvent of chloroform/methanol (10:1, v/v) gave the entitled compound (11 g, 0.03 mmol, 17%) as a brown oily substance.

MS (FAB) m/z: 418 (M+1)$^+$.
$^1$H-NMR (CDCl$_3$) δ: 1.61 (1H, br), 1.94-1.96 (1H, m), 2.13 (6H, s), 2.19 (3H, s), 2.50 (1H, br), 2.66 (3H, s), 2.94 (1H, br), 3.21-3.39 (3H, m), 3.52 (3H, s), 7.11 (1H, d, J=7.3 Hz), 7.23-7.26 (1H, m), 7.36-7.43 (3H, m).
IR (ATR): 2212, 1701, 1593, 1560, 1469 cm$^{-1}$.

Example 55

N-{4-Cyano-7-[(3S)-3-(dimethylamino)pyrrolidin-1-yl]-5-methyl-6-phenyl-1,3-benzoxazol-2-yl}-N,2,2-trimethylpropanamide (#55)

7-[3-(Dimethylamino)-1-pyrrolidin-1-yl]-5-methyl-6-phenyl-1,3-benzoxazole-4-carbonitrile (#53) (20 mg, 0.053 mmol) was dissolved in pyridine (300 μl), pivaloyl chloride (16 μl, 0.13 mmol) was added, followed by stirring at 150° C. in a sealed tube for 17 hours. Since the reaction was slow, pivalic acid anhydride (22 μl, 0.11 mmol) was added, followed by stirring in a sealed tube at 150° C. for 1 hour.

Separately, 7-[3-(dimethylamino)-1-pyrrolidinyl]-5-methyl-2-(methylamino)-6-phenyl-1,3-benzoxazole-4-carbonitrile (#53) (10 mg, 0.03 mmol) was dissolved in pyridine (200 μl), pivalic acid anhydride (27 μl, 0.13 mmol) was added, followed by stirring at 150° C. in a sealed tube for 44 hours.

The individual reaction liquid were cooled, then combined and post-treated. After fractionation with water and ethyl acetate, the organic layer was washed with saturated brine. The obtained organic layer was dried over anhydrous sodium sulfate, the solvent was evaporated away under reduced pressure. The resulting residue was subjected to preparative, silica gel column chromatography. Elution with a mixed solvent of chloroform/methanol (20:1, v/v) gave the entitled compound (17 mg, 0.04 mmol, 47%) as a yellow oily substance.

MS (EI) m/z: 459 (M)$^+$.
$^1$H-NMR (CDCl$_3$) δ: 1.23 (9H, s), 1.65 (1H, brs), 1.95 (1H, brs), 2.13 (6H, s), 2.21 (3H, s), 2.58 (1H, brs), 2.93 (1H, brs), 3.25-3.32 (2H, m), 3.37 (3H, s), 3.38-3.42 (1H, m), 7.14 (1H, d, J=7.3 Hz), 7.25 (1H, d, J=6.8 Hz), 7.37-7.42 (3H, m).
IR (ATR): 2925, 2214, 1684, 1591, 1469 cm$^{-1}$.

Reference Example 132

7-Fluoro-2-(dimethylamino)-5-methyl-6-phenyl-1,3-benzoxazole-4-carbonitrile (I-132)

2-Chloro-7-fluoro-5-methyl-6-phenyl-1,3-benzoxazole-4-cabonitrile (I-130) (0.20 g, 0.70 mmol) was dissolved in dichloromethane (7 ml), then diisopropylethylamine (0.15 ml, 0.88 mmol), dimethylamine (2.0 M tetrahydrofuran solution, 0.50 ml, 1.00 mmol) were added. After stirring in a sealed tube at an external temperature of about 60° C. for 3 hours, this was diluted with dichloromethane. After washing with water and drying over anhydrous sodium sulfate, the solvent was evaporated away under reduced pressure, and the resulting residue was purified by silica gel column chromatography (dichloromethane) to obtain a colorless solid (0.18 g, 87%).

MS (ESI) m/z: 296 (M+1)$^+$.
$^1$H-NMR (CDCl$_3$) δ: 2.34 (3H, s), 3.29 (6H, s), 7.20-7.30 (2H, m), 7.35-7.60 (3H, m).

Example 56

2-(Dimethylamino)-7-[(3S)-3-(dimethylamino)pyrrolidin-1-yl]-5-methyl-6-phenyl-1,3-benzoxazole-4-carbonitrile (#56)

7-Fluoro-2-(dimethylamino)-5-methyl-6-phenyl-1,3-benzoxazole-4-carbonitrile (I-132) (0.18 g, 0.61 mmol) was suspended in dimethyl sulfoxide (5 ml), then triethylamine (0.17 ml, 1.23 mmol) and (3S)-3-(dimethylamino)pyrrolidine (0.16 ml, 1.26 mmol) were added, followed by stirring in a sealed tube at an external temperature of about 150° C. for 4 hours. This was diluted with dichloromethane, washed with water and brine, and dried over anhydrous sodium sulfate. The solvent was evaporated away under reduced pressure, and the resulting residue was purified by silica gel column chromatography (dichloromethane:methanol=30:1), then diisopropyl ether was added, and the insoluble matter was collected by filtration to obtain a pale beige solid (78.5 mg, 33%).

MS (ESI) m/z: 390 (M+1)$^+$.

$^1$H-NMR (CDCl$_3$) δ: 1.50-1.65 (1H, m), 1.85-1.95 (1H, m), 2.12 (6H, s), 2.15 (3H, s), 2.45-2.60 (1H, m), 2.90-3.00 (1H, m), 3.10-3.35 (3H, m), 3.22 (6H, s), 7.10-7.15 (1H, m), 7.20-7.25 (1H, m), 7.30-7.40 (3H, m).

Anal. Calcd for C$_{23}$H$_{27}$N$_5$O.0.25H$_2$O: C, 70.11; H, 7.03; N, 17.77. Found: C, 70.36; H, 6.94; N, 17.83.

Example 57

2-(Dimethylamino)-5-methyl-7-[(3S)-3-(methylamino)pyrrolidin-1-yl]-5-methyl-6-phenyl-1,3-benzoxazole-4-carbonitrile (#57)

Under nitrogen atmosphere, triethylamine (749 μl, 5.22 mmol) and (3S)-3-(methylamino)pyrrolidine (584 μl, 5.48 mmol) were added to a dimethyl sulfoxide (20 ml) solution of 7-fluoro-2-(dimethylamino)-5-methyl-6-phenyl-1,3-benzoxazole-4-carbonitrile (I-132) (770 mg, 2.61 mmol), followed by heating in a sealed tube at 150° C. for 20 hours. After cooling, the reaction liquid was diluted with ethyl acetate, washed with saturated brine, and the organic layer was dried over anhydrous magnesium sulfate, then the solvent was evaporated away under reduced pressure. The resulting residue was subjected to silica gel column chromatography, and the eluate with chloroform/methanol (10:1, v/v) gave the entitled compound (617 mg, 63%) as a white solid.

mp: 146-148° C.

MS (ESI) m/z: 376 (M+1)$^+$.

$^1$H-NMR (CDCl$_3$) δ: 1.50-1.62 (1H, m), 1.86-1.95 (1H, m), 2.15 (3H, s), 2.29 (3H, s), 2.88-2.90 (1H, m), 3.00-3.08 (1H, m), 3.22 (6H, s), 3.14-3.30 (3H, m), 7.11-7.20 (2H, m), 7.30-7.41 (3H, m).

IR (ATR): 2204, 1645, 1564, 1410, 908, 696 cm$^{-1}$.

Anal. Calcd for C$_{22}$H$_{25}$N$_5$O.0.25H$_2$O: C, 69.54; H, 6.76; N, 18.43. Found: C, 69.17; H, 6.62; N, 18.18.

Reference Example 133

2-(Diethylamino)-7-fluoro-5-methyl-6-phenyl-1,3-benzoxazole-4-carbonitrile (I-133)

2-Chloro-7-fluoro-5-methyl-6-phenyl-1,3-benzoxazole-4-cabonitrile (I-130) (100 mg, 0.35 mmol) was dissolved in dichloromethane (5 ml) in a sealed tube, then methylamine hydrochloride (26 mg, 0.38 mmol) and triethylamine (122 μl, 0.87 mmol) were successively added. The reaction system was heated at 45° C. for 3 hours. After cooling to room temperature, the reaction liquid was fractionated with dichloromethane and an aqueous saturated sodium hydrogencarbonate solution. The aqueous layer was separated, this was extracted twice with dichloromethane. The organic layers were combined, washed with saturated brine, then dried over anhydrous sodium sulfate. The insoluble matter was separated by filtration, the solvent was evaporated away, and the resulting residue was purified by preparative TLC (eluent, chloroform) to obtain the entitled compound (80 mg, 82%) as a white solid.

MS (ESI) m/z: 324 (M+1)$^+$.

HRMS (ED m/z: 323.1436 (Calcd for C$_{19}$H$_{18}$FN$_3$O 323.1434).

$^1$H-NMR (CDCl$_3$) δ: 1.31 (6H, t, J=7.1 Hz), 2.33 (3H, s), 3.66 (4H, q, J=7.1 Hz), 7.21-7.27 (2H, m), 7.39-7.49 (3H, m).

IR (ATR): 2220, 1637, 1576, 1423, 1117, 781, 721 cm$^{-1}$.

Example 58

2-(Diethylamino)-7-[(3S)-3-(dimethylamino)pyrrolidin-1-yl]-5-methyl-6-phenyl-1,3-benzoxazole-4-carbonitrile (#58)

2-(Diethylamino)-7-fluoro-5-methyl-6-phenyl-1,3-benzoxazole-4-carbonitrile (I-133) (78 mg, 0.24 mmol) was dissolved in dimethyl sulfoxide (2 ml) in a sealed tube, then triethylamine (67 μl, 0.48 mmol) and (3S)-3-(dimethylamino)pyrrolidine (61 μl, 0.48 mmol) were added. The reaction system was heated at 150° C. for 4.5 hours and then at 100° C. for 60 hours. After cooling to room temperature, the reaction liquid was fractionated with ethyl acetate and saturated brine. The aqueous layer was separated, and this was extracted twice with ethyl acetate. The organic layers were combined, washed with saturated brine, and dried over anhydrous sodium sulfate. The insoluble matter was separated by filtration, the solvent was evaporated away, and the resulting residue was purified by preparative TLC (eluent, chloroform:methanol=92:8) to obtain the entitled compound (66 mg, 65%) as a brown solid.

MS (ESI) m/z: 418 (M+1)$^+$.

HRMS (EI) m/z: 417.2536 (Calcd for C$_{25}$H$_{31}$N$_5$O 417.2528).

$^1$H-NMR (CDCl$_3$) δ: 1.28 (6H, t, J=7.1 Hz), 1.50-1.61 (1H, m), 1.85-1.95 (1H, m), 2.13 (9H, s), 2.14 (3H, s), 2.45-2.55 (1H, m), 2.96 (1H, t, J=9.0 Hz), 3.11 (1H, dt, J=6.9, 10.0 Hz), 3.24 (1H, t, J=8.3 Hz), 3.33 (1H, dt, J=7.1, 9.0 Hz), 3.55-3.67 (4H, m), 7.11 (1H, d, J=7.3 Hz), 7.23 (1H, d, J=7.3 Hz), 7.28-7.40 (3H, m).

IR (ATR): 2208, 1633, 1599, 1560 cm$^{-1}$.

Anal. Calcd for C$_{25}$H$_{31}$N$_5$O.0.25H$_2$O: C, 71.15; H, 7.52; N, 16.59. Found: C, 71.09; H, 7.51; N, 16.40.

Reference Example 134

2-(Azetidin-1-yl)-7-fluoro-5-methyl-6-phenyl-1,3-benzoxazole-4-carbonitrile (I-134)

2-Chloro-7-fluoro-5-methyl-6-phenyl-1,3-benzoxazole-4-carbonitrile (I-130) (0.11 g, 0.38 mmol) was dissolved in a mixed solvent of dichloromethane (10 ml) and ethanol (7 ml), then diisopropylethylamine (0.21 ml, 1.23 mol) and azetidine hydrochloride (71.5 mg, 0.76 mmol) were added. After stirring at an external temperature of about 60° C. for 3 hours, the reaction liquid was concentrated under reduced pressure and diluted with dichloromethane. After washing with water and drying over anhydrous sodium sulfate, the solvent was evaporated away under reduced pressure and the resulting residue was purified by silica gel column chromatography (dichloromethane:methanol=100:1) to obtain a colorless solid (85 mg, 74%).

MS (ESI) m/z: 308 (M+1)$^+$.

$^1$H-NMR (CDCl$_3$) δ: 2.34 (3H, s), 2.50-2.60 (2H, m), 4.40 (4H, t, J=7.8 Hz), 7.20-7.25 (2H, m), 7.40-7.50 (3H, m).

Example 59

2-(Azetidin-1-yl)-7-[(3S)-3-(dimethylamino)pyrrolidin-1-yl]-5-methyl-6-phenyl-1,3-benzoxazole-4-carbonitrile (#59)

2-(Azetidin-1-yl)-7-fluoro-5-methyl-6-phenyl-1,3-benzoxazole-4-carbonitrile (I-134) (0.11 g, 0.36 mmol) was dissolved in dimethyl sulfoxide (3.5 ml), then triethylamine (0.10 ml, 0.72 mmol) and (3S)-3-dimethylamino)pyrrolidine (92.0 µl, 0.73 mmol) were added, followed by stirring in a sealed tube at an external temperature of about 150° C. for 4 hours. This was diluted with dichloromethane, washed with water and saturated brine, and dried over anhydrous sodium sulfate. The solvent was evaporated away under reduced pressure, and the resulting residue was purified by preparative thin-layer chromatography (dichloromethane:methanol=20:1), then diisopropyl ether was added, and the insoluble matter was collected by filtration to obtain a pale beige solid (23 mg, 17%).

MS (ESI) m/z: 402 (M+1)$^+$.

$^1$H-NMR (CDCl$_3$) δ: 1.50-1.65 (1H, m), 1.85-1.95 (1H, m), 2.12 (6H, s), 2.15 (3H, s), 2.45-2.60 (3H, m), 2.90-3.00 (1H, m), 3.10-3.20 (1H, m), 3.20-3.35 (2H, m), 4.32 (4H, t, J=7.8 Hz), 7.10 (1H, d, J=7.3 Hz), 7.20-7.25 (1H, m), 7.30-7.40 (3H, m).

Anal. Calcd for C$_{24}$H$_{27}$N$_5$O.0.5H$_2$O: C, 70.22; H, 6.87; N, 17.06. Found: C, 70.45; H, 6.83; N, 16.95.

Reference Example 135

7-Fluoro-5-methyl-6-phenyl-2-(pyrrolidin-1-yl)-1,3-benzoxazole-4-carbonitrile (I-135)

2-Chloro-7-fluoro-5-methyl-6-phenyl-1,3-benzoxazole-4-cabonitrile (I-130) (0.13 g, 0.45 mmol) was dissolved in dichloromethane (10 ml), and diisopropylethylamine (92.0 µl, 0.54 mmol) and pyrrolidine (41.0 µl, 0.50 mmol) were added. This was heated under reflux for 4 hours, and diluted with dichloromethane. After washing with water and drying over anhydrous sodium sulfate, the solvent was evaporated away under reduced pressure, and the resulting residue was purified by silica gel column chromatography (dichloromethane to dichloromethane:methanol=100:1) to obtain a pale yellow oil (0.14 g, 98%).

MS (ESI) m/z: 322 (M+1)$^+$.

$^1$H-NMR (CDCl$_3$) δ: 2.00-2.15 (4H, m), 2.34 (3H, s), 3.70-3.80 (4H, m), 7.20-7.25 (2H, m), 7.40-7.50 (3H, m).

Example 60

7-[(3S)-3-(Dimethylamino)pyrrolidin-1-yl]-5-methyl-6-phenyl-2-(pyrrolidin-1-yl)-1,3-benzoxazole-4-carbonitrile (#60)

7-Fluoro-5-methyl-6-phenyl-2-(pyrrolidin-1-yl)-1,3-benzoxazole-4-carbonitrile (I-135) (0.10 g, 0.31 mmol) was suspended in dimethyl sulfoxide (3.5 ml), then triethylamine (90.0 µl, 0.65 mmol) and (3S)-3-(dimethylamino)pyrrolidine (88.0 µl, 0.69 mmol) were added, followed by stirring in a sealed tube at an external temperature of about 150° C. for 4 hours. This was diluted with dichloromethane, washed with water and saturated brine, and dried over anhydrous sodium sulfate. The solvent was evaporated away under reduced pressure, and the resulting residue was purified by preparative thin-layer chromatography (dichloromethane:methanol=20:1), then ether and a small amount of hexane were added, and the insoluble matter was collected by filtration to obtain a beige solid (38 mg, 29%).

MS (ESI) m/z: 416 (M+1)$^+$.

$^1$H-NMR (CDCl$_3$) δ: 1.50-1.65 (1H, m), 1.85-1.95 (1H, m), 2.00-2.10 (4H, m), 2.13 (6H, s), 2.15 (3H, s), 2.45-2.60 (1H, m), 2.95-3.05 (1H, s), 3.10-3.20 (1H, m), 3.20-3.35 (2H, m), 3.60-3.75 (4H, m), 7.11 (1H, d, J=7.3 Hz), 7.22 (1H, d, J=7.6 Hz), 7.25-7.40 (3H, m).

Anal. Calcd for C$_{25}$H$_{29}$N$_5$O.0.25H$_2$O: C, 71.49; H, 7.08; N, 16.67. Found: C, 71.58; H, 7.06; N, 16.47.

Reference Example 136

7-Fluoro-5-methyl-6-phenyl-2-(piperidin-1-yl)-1,3-benzoxazole-4-carbonitrile (I-136)

2-Chloro-7-fluoro-5-methyl-6-phenyl-1,3-benzoxazole-4-cabonitrile (I-130) (0.20 g, 0.70 mmol) was dissolved in dichloromethane (10 ml), and diisopropylethylamine (0.15 ml, 0.88 mmol) and piperidine (83.0 µl, 0.84 mmol) were added. This was heated under reflux for 3 hours, and diluted with dichloromethane. After washing with water and drying over anhydrous sodium sulfate, the solvent was evaporated away under reduced pressure, and the resulting residue was purified by silica gel column chromatography (dichloromethane) to obtain a colorless solid (0.21 g, 90%).

MS (ESI) m/z: 336 (M+1)$^+$.

$^1$H-NMR (CDCl$_3$) δ: 1.65-1.80 (6H, m), 2.33 (3H, s), 3.70-3.80 (4H, m), 7.20-7.25 (2H, m), 7.40-7.50 (3H, m).

Example 61

7-[(3S)-3-(Dimethylamino)pyrrolidin-1-yl]-5-methyl-6-phenyl-2-(piperidin-1-yl)-1,3-benzoxazole-4-carbonitrile (#61)

7-Fluoro-5-methyl-6-phenyl-2-(piperidin-1-yl)-1,3-benzoxazole-4-carbonitrile (I-136) (0.21 g, 0.63 mmol) was suspended in dimethyl sulfoxide (5 ml), then triethylamine (0.91 ml, 1.37 mmol) and (3S)-3-(dimethylamino)pyrrolidine (0.16 ml, 1.26 mmol) were added, followed by stirring in a sealed tube at an external temperature of about 150° C. for 4 hours. This was diluted with dichloromethane, washed with water and saturated brine, and dried over anhydrous sodium sulfate. The solvent was evaporated away under reduced pressure, and the resulting residue was purified by silica gel column chromatography (silica gel 10 g, dichloromethane:methanol=30:1) and preparative thin-layer chromatography (dichloromethane:methanol=20:1), then isopropyl ether was added, and the insoluble matter was collected by filtration to obtain a beige solid (0.12 g, 44%).

MS (ESI) m/z: 430 (M+1)$^+$.

$^1$H-NMR (CDCl$_3$) δ: 1.50-1.65 (1H, m), 1.65-1.75 (6H, m), 1.85-1.95 (1H, m), 2.12 (6H, s), 2.15 (3H, s), 2.45-2.55 (1H, m), 2.90-2.95 (1H, m), 3.10-3.20 (1H, m), 3.20-3.30 (2H, m), 3.60-3.75 (4H, m), 7.10-7.15 (1H, m), 7.20-7.25 (1H, m), 7.30-7.40 (3H, m).

Anal. Calcd for C$_{26}$H$_{31}$N$_5$O.0.25H$_2$O: C, 71.94; H, 7.31; N, 16.13. Found: C, 72.27; H, 7.32; N, 16.05.

Reference Example 137

2-(N-tert-Butyl-N-methylamino)-7-fluoro-5-methyl-6-phenyl-1,3-benzoxazole-4-carbonitrile (I-137)

2-Chloro-7-fluoro-5-methyl-6-phenyl-1,3-benzoxazole-4-cabonitrile (I-130) (0.20 g, 0.70 mmol) was dissolved in dichloromethane (10 ml), and diisopropylethylamine (0.15 ml, 0.88 mmol) and N-methyl-tert-butylamine (0.10 ml, 0.84 mmol) were added. After heating under reflux for 3 hours, N-methyl-tert-butylamine (50.0 μl, 0.42 mmol) was added, followed by heating under reflux for 2 hours. This was diluted with dichloromethane, washed with water, and dried over anhydrous sodium sulfate. The solvent was evaporated away under reduced pressure, and the resulting residue was purified by silica gel column chromatography (dichloromethane) to obtain a pale yellow solid (0.22 g, 0.65 mmol, 93%).

MS (ESI) m/z: 338 (M+1)$^+$.

$^1$H-NMR (CDCl$_3$) δ: 1.58 (9H, s), 2.34 (3H, s), 3.29 (3H, s), 7.20-7.25 (2H, m), 7.40-7.55 (3H, m).

Example 62

2-(N-tert-Butyl-N-methylamino)-7-[(3S)-3-(dimethylamino)pyrrolidin-1-yl]-5-methyl-6-phenyl-1,3-benzoxazole-4-carbonitrile (#62)

2-(N-tert-butyl-N-methylamino)-7-fluoro-5-methyl-6-phenyl-1,3-benzoxazole-4-carbonitrile (I-137) (0.22 g, 0.65 mmol) was suspended in dimethyl sulfoxide (5 ml), then triethylamine (0.19 ml, 1.37 mmol) and (3S)-3-(dimethylamino)pyrrolidine (0.17 ml, 1.34 mmol) were added, followed by stirring in a sealed tube at an external temperature of about 150° C. for 4 hours.

This was diluted with dichloromethane, washed with water and saturated brine, and dried over anhydrous sodium sulfate. The solvent was evaporated away under reduced pressure, and the resulting residue was purified by silica gel column chromatography (dichloromethane:methanol=40:1) and preparative thin-layer chromatography (dichloromethane:methanol=20:1), then isopropyl ether was added, and the insoluble matter was collected by filtration to obtain a pale beige solid (0.12 g, 43%).

MS (ESI) m/z: 432 (M+1)$^+$.

$^1$H-NMR (CDCl$_3$) δ: 1.54 (9H, s), 1.50-1.65 (1H, m), 1.85-1.95 (1H, m), 2.13 (6H, s), 2.15 (3H, s), 2.45-2.55 (1H, m), 2.95-3.05 (1H, m), 3.05-3.20 (1H, m), 3.20-3.30 (1H, m), 3.26 (3H, s), 3.30-3.40 (1H, m), 7.05-7.15 (1H, m), 7.20-7.25 (1H, m), 7.30-7.40 (3H, m).

Anal. Calcd for C$_{26}$H$_{33}$N$_5$O: C, 72.36; H, 7.71; N, 16.23. Found: C, 72.16; H, 7.65; N, 16.22.

Reference Example 138

7-Fluoro-2-[(2-hydroxyethyl)(methyl)amino]-5-methyl-6-phenyl-1,3-benzoxazole-4-carbonitrile (I-138)

2-Chloro-7-fluoro-5-methyl-6-phenyl-1,3-benzoxazole-4-cabonitrile (I-130) (0.20 g, 0.70 mmol) was dissolved in dichloromethane (10 ml), and diisopropylethylamine (0.13 ml, 0.76 mmol) and N-methylethanolamine (62.0 μl, 0.78 mmol) were added. After heating under reflux for 3 hours, N-methylethanolamine (62.0 μl, 0.78 mmol) was added. After heated under reflux for 3 hours, this was diluted with dichloromethane. After washing with water and drying over anhydrous sodium sulfate, the solvent was evaporated away under reduced pressure, and the resulting residue was purified by silica gel column chromatography (dichloromethane:methanol=40:1) to obtain a pale yellow oil (0.21 g, 93%).

MS (ESI) m/z: 326 (M+1)$^+$.

$^1$H-NMR (CDCl$_3$) δ: 2.33 (3H, s), 2.35-2.50 (1H, br), 3.35 (3H, s), 3.81 (2H, t, J=5.1 Hz), 3.99 (2H, t, J=5.1 Hz), 7.20-7.25 (2H, m), 7.40-7.50 (3H, m).

Example 63

7-[(3S)-3-(Dimethylamino)pyrrolidin-1-yl]-2-[2-hydroxyethyl)(methyl)amino]-5-methyl-6-phenyl-1,3-benzoxazole-4-carbonitrile (#63)

7-Fluoro-2-[(2-hydroxyethyl)(methyl)amino]-5-methyl-6-phenyl-1,3-benzoxazole-4-carbonitrile (I-138) (0.21 g, 0.65 mmol) was dissolved in dimethyl sulfoxide (5 ml), then triethylamine (0.18 ml, 1.30 mmol) and (3S)-3-(dimethylamino)pyrrolidine (0.17 ml, 1.34 mmol) were added, followed by stirring in a sealed tube at an external temperature of about 150° C. for 4 hours. This was diluted with dichloromethane, washed with water and saturated brine. After drying over anhydrous sodium sulfate, the solvent was evaporated away under reduced pressure, and the resulting residue was purified by silica gel column chromatography (dichloromethane:methanol=20:1 to 10:1) and preparative thin-layer chromatography (dichloromethane:methanol=10:1), then isopropyl ether was added, and the insoluble matter was collected by filtration to obtain a pale beige solid (12 mg, 5%).

MS (ESI) m/z: 420 (M+1)$^+$.

$^1$H-NMR (CDCl$_3$) δ: 1.50-1.65 (1H, m), 1.85-1.95 (1H, m), 2.13 (6H, s), 2.14 (3H, s), 2.45-2.55 (1H, m), 2.90-3.05 (1H, m), 3.05-3.20 (1H, m), 3.20-3.35 (2H, m), 3.27 (3H, s), 3.70-3.80 (2H, m), 3.90-4.00 (2H, m), 7.10 (1H, d, J=7.3 Hz), 7.20-7.25 (1H, m), 7.25-7.40 (3H, m).

Reference Example 139

Benzyl [2-(dimethylcarbamoyl)ethyl]carbamate (I-139)

3-[N-(benzyloxycarbonyl)amino]propionic acid (0.70 g, 3.14 mmol) was dissolved in N,N-dimethylformamide (15 ml), and 1-(dimethylaminopropyl)-3-ethylcarbodiimide 1-ethyl-3-(3-dimethylaminopropyl)carbodiimide hydrochloride (0.60 g, 3.13 mmol), 1-hydroxybenzotriazole (0.48 g, 3.13 mmol) and dimethylamine (2.0 M tetrahydrofuran solution, 2.40 ml, 4.80 mmol) were added, followed by stirring at room temperature for 3 days.

The reaction liquid was concentrated under reduced pressure, diluted with ethyl acetate, washed with water, and dried over anhydrous sodium sulfate.

The solvent was evaporated away under reduced pressure, and the resulting residue was purified by silica gel column chromatography (dichloromethane:methanol=40:1) to obtain a pale yellow solid (0.71 g, 90%).

$^1$H-NMR (CDCl$_3$) δ: 2.40-2.60 (2H, m), 2.94 (3H, s), 2.96 (3H, s), 3.45-3.60 (2H, m), 5.08 (2H, s), 5.55-5.70 (1H, br), 7.25-7.40 (5H, m).

Reference Example 140

Benzyl [2-(dimethylcarbamoyl)ethyl]methylcarbamate (I-140)

Benzyl [2-(dimethylcarbamoyl)ethyl]carbamate (I-139) (0.69 g, 2.76 mmol) was dissolved in tetrahydrofuran (10 ml), and with cooling with ice, sodium hydride (oily, about 55%, 0.15 g, 3.44 mmol) was added, followed by stirring for 10 minutes. Iodomethane (0.26 ml, 4.18 mmol) was added, followed by stirring at room temperature for 18 hours, and water was added. After extraction with ethyl acetate and drying over anhydrous sodium sulfate, the solvent was evaporated away, and the resulting residue was purified by silica gel column chromatography (dichloromethane:methanol=40:1) to obtain a colorless oil (0.63 g, 86%).

$^1$H-NMR (CDCl$_3$) δ: 2.50-2.70 (2H, m), 2.85-3.10 (9H, m), 3.58 (2H, d, J=7.3 Hz), 5.13 (2H, s), 7.25-7.40 (5H, m).

Reference Example 141

N,N-Dimethyl-3-(methylamino)propionamide (I-141)

Benzyl [2-(dimethylcarbamoyl)ethyl]methylcarbamate (I-140) (0.62 g, 2.35 mmol) was dissolved in tetrahydrofuran (15 ml), and 10% palladium-carbon (containing about 50% water, 0.15 g) was added, followed by stirring for 16 hours under hydrogen gas atmosphere. The catalyst was removed by filtration, and the solvent was evaporated away under reduced pressure to obtain a yellow oil (0.31, quant.).

$^1$H-NMR (CDCl$_3$) δ: 2.44 (3H, s), 2.52 (2H, t, J=6.1 Hz), 2.85 (2H, t, J=6.1 Hz), 2.95 (3H, s), 3.00 (3H, s).

Reference Example 142

N$^3$-{4-Cyano-7-fluoro-5-methyl-6-phenyl-1,3-benzoxazol-2-yl}-N,N,N$^3$-trimethyl-β-alaninamide (I-142)

2-Chloro-7-fluoro-5-methyl-6-phenyl-1,3-benzoxazole-4-cabonitrile (I-130) (0.20 g, 0.84 mmol) was dissolved in dichloromethane (10 ml), and diisopropylethylamine (0.16 ml, 0.94 mmol) and N,N-dimethyl-3-(methylamino)propionamide (I-149) (0.11 g, 0.84 mmol) were added. After heated under reflux for 3 hours, this was diluted with dichloromethane.

After washing and drying over anhydrous sodium sulfate, the solvent was evaporated away under reduced pressure, and the resulting residue was purified by silica gel column chromatography (dichloromethane:methanol=40:1) to obtain a pale yellow oil (0.31 g, 96%).

MS (ESI) m/z: 381 (M+1)$^+$.

$^1$H-NMR (CDCl$_3$) δ: 2.34 (3H, s), 2.81 (2H, t, J=7.1 Hz), 2.96 (3H, s), 3.08 (3H, s), 3.34 (3H, s), 3.92 (2H, t, J=7.3 Hz), 7.20-7.25 (2H, m), 7.40-7.50 (3H, m).

Example 64

N$^3$-{4-Cyano-7-[(3S)-3-(dimethylamino)pyrrolidin-1-yl]-5-methyl-6-phenyl-1,3-benzoxazol-2-yl}-N,N,N$^3$-trimethyl-β-24 (#64)

N$^3$-{4-cyano-7-fluoro-5-methyl-6-phenyl-1,3-benzoxazol-2-yl}-N,N,N$^3$-trimethyl-β-alaninamide (I-142) (0.31 g, 0.81 mmol) was dissolved in dimethyl sulfoxide (30 ml), then triethylamine (0.23 ml, 1.66 mmol) and (3S)-3-(dimethylamino)pyrrolidine (0.21 ml, 1.66 mmol) were added, followed by stirring in a sealed tube at an external temperature of about 150° C. for 4 hours. This was diluted with dichloromethane, washed with water and saturated brine. After drying over anhydrous sodium sulfate, the solvent was evaporated under reduced pressure, and the resulting residue was purified by silica gel column chromatography (dichloromethane:methanol=20:1 to 10:1), then ether and diisopropyl ether were added, and the insoluble matter was collected by filtration to obtain a pale beige solid (0.23 g, 59%).

MS (ESI) m/z: 475 (M+1)$^+$.

$^1$H-NMR (CDCl$_3$) δ: 1.50-1.65 (1H, m), 1.85-1.95 (1H, m), 2.11 (6H, s), 2.14 (3H, s), 2.45-2.55 (1H, m), 2.80 (2H, t, J=6.8 Hz), 2.85-2.95 (1H, m), 2.95 (3H, s), 3.10 (3H, s), 3.10-3.25 (1H, m), 3.25-3.35 (2H, m), 3.26 (3H, s), 3.87 (2H, t, J=6.8 Hz), 7.10 (1H, d, J=7.6 Hz), 7.20-7.25 (1H, m), 7.30-7.40 (3H, m).

Anal. Calcd for C$_{27}$H$_{34}$N$_6$O$_2$: C, 68.33; H, 7.22; N, 17.71. Found: C, 68.14; H, 7.26; N, 17.58.

Reference Example 143

7-Fluoro-2-(3-hydroxyazetidin-1-yl)-5-methyl-6-phenyl-1,3-benzoxazole-4-carbonitrile (I-143)

2-Chloro-7-fluoro-5-methyl-6-phenyl-1,3-benzoxazole-4-cabonitrile (I-130) (100 mg, 0.35 mmol) was dissolved in methylene chloride (2 ml), then diisopropylethylamine (237 µl, 1.39 mmol) and 3-hydroxy-1-azetidine hydrochloride (76 mg, 0.70 mmol) were added, followed by heating under reflux in a sealed tube under nitrogen atmosphere for 6 hours. After cooling, dilution with methylene chloride and washing with water and saturated brine, the organic layer was dried over anhydrous sodium sulfate, and the solvent was evaporated away under reduced pressure. The resisting residue was recrystallized and purified with n-hexane/ethyl acetate to obtain the entitled compound (123 mg, quant) as a yellow white solid.

MS (ESI) m/z: 324 (M+1)$^+$.

$^1$H-NMR (CDCl$_3$) δ: 2.33 (3H, s), 4.26 (2H, dd, J=4.6, 10.0 Hz), 4.59 (2H, dd, J=6.8, 10.0 Hz), 4.87-4.92 (1H, m), 7.22 (2H, d, J=6.8 Hz), 7.39-7.47 (3H, m).

Example 65

7-[(3S)-3-(Dimethylamino)pyrrolidin-1-yl]-2-(3-hydroxyazetidin-1-yl)-5-methyl-6-phenyl-1,3-benzoxazole-4-carbonitrile (#65)

7-Fluoro-2-(3-hydroxyazetidin-1-yl)-5-methyl-6-phenyl-1,3-benzoxazole-4-carbonitrile (I-143) (120 mg, 0.37 mmol) was dissolved in dimethyl sulfoxide (6 ml), then (3S)-3-(dimethylamino)pyrrolidine (71 µl, 0.56 mmol) and triethylamine (189 µl, 1.11 mmol) were added, followed by stirring at 150° C. under nitrogen atmosphere for 5 hours. After cooling and fractionation with water and ethyl acetate, the organic layer was washed with saturated brine. The obtained organic layer was dried over anhydrous sodium sulfate, and the solvent was evaporated away under reduced pressure. The resulting residue was subjected to preparative silica gel column chromatography. Elution with a mixed solvent of chloroform/methanol (9:1, v/v/) gave the entitled compound (36.4 mg, 23%) as a white solid.

mp: 219-221° C. MS (ESI) m/z: 418 (M+1)$^+$.

$^1$H-NMR (DMSO-d$_6$) δ: 1.43-1.53 (1H, m), 1.78-1.86 (1H, m), 2.00 (6H, s), 2.04 (3H, s), 2.75 (1H, dd, J=8.0, 9.8 Hz), 3.07-3.24 (4H, m), 3.97-4.04 (2H, m), 4.42 (2H, t, J=7.8 Hz), 4.62-4.69 (1H, m), 7.12 (1H, d, J=7.1 Hz), 7.25 (1H, d, J=7.3 Hz), 7.32-7.45 (3H, m).

IR (ATR): 2214, 1647, 1568 cm$^{-1}$.

Anal. Calcd for C$_{24}$H$_{27}$N$_5$O$_2$.0.5H$_2$O: C, 67.59; H, 6.62; N, 16.42. Found: C, 67.49; H, 6.24; N, 16.11.

Reference Example 144

1-Benzhydrylazetidine-3-carbonyldimethylamide (I-144)

Ethyl 1-benzhydrylazetidine-3-carboxylate (0.30 g, 1.02 mmol) was dissolved in ethanol (15 ml), then 1 N sodium hydroxide (1.10 ml, 1.10 mmol) was added, followed by stirring at room temperature for 14 hours. The solvent was evaporated away under reduced pressure, and the resulting residue was dissolved in N,N-dimethylformamide (15 ml), then 1-(dimethylaminopropyl)-3-ethylcarbodiimide 1-ethyl-3-(3-dimethylaminopropyl)carbodiimide hydrochloride (0.20 g, 1.04 mmol), 1-hydroxybenzotriazole (0.16 g, 1.04 mmol) and methylamine (2.0 M tetrahydrofuran solution, 0.80 ml, 1.60 mmol) were added, followed by stirring at room temperature for 6 hours. This was diluted with ethyl acetate, washed with water, and dried over anhydrous sodium sulfate. The solvent was evaporated away under reduced pressure, and the resulting residue was purified by silica gel column chromatography (dichloromethane:methanol=40:1) to obtain a colorless oil (0.24 g, 80%).

$^1$H-NMR (CDCl$_3$) δ: 2.85 (3H, s), 2.92 (3H, s), 3.20-3.35 (2H, m), 3.40-3.50 (3H, m), 4.38 (1H, s), 7.15-7.20 (2H, m), 7.25-7.30 (4H, m), 7.35-7.45 (4H, m).

Reference Example 145

Azetidine-3-carbonyldimethylamide hydrochloride (I-145)

1-Benzhydrylazetidine-3-carbonyldimethylamide (I-144) (0.24 g, 0.82 mmol) was dissolved in ethanol (10 ml), then 1 N hydrochloric acid (0.90 m, 0.90 mmol) and 10% palladium-carbon (containing about 50% water, 0.10 g) were added, followed by stirring under hydrogen atmosphere for 16 hours. The catalyst was removed by filtration, the solvent was evaporated away under reduced pressure to obtain a mixture containing the entitled compound (0.25 g). This was used in the next reaction as it was.

Reference Example 146

1-{4-Cyano-7-fluoro-5-methyl-6-phenyl-1,3-benzoxazol-2-yl}-N,N-dimethylazetidine-3-carboxamide (I-146)

2-Chloro-7-fluoro-5-methyl-6-phenyl-1,3-benzoxazole-4-cabonitrile (I-130) (0.21 g, 0.73 mmol), (diisopropylethylamine (0.28 ml, 1.65 mmol) and azetidine-3-carbonyldimethylamide hydrochloride (I-145) (0.25 g) were dissolved in dichloromethane (10 ml). After heated under reflux for 3 hours, this was diluted with dichloromethane, washed with water, then dried over anhydrous sodium sulfate. The solvent was evaporated away under reduced pressure, and the resulting residue was purified by silica gel column chromatography (dichloromethane to dichloromethane:methanol=100:1) to obtain a colorless oil (0.24 g, 86%)

MS (ESI) m/z: 379 (M+1)$^+$.

$^1$H-NMR (CDCl$_3$) δ: 2.34 (3H, s), 2.95 (3H, s), 3.02 (3H, s), 3.80-3.90 (1H, m), 4.52 (2H, t, J=8.8 Hz), 4.60-4.65 (2H, m), 7.20-7.25 (2H, m), 7.40-7.50 (3H, m).

Example 66

1-{4-Cyano-7-[(3S)-3-(dimethylamino)pyrrolidin-1-yl]-5-methyl-6-phenyl-1,3-benzoxazol-2-yl}-N,N-dimethylazetidine-carboxamide (#66)

1-{4-Cyano-7-fluoro-5-methyl-6-phenyl-1,3-benzoxazol-2-yl}-N,N-dimethylazetidine-3-carboxamide (I-146) (0.24 g, 0.63 mmol) was dissolved in dimethyl sulfoxide (5 ml), then triethylamine (0.18 ml, 1.30 mmol) and (3S)-3-(dimethylamino)pyrrolidine (0.16 ml, 1.26 mmol) were added, followed by stirring in a sealed tube at an external temperature of about 150° C. for 4 hours. This was diluted with dichloromethane, and washed with water and brine. After drying over anhydrous sodium sulfate, the solvent was evaporated away under reduced pressure, and the resulting residue was purified by silica gel column chromatography (dichloromethane:methanol=50:1 to 20:1), then diisopropyl ether was added, and the insoluble matter was collected by filtration to obtain a beige solid (0.11 g, 37%).

MS (ESI) m/z: 473 (M+1)$^+$.

$^1$H-NMR (CDCl$_3$) δ: 1.50-1.60 (1H, m), 1.85-1.95 (1H, m), 2.11 (6H, s), 2.15 (3H, s), 2.45-2.55 (1H, m), 2.85-2.95 (1H, m), 2.94 (3H, s), 3.01 (3H, s), 3.10-3.20 (1H, m), 3.20-3.30 (2H, m), 3.75-3.85 (1H, m), 4.40-4.50 (2H, m), 4.50-4.60 (2H, m), 7.11 (1H, d, J=7.3 Hz), 7.20-7.25 (1H, m), 7.30-7.40 (3H, m).

Anal. Calcd for C$_{27}$H$_{32}$N$_6$O$_2$: C, 68.62; H, 6.82; N, 17.78. Found: C, 68.22; H, 6.86; N, 17.39.

Reference Example 147

Ethyl azetidine-3-carboxylate hydrochloride (I-147)

Ethyl 1-benzhydrylazetidine-3-carboxylate (0.51 g, 1.73 mmol) was dissolved in a mixed solvent of dichloromethane (4 ml) and ethanol (10 ml), then concentrated hydrochloric acid (0.15 ml, 1.80 mmol) was added. The solvent was evaporated away under reduced pressure, and the resulting residue was dissolved in ethanol (10 ml), then 10%-palladium-carbon (containing about 50% water, 0.10 g) was added, followed by stirring under hydrogen atmosphere for 18 hours. The catalyst was removed by filtration, the solvent was evaporated away under reduced pressure to obtain a crude product of the entitled compound (0.55 g). This was used in the next reaction as such.

Reference Example 148

Ethyl 1-(4-cyano-7-fluoro-5-methyl-6-phenyl-1,3-benzoxazol-2-yl)azetidine-3-carboxylate (I-148)

2-Chloro-7-fluoro-5-methyl-6-phenyl-1,3-benzoxazole-4-cabonitrile (I-130) (0.45 g, 1.57 mmol) was dissolved in dichloromethane (15 ml), then diisopropylethylamine (0.6 ml, 3.53 mmol) and ethyl azetidine-3-carboxylate hydrochloride (I-147) (0.55 g) were added. After heated under reflux for 3 hours, this was diluted with dichloromethane. After washing with water and drying over anhydrous sodium sulfate, the solvent was evaporated away under reduced pressure, and the resulting residue was purified by silica gel column chromatography (dichloromethane to dichloromethane:methanol=70:1) to obtain a brown oil (0.60 g, quant).

MS (ESI) m/z: 380 (M+1)$^+$.

$^1$H-NMR (CDCl$_3$) δ: 1.32 (3H, t, J=7.1 Hz), 2.35 (3H, s), 3.60-3.70 (1H, m), 4.26 (2H, q, J=7.1 Hz), 4.54 (4H, d, J=7.6 Hz), 7.20-7.25 (2H, m), 7.40-7.50 (3H, m).

Example 67

1-{4-Cyano-7-[(3S)-3-(dimethylamino)pyrrolidin-1-yl]-5-methyl-6-phenyl-1,3-benzoxazol-2-yl}-azetidine-3-carboxylic acid (#67)

Ethyl 1-(4-cyano-7-fluoro-5-methyl-6-phenyl-1,3-benzoxazol-2-yl)azetidine-3-carboxylate (I-148) (0.50 g, 1.32 mmol) was dissolved in dimethyl sulfoxide (7 ml), then triethylamine (0.38 ml, 2.74 mmol) and (3S)-(−)-(dimethylamino)pyrrolidine (0.34 ml, 2.68 mmol) were added, followed by stirring in a sealed tube at an external temperature of about 150° C. for 4 hours. This was diluted with dichloromethane, and washed with water and brine. After drying over anhydrous sodium sulfate, the solvent was evaporated away under reduced pressure, and the resulting residue was purified by silica gel column chromatography (dichloromethane to dichloromethane:methanol=70:1 to 20:1) and gel permeation (Sephadex (trade name) LH-20, methanol), then dissolved in tetrahydrofuran (10 ml). 1N Sodium hydroxide (0.60 ml, 0.60 mmol) was added, followed by stirring at room temperature for 16 hours, then 1 N hydrochloric acid (0.60 ml, 0.60 mmol) was added. The solvent was evaporated away under reduced pressure, and the resulting residue was purified by silica gel column chromatography (chloroform:methanol:water=8:3:0.5), then ether and a small amount of methanol were added, and the insoluble matter was collected by filtration to obtain a pale red amorphous substance (0.17 g, 27%).

MS (ESI) m/z: 446 (M+1)$^+$.

$^1$H-NMR (CDCl$_3$) δ: 1.80-1.95 (2H, m), 2.11 (3H, s), 2.30-2.70 (7H, m), 2.85-3.20 (2H, m), 3.45-3.70 (2H, m), 3.80-4.00 (1H, m), 4.30-4.60 (4H, m), 7.00-7.10 (1H, m), 7.10-7.20 (1H, m), 7.30-7.40 (3H, m).

Reference Example 149 tert-Butyl N-(1-benzhydrylazetidin-3-yl)-N-methylcarbamate (I-149)

N-(1-Benzhydrylazetidin-3-yl)-N-methylamine (0.30 g, 1.19 mmol) was dissolved in dichloromethane (6 ml), then a dichloromethane solution (dichloromethane, 4 ml) of di-tert-butyl dicarbonate (0.32 g, 1.47 mmol) was added, followed by stirring at room temperature for 1 hour. The reaction liquid was purified by silica gel column chromatography (dichloromethane:methanol=50:1) to obtain a colorless solid (0.40 g, 95%).

$^1$H-NMR (CDCl$_3$) δ: 1.41 (9H, m), 2.86 (3H, s), 2.95-3.05 (2H, m), 3.40-3.50 (2H, m), 4.32 (1H, s), 4.40-4.60 (1H, br), 7.15-7.30 (6H, m), 7.35-7.45 (4H, m).

Reference Example 150 tert-Butyl N-(1-acetylazetidin-3-yl)-N-methylcarbamate (I-150)

tert-Butyl N-(1-benzhydrylazetidin-3-yl)-N-methylcarbamate (I-149) (0.40 g, 1.13 mmol) was dissolved methanol (20 ml), then 20% palladium hydroxide-carbon (containing about 50% water, 20 g) was added, followed by stirring at room temperature under hydrogen atmosphere for 15 hours, and the catalyst was removed by filtration. The solvent was evaporated away under reduced pressure, the resulting residue was dissolved in dichloromethane (10 ml), and triethylamine (0.20 ml, 3.44 mmol) and acetyl chloride (90.0 μl, 26 mmol) were added.

After stirring at room temperature for 3 days, the reaction liquid was concentrated under reduced pressure, and ethyl acetate and water were added. The organic layer was separated, dried over anhydrous sodium sulfate, the solvent was evaporated away under reduced pressure, and the resulting residue was purified by silica gel column chromatography (dichloromethane:methanol=50:1) to obtain a colorless oil (99.0 mg, 38%).

MS (ESI) m/z: 229 (M+1)$^+$.

$^1$H-NMR (CDCl$_3$) δ: 1.47 (9H, m), 1.89 (3H, s), 2.91 (3H, s), 4.00-4.10 (1H, m), 4.10-4.20 (2H, m), 4.25-4.35 (1H, m), 4.70-5.10 (1H, br).

Reference Example 151

N-(1-Acetylazetidin-3-yl)methylamine trifluoroacetate (I-151)

tert-Butyl N-(1-acetylazetidin-3-yl)-N-methylcarbamate (I-150) (99.0 mg, 0.43 mmol) was dissolved in dichloromethane (2 ml), then trifluoroacetic acid (2 ml) was added, followed by stirring at room temperature for 45 minutes. The reaction liquid was evaporated under reduced pressure to obtain a colorless oil (0.11 g) this was used in the next reaction as such.

Reference Example 152

2-[1-Acetylazetidin-3-yl)(methyl)amino]-7-fluoro-5-methyl-6-fluoro-1,3-benzoxazole-4-carbonitrile (I-152)

2-Chloro-7-fluoro-5-methyl-6-phenyl-1,3-benzoxazole-4-cabonitrile (I-130) (0.12 g, 0.42 mmol) was dissolved in dichloromethane (10 ml), then diisopropylethylamine (0.21 ml, 1.23 mmol) and N-(1-acetylazetidin-3-yl)methylamine trifluoroacetate (I-151) (0.11 g, 0.45 mmol) were added. After heated under reflux for 3 hours, this was diluted with dichloromethane. After washing with water and drying over anhydrous sodium sulfate, the solvent was evaporated away under reduced pressure, and the resulting residue was purified by silica gel column chromatography (dichloromethane:methanol=100:1 to 30:1) to obtain a pale yellow oil (0.15 g, 95%).

MS (ESI) m/z: 379 (M+1)$^+$.

$^1$H-NMR (CDCl$_3$) δ: 1.95 (3H, s), 2.35 (3H, s), 3.35 (3H, s), 4.20-4.25 (1H, m), 4.30-4.40 (2H, m), 4.50-4.60 (1H, m), 5.20-5.30 (1H, m), 7.20-7.25 (2H, m), 7.40-7.50 (3H, m).

Example 68

2-[(1-Acetylazetidin-3-yl)(methyl)amino]-7-[(3S)-3-(dimethylamino)pyrrolidin-1-yl]-5-methyl-6-phenyl-1,3-benzoxazole-4-carbonitrile (#68)

2-[(1-Acetylazetidin-3-yl)(methyl)amino]-7-fluoro-5-methyl-6-fluoro-1,3-benzoxazole-4-carbonitrile (I-152) (0.15 g, 0.40 mmol) was dissolved in dimethyl sulfoxide (5 ml), then triethylamine (0.11 ml, 0.79 mmol) and (3S)-3-(dimethylamino)pyrrolidine (0.11 ml, 0.87 mmol) were added, followed by stirring in a sealed tube at an external temperature of about 150° C. for 4 hours. This was diluted with dichloromethane, and washed with water and brine. After drying over anhydrous sodium sulfate, the solvent was evaporated away under reduced pressure, and the resulting residue was purified by silica gel column chromatography (dichloromethane:methanol=20:1 to 10:1), then diisopropyl ether was added and the insoluble matter was collected by filtration to obtain a pale beige amorphous substance (89.0 mg, 48%).

MS (ESI) m/z: 473 (M+1)$^+$.

$^1$H-NMR (CDCl$_3$) δ: 1.50-1.65 (1H, m), 1.90-2.00 (1H, m), 1.95 (3H, s), 2.12 (6H, s), 2.15 (3H, s), 2.45-2.55 (1H, m), 2.85-2.95 (1H, m), 3.15-3.35 (3H, m), 3.26 (3H, s), 4.15-4.25 (1H, m), 4.30-4.40 (2H, m), 4.45-4.55 (1H, m), 5.10-5.25 (1H, m), 7.10 (1H, d, J=7.3 Hz), 7.22 (1H, d, J=7.3 Hz), 7.30-7.45 (3H, m). Anal. Calcd for C$_{27}$H$_{32}$N$_6$O$_2$: C, 68.62; H, 6.82; N, 17.78. Found: C, 68.24; H, 6.58; N, 17.43.

Reference Example 153

Benzyl (3-dimethylcarbamoylpropyl)carbamate (I-153)

4-(Benzyloxycarbonylamino)butyric acid (0.74 g, 3.12 mmol) was dissolved in N,N-dimethylformamide, then 1-(dimethylaminopropyl)-3-ethylcarbodiimide 1-ethyl-3-(3-dimethylaminopropyl)carbodiimide hydrochloride (0.60 g, 3.13 mmol), 1-hydroxybenzotriazole (0.48 g, 3.13 mmol) and dimethylamine (2.0 M tetrahydrofuran solution, 2.40 ml, 4.80 mmol) were added, followed by stirring at room temperature for 3 days. The reaction liquid was concentrated under reduced pressure, diluted with ethyl acetate, washed with water, and dried over anhydrous sodium sulfate. The solvent was evaporated away under reduced pressure, and the resulting residue was purified by silica gel column chromatography (dichloromethane:methanol=70:1 to 40:1) to obtain a yellow solid (0.68 g, 82%).

$^1$H-NMR (CDCl$_3$) δ: 1.80-1.90 (2H, m), 2.30-2.40 (2H, m), 2.93 (3H, s), 2.97 (3H, s), 3.20-3.30 (2H, m), 5.09 (2H, s), 5.10-5.25 (1H, br), 7.25-7.40 (5H, m).

Reference Example 154

Benzyl [3-dimethylcarbamoyl)propyl]methylcarbamate (I-154)

Benzyl (3-dimethylcarbamoylpropyl)carbamate (I-153) (0.68 g, 2.57 mmol) was dissolved in tetrahydrofuran (10 ml), and with codling with ice, sodium hydride (oily, about 55%, 0.16 g, 3.67 mmol) was added, followed by stirring for 10 minutes. Iodomethane (0.25 ml, 4.02 mmol) was added, followed by stirring at room temperature for 1 day, and water was added. After extraction with ethyl acetate and drying over anhydrous sodium sulfate, the solvent was evaporated away under reduced pressure, and the resulting residue was purified by silica gel column chromatography (dichloromethane: methanol=40:1) to obtain a pale yellow oil (0.66 g, 92%).

$^1$H-NMR (CDCl$_3$) δ: 1.85-1.95 (2H, m), 2.20-2.35 (2H, m), 2.85-3.00 (9H, m), 3.35 (2H, d, J=7.1 Hz), 5.12 (2H, s), 7.25-7.40 (5H, m).

Reference Example 155

N,N-Dimethyl-4-methylamino)butylamide (I-155)

Benzyl [3-(dimethylcarbamoyl)propyl]methylcarbamate (I-154) (0.26 g, 0.93 mmol) was dissolved in tetrahydrofuran (10 ml), then 10% palladium-carbon (containing about 50% water, 90.0 mg) was added, followed by stirring under hydrogen atmosphere for 15 hours. The catalyst was removed by filtration, the solvent was evaporated away under reduced pressure to obtain a yellow oil (0.31 g, quant.).

$^1$H-NMR (CDCl$_3$) δ: 1.75-1.90 (2H, m), 2.39 (2H, t, J=7.6 Hz), 2.43 (3H, s), 2.63 (2H, t, J=7.1 Hz), 2.95 (3H, s), 3.01 (3H, s).

Reference Example 156

4-{[4-Cyano-7-fluoro-5-methyl-6-phenyl-1,3-benzoxazol-2-yl}(methyl)amino]-N,N-dimethylbutanamide (I-156)

2-Chloro-7-fluoro-5-methyl-6-phenyl-1,3-benzoxazole-4-cabonitrile (I-130) (0.24 g, 0.84 mmol) was dissolved in dichloromethane (10 ml), then diisopropylethylamine (0.14 ml, 0.82 mmol) and N,N-dimethyl-4-(methylamino/butylamide (I-155) (0.13 g, 0.90 mmol) were added. After heated under reflux for 3 hours, this was diluted with dichloromethane. After washing with water and drying over anhydrous sodium sulfate, the solvent was evaporated away under reduced pressure, and the resulting residue was purified by silica gel column chromatography (dichloromethane:methanol=40:1) to obtain a pale yellow oil (0.32 g, 96%).

MS (ESI) m/z: 395 (M+1)$^+$.

$^1$H-NMR (CDCl$_3$) δ: 2.00-2.15 (2H, m), 2.34 (3H, s), 2.43 (2H, t, J=7.1 Hz), 2.94 (3H, s), 2.99 (3H, s), 3.28 (3H, s), 3.69 (2H, t, J=7.1 Hz), 7.20-7.30 (2H, m), 7.40-7.50 (3H, m).

Example 69

4-[{4-Cyano-7-[(3S)-3-(dimethylamino)pyrrolidin-1-yl]-5-methyl-6-phenyl-1,3-benzoxazol-2-yl}(methyl)amino]-N,N-dimethylbutanamide (#69)

4-[{4-Cyano-7-fluoro-5-methyl-6-phenyl-1,3-benzoxazol-2-yl}(methyl)amino]-N,N-dimethylbutanamide (I-156) (0.32 g, 0.81 mmol) was dissolved in dimethyl sulfoxide (5 ml), then triethylamine (0.24 ml, 1.73 mmol) and (3S)-3-(dimethylamino)pyrrolidine (0.21 ml, 1.66 mmol) were added, followed by stirring in a sealed tube at an external temperature of about 150° C. for 4 hours. This was diluted with dichloromethane, and washed with water and brine. After drying over anhydrous sodium sulfate, the solvent was evaporated away under reduced pressure, and the resulting residue was purified by silica gel column chromatography (dichloromethane:methanol=20:1 to 10:1), then diisopropyl ether was added and the insoluble matter was collected by filtration to obtain a colorless solid (0.22 g, 56%).

MS (ESI) m/z: 489 (M+1)$^+$.

$^1$H-NMR (CDCl$_3$) δ: 1.50-1.65 (1H, m), 1.85-1.95 (1H, m), 2.00-2.10 (2H, m), 2.11 (6H, s), 2.15 (3H, s), 2.41 (2H, t, J=7.1 Hz), 2.45-2.60 (1H, br), 2.80-2.95 (1H, m), 2.93 (3H, s), 2.98 (3H, s), 3.15-3.30 (3H, m), 3.21 (3H, s), 3.60-3.70 (2H, m), 7.11 (1H, d, J=7.3 Hz), 7.20-7.25 (1H, m), 7.25-7.40 (3H, m).

Anal. Calcd for C$_{28}$H$_{36}$N$_6$O$_2$: C, 68.83; H, 7.43; N, 17.20. Found: C, 68.75; H, 7.48; N, 16.88.

Reference Example 157

Ethyl 3-(benzyloxycarbonylamino)propionate (I-157)

Ethyl 3-aminopropionate hydrochloride (2.00 g, 13.0 mmol) was dissolved in dichloromethane (40 ml), and benzyl chloroformate (2.00 ml, 14.1 mmol) was added. With cooling with ice, triethylamine (4.00 ml, 28.9 mmol) was added, followed by stirring at room temperature for 15 hours, then the reaction, liquid was concentrated. Ethyl acetate and water were added, the organic layer was collected, and dried over anhydrous sodium sulfate. The solvent was evaporated away under reduced pressure, the resulting residue was purified by silica gel column chromatography (dichloromethane to dichloromethane:methanol=70:1) to obtain a pale yellow oil (3.26 g, quant).

$^1$H-NMR (CDCl$_3$) δ: 1.26 (3H, t, J=7.1 Hz), 2.50-2.60 (2H, m), 3.40-3.50 (2H, m), 4.15 (2H, q, J=7.1 Hz), 5.10 (2H, s), 5.20-5.30 (1H, br), 7.25-7.40 (5H, m).

Reference Example 158

Ethyl 3-[N-(benzyloxycarbonyl)methylamino]propionate (I-158)

Ethyl 3-(benzyloxycarbonylamino)propionate (I-157) (3.26 g, 13.0 mmol) was dissolved in tetrahydrofuran (40 ml), and with cooling with ice, sodium hydride (oily, about 55%, 0.70 g, 16.0 mmol) was added, followed by stirring for 1 hour with cooling with ice. Iodomethane (1.20 ml, 19.3 mmol) was added, followed by stirring at room temperature for 17 hours, and water was added. After extraction with ethyl acetate, this was dried over anhydrous sodium sulfate. The solvent was evaporated away under reduced pressure, and the resulting residue was purified by silica gel column chromatography (dichloromethane to dichloromethane:methanol=50:1) to obtain the entitled compound (2.93 g, 85%) as a brown oil.

$^1$H-NMR (CDCl$_3$) δ: 1.25 (3H, t, J=7.1 Hz), 2.50-2.65 (2H, m), 2.95 (3H, s), 3.58 (2H, t, J=7.1 Hz), 4.05-4.20 (2H, m), 5.10-5.20 (2H, m), 7.30-7.40 (5H, m).

Reference Example 159

Ethyl 3-(methylamino)propionate hydrochloride (I-159)

Ethyl 3-[N-(benzyloxycarbonyl)methylamino]propionate (I-158) (0.50 g, 1.88 mmol) was dissolved in ethanol (15 ml), then 10% palladium-carbon (containing about 50% water, 0.10 g) was added, followed by stirring under hydrogen atmosphere for 4 hours. The catalyst was removed by filtration, then 1 N hydrochloric acid (2.00 ml) was added to the filtrate. The solvent was evaporated away under reduced pressure to obtain a colorless oil (0.32 g). This was used in the next reaction as such.

Reference Example 160

Ethyl 3-[N-(4-cyano-7-fluoro-5-methyl-6-phenyl-1,3-benzoxazol-2-yl)methylamino]propionate (I-160)

2-Chloro-7-fluoro-5-methyl-6-phenyl-1,3-benzoxazole-4-cabonitrile (I-130) (0.49 g, 1.71 mmol), diisopropylethylamine (0.70 ml, 4.12 mmol) and ethyl 3-(methylamino)propionate hydrochloride (I-159) (0.32 g, 1.91 mmol) were dissolved in dichloromethane (15 ml). After heated under reflux for 3 hours, this was diluted with dichloromethane. After washed with water and drying over anhydrous sodium sulfate, the solvent was evaporated away under reduced pressure, and the resulting residue was purified by silica gel column chromatography (dichloromethane to dichloromethane:methanol=70; 1), then again purified by silica gel column chromatography (hexane:ethyl acetate=4:1 to 2:1) to obtain the entitled compound (0.53 g, 81%) as a brown oil.

MS (ESI) m/z: 382 (M+1)$^+$.

$^1$H-NMR (CDCl$_3$) δ: 1.27 (3H, t, J=7.3 Hz), 2.34 (3H, s), 2.77 (2H, t, J=6.8 Hz), 3.31 (3H, s), 3.92 (2H, t, J=6.8 Hz), 4.17 (2H, q, J=7.3 Hz), 7.20-7.30 (2H, m), 7.40-7.50 (3H, m).

Example 70

N-{4-Cyano-7-[(3S)-3-(dimethylamino)pyrrolidin-1-yl]-5-methyl-6-phenyl-1,3-benzoxazol-2-yl}-N-methyl-β-alanine (#70)

Ethyl 3-[N-(4-cyano-7-fluoro-5-methyl-6-phenyl-1,3-benzoxazol-2-yl)methylamino]propionate (I-160) (0.53 g, 1.39 mmol) was dissolved in dimethyl sulfoxide (7 ml), then triethylamine (0.42 ml, 3.03 mmol) and (3S)-3-(dimethylamino)pyrrolidine (0.38 ml, 3.00 mmol) were added, followed by stirring in a sealed tube at an external temperature of about 150° C. for 4 hours. This was diluted with, dichloromethane, and washed with water and brine. After drying over anhydrous sodium sulfate, the solvent was evaporated away under reduced pressure, and the resulting residue was purified by silica gel column chromatography (dichloromethane to dichloromethane:methanol=70:1 to 10:1), then dissolved in tetrahydrofuran (10 ml). 1 N Sodium hydroxide (0.60 ml) was added, followed by stirring at room temperature for 16 hours. 1 N Hydrochloric acid (0.60 ml) was added, then the solvent was evaporated away under reduced pressure, and the resulting residue was purified by silica gel column chromatography (chloroform:methanol:water=8:3:0.5) and preparative thin-layer chromatography (chloroform:methanol:water=8:3:0/5), then ethanol and a small amount of ether were added, and the insoluble matter was collected by filtration to obtain a colorless solid (0.11 g, 17%).

MS (ESI) m/z: 448 (M+1)$^+$.

$^1$H-NMR (CDCl$_3$) δ: 1.80-1.90 (2H, m), 2.16 (3H, s), 2.37 (6H, s), 2.50-2.75 (3H, m), 2.90-3.05 (1H, m), 3.10-3.20 (1H, m), 3.29 (3H, s), 3.40-3.50 (1H, m), 3.65-3.90 (3H, m), 7.10 (1H, d, J=7.3 Hz), 7.18 (1H, d, J=7.3 Hz), 7.30-7.45 (3H, m).

Anal. Calcd for C$_{25}$H$_{29}$N$_5$O$_3$.0.25H$_2$O: C, 66.43; H, 6.58; N, 15.49. Found: C, 66.35; H, 6.55; N, 15.25.

Reference Example 161

Ethyl 1-(4-cyano-7-fluoro-5-methyl-6-phenyl-1,3-benzoxazol-2-yl)piperidine-4-carboxylate (I-161)

2-Chloro-7-fluoro-5-methyl-6-phenyl-1,3-benzoxazole-4-carbonitrile (I-130) (0.20 g, 0.70 mmol) was dissolved in dichloromethane (10 ml), then ethyl isonipecotate (0.12 ml, 0.78 mmol) and diisopropylethylamine (0.15 ml, 0.88 mmol) were added, followed by heating under reflux for 3 hours. This was diluted with dichloromethane, washed with water, and dried over anhydrous sodium sulfate. The solvent was evaporated away under reduced pressure, and the resulting residue was purified by silica gel column chromatography (dichloromethane:methanol=100:1) to obtain a yellow oil (0.27 g, 94%).

MS (ESI) m/z: 408 (M+1)$^+$.

$^1$H-NMR (CDCl$_3$) δ: 1.28 (3H, t, J=7.3 Hz), 1.80-1.95 (2H, m), 2.05-2.15 (2H, m), 2.34 (3H, s), 2.55-2.65 (1H, m), 3.25-

3.40 (2H, m), 4.18 (2H, q, J=7.3 Hz), 4.25-4.35 (2H, m), 7.20-7.25 (2H, m), 7.40-7.50 (3H, m).

Reference Example 162

Ethyl 1-{4-cyano-7-[(3S)-3-(dimethylamino)pyrrolidin-1-yl]-5-methyl-6-phenyl-1,3-benzoxazol-2-yl}piperidine-4-carboxylate (I-162)

Ethyl 1-(4-cyano-7-fluoro-5-methyl-6-phenyl-1,3-benzoxazol-2-yl)piperidine-4-carboxylate (I-161) (0.27 g, 0.66 mmol) was dissolved in dimethyl sulfoxide (5 ml), then triethylamine (0.19 ml, 1.37 mmol) and (3S)-3-(dimethylamino)pyrrolidine (0.17 ml, 1.34 mmol) were added, followed by stirring in a sealed tube at an external temperature of about 150° C. for 4 hours.

This was diluted with dichloromethane, and washed with water and brine. After drying over anhydrous sodium sulfate, the solvent was evaporated away under reduced pressure, and the resulting residue was purified by silica gel column chromatography (dichloromethane:methanol=100:1 to 20:1) to obtain a brown oil (0.26 g, 79%).

$^1$H-NMR (CDCl$_3$) δ: 1.28 (3H, t, J=7.1 Hz), 1.55-1.70 (1H, m), 1.80-2.00 (3H, m), 2.00-2.10 (2H, m), 2.12 (6H, s), 2.15 (3H, s), 2.45-2.60 (2H, m), 2.90-3.00 (1H, m), 3.10-3.20 (1H, m), 3.20-3.30 (4H, m), 4.18 (2H, q, J=7.1 Hz), 4.20-4.30 (2H, m), 7.11 (1H, d, J=7.3 Hz), 7.20-7.25 (1H, m), 7.30-7.40 (3H, m).

Example 71

1-{4-Cyano-7-[(3S)-3-(dimethylamino)pyrrolidin-1-yl]-5-methyl-6-phenyl-1,3-benzoxazol-2-yl}piperidine-4-carboxylic acid (#71)

Ethyl 1-{4-cyano-7-[(3S)-3-(dimethylamino)pyrrolidin-1-yl]-5-methyl-6-phenyl-1,3-benzoxazol-2-yl}piperidine-4-carboxylate (I-162) (0.26 g, 0.52 mmol) was dissolved in tetrahydrofuran (10 ml), then 1 N sodium hydroxide (0.60 ml, 0.60 mmol) was added. After stirring at room temperature for 19 hours, 1 N sodium hydroxide (0.40 ml, 0.40 mmol) was further added, followed by stirring at room temperature for 24 hours. 1 N Hydrochloric acid (1.00 ml, 1.00 mmol) was added, then the solvent was evaporated away under reduced pressure. The resulting residue was purified by silica gel column chromatography (chloroform:methanol:water=8:3:0.5), then ethanol and a small amount of ether were added, and the insoluble matter was collected by filtration to obtain a colorless solid (0.18 g, 71%).

MS (ESI) m/z: 474 (M+1)$^+$.

$^1$H-NMR (CDCl$_3$) δ: 1.70-1.90 (4H, m), 2.00-2.10 (2H, m), 2.15 (3H, s), 2.37 (6H, s), 2.40-2.50 (2H, m), 2.80-2.90 (1H, m), 2.95-3.05 (1H, m), 3.20-3.30 (2H, m), 3.60-3.70 (1H, m), 3.85-3.95 (1H, m), 4.20-4.40 (2H, m), 7.10 (1H, d, J=7.3 Hz), 7.19 (1H, d, J=7.3 Hz), 7.30-7.45 (3H, m).

Anal. Calcd for C$_{27}$H$_{31}$N$_5$O$_3$·H$_2$O: C, 65.97; H, 6.77; N, 14.25. Found: C, 66.25; H, 6.79; N, 14.04.

Reference Example 163

N-[[2-(4-Methoxybenzyl)-2H-[1,2,4]triazol-3-yl]methyl]methylamine (I-163)

[2-(4-Methoxybenzyl)-2H-[1,2,4]triazol-3-yl]methanol (0.50 g, 2.28 mmol) was dissolved in dichloromethane (10 ml), then triethylamine (0.36 ml, 2.60 mmol) was added. With cooling with ice, methanesulfonyl chloride (0.20 ml, 2.58 mmol) was added, followed by stirring at room temperature for 2 hours. The reaction liquid was concentrated, ethyl acetate was added, followed by washing. After drying over anhydrous sodium sulfate, the solvent was evaporated away under reduced pressure, and the resulting residue was dissolved in tetrahydrofuran (25 ml), then aqueous methylamine solution (40%, 5 ml) was added. After stirring at room temperature for 3 days, the reaction liquid was concentrated. This was diluted with ethyl acetate, washed with water, and dried over anhydrous sodium sulfate. The solvent was evaporated away under reduced pressure to obtain a pale yellow oil (0.44 g, 83%).

$^1$H-NMR (CDCl$_3$) δ: 1.55-1.70 (1H, br), 2.42 (3H, s), 3.79 (3H, s), 3.84 (2H, s), 5.35 (2H, s), 6.85-6.90 (2H, m), 7.18 (2H, d, J=8.8 Hz), 7.84 (1H, s).

Reference Example 164

7-Fluoro-2-[N-[[2-(4-methoxybenzyl)-2H-[1,2,4]triazol-3-yl]methyl]methylamino]-5-methyl-6-phenyl-1,3-benzoxazole-4-carbonitrile (I-164)

2-Chloro-7-fluoro-5-methyl-6-phenyl-1,3-benzoxazole-4-cabonitrile (I-130) (0.20 g, 0.70 mmol), N-[[2-(4-methoxybenzyl)-2H-[1,2,4]triazol-3-yl]methyl]methylamine (I-163) (0.18 g, 0.77 mmol) and diisopropylethylamine (0.13 ml, 0.76 mmol) were dissolved in dichloromethane (10 ml), followed by heating under reflux for 3 hours. This was diluted with dichloromethane, washed with water, and dried over anhydrous sodium sulfate.

The solvent was evaporated away under reduced pressure, and the resulting residue was purified by silica gel column chromatography (dichloromethane:methanol=50:1) to obtain a yellow oil (0.33 g, 97%).

MS (ESI) m/z: 483 (M+1)$^+$.

$^1$H-NMR (CDCl$_3$) δ: 2.36 (3H, s), 3.25 (3H, s), 3.76 (3H, s), 4.92 (2H, s), 5.61 (2H, s), 6.75-6.85 (2H, m), 7.15 (2H, d, J=8.8 Hz), 7.20-7.25 (2H, m), 7.40-7.50 (3H, m), 7.93 (1H, s).

Reference Example 165

7-Fluoro-5-methyl-2-[methyl(1H-1,2,4-triazol-5-ylmethyl)amino]-6-phenyl-1,3-benzoxazole-4-carbonitrile (I-165)

7-Fluoro-2-[N-[[2-(4-methoxybenzyl)-2-H-[1,2,4]triazol-3-yl]methyl]methylamino]-5-methyl-6-phenyl-1,3-benzoxazole-4-carbonitrile (I-164) (0.33 g, 0.68 mmol) was dissolved in trifluoroacetic acid (5 ml), and stirred at room temperature for 16 hours, then at an external temperature of about 60° C. for 6 hours. The solvent was evaporated away under reduced pressure, then ethyl acetate and aqueous sodium hydrogencarbonate solution were added, and the organic layer was separated. After drying over anhydrous sodium sulfate, the solvent was evaporated away under reduced pressure, and the resulting residue was purified by silica gel column chromatography (dichloromethane:methanol=20:1) to obtain a colorless solid (0.24 g, 97%).

$^1$H-NMR (CDCl$_3$) δ: 2.33 (3H, s), 3.37 (3H, s), 4.96 (2H, s), 7.20-7.25 (2H, m), 7.40-7.50 (3H, m), 8.18 (1H, s).

Example 72

7-[(3S)-3-(Dimethylamino)pyrrolidin-1-yl]-5-methyl-2-[methyl(1H-1,2,4-triazol-5-ylmethyl)amino]-6-phenyl-1,3-benzoxazole-4-carbonitrile (#72)

7-Fluoro-5-methyl-2-[methyl(1H-1,2,4-triazol-5-ylmethyl)amino]-6-phenyl-1,3-benzoxazole-4-carbonitrile (I-165) (0.24 g, 0.66 mmol) was dissolved in dimethyl sulfoxide (5 ml), then triethylamine (0.19 ml, 1.37 mmol) and (3S)-3-(dimethylamino)pyrrolidine (0.17 ml, 1.34 mmol) were added, followed by stirring in a sealed tube at an external temperature of about 150° C. for 4 hours. This was diluted with dichloromethane, and washed with water and brine. After drying over anhydrous sodium sulfate, the solvent was evaporated away under reduced pressure, and the resulting residue was purified by silica gel column chromatography (dichloromethane:methanol=10:1), then diisopropyl ether was added and the insoluble matter was collected by filtration to obtain a beige solid (0.13 g, 42%).

MS (ESI) m/z: 457 (M+1)$^+$.

$^1$H-NMR (CDCl$_3$) δ: 1.50-1.65 (1H, m), 1.85-1.95 (1H, m), 2.13 (3H, s), 2.34 (6H, s), 2.45-2.60 (1H, m), 2.95-3.15 (2H, m), 3.20-3.30 (2H, m), 3.33 (3H, s), 4.83 (1H, d, J=15.8 Hz), 4.90 (1H, d, J=15.8 Hz), 7.07 (1H, d, J=7.1 Hz), 7.20 (1H, d, J=7.6 Hz), 7.30-7.40 (3H, m), 8.07 (1H, s).

Reference Example 166

7-Fluoro-5-methyl-2-(1-methyl-1H-pyrrol-2-yl)-6-phenyl-1,3-benzoxazole-4-carbonitrile (I-166)

Tributylstannyl-1-methylpyrrole (389 mg, 1.05 mmol), bis(triphenylphosphine)palladium(II) dichloride (49 mg, 0.07 mmol), and a catalytic amount of 2,6-di-tert-butylcresol (2 mg) were added to a toluene (20 ml) solution of 2-chloro-7-fluoro-5-methyl-6-phenyl-1,3-benzoxazole-4-cabonitrile (I-130) (200 mg, 0.70 mol), followed by stirring under heat under nitrogen atmosphere for 3 hours. After cooling, the reaction liquid was filtered, and the solvent of the filtrate was evaporate away under reduced pressure. The resulting residue was subjected to silica gel column chromatography, and eluted with a mixed solvent of n-hexane/ethyl acetate (9:1, v/v→5:1, v/v) to obtain a main product. After washing with isopropyl ether, the entitled compound (50 mg, 22%) was collected by filtration as a pale yellow solid.

$^1$H-NMR (CDCl$_3$) δ: 2.42 (3H, s), 4.19 (3H, s), 6.28 (1H, dd, J=2.8, 4.0 Hz), 6.96 (1H, t, J=2.0 Hz) 7.19-7.22 (1H, m), 7.25-7.32 (2H, m), 7.46-7.53 (3H, m).

Example 73

7-[(3S)-3-(Dimethylamino)pyrrolidin-1-yl]-5-methyl-2-(1-methyl-1H-pyrrol-2-yl)-6-phenyl-1,3-benzoxazole-4-carbonitrile (#73)

(3S)-3-(Dimethylamino)pyrrolidine (53 μl, 0.42 mmol) and triethylamine (100 μl) were added to a dimethyl sulfoxide (2 ml) solution of 7-fluoro-5-methyl-2-(1-methyl-1H-pyrrol-2-yl)-6-phenyl-1,3-benzoxazole-4-carbonitrile (I-166) (69 mg, 0.21 mmol). The system was purged with nitrogen, then sealed up, and heated at 110° C. for 3.5 hours. After cooling, the solvent was evaporated away under reduced pressure, the resulting residue was dissolved in chloroform and washed with water. The organic layer was dried over anhydrous sodium sulfate, then the solvent was evaporated away under reduced pressure, and the resulting residue was separated and purified by preparative TLC to obtain a main product. This was washed with a mixed solvent of isopropyl ether and ethanol, and the solid was collected by filtration to obtain the entitled compound (24 mg, 27%) as a colorless solid.

mp: 1.88-191° C. MS (EI) m/z: 425 (M$^+$).

$^1$H-NMR (CDCl$_3$) δ: 1.58-1.67 (1H, m), 1.93-2.01 (1H, m), 2.15 (6H, s), 2.21 (3H, s), 2.53 (1H, brs), 3.01 (1H, t, J=8.8 Hz), 3.30-3.47 (3H, m), 4.19 (3H, s), 6.24 (1H, dd, J=2.8, 4.0 Hz), 6.89 (1H, t, J=2.0 Hz), 6.99 (1H, dd, J=2.0, 4.0 Hz), 7.14 (1H, d, J=7.2 Hz), 7.25-7.29 (1H, m), 7.35-7.45 (3H, m).

IR (ATR): 2206, 1616, 1589, 1565, 1457, 1400, 1361, 1090 cm$^{-1}$.

Anal. Calcd for C$_{26}$H$_{27}$N$_5$O.0.5H$_2$O: C, 71.87; H, 6.49; N, 16.12. Found: C, 72.12; H, 6.30; N, 16.22.

Example 74

7-[(3S)-3-(Dimethylamino)pyrrolidin-1-yl]-5-methyl-2-(1-methyl-1H-pyrazol-4-yl)-6-phenyl-1,3-benzoxazole-4-carbonitrile (#74)

1-Methyl-4-(4,4,5,5-tetramethyl-1,3,2-dioxaboroan-2-yl)pyrazole (291 mg, 1.40 mmol), tetrakistriphenylphosphine palladium(0) (81 mg, 0.07 mmol), tripotassium phosphate (297 mg, 1.40 mmol) and water (1 ml) were added to a 1,4-dioxane (15 ml) solution of 2-chloro-7-fluoro-5-methyl-6-phenyl-1,3-benzoxazole-4-cabonitrile (I-130) (200 mg, 0.70 mmol), followed by heating under reflux under nitrogen atmosphere for 1.5 hours. After cooling, the reaction liquid was filtered, and the solvent of the filtrate was evaporated away under reduced pressure. The resulting residue was subjected to silica gel column chromatography, eluted with a mixed solvent of n-hexane/ethyl acetate (5:1, v/v→3:1, v/v), then eluted with a mixed solvent of chloroform/methanol (95:5, v/v) to obtain a main product. This was dissolved in toluene (20 ml), and heated under reflux in the presence of a catalytic amount of p-tosylic acid in a Dan-Stark device. After cooling, the reaction liquid was washed with water, the organic layer was dried over anhydrous sodium sulfate, then the solvent was evaporated away under reduced pressure.

(3S)-3-(Dimethylamino)pyrrolidine (317 μl, 2.5 mmol) and triethylamine (350 μl) were added to a dimethyl sulfoxide (8 ml) suspension of the resulting residue. The system was purged with nitrogen, then sealed up, and heated at 110° C. for 1 hour. After cooling, the solvent was evaporated away under reduced pressure, and the resulting residue was dissolved in chloroform and washed with water. The organic layer was dried over anhydrous sodium sulfate, then the solvent was evaporated away under reduced pressure, and the resulting residue was separated and purified by preparative TLC to obtain a main product. This was washed with a mixed solvent of isopropyl ether and ethanol, and the solid was collected by filtration to obtain the entitled compound (82 mg, 28%) as a colorless solid.

mp: 214-222° C. MS (EI) m/z: 426 (M$^+$).

$^1$H-NMR (CDCl$_3$) δ: 1.60-1.70 (1H, m), 1.92-2.02 (1H, m), 2.16 (6H, s), 2.21 (3H, s), 2.50-2.58 (1H, m), 3.03 (1H, t, J=9.2 Hz), 3.30-3.48 (3H, m), 4.01 (3H, s), 7.13 (1H, d, J=7.6

Hz), 7.24-7.27 (1H, m), 7.32-7.45 (3H, m), 8.08 (1H, s), 8.13 (1H, s).

IR (ATR): 2200, 1637, 1597, 1471, 1444, 1227, 991 cm$^{-1}$.

Anal. Calcd for $C_{25}H_{26}N_6O \cdot 0.75H_2O$: C, 68.24; H, 6.30; N, 19.10. Found: C, 68.07; H, 6.32; N, 19.10.

Reference Example 167

6-Bromo-2-chloro-7-fluoro-5-methyl-1,3-benzoxazole-4-carbonitrile (I-167)

2-Amino-5-bromo-4-fluoro-3-hydroxy-6-methylbenzonitrile (I-75) (1.54 g, 6.28 mmol) was dissolved in pyridine (80 ml), then potassium O-ethyl dithiocarbonate (3.10 g, 19.3 mmol) was added, followed by heating under reflux for 3 hours. The solvent was evaporated away under reduced pressure, then ethyl acetate and diluted hydrochloric acid were added for liquid-liquid separation of the organic layer. After washing with water and saturated brine and drying over anhydrous sodium sulfate, the solvent was evaporated away under reduced pressure. Again using 2-amino-5-bromo-4-fluoro-3-hydroxy-6-methylbenzonitrile (I-75) (1.45 g, 5.92 mmol), pyridine (75 ml) and potassium O-ethyl dithiocarbonate (2.90 g, 18.1 mmol), the same reaction was carried out, and the resulting residues were combined, dissolved in thionyl chloride (70 ml). N,N-dimethylformamide (0.70 ml) was added, followed by stirring at an external temperature of about 70° C. for 1 hour, then the reaction liquid was concentrated under reduced pressure. Dichloromethane and aqueous sodium hydrogencarbonate solution were added, and the organic layer was separated. After extraction with dichloromethane, the organic layers were combined, and dried over anhydrous sodium sulfate. The solvent was evaporated away under reduced pressure, and the resulting residue was purified by silica gel column chromatography (dichloromethane) to obtain the entitled compound (1.93 g, 55%) as a brown solid.

Reference Example 168

6-Bromo-2-(dimethylamino)-7-fluoro-5-methyl-1,3-benzoxazole-4-carbonitrile (I-168)

6-Bromo-2-chloro-7-fluoro-5-methyl-1,3-benzoxazole-4-carbonitrile (I-167) (1.93 g, 6.67 mmol) was dissolved in dichloromethane (40 ml), then diisopropylethylamine (1.20 ml, 7.06 mmol) and dimethylamine (2.0 M tetrahydrofuran solution, 5.00 ml, 10.0 mmol) were added. After stirring with heating under reflux overnight, this was diluted with dichloromethane. After washing with water and drying over anhydrous sodium sulfate, the solvent was evaporated away under reduced pressure, then the resulting residue was purified by silica gel column chromatography (dichloromethane to dichloromethane:methanol=70:1) to obtain a yellow solid (1.12 g, 56%).

MS (ESI) m/z: 298 [(M+1)$^+$, Br$^{79}$], 300 [(M+1)$^+$, Br$^{81}$].

$^1$H-NMR (CDCl$_3$) δ: 2.65 (3H, s), 3.28 (6H, s).

Reference Example 169

6-(1-Ethoxyvinyl)-2-(dimethylamino)-7-fluoro-5-methyl-1,3-benzoxazole-4-carbonitrile (I-169)

6-Bromo-2-(dimethylamino)-7-fluoro-5-methyl-1,3-benzoxazole-4-carbonitrile (I-168) (0.80 g, 2.68 mmol) was dissolved in toluene (25 ml), then tributyl(1-ethoxyvinyl)tin (1.30 ml, 3.85 mmol), 2,6-di-tert-butylcresol (12 mg, 0.05 mmol) and bis(triphenylphosphine)palladium(II) dichloride (0.10 g, 0.14 mmol) were added followed by heating under reflux for 3 days. The insoluble matter was removed by filtration through Celite, followed by washing with ethyl acetate. The solvent was evaporated away under reduced pressure, and the resulting residue was purified by silica gel column chromatography (dichloromethane:hexane=1:2 to 2:3 to 9:1 to dichloromethane:methanol=200:1) to obtain a brown solid (0.51 g, 66%).

$^1$H-NMR (CDCl$_3$) δ: 1.36 (3H, t, J=7.1 Hz), 2.52 (3H, s), 3.2 (6H, s), 3.92 (2H, q, J=7.1 Hz), 4.20 (1H, d, J=2.5 Hz), 4.55 (1H, d, J=2.5 Hz).

Reference Example 170

6-(Bromoacetyl)-2-(dimethylamino)-7-fluoro-5-methyl-1,3-benzoxazole-4-carbonitrile (I-170)

6-(1-Ethoxyvinyl)-2-(dimethylamino)-7-fluoro-5-methyl-1,3-benzoxazole-4-carbonitrile (I-169) (0.51 g, 1.76 mmol) was dissolved in tetrahydrofuran (10 ml), then water (1.0 ml), N-bromosuccinimide (0.30 g, 1.69 g) were added. After stirring at room temperature for 30 minutes, the solvent was evaporated away under reduced pressure, and the resulting residue was purified by silica gel column chromatography (dichloromethane to dichloromethane:methanol=100:1) to obtain a pale brown solid (0.60 g, 100%).

$^1$H-NMR (CDCl$_3$) δ: 2.57 (3H, s), 3.31 (6H, s), 4.32, 4.33 (2H, each s).

Reference Example 171

2-(Dimethylamino)-7-fluoro-5-methyl-6-(2-methyl-1,3-thiazol-4-yl)-1,3-benzoxazole-4-carbonitrile (I-171)

6-(Bromoacetyl)-2-(dimethylamino)-7-fluoro-5-methyl-1,3-benzoxazole-4-carbonitrile (I-170) (0.60 g, 1.76 mmol) was dissolved in toluene (30 ml), then thioacetamide (0.16 g, 2.13 mmol) and cesium carbonate (0.75 g, 2.30 mmol) were added, followed by stirring at an external temperature of 100° C. for 16 hours. The reaction liquid was diluted with ethyl acetate, washed with water, and dried over anhydrous sodium sulfate. The solvent was evaporated away under reduced pressure, and the resulting residue was purified by silica gel column chromatography (hexane:ethyl acetate=2:1 to 1:1) to obtain a yellow solid (0.44 g, 79%).

$^1$H-NMR (CDCl$_3$) δ: 2.45 (3H, s), 2.79 (3H, s), 3.29 (6H, s).

Example 75

2-(Dimethylamino)-7-[(3S)-3-(dimethylamino)pyrrolidin-1-yl]-5-methyl-6-(2-methyl-1,3-thiazol-4-yl)-1,3-benzoxazole-4-carbonitrile (#75)

2-(Dimethylamino)-7-fluoro-5-methyl-6-(2-methyl-1,3-thiazol-4-yl)-1,3-benzoxazole-4-carbonitrile (I-171) (0.44 g, 1.39 mmol) was suspended in dimethyl sulfoxide (10 ml), then triethylamine (0.42 ml 3.03 mmol) and (3S)-3-(dimethylamino)pyrrolidine (0.38 ml, 3.00 mmol) were added, followed by stirring at an external temperature of about 110° C. for 4 hours. This was diluted with ethyl acetate, washed with water, and dried over anhydrous sodium sulfate. The solvent was evaporated away under reduced pressure, and the resulting residue was purified by silica gel column chromatography (dichloromethane:methanol=50:1 to 10:1) to obtain a brown amorphous substance (0.51 g, 83%).

MS (ESI) m/z: 411 (M+1)$^+$.

$^1$H-NMR (CDCl$_3$) δ: 1.55-1.70 (1H, m), 1.95-2.05 (1H, m), 2.16 (3H, s), 2.17 (6H, s), 2.50-2.60 (1H, m), 2.76 (3H, s), 2.90-3.00 (1H, m), 3.21 (6H, s), 3.25-3.50 (3H, m), 6.93 (1H, s).

Anal. Calcd for C$_{21}$H$_{26}$N$_6$OS; C, 61.44; H, 6.38; N, 20.47; S, 7.81. Found: C, 61.38; H, 6.42; N, 20.43; S, 7.85.

Reference Example 172

2-Amino-7-fluoro-5-methyl-6-phenyl-1,3-benzoxazole-4-carbonitrile (I-172)

4-Amino-6-fluoro-5-hydroxy-2-methylbiphenyl-3-carbonitrile (I-41) (1.66 g, 6.86 mmol) and di(imidazol-1-yl) methanimine (2.821 g) were suspended in tetrahydrofuran (33 ml), and stirred under reflux under nitrogen atmosphere for 120 hours. After cooling to room temperature, the solvent was evaporated away under reduced pressure. The residue was fractionated with 10% methanol-containing chloroform and water. The organic layer was separated, and dried over anhydrous sodium sulfate. The insoluble matter was separated by filtration, and the solvent was evaporated away under reduced pressure. The residue was recrystallized form methanol to obtain the entitled compound (1.60 g, 87%) as a pale brown solid.

MS (LC) m/z: 268 (M+1)$^+$.

HRMS (EI) m/z: 267.0818 (Calcd for C$_{18}$H$_{10}$FN$_3$O 267.0807).

$^1$H-NMR (CDCl$_3$) δ: 2.23 (3H, s), 7.30-7.33 (2H, m), 7.40-7.51 (3H, m), 8.32 (2H, s).

IR (ATR): 3327, 3111, 2227, 1680, 1560, 1429, 1288, 1124, 1107, 939, 744, 717, 694 cm$^{-1}$.

Example 76

2-Amino-7-[(3S)-3-(dimethylamino)pyrrolidin-1-yl]-5-methyl-6-phenyl-1,3-benzoxazole-4-carbonitrile (#76)

2-Amino-7-fluoro-5-methyl-6-phenyl-1,3-benzoxazole-4-carbonitrile (I-172) (200 mg, 0.75 mmol), (3S)-3-(dimethylamino)pyrrolidine (190 μl, 1.50 mmol) and triethylamine (209 μl, 1.50 mmol) were dissolved in dimethyl sulfoxide (4 ml), and the mixture was heated in a sealed tube at 150° C. for 4 hours. After cooling to room temperature, the reaction liquid was fractionated with ethyl acetate and saturated brine. The aqueous layer was separated, and this was extracted twice with ethyl acetate. The organic layers were combined, washed with saturated brine, and dried over anhydrous sodium sulfate. The insoluble matter was separated by filtration, and the solvent was evaporated away under reduced pressure. The solvent was evaporated away, and the resulting residue was purified by preparative TLC (eluent; 7 N ammonia-containing methanol solution:chloroform=8:92) to obtain the entitled compound (81 mg, 30%) as a roughly-purified product. This was further recrystallized from ethyl acetate-hexane to obtain a brown solid (62 mg).

MS (ESI) m/z: 362 (M+1)$^+$.

HRMS (EI) m/z: 361.1904 (Calcd for C$_{21}$H$_{23}$N$_5$O 361.1903).

$^1$H-NMR (CDCl$_3$) δ: 1.38-1.49 (1H, m), 1.79-1.86 (1H, m), 1.96 (6H, s), 2.01 (3H, s), 2.38-2.47 (1H, m), 2.67 (1H, t, J=8.3 Hz), 3.07-3.27 (3H, m), 7.09-7.12 (1H, m), 7.27-7.30 (1H, m), 7.32-7.45 (3H, m), 7.73 (2H, s).

IR (ATR): 3228, 2210, 1672, 1560, 1466, 1408, 1286, 739 cm$^{-1}$.

Anal. Calcd for C$_{21}$H$_{23}$N$_5$O.0.25H$_2$O; C, 68.92; H, 6.47; N, 19.14. Found: C, 68.68; H, 6.41; N, 18.79.

Example 77

N-{4-Cyano-7-[(3S)-3-(dimethylamino)pyrrolidin-1-yl]-5-methyl-6-phenyl-1,3-benzoxazol-2-yl}-N-acetamide (#17)

2-Amino-7-[(3S)-3-(dimethylamino)pyrrolidin-1-yl]-5-methyl-6-phenyl-1,3-benzoxazole-4-carbonitrile (#76) (80 mg, 0.22 mmol) was dissolved in pyridine (2.4 ml), then acetyl chloride (32 μl, 0.44 mmol) was added, followed by stirring under nitrogen atmosphere at 90° C. for 5 hours. After cooling and fractionating with water and ethyl acetate, the organic layer was washed with saturated brine. The obtained organic layer was dried over anhydrous sodium sulfate, then the solvent was evaporated away under reduced pressure. The resulting residue was subjected to preparative silica gel column chromatography. Elution with a mixed solvent of chloroform/methanol (10:1, v/v) followed by recrystallization and purification in a mixed liquid of diisopropyl ether/ethyl acetate/n-hexane gave the entitled compound (28.8 mg, 32%) as a white solid.

mp: 111-113° C. MS (ESI) m/z: 404 (M+1)$^+$.

$^1$H-NMR (CDCl$_3$) δ: 1.57-1.68 (1H, m), 1.90-1.97 (1H, m), 2.13 (6H, s), 2.18 (3H, s), 2.47 (3H, s), 2.54 (1H, br s), 2.91-2.97 (1H, m), 3.26-3.44 (3H, m), 7.13 (1H, d, J=7.3 Hz), 7.24 (1H, d, J=7.3 Hz), 7.33-7.42 (3H, m).

IR (ATR): 2210, 1601, 1558, 1365 cm$^{-1}$.

Anal. Calcd for C$_{23}$H$_{25}$N$_5$O$_2$.0.25H$_2$O: C, 67.71; H, 6.30; N, 17.17. Found: C, 67.36; H, 6.56; N, 15.99.

Example 78

N-{4-Cyano-7-[(3S)-3-(dimethylamino)pyrrolidin-1-yl]-5-methyl-6-phenyl-1,3-benzoxazol-2-yl}methanesulfonamide (#78)

2-Amino-7-[3-(dimethylamino)pyrrolidin-1-yl]-5-methyl-6-phenyl-1,3-benzoxazole-4-carbonitrile (#76) was suspended in dichloromethane (3.4 ml), then triethylamine (94.9 μl, 681 μmol) and methanesulfonyl chloride (52.7 μl, 681 μmol) were added with cooling with ice, then dichloromethane (10 ml) was added, followed by stirring with cooling with ice for 5 hours. Further, triethylamine (94.9 μl, 681 μmol) and methanesulfonyl chloride (52.7 μl, 681 μmol) were added with cooling with ice, followed by stirring at room temperature for 15 hours. Aqueous 1 N sodium hydroxide solution (5 ml) and water (5 ml) were added to the reaction liquid, and the aqueous layer was washed with diethyl ether (20 ml×2).

The aqueous layer was controlled at pH=7.4, followed by extraction with chloroform (100 ml×2). The organic layer was dried over anhydrous sodium sulfate, the insoluble matter was separated by filtration, and the solvent was evaporated away under reduced pressure. The resulting residue was purified by PTLC (lower layer of eluent, chloroform:methanol:water=7:3:1) to obtain the entitled compound (40.0 mg, 25.2%) as a pale yellow powder.

MS (ESI) m/z: 440 (M+1)$^+$.

$^1$H-NMR (CDCl$_3$) δ: 1.96-2.07 (1H, m), 2.07-2.17 (1H, m), 2.14 (3H, s), 2.74 (6H, s), 2.97-3.08 (1H, m), 3.13 (3H, s), 3.23-3.32 (1H, m), 3.45-3.56 (2H, m), 3.63-3.74 (1H, m), 7.04 (1H, d, J=7.8 Hz), 7.31-7.44 (4H, m).

IR (ATR): 3051, 3024, 2208, 1601, 1529, 1466, 1439, 1412, 1367, 1302, 1255, 1178, 1157, 1115, 980, 951, 889, 833, 775, 748, 731, 704 cm$^{-1}$.

Anal. Calcd for $C_{22}H_{25}N_5O_3S\cdot1.5H_2O$: C, 56.64; H, 6.05; N, 15.01; S, 7.87. Found: C, 56.59; H, 5.68; N, 14.82; S, 7.60.

Reference Example 173

2-Cyclopropyl-7-fluoro-5-methyl-6-phenyl-1,3-benzoxazole-4-carbonitrile (I-173)

6-Bromo-2-cyclopropyl-7-fluoro-5-methyl-1,3-benzoxazole-4-carbonitrile (I-77) (300 mg, 1.02 mmol), phenylboronic acid (256 mg, 2.03 mmol) and tripotassium phosphate (432 mg, 2.03 mmol) were dissolved in 1,4-dioxane (6 ml), then tetrakis(triphenylphosphine)palladium(0) (118 mg, 0.10 mmol) was added at room temperature. The solution was stirred under nitrogen atmosphere at 100° C. for 17 hours. After cooling to room temperature, aqueous saturated ammonium chloride solution was added to the reaction liquid, followed by stirring at room temperature for 10 minutes. The insoluble matter was separated by filtration with washing with ethyl acetate, and further the aqueous layer of the filtrate was extracted twice with ethyl acetate. The organic layers were combined, washed with saturated brine, and dried over anhydrous sodium sulfate. The insoluble matter was separated by filtration, the solvent was evaporated away, and the resulting residue was purified by middle-pressure liquid chromatography (eluent, hexane:ethyl acetate=8:1) to obtain the entitled compound (275 mg, 92%) as a white solid.

MS (ESI) m/z: 293 (M+1)$^+$.

$^1$H-NMR (CDCl$_3$) δ: 1.26-2.01 (2H, m), 2.38-2.42 (2H, m), 2.28-2.34 (1H, m), 2.40 (3H, s), 7.21-7.26 (2H, m), 7.42-7.51 (1H, m).

Example 79

2-Cyclopropyl-7-[(3S)-3-(dimethylamino)pyrrolidin-1-yl]-5-methyl-6-phenyl-1,3-benzoxazole-4-carbonitrile (#79)

2-Cyclopropyl-7-fluoro-5-methyl-6-phenyl-1,3-benzoxazole-4-carbonitrile (I-173) (70 mg, 0.24 mmol) was dissolved in dimethyl sulfoxide (2 ml), then at room temperature, triethylamine (50 µl, 0.36 mmol) and (3S)-3-(dimethylamino)pyrrolidine (40 µl, 0.31 mmol) were added. After cooling to room temperature, the reaction liquid was fractionated with ethyl acetate and saturated brine. The aqueous layer was further extracted twice with ethyl acetate. The organic layers were combined, washed with saturated brine, and dried over anhydrous sodium sulfate. The insoluble matter was separated by filtration, then the solvent was evaporated away, and the resulting residue was purified by preparative TLC (eluent, chloroform:methanol=97:3) to obtain a roughly-purified product (64 mg, 69%).

This was recrystallized from diethyl ether to obtain the entitled compound (34 mg) as a white solid.

MS (ESI) m/z: 387 (M+1)$^+$.

HRMS (EI) m/z: 386.2111 (Calcd for $C_{24}H_{26}N_4O$ 386.2107).

$^1$H-NMR (CDCl$_3$) δ: 1.17-2.30 (4H, m), 1.55-1.67 (1H, m), 1.90-1.98 (1H, m), 2.14 (6H, s), 2.17 (3H, s), 2.24 (1H, ddd, J=5.1, 8.5, 13.0 Hz), 2.48-2.57 (1H, m), 2.94 (1H, t, J=9.3 Hz), 3.22-3.39 (3H, m), 7.10 (1H, d, J=7.6 Hz), 7.23 (1H, d, J=7.6 Hz), 7.31-7.42 (3H, m).

IR (ATR): 2206, 1585, 1560, 1466, 1152, 712, 702 cm$^{-1}$.

Anal. Calcd for $C_{24}H_{26}N_4O\cdot0.25H_2O$: C, 73.72; H, 6.83; N, 14.33. Found: C, 74.08; H, 6.76; N, 14.35.

Reference Example 174

2-Cyclopropyl-7-fluoro-6-(3-fluorophenyl)-5-methyl-1,3-benzoxazole-4-carbonitrile (I-174)

6-Bromo-2-cyclopropyl-7-fluoro-5-methyl-1,3-benzoxazole-4-carbonitrile (I-77) (200 mg, 0.68 mmol), 3-fluorophenylboronic acid (380 mg, 2.71 mmol) and tripotassium phosphate (288 mg, 1.36 mmol) were dissolved in 1,4-dioxane (8 ml), then at room temperature, tetrakis(triphenylphosphine)palladium(0) (157 mg, 0.14 mmol) was added. The solution was stirred under nitrogen atmosphere at 95° C. for 17 hours. After cooling to room temperature, the reaction liquid was fractionated with ethyl acetate and aqueous saturated ammonium chloride solution. The aqueous layer was further extracted twice with ethyl acetate. The organic layers were combined, washed with saturated brine, and dried over anhydrous sodium sulfate. The insoluble matter was separated by filtration, the solvent was evaporated away, and the resulting residue was purified by middle-pressure liquid chromatography (eluent, hexane:ethyl acetate=8:1) to obtain the entitled compound (151 mg, 72%) as a white solid.

MS (ESI) m/z: 311 (M+1)$^+$.

HRMS (EI) m/z: 310.0909 (Calcd for $C_{18}H_{12}F_2N_2O$ 310.0918).

$^1$H-NMR (CDCl$_3$) δ: 1.26-1.32 (2H, m) 1.37-1.42 (2H, m), 2.28-2.35 (1H, m), 2.41 (3H, s), 6.97 (1H, dt, J=2.2, 9.3 Hz), 7.03 (1H, d, J=7.8 Hz), 7.17 (1H, ddt, J=1.0, 2.7, 8.5 Hz), 7.43-7.50 (1H, m).

IR (ATR): 2227, 1562, 1410, 1155, 1120, 881, 779, 742 cm$^{-1}$.

Example 80

2-Cyclopropyl-7-[(3S)-3-(dimethylamino)pyrrolidin-1-yl]-6-(3-fluorophenyl)-5-methyl-1,3-benzoxazole-4-carbonitrile 2-Cyclopropyl-7-fluoro-6-(3-fluorophenyl)-5-methyl-1,3-benzoxazole-4-carbonitrile (I-174) (150 mg, 0.48 mmol) was dissolved in dimethyl sulfoxide (3 ml), then at room temperature, triethylamine (101 µl, 0.73 mmol) and (3S)-3-(dimethylamino)pyrrolidine (80 µl, 0.63 mmol) were added. The solution was stirred under nitrogen atmosphere at 90° C. for 10 hours.

After cooling to room temperature, the reaction liquid was fractionated with ethyl acetate and an aqueous saturated sodium hydrogencarbonate solution. The aqueous layer was further extracted once with ethyl acetate. The organic layers were combined, washed with saturated brine, and dried over anhydrous sodium sulfate. The insoluble matter was separated by filtration, then the solvent was evaporated away, and the resulting residue was purified by preparative TLC (eluent, chloroform:methanol=97:3) to obtain a roughly-purified product (158 mg, 81%) as a white solid. This was recrystallized from diisopropyl ether and hexane to obtain the entitled compound (115 mg) as a white solid.

MS (ESI) m/z: 405 (M+1)$^+$.

HRMS (EI) m/z: 404.2019 (Calcd for $C_{24}H_{25}FN_4O$ 404.2012).

¹H-NMR (CDCl₃) δ: 1.18-1.31 (4H, m), 1.57-1.67 (1H, m), 1.92-2.00 (1H, m), 2.15 (3H, s), 2.18 (1.5H, s), 2.19 (1.5H, s), 2.20-2.27 (1H, m), 2.49-2.58 (1H, m), 2.99 (0.5H, t, J=9.0 Hz), 3.02 (0.5H, t, J=9.0 Hz), 3.21-3.40 (3H, m), 6.84 (0.5H, ddd, J=1.5, 2.4, 9.5 Hz), 6.91 (0.5H, dt, J=1.5, 7.6 Hz), 6.97 (0.5H, ddd, J=1.5, 2.4, 9.5 Hz), 7.03-7.09 (1.5H, m), 7.33-7.41 (1H, m).

IR (ATR): 2202, 1608, 1589, 1562, 1470, 1446, 1365, 1192, 779 cm⁻¹.

Anal. Calcd for $C_{25}H_{24}FN_4O$: C, 71.27; H, 6.23; N, 13.85. Found: C, 70.93; H, 6.21; N, 13.66.

Reference Example 175

2-Cyclopropyl-7-fluoro-6-(2-fluorophenyl)-5-methyl-1,3-benzoxazole-4-carbonitrile (I-175)

6-Bromo-2-cyclopropyl-7-fluoro-5-methyl-1,3-benzoxazole-4-carbonitrile (I-77) (200 mg, 0.68 mmol), 2-fluorophenylboronic acid (380 mg, 2.71 mmol) and tripotassium phosphate (288 mg, 1.36 mmol) were dissolved in 1,4-dioxane (8 ml), then at room temperature, tetrakis(triphenylphosphine)palladium(0) (157 mg, 0.14 mmol) was added. The solution was stirred under nitrogen atmosphere at 95° C. for 48 hours. After cooling to room temperature, aqueous saturated ammonium chloride solution was added to the reaction liquid, followed by stirring at room temperature for 5 minutes. This was extracted twice with ethyl acetate.

The organic layers were combined, washed with saturated brine, and dried over anhydrous sodium sulfate. The insoluble matter was separated by filtration, the solvent was evaporated away, and the resulting residue was purified by middle-pressure liquid chromatography (eluent, hexane:ethyl acetate=8:1) to obtain the entitled compound (148 mg, 70%) as a colorless gel.

MS (ESI) m/z: 311 (M+1)⁺.

HRMS (EI) m/z: 310.0914 (Calcd for $C_{18}H_{12}F_2N_2O$ 310.0917).

¹H-NMR (CDCl₃) δ: 1.27-1.42 (4H, m), 2.28-2.35 (1H, m), 2.42 (3H, s), 7.20-7.31 (3H, m), 7.45-7.51 (1H, m).

IR (ATR): 2227, 1570, 1126, 756 cm⁻¹.

Example 81

2-Cyclopropyl-7-[(3S)-3-(dimethylamino)pyrrolidin-1-yl]-6-(2-fluorophenyl)-5-methyl-1,3-benzoxazole-4-carbonitrile (#81)

2-Cyclopropyl-7-fluoro-6-(2-fluorophenyl)-5-methyl-1,3-benzoxazole-4-carbonitrile (I-175) (147 mg, 0.47 mmol) was dissolved in dimethyl sulfoxide (3 ml), then at room temperature, triethylamine (99 μl, 0.71 mmol) and (3S)-3-(dimethylamino)pyrrolidine (78 μl, 0.62 mmol) were added. The solution was stirred under nitrogen atmosphere at 90° C. for 10 hours. After cooling to room temperature, the reaction liquid was fractionated with ethyl acetate and an aqueous saturated sodium hydrogencarbonate solution.

The aqueous layer was further extracted once with ethyl acetate. The organic layers were combined, washed with saturated brine, and dried over anhydrous sodium sulfate. The insoluble matter was separated by filtration, then the solvent was evaporated away, and the resulting residue was purified by preparative TLC (eluent, chloroform:methanol=97:3) to obtain a roughly-purified product (159 mg, 83%) as a white solid. This was recrystallized from diisopropyl ether and hexane to obtain the entitled compound (105 mg) as a white solid.

MS (ESI) m/z: 405 (M+1)⁺.

HRMS (EI) m/z: 404.2000 (Calcd for $C_{24}H_{25}FN_4O$ 404.2012).

¹H-NMR (CDCl₃) δ: 1.17-1.30 (4H, m), 1.56-1.71 (1H, m), 1.90-2.03 (1H, m), 2.14 (3.6H, s), 2.15 (2.4H, s), 2.19 (3H, s), 2.20-2.29 (1H, m), 2.47-2.61 (1H, m), 2.91 (0.6H, t, J=9.0 Hz), 3.04 (0.4H, t, J=9.0 Hz), 3.26-3.44 (3H, m), 7.03-7.24 (3H, m), 7.34-7.41 (1H, m).

IR (ATR): 2204, 1606, 1587, 1558, 1470, 1446, 756 cm⁻¹.

Anal. Calcd for $C_{25}H_{24}FN_4O$: C, 71.27; H, 6.23; N, 13.85. Found: C, 71.11; H, 6.20; N, 13.66.

Reference Example 176

2-Cyclopropyl-6-(3,5-difluorophenyl)-7-fluoro-5-methyl-1,3-benzoxazole-4-carbonitrile (I-176)

6-Bromo-2-cyclopropyl-7-fluoro-5-methyl-1,3-benzoxazole-4-carbonitrile (I-77) (200 mg, 0.68 mmol), 3,5-difluorophenylboronic acid (428 mg, 2.71 mmol) and tripotassium phosphate (288 mg, 1.36 mmol) were dissolved in 1,4-dioxane (8 ml), then at room temperature, tetrakis(triphenylphosphine)palladium(0) (157 mg, 0.14 mmol) was added. The solution was stirred under nitrogen atmosphere at 95° C. for 60 hours. After cooling to room temperature, aqueous saturated ammonium chloride solution was added to the reaction liquid, followed by stirring at room temperature for 5 minutes. This was extracted twice with ethyl acetate. The organic layers were combined, washed with saturated brine, and dried over anhydrous sodium sulfate. The insoluble matter was separated by filtration, the solvent was evaporated away, and the resulting residue was purified by middle-pressure liquid chromatography (eluent, hexane:ethyl acetate=8:1) to obtain the entitled compound (240.5 mg containing impurities (reference)) as a white solid. Since the impurities were difficult to separate, they are separated in the next step.

MS (ESI) m/z: 329 (M+1)⁺.

¹H-NMR (CDCl₃) δ: 1.22-1.44 (4H, m), 2.17-2.23 (0.15H, m), 2.29-2.37 (0.85H, m), 2.41 (0.45H, s), 2.42 (2.55H, s), 6.56 (0.15H, ddt, J=2.2, 8.8, 8.8 Hz), 6.69-6.73 (0.3H, m), 6.78-6.86 (1.7H, m), 6.93 (0.85H, ddt, J=2.2, 8.8, 8.8 Hz).

Example 82

2-Cyclopropyl-6-(3,5-difluorophenyl)-7-[(3S)-3-(dimethylamino)pyrrolidin-1-yl]-5-methyl-1,3-benzoxazole-4-carbonitrile (#82)

2-Cyclopropyl-6-(3,5-difluorophenyl)-7-fluoro-5-methyl-1,3-benzoxazole-4-carbonitrile (I-176) (including impurities, estimated as 0.68 mmol) was dissolved in dimethyl sulfoxide (5 ml), then at room temperature, triethylamine (142 μl, 1.02 mmol) and (3S)-3-(dimethylamino)pyrrolidine (112 μl, 0.88 mmol) were added, the solution was stirred under nitrogen atmosphere at 90° C. for 15 hours. After cooling to room temperature, the reaction liquid was fractionated with ethyl acetate and an aqueous saturated sodium hydrogencarbonate solution. The aqueous layer was further extracted twice with ethyl acetate. The organic layers were combined, washed with saturated brine, and dried over anhydrous sodium sulfate. The insoluble matter was separated by filtration, then the solvent was evaporated away, and the resulting residue was purified by preparative TLC (eluent, chloroform:methanol=96:4) to obtain a roughly-purified product (211 mg, 74% for 2 steps) as a white solid. This was recrystallized from ethyl acetate and diisopropyl ether to obtain the entitled compound (46 mg) as a white solid.

MS (ESI) m/z: 423 (M+1)+.

HRMS (EI) m/z: 422.1935 (Calcd for $C_{24}H_{24}F_2N_4O$ 422.1918).

$^1$H-NMR (CDCl$_3$) δ: 1.18-1.31 (4H, m), 1.62-1.73 (1H, m), 1.97-2.04 (1H, m), 2.20 (3H, s), 2.21 (6H, s), 2.20-2.27 (1H, m), 2.57-2.65 (1H, m), 3.10 (01H, t, J=9.0 Hz), 3.27 (1H, dt, J=6.6, 10.3 Hz), 3.33-3.42 (2H, m), 6.68 (1H, d, J=8.8 Hz), 6.80-6.86 (2H, m).

IR (ATR): 2206, 1585, 1560, 365, 1115, 982 cm$^{-1}$.

Anal. Calcd for $C_{24}H_{24}F_2N_4O \cdot 0.25H_2O$: C, 67.5-1; H, 5.78; N, 13.12. Found: C, 67.44; H, 5.67; N, 13.05.

Reference Example 177

2-Cyclopropyl-6-(2,3-difluorophenyl)-7-fluoro-5-methyl-1,3-benzoxazole-4-carbonitrile (I-177)

6-Bromo-2-cyclopropyl-7-fluoro-5-methyl-1,3-benzoxazole-4-carbonitrile (I-77) (190 mg, 0.64 mmol), 2,3-difluorophenylboronic acid (407 mg, 2.58 mmol) and tripotassium phosphate (274 mg, 1.29 mmol) were dissolved in 1,4-dioxane (6 ml), then at room temperature, tetrakis(triphenylphosphine)palladium(0) (149 mg, 0.13 mmol) was added. The suspension was stirred under nitrogen atmosphere at 95° C. for 86 hours. After cooling to room temperature, the solution was fractionated with ethyl acetate and aqueous saturated ammonium chloride solution. The aqueous layer was extracted twice with ethyl acetate. The organic layers were combined, washed with saturated brine, and dried over anhydrous sodium sulfate. The solvent was evaporated away, and the resulting residue was purified by middle-pressure liquid chromatography (eluent, hexane:ethyl acetate=9:1) to obtain the entitled compound (111 mg, 53%) as a white solid.

MS (ESI) m/z: 329 (M+1)+.

HRMS (EI) m/z: 328.0826 (Calcd for $C_{18}H_{11}N_2F_3O$ 328.0823).

$^1$H-NMR (CDCl$_3$) δ: 1.27-1.44 (4H, m), 2.28-2.35 (1H, m), 2.42 (3H, s), 6.98-7.02 (1H, m), 7.19-7.34 (2H, m).

IR (ATR): 2227, 1572, 1473, 1414, 1325, 1271, 1130, 1028, 951, 920, 879, 833, 800, 762, 742 cm$^{-1}$.

Example 83

2-Cyclopropyl-6-(2,3-difluorophenyl)-7-[(3S)-3-(dimethylamino)pyrrolidin-1-yl]-5-methyl-1,3-benzoxazole-4-carbonitrile (#83)

2-Cyclopropyl-6-(2,3-difluorophenyl)-7-fluoro-5-methyl-1,3-benzoxazole-4-carbonitrile (I-177) (109 mg, 0.33 mmol) was dissolved in dimethyl sulfoxide (3 ml), then at room temperature, triethylamine (70 µl, 0.50 mmol) and (3S)-3-(dimethylamino)pyrrolidine (55 µl, 0.43 mmol) were added. The solution was stirred under nitrogen atmosphere at 90° C. for 23 hours. After cooling to room temperature, the reaction liquid was fractionated with ethyl acetate and an aqueous saturated sodium hydrogencarbonate solution. The aqueous layer was further extracted twice with ethyl acetate. The organic layers were combined, washed with saturated brine, and dried over anhydrous sodium sulfate. The insoluble matter was separated by filtration, then the solvent was evaporated away, and the resulting residue was purified by preparative TLC (eluent, chloroform:methanol=92:8) to obtain a roughly-purified product (119 mg, 85%) as a white solid. This was recrystallized from diisopropyl ether to obtain the entitled compound (71 mg) as a white solid.

MS (ESI) m/z: 423 (M+1)+.

HRMS (EI) m/z: 422.1910 (Calcd for $C_{24}H_{24}F_2N_4O$ 422.1918).

$^1$H-NMR (CDCl$_3$) δ: 1.19-1.30 (4H, m), 1.59-1.75 (1H, m), 1.95-2.07 (1H, m), 2.17 (6H, s), 2.19 (1.5H, s), 2.20 (1.5H, s), 2.20-2.30 (1H, m), 2.52-2.66 (1H, m), 2.99 (0.5H, t, J=9.2 Hz), 3.08 (0.5H, t, J=9.2 Hz), 3.29-3.45 (3H, m), 6.87 (0.5H, dd, J=6.3, 7.3 Hz), 7.03 (0.5H, dd, J=6.3, 7.3 Hz), 7.11-7.28 (2H, m).

IR (ATR): 2212, 1606, 1587, 1471, 1365, 1267, 1173, 1059, 1038, 935, 831, 800, 762, 742 cm$^{-1}$.

Anal. Calcd for $C_{24}H_{24}F_2N_4O \cdot 0.25H_2O$: C, 67.51; H, 5.78; N, 13.12. Found: C, 67.41; H, 5.60; N, 12.94.

Reference Example 178

6-(3-Aminophenyl)-2-cyclopropyl-7-fluoro-5-methyl-1,3-benzoxazole-4-carbonitrile (I-178)

6-Bromo-2-cyclopropyl-7-fluoro-5-methyl-1,3-benzoxazole-4-carbonitrile (I-77) (150 mg, 0.51 mmol) and 3-aminophenylboronic acid monohydrate (315 mg, 2.03 mmol) were dissolved in 1,4-dioxane (5 ml), then at room temperature, tripotassium phosphate (216 mg, 1.02 mmol) and then tetrakis(triphenylphosphine)palladium(0) (118 mg, 0.10 mmol) were added. The suspension was stirred under nitrogen atmosphere at 95° C. for 12 hours. After cooling to room temperature, the solution was fractionated with ethyl acetate and saturated brine. The aqueous layer was extracted twice with ethyl acetate. The organic layers were combined, washed with saturated brine, and dried over anhydrous sodium sulfate. The insoluble matter was separated by filtration, the solvent was evaporated away, and the resulting residue was purified by middle-pressure liquid chromatography (eluent, hexane:ethyl acetate=2:1) to obtain the entitled compound (170 mg, quant.) as a white amorphous substance.

MS (ESI) m/z: 308 (M+1)+.

HRMS (EI) m/z: 307.1116 (Calcd for $C_{18}H_{14}FN_3O$ 307.1121).

$^1$H-NMR (CDCl$_3$) δ: 1.24-1.31 (2H, m), 1.37-1.42 (2H, m), 2.27-2.33 (1H, m), 2.41 (3H, s), 3.00-4.30 (2H, br), 6.54 (1H, t, J=2.2 Hz), 6.60 (1H, dt, J=1.0, 8.0 Hz), 6.76 (1H, ddd, J=1.0, 2.2, 8.0 Hz), 7.26 (1H, t, J=8.0 Hz).

IR (ATR): 3371, 2225, 1603, 1412, 1309, 1120, 874, 779, 741 cm$^{-1}$.

Example 84

6-(3-Aminophenyl)-2-cyclopropyl-7-[(3S)-3-(dimethylamino)pyrrolidin-1-yl]-5-methyl-1,3-benzoxazole-4-carbonitrile (#84)

6-(3-Aminophenyl)-2-cyclopropyl-7-fluoro-5-methyl-1,3-benzoxazole-4-carbonitrile (I-178) (200 mg, 0.65 mmol) was dissolved in dimethyl sulfoxide (4 ml), then at room temperature, triethylamine (136 µl, 0.98 mmol) and (3S)-3-(dimethylamino)pyrrolidine (124 µl, 0.98 mmol) were added. The solution was stirred under nitrogen atmosphere at 90° C. for 19 hours, then cooled to room temperature. This was fractionated with ethyl acetate and an aqueous saturated sodium hydrogencarbonate solution.

The aqueous layer was further extracted twice with ethyl acetate. The organic layers were combined, washed with saturated brine, and dried over anhydrous sodium sulfate. The insoluble matter was separated by filtration, then the solvent was evaporated away, and the resulting residue was purified by preparative TLC (eluent, chloroform:methanol=9:1) to obtain the entitled compound (247 mg, 94%) as a white solid.

MS (ESI) m/z: 402 (M+1)$^+$.

HRMS (EI) m/z; 401.2213 (Calcd for $C_{24}H_{27}N_5O$ 401.2216).

$^1$H-NMR (CDCl$_3$) δ: 1.17-1.30 (4H, m), 1.57-1.68 (1H, m), 1.89-2.01 (1H, m), 2.16 (3H, s), 2.17 (3H, s), 2.20 (1.5H, s), 2.22 (1.5H, s), 2.18-2.28 (1H, m), 2.49-2.59 (1H, m), 3.06 (0.5H, t, J=9.3 Hz), 3.14 (0.5H, t, J=9.3 Hz), 3.26 (0.5H, dt, J=6.6, 10.3 Hz), 3.31-3.46 (2.5H, m), 3.50-4.00 (2H, br), 6.42 (0.5H, t, J=2.2 Hz), 6.50 (0.5H, d, J=7.6 Hz), 6.54 (0.5H, t, J=2.2 Hz), 6.62 (0.5H, d, J=7.6 Hz), 6.64-6.68 (1H, m), 7.16 (1H, q, J=7.6 Hz).

IR (ATR): 3365, 2204, 1587, 1560, 468, 1448, 1396, 1362, 1308, 1159, 868 cm$^{-1}$.

Anal. Calcd for $C_{24}H_{27}N_5O \cdot 0.25H_2O$: C, 71.00; H, 6.83; N, 17.25. Found: C, 70.88; H, 6.81; N, 16.88.

Reference Example 179

2-Cyclopropyl-7-fluoro-6-(2-methoxy-1,3-thiazol-4-yl)-5-methyl-1,3-benzoxazole-4-carbonitrile (I-179)

6-Bromo-2-cyclopropyl-7-fluoro-5-methyl-1,3-benzoxazole-4-carbonitrile (I-77) (150 mg, 0.51 mmol), 2-methoxy-4-(tributylstannyl)thiazole (257 mg, 0.61 mmol) and 2,6-di-tert-butylcresol (1 grain) were dissolved in 1,4-dioxane (5 ml), then at room temperature, dichlorobis(triphenylphosphine)palladium(0) (36 mg, 0.05 mmol) was added. After stirred under nitrogen atmosphere at 95° C. for 37 hours, this was cooled to room temperature.

The reaction liquid was fractionated with ethyl acetate and saturated brine. The aqueous layer was extracted twice with ethyl acetate. The organic layers were combined, washed with saturated brine, and dried over anhydrous sodium sulfate. The insoluble matter was separated by filtration, the solvent was evaporated away. The resulting residue was dissolved in tetrahydrofuran (3 ml) and water (1.5 ml), then at room temperature, potassium fluoride (591 mg, 10.2 mmol) was added, followed by stirring for 21 hours. This was fractionated with ethyl acetate and saturated brine. The aqueous layer was further extracted twice with ethyl acetate. The organic layers were combined, washed with saturated brine, and dried over anhydrous sodium sulfate. The insoluble matter was separated by filtration, the solvent was evaporated away, and the resulting residue was purified by middle-pressure liquid chromatography (eluent, hexane:ethyl acetate=5: 1) to obtain the entitled compound (120 mg, 72%) as a white solid.

HRMS (EI) m/z: 329.0617 (Calcd for $C_{16}H_{12}FN_3O_2S$ 329.0634).

$^1$H-NMR (CDCl$_3$) δ: 1.26-1.42 (4H, m), 0.27-2.34 (1H, m), 2.57 (3H, s), 4.10 (3H, s), 6.73 (1H, d, J=1.0 Hz).

IR (ATR): 2231, 1568, 1525, 1417, 1329, 1313, 1281, 1250, 1232, 1111, 1024, 926, 877 cm$^{-1}$.

Example 85

2-Cyclopropyl-7-[(3S)-3-(dimethylamino)pyrrolidin-1-yl]-6-(2-methoxy-1,3-thiazole-4-yl)-5-methyl-1,3-benzoxazole-4-carbonitrile (#85)

2-Cyclopropyl-7-fluoro-6-(2-methoxy-1,3-thiazol-4-yl)-5-methyl-1,3-benzoxazole-4-carbonitrile (I-179) (120 mg, 0.36 mmol) was dissolved in dimethyl sulfoxide (2.4 ml), then at room temperature, triethylamine (76 μl, 0.55 mmol) and (3S)-3-(dimethylamino)pyrrolidine (56 μl, 0.44 mmol) were added. The solution was stirred under nitrogen atmosphere at 90° C. for 18 hours, then cooled to room temperature. This was fractionated with ethyl acetate and an aqueous saturated sodium hydrogencarbonate solution. The aqueous layer was further extracted twice with ethyl acetate. The organic layers were combined, washed with saturated brine, and dried over anhydrous sodium sulfate. The insoluble matter was separated by filtration, then the solvent was evaporated away, and the resulting residue was purified by preparative TLC, in which, as the mobile layer, chloroform:methanol=9:1 was first used and then chloroform:7 N ammonia-containing methanol solution=97:3 was used, thereby obtaining a roughly-purified product (17 mg). This was washed with diisopropyl ether to obtain the entitled compound (6.5 mg, 4.2%) as a white solid.

MS (ESI) m/z: 424 (M+1)$^+$.

HRMS (EI) m/z: 423.1735 (Calcd for $C_{22}H_{25}N_5O_2S$ 423.1729).

$^1$H-NMR (CDCl$_3$) δ: 1.16-1.30 (4H, m), 1.68-1.81 (1H, m), 2.02-2.10 (1H, m), 2.19-2.27 (1H, m), 2.24 (6H, s), 2.27 (3H, s), 2.57-2.67 (1H, m), 3.18 (1H, t, J=9.3 Hz), 3.47-3.61 (3H, m), 4.09 (3H, s), 6.45 (3H, s).

IR (ATR): 2206, 1520, 1254 cm$^{-1}$.

Anal. Calcd for $C_{22}H_{25}N_5O_2S \cdot 0.75H_3O$: C, 60.46; H, 6.11; N, 16.02. Found: C, 60.26; H, 6.10; N, 15.35.

Reference Example 180

2-Cyclopropyl-7-fluoro-5-methyl-6-vinyl-1,3-benzoxazole-4-carbonitrile (I-180)

6-Bromo-2-cyclopropyl-7-fluoro-5-methyl-1,3-benzoxazole-4-carbonitrile (I-77) (300 mg, 1.02 mmol), vinyl-tri-n-butyltin (97%) (398 μl, 1.32 mmol) and 2,6-di-tert-butylcresol (2 grains) were dissolved in 1,4-dioxane (6 ml), then at room temperature, tetrakis(triphenylphosphine)palladium(0) (118 mg, 0.10 mmol) was added.

The reaction liquid was stirred at 100° C. for 21 hours, then cooled to room temperature. The insoluble matter was separated by filtration, the filtrate was fractionated with ethyl acetate and aqueous saturated potassium fluoride solution. The organic layer was washed with saturated brine, then dried over anhydrous sodium sulfate. The insoluble matter was separated by filtration, then the solvent was evaporated away under reduced pressure, and the resulting residue was dissolved in dichloromethane (6 ml), and at room temperature, water (0.3 ml) and potassium fluoride (591 mg, 10.17 mmol) were added. This was vigorously stirred at the same temperature for 3 hours. The insoluble matter was separated by filtration with washing with water, and the filtrate was washed with saturated brine, then dried over anhydrous sodium sulfate. The insoluble matter was separated by filtration, the solvent was evaporated away, and the resulting residue was purified by middle-pressure liquid chromatography (eluent, hexane:ethyl acetate=8:1) to obtain the entitled compound (218 mg, 88%) as a white solid.

MS (ESI) m/z: 243 (M+1)$^+$.

HRMS (EI) m/z: 242.0849 (Calcd for $C_{14}H_{11}FN_2O$ 242.0855).

$^1$H-NMR (CDCl$_3$) δ: 1.25-1.30 (2H, m) 1.36-1.40 (2H, m), 2.26-2.32 (1H, m), 2.61 (3H, s), 5.72 (1H, dt, J=1.2, 11.5 Hz), 5.75 (1H, dt, J=1.2, 17.8 Hz), 6.62 (1H, dd, J=11.5, 17.8 Hz).

IR (ATR): 2224, 1564, 1406, 1313, 1240, 1146, 1030, 999, 924, 874 cm$^{-1}$.

Example 86

2-Cyclopropyl-7-[(3S)-3-(dimethylamino)pyrrolidin-1-yl]-5-methyl-6-vinyl-1,3-benzoxazole-4-carbonitrile (#86)

2-Cyclopropyl-7-fluoro-5-methyl-6-vinyl-1,3-benzoxazole-4-carbonitrile (I-180) (100 mg, 0.41 mmol) was dissolved in dimethyl sulfoxide (2 ml), then at room temperature, triethylamine (86 μl, 0.62 mmol) and (3S)-3-(dimethylamino)pyrrolidine (68 μl, 0.54 mmol) were added. The solution was stirred under nitrogen atmosphere at 90° C. for 4.5 hours. After cooling to room temperature, the reaction liquid was fractionated with ethyl acetate and an aqueous saturated sodium hydrogencarbonate solution. The aqueous layer was further extracted twice with ethyl acetate. The organic layers were combined, washed with saturated brine, and dried over anhydrous sodium sulfate. The insoluble matter was separated by filtration, then the solvent was evaporated away, and the resulting residue was purified by preparative TLC (eluent, chloroform:methanol=9:1) to obtain a roughly-purified product (123 mg, 89%) as a pale brown solid. This was recrystallized from diisopropyl ether and hexane to obtain the entitled compound (79 mg) as a white solid.

MS (ESI) m/z: 337 (M+1)$^+$.

HRMS (EI) m/z: 336.1954 (Calcd for $C_{20}H_{24}N_4O$ 336.1950).

$^1$H-NMR (CDCl$_3$) δ: 1.17-1.29 (4H, m), 1.76-1.87 (1H, m), 2.13-2.26 (2H, m), 2.28 (6H, s), 2.47 (3H, s), 2.70-2.79 (1H, m), 3.52-3.61 (2H, m), 3.67 (1H, t, J=8.6 Hz), 3.89 (1H, dt, J=6.6, 10.0 Hz), 5.14 (1H, dd, J=1.8, 17.8 Hz), 5.58 (1H, dd, J=1.8, 11.2 Hz), 6.68 (1H, dd, J=11.2, 17.8 Hz).

IR (ATR): 2210, 1604, 1587, 1560, 1468, 1363, 1192, 1155 cm$^{-1}$.

Anal. Calcd for $C_{20}H_{24}N_4O$: C, 71.40; H, 7.19; N, 16.65. Found: C, 71.16; H, 7.20; N, 16.45.

Reference Example 181

2-Cyclopropyl-6-ethyl-7-fluoro-5-methyl-1,3-benzoxazole-4-carbonitrile (I-181)

2-Cyclopropyl-7-fluoro-5-methyl-6 vinyl-1,3-benzoxazole-4-carbonitrile (I-180) (114 mg, 0.47 mmol) was dissolved in ethyl acetate (2.5 ml), then at room temperature, 10% palladium-carbon (23 mg) was added. The suspension was stirred at the same temperature under atmospheric pressure of hydrogen for 16 hours. The catalyst was separated by filtration with washing with ethyl acetate, and the filtrate was concentrated under reduced pressure. The residue was purified by preparative TLC (eluent, ethyl acetate:hexane=1:2) to obtain the entitled compound (110 mg, 96%) as a white solid.

MS (ESI) m/z: 245 (M+1)$^+$.

HRMS (EI) m/z: 244.1031 (Calcd for $C_{14}H_{13}FN_2O$ 244.1012).

$^1$H-NMR (CDCl$_3$) δ: 1.18 (3H, t, J=7.3 Hz), 1.23-1.38 (4H, m), 2.24-2.31 (1H, m), 2.61 (3H, s), 2.80 (2H, dq, J=2.7, 7.3 Hz).

IR (ATR): 2220, 1578, 1319, 1240, 1130, 1043, 933, 874 cm$^{-1}$.

Example 87

2-Cyclopropyl-7-[(3S)-3-(dimethylamino)pyrrolidin-1-yl]-6-ethyl-5-methyl-1,3-benzoxazole-4-carbonitrile (#87)

2-Cyclopropyl-6-ethyl-7-fluoro-5-methyl-1,3-benzoxazole-4-carbonitrile (I-181) (108 mg, 0.44 mmol) was dissolved in dimethyl sulfoxide (3 ml), then at room temperature, triethylamine (93 μl, 0.66 mmol) and (3S)-3-(dimethylamino)pyrrolidine (73 μl, 0.57 mmol) were added. The solution was stirred under nitrogen atmosphere at 90° C. for 13 hours, then cooled to room temperature. This was fractionated with ethyl acetate and an aqueous saturated sodium hydrogencarbonate solution. The aqueous layer was further extracted twice with ethyl acetate. The organic layers were combined, washed with saturated brine, and dried over anhydrous sodium sulfate. The insoluble matter was separated by filtration, then the solvent was evaporated away, and the resulting residue was purified by preparative TLC (eluent, chloroform:methanol=93:7) to obtain the entitled compound (87 mg, 58%) as a white solid.

MS (ESI) m/z: 339 (M+1)$^+$.

HRMS (EI) m/z: 338.2106 (Calcd for $C_{20}H_{26}N_4O$ 338.2107).

$^1$H-NMR (CDCl$_3$) δ: 1.15 (3H, t, J=7.6 Hz), 1.17-1.30 (4H, m), 1.94 (1H, dq, J=8.8, 12.0 Hz), 2.19-2.27 (2H, m), 2.33 (6H, s), 2.57 (3H, s), 2.73-2.96 (3H, m), 3.45 (1H, dt, J=3.28-8 Hz), 3.47 (2H, d, J=7.6 Hz), 3.62 (1H, dt, J=7.1, 8.8 Hz).

IR (ATR): 2218, 1562, 1460, 1448, 1396, 1352, 1309, 1161, 1057, 1032, 899, 866 cm$^{-1}$.

Anal. Calcd for $C_{20}H_{26}N_4O$: C, 70.98; H, 7.74; N, 16.55. Found: C, 70.72; H, 7.76; N, 16.31.

Reference Example 182

2-Cyclopropyl-7-fluoro-6-formyl-5-methyl-1,3-benzoxazole-4-carbonitrile (I-182)

2-Cyclopropyl-7-fluoro-5-methyl-6-vinyl-1,3-benzoxazole-4-(carbonitrile (I-180) (500 mg, 2.06 mmol) was dissolved in 1,4-dioxane (7.5 ml) and water (2.5 ml), then at room temperature, 2,6-lutidine (481 μl, 4.13 mmol), a catalytic amount of osmium tetroxide and sodium metaperiodate (1.766 g, 8.26 mmol) were added. After stirring at the same temperature for 13 hours, sodium sulfite (purity 90%, 1.61 g, 12.38 mmol) and water (5 ml) were added. The solution was fractionated with ethyl acetate and saturated brine. The aqueous layer was further extracted twice with ethyl acetate. The organic layers were combined, washed with saturated brine, and dried over anhydrous sodium sulfate. The insoluble matter was separated by filtration, the solvent was evaporated away under reduced pressure, and the resulting residue was purified by middle-pressure liquid chromatography (eluent, hexane:ethyl acetate=6:1) to obtain the entitled compound (435 mg, 86%) as a white solid.

MS (ESI) m/z: 245 (M+1)$^+$. HRMS (EI) m/z: 244.0640 (Calcd for $C_{13}H_9N_2O_2$ 244.0648).

$^1$H-NMR (CDCl$_3$) δ: 135-1.50 (4H, m), 2.30-2.38 (1H, m), 2.92 (3H, s), 10.54 (1H, s).

IR (ATR): 2231, 1691, 1560, 1321, 1246, 1136 1036 cm$^{-1}$.

Example 88

2-Cyclopropyl-7-[(3S)-3-(dimethylamino)pyrrolidin-1-yl]-6-formyl-5-methyl-1,3-benzoxazole-4-carbonitrile hydrochloride (#88)

2-Cyclopropyl-7-fluoro-6-formyl-5-methyl-1,3-benzoxazole-4-carbonitrile (I-182) (150 mg, 0.92 mmol) was dissolved in dimethyl sulfoxide (3 ml), then at room temperature, triethylamine (128 μl, 0.92 mmol) and (3S)-3-(dimethylamino)pyrrolidine (101 μl, 0.80 mmol) were added. The solution was stirred under nitrogen atmosphere at 90° C. for 12 hours, then cooled to room temperature. This was fractionated with ethyl acetate and an aqueous saturated sodium hydrogencarbonate solution. The aqueous layer was further extracted twice with ethyl acetate. The organic layers were combined, washed with saturated brine, and dried over anhydrous sodium sulfate. The insoluble matter was separated by filtration, then the solvent was evaporated away, and file resulting residue was purified by preparative TLC (eluent, chloroform:methanol=9:1) to 2-cyclopropyl-7-[(3S)-3-(dimethylamino)pyrrolidin-1-yl]-6-formyl-5-methyl-1,3-benzoxazole-4-carbonitrile (172 mg, 83%) as a brown gel. The analytical data are shown below.

MS (ESI) m/z: 339 (M+1)$^+$.
HRMS (EI) m/z: 338.1729 (Calcd for $C_{19}H_{22}N_4O_2$ 338.1743).
$^1$H-NMR (CDCl$_3$) δ: 1.22-1.33 (4H, m), 1.88-1.98 (1H, m), 2.18-2.28 (2H, m), 2.31 (6H, s), 2.79-2.86 (12H, m), 2.82 (3H, s), 3.55-3.71 (3H, m), 3.90 (1H, dt, J=6.6, 10.5 Hz), 10.20 (1H, s).
IR (ATR): 2214, 1662, 1661, 1550, 1468 cm$^{-1}$.

The above-obtained 2-cyclopropyl-7-[(3S)-3-(dimethylamino)pyrrolidin-1-yl]-6-formyl-5-methyl-1,3-benzoxazole-4-carbonitrile (50 mg, 0.15 mmol) was dissolved in ethanol (0.5 ml) and diethyl ether (1 ml), then at room temperature, 1 mol hydrochloric acid/ethanol solution (162 μl, 0.16 mmol) was added. After stirring under nitrogen atmosphere at the same temperature for 3 hours, the solvent was evaporated away under reduced pressure. Diethyl ether was added to the residue, and this was concentrated under reduced pressure. This operation was repeated further twice.

The residue was collected by filtration with washing with diethyl ether, and further dried under reduced pressure at 60° C. for 88 hours to obtain the entitled compound (46 mg, 82%) as a pale brown powder.

MS (ESI) m/z: 339 (M+1)$^+$.
HRMS (EI) m/z: 338.1735 (Calcd for $C_{19}H_{22}N_4O_2$ 338.1743).
$^1$H-NMR (CD$_3$OD) δ: 1.30-1.36 (4H, m), 2.26-2.37 (2H, m), 2.53-2.62 (1H, m), 2.80 (3H, s), 2.97 (6H, s), 3.81-4.05 (5H, m), 10.26 (12H, s).
IR (ATR): 2328, 2208, 1662, 1603, 1587, 1550, 1450, 1398, 1255 cm$^{-1}$.
Anal. Calcd for $C_{19}H_{22}N_4O_2 \cdot HCl \cdot 0.25H_2O$: C, 60.15; H, 6.24; N, 14.77; Cl, 9.35. Found: C, 59.84; H, 6.26; N, 14.56; Cl, 9.36.

Example 89

2-Cyclopropyl-7-[(3S)-3-(dimethylamino)pyrrolidin-1-yl]-6-hydroxymethyl-5-methyl-1,3-benzoxazole-4-carbonitrile (#89)

2-Cyclopropyl-7-[(3S)-3-(dimethylamino)pyrrolidin-1-yl]-6-formyl-5-methyl-1,3-benzoxazole-4-carbonitrile (free form of #88) (120 mg, 0.35 mmol) was dissolved in methanol (2.4 ml) and dichloromethane (0.8 ml), then at 0° C., sodium borohydride (18 mg, 0.43 mmol) was added, followed by stirring at the same temperature for 1 hour. Next, at the same temperature, sodium borohydride (9 mg, 0.22 mmol) was further added, followed by stirring at the same temperature for 1 hour. An aqueous saturated sodium hydrogencarbonate solution was added, followed by farmer stirring for 5 minutes. The solution was extracted three times with chloroform. The organic layers were combined, washed with saturated brine, and dried over anhydrous sodium sulfate. The insoluble matter was separated by filtration, the solvent was evaporated away, and the resulting residue was purified by preparative TLC (eluent, chloroform:methanol=9:1) to obtain the entitled compound (91 mg) as a roughly-purified product. This was washed with isopropyl ether to obtain the entitled compound (85 mg, 70%) as a white solid.

MS (ESI) m/z: 341 (M+1)$^+$.
HRMS (EI) m/z: 340.1905 (Calcd for $C_{19}H_{24}N_4O_2$ 340.1900).
$^1$H-NMR (CDCl$_3$) δ: 1.20-1.33 (4H, m), 1.95 (1H, dq, J=8.5, 32.0 Hz), 2.18-2.27 (2H, m), 2.32 (6H, s), 2.20-2.50 (1H, br), 2.63 (3H, s), 2.88 (1H, dq, J=7.8, 7.8 Hz), 3.56-3.77 (4H, m), 4.79 (1H, d, J=12.5 Hz), 4.85 (1H, d, J=12.5 Hz).
IR (ATR): 3053, 2204, 1608, 1587, 3560, 3466, 3448, 3363, 100, 1034, 1012, 958, 878 cm$^{-1}$.
Anal. Calcd for $C_{19}H_{22}N_4O_2 \cdot 0.75H_2O$: C, 64.48; H, 7.26; N, 145.83. Found: C, 64.43; H, 6.92; N, 15.47.

Reference Example 183

Methyl 4-cyano-2-cyclopropyl-7-fluoro-5-methyl-1,3-benzoxazole-6-carboxylate (I-183)

2-Cyclopropyl-7-fluoro-6-formyl-5-methyl-1,3-benzoxazole-4-carbonitrile (I-182) (280 mg, 1.15 mmol) was dissolved in tert-butanol (8 ml), tetrahydrofuran (6 ml) and water (6 ml), then at 0° C., sodium dihydrogenphosphate dihydrate (268 mg, 1.72 mmol), 2-methyl-2-butene (515 μl, 4.59 mmol), then sodium chlorite (purity 80%, 389 mg, 3.44 mmol) were added. After stirring at room temperature for 6 hours, the solvent was evaporated away under reduced pressure. The residue was fractionated with ethyl acetate and aqueous 1 mol hydrochloric acid solution. The aqueous layer was further extracted twice with ethyl acetate. The organic layers were combined, washed with saturated brine, and dried over anhydrous sodium sulfate. The insoluble matter was separated by filtration, then the solvent was evaporated away under reduced pressure. Benzene (6 ml) and methanol (2 ml) were added to it, then at 0° C., 2 M trimethylsilyldiazomethane/diethyl ether solution (1.15 ml, 2.29 mmol) was added. After stirring at room temperature for 18 hours, an aqueous saturated sodium hydrogencarbonate solution was added at 0° C. The solution was extracted three times with ethyl acetate. The organic layers were combined, washed with saturated brine, and dried over anhydrous sodium sulfate.

The insoluble matter was separated by filtration, the solvent was evaporated away, and the residue was purified with middle-pressure liquid chromatography (eluent, hexane:ethyl acetate=6:1) to obtain the entitled compound (260 mg, 83%) as a white solid.

HRMS (EI) m/z: 274.0758 (Calcd for $C_{14}H_{11}FN_2O_3$ 274.0753).
$^1$H-NMR (CDCl$_3$) δ: 1.30-1.44 (4H, m), 2.27, 2.34 (1H, s), 2.66 (3H, s), 3.99 (3H, s).
IR (ATR): 2233, 1732, 1566, 1265, 1211, 1030, 872, 752 cm$^{-1}$.

Example 90

Methyl 4-cyano-2-cyclopropyl-7-[(3S)-3-(dimethylamino)pyrrolidin-1-yl]-5-methyl-1,3-benzoxazole-6-carboxylate (#90)

Methyl 4-cyano-2-cyclopropyl-7-fluoro-5-methyl-1,3-benzoxazole-6-carboxylate (I-183) (100 mg, 0.37 mmol) was dissolved in dimethyl, then at room temperature, triethylamine (76 µl, 0.55 mmol) and (3S)-3-(dimethylamino)pyrrolidine (56 µl, 0.44 mmol) were added. The solution was stirred under nitrogen atmosphere at 90° C. for 10 hours, then cooled to room temperature. This was fractionated with ethyl acetate and an aqueous saturated sodium hydrogencarbonate solution. The aqueous layer was further extracted twice with ethyl acetate. The organic layers were combined, washed with saturated brine, and dried over anhydrous sodium sulfate. The insoluble matter was separated by filtration, then the solvent was evaporated away, and the resulting residue was purified by preparative TLC (eluent, chloroform:methanol=92:8) to obtain the entitled compound (118 mg) as a roughly-purified product. This was washed with diisopropyl ether to obtain the entitled compound (109 mg, 81%) as a white solid.

MS (ESI) m/z: 369 (M+1)$^+$.

HRMS (EI) m/z: 368.1865 (Calcd for $C_{20}H_{34}N_4O_3$ 368.1849).

$^1$H-NMR (CDCl$_3$) δ: 1.17-1.29 (4H, m), 1.82-1.92 (1H, m), 2.13-2.25 (2H, m), 2.30 (6H, s), 2.45 (3H, s), 2.72-2.81 (1H, m), 3.56 (1H, t, J=9.0 Hz), 3.71-3.81 (3H, m), 3.90 (3H, s).

IR (ATR): 2210, 1720, 1606, 1589, 1556, 1475, 1298, 1223, 1151, 1057, 1038 cm$^{-1}$.

Anal. Calcd for $C_{20}H_{24}N_4O_3$: C, 64.41; H, 6.62; N, 15.02. Found: C, 64.57; H, 6.61; N, 14.91.

Reference Example 184

4-Cyano-7-fluoro-6-(3-fluorophenyl)-N,N,5-trimethyl-1,3-benzoxazole-2-carboxamide (I-184)

6-Bromo-4-cyano-7-fluoro-N,N,5-trimethyl-1,3-benzoxazole-2-carboxamide (I-127) (200 mg, 0.61 mmol), 3-fluorophenylboronic acid (343 mg, 2.45 mmol) and tripotassium phosphate (261 mg, 1.23 mmol) were suspended in 1,4-dioxane (6 ml), and at room temperature, tetrakis(triphenylphosphine)palladium(0) (142 mg, 0.12 mmol) was added. The suspension was stirred under nitrogen atmosphere at 95° C. for 62 hours, followed by cooling to room temperature. The solution was fractionated with ethyl acetate and aqueous saturated ammonium chloride solution. The aqueous layer was extracted twice with ethyl acetate. The organic layers were combined, washed with saturated brine, and dried over anhydrous sodium sulfate. The insoluble matter was separated by filtration, the solvent was evaporated away, and the resulting residue was purified by middle-pressure liquid chromatography (eluent, hexane:ethyl acetate=5:2) to obtain the entitled compound (76 mg, 36%) as a white solid.

MS (ESI) m/z: 342 (M+1)$^+$.

HRMS (EI) m/z: 341.0996 (Calcd for $C_{18}H_{13}F_2N_3O_2$ 341.0975).

$^1$H-NMR (CDCl$_3$) δ: 2.48 (3H, s), 3.24 (3H, s), 3.54 (3H, s), 7.00 (1H, odd, J=1.7, 2.4, 9.0 Hz), 7.05 (1H, d, J=7.8 Hz), 7.20 (1H, ddt, J=1.0, 2.4, 9.0 Hz), 7.50 (1H, dt, J=5.9, 7.8 Hz).

IR (ATR): 2231, 1658, 1537, 1475, 1400, 1257, 1151, 1099, 800, 779, 742 cm$^{-1}$.

Example 91

4-Cyano-6-(3-fluorophenyl)-N,N,5-trimethyl-7-[(3S)-3-methylaminopyrrolidin-1-yl]-1,3-benzoxazole-2-carboxamide (#91)

4-Cyano-7-fluoro-6-(3-fluorophenyl)-N,N,5-trimethyl-1,3-benzoxazole-2-carboxamide (I-184) (75 mg, 0.22 mmol) was dissolved in dimethyl sulfoxide (3.5 ml), then at room temperature, triethylamine (40 µl, 0.29 mmol) was added. The solution was heated at 150° C., a solution of (3S)-3-(dimethylamino)pyrrolidine (30 µl, 0.29 mmol) dissolved in dimethyl sulfoxide (1 ml) was added all at a time. The solution was stirred under nitrogen atmosphere at the same temperature for 1 hour. After cooling to room temperature, the solvent was evaporated away under reduced pressure. The residue was fractionated with chloroform and an aft aqueous saturated sodium hydrogencarbonate solution. The aqueous layer was further extracted twice with chloroform. The organic layers were combined, washed with saturated brine, and dried over anhydrous sodium sulfate. The insoluble matter was separated by filtration, the solvent was evaporated away under reduced pressure, and the resulting residue was purified first by preparative TLC (eluent, chloroform:methanol=9:1) to obtain a roughly-purified form (54 mg). This was further purified by preparative TLC (eluent, chloroform:7 N ammonia-containing methanol solution=95:5), then recrystallized from diisopropyl ether to obtain the entitled compound (12 tag, 13%) as a white solid.

MS (ESI) m/z: 422 (M+1)$^+$.

HRMS (EI) m/z: 421.1913 (Calcd for $C_{23}H_{24}FN_5O_2$ 421.1914).

$^1$H-NMR (CDCl$_3$) δ: 150-1.65 (1H, br), 1.60-1.70 (1H, m), 1.94 (1H, dq, J=5.9, 6.8 Hz), 2.22 (3H, s), 2.33 (3H, d, J=1.2 Hz), 3.01 (1H, dt, J=4.6, 10.3 Hz), 3.09-3.13 (1H, m), 3.20 (3H, s), 3.31-3.54 (3H, m), 3.55 (3H, s), 6.94 (1H, ddd, J=1.5, 2.4, 9.3 Hz), 7.01 (1H, d, J=7.6 Hz), 7.09 (1H, dt, J=2.4, 8.6 Hz), 7.40 (1H, dt, J=6.1, 7.6 Hz).

IR (ATR): 2212, 1655, 1606, 1577, 1469, 1396, 1369, 1113, 796, 777 cm$^{-1}$.

Anal. Calcd for $C_{23}H_{24}FN_5O_2 \cdot 0.25H_2O$: C, 64.85; H, 5.80; N, 16.44. Found: C, 64.65; H, 5.70; N, 15.97.

Reference Example 185

4-Cyano-7-fluoro-N,N,5-trimethyl-6-vinyl-1,3-benzoxazole-2-carboxamide (I-185)

6-Bromo-4-cyano-7-fluoro-N,N,5-trimethyl-1,3-benzoxazole-2-carboxamide (I-127) (500 mg, 1.53 mmol), 2,6-di-tert-butylcresol (3 grains) and tetrakis(triphenylphosphine)palladium(0) (177 mg, 0.15 mmol) were dissolved in 1,4-dioxane (10 ml), then at room temperature, tributylvinyltin (601 µl, 1.99 mmol) was added, followed by stirring under nitrogen atmosphere at 100° C. for 17 hours. After cooling to room temperature, the insoluble matter was separated by filtration with washing with ethyl acetate. The filtrate was washed with saturated brine, then dried over anhydrous sodium sulfate. The insoluble matter was separated by filtration, the organic layer was washed with water, and dried over anhydrous sodium sulfate. The solvent was evaporated away, the resulting residue was dissolved in tetrahydrofuran (10 ml) and water (5 ml), and at room temperature, potassium fluoride (1.782 g, 30.66 mmol) was added. After vigorously stirring at the same temperature for 23 hours, the reaction liquid was fractionated with ethyl acetate and saturated brine. The aqueous layer was further extracted twice with ethyl acetate. The organic layers were combined, washed with saturated brine, then dried over anhydrous sodium sulfate. The insoluble matter was separated by filtration, the solvent was evaporated away, and the resulting residue was purified by middle-pressure liquid chromatography (eluent, hexane:ethyl acetate=3:1) to obtain the entitled compound (261 mg, 62%) as a white solid.

MS (ESI) m/z: 274 (M+1)$^+$.

HRMS (EI) m/z: 273.0905 (Calcd for $C_{14}H_{12}FN_3O_2$ 273.0913).

$^1$H-NMR (CDCl$_3$) δ: 2.68 (3H, s), 3.232 (3H, s), 3.53 (3H, s), 5.80-5.86 (2H, m), 6.65 (1H, dd, J=11.7, 17.8 Hz).

IR (ATR): 2229, 1666, 1485, 1394, 1219, 1092, 947 cm$^{-1}$.

Example 92

4-Cyano-7-[(3S)-3-(dimethylamino)pyrrolidin-1-yl]-N,N,5-trimethyl-6-vinyl-1,3-benzoxazole-2-carboxamide (#92)

4-Cyano-7-fluoro-N,N,5-trimethyl-6-vinyl-1,3-benzoxazole-2-carboxamide (I-185) (130 mg, 0.48 mmol) was dissolved in dimethyl sulfoxide (8 ml), then at room temperature, triethylamine (100 μl, 0.48 mmol) was added. The solution was gradually heated from room temperature up to 150° C. under nitrogen atmosphere, a solution of (3S)-3-(dimethylamino)pyrrolidine (79 μl, 0.62 mmol) dissolved in dimethyl sulfoxide (1 ml) was added all at a time. The solution was stirred at the same temperature for 1.25 hours, and the cooled to room temperature. This was fractionated with ethyl acetate and an aqueous saturated sodium hydrogencarbonate solution. The aqueous layer was further extracted twice with ethyl acetate. The organic layers were combined, washed with saturated brine, and dried over anhydrous sodium sulfate. The insoluble matter was separated by filtration, the solvent was evaporated away under reduced pressure, and the resulting residue was purified by preparative TLC (eluent, chloroform:methanol=93:7) to obtain a roughly-purified product (124 mg). This was washed with diisopropyl ether to obtain the entitled compound (87 mg, 50%) as a yellow solid.

MS (ESI) m/z: 368 (M+1)$^+$.

HRMS (EI) m/z: 367.2004 (Calcd for $C_{20}H_{25}N_5O_2$ 367.2008).

$^1$H-NMR (CDCl$_3$) δ: 1.79-1.89 (1H, m), 2.13-2.12 (1H, m), 2.30 (6H, s), 2.52 (3H, s), 2.69-2.77 (1H, m), 3.20 (3H, s), 3.50-3.53 (1H, m), 3.53 (3H, s), 3.70-3.80 (2H, m), 4.04 (1H, dt, J=6.3, 10.3 Hz), 5.14 (1H, dd, J=1.7, 17.8 Hz), 5.64 (1H, dd, J=1.7, 11.2 Hz), 6.73 (1H, dd, J=11.2, J=7.8 Hz).

IR (ATR): 2214, 1662, 1604, 1469, 1360, 1107, 955 cm$^{-1}$.

Anal. Calcd for $C_{20}H_{25}N_5O_2$; C, 64.58; H, 6.91; N, 18.83. Found: C, 64.42; H, 6.78; N, 18.52.

Reference Example 186

7-Fluoro-5-methyl-6-phenyl-2-(1,3-thiazol-2-yl)-1,3-benzoxazole-4-carbonitrile (I-186)

2-Tri-n-butylstannylthiazole (392 mg, 1.05 mmol), dichlorobis(triphenylphosphine)palladium(II) (49.0 mg, 0.070 mmol) and 2,6-di-tert-butylcresol (30.7 mg, 0.14 mmol) were added to a toluene (20 ml) solution of 2-chloro-7-fluoro-5-methyl-6-phenyl-1,3-benzoxazole-4-cabonitrile (I-130) (200 mg, 0.698 mmol), followed by heating under reflux in an oil bath at 125° C. for 5 hours in an argon atmosphere. The solvent was evaporated away under reduced pressure, then the residue was purified by silica gel column chromatography (eluent, hexane:ethyl acetate=9:1→2:1) to obtain the entitled compound (70.0 mg, 29.9%) as a pale yellow solid.

MS (ESI) m/z: 336 (M+1)$^+$.

$^1$H-NMR (CDCl$_3$) δ: 2.48 (3H, s), 7.20-7.53 (5H, m), 7.75 (1H, d, J=3.2 Hz), 8.16 (1H, d, J=3.2 Hz).

Example 93

7-[(3S)-3-(Dimethylamino)pyrrolidin-1-yl]-5-methyl-6-phenyl-2-(1,3-thiazol-2-yl)-1,3-benzoxazole-4-carbonitrile (#93)

(3S)-3-(Dimethylamino)pyrrolidine (48.4 μl, 0.382 mmol) and triethylamine (53.2 μl, 0.382 mmol) were added to a dimethyl sulfoxide (1 ml) solution of 7-fluoro-5-methyl-6-phenyl-2-(1,3-thiazol-2-yl)-1,3-benzoxazole-4-carbonitrile (I-186) (64.0 mg, 0.191 mmol), followed by stirring in an oil bath at 100° C. for 3 hours.

The reaction liquid was concentrated under reduced pressure, the residue was dissolved in chloroform (50 ml), washed with water (50 ml) and saturated brine (50 ml). After drying over anhydrous sodium sulfate, the solvent was evaporated away, and the resulting residue was purified by preparative TLC (eluent, chloroform:methanol=10:1) to obtain the entitled compound (14.0 mg, 16.9%) as a pale yellow solid.

MS (ESI) m/z: 430 (M+1)$^+$.

$^1$H-NMR (CDCl$_3$) δ: 1.55-1.74 (1H, m), 1.98-2.08 (1H, m), 2.10 (6H, s), 2.24 (3H, s), 2.44-2.57 (1H, m), 2.72-2.83 (1H, m), 3.17-3.30 (1H, m), 3.61-3.77 (2H, m), 7.12-7.51 (5H, m), 7.65 (1H, d, J=3.2 Hz), 8.08 (1H, d, J=3.2 Hz).

IR (ATR): 3057, 2958, 2929, 2887, 2825, 2767, 2206, 1720, 1672, 1606, 1581, 1464, 1441, 1394, 1365, 1306, 1190, 1157, 1099, 1043, 1014, 922 cm$^{-1}$.

Anal. Calcd for $C_{24}H_{23}N_5OS.0.25H_2O$: C, 66.41; H, 5.46; N, 16.13; S, 7.39. Found: C, 66.54; H, 5.40; N, 16.05; S, 7.36.

Reference Example 187

7-Fluoro-5-methyl-6-phenyl-2-(pyrazin-2-yl)-1,3-benzoxazole-4-carbonitrile (I-187)

2-Tri-n-butylstannylpyrazine (409 mg, 1.11 mmol), dichlorobis(triphenylphosphine)palladium(II) (51.9 mg, 0.074 mmol) and 2,6-di-tert-butylcresol (32.6 mg, 0.148 mmol) were added to a toluene (20 ml) solution of 2-chloro-7-fluoro-5-methyl-6-phenyl-1,3-benzoxazole-4-cabonitrile (I-130) (212 mg, 0.739 mmol), followed by heating under reflux in an oil bath at 125° C. for 2 hours. The solvent was evaporated away under reduced pressure, then the residue was purified by silica gel column chromatography (eluent, hexane:ethyl acetate=2:1) to obtain the entitled compound (146 mg, 59.8%) as a colorless solid.

MS (ESI) m/z: 331 (M+1)$^+$.

$^1$H-NMR (CDCl$_3$) δ: 2.49 (3H, s), 7.26-7.56 (5H, m), 8.82-8.84 (2H, m), 9.71 (1H, d, J=1.2 Hz).

Example 94

7-[(3S)-3-(Dimethylamino)pyrrolidin-1-yl]-5-methyl-6-phenyl-2-(pyrazin-2-yl)-1,3-benzoxazole-4-carbonitrile (#94)

(3S)-3-(Dimethylamino)pyrrolidine (93.4 μl, 0.736 mmol) and triethylamine (121 μl, 0.866 mmol) were added to a dimethyl sulfoxide (4 ml) solution of 7-fluoro-5-methyl-6-phenyl-2-(pyrazin-2-yl)-1,3-benzoxazole-4-carbonitrile (I-187) (143 mg, 0.433 mmol), followed by stirring in an oil bath at 95° C. for 0.2 hours. The reaction liquid was concentrated under reduced pressure, the residue was dissolved in chloroform (100 ml), washed with saturated brine (50 ml). After drying over anhydrous sodium sulfate, the solvent was evaporated away, and the resulting residue was purified by silica gel column chromatography (eluent, chloroform:methanol=9:1), the eluate was recrystallized from isopropanol to obtain the entitled compound (71.0 mg, 38.6%) as a pale yellow acicular crystal.

MS (ESI) m/z: 425 (M+1)$^+$.

$^1$H-NMR (CDCl$_3$) δ: 1.60-1.73 (1H, m), 1.98-2.08 (1H, m), 2.13 (6H, s), 2.25 (3H, s), 2.48-2.61 (1H, m), 2.93 (1H, t, J=9.2 Hz), 3.33 (1H, dd, J=9.8, 7.1 Hz), 3.58-3.63 (2H, m), 7.13-7.18 (1H, m), 7.26-7.31 (1H, m), 7.35-7.47 (3H, m), 8.74-8.77 (2H, m), 9.61 (1H, d, J=1.5 Hz).

IR (ATR): 3053, 2983, 2951, 2871, 2825, 2779, 2200, 1606, 1577, 1469, 1444, 1396, 1358, 1302, 1200, 1169, 1113, 1045, 1014, 980, 924, 858, 785, 754, 708 cm$^{-1}$.

Anal. Calcd for C$_{25}$H$_{24}$N$_6$O: C, 70.73; H, 5.70; N, 19.80. Found: C, 70.56; H, 5.70; N, 19.50.

Reference Example 188

7-Fluoro-5-methyl-2-(4-methyl-3-oxopiperazin-1-yl)-6-phenyl-1,3-benzoxazole-4-carbonitrile (I-188)

Diisopropylethylamine (232 μl, 1.36 mmol) and 1-methylpiperazin-2-one hydrochloride (103 mg, 0-682 mmol) were added to a dichloromethane (6 ml) solution of 2-chloro-7-fluoro-5-methyl-6-phenyl-1,3-benzoxazole-4-cabonitrile (I-130) (163 mg, 0.569 mmol), followed by stirring at room temperature for 30 minutes. Chloroform (50 ml) was added to the reaction liquid, followed by washing with saturated brine (50 ml). After drying over anhydrous sodium sulfate and concentration under reduced pressure, the resulting residue was purified by silica gel column chromatography (eluent, chloroform:methanol=20:1) to obtain the entitled compound (207 mg, 99.9%) as a colorless solid.

MS (ESI) m/z: 365 (M+1)$^+$.

$^1$H-NMR (CDCl$_3$) δ: 2.36 (3H, s), 3.07 (3H, s), 3.57 (2H, t, J=5.5 Hz), 4.08 (2H, t, J=5.5 Hz), 4.41 (2H, s), 7.22-7.27 (2H, m), 7.40-7.52 (3H, m).

Example 95

7-[(3S)-3-(Dimethylamino)pyrrolidin-1-yl]-5-methyl-2-(4-methyl-3-oxopiperazin-1-yl)-6-phenyl-1,3-benzoxazole-4-carbonitrile (#95)

(3S)-3-(Dimethylamino)pyrrolidine (67.9 μl, 0.535 mmol) and triethylamine (86.1 μl, 0.618 mmol) were added to a dimethyl sulfoxide (5 ml) solution of 7-fluoro-5-methyl-2-(4-methyl-3-oxopiperazin-1-yl)-6-phenyl-1,3-benzoxazole-4-carbonitrile (I-188) (150 mg, 0.412 mmol), followed by stirring in an oil bath at 130° C. for 3 hours. The reaction liquid was concentrated under reduced pressure, the residue was dissolved in chloroform (50 ml), washed with saturated brine (50 ml). After drying over anhydrous sodium sulfate and concentration under reduced pressure, the resulting residue was purified by preparative TLC (eluent, chloroform:methanol=10:1) to obtain the entitled compound (109 mg, 54.5%) as a colorless foamy substance.

MS (ESI) m/z: 459 (M+1)$^+$.

$^1$H-NMR (CDCl$_3$) δ: 1.50-1.67 (1H, m), 1.89-1.97 (1H, m), 2.09 (6H, s), 2.15 (3H, s), 2.41-2.53 (1H, m), 2.73 (1H, t, J=9.0 Hz), 3.07 (3H, s), 3.15 (1H, dd, J=9.4, 7.2 Hz), 3.31-3.41 (2H, m), 3.55 (2H, t, J=5.5 Hz), 4.00-4.07 (2H, m), 4.28-4.32 (2H, m), 7.10-7.41 (5H, m).

IR (ATR): 2947, 2868, 2773, 2206, 1630, 1595, 1560, 1502, 1439, 1408, 1365, 1313, 1244, 1194, 1155, 1057, 984, 918, 903, 833, 785, 760, 723 cm$^{-1}$.

Anal. Calcd for C$_{26}$H$_{30}$N$_6$O$_2$·1.5H$_2$O: C, 64.31; H, 6.85; N, 17.31. Found: C, 64.24; H, 6.59; N, 17.22.

Reference Example 189

7-Fluoro-5-methyl-2-[methyl(pyridin-2-yl)amino]-6-phenyl-1,3-benzoxazole-4-carbonitrile (I-189)

Diisopropylethylamine (169 μl, 0.944 mmol) and 2-(methylamino)pyridine (102 μl, 0.994 mmol) were added to a dichloromethane (10 ml) solution of 2-chloro-7-fluoro-5-methyl-6-phenyl-1,3-benzoxazole-4-cabonitrile (I-130) (190 mg, 0.663 mmol), followed by heating under reflux in an oil bath at 50° C. for 3 hours. The reaction liquid was cooled to room, temperature, ethyl acetate (70 ml) was added, followed by washing with water (50 ml) and saturated brine (50 ml). After drying over anhydrous sodium sulfate and concentration under reduced pressure, the resulting residue was purified by silica gel column chromatography (eluent, hexane:ethyl acetate=4:1) to obtain the entitled compound (137 mg, 57.5%) as a colorless solid.

MS (ESI) m/z: 359 (M+1)$^+$.

$^1$H-NMR (CDCl$_3$) δ: 2.39 (3H, s), 3.88 (3H, s), 7.14 (1H, dd, J=7.3, 4.9 Hz), 7.24-7.28 (2H, m), 7.41-7.53 (3H, m), 7.82 (1H, ddd, J=8.3, 7.6, 2.2 Hz), 8.31 (1H, d, J=8.5 Hz), 8.47 (1H, dd, J=4.6, 1.5 Hz).

Example 96

7-[(3S)-3-(Dimethylamino)pyrrolidin-1-yl]-5-methyl-2-[methyl(pyridin-2-yl)amino]-6-phenyl-1,3-benzoxazole-4-carbonitrile (#96)

(3S)-3-(Dimethylamino)pyrrolidine (63.2 μl, 0.498 mmol) and triethylamine (81.7 μl, 0.586 mmol) were added to a dimethyl sulfoxide (3 ml) solution of 7-fluoro-5-methyl-2-methylpyridin-2-ylamino-6-phenyl-1,3-benzoxazole-4-carbonitrile (I-189) (105 mg, 0.293 mmol), followed by stirring in an oil bath at 95° C. for 2 hours. The reaction liquid was concentrated under reduced pressure, the residue was dissolved in chloroform (50 ml), washed with saturated brine (50 ml). After drying over anhydrous sodium sulfate and concentration, the resulting residue was purified by preparative TLC (eluent, chloroform:methanol=20:1), and the obtained eluate was recrystallized from isopropanol to obtain the entitled compound (35.0 mg, 26.4%) as a colorless solid.

MS (ESI) m/z: 453 (M+1)$^+$.

$^1$H-NMR (CDCl$_3$) δ: 1.50-1.67 (1H, m), 1.87-1.96 (1H, m), 2.11 (6H, s), 2.19 (3H, s), 2.44-2.56 (1H, m), 2.96 (1H, t, J=9.0 Hz), 3.17 (1H, td, J=10.2, 6.7 Hz), 3.27-3.36 (2H, m), 3.82 (3H, s), 7.05-7.14 (2H, m), 7.23-7.43 (4H, m), 7.75-7.79 (1H, m), 8.26 (1H, d, J=8.5 Hz), 8.42-8.45 (1H, m).

IR (ATR): 2976, 2947, 2870, 2819, 2775, 2208, 1620, 1597, 1550, 1469, 1431, 1383, 1306, 1198, 1153, 1101, 1059, 989, 962, 918, 872, 829, 777, 754 cm$^{-1}$.

Anal. Calcd for C$_{27}$H$_{28}$N$_6$O: C, 71.66; H, 6.24; N, 18.57. Found: C, 71.37; H, 6.21; N, 18.35.

Reference Example 190

Ethyl [1-(4-cyano-7-fluoro-5-methyl-6-phenyl-1,3-benzoxazol-2-yl)azetidin-3-yl]acetate (I-190)

Under nitrogen atmosphere, 2-chloro-7-fluoro-5-methyl-6-phenyl-1,3-benzoxazole-4-cabonitrile (I-130) (400 mg, 1.40 mmol) was dissolved in methylene chloride (15 ml), then diisopropylethylamine (537 µl, 3.08 mmol) and ethyl azetidine-3-acetate (503 mg, 2.80 mmol) dissolved in methylene chloride (5 ml) were added, followed by heating under reflux for 19 hours. After cooling, diluting with chloroform and washing with water, the organic layer was dried over anhydrous magnesium sulfate, then the solvent was evaporated away under reduced pressure. The resulting residue was subjected to preparative silica gel column chromatography. From the eluate with ethyl acetate/hexane (1:1, v/v), the entitled compound (420 mg, 76%) was obtained as a colorless oil.

MS (ESI) m/z: 394 (M+1)$^+$.

$^1$H-NMR (CDCl$_3$) δ: 1.28 (3H, t, J=7.2 Hz), 2.34 (3H, s), 2.75 (2H, d, J=7.2 Hz), 3.20-3.30 (1H, m), 4.05-4.11 (2H, m), 4.17 (2H, q, J=7.2 Hz), 4.54 (2H, t, J=8.7 Hz), 7.22-7.26 (3H, m), 7.40-7.50 (3H, m).

Reference Example 191

Ethyl (1-{4-cyano-7-[(3S)-3-(dimethylamino)pyrrolidin-1-yl]-5-methyl-6-phenyl-1,3-benzoxazol-2-yl}azetidin-3-yl)acetate (I-191)

Ethyl [1-(4-cyano-7-fluoro-5-methyl-6-phenyl-1,3-benzoxazol-2-yl)azetidin-3-yl]acetate (I-190) (428 mg, 1.09 mmol) was dissolved in dimethyl sulfoxide (10 ml), then triethylamine (312 µl, 2.18 mmol) and (3S)-3-(dimethylamino)pyrrolidine (290 µl, 2.29 mmol) were added, followed by stirring in a sealed tube at 150° C. for 6 hours. After cooling, concentration under reduced pressure, dilution with chloroform, and washing with water, the organic layer was dried over anhydrous magnesium sulfate, then the solvent was evaporated away under reduced pressure. The resulting residue was subjected to silica gel column chromatography, and the eluate with chloroform/methanol (10:1, v/v) gave the entitled compound (220 mg, 41.4%) as a white solid.

MS (ESI) m/z: 488 (M+1)$^+$.

$^1$H-NMR (CDCl$_3$) δ: 1.25-1.30 (3H, m), 1.50-1.61 (1H, m), 1.84-1.94 (1H, m), 2.10 (6H, s), 2.15 (3H, s), 2.41-2.52 (1H, m), 2.74 (2H, d, J=7.8 Hz), 2.87 (1H, t, J=9.0 Hz), 3.12-3.29 (4H, m), 3.98-4.04 (2H, m), 4.17 (2H, q, J=7.2 Hz), 4.46 (2H, t, J=8.5 Hz), 7.08-7.12 (1H, m), 7.20-7.24 (1H, m), 7.29-7.41 (3H, m).

Example 97

(1-{4-Cyano-7-[(3S)-3-(dimethylamino)pyrrolidin-1-yl]-5-methyl-6-phenyl-1,3-benzoxazol-2-yl}azetidin-3-yl)acetic acid (#97)

Ethyl (1-{4-cyano-7-[(3S)-3-(dimethylamino)pyrrolidin-1-yl]-5-methyl-6-phenyl-1,3-benzoxazol-2-yl}azetidin-3-yl)acetate (I-191) (220 mg, 0.45 mmol) was dissolved in tetrahydrofuran (5 ml), then 1 N sodium hydroxide (4.5 ml, 4.5 mmol) was added, followed by stirring at room temperature for 18 hours. After the reaction, the solvent was evaporated away under reduced pressure, then 1 N hydrochloric acid (4.5 ml, 4.5 mmol) was added, followed by extraction with a mixed solvent of chloroform:methanol (10:1) and by washing with saturated sodium hydrogencarbonate solution, then the organic layer was dried over anhydrous magnesium sulfate, and the solvent was evaporated away under reduced pressure. The resulting residue was subjected to preparative silica gel column chromatography. The eluate with chloroform/methanol (4:1, v/v) gave the entitled compound (35 mg, 17%) as a pale yellow crystal.

mp: 125-128° C. MS (ESI) m/z: 460 (M+1)$^+$.

$^1$H-NMR (CD$_3$OD) δ: 1.66-1.81 (1H, m), 2.10 (3H, s), 2.10-2.14 (1H, m), 2.48 (6H, s), 2.67 (2H, d, J=7.6 Hz), 3.06-3.14 (1H, m), 3.22-3.35 (6H, m), 3.39-3.46 (1H, m), 4.01-4.09 (2H, m), 4.41-4.49 (2H, m), 7.15-7.21 (1H, m), 7.26-7.32 (1H, m), 7.36-7.49 (3H, m).

IR (ATR): 2208, 1597, 1560, 1465, 1309, 935, 700 cm$^{-1}$.

Anal. Calcd for C$_{26}$H$_{29}$N$_5$O$_2$.3H$_2$O: C, 60.80; H, 6.87; N, 13.64. Found: C, 60.94; H, 6.72; N, 13.26.

Reference Example 192

7-Fluoro-2-[3-(hydroxymethyl)azetidin-1-yl]-5-methyl-6-phenyl-1,3-benzoxazole-4-carbonitrile (I-192)

Under nitrogen atmosphere, 2-chloro-7-fluoro-5-methyl-6-phenyl-1,3-benzoxazole-4-cabonitrile (I-130) (240 mg, 0.84 mmol) was dissolved in methylene chloride (10 ml), then diisopropylethylamine (584 µl, 3.35 mmol) and 3-hydroxymethylazetidine (206 mg, 1.67 mmol) dissolved in methylene chloride (5 ml) were added, followed by heating under reflux in a sealed tube for 5 hours. After cooling, diluting with chloroform and washing with water, the organic layer was dried over anhydrous magnesium sulfate, then the solvent was evaporated away under reduced pressure. The resulting residue was subjected to preparative silica gel column chromatography. The eluate with chloroform/methanol (10:1, v/v) gave the entitled compound (208 mg, 74%) as a white solid.

MS (ESI) m/z: 338 (M+1)$^+$.

$^1$H-NMR (CDCl$_3$) δ: 2.34 (3H, s), 3.02-3.13 (1H, m), 3.90 (2H, d, J=5.9 Hz), 4.43 (2H, t, J=8.7 Hz), 7.22-7.25 (5H, m), 7.39-7.49 (3H, m).

Example 98

7-[(3S)-3-(Dimethylamino)pyrrolidin-1-yl]-2-[3-(hydroxymethyl)azetidin-1-yl]-5-methyl-6-phenyl-1,3-benzoxazole-4-carbonitrile (#98)

7-Fluoro-2-[3-(hydroxymethyl)azetidin-1-yl]-5-methyl-6-phenyl-1,3-benzoxazole-4-carbonitrile (I-192) (220 mg, 0.37 mmol) was dissolved in dimethyl sulfoxide (5 ml), then triethylamine (166 µl, 1.19 mmol) and (3S)-3-(dimethylamino)pyrrolidine (159 µl, 1.25 mmol) were added, followed by stirring in a sealed tube at 150° C. for 19 hours. After cooling, concentration under reduced pressure, dilution with methylene chloride and washing with water, the organic layer was dried over anhydrous magnesium sulfate, then the solvent was evaporated away under reduced pressure. The resulting residue was subjected to preparative silica gel column chromatography. The eluate with chloroform/methanol (10:1, v/v) gave the entitled compound (208 mg, 74%) as a white amorphous substance.

mp: 48-51° C. MS (ESI) m/z; 401 (M+1)$^+$.

$^1$H-NMR (CDCl$_3$) δ: 1.51-1.63 (1H, m), 1.86-2.05 (1H, m), 2.13 (6H, s), 2.14 (3H, s), 2.47-2.57 (1H, m), 2.91-3.15 (3H, m), 3.39-3.30 (2H, m), 3.87 (2H, d, J=6.1 Hz), 4.10-4.16 (2H, m), 4.36 (2H, t, J=8.5 Hz), 7.08-7.32 (1H, m), 7.20-7.24 (1H, m), 7.29-7.41 (3H, m). IR (ATR): 2206, 1635, 1560, 1041, 700 cm$^{-1}$.

Anal. Calcd for $C_{25}H_{29}N_5O_2 \cdot 1.75H_2O$: C, 64.85; H, 7.07; N, 15.12. Found: C, 65.53; H, 6.67; N, 14.34.

Reference Example 193

7-Fluoro-2-(3-hydroxy-3-methylazetidin-1-yl)-5-methyl-6-phenyl-1,3-benzoxazole-4-carbonitrile (I-193)

Under nitrogen atmosphere, 2-chloro-7-fluoro-5-methyl-6-phenyl-1,3-benzoxazole-4-cabonitrile (I-130) (216 mg, 0.753 mmol) was dissolved in N,N-dimethylsulfoamide (10 ml), then N,N-diisopropylethylamine (584 µl, 3.35 mmol) and 3-hydroxy-3-methylazetidine (132 mg, 1.51 mmol) dissolved in N,N-dimethylsulfoamide (5 ml) were added, followed by stirring under heat at 100° C. for 20 hours. After cooling, diluting with chloroform and washing with water, the organic layer was dried over anhydrous magnesium, sulfate, then the solvent was evaporated away under reduced pressure. The resulting residue was subjected to preparative silica gel column chromatography. The eluate with chloroform/methanol (10:1, v/v) gave the entitled compound (234 mg, 92%) as a white solid.
MS (ESI) m/z: 338 (M+1)$^+$.
$^1$H-NMR (CDCl$_3$) δ: 1.67 (3H, s), 2.21 (3H, s), 4.25-4.34 (4H, m), 7.22-7.26 (2H, m), 7.42-7.49 (3H, m).

Example 99

7-[(3S)-3-(Dimethylamino)-1-pyrrolidinyl]-2-(3-hydroxy-3-methylazetidin-1-yl)-5-methyl-6-phenyl-1,3-benzoxazole-4-carbonitrile (#99)

7-Fluoro-2-(3-hydroxy-3-methylazetidin-1-yl)-5-methyl-6-phenyl-1,3-benzoxazole-4-carbonitrile (I-193) (230 mg, 0.68 mmol) was dissolved in DMSO (5 ml), then triethylamine (195 µl, 1.36 mmol) and (3S)-3-(dimethylamino)pyrrolidine (181 µl, 1.43 mmol) were added, followed by stirring at 150° C. for 4 hours. After cooling, concentration under reduced pressure, dilution with ethyl acetate and washing with water, the organic layer was dried over anhydrous magnesium sulfate, then the solvent was evaporated away under reduced pressure. The resulting residue was subjected to silica gel column chromatography, and the eluate with chloroform/methanol (10:1, v/v) gave the entitled compound (32 mg, 11%) as a white solid.
m.p: 167-169° C. MS (ESI) m/z: 432 (M+1)$^+$.
$^1$H-NMR (CDCl$_3$) δ: 1.53-1.63 (1H, m), 1.64 (3H, s), 1.85-1.93 (1H, m), 2.12 (6H, s), 2.14 (3H, s), 2.44-2.54 (1H, m), 2.92 (1H, t, J=8.9 Hz), 3.08-3.16 (1H, m), 3.19-3.29 (2H, m), 4.18-4.28 (2H, m), 7.08-7.12 (1H, m), 7.19-7.24 (1H, m), 7.30-7.41 (3H, m).
IR (ATR): 2206, 1635, 1597, 1566, 1463, 1171, 700 cm$^{-1}$.
Anal. Calcd for $C_{25}H_{29}N_5O_2 \cdot 0.5H_3O$: C, 68.16; H, 6.86; N, 15.90. Found: C, 68.42; H, 6.82; N, 15.47.

Reference Example 194 tert-Butyl [1-(4-cyano-7-fluoro-5-methyl-6-phenyl-1,3-benzoxazol-2-yl)azetidin-3-yl]carbamate (I-194)

Diisopropylethylamine (787 µl, 4.63 mmol) and tert-butyl azetidin-3-ylcarbamate hydrochloride (483 mg, 2.31 mmol) were added to a dichloromethane (20 ml) solution of 2-chloro-7-fluoro-5-methyl-6-phenyl-1,3-benzoxazole-4-cabonitrile (I-130) (553 mg, 1.93 mmol), followed by stirring at room temperature for 30 minutes. With cooling with ice, aqueous 10% citric acid solution (10 ml) was added to the reaction liquid, followed by extraction with chloroform (50 ml), then the organic layer was washed with saturated brine (50 ml). After drying over anhydrous sodium sulfate and concentration under reduced pressure, the resulting residue was purified by silica gel column chromatography (eluent, hexane:ethyl acetate=2:1) to obtain the entitled compound (815 mg, 100%) as a colorless oily substance.
MS (ESI) m/z: 423 (M+1)$^+$.
$^1$H-NMR (CDCl$_3$) δ: 1.47 (9H, s), 2.34 (3H, s), 4.20-4.26 (2H, m), 4.60-4.67 (2H, m), 4.67-4.77 (1H, m), 4.99-5.14 (1H, m), 7.21-7.25 (2H, m), 7.40-7.51 (3H, m).

Reference Example 195 tert-Butyl (1-{4-cyano-7-[(3S)-3-(dimethylamino)pyrrolidin-1-yl]-5-methyl-6-phenyl-1,3-benzoxazol-2-yl}azetidin-3-yl)carbamate (I-195)

(3S)-3-(Dimethylamino)pyrrolidine (180 µl, 1.42 mmol) and triethylamine (238 µl, 1.70 mmol) were added to a dimethyl sulfoxide (5 ml) solution of tert-butyl [1-(4-cyano-7-fluoro-5-methyl-6-phenyl-1,3-benzoxazol-2-yl)azetidin-3-yl]carbamate (I-194) (400 mg, 0.947 mmol), followed by stirring in an oil bath at 130° C. for 3 hours. The reaction liquid was concentrated under reduced pressure, the residue was dissolved in chloroform (100 ml) and washed with saturated brine (100 ml). After drying over anhydrous sodium sulfate and concentration, the resulting residue was purified by silica gel column chromatography (eluent, chloroform:methanol=10:1) to obtain the entitled compound (260 mg, 53.2%) as a colorless solid.
MS (ESI) m/z: 517 (M+1)$^+$.
$^1$H-NMR (CDCl$_3$) δ: 1.46 (9H, s), 1.52-1.60 (1H, m), 1.86-1.94 (1H, m), 2.11 (6H, s), 2.14 (3H, s), 2.44-2.49 (1H, m), 2.87 (1H, t, J=9.0 Hz), 3.15 (1H, td, J=10.1, 6.6 Hz), 3.21-3.27 (2H, m), 4.12-4.16 (2H, m), 4.57 (2H, t, J=8.3 Hz), 4.68 (1H, brs), 5.06 (1H, s), 7.01-7.57 (5H, m).

Example 100

N-(1-{4-Cyano-7-[(3S)-3-(dimethylamino)pyrrolidin-1-yl]-5-methyl-6-phenyl-1,3-benzoxazol-2-yl}azetidin-3-yl)methanesulfonamide (#100)

With cooling with ice, trifluoroacetic acid (1 ml) was added to a dichloromethane (2 ml) solution of tert-butyl (1-{4-cyano-7-[(3S)-3-(dimethylamino)pyrrolidin-1-yl]-5-methyl-6-phenyl-1,3-benzoxazol-2-yl}azetidin-3-yl)carbamate (I-195) (77.6 mg, 0.15 mmol), followed by stirring with cooling with ice for 1 hour. The reaction liquid was concentrated under reduced pressure, dissolved in dichloromethane (2 ml), and with cooling with ice, triethylamine (210 ml, 1.52 mmol) and methanesulfonyl chloride (25.6 µl, 0.33 mmol) were added, followed by stirring at room temperature for 1 hour. The reaction liquid was concentrated under reduced pressure, the residue was dissolved in chloroform (50 ml), and washed with saturated brine (50 ml). After drying over anhydrous sodium sulfate and concentration, the resulting residue was purified by preparative TLC (eluent, chloroform:methanol=10:1) to obtain the entitled compound (15.0 mg, 19.7%) as a colorless solid.
MS (BSI) m/z: 495 (M+1)$^+$.
$^1$H-NMR (CDCl$_3$) δ: 1.50-1.63 (1H, m), 1.86-1.95 (1H, m), 2.11 (6H, s), 2.13 (3H, s), 2.44-2.55 (1H, m), 2.87 (1H, t, J=9.2 Hz), 3.03 (3H, s), 3.13-3.27 (3H, m), 4.25-4.31 (2H, m), 4.50-4.58 (1H, m), 4.61-4.68 (2H, m), 7.09 (1H, d, J=7.3 Hz), 7.21 (1H, d, J=7.3 Hz), 7.29-7.42 (3H, m).

IR (ATR): 3059, 2952, 2873, 2823, 2775, 2206, 1635, 1595, 1562, 1466, 1410, 1385, 1365, 1317, 1246, 1194, 1146, 1057, 1011, 974, 906, 862, 831, 760 cm$^{-1}$.

Anal. Calcd for $C_{25}H_{30}N_6O_3S.0.75H_2O$: C, 59.09; H, 6.25; N, 16.54. Found: C, 59.20; H, 6.28; N, 16.25.

Reference Example 196

4-Cyano-7-fluoro-5-methyl-6-phenyl-1,3-benzoxazole-2-carboxamide (I-196)

At room temperature, trimethylaluminium (4.49 ml, 4.63 mmol, 1.03 M hexane solution was added to an anhydrous dichloromethane (6 ml) suspension of ammonium chloride (247 mg, 4.62 mmol), followed by stirring at room temperature for 20 minutes. A dichloromethane (4 ml) solution of ethyl 4-cyano-7-fluoro-5-methyl-6-phenyl-1,3-benzoxazole-2-carboxylate (I-111) (500 mg, 1.54 mmol) was added, followed by stirring for 4 hours and by heating under reflux in an oil bath at 45° C. for 48 hours. With cooling with ice, 1 N hydrochloric acid (10 ml) was added to the reaction liquid, then water (20 ml) was added, followed by extraction with chloroform (100 ml×2). The organic layer was washed with saturated brine (100 ml), then dried over anhydrous sodium sulfate, concentrated under reduced pressure, and the resulting residue was purified in slurry with diethyl ether to obtain the entitled compound (368 mg, 80.8%) as a pale yellow solid.

$^1$H-NMR (CDCl$_3$) δ: 2.48 (3H, s), 7.16-7.58 (5H, m).

Reference Example 196-1

4-Cyano-7-fluoro-5-methyl-6-phenyl-1,3-benzoxazole-2-carbothioamide (I-196-1)

Lawesson's reagent (458 mg, 1.13 mmol) was added to a toluene solution of 4-cyano-7-fluoro-5-methyl-6-phenyl-1,3-benzoxazole-2-carboxamide (I-196) (304 mg, 1.03 mmol), followed by heating under reflux in an oil bath at 125° C. for 10 minutes. After cooling to room temperature, the reaction liquid was concentrated, and the resulting residue was purified by silica gel column chromatography (eluent, chloroform:ethyl acetate=20:1→10:1) to obtain the entitled compound (134 mg, 41.8%) as a yellow solid.

MS (ESI) m/z: 312 (M+1)$^+$.

$^1$H-NMR (CDCl$_3$) δ: 2.47 (3H, s), 7.25-7.55 (5H, m).

Reference Example 197

Ethyl 2-(4-cyano-7-fluoro-5-methyl-6-phenyl-1,3-benzoxazol-2-yl)-1,3-thiazole-4-carboxylate (I-197)

Ethyl 3-bromopyruvate (72.2 μl, 0.518 mmol) was added to a toluene (10 ml) solution of 4-cyano-7-fluoro-5-methyl-6-phenyl-1,3-benzoxazole-2-carbothioamide (I-196-1) (124 mg, 0.398 mmol), followed by heating under reflux in an oil bath at 125° C. for 2 hours. After cooling to room temperature, p-toluenesulfonic acid monohydrate (15.2 mg, 0.080 mmol) was added to the reaction liquid, followed by heating under reflux in an oil bath at 125° C. for 15 hours. After cooling to room temperature, an aqueous saturated sodium hydrogencarbonate solution (50 ml) and water (50 ml) were added, followed by extraction with ethyl acetate (50 ml×2). The organic layer was washed with an aqueous saturated sodium hydrogencarbonate solution (50 ml) and saturated brine (50 ml), and dried over anhydrous sodium sulfate. After concentration, the resulting residue was purified by silica gel column chromatography (eluent, chloroform:ethyl acetate=100:1→25:1) to obtain the entitled compound (148 mg, 91.2%) as a pale yellow solid.

MS (ESI) m/z: 408 (M+1)$^+$.

$^1$H-NMR (CDCl$_3$) δ: 1.46 (3H, t, J=7.1 Hz), 2.48 (3H, s), 4.51 (2H, q, J=7.2 Hz), 7.26-7.31 (2H, m), 7.46-7.57 (3H, m), 8.49 (1H, s).

Reference Example 198

Ethyl 2-{4-cyano-7-[(3S)-3-(dimethylamino)pyrrolidin-1-yl]-5-methyl-6-phenyl-1,3-benzoxazol-2-yl}-1,3-thiazole-4-carboxylate (I-198)

(3S)-3-(Dimethylamino)pyrrolidine (91.6 μl, 0.722 mmol) and triethylamine (101 μl, 0.722 mmol) were added to a dimethyl sulfoxide (2 ml) solution of ethyl 2-(4-cyano-7-fluoro-5-methyl-6-phenyl-1,3-benzoxazol-2-yl)-1,3-thiazole-4-carboxylate (I-197) (147 mg, 0.361 mmol), followed by stirring in an oil bath at 100° C. for 3 hours. The reaction liquid was concentrated under reduced pressure, the residue was dissolved in chloroform (100 ml) and washed with water (50 ml) and saturated brine (50 ml). After drying over anhydrous sodium sulfate and concentration, the resulting residue was purified by silica gel column chromatography (eluent, chloroform:methanol=100:1→100:3), and the obtained yellow solid was purified in slurry with isopropanol (3 ml) to obtain the entitled compound (120 mg, 66.3%) as a pale yellow solid.

MS (ESI) m/z: 502 (M+1)$^+$.

$^1$H-NMR (CDCl$_3$) δ: 1.45 (3H, t, J=7.1 Hz), 1.56-1.71 (1H, m), 1.97-2.09 (1H, m), 2.11 (6H, s), 2.23 (3H, s), 2.46-2.58 (1H, m), 2.75-2.85 (1H, m), 3.23-3.32 (1H, m), 3.62 (1H, t, J=8.9 Hz), 3.67-3.78 (1H, m), 4.47 (2H, q, J=7.2 Hz), 7.10-7.50 (5H, m), 8.41 (1H, s).

IR (ATR): 3130, 2976, 2870, 2823, 2775, 2208, 1738, 1606, 1579, 1473, 1434, 1396, 1367, 1329, 1304, 1238, 1198, 1155, 1095, 1035, 1014, 955, 912, 823, 769 cm$^{-1}$.

Anal. Calcd for $C_{27}H_{27}N_5O_3S.0.25H_2O$: C, 64.08; H, 5.48; N, 13.84; S, 6.34. Found: C, 64.07; H, 5.28; N, 13.84; S, 6.49.

Example 101

2-{4-Cyano-7-[(3S)-3-(dimethylamino)pyrrolidin-1-yl]-5-methyl-6-phenyl-1,3-benzoxazol-2-yl}-1,3-thiazole-4-carboxylic acid (#101)

Aqueous 1 N sodium hydroxide solution (225 μl, 0.225 mmol) was added to an ethanol (1.7 ml) solution of ethyl 2-{4-cyano-7-[(3S)-3-(dimethylamino)pyrrolidin-1-yl]-5-methyl-6-phenyl-1,3-benzoxazol-2-yl}-1,3-thiazole-4-carboxylate (I-198) (87.0 mg, 0.173 mmol), followed by stirring in an oil bath at 45° C. for 1 hour. With cooling with ice, 1 N hydrochloric acid (225 μl, 0.225 mmol) was added to the reaction liquid, followed by concentration, under reduced pressure, and the obtained pale yellow solid was purified in slurry with a mixed solvent of ethanol:water=9:1 to obtain the entitled compound (50.0 mg, 59.7%) as a pale yellow solid.

MS (ESI) m/z: 474 (M+1)$^+$.

$^1$H-NMR (DMSO-d$_6$) δ: 1.55-1.66 (1H, m), 1.90-1.99 (1H, m), 2.06 (6H, s), 2.15 (3H, s), 2.61-2.69 (1H, m), 2.91 (1H, dd, J=9.9, 7.6 Hz), 3.30 (1H, dd, J=9.9, 7.3 Hz), 3.39-3.53 (2H, m), 7.22 (1H, d, J=7.3 Hz), 7.35 (1H, d, J=7.3 Hz), 7.39-7.51 (3H, m), 8.72 (1H, s).

IR (ATR): 3091, 3047, 2970, 2214, 1608, 1581, 1477, 1442, 1433, 1392, 1363, 1329, 1304, 1273, 1242, 1159, 1090, 1047, 1011, 949, 910, 858, 785, 768 cm$^{-1}$.

Anal. Calcd for $C_{25}H_{23}N_5O_3S \cdot 0.5H_2O$: C, 62.23; H, 5.01; N, 14.51; S, 6.64. Found: C, 62.01; H, 4.80; M, 14.50; S, 6.75.

Reference Example 199 tert-Butyl [(4-cyano-7-fluoro-5-methyl-6-phenyl-1,3-benzoxazole-2-carbonyl)methylamino]acetate (I-199)

Under nitrogen atmosphere, trimethylaluminium (1.03 M n-hexane solution, 4.50 ml, 4.63 mmol) was dropwise added at room temperature to a dichloromethane (6 ml) solution of N-methylglycine tert-butyl ester hydrochloride (840 mg, 4.63 mmol), followed by stirring for 25 hours. Subsequently, a dichloromethane (4 ml) solution of ethyl 4-cyano-7-fluoro-5-methyl-6-phenyl-1,3-benzoxazole-2-carboxylate (I-111) (500 mg, 1.54 mmol) was dropwise added, followed by stirring for 23 hours. After the reaction, aqueous 1 N hydrochloric acid solution was added to the reaction liquid with cooling with ice, followed by stirring at room temperature, and the reaction liquid was extracted with chloroform. Next, the obtained organic layers were combined, dried over anhydrous magnesium sulfate, filtered, and the filtrate was concentrated under reduced pressure. The resulting residue was suspended and washed in diethyl ether to obtain the entitled compound (569 mg, 87%) as a white solid.

MS (ESI) m/z: 368 (M−55)$^+$.

$^1$H-NMR (CDCl$_3$) δ: 1.51 (3.42H, s), 1.52 (5.58H, s), 2.46 (1.86H, s), 2.47 (1.14H, s), 3.28 (1.86H, s), 3.63 (1.14H, s), 4.24 (0.76H, s), 4.69 (1.24H, s), 7.24-7.28 (2H, m), 7.45-7.55 (3H, m).

IR (ATR): 2227, 1741, 1653, 1259, 1228, 1155, 1134 cm$^{-1}$.

Reference Example 200 tert-Butyl [[4-cyano-7-(3S)-3-(dimethylamino)pyrrolidin-1-yl]-5-methyl-6-phenyl-1,3-benzoxazole-2-carbonyl]methylamino]acetate (I-200)

Under nitrogen atmosphere at 140 to 150° C., a dimethyl sulfoxide (1 ml) solution of (3S)-3-(dimethylamino)pyrrolidin (114 μl, 901 μmol) was added to a dimethyl sulfoxide (14 ml) solution of tert-butyl [(4-cyano-7-fluoro-5-methyl-6-phenyl-1,3-benzoxazole-2-carbonyl)methylamino]acetate (I-199) (318 mg, 751 μmol) and trimethylamine (136 μl, 976 μmol), followed by stirring at the same temperature for 40 minutes. After cooling, saturated brine was added to the reaction liquid, and the reaction liquid was extracted with ethyl acetate. Next, the combined organic layer was washed with saturated brine, dried over anhydrous sodium sulfate, filtered, and the filtrate was concentrated under reduced pressure. The resulting residue was subjected to silica gel column chromatography, and the eluate with dichloromethane/methanol (20:1, v/v) gave the entitled compound (183 mg, 47%) as a yellow oil.

MS (ESI) m/z: 518 (M+1)$^+$.

$^1$H-NMR (CDCl$_3$) δ: 1.51 (3.33H, s), 1.52 (5.67H, s), 1.54-1.65 (3H, m), 3.93-2.02 (1H, m), 2.08 (6H, s), 2.20 (1.89H, s), 2.22 (1.11H, s), 2.43-2.54 (1H, m), 2.69-2.78 (1H, m), 3.18-3.24 (1H, m), 3.24 (1.89H, s), 3.58-3.70 (2H, m), 3.64 (1.11H, s), 4.22 (0.74H, s), 4.77 (1.26H, s), 7.10-7.15 (1H, m), 7.23-7.27 (1H, m), 7.33-7.44 (3H, m).

IR (ATR): 2212, 1739, 1660, 1603, 1473, 1394, 1367, 1153 cm$^{-1}$.

Example 102

N-({4-Cyano-7-[(3S)-3-(dimethylamino)pyrrolidin-1-yl]-5-methyl-6-phenyl-1,3-benzoxazol-2-yl}carbonyl)-N-methylglycine (#102)

With cooling with ice, trifluoroacetic acid (500 μl) was added to a dichloromethane (2 ml) solution of tert-butyl [[4-cyano-7-(3S)-3-(dimethylamino)pyrrolidin-1-yl]-5-methyl-6-phenyl-1,3-benzoxazole-2-carbonyl]methylamino]acetate (I-200) (86 mg, 166 μmol), followed by stirring at room temperature for 23 hours. The solvent was evaporated away under reduced pressure, then the residue was azeotroped with toluene. Next, the resulting residue was made alkaline with aqueous 1 N sodium hydroxide solution (664 μl) added thereto, and the mixture was washed with ethyl acetate. Subsequently, the aqueous layer was made neutral with aqueous 1 N hydrochloric acid solution (166 μl) added thereto, followed by extraction with a mixed solvent of chloroform/methanol (10:1, v/v). The obtained organic layers were combined, dried over anhydrous magnesium sulfate, filtered, and the filtrate was concentrated under reduced pressure. The resulting residue was suspended and washed in diethyl ether to obtain the entitled compound (33 mg, 43%) as a brown solid.

MS (ESI) m/z: 462 (M+1)$^+$.

1H-NMR (CDCl$_3$) δ: 1.93-2.11 (2H, m), 2.22 (3H, s), 2.40 (1H, s), 2.68 (6H, s), 3.08-3.15 (1H, m), 3.28 (3H, s), 3.30-3.37 (1H, m), 3.51-3.57 (1H, m), 3.94 (1H, d, J=18.1 Hz), 3.99-4.06 (1H, m), 4.20 (1H, d, J=18.1 Hz), 7.02-7.06 (1H, m), 7.26-7.29 (1H, m), 7.35-7.48 (3H, m).

IR (ATR): 2212, 1653, 1604, 1471, 3396, 3365 cm$^{-1}$.

Anal. Calcd for $C_{25}H_{27}N_5O_4 \cdot 1.75H_2O$: C, 60.90; H, 6.24; N, 14.20. Found: C, 61.20; H, 5.94; N, 13.29.

Reference Example 201

2-(tert-Butyldiphenylsiloxy)ethylamine (I-201)

Under nitrogen atmosphere and with cooling with ice, imidazole (3.56 g, 52.4 mmol) was added to an N,N-dimethylformamide (120 ml) solution of ethanolamine hydrochloride (3.00 g, 30.8 mmol), then an N,N-dimethylformamide (30 ml) solution of tert-butylchlorodiphenylsilane (4.23 g, 15.4 mmol) was dropwise added at the same temperature, followed by stirring at room temperature for 25.5 hours. The solvent was evaporated away under reduced pressure, then the residue was dissolved in ethyl acetate, and the solution was washed with saturated sodium hydrogencarbonate water. Next, the aqueous layer was extracted with ethyl acetate. Subsequently, the organic layers were combined, dried over anhydrous magnesium sulfate, filtered and the filtrate was concentrated under reduced pressure.

The resulting residue was subjected to silica gel column chromatography, and the eluate with dichloromethane/methanol (10:1, v/v) gave the entitled compound (2.81 g, 61%) as a pale yellow oil.

MS (ESI) m/z: 300 (M+1)$^+$.

$^1$H-NMR (CDCl$_3$) δ: 1.06 (9H, s), 1.91 (2H, brs), 2.81-2.85 (2H, m), 3.67-3.71 (2H, m), 7.35-7.45 (6H, m), 7.64-7.69 (4H, m).

IR (ATR): 2929, 2856, 1471, 1427, 1105 cm$^{-1}$.

Example 103

4-Cyano-7-[(3S)-3-(dimethylamino)pyrrolidin-1-yl]-N-[(2-hydroxyethyl)-5-methyl-6-phenyl-1,3-benzoxazole-2-carboxamide (#103)

Under nitrogen atmosphere, trimethylaluminium (1.03 M n-hexane solution, 1.19 ml, 1.23 mmol) was dropwise added at room temperature to a dichloromethane (2 ml) solution of 2-(tert-butyldiphenylsiloxy)ethylamine (I-201) (369 mg, 1.23 mmol), followed by stirring for 30 minutes. Subsequently, a dichloromethane (2 ml) solution of ethyl 4-cyano-7-fluoro-5-methyl-6-phenyl-1,3-benzoxazole-2-carboxylate (I-111) (200 mg, 617 μmol) was dropwise added, followed by stirring for 17 hours. After the reaction, aqueous 1 N hydrochloric acid solution was added to the reaction liquid with cooling with ice, followed by stirring at room temperature, and the reaction liquid was extracted with chloroform. Next, the obtained organic layers were combined, dried over anhydrous magnesium sulfate, filtered, and the filtrate was concentrated under reduced pressure. The resulting residue was subjected to silica gel column chromatography, and the eluate with n-hexane/ethyl acetate (4:1, v/v) gave an amorphous substance.

A dimethyl sulfoxide (1 ml) solution of (3S)-3-(dimethylamino)pyrrolidine (87 μl, 690 μmol) was added to a dimethyl sulfoxide (11 ml) solution of the above amorphous substance and triethylamine (104 μl, 748 μmol) at 140 to 150° C., followed by stirring at the same temperature for 18 hours. After cooling, saturated brine was added to the reaction liquid, and the reaction liquid was extracted with ethyl acetate. Next, the combined organic layer was washed with saturated brine, dried over anhydrous magnesium sulfate, filtered, and the filtrate was concentrated under reduced pressure. The resulting residue was subjected to silica gel column chromatography, and the eluate with dichloromethane/methanol (10:1, v/v) gave the entitled compound (34 mg, 13%) as an amorphous substance.

MS (ESI) m/z: 434 (M+1)$^+$.

$^1$H-NMR (CDCl$_3$) δ: 1.60-1.81 (1H, m), 1.96-2.05 (1H, m), 2.15 (6H, s), 2.21 (3H, m), 2.53-2.62 (1H, m), 2.92-3.01 (1H, m), 3.32 (1H, dd, J=10.0, 7.1 Hz), 3.46-3.61 (2H, m), 3.63-3.76 (2H, m), 3.88-3.93 (2H, m), 7.10-7.14 (1H, m), 7.26-7.31 (1H, m), 7.34-7.46 (3H, m), 7.87-7.94 (1H, m).

IR (ATR): 3410, 2210, 1685, 1603, 1576, 1556, 1471, 1441, 1394, 1363, 1304 cm$^{-1}$.

Anal. Calcd for C$_{24}$H$_{27}$N$_5$O$_3$·0.75H$_2$O: C, 64.49; H, 6.43; N, 15.67. Found: C, 64.65; H, 6.42; N, 14.97.

Reference Example 202

[2-tert-Butoxycarbonylmethylamino)ethyl]methylamine (I-202)

Under nitrogen atmosphere, a dichloromethane (34 ml) solution of di-tert-butyl dicarbonate (2.48 g, 11.3 mmol) was dropwise added to a dichloromethane (80 ml) solution of N,N'-dimethylethylenediamine (2.00 g, 22.7 mmol) and triethylamine (2.21 ml 15.9 mmol) with cooling with ice, followed by stirring at room temperature for 29.5 hours. The solvent was evaporated away under reduced pressure, and the resulting residue was subjected to silica gel column chromatography, in which the eluate with dichloromethane/methanol (5:1, v/v) gave the entitled compound (1.55 g, 73%) as a pale yellow solid.

MS (ESI) m/z: 189 (M+1)$^+$.

$^1$H-NMR (CDCl$_3$) δ: 1.46 (9H, s), 2.51 (3H, brs), 2.62 (2H, brs), 2.89 (3H, s), 3.39 (2H, brs).

IR (ATR): 1685, 1390, 1365, 1155 cm$^{-1}$.

Reference Example 203

N-[2-(tert-Butoxycarbonylmethylamino)ethyl]-N-methylacetamide (I-203)

Under nitrogen atmosphere, acetic anhydride (1.16 ml, 12.3 mmol) and triethylamine (2.28 ml, 16.4 mmol) were added to a dichloromethane (41 ml) solution of [2-(tert-butoxycarbonylmethylamino)ethyl]methylamine (I-202) (1.54 g, 8.18 mmol) with cooling with ice, followed by stirring at room temperature for 15 hours. The solvent was evaporated away under reduced pressure, then the resulting residue was subjected to silica gel column chromatography, and the eluate with dichloromethane/methanol (10:1, v/v) gave the entitled compound (1.88 g, 100%) as a colorless oil.

MS (ESI) m/z; 131 (M−99)$^+$.

$^1$H-NMR (CDCl$_3$) δ: 1.46 (9H, s), 2.08-2.11 (3H, m), 2.88 (3H, s), 2.95 (1.17H, s), 3.03 (1.83H, s), 3.32-3.55 (4H, m).

IR (ATR): 1689, 1647, 1612, 1392, 1365, 1232, 1155 cm$^{-1}$.

Reference Example 204

N-{2-[Acetyl(methyl)amino]ethyl}-4-cyano-N,5-dimethyl-7-fluoro-6-phenyl-1,3-benzoxazole-2-carboxamide (I-204)

At room temperature, 4 N hydrochloric acid/1,4-dioxane solution (923 μl, 3.69 mmol) was added to a 1,4-dioxane (11 ml) solution of N-[2-(tert-butoxycarbonylmethylamino)ethyl]-N-methylacetamide (I-203) (284 mg, 1.23 mmol), followed by stirring for 20 hours, then 4 N hydrochloric acid/1,4-dioxane solution (923 μl, 3.69 mmol) was added at the same temperature, followed by stirring for 6 hours. After the reaction, the solvent was evaporated away under reduced pressure to obtain a white solid.

Under nitrogen atmosphere, trimethylaluminium (1.03 M n-hexane solution, 2.40 ml, 2.47 mmol) was dropwise added at room temperature to a toluene (6 ml) solution of the above white solid, followed by stirring for 1 hour. Subsequently, a dichloromethane (2 ml) solution of ethyl 4-cyano-7-fluoro-5-methyl-6-phenyl-1,3-benzoxazole-2-carboxylate (I-111) (200 mg, 617 μmol) was dropwise added at the same temperature, followed by stirring at 100° C. for 23 hours. After the reaction, aqueous 1N hydrochloric acid solution was added to the reaction liquid with cooling with ice, followed by stirring at room temperature, and the reaction liquid was extracted with chloroform. Next, the obtained organic layers were combined, dried over anhydrous magnesium sulfate, filtered, and the filtrate was concentrated under reduced pressure. The resulting residue was subjected to silica gel column chromatography, and the eluate with dichloromethane/methanol (30:1, v/v) gave the entitled compound (94 mg, 37%) as a pale yellow solid.

MS (ESI) m/z: 409 (M+1)$^+$.

$^1$H-NMR (CDCl$_3$) δ: 2.10 (3H, s), 2.47 (3H, s), 3.14 (1.23H, s), 3.22 (1.77H, s), 3.29 (1.77H, s), 3.56 (1.23H, s), 3.69-3.84 (3H, m), 3.97-4.03 (1H, m), 7.25-7.28 (2H, m), 7.46-7.56 (3H, m).

IR (ATR): 2227, 1655, 1635, 1475, 1429, 1400, 1194, 1126, 1084 cm$^{-1}$.

Example 104

N-{2-[Acetyl(methyl)amino]ethyl}-4-cyano-7-[(3S)-3-(dimethylamino)pyrrolidin-1-yl]-N,5-dimethyl-6-phenyl-1,3-benzoxazole-2-carboxamide (#104)

Under nitrogen atmosphere at 140 to 150° C., a dimethyl sulfoxide (1 ml) solution of (3S)-3-(dimethylamino)pyrrolidin (32 μl, 256 μmol) was added to a dimethyl sulfoxide (3 ml) solution of N-{2-[acetyl(methyl)amino]ethyl}-4-cyano-N,5-dimethyl-7-fluoro-6-phenyl-1,3-benzoxazole-2-carboxamide (I-204) (87 mg, 213 μmol) and triethylamine (39 μl, 277 μmol), followed by stirring at the same temperature for 45 minutes. After cooling, the solvent was evaporated away under reduced pressure, the residue was dissolved in chloroform. The organic layer was washed with saturated brine, dried over anhydrous magnesium sulfate, then filtered, and the filtrate was concentrated under reduced pressure. The resulting residue was subjected to silica gel column chromatography, and the eluate with dichloromethane/methanol (10:1, v/v) gave the entitled compound (47 mg, 44%) as an amorphous substance.

MS (ESI) m/z; 503 (M+1)$^+$.

$^1$H-NMR (CDCl$_3$) δ: 1.95-2.04 (1H, m), 2.10 (6H, s), 2.11 (3H, s), 2.17-2.24 (4H, m), 2.46-2.60 (1H, m), 2.73-2.89 (1H, m), 3.13 (1H, s), 3.23 (1H, s), 3.26 (2H, s), 3.27 (2H, s), 3.55-3.86 (6H, m), 4.00-4.09 (1H, m), 7.13 (1H, d, J=7.1 Hz), 7.24-7.27 (1H, m), 7.35-7.46 (3H, m).

IR (ATR): 2210, 1645, 1604, 1576, 1471, 1439, 1396, 1365, 1304, 1198 cm$^{-1}$.

Anal. Calcd for C$_{28}$H$_{34}$N$_6$O$_3$·0.5H$_2$O: C, 65.73; H, 6.90; N, 16.43. Found: C, 65.51; H, 6.97; N, 16.09.

Reference Example 205

1-Acetyl-3-(tert-butoxycarbonylmethylamino)pyrrolidine (I-205)

Under nitrogen atmosphere, acetic anhydride (707 μl, 7.49 mmol) and triethylamine (1.39 ml, 9.98 mmol) were added to a dichloromethane (25 ml) solution of 3-(tert-butoxycarbonylmethylamino)pyrrolidine (1.00 g, 4.99 mmol) with cooling with ice, followed by stirring at room temperature for 17 hours. The solvent was evaporated away under reduced pressure, then the resulting residue was subjected to silica gel column chromatography, and the eluate with ethyl acetate gave the entitled compound (1.10 g, 91%) as a pale yellow oil.

MS (ESI) m/z: 243 (M+1)$^+$.

$^1$H-NMR (CDCl$_3$) δ: 1.47 (4.5H, s), 1.48 (4.5H, s), 1.93-2.15 (2H, m), 2.05 (3H, s), 2.78 (1.5H, s), 2.80 (1.5H, s), 3.24-3.49 (2H, m), 3.55-3.76 (2H, m), 4.75 (1H, brs).

IR (ATR): 1685, 1643, 1439, 1419, 1410, 1363, 1352, 1144 cm$^{-1}$.

Reference Example 206

N-(1-Acetylpyrrolidin-3-yl)-4-cyano-7-fluoro-N,5-dimethyl-6-phenyl-1,3-benzoxazole-2-carboxamide (I-206)

At room temperature, 4 N hydrochloric acid/1,4-dioxane solution (1.54 ml, 6.15 mmol) was added to a 1,4-dioxane (6.15 ml) solution of 1-acetyl-3-(tert-butoxycarbonylmethylamino)pyrrolidine (I-206) (298 mg, 1.23 mmol), followed by stirring for 20 hours. After the reaction, the solvent was evaporated away under reduced pressure to obtain a white solid.

Under nitrogen atmosphere, trimethylaluminium (1.03 M n-hexane solution, 2.39 ml, 2.47 mmol) was dropwise added at room temperature to a toluene (6 ml) solution of the above white solid, followed by stirring for 65 minutes. Subsequently, a dichloromethane (2 ml) solution of ethyl 4-cyano-7-fluoro-5-methyl-6-phenyl-1,3-benzoxazole-2-carboxylate (I-111) (200 mg, 617 μmol) was dropwise added at the same temperature, followed by stirring at 100° C. for 18.5 hours. After the reaction, aqueous 1 N hydrochloric acid solution was added to the reaction liquid with cooling with ice, followed by stirring at room temperature, and the reaction liquid was extracted with chloroform. Next, the obtained organic layers were combined, dried over anhydrous magnesium sulfate, filtered, and the filtrate was concentrated under reduced pressure. The resulting residue was subjected to silica gel column chromatography, and the eluate with dichloromethane/methanol (30:1, v/v) gave the entitled compound (240 mg, 93%) as an amorphous substance.

MS (ESI) m/z: 421 (M+1)$^+$.

$^1$H-NMR (CDCl$_3$) δ: 2.08-2.15 (3H, m), 2.17-2.36 (2H, m), 2.47-2.49 (3H, m), 3.13 (0.6H, s), 3.16 (0.6H, s), 3.42 (0.9H, s), 3.44 (0.9H, s), 3.46-3.64 (2H, m), 3.68-3.91 (2H, m), 5.26-5.50 (1H, m), 7.24-7.28 (2H, m), 7.47-7.56 (3H, m).

IR (ATR): 2227, 1643, 1441, 1415, 1126, 1092 cm$^{-1}$.

Example 105

N-(1-Acetylpyrrolidin-3-yl)-4-cyano-7-[(3S)-3-(dimethylamino)pyrrolidin-1-yl]-N,5-dimethyl-6-phenyl-1,3-benzoxazole-2-carboxamide (#105)

Under nitrogen atmosphere at 140 to 150° C., a dimethyl sulfoxide (1 ml) solution of (3S)-3-(dimethylamino)pyrrolidin (86 μl, 679 μmol) was added to a dimethyl sulfoxide (10 ml) solution of N-(1-acetylpyrrolidin-3-yl)-4-cyano-7-fluoro-N,5-dimethyl-6-phenyl-1,3-benzoxazole-2-carboxamide (I-206) (238 mg, 566 μmol) and triethylamine (103 μl, 736 μmol), followed by stirring at the same temperature for 45 minutes. After cooling, the solvent was evaporated away under reduced pressure, the residue was dissolved in ethyl acetate. The organic layer was washed with saturated brine, then the aqueous layer was extracted with ethyl acetate. Next, saturated sodium hydrogencarbonate water was added to the aqueous layer, followed by extraction with chloroform. The combined organic layer was dried over anhydrous magnesium sulfate, then filtered, and the filtrate was concentrated under reduced pressure. The resulting residue was subjected to silica gel column chromatography, and the eluate with dichloromethane/methanol (10:1, v/v) gave the entitled compound (153 mg, 53%) as an amorphous substance.

MS (ESI) m/z: 515 (M+1)$^+$.

$^1$H-NMR (CDCl$_3$) δ: 1.93-2.03 (1H, m), 2.05-2.15 (9H, m), 2.21-2.36 (2H, m), 2.22 (3H, s), 2.46-2.61 (1H, m), 2.73-2.90 (1H, m), 3.10 (0.6H, s), 3.13 (0.6H, s), 3.19-3.33 (1H, m), 3.42-3.89 (7H, m), 3.43 (0.9H, s), 3.47 (0.9H, s), 5.23-5.65 (1H, m), 7.10-7.15 (1H, m), 7.24-7.29 (1H, m), 7.34-7.46 (3H, m).

IR (ATR): 2210, 1643, 1604, 1471, 1439, 1415, 1396, 1365, 1304, 1095 cm$^{-1}$.

Anal. Calcd for $C_{29}H_{34}N_6O_3 \cdot 0.5H_2O$: C, 66.52; H, 6.74; N, 16.05. Found: C, 66.42; H, 6.84; N, 15.59.

Reference Example 207

4-Amino-5-cyano-2-fluoro-6-methylbiphenyl-3-yl cyclobutanecarboxylate (I-207)

Under nitrogen atmosphere, 2-amino-5-phenyl-4-fluoro-3-hydroxy-6-methylbenzonitrile (I-41) (250 mg, 1.03 mmol) was dissolved in acetonitrile (0.10 ml), and cooled to 0° C. Triethylamine (244 µl, 1.75 mmol) and cyclobutanecarbonyl chloride (177 µl, 1.55 mmol) were dropwise added to the solution, followed by stirring at room temperature for 1 hour. 10% citric acid was added to the reaction liquid, and the solvent was evaporated away under reduced pressure. Ethyl acetate was added to the resulting residue, followed by washing with saturated brine. The organic layer was dried over anhydrous magnesium sulfate, and the solvent was evaporated away under reduced pressure. The resulting residue was subjected to silica gel column chromatography, and the eluate with ethyl acetate/hexane (1:4, v/v) gave the entitled compound (283 mg, 85%) as a white solid.

MS (ESI) m/z: 325 (M+1)$^+$. $^1$H-NMR (CDCl$_3$) δ: 2.01-2.11 (2H, m), 2.28 (3H, s), 2.34-2.47 (4H, m), 3.42-3.49 (1H, m), 4.48 (2H, brs), 7.21-7.26 (2H, m), 7.37-7.45 (3H, m).

Reference Example 208

2-Cyclobutyl-7-fluoro-5-methyl-6-phenyl-1,3-benzoxazole-4-carbonitrile (I-208)

4-Amino-3-cyano-2-fluoro-6-methylbiphenyl-3-yl cyclobutanecarboxylate (I-207) (283 mg, 0.88 mmol) was dissolved in toluene (20 ml), then p-toluenesulfonic acid monohydrate (10 mg) was added, followed by heating under reflux for 18 hours. After cooled to room temperature, this was diluted with ethyl acetate, and washed with saturated brine. The obtained organic layer was dried over anhydrous magnesium sulfate, and the solvent was evaporated away under reduced pressure. The resulting residue was subjected to silica gel column chromatography, and eluted with a mixed solvent of n-hexane/ethyl acetate (4:1, v/v) to obtain the entitled compound (244 mg, 0.80 mmol, 91%) as a white crystal.

$^1$H-NMR (CDCl$_3$) δ: 2.06-2.25 (2H, m), 2.42 (3H, s), 2.45-2.68 (4H, m), 3.83-3.93 (1H, m), 7.23-7.27 (3H, m), 7.44-7.53 (3H, m).

Example 106

2-Cyclobutyl-7-[(3S)-3-(dimethylamino)pyrrolidin-1-yl]-5-methyl-6-phenyl-1,3-benzoxazole-4-carbonitrile (#106)

2-Cyclobutyl-7-fluoro-5-methyl-6-phenyl-1,3-benzoxazole-4-carbonitrile (I-208) (244 mg, 0.80 mmol) was dissolved in dimethyl sulfoxide (8 ml), then triethylamine (228 µl, 1.59 mmol) and (3S)-3-(dimethylamino)pyrrolidine (212 µl, 1.67 mmol) were added, followed by stirring at 95° C. for 5 hours. After cooled, this was reduced under reduced pressure, diluted with chloroform, washed with saturated brine. The organic layer was dried over anhydrous magnesium sulfate, then the solvent was evaporated away under reduced pressure.

The resulting residue was subjected to preparative silica gel column chromatography. The eluate with chloroform/methanol (10:1, v/v) gave the entitled compound (151 mg, 47%) as a white amorphous substance.

MS (ESI) m/z: 401 (M+1)$^+$.
$^1$H-NMR (CDCl$_3$) δ: 1.56-1.68 (1H, m), 2.14 (6H, s), 2.19 (3H, s), 2.06-2.20 (3H, m), 2.41-2.56 (5H, m), 2.99 (1H, t, J=9.3 Hz), 3.27-3.43 (3H, m), 3.77-3.86 (1H, m), 7.09-7.13 (1H, m), 7.23-7.27 (1H, m), 7.32-7.44 (3H, m).
IR (ATR): 2210, 1604, 1583, 1468, 1362, 1153, 701 cm$^{-1}$.
Anal. Calcd for $C_{23}H_{28}N_4O \cdot 0.25H_2O$: C, 74.14; H, 7.09; N, 13.83. Found: C, 74.50; H, 7.09; N, 13.72.

Reference Example 209

7-Fluoro-5-methyl-6-phenyl-2-(pyridin-3-yl)-1,3-benzoxazole-4-carbonitrile (I-209)

Nicotinyl chloride hydrochloride (192 mg, 1.08 mmol) and triethylamine (301 µl, 2.16 mmol) were added to a dichloromethane (9 ml) solution of 4-amino-6-fluoro-5-hydroxy-2-methylbiphenyl-3-carbonitrile (I-41) (218 mg, 0.900 mmol), followed by stirring at room temperature for 2 hours. Ethyl acetate (100 ml) was added to the reaction liquid, followed by washing with water (50 ml) and saturated brine (50 ml).

After drying over anhydrous sodium sulfate and concentration under reduced pressure, the resulting residue was dissolved in xylene (30 ml), then pyridinium p-toluenesulfonate (218 mg) was added, followed by heating under reflux in an oil bath at 150° C. for 5 hours. The reaction liquid was concentrated under reduced pressure, the residue was dissolved in chloroform (100 ml), and washed with an aqueous saturated sodium hydrogencarbonate solution (50 ml). After drying over anhydrous sodium sulfate and concentration under reduced pressure, the resulting residue was purified by silica gel column chromatography (eluent, chloroform:ethyl acetate=4:1) to obtain the entitled compound (256 mg, 86.4%) as a colorless solid.

MS (ESI) m/z: 330 (M+1)$^+$.
$^1$H-NMR (CDCl$_3$) δ: 2.47 (3H, s), 7.23-7.57 (6H, m), 8.63 (1H, dt, J=8.1, 2.0 Hz), 8.85 (1H, dd, J=4.8, 1.6 Hz), 9.55 (1H, d, J=2.0 Hz).

Example 107

7-[(3S)-3-(Dimethylamino)pyrrolidin-1-yl]-5-methyl-6-phenyl-2-(pyridin-3-yl)-1,3-benzoxazole-4-carbonitrile (#107)

(3S)-3-(Dimethylamino)pyrrolidine (123 µl, 0.970 mmol) and triethylamine (135 µl, 0.970 mmol) were added to a dimethyl sulfoxide (6 ml) solution of 7-fluoro-5-methyl-6-phenyl-2-(pyridin-3-yl)-1,3-benzoxazole-4-carbonitrile (I-209) (213 mg, 0.647 mmol), followed by stirring in an oil bath at 95° C. for 2 hours. The reaction liquid was concentrated under reduced pressure, the residue was dissolved in chloroform (100 ml), then washed with water (50 ml) and saturated brine (50 ml). After drying over anhydrous sodium sulfate and concentration, the residue was purified by silica gel column chromatography (eluent, chloroform/methanol=10:1), and the eluate was recrystallized from isopropanol to obtain the entitled compound (190 mg, 69.4%) as a yellow crystal.

MS (ESI) m/z: 424 (M+1)$^+$.
$^1$H-NMR (CDCl$_3$) δ: 1.60-1.72 (1H, m), 1.97-2.06 (1H, m), 2.16 (6H, s), 2.23 (3H, s), 2.50-2.60 (1H, m), 3.02 (1H, t, J=9.2 Hz), 3.37-3.56 (3H, m), 7.13-7.17 (1H, m), 7.26-7.30 (1H, m), 7.34-7.51 (4H, m), 8.56 (1H, dt, J=8.1, 1.7 Hz), 8.79 (1H, dd, J=4.9, 1.7 Hz), 9.41 (1H, dd, J=2.2, 0.7 Hz).

IR (ATR): 2968, 2945, 2868, 2823, 2777, 2206, 1593, 1549, 1471, 1446, 1396, 1367, 1302, 1277, 1192, 1163, 1091, 1059, 1014, 935, 862, 820, 789, 723 cm$^{-1}$.

Anal. Calcd for $C_{26}H_{25}N_5O$: C, 73.74; H, 5.95; N, 16.54. Found: C, 73.54; H, 5.92; N, 16.44.

Example 108

7-[(3S)-3-(Dimethylamino)pyrrolidin-1-yl]-5-methyl-6-phenyl-2-(pyridin-2-ylmethyl)-1,3-benzoxazole-4-carbonitrile (#108)

With cooling with ice, oxalyl chloride (262 μl, 3 mmol) and a catalytic amount of dimethyl formamide were added to a dichloromethane (7 ml) suspension of 2-pyridylacetic acid hydrochloride (382 mg, 2.2 mmol), followed by stirring at the same temperature for 10 minutes and at room temperature for 10 minutes. Again after cooling with ice, a dichloromethane suspension of 4-amino-6-fluoro-5-hydroxy-2-methyl-biphenyl-3-carbonitrile (I-41) (485 mg, 2.0 mmol) and diisopropylethylamine (697 μl, 4 mmol) were added, followed by stirring at room temperature for 1.5 hours. The reaction liquid was diluted with chloroform, then the organic layer was washed with water, dried over anhydrous sodium sulfate, and the solvent was evaporated away under reduced pressure. In a mixed solvent of xylene/tetrahydrofuran (ca. 5:1, 20 ml) in the presence of a catalytic amount of p-tosylic acid, the resulting residue was heated under reflux for 2 hours with a Dean-Stark device. After cooling, the solvent was evaporated away, and the resulting residue was dissolved in chloroform, washed with water, dried over anhydrous sodium sulfate, then the solvent was evaporated away under reduced pressure. The resulting residue was subjected to silica gel column chromatography, and eluted with a mixed solvent of chloroform/methanol (99:1, v/v) to obtain a main product.

This was dissolved in dimethyl sulfoxide (7 ml), and (3S)-3-(dimethylamino)pyrrolidine (83 μl, 0.65 mmol) and triethylamine (100 μl) were added. The system was purged with nitrogen, then sealed up, and heated at 120° C. for 1.5 hours. After cooling, the solvent was evaporated away under reduced pressure, then the resulting residue was dissolved in chloroform, washed with water. The organic layer was dried over anhydrous sodium sulfate, then the solvent was evaporated away under reduced pressure, and the resulting residue was separated and purified by preparative TLC to obtain a main product. Silica gel column chromatography with elution with a mixed solvent of chloroform/methanol (97:3, v/v) gave the entitled compound (8.9 mg, 1%) as a yellow oil.

MS (ESI) m/z: 438 (M+1)$^+$.
$^1$H-NMR (CDCl$_3$) δ: 1.80-1.92 (1H, m), 1.85-1.95 (1H, m), 2.09 (6H, s), 2.19 (3H, s), 2.40-2.50 (1H, m), 2.80-2.93 (1H, m), 3.18-3.38 (3H, m), 4.51 (2H, s), 7.09 (1H, d, J=2.0, 6.8 Hz), 7.22-7.28 (2H, m), 7.34-7.42 (4H, m), 7.68-7.70 (1H, m), 8.57 (1H, d, J=4.0 Hz).

Reference Example 210

7-Fluoro-5-methyl-2-(2-nitrophenyl)-6-phenyl-1,3-benzoxazole-4-carbonitrile (I-210)

Diisopropylethylamine (523 μl, 3 mmol) was added to a dichloromethane (10 ml) solution of 4-amino-6-fluoro-5-hydroxy-2-methyl-biphenyl-3-carbonitrile (I-41) (485 mg, 2.0 mmol), and after cooling with ice, 2-nitrobenzoyl chloride (408 mg, 2.2 mmol) was added, followed by stirring at the same temperature for 1 hour. With cooling with ice, water was added, followed by extraction with ethyl acetate. The organic layer was washed with saturated brine, dried over anhydrous sodium sulfate, then the solvent was evaporated away under reduced pressure. In xylene (30 ml) in the presence of a catalytic amount of p-tosylic acid, the resulting residue was heated under reflux for 16 hours with a Dean-Stark device. After cooling, the solvent was evaporated away, and the resulting residue was dissolved in chloroform, washed with saturated sodium bicarbonate water, then dried over anhydrous sodium sulfate, and the solvent was evaporated away under reduced pressure. The resulting residue was subjected to silica gel column chromatography. Elution with chloroform gave the entitled compound (576 mg, 77%) as a colorless solid.

MS (EI) m/z: 373 (M$^+$).
$^1$H-NMR (CDCl$_3$) δ: 2.47 (3H, s), 7.25-7.28 (2H, m), 7.48-7.55 (3H, m), 7.80-7.86 (2H, m), 8.09-8.12 (1H, m), 8.15-8.18 (1H, m).

Reference Example 211

7-[(3S)-3-(Dimethylamino)pyrrolidin-1-yl]-5-methyl-2-(2-nitrophenyl)-6-phenyl-1,3-benzoxazole-4-carbonitrile (I-211)

(3S)-3-(Dimethylamino)pyrrolidine (90 μl, 0.71 mmol) and triethylamine (200 μl) were added to a dimethyl sulfoxide (5 ml) solution of 7-fluoro-5-methyl-2-(2-nitrophenyl)-6-phenyl-1,3-benzoxazole-4-carbonitrile (I-210) (204 mg, 0.55 mmol). The system was purged with nitrogen, then sealed up, and heated at 100° C. for 1.5 hours. After cooling, the solvent was evaporated away under reduced pressure, then the resulting residue was dissolved in chloroform, and washed with water and saturated brine. The organic layer was dried over anhydrous sodium sulfate, then the solvent was evaporated away under reduced pressure, and the resulting residue was subjected to silica gel column chromatography. Elution with a mixed solvent of chloroform/methanol (98:2, v/v) gave a main product. This was washed with a mixed solvent of isopropyl ether and ethanol, and the solid was collected by filtration to obtain the entitled compound (137 mg, 54%) as a yellow solid.

mp: 139-142° C. MS (EI) m/z: 467 (M$^+$).
$^1$H-NMR (CDCl$_3$) δ: 1.58-1.70 (1H, m), 1.91-2.00 (1H, m), 2.14 (6H, s), 2.22 (3H, s), 2.47-2.55 (1H, m), 2.90 (1H, t, J=9.2 Hz), 3.18-3.27 (1H, m), 3.30-3.40 (2H, m), 7.13 (1H, d, J=7.2 Hz), 7.25-7.28 (1H, m), 7.33-7.44 (3H, m), 7.68-7.80 (2H, m), 7.85 (1H, dd, J=1.6, 8.0 Hz), 8.35 (1H, dd, J=1.6, 8.0 Hz).

IR (ATR): 2206, 1597, 1544, 1473, 1441, 1367 cm$^{-1}$.
Anal. Calcd for $C_{26}H_{25}N_5O$: C, 69.36; H, 5.39; N, 14.98. Found: C, 69.30; H, 5.39; N, 14.85.

Example 109

2-(2-Aminophenyl)7-[(3S)-3-(dimethylamino)pyrrolidin-1-yl]-5-methyl-6-phenyl-1,3-benzoxazole-4-carbonitrile (#109)

10% Palladium-carbon (150 mg) was added to an ethyl acetate (30 ml) solution of 5-methyl-7-[(3S)-3-(dimethylamino)pyrrolidin-1-yl]-2-(2-nitrophenyl)-6-phenyl-1,3-benzoxazole-4-carbonitrile (I-211) (128 mg, 0.27 mmol), followed by stirring at the same temperature under atmospheric pressure of hydrogen for 1.5 hours. The catalyst was removed by filtration with washing with ethyl acetate, the filtrate was concentrated under reduced pressure, and the resulting residue was subjected to silica gel column chromatography. Elution with a mixed solvent of chloroform/methanol (99:1→96:4, v/v) gave the entitled compound (65 mg, 55%) as a pale yellow solid.

mp: 259-263° C. MS (EI) m/z: 437 (M⁺).

$^1$H-NMR (CDCl$_3$) δ: 1.60-1.71 (1H, m), 1.98-2.04 (1H, m), 2.18 (6H, s), 2.22 (3H, s), 2.50-2.61 (1H, m), 3.02 (1H, t, J=9.2 Hz), 3.37-3.53 (3H, m), 6.27 (2H, brs), 6.74 (1H, t, J=7.2 Hz), 6.81 (1H, d, J=8.8 Hz), 7.16 (1H, d, J=2.0 Hz), 7.25-7.32 (2H, m), 7.37-7.46 (3H, m), 7.88 (1H, dd, J=1.6, 7.6 Hz).

IR (ATR): 3442, 3336, 2206, 1599, 1535, 1469 cm$^{-1}$.

Anal. Calcd for C$_{27}$H$_{27}$N$_5$O.0.25H$_2$O: C, 73.36; H, 6.27; N, 15.84. Found: C, 73.60; H, 6.27; N, 15.68.

Reference Example 212

7-Fluoro-2-(2-hydroxyphenyl)-5-methyl-6-phenyl-1,3-benzoxazole-4-carbonitrile (I-212)

Diisopropylethylamine (435 μl, 2.5 mmol) was added to a dichloromethane (10 ml) solution of 4-amino-6-fluoro-5-hydroxy-2-methyl-biphenyl-3-carbonitrile (I-41) (353 mg, 1.46 mmol), then after cooling with ice, O-acetylsalicyloyl chloride (318 mg, 1.6 mmol) was added, followed by stirring at the same temperature for 30 minutes. With cooling with ice, water was added, followed by extraction with ethyl acetate. The organic layer was washed with saturated brine, dried over anhydrous sodium sulfate, then the solvent was evaporated away under reduced pressure. In xylene (30 ml) and in the presence of a catalytic amount of p-tosylic acid, the resulting residue was heated under reflux for 2 hours with a Dean-Stark device. After cooling, the solvent was evaporated away, and the resulting residue was dissolved in chloroform, washed with saturated sodium bicarbonate water, then dried over anhydrous sodium sulfate, and the solvent was evaporated away under reduced pressure. The resulting residue was washed with a mixed solvent of isopropyl ether and ethanol, and the solid was collected by nitration to obtain the entitled compound (320 mg, 64%) as a pale yellow solid.

MS (ESI) m/z; 345 (M+1)⁺.

$^1$H-NMR (CDCl$_3$) δ: 2.46 (3H, s), 7.04-7.10 (1H, m), 7.18 (1H, d, J=8.4 Hz), 7.28-7.35 (2H, m), 7.48-7.60 (4H, m), 8.08 (1H, dd, J=1.6, 8.0 Hz), 10.81 (1H, brs).

Example 110

7-[(3S)-3-(Dimethylamino)pyrrolidin-1-yl]-2-(2-hydroxyphenyl)-5-methyl-6-phenyl-1,3-benzoxazole-4-carbonitrile (#110)

(3S)-3-(Dimethylamino)pyrrolidine (100 μl, 0.79 mmol) and triethylamine (220 μl) were added to a dimethyl sulfoxide (5 ml) solution of 7-fluoro-2-(2-hydroxyphenyl)-5-methyl-6-phenyl-1,3-benzoxazole-4-carbonitrile (I-212) (204 mg, 0.59 mmol). The system was purged with nitrogen, then sealed up, and heated at 120° C. for 30 minutes. After cooling, the solvent was evaporated away under reduced pressure, then the resulting residue was dissolved in chloroform, and washed with water and saturated brine. The organic layer was dried over anhydrous sodium sulfate, then the solvent was evaporated away under reduced pressure, and the resulting residue was subjected to silica gel column chromatography. Elution with a mixed solvent of chloroform/methanol (97:3, v/v) gave a main product. This was washed with a mixed solvent of isopropyl ether and ethanol, and the solid was collected by filtration to obtain the entitled compound (64 mg, 24%) as a pale yellow solid.

mp: 159-162° C.

MS (EI) m/z: 438 (M*).

$^1$H-NMR (CDCl$_3$) δ: 1.60-1.72 (1H, m), 1.98-2.09 (1H, m), 2.16 (6H, s), 2.22 (3H, s), 2.50-2.61 (1H, m), 3.02 (1H, t, J=9.2 Hz), 3.39-3.58 (3H, m), 6.95-6.99 (1H, m), 7.11-7.15 (2H, m), 7.25-7.33 (1H, m), 7.38-7.50 (4H, m), 7.86 (1H, dd, J=1.6, 8.0 Hz), 11.10 (1H, brs).

IR (ATR): 2208, 1602, 1540, 1471, 1438, 1254, 1155 cm$^{-1}$.

Anal. Calcd for C$_{27}$H$_{26}$N$_4$O$_2$.0.25H$_2$O: C, 73.20; H, 6.03; N, 12.65. Found: C, 72.85; H, 5.89; N, 12.61.

Reference Example 213

4-Amino-5-cyano-2-fluoro-6-methylbiphenyl-3-yl cyclopentenecarboxylate (I-213)

Under nitrogen atmosphere, 2-amino-5-phenyl-4-fluoro-3-hydroxy-6-methylbenzonitrile (I-41) (200 mg, 0.83 mmol) was dissolved in acetonitrile (10 ml), and cooled to 0° C. Triethylamine (195 μl, 1.4 mmol) and cyclopentenecarbonyl chloride (162 mg, 1.24 mmol) were dropwise added to the solution, followed by stirring at room temperature for 1 hour. 10% citric acid was added to the reaction liquid, and the solvent was evaporated away under reduced pressure. Ethyl acetate was added to the resulting residue, followed by washing with saturated brine. The organic layer was dried over anhydrous magnesium sulfate, and the solvent was evaporated away under reduced pressure. The resulting residue was subjected to preparative silica gel column chromatography, and the eluate with ethyl acetate/hexane (1:3, v/v) gave the entitled compound (180 mg, 77%) as a white solid.

$^1$H-NMR (CDCl$_3$) δ: 1.98-2.07 (2H, m), 2.28 (3H, s), 2.55-2.63 (2H, m), 2.65-2.73 (2H, m), 4.60 (2H, brs), 7.09-7.24 (2H, m), 7.33-7.44 (3H, m).

Reference Example 214

2-(Cyclopent-1-en-1-yl)-7-fluoro-5-methyl-6-phenyl-1,3-benzoxazole-4-carbonitrile (I-214)

4-Amino-5-cyano-2-fluoro-6-methylbiphenyl-3-yl cyclopentenecarboxylate (I-213) (180 mg, 0.54 mmol) was dissolved in xylene (50 ml), pyridinium p-toluenesulfonate (50 mg) was added, followed by heating under reflux for 5 hours. After cooling to room temperature, the solvent was evaporated away under reduced pressure. The resulting residue was diluted with ethyl acetate, and washed with saturated brine. The obtained organic layer was dried over anhydrous sodium sulfate, the solvent was evaporated away under reduced pressure. The resulting residue was subjected to silica gel column chromatography, and eluted with a mixed solvent of n-hexane/ethyl acetate (4:1, v/v) to obtain the entitled compound (148 mg, 87%) as a white crystal.

$^1$H-NMR (CDCl$_3$) δ: 2.08-2.17 (2H, m), 2.42 (3H, s), 2.66-2.73 (2H, m), 2.92-2.99 (1H, m), 7.07-7.11 (1H, m), 7.25-7.29 (1H, m), 7.44-7.54 (3H, m).

Example 111

2-(Cyclopent-1-en-1-yl)-7-[(3S)-3-(dimethylamino)pyrrolidin-1-yl]-5-methyl-6-phenyl-1,3-benzoxazole-4-carbonitrile (#111)

2-(Cyclopent-1-en-1-yl)-7-fluoro-5-methyl-6-phenyl-1,3-benzoxazole-4-carbonitrile (I-214) (145 mg, 0.46 mmol) was dissolved in dimethyl sulfoxide (5 ml), then triethylamine (130 μl, 0.91 mmol) and (3S)-3-(dimethylamino)pyrrolidine (121 μl, 0.96 mmol) were added, followed by stirring at 95° C. for 4 hours. After cooled, this was concentrated under reduced pressure, diluted with chloroform, and washed with saturated brine. The organic layer was dried over anhydrous magnesium sulfate, then the solvent was evaporated away under reduced pressure. The resulting residue was subjected to preparative silica gel column chromatography. The eluate with chloroform/methanol (5:1, v/v) gave the entitled compound (34 mg, 18%) as a pale yellow amorphous substance.

MS (ESI) m/z: 413 (M+1)+.

$^1$H-NMR (CDCl$_3$) δ: 1.57-1.60 (1H, m), 1.89-1.99 (1H, m), 2.13 (6H, s), 2.05-2.16 (2H, m), 2.20 (3H, s), 2.44-2.55 (1H, m), 2.60-2.68 (2H, m), 2.88-3.03 (3H, m), 3.25-3.42 (3H, m), 6.87 (1H, brs), 7.12 (1H, d, J=7.6 Hz), 7.25-7.27 (1H, m), 7.31-7.44 (3H, m).

IR (ATR): 2202, 1603, 1.466, 1442, 1362, 1302, 706 cm$^{-1}$.

Anal. Calcd for C$_{26}$H$_{28}$N$_4$O.1.0H$_2$O: C, 72.53; H, 7.02; N, 13.01. Found: C, 72.62; H, 6.99; N, 12.70.

Reference Example 215

1-(4-Amino-5-cyano-2-fluoro-6-methyl-1-biphenyl-3-yl)-2-ethyl (1R*,2R*)-cyclopropane-1,2-dicarboxylate (I-215)

Under nitrogen atmosphere, 2-amino-5-phenyl-4-fluoro-3-hydroxy-6-methylbenzonitrile (I-41) (250 mg, 1.03 mmol) was dissolved in acetonitrile (10 ml), and cooled to 0° C. Ethyl (1R*,2R*)-2-chlorocarbonylcyclopropanecarboxylate (273 mg, 1.55 ml) prepared from ethyl (1R*,2R*)-cyclopropane-1,2-dicarboxylate, and triethylamine (244 μl, 1.75 mmol) were dropwise added to the solution, followed by stirring at room temperature for 1 hour. 10% citric acid was added to the reaction liquid, and the solvent was evaporated away under reduced pressure. Ethyl acetate was added to the resulting residue, followed by washing with saturated brine. The organic layer was dried over anhydrous magnesium sulfate, and the solvent was evaporated away under reduced pressure. The resulting residue was subjected to silica gel column chromatography, and the eluate with ethyl acetate/hexane (1:2, v/v) gave the entitled compound (210 mg, 53%) as a white solid.

MS (ESI) m/z: 383 (M+1)+.

$^1$H-NMR (CDCl$_3$) δ: 1.30 (3H, t, J=7.2 Hz), 1.80-1.89 (2H, m), 2.41 (3H, s), 2.49-2.55 (1H, m), 4.21 (2H, q, J=7.2 Hz), 7.22-7.26 (2H, m), 7.44-7.53 (3H, m).

Reference Example 216

Ethyl (1R*,2R*)-2-[4-cyano-7-fluoro-5-methyl-6-phenyl-1,3-benzoxazol-2-yl]cyclopropanecarboxylate (I-216)

1-(4-Amino-5-cyano-2-fluoro-6-methyl-1-biphenyl-3-yl)-2-ethyl(1R*,2R*)-cyclopropane-1,2-dicarboxylate (I-215) (180 mg, 0.54 mmol) was dissolved in xylene (50 ml), pyridinium p-toluenesulfonate (50 mg) was added, followed by heating under reflux for 25 hours.

After cooling to room temperature, the solvent was evaporated away under reduced pressure. The resulting residue was diluted with ethyl acetate, and washed with saturated brine. The obtained organic layer was dried over anhydrous sodium sulfate, the solvent was evaporated away under reduced pressure. The resulting residue was subjected to preparative TLC, and the eluate with ethyl acetate/hexane (1:4, v/v) gave the entitled compound (200 mg, quant.) as a white solid.

$^1$H-NMR (CDCl$_3$) δ: 1.30 (3H, t, J=7.2 Hz), 1.80-1.89 (2H, m), 2.41 (3H, s), 2.49-2.55 (1H, m), 4.21 (2H, q, J=7.2 Hz), 7.22-7.26 (2H, m), 7.44-7.53 (3H, m).

Example 112

Ethyl (1R*,2R*)-2-{4-cyano-7-[(3S)-3-(dimethylamino)pyrrolidin-1-yl]-5-methyl-6-phenyl-1,3-benzoxazol-2-yl}cyclopropanecarboxylate (#112)

Ethyl (1R*,2R*)-2-[4-cyano-7-fluoro-5-methyl-6-phenyl-1,3-benzoxazole-2-yl]cyclopropanecarboxylate (I-216) (200 mg, 0.55 mmol) was dissolved in dimethyl sulfoxide (5 ml), then triethylamine (146 μl, 1.10 mmol) and (3S)-3-(dimethylamino)pyrrolidine (146 μl, 1.15 mmol) were added, followed by stirring at 95° C. for 4 hours. After cooled, this was concentrated under reduced pressure, diluted with chloroform, and washed with saturated brine. The organic layer was dried over anhydrous magnesium sulfate, then the solvent was evaporated away under reduced pressure. The resulting residue was subjected to preparative TLC. The eluate with chloroform/methanol (5:1, v/v) gave the entitled compound (105 mg, 42%) as a red brown solid.

MS (ESI) m/z: 459 (M+1)+.

$^1$H-NMR (CDCl$_3$) δ: 1.30 (3H, t, J=7.2 Hz), 1.56-1.64 (4H, m), 1.72-1.82 (2H, m), 1.90-1.99 (1H, m), 2.12 (6H, s), 2.18 (3H, s), 2.38-2.54 (2H, m), 2.74-2.93 (2H, m), 3.23-3.42 (3H, m), 4.21 (2H, q, J=7.2 Hz), 7.10 (1H, d, J=6.8 Hz), 7.21-7.26 (6H, m), 7.32-7.44 (3H, m).

IR (ATR): 2206, 1724, 1587, 1178, 701 cm$^{-1}$.

Anal. Calcd for C$_{27}$H$_{30}$N$_4$O$_3$.0.25H$_2$O: C, 70.03; H, 6.64; N, 12.10. Found: C, 69.83; H, 6.62; N, 11.86.

Example 113

(1R*,2R*)-2-{4-cyano-7-[(3S)-3-(dimethylamino)pyrrolidin-1-yl]-5-methyl-6-phenyl-1,3-benzoxazol-2-yl}cyclopropanecarboxylic acid (#113)

Ethyl (1R*,2R*)-2-{4-cyano-7-[(3S)-3-(dimethylamino)pyrrolidin-1-yl]-5-methyl-6-phenyl-1,3-benzoxazol-2-yl}cyclopropanecarboxylate (#112) (81 mg, 0.177 mmol) was dissolved in tetrahydrofuran (5 ml), then aqueous 1 N sodium hydroxide solution (33 μl, 0.883 mmol) was added, followed by stirring at room temperature for 18 hours. After the reaction, this was concentrated under reduced pressure, diluted with chloroform, and washed with saturated brine. The organic layer was dried over anhydrous sodium sulfate, then the solvent was evaporated away under reduced pressure. The resulting residue was subjected to preparative TLC.

The eluate with chloroform/methanol (5:1, v/v) gave the entitled compound (105 mg, 42%) as a red brown solid.

MS (ESI) m/z: 459 (M+1)+.

$^1$H-NMR (CDCl$_3$) δ: 1.30 (3H, t, J=7.2 Hz), 1.56-1.64 (4H, m), 1.72-1.82 (2H, m), 1.90-3.99 (1H, m), 2.12 (6H, s), 2.18 (3H, s), 2.38-2.54 (2H, m), 2.74-2.93 (2H, m), 3.23-3.42 (3H, m), 4.21 (2H, q, J=7.2 Hz), 7.10 (1H, d, J=6.8 Hz), 7.21-7.26 (6H, m), 7.32-7.44 (3H, m).

IR (ATR): 2206, 1724, 1587, 1178, 701 cm$^{-1}$.

Anal. Calcd for C$_{27}$H$_{30}$N$_4$O$_3$.0.25H$_2$O: C, 70.03; H, 6.64; N, 12.10. Found: C, 69.83; H, 6.62; N, 11.86.

Reference Example 217

N-(5-Cyano-2-fluoro-3-hydroxy-6-methyl-biphenyl-4-yl)-2-hydroxyacetamide (I-217)

A catalyst 10%-palladium carbon (40.0 mg) was added to an ethanol (10 ml) solution of 2-(benzyloxy)-N-(5-cyano-2-fluoro-3-hydroxy-6-methylbiphenyl-4-yl)acetamide (I-89) (120 mg, 0.307 mmol), followed by stirring under hydrogen atmosphere at room temperature for 15 hours. After the reaction, the insoluble matter was removed by filtration, the filtrate was concentrated under reduced pressure to obtain the entitled compound. Not purified, this was used in the next reaction as such.

Reference Example 218

7-Fluoro-2-hydroxymethyl-5-methyl-6-phenyl-1,3-benzoxazole-4-carbonitrile (I-218)

N-(5-Cyano-2-fluoro-3-hydroxy-6-methyl-biphenyl-4-yl)-2-hydroxyacetamide (I-217) obtained in the above was dissolved in xylene (20 ml), then pyridinium p-toluenesulfonate (20 mg) was added, followed by heating under reflux in an oil bath at 155° C. for 24 hours. The reaction liquid was concentrated under reduced pressure, then the residue was dissolved in chloroform (100 ml), and washed with an aqueous saturated sodium hydrogencarbonate solution (50 ml). After drying over anhydrous sodium sulfate and concentration under reduced pressure, the resulting residue was purified by silica gel column chromatography (eluent, chloroform:ethyl acetate=2:1) to obtain the entitled compound (55.0 mg, 63.4% from I-89) as a colorless solid.

MS (ESI) m/z: 283 (M+1)$^+$.

$^1$H-NMR (CDCl$_3$) δ: 2.44 (3H, s), 2.69-2.77 (1H, m), 5.02 (2H, d, J=6.6 Hz), 7.19-7.54 (5H, m).

Example 114

7-[(3S)-3-(Dimethylamino)pyrrolidin-1-yl]-2-hydroxymethyl-5-methyl-6-phenyl-1,3-benzoxazole-4-carbonitrile (#114)

(3S)-3-(Dimethylamino)pyrrolidine (18.2 μl, 0.143 mmol) and triethylamine (26.7 μl, 0.191 mmol) were added to a dimethyl sulfoxide (0.5 ml) solution of 7-fluoro-2-hydroxymethyl-5-methyl-6-phenyl-1,3-benzoxazole-4-carbonitrile (I-218) (27.0 mg, 0.096 mmol), followed by stirring in an oil bath at 95° C. for 3 hours. The reaction liquid was concentrated under reduced pressure, the residue was dissolved in chloroform (10 ml), and washed with saturated brine (10 ml). After drying over anhydrous sodium sulfate and concentration, the resulting residue was purified by preparative TLC (eluent, chloroform:methanol-10:1), and the eluate was purified in slurry with diethyl ether to obtain the entitled compound (4.00 mg, 11.1%) as a pale yellow solid.

MS (ESI) m/z: 377 (M+1)$^+$.

HRMS (EI) m/z: 376.1895 (Calcd for C$_{22}$H$_{24}$N$_4$O$_2$ 376.1899).

$^1$H-NMR (CDCl$_3$) δ: 1.61-1.71 (1H, m), 1.91-1.99 (1H, m), 2.15 (6H, s), 2.20 (3H, s), 2.50-2.60 (1H, m), 3.01 (1H, t, J=9.0 Hz), 3.24-3.34 (2H, m), 3.38-3.45 (1H, m), 4.93 (2H, s), 7.10 (1H, d, J=7.1 Hz), 7.24-7.27 (1H, m), 7.33-7.45 (3H, m).

IR (ATR): 2951, 2883, 2777, 2206, 1604, 1560, 1462, 1439, 1400, 1363, 1304, 1242, 1213, 1157, 1095, 1038, 989, 960, 914, 837, 789, 752 cm$^{-1}$.

Example 115

7-[(3S)-3-(Dimethylamino)pyrrolidin-1-yl]-5-methyl-6-phenyl-2-(1,2,4-triazol-1-yl)methyl-1,3-benzoxazole-4-carbonitrile (#114)

Triethylamine (6.22 μl, 0.045 mmol) and methanesulfonyl chloride (3.00 μl, 0.038 mmol) were added to a dichloromethane (0.3 ml) solution of 7-[(3S)-3-(dimethylamino) pyrrolidin-1-yl]-2-hydroxymethyl-5-methyl-6-phenyl-1,3-benzoxazole-4-carbonitrile (#114) (12.0 mg, 0.032 mmol), followed by stirring for 1 hour with cooling with ice. The reaction liquid was concentrated under reduced pressure, the residue was dissolved in ethyl acetate (50 ml), washed with saturated brine (30 ml). After drying over anhydrous sodium sulfate and concentration, the resulting residue was dissolved in tetrahydrofuran (0.3 ml), then 1,2,4-triazole (12.6 mg, 0.182 mmol), sodium hydride (7.67 mg, 0.175 mmol) and dimethylformamide (0.1 ml) were added, followed by stirring at room temperature for 3 days. With cooling with ice, water (15 ml) was added to the reaction liquid, followed by extraction with ethyl acetate (20 ml). The organic layer was washed with saturated brine (15 ml), dried over anhydrous sodium sulfate, then concentrated, and the resulting residue was purified by preparative TLC (eluent, chloroform:methanol=10:1), and the eluate was purified in slurry with diethyl ether to obtain the entitled compound (7.00 mg, 51.4%) as a colorless solid.

MS (ESI) m/z: 428 (M+1)$^+$.

HRMS (EI) m/z; 428.2177 (Calcd for 428.2199).

$^1$H-NMR (CDCl$_3$) δ: 1.47-1.63 (1H, m), 1.86-1.97 (1H, m), 2.09 (6H, s), 2.19 (3H, s), 2.38-2.50 (1H, m), 2.79-2.87 (1H, m), 3.17-3.30 (2H, m), 3.32-3.39 (1H, m), 5.69 (2H, s), 6.95-7.56 (5H, m), 8.01 (1H, s), 8.34 (1H, s).

IR (ATR): 3118, 2952, 2871, 2823, 2775, 2210, 1608, 1587, 1506, 1469, 1441, 1398, 1365, 1302, 1273, 1207, 1155, 1136, 1059, 1014, 974, 916, 862, 839, 785, 725 cm$^{-1}$.

Reference Example 219

2-Amino-5-bromo-3-hydroxybenzoic acid (I-219)

3-Hydroxyanthranilic acid (6.28 g, 41.0 mmol) was dissolved in acetic acid (550 ml), then a solution of bromine (13.1 g, 82.0 mmol) dissolved in acetic acid (50 ml) was gradually and dropwise added at room temperature, taking 20 minutes. After stirring at room temperature for 2.5 hours, methanol (70 ml) and water (300 ml) were added to the solution, followed by stirring at room temperature for 15 hours. The formed solid was collected by nitration, and dried under reduced pressure to obtain the entitled compound (9.129 g, 97%) as a brown powder.

MS (ESI) m/z: 234 (M+1)$^+$.

$^1$H-NMR (DMSO-d$_6$) δ: 6.89 (1H, d, J=2.4 Hz), 7.30 (1H, d, J=2.4 Hz), 10.19 (1H, brs).

Reference Example 220

5-Bromo-2-(2,2-dimethylpropionylamino)-3-hydroxybenzoic acid (I-220)

2-Amino-5-bromo-3-hydroxybenzoic acid (I-219) (11.92 g, 51.37 mmol) was dissolved in benzene (360 ml), and pyridine (12.5 m, 154.12 mmol) and pivaloyl chloride (19.0 ml, 154.12 mmol) were added at room temperature. After stirred at 85° C. under nitrogen atmosphere for 3.5 hours, this was cooled to room temperature. The solution was fractionated with ethyl acetate and aqueous 1 M hydrochloric acid solution. The organic layer was washed with saturated brine, and dried over anhydrous sodium sulfate. The solvent was evaporated away under reduced pressure, and the resulting residue was subjected to column chromatography with silica gel, and the fraction with hexane:ethyl acetate=95:5 gave the entitled compound (15.98 g, 98.4%) as a brown solid.

HRMS m/z: 316.0232 (Calcd for $C_{12}H_{13}O_4NBr$ 315.9752).

$^1$H-NMR (CDCl$_3$) δ: 1.41 (9H, s), 7.04 (1H, s), 7.45 (1H, d, J=2.2 Hz), 7.80 (1H, d, J=2.2 Hz).

IR (ATR): 3360, 1749, 1583, 1466, 1302, 1088, 858, 789, 754 cm$^{-1}$.

Reference Example 221

5-Bromo-2-(2,2-dimethylpropionylamino)-3-hydroxy-4-nitrobenzoic acid (I-221)

5-Bromo-2-(2,2-dimethylpropionylamino)-3-hydroxybenzoic acid (I-220) was dissolved in acetic acid (3 ml), then fuming nitric acid (22 μl, 0.52 mmol) was added at room temperature. After stirring at room temperature for 1 hour, the solvent was evaporated away under reduced pressure. The residue was fractionated with ethyl acetate and saturated brine. The organic layer was again washed with saturated brine, and dried over anhydrous sodium sulfate. After filtration, the solvent was evaporated away and the resulting residue was subjected to column chromatography with silica gel, and the fraction with hexane:ethyl acetate=3:1 gave 5-bromo-2-(2,2-dimethylpropionylamino)-3-hydroxy-6-nitrobenzoic acid (61 mg, 36) and the entitled compound (22 mg, 13%).

$^1$H-NMR (CDCl$_3$) δ: 1.43 (9H, s), 7.95 (1H, s).

Reference Example 222

6-Bromo-2-tert-butyl-7-nitro-1,3-benzoxazole-4-carboxylic acid (I-222)

5-Bromo-2-(2,2-dimethylpropionylamino)-3-hydroxy-4-nitrobenzoic acid (I-221) (1.90 g, 5.26 mmol) was dissolved in benzene (38 ml), then p-toluenesulfonic acid monohydrate (1.00 g, 5.26 mmol) was added at room temperature. Under nitrogen atmosphere, the reaction liquid was heated under reflux for 21 hours, then cooled to room temperature. The reaction liquid was fractionated with ethyl acetate and saturated brine. The organic layer was washed with saturated brine, and dried over anhydrous sodium sulfate. The insoluble matter was removed by filtration, the solvent was evaporated away and the resulting residue was purified by middle-pressure liquid chromatography (eluent, ethyl acetate:methanol=4:1) to obtain the entitled compound (1.80 g, 98%) as a brown solid.

MS (ESI) m/z: 343, 345 (M+1)$^+$.

HREI-MS m/z: 341.9821 (Calcd for $C_{12}H_{11}O_5N_2{}^{79}Br$ 341.9852), 343.9803 (Calcd for $C_{12}H_{11}O_5N_2{}^{81}Br$ 343.9831).

$^1$H-NMR (CD$_3$OD) δ: 1.52 (9H, s), 8.20 (1H, s).

IR (ATR): 1705, 1533, 1190, 1136, 808 cm$^{-1}$.

Reference Example 223

2-tert-Butyl-7-nitro-6-phenyl-1,3-benzoxazole-4-carboxylic acid (I-223)

6-Bromo-2-tert-butyl-7-nitro-1,3-benzoxazole-4-carboxylic acid (I-222) (2.15 g, 6.27 mmol), phenylboronic acid (1.53 g, 12.53 mmol) and aqueous 2 M sodium carbonate solution (20 ml) were suspended in toluene (40 ml) and ethanol (30 ml). Tetrakis(triphenylphosphine)palladium(0) (724 mg, 0.63 mmol) was added at room temperature to the suspension. The mixture was stirred at 85° C. for 22 hours, then cooled to room temperature. The reaction liquid was fractionated with ethyl acetate and aqueous 1 M hydrochloric acid solution. The organic layer was washed with saturated brine, and dried over anhydrous sodium sulfate. The insoluble matter was removed by filtration, the solvent was evaporated away and the resulting residue was purified by middle-pressure liquid chromatography (eluent, chloroform:methanol=9:1) to obtain the entitled compound (3.00 g) as a brown gel. This was used in the next reaction as such.

MS (ESI) m/z: 341 (M+1)$^+$.

HREI-MS m/z: 340.1064 (Calcd for $C_{12}H_{16}O_5N_2$ 340.1059).

$^1$H-NMR (CDCl$_3$) δ: 1.41 (9H, s), 7.26-7.32 (2H, m), 7.38-7.45 (3H, m), 7.94 (1H, s).

IR (ATR): 2976, 1711, 1533, 1358, 1236, 1115, 812, 698 cm$^{-1}$.

Reference Example 224

7-Amino-2-tert-butyl-6-phenyl-1,3-benzoxazole-4-carboxylic acid (I-224)

2-tert-Butyl-7-nitro-6-phenyl-1,3-benzoxazole-4-carboxylic acid (I-223) (6.27 mmol) was dissolved in methanol (30 ml), then at room temperature, 10% palladium-carbon (430 mg) was added. The suspension was stirred at room temperature under atmospheric pressure of hydrogen for 16 hour. The catalyst was removed by filtration with washing with methanol, and the filtrate was concentrated under reduced pressure. The resulting residue was purified by middle-pressure liquid chromatography (eluent, chloroform:methanol=98:2) to obtain the entitled compound (1.274 g, 66% from I-222) as a pale brown powder.

MS (ESI) m/z: 311 (M+1)$^+$.

HREI-MS m/z: 310.1295 (Calcd for $C_{18}H_{18}O_3N_2$ 310.1318).

$^1$H-NMR (CDCl$_3$) δ: 1.52 (9H, s), 4.62 (2H, br), 7.35-7.50 (5H, m) 7.89 (1H, s).

IR (ATR): 3323, 3209, 1724, 1635, 1556, 1363, 1329, 1227, 1153, 1109, 775, 702 cm$^{-1}$.

Reference Example 225

7-Bromo-2-tert-butyl-6-phenyl-1,3-benzoxazole-4-carboxylic acid (I-225)

Copper(II) bromide (1.98 g, 8.86 mmol) was suspended in acetonitrile (20 ml), and under nitrogen atmosphere at room temperature, tertiary butyl nitrite (90% purity, 1.07 ml, 8.06 mmol) was added. Next, the solution was stirred at 60° C. for 5 minutes, and at the same temperature, a solution of 7-amino-2-tert-butyl-6-phenyl-1,3-benzoxazole-4-carboxylic acid (I-223) (1.25 g, 4.03 mmol) dissolved in acetonitrile (110 ml) was gradually added. The reaction liquid was further stirred for 50 minutes, then cooled to room temperature. The reaction liquid was fractionated with ethyl acetate and an aqueous 0.5 M hydrochloric acid solution. The organic layer was washed with saturated brine, and dried over anhydrous sodium sulfate. The insoluble matter was removed by filtration, the solvent was evaporated away, and the resulting residue was purified with middle-pressure liquid chromatography (eluent, chloroform:methanol=98:2) to obtain the entitled compound (1.37 g, 91%) as a brown solid.

MS (ESI) m/z: 0374, 376 (M+1)⁺.
HRMS (EI) m/z: 373.0312 (Calcd for $C_{18}H_{16}O_3N^{79}Br$ 373.0314), 375.0291 (Calcd for $C_{18}H_{16}O_3N^{81}Br$ 375.0295).
$^1$H-NMR (CDCl$_3$) δ: 1.55 (9H, s), 7.38-7.52 (5H, m), 8.04 (1H, brs).
IR (ATR): 2974, 1689, 1545, 1236, 1117, 931, 742, 698 cm$^{-1}$.

Reference Example 226

7-Bromo-2-tert-butyl-6-phenyl-1,3-benzoxazole-4-carbonitrile (I-226)

7-Bromo-2-tert-butyl-6-phenyl-1,3-benzoxazole-4-carboxylic acid (I-225) (1.37 g, 3.66 mmol) was dissolved in dichloromethane (20 ml), and under nitrogen atmosphere at 0° C., N,N-dimethylformamide (2 drops) and oxalyl chloride (479 μl, 5.49 mmol) were added. The reaction liquid was stirred at room temperature for 2 hours, then the solvent was evaporated away under reduced pressure. Toluene was added to the residue, followed by azeotropic distillation under reduced pressure. This operation was repeated once again. The residue was dried under reduced pressure, ethyl acetate (40 ml) was added to it, followed by stirring at 0° C. for 5 minutes. Aqueous 28% ammonia (20 ml) was gradually added to the solution, followed by further stirring at room temperature for 11 hours. Ethyl acetate was evaporated away under reduced pressure, and the residue was extracted with 10% methanol-containing chloroform. The organic layer was washed with saturated brine, and dried over anhydrous sodium sulfate. The insoluble matter was removed by filtration, then the solvent was evaporated away under reduced pressure. Next, the residue was dissolved in pyridine (15 ml), and at 0° C., 4-dimethylaminopyridine (90 mg, 0.73 mmol) and then trifluoromethanesulfonic acid anhydride (1.85 ml, 10.98 mmol) were added.

The reaction liquid was stirred at room temperature for 1 hour, and fractionated with ethyl acetate and aqueous 0.5 M hydrochloric acid. The organic layer was washed with an aqueous saturated sodium hydrogencarbonate solution and then with saturated brine, and dried over anhydrous sodium sulfate. The solvent was evaporated away and the resulting residue was purified by middle-pressure liquid chromatography (eluent, hexane:ethyl acetate=9:1) to obtain the entitled compound (809 mg, 62%) as a colorless solid.

MS (LC) m/z: 355, 357 (M+1)⁺.
HREI-MS m/z: 374.0368 (Calcd for $C_{18}H_{15}ON_2{}^{79}Br$ 354.0368).
$^1$H-NMR (CDCl$_3$) δ: 1.56 (9H, s), 7.38-7.51 (5H, m), 7.60 (1H, s). IR (ATR): 2231, 1726, 1556, 1460, 1385, 1250, 1124, 1043, 771, 708 cm$^{-1}$.

Example 116

2-tert-Butyl-7-[(3S)-3-(dimethylamino)pyrrolidin-1-yl]-6-phenyl-1,3-benzoxazole-4-carbonitrile hydrochloride (#116)

Racemic BINAP (13.2 mg, 0.02 mmol) was suspended in toluene (2 ml), and heated under nitrogen atmosphere at 80° C. to be a transparent solution. The solution was pooled to room temperature, and palladium acetate (3.2 mg, 0.014 mmol) was added, followed by stirring at the same temperature for 5 minutes. Next, 7-bromo-2-tert-butyl-6-phenyl-1,3-benzoxazole-4-carbonitrile (I-226) (50 mg, 0.14 mmol), (3S)-3-(dimethylamino)pyrrolidine (22 μl, 0.17 mmol) and sodium t-butoxide (19 mg, 0.20 mmol) were added, followed by stirring at 80° C. for 14 hours. The solution was cooled to room temperature, then the insoluble matter was removed by filtration with washing with ethyl acetate. The filtrate was fractionated with ethyl acetate and saturated brine. The organic layer was washed with saturated brine, and dried over anhydrous sodium sulfate.

The insoluble matter was separated by filtration, the solvent was evaporated away and the resulting residue was purified by preparative TLC (eluent, chloroform:methanol=95:5) to obtain a non-salt form of the entitled compound (18.5 mg, 34%) as a pale brown gel. A part of this (10 mg, 0.026 mg) was dissolved in diethyl ether (2 ml), then at room temperature, 1 M hydrochoric acid/ethanol solution (28 μl, 0.028 mmol) was added. After stirring under nitrogen atmosphere at the same temperature for 2 hours, the solvent was evaporated away under reduced pressure. Diethyl ether was added to the residue, followed by evaporation under reduced pressure. This operation was repeated further twice. The residue was dried at 60° C. under reduced pressure to obtain a white solid (9.5 mg, 87%).

MS (ESI) m/z: 389 (M+1)⁺.
HRMS (EI) m/z: 388.2251 (Calcd for $C_{24}H_{28}N_4O$ 388.2251).
IR (ATR): 2216, 1610, 1483, 1406, 1140, 714 cm$^{-1}$.
Anal. Calcd for $C_{24}H_{28}N_4O \cdot 0.75H_2O \cdot HCl$: C, 65.74; H, 7.01; N, 12.78; Cl, 8.09. Found: C, 65.51; H, 6.73; N, 12.25; Cl, 8.24.

Reference Example 227

5-Bromo-4-fluoro-2-hydroxybenzoic acid (I-227)

4-Fluoro-2-hydroxybenzoic acid (29.01 g, 0.186 mol) was dissolved in acetic acid (290 ml), then a solution of bromine (31.18 g, 0.195 mol) dissolved in acetic acid (15 ml) was gradually dropwise added at room temperature (1 hour). After stirred at 60° C. for 24 hours, this was cooled to room temperature. The reaction liquid was dried to solidness under reduced pressure, the residue was dissolved in methanol (100 ml), and this was poured into water (600 ml). After stirring at room temperature for 15 minutes, the precipitated crystal was washed and collected by filtration, and dried to obtain the entitled compound (35.36 g, 93%) as a colorless solid.

$^1$H-NMR (DMSO-d$_6$) δ: 7.03 (1H, d, J=10.3 Hz), 7.98 (1H, d, J=8.1 Hz).

Reference Example 228

5-Bromo-4-fluoro-2-hydroxy-3-nitrobenzoic acid (I-228)

5-Bromo-4-fluoro-2-hydroxybenzoic acid (I-227) (34.39 g, 0.146 mol) was dissolved in concentrated sulfuric acid (260 ml), and cooled at 0° C. At the same temperature, fuming nitric acid (d=1.52) (6.67 ml, 0.161 mol) was dropwise added with keeping the inner temperature at 0° C. or lower (about 20 minutes). After the addition, the disappearance of the starting material was confirmed by TLC, then the reaction liquid was gradually poured into ice. The aqueous layer was extracted with ethyl acetate, the organic layer was washed with saturated brine, then dried over anhydrous sodium sulfate, and the solvent was evaporated away. N-hexane was added to the residue, the crystal was ground, the suspension was stirred at room temperature for 1 hour (optionally with sonication). The crystal was washed with n-hexane, followed by filtration and drying to obtain the entitled compound (33.82 g, 83%) as an orange solid.

MS (ESI) m/z: 280, 282 (M+1)⁺.

HRMS (EI) m/z: 278.9169 (Calcd for $C_7H_3BrNO_5$ 278.9170).

¹H-NMR (CDCl₃) δ: 6.08 (1H, br), 8.29 (1H, d, J=7.3 Hz), 11.31 (1H, br s).

IR (ATR): 3076, 2860, 1668, 1541, 1431, 1228, 1213, 1167, 1072, 685, 654 cm⁻¹.

Reference Example 229

Methyl
5-bromo-4-fluoro-2-methoxy-3-nitrobenzoate
(I-229)

5-Bromo-4-fluoro-2-hydroxy-3-nitrobenzoic acid (I-228) (35.89 g, 0.128 mol) was dissolved in acetonitrile (600 ml), then at room temperature, potassium carbonate (53.1 g, 0.358 mol) was added, and dimethyl sulfate (30.3 ml, 0.32 mol was dropwise added. After staring at 60° C. for 2.5 hour and then cooling to room temperature, the insoluble matter was removed by filtration (with washing with acetonitrile (400 ml)). The filtrate was concentrated under reduced pressure (about 800 ml of acetonitrile was evaporated away), and water (800 ml) was added to the residue, followed by stirring at room temperature. The precipitated crystal was washed with water and dried to obtain the entitled compound (36.5 g, 92%) as a pale yellow solid.

MS (EI) m/z: 307, 309 (M⁺).

HRMS (EI) m/z: 306.9494 (Calcd for $C_9H_7{}^{79}BrFNO_5$ 306.9492), 308.9481 (Calcd for $C_9H_7{}^{81}BrFNO_5$ 308.9472).

¹H-NMR (CDCl₃) δ: 3.97 (3H, s), 4.00 (3H, s), 8.26 (1H, d, J=7.6 Hz).

IR (ATR): 1722, 1537, 1296, 1255, 1147, 1078, 991, 673, 636 cm⁻¹.

Reference Example 230

Methyl
3-amino-5-bromo-4-fluoro-2-methoxybenzoate
(I-230)

Methyl 5-bromo-4-fluoro-2-methoxy-3-nitrobenzoate (I-229) (1.0 g, 3.25 mmol) was dissolved in acetic acid (10 ml), and at room temperature, iron powder (544 mg, 9.74 mmol) was added, followed by stirring at 130° C. for 4 hours. After cooling to room temperature, the insoluble matter was separated by filtration with washing with ethyl acetate. The organic layer of the filtrate was evaporated under reduced pressure, and the resulting residue was fractionated with ethyl acetate and aqueous 1 M sodium hydroxide solution. The organic layer was washed with saturated brine, and dried over anhydrous sodium sulfate. The solvent was evaporated away, and the resulting residue was purified by middle-pressure liquid chromatography (eluent, hexane:ethyl acetate=4:1) to obtain the entitled compound (798 mg, 88%) as a colorless gel substance.

MS (ESI) m/z: 278, 280 (M+1)⁺.

MS (EI) m/z: 277, 279 (M⁺).

HRMS (EI) m/z: 276.9759 (Calcd for $C_9H_9{}^{79}BrFNO_3$ 276.9750), 278.9748 (Calcd for $C_9H_9{}^{81}BrFNO_3$ 278.9729).

¹H-NMR (CDCl₃) δ: 3.87 (3H, s), 3.90 (3H, s), 4.80 (2H, br s), 7.43 (1H, d, J=7.8 Hz).

IR (ATR): 3475, 1724, 1614, 1466, 1435, 1319, 1294, 1205, 1009, 924, 787 cm⁻¹.

Reference Example 231

Methyl
5-amino-6-fluoro-4-methoxybiphenyl-3-carboxylate
(I-231)

Methyl 3-amino-5-bromo-4-fluoro-2-methoxybenzoate (I-230) (504 mg, 1.81 mmol) was dissolved in 1,4-dioxane (10 ml), then under nitrogen atmosphere at room temperature, phenylboronic acid (456 mg, 3.62 mmol), tripotassium phosphate (770 mg, 3.62 mmol) and tetrakis(triphenylphosphine)palladium(0) (210 mg, 0.18 mmol) were added. After stirred at 90° C. for 36 hours, this was cooled to room temperature. The insoluble matter was separated by filtration with washing with ethyl acetate, the filtrate was fractionated with ethyl acetate and saturated brine. The organic layer was washed with saturated brine, dried over anhydrous sodium sulfate. The solvent was evaporated away, and the resulting residue was purified by middle-pressure liquid chromatography (eluent, hexane:ethyl acetate=3:1) to obtain the entitled compound (459 mg, 92%) as a colorless gel substance.

MS (EI) m/z: 275 (M⁺).

HRMS (EI) m/z: 275.0967 (Calcd for $C_{15}H_{14}FNO_3$ 275.0958).

¹H-NMR (CDCl₃) δ: 3.90 (3H, s), 3.91 (3H, s), 4.02 (2H, br), 7.32-7.38 (2H, m), 7.39-7.45 (2H, m), 7.49-7.52 (2H, m).

IR (ATR): 3371, 1724, 1468, 1425, 1238, 1203, 1009, 700 cm⁻¹.

Reference Example 232

5-Amino-6-fluoro-4-methoxybiphenyl-3-carboxamide
(I-232)

Methyl 5-amino-6-fluoro-4-methoxybiphenyl-3-carboxylate (I-231) (3.0 g, 10.90 mmol) was dissolved in tetrahydrofuran (90 ml) and water (45 ml), and at 0° C., lithium hydroxide monohydrate (4.57 g, 108.98 mmol) was gradually added. After heated under reflux for 5 hours, this was cooled to room temperature. Under reduced pressure, the organic layer was evaporated, and the resulting residue was cooled at 0° C., and 2 N hydrochloric acid (55 ml) was gradually added.

After the addition, the mixture was extracted with ethyl acetate. The organic layer was washed with saturated brine, and dried over anhydrous sodium sulfate. The insoluble matter was separated by filtration, the solvent was evaporated away under reduced pressure to obtain 5-amino-6-fluoro-4-methoxybiphenyl-3-carboxylic acid as a white solid. Not purified, this was dissolved in N,N-dimethylformamide (60 ml), and at room temperature, 1-(3-dimethylaminopropyl)-3-ethylcarbodiimide hydrochloride (3.14 g, 16.35 mmol), 1-hydroxybenzotriazole (2.21 g, 16.35 mmol) and further aqueous 28% ammonia (2.0 ml, 32.70 mmol) were gradually added. The solution was stirred at room temperature for 11 hours, then fractionated with ethyl acetate and saturated brine. The organic layer was washed with saturated brine, and dried over anhydrous sodium sulfate. The solvent was evaporated away, and the resulting residue was purified by middle-pressure liquid chromatography (eluent, chloroform:methanol=98:2) to obtain the entitled compound (2.83 g, 99.8%) as a white solid.

MS (EI) m/z: 260 (M⁺).

HRMS (EI) m/z: 260.0959 (Calcd for $C_{14}H_{13}FN_2O_2$ 260.0961).

¹H-NMR (CDCl₃) δ: 3.87 (3H, s), 4.02 (2H, brs), 6.67 (1H, br s), 7.32-7.44 (3H, m), 7.51-7.65 (4H, m).

Reference Example 233

N-(5-Cyano-2-fluoro-4-methoxybiphenyl-3-yl)-2,2,2-trifluoroacetamide (I-233)

5-Amino-6-fluoro-4-methoxybiphenyl-3-carboxamide (I-232) (2.28 g, 8.76 mmol) was dissolved in tetrahydrofuran (36 ml), and at 0° C., a solution of triethylamine (4.88 ml, 35.04 mmol) and trifluoroacetic anhydride (3.71 ml, 26.28 mmol) dissolved in tetrahydrofuran (10 ml) was gradually added. After stirring at 0° C. for 2 hours, water (46 ml) was added, followed by vigorously stirring for 5 minutes. Tetrahydrofuran was evaporated away under reduced pressure, and the residue was extracted with ethyl acetate. The organic layer was washed with saturated brine, and dried over anhydrous sodium sulfate. The solvent was evaporated away, and the resulting residue was purified by middle-pressure liquid chromatography (eluent, hexane:ethyl acetate=4:1) to obtain the entitled compound (2.782 g, 94%) as a white solid.

MS (FAB) m/z: 339 (M+1)$^+$.
HRMS (FAB) m/z: 339.0760 (Calcd for $C_{16}H_{11}F_4N_2O_2$ 339.0757).
$^1$H-NMR (CDCl$_3$) δ: 4.16 (3H, s), 7.39-7.50 (5H, m), 7.63 (1H, d, J=7.8 Hz), 8.03 (1H, brs).
IR (ATR): 3232, 2231, 1726, 1479, 1433, 1417, 1207, 1153, 1059, 958, 908, 766, 692 cm$^{-1}$.

Reference Example 234

5-Amino-6-fluoro-4-methoxybiphenyl-3-carbonitrile (I-234)

N-(5-Cyano-2-fluoro-4-methoxybiphenyl-3-yl)-2,2,2-trifluoroacetamide 233) (2.78 g, 8.22 mmol) was dissolved in methanol (31.8 ml), and at room temperature, aqueous 15 wt. % potassium carbonate solution (31.8 ml, 34.5 mmol) was added. This was stirred at 70° C. for 38 hours. After cooling to room temperature, methanol was evaporated away under reduced pressure, and the resulting residue was extracted with ethyl acetate. The organic layer was separated, and the aqueous layer was again extracted with ethyl acetate. The organic layers were combined, washed with saturated brine, and dried over anhydrous sodium sulfate. The solvent was evaporated away, and the resulting residue was purified by middle-pressure liquid chromatography (eluent, hexane:ethyl acetate=4:1) to obtain the entitled compound (1.833 g, 92%) as a colorless gel substance.

MS (EI) m/z; 242 (M$^+$).
HRMS (EI) m/z: 242.0854 (Calcd for $C_{14}H_{11}FN_2O$ 242.0855).
$^1$H-NMR (CDCl$_3$) δ: 4.09 (3H, s), 4.05-4.20 (2H, br), 7.00 (1H, d, J=8.1 Hz), 7.38-7.49 (5H, m).
IR (ATR): 3477, 3367, 2229, 1618, 1481, 1470, 1427, 1254, 1188, 1170, 1153, 1049, 1001, 770, 698 cm$^{-1}$.

Reference Example 235

5-Amino-2-bromo-6-fluoro-4-methoxybiphenyl-3-carbonitrile (I-235)

5-Amino-6-fluoro-4-methoxybiphenyl-3-carbonitrile (I-234) (500 mg, 2.06 mmol) was dissolved in acetic acid (9.5 ml), and at room temperature, N-bromosuccinimide (441 mg, 2.48 mmol) was gradually added. After stirring under nitrogen atmosphere at room temperature for 1 hour, the solvent was evaporated away under reduced pressure. The residue was fractionated with ethyl acetate and aqueous 1M sodium hydroxide solution. The organic layer was washed with saturated brine, and dried over anhydrous sodium sulfate. After filtration, the solvent was evaporated away, and the resulting residue was purified by middle-pressure liquid chromatography (eluent, hexane:ethyl acetate=3:1) to obtain the entitled compound (592 mg, 89%) as a pale brown solid.

MS (EI) m/z: 320, 322 (M$^+$).
HRMS (EI) m/z: 319.9984 (Calcd for $C_{14}H_{10}Br^{79}FN_2O$ 319.9960), 321.9958 (Calcd for $C_{14}H_{10}Br^{81}FN_2O$ 321.9940).
$^1$H-NMR (CDCl$_3$) δ: 4.05-4.10 (2H, br), 4.08 (3H, s), 7.24-7.29 (2H, m), 7.42-7.50 (3H, m).
IR (ATR): 3369, 2231, 1616, 1465, 1452, 1434, 1417, 1190, 1155, 1061, 1011, 937, 775, 716, 698 cm$^{-1}$.

Reference Example 236

5-Amino-6-fluoro-4-methoxy-2-methylbiphenyl-3-carbonitrile (I-236)

5-Amino-2-bromo-6-fluoro-4-methoxy-2-methylbiphenyl-3-carbonitrile (I-235) (2.02 g, 6.29 mmol), potassium carbonate (2.61 g, 18.87 mmol) and tetrakis(triphenylphosphine)palladium(0) (727 mg, 0.63 mmol) were dissolved in 10% water-containing 1,4-dioxane (50 ml), and at room temperature, trimethylboroxine (50 wt. % tetrahydrofuran solution, 1.90 ml, 7.55 mmol) was added. After stirring under nitrogen atmosphere at 110° C. for 8 hours and then cooling to room temperature, tetrakis(triphenylphosphine)palladium (0) (727 mg, 0.63 mmol) was added, followed by further stirring at 110° C. for 11 hours. After cooling to room temperature, the insoluble matter was separated by filtration, the filtrate was fractionated with ethyl acetate and saturated brine. The organic layer was separated, the aqueous layer was again extracted with ethyl acetate.

The organic layers were combined, washed with saturated brine, and dried over anhydrous sodium sulfate. After filtration, the solvent was evaporated away, the resulting residue was dissolved in a small amount of chloroform, then silica gel (20 g) was added, and the excessive solvent was evaporated away. The powder was subjected to column chromatography with silica gel, and the fraction with, ethyl acetate:hexane=4:1 gave the entitled compound (1.567 g, 97%) as a pale brown solid.

MS (EI) m/z: 256 (M$^+$).
HRMS (EI) m/z: 256.1014 (Calcd for $C_{15}H_{13}FN_2O$ 256.1012).
$^1$H-NMR (CDCl$_3$) δ: 2.22 (3H, s), 3.88 (2H, brs), 4.05 (3H, s), 7.18-7.23 (2H, m), 7.38-7.48 (3H, m).
IR (ATR): 3367, 2224, 1477, 1431, 1358, 1296, 1151, 1059, 939, 775, 711 cm$^{-1}$.

Reference Example 237

N-(5-Cyano-2-fluoro-4-methoxy-6-methylbiphenyl-3-yl)-2,2-dimethylpropionamide (I-237)

5-Amino-6-fluoro-4-methoxy-2-methylbiphenyl-3-carbonitrile (I-236) (300 mg, 1.17 mmol) was dissolved in pyridine (3 ml), and under nitrogen atmosphere at 0° C., pivaloyl chloride (433 μl, 3.51 mmol) was dropwise added. After stirring at roam temperature for 20 hours, aqueous 1 M hydrochloric acid solution was added to the reaction liquid at 0° C.

The solution was extracted twice with ethyl acetate. The organic layer was washed with saturated brine, then dried over anhydrous sodium sulfate.

The insoluble matter was separated by filtration, the solvent was evaporated away under reduced pressure, and the resulting residue was purified by middle-pressure liquid chromatography (eluent, hexane/ethyl acetate=4:1) to obtain the entitled compound (410 mg, 103%, as containing a small amount of impurities), as a white solid.

HRMS (EI) m/z: 340.1571 (Calcd for $C_{20}H_{21}FN_2O_2$ 340.1587).

$^1$H-NMR (CDCl$_3$) δ: 1.34 (9H, s), 2.32 (3H, s), 4.04 (3H, s), 6.94 (1H, brs), 7.19-7.23 (2H, m), 7.38-7.47 (3H, m).

IR (ATR): 3259, 2225, 1658, 1514, 1473, 1415, 1350, 1088, 756, 708 cm$^{-1}$.

Reference Example 238

N-(5-Cyano-2-fluoro-4-hydroxy-6-methylbiphenyl-3-yl)-2,2-dimethylpropionamide (I-238)

N-(5-Cyano-2-fluoro-4-methoxy-6-methylbiphenyl-3-yl)-2,2-dimethylpropionamide (I-237) (200 mg, 0.59 mmol) was dissolved in dichloromethane (5 ml), and under nitrogen atmosphere at −78° C., 1 M borondichloromethane tribromide solution (1.76 ml, 1.76 mmol) was dropwise added. With stirring, the solution was heated up to 0° C., taking 3 hours. At the same temperature, water with ice was gradually dropwise added to it, followed by stirring for 5 minutes. Further, an aqueous saturated sodium hydrogencarbonate solution was added to the solution to make pH=7. The solution was extracted twice with dichloromethane. The organic layer was washed with saturated brine, then dried over anhydrous sodium sulfate. The insoluble matter was separated by filtration, the solvent was evaporated away, and the resulting residue was purified by middle-pressure liquid chromatography (eluent, hexane:ethyl acetate=4:1) to obtain the entitled compound (125 mg, 65%) as a white solid.

MS (ESI) m/z: 327 (M+1)$^+$.

HRMS (EI) m/z: 326.1432 (Calcd for $C_{19}H_{19}FN_2O_2$ 326.1431).

$^1$H-NMR (CDCl$_3$) δ: 1.36 (9H, s), 2.29 (3H, s), 7.17-7.21 (3H, m), 7.39-7.49 (3H, m), 7.73 (1H, br), 11.21 (1H, br).

IR (ATR): 3275, 2229, 1643, 1591, 1369, 1082, 706 cm$^{-1}$.

Reference Example 239

2-tert-Butyl-4-fluoro-6-methyl-5-phenyl-1,3-benzoxazole-7-carbonitrile (I-239)

N-(5-Cyano-2-fluoro-4-hydroxy-6-methylbiphenyl-3-yl)-2,2-dimethylpropionamide (I-238) (124 mg, 0.38 mol) was dissolved in toluene (5 ml), and at room temperature, para-toluenesulfonic acid monohydrate (20 mg, 0.11 mmol) was added. The reaction liquid was heated under reflux under nitrogen atmosphere for 4.5 hours. After cooling to room temperature, the solution was fractionated with ethyl acetate and an aqueous saturated sodium hydrogencarbonate solution. The aqueous layer was separated, this was extracted with ethyl acetate. The organic layer was washed with saturated brine, dried over anhydrous sodium sulfate. The insoluble matter was separated by filtration, the solvent was evaporated away, and the resulting residue was purified by middle-pressure liquid chromatography (eluent, hexane:ethyl acetate=9:1) to obtain the entitled compound (106 mg, 90%) as a white solid.

MS (ESI) m/z: 309 (M+1)$^+$.

HRMS (EI) m/z: 308.1326 (Calcd for $C_{19}H_{17}FN_2O$ 308.1325).

$^1$H-NMR (CDCl$_3$) δ: 1.54 (9H, s), 2.42 (3H, s), 7.20-7.26 (2H, m), 7.42-7.52 (3H, m).

IR (ATR): 2224, 1612, 1408, 1296, 1271, 1113, 960, 918, 777, 719 cm$^{-1}$.

Example 117

2-tert-Butyl-4-[(3S)-3-(dimethylamino)pyrrolidin-1-yl]-6-methyl-6-phenyl-1,3-benzoxazole-7-carbonitrile (#117)

2-tert-Butyl-4-fluoro-6-methyl-5-phenyl-1,3-benzoxazole-7-carbonitrile (I-239) (105 mg, 0.34 mmol) was dissolved in dimethyl sulfoxide (2 ml), and at room temperature, triethylamine (95 μl, 0.68 mmol) and (3S)-3-(dimethylamino)pyrrolidine (65 μl, 0.51 mmol) were added. The solution was stirred under nitrogen atmosphere at 90° C. for 6 hours. After cooling to room temperature, the reaction liquid was fractionated with ethyl acetate and an aqueous saturated sodium hydrogencarbonate solution. The aqueous layer was further extracted with ethyl acetate. The organic layers were combined, washed with saturated brine, then dried over anhydrous sodium sulfate. The insoluble matter was separated by filtration, then the solvent was evaporated away, and the resulting residue was purified by middle-pressure liquid chromatography (eluent, chloroform:methanol=98:2) to obtain the entitled compound (119 mg, 87%) as a pale yellow solid.

MS (ESI) m/z: 403 (M+1)$^+$.

HRMS (EI) m/z: 402.2399 (Calcd for $C_{25}H_{30}N_4O$ 402.2420).

$^1$H-NMR (CDCl$_3$) δ: 1.46 (9H, s), 1.48-1.62 (1H, m), 1.90-1.98 (1H, m), 2.12 (6H, s), 2.17 (3H, s), 2.42-2.51 (1H, m), 3.11 (1H, dd, J=9.0, 10.5 Hz), 3.45-3.53 (3H, m), 7.08-7.10 (1H, m), 7.23-7.26 (1H, m), 7.30-7.41 (3H, m).

IR (ATR): 2210, 1612, 1458, 1369, 1298, 1117, 704 cm$^{-1}$.

Anal. Calcd for $C_{25}H_{30}N_4O\cdot0.25H_2O$: C, 73.77; H, 7.55; N, 13.76. Found: C, 74.05; H, 7.42; N, 13.18.

Reference Example 240

5-Bromo-4-fluoro-2-nitrobenzonitrile (I-240)

3-Bromo-4-fluorobenzonitrile (25 g, 0.125 mol) was dissolved in concentrated sulfuric acid (200 ml), and at 0° C., fuming nitric acid was dropwise added at 0° C., taking 1 hour. After stirred for 30 minutes at the same temperature, this was heated up to room temperature, taking 1.5 hours. This was gradually poured into ice. The formed precipitate was collected by filtration with washing with water, and dried under reduced pressure. The collected yellow powder was fractionated with chloroform and aqueous 1 M sodium hydroxide solution. The organic layer was washed with saturated brine, then dried over anhydrous sodium sulfate. The solvent was evaporated away, and the resulting residue was well dried under reduced pressure to obtain the entitled compound (14.7 g, 48%) as a yellow powder.

¹H-NMR (CDCl₃) δ: 8.11 (1H, d, J=7.3 Hz), 8.16 (1H, d, J=6.4 Hz).

Reference Example 241

6-Fluoro-4-nitrobiphenyl-3-carbonitrile (I-241)

5-Bromo-4-fluoro-2-nitrobenzonitrile (I-240) (9.1 g, 37.14 mmol) was dissolved in tetrahydrofuran (270 ml), and at room temperature, phenylboronic acid (9.06 g, 74.28 mmol), tripotassium phosphate (15.77 g, 74.28 mmol) and tetrakis(triphenylphosphine)palladium (2.15 g, 1.86 mmol) were added. After stirred under nitrogen atmosphere at 75° C. for 48 hours, this was cooled to room temperature. The insoluble matter was separated by filtration, the filtrate was concentrated under reduced pressure. The residue was fractionated with chloroform and aqueous saturated ammonium chloride solution. The organic layer was washed with saturated brine, and dried over anhydrous sodium sulfate.

The insoluble matter was separated by filtration, the solvent was evaporated away, and the resulting residue was subjected to column chromatography with silica gel, and the fraction with chloroform:hexane=1:1 gave the entitled compound (7.75 g, 86%) as a brown powder.

¹H-NMR (CDCl₃) δ: 7.52-7.60 (5H, m), 8.02 (1H, d, J=7.1 Hz), 8.17 (1H, d, J=9.5 Hz).

Reference Example 242

6-[(3S)-3-(Dimethylamino)pyrrolidin-1-yl]-4-nitro-biphenyl-3-carbonitrile (I-242)

6-Fluoro-4-nitrobiphenyl-3-carbonitrile (I-241) (6.0 g, 24.77 mmol) was dissolved in dimethyl sulfoxide (60 ml), and at room temperature, triethylamine (6.9 ml, 49.54 mmol) and (3S)-3-(dimethylamino)pyrrolidine (3.77 ml, 29.73 mmol) were added. After stirring at the same temperature for 19 hours, the reaction liquid was fractionated with ethyl acetate and an aqueous saturated sodium hydrogencarbonate solution. The organic layer was washed with saturated brine, then dried over anhydrous sodium sulfate. The insoluble matter was separated by filtration, the solvent was evaporated away, and the resulting residue was subjected to column chromatography with silica gel, and the fraction with chloroform:methanol=95:5 gave the entitled compound (7.90 g, 95%) as an orange powder.

HRMS (EI) m/z: 322.1428 (Calcd for $C_{18}H_{18}N_4O_2$ 322.1428).

¹H-NMR (CDCl₃) δ: 1.43 (1H, br), 1.72-1.81 (1H, m), 1.99-2.08 (1H, m), 2.34 (3H, s), 2.81 (1H, dd, J=3.7, 9.8 Hz), 3.12-3.24 (3H, m), 3.26-3.32 (1H, m), 7.30-7.33 (2H, m), 7.36-7.44 (3H, m), 7.50 (1H, s), 7.57 (1H, s).

IR (ATR): 3330, 2220, 1608, 1520, 1419, 1336, 901, 827, 754, 702 cm⁻¹.

Reference Example 243

4-Amino-6-[(3S)-3-(dimethylamino)pyrrolidin-1-yl]biphenyl-3-carbonitrile (I-243)

6-[(3S)-3-(Dimethylamino)pyrrolidin-1-yl]-4-nitrobiphenyl-3-carbonitrile (I-242) (7.9 g, 23.5 mmol) was dissolved in concentrated hydrochloric acid (40 ml), and at room temperature, acetic acid (4.0 ml, 70.5 mmol) and methanol (10 ml) were added, followed by cooling at 0° C., and tin(II) chloride dihydrate (15.9 g, 70.5 mmol) was gradually added. After stirred at the same temperature for 20 minutes, this was further stirred at room temperature for 20 minutes. At room temperature, methanol (30 ml) was added to the suspension, followed by stirring at the same temperature for 24 hours. The reaction liquid was fractionated with ethyl acetate and aqueous 1 M sodium hydroxide solution. The organic layer was washed with saturated brine, then dried over anhydrous sodium sulfate. The insoluble matter was separated by filtration, the solvent was evaporated away, and the resulting residue was subjected to column chromatography with silica gel, and the fraction with chloroform:methanol=95:5 gave the entitled compound (6.475 g, 90%) as a pale brown gel.

MS (ESI) m/z: 307 (M+1)⁺.

HRMS (EI) m/z: 306.1841 (Calcd for $C_{19}H_{22}N_4$ 306.1845).

¹H-NMR (CDCl₃) δ: 1.60-1.70 (1H, m), 1.93-2.10 (1H, m), 2.12 (6H, s), 2.50-2.59 (1H, m), 2.82 (1H, t, J=9.0 Hz), 2.99-3.09 (3H, m), 4.35 (2H, br), 6.04 (1H, s), 7.11 (1H, s), 7.22-7.34 (5H, m).

IR (ATR): 3359, 2198, 1606, 1477, 1435, 1348, 1157 cm⁻¹.

Reference Example 244

N-[5-Cyano-2-((3S)-3-(dimethylamino)pyrrolidin-1-yl)biphenyl-4-yl]-2,2-dimethylpropionamide (I-244)

4-Amino-6-[(3S)-3-(dimethylamino)pyrrolidin-1-yl]biphenyl-3-carbonitrile (I-243) (300 mg, 0.98 mmol) was dissolved in pyridine (3 ml), and under nitrogen atmosphere at room temperature, pivaloyl chloride (181 μl, 1.47 mmol) was added. After stirring at room temperature for 3 days, the reaction liquid was fractionated with ethyl acetate and aqueous 1 M sodium hydroxide solution. The organic layer was washed with saturated brine, then dried over anhydrous sodium sulfate. The insoluble matter was separated by filtration, then the solvent was evaporated away and the resulting residue was purified by middle-pressure liquid chromatography (eluent, chloroform:methanol=98:2) to obtain the entitled compound (364 mg, 95%) as a pale yellow gel.

MS (ESI) m/z: 391 (M+1)⁺.

¹H-NMR (CDCl₃) δ: 1.37 (9H, s), 1.62-1.74 (1H, m), 1.96-2.04 (1H, m), 2.10 (6H, s), 2.48-2.58 (1H, m), 2.86 (1H, t, J=8.8 Hz), 3.02 (1H, dd, J=7.1, 10.0 Hz), 3.14-3.27 (2H, m), 7.25-7.37 (6H, m), 7.94 (1H, brs), 7.95 (1H, s).

Example 118

2-tert-Butyl-7-[(3S)-3-(dimethylamino)pyrrolidin-1-yl]-6-phenyl-1,3-benzothiazole-4-carbonitrile (#118)

N-[5-Cyano-2-((3S)-3-(dimethylamino)pyrrolidin-1-yl)biphenyl-4-yl]-2,2-dimethylpropionamide (I-244) (364 mg, 0.93 mmol) was dissolved in toluene (10 ml), and a Lawesson's recent (377 mg, 0.93 mmol) was added at room temperature. After stirred under nitrogen atmosphere at 80° C. for 4 hours, this was cooled to room temperature. The reaction liquid was fractionated with ethyl acetate and aqueous 1 M sodium hydroxide solution. The organic layer was washed with saturated brine, and dried over anhydrous sodium sulfate. The insoluble matter was separated by filtration, the solvent was evaporated away, and the resulting residue was roughly purified by middle-pressure liquid chromatography (eluent, chloroform:methanol=98:2) to remove the starting material. The roughly-purified residue was dissolved in water (3 ml) and ethanol (0.3 ml), and at room temperature, sodium hydroxide (44 mg, 1.1 mmol) was added. After stirring at the same temperature for 5 minutes, a solution of potassium ferricyanide (162 mg, 0.49 mmol) dissolved in water (1 ml)

was added to it. The solution was stirred at room temperature for 15 hours, and then fractionated with ethyl acetate and aqueous 1 M sodium hydroxide solution. The organic layer was washed with saturated brine, then dried over anhydrous sodium sulfate. The insoluble matter was separated by filtration, the solvent was evaporated away and the resulting residue was purified by preparative TLC (eluent, chloroform:methanol=9:1) to obtain the entitled compound (2 mg, 4%) as a yellow gel. This was again purified by preparative TLC (eluent, chloroform:methanol=9:1) to obtain the entitled compound (1.10 mg).

MS (ESI) m/z: 405 (M+1)$^+$.

$^1$H-NMR (CDCl$_3$) δ: 1.54 (9H, s), 1.65-1.75 (1H, m), 1.95-2.05 (1H, m), 2.19 (6H, s), 2.60-2.70 (1H, m), 3.21 (1H, t, J=9.0 Hz), 3.29-3.1 (3H, m), 7.27-7.42 (5H, m), 7.53 (1H, s).

Reference Example 245

4-Amino-6-[(3S)-3-(dimethylamino)pyrrolidin-1-yl]-5-iodobiphenyl-3-carbonitrile (I-245)

4-Amino-6-[(3S)-3-(dimethylamino)pyrrolidin-1-yl]biphenyl-3-carbonitrile (I-243) (75 mg, 0.25 mmol) was dissolved in acetic acid (1 ml), and at room temperature, N-iodosuccinimide (66 mg, 0.29 mmol) was added. After stirring under nitrogen atmosphere at the same temperature for 6 hours, the reaction liquid was fractionated with chloroform and aqueous 1 M sodium hydroxide solution. The organic layer was washed with saturated brine, then dried over anhydrous sodium sulfate. The insoluble matter was separated by filtration, the solvent was evaporated away, and the resulting residue was purified by preparative TLC (eluent, chloroform:methanol=9:1) to obtain the entitled compound (67 mg, 63%) as a brown gel.

MS (ESI) m/z: 433 (M+1)$^+$.

$^1$H-NMR (CDCl$_3$) δ: 1.58-1.70 (1H, m), 1.91-2.01 (1H, m), 2.15 (6H, s), 2.55-2.65 (1H, m), 2.93 (1H, t, J=8.3 Hz), 3.10 (2H, dd, J=4.9, 8.8 Hz), 3.25 (1H, t, J=8.3 Hz), 4.99 (2H, brs), 7.19-7.42 (6H, m).

Reference Example 246

4-Amino-6-[(3S)-3-(dimethylamino)pyrrolidin-1-yl]-5-(3,3-dimethylbutyn-1-yl)biphenyl-3-carbonitrile (I-246)

4-Amino-6-[(3S)-3-(dimethylamino)pyrrolidin-4-yl]-5-iodobiphenyl-3-carbonitrile (I-245) (65 mg, 0.15 mmol), bis(triphenylphosphine)palladium(II) dichloride (11 mg, 0.015 mmol), copper(I) iodide (4 mg, 0.02 mmol) and triethylamine (1 ml) were dissolved in 1,4-dioxane (1 ml), and at room temperature, 3,3-dimethyl-1-butyne (184 µl, 1.50 mmol) was added. After stirring at the same temperature under nitrogen atmosphere for 2 hours, 3,3-dimethyl-1-butyne (184 µl, 1.50 mmol) was again added, followed by further stirring for 14 hours. The reaction liquid was fractionated with chloroform and an aqueous saturated sodium hydrogencarbonate solution.

The organic layer was washed with saturated brine, then dried over anhydrous sodium sulfate. The solvent was evaporated away and the resulting residue was purified by preparative TLC (eluent, chloroform:methanol=9:1) to obtain the entitled compound (55 mg, 95%) as a pale brown gel.

MS (ESI) m/z: 387 (M+1)$^+$.

$^1$H-NMR (CDCl$_3$) δ: 1.07 (9H, s), 1.23-1.34 (1H, m), 1.56-1.64 (1H, m), 1.84 (6H, s), 2.27 (1H, quint, J=8.1 Hz), 2.78 (1H, t, J=9.0 Hz), 2.92-3.09 (2H, m), 3.17 (1H, t, J=9.0 Hz), 4.62 (2H, brs), 6.77 (1H, s), 6.89-7.08 (5H, m).

Example 119

2-tert-Butyl-4-[(3S)-3-(dimethylamino)pyrrolidin-1-yl]-5-phenyl-1H-indole-7-carbonitrile (#119)

4-Amino-6-[(3S)-3-(dimethylamino)pyrrolidin-1-yl]-5-(3,3-dimethylbutyn-1-yl)biphenyl-3-carbonitrile (I-246) (54 mg, 0.14 mmol) was dissolved in acetonitrile (3 ml), and at room temperature, bis(acetonitrile)palladium(II) dichloride (7.3 mg, 0.28 mmol) was added, followed by heating under reflux for 3 hours. After cooling to room temperature, the reaction liquid was fractionated with chloroform and an aqueous saturated sodium hydrogencarbonate solution. The organic layer was washed with saturated brine, then dried over anhydrous sodium sulfate. The insoluble matter was separated by filtration, the solvent was evaporated away, and the resulting residue was purified by preparative TLC (eluent, chloroform:methanol=95:5) to obtain a crude product of the entitled compound (32 mg, 60%) as a pale brown gel. This was recrystallized from hexane/diethyl ether to obtain the entitled compound (15 mg) as a pale brown powder.

MS (ESI) m/z: 387 (M+1)$^+$.

HRMS (EI) m/z: 386.2495 (Calcd for C$_{25}$H$_{30}$N$_4$ 386.2471).

$^1$H-NMR (CDCl$_3$) δ: 1.41 (9H, s), 1.63-1.73 (1H, m), 1.96-2.03 (1H, m), 2.18 (6H, s), 2.56-2.65 (1H, m), 3.24 (1H, t, J=9.0 Hz), 3.38-3.49 (3H, m), 6.56 (1H, d, J=2.4 Hz), 7.23-7.37 (6H, m), 8.84 (1H, brs).

IR (ATR): 3292, 2964, 2204, 1597, 1460, 1439, 1358, 754, 706 cm$^{-1}$.

Reference Example 247

Methyl 4-aminosalicylate (I-247)

Produced according to the method described in a patent (U.S. Pat. No. 6,482,982).

Concentrated sulfuric acid (80 ml, 1.5 mol) was carefully added to a methanol (40 ml) suspension of 4-aminosalicylic add (92 g, 0.6 mol). After stirring with heating under heat for 2 hours, then cooling with ice, concentrated ammonia water was added for pH control to 9, and the precipitated matter was collected by filtration, washed with water, dried to obtain the entitled compound (52 g, 52%) as a red solid.

MS (FAB) m/z: 168 (M+1)$^+$.

$^1$H-NMR (CDCl$_3$) δ: 3.87 (3H, s), 4.10 (2H, brs), 6.13-6.16 (2H, m), 7.59-7.63 (1H, m), 10.9 (1H, s).

Reference Example 248

Methyl 4-acetylaminosalicylate (I-248)

Produced according to the method described in a patent (U.S. Pat. No. 6,482,982, JP-A 63-313732).

An acetic anhydride (310 ml) solution of methyl 4-aminosalicylate (I-247) (52 g, 310 mmol) was stirred at 75° C. for 10 minutes, then cooled, and water (520 ml) was added and concentrated under reduced pressure. The residue was recrystallized from water/methanol to obtain the entitled compound (61.5 g, 95%) as a brown crystal.

MS (FAB) m/z: 210 (M+1)$^+$.

$^1$H-NMR (CDCl$_3$) δ: 2.20 (3H, s), 3.92 (3H, s), 7.06-7.10 (1H, m), 7.17 (1H, m), 7.61 (1H, brs), 7.76 (1H, d, J=8.7 Hz), 10.9 (1H, s).

Reference Example 249

Methyl 4-acetylamino-5-bromosalicylate (I-249)

N-Bromosuccinimide (0.94 g, 5.3 mmol) was added to an N,N-dimethylformamide (8 ml) solution of methyl 4-acetylaminosalicylate (I-248) (1.1 g, 5.0 mmol), followed by stirring with heating under reflux at 70 to 75° C. for 2 hours and a half. After cooling to room temperature, ethyl acetate was added, followed by washing twice with saturated brine and drying over anhydrous magnesium sulfate. After filtration and concentration under reduced pressure, the resulting residue was subjected to column chromatography, and the eluate with chloroform/methanol (100:1) gave the entitled compound (0.64 g, 45%) as a pale red solid.

MS (FAB) m/z: 288 (M+1 for $^{79}$Br)$^+$, 290 (M+1 for $^{81}$Br)$^+$.
$^1$H-NMR (CDCl$_3$) δ: 2.26 (3H, s), 3.94 (3H, s), 7.73 (1H, brs), 8.00 (1H, s), 8.16 (1H, s), 10.73 (1H, s).

Reference Example 250

Methyl 4-acetylamino-5-bromo-3-iodosalicylate (I-250)

Methyl 4-acetylamino-5-bromosalicylate (I-249) (576 mg, 2.0 mmol) was dissolved in a mixed liquid of methylene chloride (20 ml) and methanol (10 ml), then benzyltrimethylammonium dichloroiodate (835 mg, 2.4 mmol) and sodium bicarbonate (1.1 g, 13.0 mmol) were added, followed by stirring at room temperature for 30 hours. The reaction liquid was filtered, the filtrate was concentrated under reduced pressure, then saturated ammonium chloride water was added to the residue, followed by extraction twice with chloroform, then the organic layer was washed with saturated sodium thiosulfate water, and dried over anhydrous magnesium sulfate. After filtration and concentration under reduced pressure, the resulting residue was subjected to column chromatography, and the eluate with chloroform/methanol (50:1) gave the entitled compound (889 mg, quant.) as a pale yellow solid.

MS (FAB) m/z: 414 (M+1 for $^{79}$Br)$^+$, 416 (M+1 for $^{81}$Br)$^+$.
$^1$H-NMR (CDCl$_3$) δ: 2.26 (3H, s), 4.00 (3H, s), 7.13 (1H, brs), 8.12 (1H, s), 11.73 (1H, s).

Reference Example 251

Methyl 4-acetylamino-5-bromo-3-(3,3-dimethyl-1-butynyl)salicylate (I-251)

Under nitrogen atmosphere, methyl 4-acetylamino-5-bromo-3-iodosalicylate (I-250) (414 mg, 1.0 mmol), bis(triphenylphosphine)palladium(II) chloride (49 mg, 0.07 mmol), copper(I) iodide (19 mg, 0.1 mmol) and 3,3-dimethyl-1-butyne (0.13 ml, 1.1 mmol) were added to a mixed liquid of triethylamine (4 ml) and dioxane (6 ml), followed by stirring at 30° C. for 2 hours. The reaction liquid was concentrated under reduced pressure, then saturated ammonium chloride water was added to the residue, followed by extraction twice with chloroform, the organic layer was washed with saturated brine, then dried over anhydrous magnesium sulfate. After filtration and concentration under reduced pressure, the resulting residue was subjected to column, chromatography, and the eluate with n-hexane/ethyl acetate (2:1) gave the entitled compound (243 mg, 66.5) as a white solid.

MS (FAB) m/z: 368 (M+1 for $^{79}$Br)$^+$, 370 (M+1 for $^{81}$Br)$^+$.
$^1$H-NMR (CDCl$_3$) δ: 1.35 (9H, s), 2.18 (3H, s), 3.96 (3H, s), 7.08 (1H, brs), 8.00 (1H, s), 11.23 (1H, s).

Reference Example 252

Methyl 4-acetylamino-5-bromo-2-tert-butyl-1-benzofuran-7-carboxylate (I-252)

Methyl 4-acetylamino-5-bromo-3-(3,3-dimethyl-1-butynyl)salicylate (I-250) (202 mg, 0.55 mmol) was dissolved in a mixed liquid of triethylamine (4 ml) and toluene (10 ml), and stirred with heating under reflux for 2 hours. After cooling to room temperature, the reaction liquid was concentrated under reduced pressure, the resulting residue was subjected to column chromatography, and the eluate with n-hexane/ethyl acetate (2:1) gave the entitled compound (165 mg, 82%) as a white solid.

MS (FAB) m/z: 368 (M+1 for $^{79}$Br)$^+$, 370 (M+1 for $^{81}$Br)$^+$.
$^1$H-NMR (CDCl$_3$) δ: 1.40 (9H, s), 2.30 (3H, s), 3.98 (3H, s), 6.38 (1H, s), 7.45 (1H, brs), 8.05 (1H, s).

Reference Example 253

Methyl 4-acetylamino-2-tert-butyl-5-phenyl-4-benzofuran-7-carboxylate (I-253)

Under nitrogen atmosphere, methyl 4-acetylamino-5-bromo-2-tert-butyl-1-benzofuran-7-carboxylate (I-252) (147 mg, 0.4 mmol), phenylboronic acid (61 mg, 0.5 mmol), aqueous 2 M cesium carbonate solution (0.5 ml, 1.0 mmol) and tetrakistriphenylphosphine palladium(0) (23 mg, 0.02 mmol) were added, followed by stirring at 100° C. for 6 hours. After cooling to room temperature, ethyl acetate was added to the reaction liquid, followed by washing with saturated sodium bicarbonate water and saturated brine and drying over anhydrous magnesium sulfate. After filtration and concentration under reduced pressure, the resulting residue was subjected to column chromatography, and the eluate with n-hexane/ethyl acetate (2:1) gave the entitled compound (117 mg, 80%) as a white solid.

MS (FAB) m/z: 366 (M+1)$^+$.
$^1$H-NMR (CDCl$_3$) δ: 1.43 (9H, s), 2.12 (3H, s), 3.98 (3H, s), 6.40 (1H, s), 7.03 (1H, brs), 7.35-7.49 (5H, m), 7.83 (1H, s).

Reference Example 254

Methyl 4-amino-2-tert-butyl-5-phenyl-1-benzofuran-7-carboxylate (I-254)

A methanol (60 ml) solution of methyl 4-acetylamino-2-tert-butyl-5-phenyl-1-benzofuran-7-carboxylate (I-253) (2.28 g, 6.24 mmol) and 4 N hydrogen carbonate/1,4-dioxane solution (15.6 ml, 62.4 mmol) were stirred overnight at room temperature, then heated up to 50° C. and stirred for 5 hours. The reaction liquid was put into saturated sodium bicarbonate water (300 ml), followed by extraction with ethyl acetate (200 ml). The organic layer was dried over anhydrous sodium sulfate, concentrated under reduced pressure, and the residue was purified by silica gel column chromatography (n-hexane: ethyl acetate=3:1→1:1) to obtain the entitled compound (972 mg, 48%) as a yellow white solid. Starting material recovery, 1.10 g (48%).

MS (FAB) m/z: 324 (M+1)⁺.

¹H-NMR (CDCl₃) δ: 1.43 (9H, s), 3.93 (3H, s), 4.35 (2H, brs), 6.31 (1H, s), 7.31-7.50 (5H, m), 7.74 (1H, s).

Reference Example 255

Methyl 4-bromo-2-tert-butyl-5-phenyl-1-benzofuran-7-carboxylate (I-255)

An acetonitrile (50 ml) mixed liquid of tert-butyl nitrite (1.38 ml, 11.6 mmol) and anhydrous copper(II) bromide (2.07 g, 9.28 mmol) was stirred at 75° C. for 5 minutes, then an acetonitrile (50 ml) suspension of methyl 4-amino-2-tert-butyl-5-phenyl-1-benzofuran-7-carboxylate (I-254) (2.50 g, 7.73 mmol) was put into it, and stirred at the same temperature for 20 minutes. After cooling, the reaction liquid was evaporated under reduced pressure, then aqueous saturated ammonium chloride solution (200 ml) and sodium thiosulfate (5 g) were added, followed by extraction with chloroform (300 ml×2). The organic layer was washed with saturated brine (300 ml), then dried over anhydrous magnesium sulfate, concentrated under reduced pressure, and the residue was purified by silica gel column chromatography (n-hexane:ethyl acetate=8:1) to obtain the entitled compound (2.95 g, 99%) as a yellow oily substance.

MS (FAB) m/z: 387 (M+1 for ⁷⁹Br)⁺, 389 (M+1 for ⁸¹Br)⁺.

¹H-NMR (CDCl₃) δ: 1.45 (9H, s), 3.99 (3H, s), 6.52 (1H, s), 7.35-7.47 (5H, m), 7.84 (1H, s).

Reference Example 256

4-Bromo-2-tert-butyl-5-phenyl-1-benzofuran-7-carboxylic acid (I-256)

A methanol (12 ml) solution of potassium hydroxide (1.26 g, 22.5 mol) was put into a tetrahydrofuran (50 ml) solution of methyl 4-bromo-2-tert-butyl-5-phenyl-1-benzofuran-7-carboxylate (I-255) (2.90 g, 7.49 mmol), followed by stirring at room temperature for 3.5 hours. The reaction liquid was concentrated under reduced pressure, then 1 N hydrochloric acid (100 ml) and water (100 ml) were added, the product was extracted with ethyl acetate (200 ml×2). The organic layer was washed with saturated brine (50 ml×2), then dried over anhydrous magnesium sulfate, concentrated under reduced pressure to obtain the entitled compound (2.64 g, 95%) as a yellow white solid.

MS (FAB) m/z: 373 (M+1 for ⁷⁹Br)⁺, 375 (M+1 for ⁸¹Br)⁺.

¹H-NMR (CDCl₃) δ: 1.46 (9H, s), 6.55 (1H, s), 7.37-7.50 (5H, m), 7.94 (1H, s).

Reference Example 257

4-Bromo-2-tert-butyl-5-phenyl-1-benzofuran-7-carboxamide (I-257)

1-Ethyl-3-[3-(dimethylamino)propyl]carbodiimide hydrochloride (1.61 g, 8.42 mmol) was added to an N,N-dimethylformamide (80 ml) solution of 4-bromo-2-tert-butyl-5-phenyl-1-benzofuran-7-carboxylic acid (I-256) (2.62 g, 7.02 mmol) and hydroxybenzotriazole (1.14 g, 8.42 mmol), followed by stirring at room temperature for 1 hour. The reaction liquid was cooled at 0° C., then aqueous 28% ammonia (1.42 ml, 21.1 mmol) was put into it, followed by further stirring at room temperature for 1 hour. The reaction liquid was concentrated under reduced pressure, then saturated sodium bicarbonate water (200 ml) was added, the product was extracted with ethyl acetate (200 ml×2). The organic layer was washed with saturated brine (50 ml), then dried over anhydrous magnesium sulfate, concentrated under reduced pressure, and the residue was purified by silica gel column chromatography (n-hexane/ethyl acetate=3:2) to obtain the entitled compound (2.59 g, 99%) as a yellow white solid.

MS (FAB) m/z; 372 (M+1 for ⁷⁹Br)⁺, 374 (M+1 for ⁸¹Br)⁺.

¹H-NMR (CDCl₃) δ: 1.45 (9H, s), 6.32 (1H, brs), 6.59 (1H, s), 7.26 (1H, brs, overlapping with chloroform), 7.35-7.47 (5H, m), 8.02 (1H, s).

Reference Example 258

4-Bromo-2-tert-butyl-7-cyano-5-phenyl-1-benzofuran (I-258)

Triethylamine (1.92 ml, 13.8 mmol) was added to a dichloromethane (100 ml) solution of 4-bromo-2-tert-butyl-5-phenyl-1-benzofuran-7-carboxamide (I-257) (2.56 g, 6.88 mmol), and cooled at −12° C.

Trifluoromethanesulfonic acid anhydride (1.28 ml, 7.56 mmol) was dropwise added to it, followed by stirring at room temperature for 1 hour. The reaction liquid was cooled at 0° C., then triethylamine (959 μl, 6.88 mmol) and trifluoromethanesulfonic acid anhydride (581 μl, 3.44 mmol) were further added, followed by further stirring at room temperature for 2 hours. Water (100 ml) was added to the reaction liquid, the product was extracted with chloroform (100 ml×2), the organic layer was washed with saturated brine (50 ml), dried over anhydrous magnesium sulfate, concentrated under reduced pressure. The residue was purified twice by silica gel column chromatography (n-hexane:ethyl acetate=10:1), (n-hexane:ethyl acetate=12:1) to obtain the entitled compound (2.11 g, 87%) as a yellow solid.

MS (FAB) m/z: 354 (M+1 for ⁷⁹Br)⁺, 356 (M+1 for ⁸¹Br)⁺.

¹H-NMR (CDCl₃) δ: 1.44 (9H, s), 6.54 (1H, s), 7.35-7.50 (6H, m).

Example 120

2-tert-Butyl-4-[(3S)-3-(dimethylamino)pyrrolidin-1-yl]-5-phenyl-1-benzofuran-7-carbonitrile (#120)

(R)-(+)-2,2'-Bis(diphenylphosphino)-1,1'-binaphthyl (65.9 mg, 106 μmol) was dissolved under heat in toluene (1.5 ml), then cooled to room temperature, and palladium(II) acetate (15.8 mg, 70.6 μmol) was added, followed by stirring for 1 minute. 4-Bromo-2-tert-butyl-7-cyano-5-phenyl-1-benzofuran (I-258) (500 mg, 1.41 mmol), (3S)-3-(dimethylamino)pyrrolidine (215 μl, 1.69 mmol), sodium tert-butoxide (190 mg, 1.98 mmol) and toluene (1.5 ml) were successively put into it, followed by stirring at 80° C. for 14 hours. Water (30 ml) was added to the reaction liquid, the product was extracted with chloroform (50 ml×3). The organic layer was washed with saturated brine (50 ml), dried over anhydrous magnesium sulfate, concentrated under reduced pressure. The residue was purified twice by silica gel column chromatography (chloroform:methanol=200:1) to obtain the entitled compound (180 mg, 33%) as a yellow solid.

mp: 46-48° C. MS (FAB) m/z: 388 (M+1)⁺.

¹H-NMR (CDCl₃) δ: 1.39 (9H, s), 1.60-1.74 (1H, m), 1.92-2.04 (1H, m), 2.15 (6H, s), 2.50-2.61 (1H, m), 3.13 (1H, t, J=9.0 Hz), 3.31-3.42 (3H, m), 6.65 (1H, s), 7.24-7.38 (6H, m).

Reference Example 259

N-(4-Fluoro-2-methylphenyl)acetamide (I-259)

Acetic anhydride (17.7 ml, 0.19 mol) was dropwise added to 4-fluoro-2-methylaniline (234 g, 0.19 mol). The solidified reaction mixture was dissolved in chloroform, washed with an aqueous saturated sodium hydrogencarbonate solution and saturated brine, then dried over anhydrous sodium sulfate. The solvent was evaporated away under reduced pressure, and the residue was dried with a vacuum pump to obtain the entitled compound (31.7 g, 99%) as a pale red solid.

$^1$H-NMR (CDCl$_3$) δ: 2.18 (3H, s), 2.23 (3H, s), 6.85-7.02 (3H, m), 7.57 (1H, m).

Reference Example 260

N-(4-Fluoro-2-methyl-6-nitrophenyl)acetamide (I-260)

With cooling with ice, fuming nitric acid (25 ml) was dropwise added to an acetic acid (100 ml) solution of N-(4-fluoro-2-methylphenyl)acetamide (I-259) (10.0 g, 59.8 mmol), taking 50 minutes. After the addition, then restoration to room temperature and stirring for 23 hours, the reaction liquid was poured into ice. The precipitated solid was collected by filtration, washed with water, then dried to obtain the entitled compound (11.1 g, 87%) as a pale brown solid.

$^1$H-NMR (CDCl$_3$) δ: 2.23 (3H, s), 2.34 (3H, s), 7.27 (1H, m), 7.58 (1H, m), 8.08 (1H, broad s).

Reference Example 261

4-Fluoro-2-methyl-6-nitroamine (I-261)

Concentrated hydrochloric acid (120 ml) was added to an ethanol (120 ml) suspension of N-(4-fluoro-2-methyl-6-nitrophenyl)acetamide (I-260) (28.9 g, 136 mmol), followed by healing under reflux for 8 hours. After cooling the reaction liquid was poured into water with ice, then neutralized with aqueous sodium hydroxide solution. The precipitated solid was collected by filtration, washed with water, and dried to obtain the entitled compound (21.0 g, 91%) as an orange red solid.

$^1$H-NMR (CDCl$_3$) δ: 2.27 (3H, s), 6.05 (2H, broad s), 7.12 (1H, dd, J=3.1, 8.1 Hz), 7.75 (1H, dd, J=3.1, 9.2 Hz).

Reference Example 262

5-Fluoro-2-iodo-1-methyl-3-nitrobenzene (I-262)

With cooling with ice, aqueous sodium nitrite solution (7.3 M, 25 ml) was dropwise added to a concentrated hydrochloric acid (100 ml) suspension of 4-fluoro-2-methyl-6-nitroaniline (I-261) (20.6 g, 121 mmol), taking 20 minutes. After the addition and stirring at the same temperature (cooling with ice) for 30 minutes, aqueous potassium iodide solution (3.2 M, 75 ml) was dropwise added, taking 20 minutes. After the addition, this was gradually restored to room temperature and stirred for 18 hours. Aqueous 10% sodium thiosulfate solution (400 ml) was added to the reaction mixture liquid, then stirred, and the reaction mixture liquid was poured into water with ice. The precipitated solid was collected by filtration, washed with water, and dried to obtain a crude product of the entitled compound (34.0 g) as a dark brown solid.

$^1$H-NMR (CDCl$_3$) δ: 2.59 (3H, s), 7.21-7.26 (2H, m).

Reference Example 263

4-Fluoro-2-methyl-6-nitrobenzonitrile (I-263)

Copper cyanide (11.9 g, 133 mmol) was added to an N,N-dimethylformamide (240 ml) solution of 5-fluoro-2-iodo-1-methyl-3-nitrobenzene (I-262) (34.0 g, crude product), followed by heating at 130° C. for 3.5 hours. After cooling, the insoluble matter was removed by filtration under suction, water was added to the filtrate, and the precipitated insoluble matter was removed by filtration through Celite under suction. The filtrate was extracted with ethyl acetate, the organic layer was washed with saturated brine, then dried over anhydrous sodium sulfate. The solvent was evaporated away under reduced pressure, then the residue was subjected to column chromatography, and eluted with a mixed solvent of n-hexane/ethyl acetate (3:1, v/v) to obtain the entitled compound (17.6 g, 81% from I-235) as a red brown solid.

MS (EI) m/z: 180 (M$^+$).

$^1$H-NMR (CDCl$_3$) δ: 2.71 (3H, s), 7.42 (1H, dd, J=2.6, 7.9 Hz), 7.86 (1H, dd, J=2.6, 7.8 Hz).

IR (ATR): 3100, 2227, 1629, 1579, 1533, 1473, 1446 cm$^{-1}$.

Reference Example 264

2-Amino-4-fluoro-6-methylbenzonitrile (I-264)

Acetic acid (16.0 ml, 28 mmol) was added to a concentrated hydrochloric acid (90 ml) solution of tin chloride dihydrate (63.1 g, 280 mmol), and 4-fluoro-2-methyl-6-nitrobenzonitrile (I-263) (16.8 g, 93.3 mmol) was added, then methanol (8 ml) was added. Since the reaction liquid greatly generated heat, it was cooled with ice. After stirring for 1 hour, the reaction mixture liquid was poured into aqueous sodium hydroxide solution (4.6 M, 500 ml) with ice therein. The precipitated solid was collected by filtration, washed with water, then dried to obtain the entitled compound (14.7 g, 99%) as a gray solid.

MS (EI) m/z: 150 (M$^+$).

$^1$H-NMR (CDCl$_3$) δ: 2.43 (3H, s), 4.49 (2H, broad s), 6.26 (1H, dd, J=0.9, 10.1 Hz), 6.33 (1H, dd, J=0.9, 9.5 Hz).

IR (ATR): 3407, 3338, 3230, 2215, 1644, 1600, 1589, 1459 cm$^{-1}$.

Reference Example 265

6-Amino-3-bromo-4-fluoro-2-methylbenzonitrile (I-265)

N-Bromosuccinimide (16.6 g, 93.3 mmol) was gradually added to an N,N-dimethylformamide (250 ml) solution of 2-amino-4-fluoro-6-methylbenzonitrile (I-264) (14.0 g, 93.3 mmol). After stirring for 6 hours, the reaction liquid was poured into water with ice (750 ml), the precipitated solid was collected by filtration. The solid was washed with water, then dried to obtain the entitled compound (20.2 g, 95%) as a gray solid.

MS (EI) m/z: 228, 230 (M$^+$).

IR (ATR): 3388, 3322, 3220, 2217, 1648, 1592, 1573, 1465, 140 cm$^{-1}$.

IR (diffuse reflectance spectroscopy): 2969, 2869, 2774, 2218, 1602, 1466 cm$^{-1}$.

Anal. Calcd for C$_{25}$H$_{29}$N$_3$O.H$_2$O: C, 74.04; H, 7.70; N, 10.36. Found: C, 73.82; H, 7.17; N, 10.12.

Reference Example 266

2-Amino-5-bromo-4-fluoro-6-methyl-3-nitrobenzonitrile (I-266)

With cooling with ice, potassium nitrate (2.43 g, 21.8 mmol) was gradually added to a concentrated sulfuric acid (20 ml) solution of 6-amino-3-bromo-4-fluoro-2-methylbenzonitrile (I-265) (5.00 g, 21.8 mmol). After stirring for 10 minutes, the reaction liquid was poured into ice and stirred.

After extracted with ethyl acetate, this was washed with saturated brine, and dried over anhydrous sodium sulfate. The solvent was evaporated away under reduced pressure, the residue was subjected to column chromatography, and eluted with a mixed solvent of n-hexane/ethyl acetate (4:1, v/v) to obtain the entitled compound (3.00 g, 50%) as a yellow solid.

MS (EI) m/z: 273, 275 (M$^+$).
$^1$H-NMR (CDCl$_3$) δ: 2.66 (2H, s), 6.53 (2H, broad s).
IR (ATR): 3455, 3324, 2227, 1625, 1589, 1560, 1508 cm$^{-1}$.

Reference Example 267

2-Amino-5-bromo-4-[(3S)-3-(dimethylamino)pyrrolidin-1-yl]-6-methyl-3-nitrobenzonitrile (I-267)

(3S)-3-(Dimethylamino)pyrrolidine (140 μl, 1.10 mmol) was added to a dimethyl sulfoxide (2 ml) solution of 2-amino-5-bromo-4-fluoro-6-methyl-3-nitrobenzonitrile (I-266) (274 mg, 1.00 mmol) and triethylamine (209 μl, 1.50 mmol), followed by stirring at room temperature for 30 minutes. The reaction liquid was poured into water, and the precipitated solid was collected by filtration, washed with water, and dried to obtain the entitled compound (359 mg, 97%) as a yellow solid.

MS (EI) m/z: 366, 368 (M$^+$).
$^1$H-NMR (CDCl$_3$) δ: 1.90 (1H, m), 2.15 (1H, m), 2.28 (6H, s), 2.61 (3H, s), 2.92 (1H, m), 3.29-3.45 (4H, m), 5.56 (2H, broad s).
IR (ATR): 3424, 3301, 2977, 2873, 2834, 2792, 2215, 1650, 1575, 1519, 1452 cm$^{-1}$.

Reference Example 268

4-Amino-6-[(3S)-3-(dimethylamino)pyrrolidin-1-yl]-2-methyl-5-nitrobiphenyl-3-carbonitrile (I-268)

Potassium phosphate (115 mg, 0.54 mmol) and Pd(PPh$_3$)$_4$ (16 mg, 5 mol %) were added to a dioxane (3 ml) solution of 2-amino-5-bromo-4-[(3S)-3-(dimethylamino)pyrrolidin-1-yl]-6-methyl-3-nitrobenzonitrile (I-267) (100 mg, 0.27 mmol) and phenylboronic acid (40 mg, 0.33 mmol), followed by purging with nitrogen and heating under reflux for 18 hours. After cooling, water was added, followed by extraction with ethyl acetate. The organic layer was washed with saturated brine, then dried over anhydrous sodium sulfate. The solvent was evaporated away under reduced pressure, and the residue was subjected to column chromatography, and eluted with a mixed solvent of chloroform/methanol (2:1, v/v) to obtain the entitled compound (89 mg, 90%) as a dark red solid.

MS (FAB) m/z: 366 (M+1)$^+$.
$^1$H-NMR (CDCl$_3$) δ: 1.54 (1H, m), 1.83 (1H, m), 2.06 (6H, s), 2.12 (3H, s), 2.50 (1H, m), 2.65 (1H, m), 2.90-2.99 (3H, m), 5.73 (2H, broad s), 7.12-7.16 (2H, m), 7.34-7.50 (3H).
IR (ATR): 3326, 3210, 2827, 2776, 2208, 1623, 1571 cm$^{-1}$.

Reference Example 269

4,5-Diamino-6-[(3S)-3-(dimethylamino)pyrrolidin-1-yl]-2-methylbiphenyl-3-carbonitrile (I-269)

An aqueous solution (14 ml) of iron chloride hexahydrate (0.83 g, 3.06 mmol) and zinc (5.01 g, 76.6 mmol) were added to an N,N-dimethylformamide (35 ml) solution of 4-amino-6-[(3S)-3-(dimethylamino)pyrrolidin-1-yl]-2-methyl-5-nitrobiphenyl-3-carbonitrile (I-268) (1.40 g, 3.83 mmol), followed by stirring at room temperature for 1 hour. The insoluble matter was removed by filtration under suction, then the filtrate was diluted with ethyl acetate, washed with aqueous saturated sodium carbonate solution and saturated brine in that order, and dried over anhydrous sodium sulfate. The solvent was evaporated away under reduced pressure, followed by drying with a vacuum pump to obtain the entitled compound (1.25 g, 97%) as a dark brown solid.

MS (FAB) m/z: 336 (M+1)$^+$.
$^1$H-NMR (CDCl$_3$) δ: 1.64 (1H, m), 1.80 (1H, m), 2.06 (6H, s), 2.16 (3H, s), 2.35 (1H, m), 2.76 (1H, m), 2.890-2.96 (3H, m), 4.09 (2H, broads), 7.10-7.14 (2H, m), 7.34-7.49 (3H).
IR (ATR): 3357, 3284, 2944, 2821, 2775, 2200, 1666, 1583, 1459, 1436 cm$^{-1}$.

Reference Example 270

N-[4-Amino-5-cyano-2-[(3S)-3-(dimethylamino)pyrrolidin-1-yl]-6-methylbiphenyl-3-yl]-2,2-dimethylpropionamide (I-270)

With cooling with ice, pivaloyl chloride (0.46 ml, 3.73 mmol) was dropwise added to a chloroform (40 ml) solution of 4,5-diamino-6-[(3S)-3-(dimethylamino)pyrrolidin-1-yl]-2-methylbiphenyl-3-carbonitrile (I-269) (1.25 g, 3.73 mmol). After stirring for 3 hours, water was added to the reaction liquid to stop the reaction, followed by extraction with chloroform. The organic layer was washed with an aqueous saturated sodium hydrogencarbonate solution and saturated brine, then dried over anhydrous sodium sulfate. The solvent was evaporated away under reduced pressure, then the residue was subjected to column chromatography, and eluted with a mixed solvent of chloroform/methanol (95:5, v/v) to obtain the entitled compound (675 mg, 43%) as a brown amorphous substance.

MS (EI) m/z: 419 (M$^+$).
$^1$H-NMR (CDCl$_3$) δ: 1.35 (9H, s), 1.54 (1H, m), 1.83 (1H, m), 2.05 (6H, s), 2.11 (3H, s), 2.26 (1H, m), 2.55 (1H, m), 2.80-2.94 (3H, m), 4.96 (2H, broad s), 7.11 (2H, d, J=7.1 Hz), 7.34-7.46 (3H, m), 7.97 (1H, broads).
IR (ATR): 3330, 2964, 2865, 2773, 2202, 1658, 1612, 1577, 1457 cm$^{-1}$.

Example 121

2-tert-Butyl-7-[(3S)-3-(dimethylamino)pyrrolidin-1-yl]-5-methyl-6-phenyl-1H-benzimidazole-4-carbonitrile (#121)

An acetic acid (5 ml) solution of N-[4-amino-5-cyano-2-[(3S)-3-(dimethylamino)pyrrolidin-1-yl]-6-methylbiphenyl-3-yl]-2,2-dimethylpropionamide (I-270) (300 mg, 0.72 mmol) was heated at 80° C. for 2.5 hours. After cooling, the reaction solution was poured into aqueous sodium hydroxide solution (6.7 M, 15 ml).

The precipitated solid was collected by filtration, and dried. The obtained solid was purified by column chromatography, and eluted with a mixed solvent of ethyl acetate/acetone (1:1, v/v) to obtain the entitled compound 228 mg (79%) as a colorless solid.

MS (EI) m/z: 401 (M+).

$^1$H-NMR (CDCl$_3$) δ: 1.45 and 1.49 (total 9H, each s), 1.51-1.20 (2H, m), 2.14 and 2.28 (total 6H, each s), 2.18 and 2.28 (total 3H, each s), 2.45-3.66 (5H, m), 7.09-7.43 (5H, m), 9.16 (1H, broad s).

IR (ATR): 3241, 2969, 2813, 2765, 2204, 1602, 1565, 1455 cm$^{-1}$.

Anal. Calcd for C$_{25}$H$_{31}$N$_5$: C, 74.78; H, 7.78; N, 17.44. Found: C, 74.76; H, 7.85; N, 17.28.

Reference Example 271

7-Fluoro-2-(2-furylmethyl)-5-methyl-6-phenyl-1,3-benzoxazole-4-carbonitrile (I-271)

With cooling with ice, 1-hydroxybenzotriazole (134 mg, 0.991 mmol), 1-ethyl-3-(3-dimethylaminopropyl)carbodiimide (174 mg, 0.908 mmol) and triethylamine (127 μl, 0.980 mmol) were added to an acetonitrile (8 ml) solution of 4-amino-6-fluoro-5-hydroxy-2-methylbiphenyl-3-carbonitrile (I-41) (200 mg, 0.826 mmol) and 2-furylacetic acid (115 mg, 0.908 mmol), followed by stirring at room temperature for 16 hours. The reaction liquid was concentrated under reduced pressure, the residue was dissolved in ethyl acetate, and washed with water and saturated brine. The organic layer was dried over anhydrous sodium sulfate, then concentrated under reduced pressure, and the resulting residue was dissolved in xylene (20 ml), then pyridinium p-toluenesulfonate (50 mg) was added, followed by heating under reflux in an oil bath at 160° C. for 1 hour. The reaction liquid was concentrated under reduced pressure, then the residue was dissolved in ethyl acetate, washed with saturated brine. After drying over anhydrous sodium sulfate, the insoluble matter was separated by filtration, and the residue obtained by concentration under reduced pressure was purified by silica gel column chromatography (eluent, n-hexane:ethyl acetate=4:1, v/v) to obtain the entitled compound (155 mg, 57%) as a pale yellow solid.

MS (FAB) m/z: 333 (M+1)+.

HRMS (FAB) m/z: 333.1031 (Calcd for C$_{20}$H$_{14}$FN$_2$O$_2$ 333.1039).

$^1$H-NMR (CDCl$_3$) δ: 2.42 (3H, s), 4.43 (2H, s), 6.35-6.40 (2H, m), 7.22-7.26 (2H, m), 7.39-7.53 (4H, m).

IR (ATR): 3028, 2925, 2889, 2854, 2227, 1637, 1618, 1583, 1502, 1477, 1444, 1412, 1338, 1315, 1225, 1205, 1178, 1157, 1117, 1070, 1009, 958, 885 cm$^{-1}$.

Example 122

7-[(3S)-3-(Dimethylamino)pyrrolidin-1-yl]-2-(2-furylmethyl)-5-methyl-6-phenyl-1,3-benzoxazole-4-carbonitrile (#122)

(3S)-3-(Dimethylamino)pyrrolidine (88 μl, 0.695 mmol) and triethylamine (97 μl, 0.695 mmol) were added to a dimethyl sulfoxide (4 ml) solution of 7-fluoro-2-(2-furylmethyl)-5-methyl-6-phenyl-1,3-benzoxazole-4-carbonitrile (I-271) (154 mg, 0.463 mmol), followed by stirring in an oil bath at 95° C. for 1 hour. The reaction liquid was concentrated under reduced pressure, then the residue was dissolved in ethyl acetate, and washed with water and saturated brine. After drying over anhydrous sodium sulfate, the insoluble matter was separated by filtration, and the residue obtained by concentration was purified by silica gel column chromatography and preparative TLC (eluent, chloroform:methanol=20:1, v/v) to obtain the entitled compound (27 mg, 14%) as a pale brown foamy substance.

MS (FAB) m/z: 427 (M+1)+.

HRMS (FAB) m/z: 427.2147 (Calcd for C$_{26}$H$_{27}$N$_4$O$_2$ 427.2134).

$^1$H-NMR (CDCl$_3$) δ: 1.53-1.61 (1H, m), 1.88-1.95 (1H, m), 2.11 (6H, s), 2.18 (3H, s), 2.41-2.52 (1H, m), 2.93 (1H, t, J=9.3 Hz), 3.18-3.37 (3H, m), 4.35 (2H, s), 6.29-6.31 (1H, m), 6.35 (1H, dd, J=3.2, 2.0 Hz), 7.07-7.12 (1H, m), 7.21-7.45 (5H, m).

IR (ATR): 2974, 2949, 2870, 2819, 2773, 2210, 1604, 1587, 1562, 1469, 1439, 1400, 1365, 1302, 1238, 1192, 1153, 1061, 1011, 964, 918, 883, 837, 789, 727, 702 cm$^{-1}$.

Reference Example 272

Benzyl [(4-cyano-7-fluoro-5-methyl-6-phenyl-1,3-benzoxazol-2-yl)methyl]methylcarbamate (I-272)

At room temperature, 1-hydroxybenzotriazole (184 mg, 1.36 mmol), 1-ethyl-3-[3-(dimethylamino)propyl]carbodiimide hydrochloride (249 mg, 1.30 mmol) and triethylamine (190 μl, 1.36 mmol) were added to an acetonitrile (12 ml) solution of 4-amino-6-fluoro-5-hydroxy-2-methylbiphenyl-3-carbonitrile (I-41) (300 mg, 1.24 mmol) and N-[(benzyloxy)carbonyl]-N-methylglycine (290 mg, 1.30 mmol), followed by stirring at room temperature for 16 hours. The reaction liquid was concentrated under reduced pressure, dissolved in ethyl acetate, and washed with water and saturated brine. After drying over anhydrous sodium sulfate, the insoluble matter was separated by filtration, the residue obtained by concentration was dissolved in xylene (20 ml), then pyridinium p-toluenesulfonate (120 mg) was added, followed by heating under reflux in an oil bath at 160° C. for 6 hours. The reaction liquid was concentrated under reduced pressure, dissolved in ethyl acetate, washed with saturated brine. After drying over anhydrous sodium sulfate, the insoluble matter was separated by filtration, and the residue obtained by filtration was purified by silica gel column chromatography (eluent, n-hexane:ethyl acetate=3:1, v/v) to obtain the entitled compound (242 mg, 46%) as a colorless foamy substance.

MS (FAB) m/z: 430 (M+1)+.

HRMS (FAB) m/z: 430.1573 (Calcd for C$_{25}$H$_{21}$FN$_3$O$_3$ 430.1567).

$^1$H-NMR (CDCl$_3$) δ: 2.43 (2.5H, s), 2.66 (0.5H, s), 3.14 (0.5H, s), 3.15 (2.5H, s), 4.77-4.89 (2H, m), 5.15-5.23 (2H, m), 7.14-7.58 (10H, m).

IR (ATR): 3423, 3060, 3032, 2925, 2854, 2227, 1705, 1633, 1572, 1477, 1454, 1404, 1363, 1325, 1306, 1215, 1201, 1151, 1120, 1059, 985, 957 cm$^{-1}$.

Reference Example 273

7-Fluoro-5-methyl-2-[(methylamino)methyl]-6-phenyl-1,3-benzoxazole-4-carbonitrile (I-273)

A catalyst 10% palladium-carbon (100 mg) was added to an ethanol (6 ml) solution of benzyl [(4-cyano-7-fluoro-5-methyl-6-phenyl-1,3-benzoxazol-2-yl)methyl]methylcarbamate (I-272) (242 mg, 0.564 mmol), followed by stirring under hydrogen atmosphere at room temperature for 6 hours. The insoluble matter was separated by filtration, the filtrate was concentrated, and the resulting residue was purified by silica gel column chromatography (eluent, chloroform:

methanol=10:1, v/v) to obtain the entitled compound (115 mg, 69%) as a colorless oily substance.

MS (ESI) m/z: 296 (M+1)$^+$.

$^1$H-NMR (CDCl$_3$) δ: 2.42 (3H, s), 2.57 (3H, s), 4.12 (2H, s), 7.23-7.25 (2H, m), 7.44-7.52 (3H, m).

IR (ATR): 3199, 3057, 2924, 2852, 2235, 1651, 1604, 1506, 1458, 1437, 1406, 1350, 1329, 1234, 1184, 1124, 1084, 1066, 1030, 957, 931, 910 cm$^{-1}$.

Example 123

N-({4-Cyano-7-[(3S)-3-(dimethylamino)pyrrolidin-1-yl]-5-methyl-6-phenyl-1,3-benzoxazol-2-yl}methyl)-N-methylacetamide (#123)

(3S)-3-(Dimethylamino)pyrrolidine (74 μl, 0.579 mmol) and triethylamine (81 μl, 0.579 mmol) were added to a dimethyl sulfoxide (4 ml) solution of 7-fluoro-5-methyl-2-[(methylamino)methyl]-6-phenyl-1,3-(I-273) (114 mg, 0.386 mmol), followed by stirring in an oil bath at 95° C. for 2 hours. The reaction liquid was concentrated under reduced pressure, then the residue was dissolved in chloroform, and washed with saturated brine. After drying over anhydrous sodium sulfate, the insoluble matter was separated by filtration, and the residue obtained by concentration was purified by preparative TLC (eluent, chloroform:methanol=10:1, v/v). The obtained eluate was dissolved in pyridine (1 ml), and with cooling with ice, acetic anhydride (18 μl 0.194 mmol) was added, followed by stirring at room temperature for 2 hours. The reaction liquid was concentrated under reduced pressure, the residue was dissolved in chloroform, and washed with saturated brine. After drying over anhydrous sodium sulfate, the insoluble matter was separated by filtration, and the residue obtained by concentration was purified by preparative TLC (eluent, chloroform:methanol=10:1, v/v) to obtain the entitled compound (18.0 mg, 10%) as a brown foamy substance.

MS (ESI) m/z: 432 (M+1)$^+$.

HRMS (EI) m/z: 431.2313 (Calcd for C$_{25}$H$_{29}$N$_5$O$_2$ 431.2321).

$^1$H-NMR (CDCl$_3$) δ: 1.49-1.63 (1H, m), 1.90-1.99 (1H, m), 2.11 (6H, s), 2.19 (3H, s), 2.20 (3H, s), 2.43-2.55 (1H, m), 2.83-2.96 (1H, m), 3.20 (3H, s), 3.25-3.48 (3H, m), 4.76-4.92 (2H, m), 7.08-7.12 (1H, m), 7.20-7.30 (1H, m), 7.32-7.45 (3H, m).

IR (ATR): 2976, 2949, 2871, 2823, 2775, 2210, 1651, 1606, 1587, 1469, 1439, 1398, 1363, 1302, 1246, 1201, 1155, 1038, 989, 960, 918, 839 cm$^{-1}$.

Anal. Calcd for C$_{25}$H$_{29}$N$_5$O$_2$·1.5H$_2$O: C, 65.48; H, 7.03; N, 15.27. Found: C, 65.64; H, 6.79; N, 15.46.

Reference Example 274

4-Amino-5-cyano-2-fluoro-6-methylbiphenyl-3-yl cyclopentanecarboxylate (I-274)

Under nitrogen atmosphere, 2-amino-5-phenyl-4-fluoro-3-hydroxy-6-methylbenzonitrile (I-41) (200 mg, 0.83 mmol) was dissolved in acetonitrile (10 ml), and cooled at 0° C. Triethylamine (138 μl, 1.36 mmol) and cyclopentanecarbonyl chloride (138 μl, 1.36 mmol) were dropwise added to the solution, followed by stirring at room temperature for 2 hours. 10% citric acid was added to the reaction liquid, and the solvent was evaporated away under reduced pressure. Ethyl acetate was added to the resulting residue, followed by washing with saturated brine. The organic layer was dried over anhydrous magnesium sulfate, and the solvent was evaporated away under reduced pressure. The resulting residue was purified by preparative TLC (ethyl acetate:n-hexane=1:3, v/v) to obtain the entitled compound (200 mg, 72%) as a colorless oil.

$^1$H-NMR (CDCl$_3$) δ: 1.62-1.86 (4H, m), 1.92-2.12 (4H, m), 2.56 (3H, s), 3.03-3.12 (1H, m), 4.50 (2H, brs), 7.21-7.26 (2H, m), 7.39-7.44 (3H, m).

Reference Example 275

2-Cyclopentyl-7-fluoro-5-methyl-6-phenyl-1,3-benzoxazole-4-carbonitrile (I-275)

(4-Amino-5-cyano-2-fluoro-6-methylbiphenyl-3-yl)cyclopentanecarboxylate (I-274) (200 mg, 0.83 mmol) was dissolved in xylene (50 ml), then pyridinium p-toluenesulfonate (50 mg) was added, followed by heating under reflux for 18 hours. After cooling to room temperature, the solvent was evaporated away under reduced pressure. The resulting residue was diluted with ethyl acetate, washed with saturated brine. The obtained organic layer was dried over anhydrous magnesium sulfate, and the solvent was evaporated away under reduced pressure. The resulting residue was purified by preparative TLC (ethyl acetate:n-hexane=1:2, v/v) to obtain the entitled compound (112 mg, 59%) as a colorless amorphous substance.

$^1$H-NMR (CDCl$_3$) δ: 1.72-1.89 (4H, m), 1.98-2.22 (4H, m), 2.41 (3H, s), 3.41-3.49 (1H, m), 7.25-7.29 (2H, m), 7.43-7.54 (3H, m).

Example 124

2-Cyclopentene-7-[(3S)-3-(dimethylamino)pyrrolidinyl]-5-methyl-6-phenyl-1,3-benzoxazole-4-carbonitrile (#124)

2-Cyclopentyl-7-fluoro-5-methyl-6-phenyl-1,3-benzoxazole-4-carbonitrile (I-275) (112 mg, 0.24 mmol) was dissolved in dimethyl sulfoxide (5 ml), then triethylamine (100 μl, 0.36 mmol) and (3S)-3-(dimethylamino)pyrrolidine (93 μl, 0.31 mmol) were added, followed by stirring under nitrogen atmosphere at 95° C. for 4 hours. After cooling, this was concentrated under reduced pressure, diluted, with chloroform, washed with saturated brine. The organic layer was dried over anhydrous magnesium sulfate, then the solvent was evaporated away under reduced pressure. The resulting residue was purified by preparative TLC (chloroform:methanol=10:1, v/v) to obtain the entitled compound (48 mg, 33%) as a white crystal.

mp.: 120-122° C.

MS (ESI) m/z: 415 (M+1)$^+$.

$^1$H-NMR (CDCl$_3$) δ: 1.53-2.09 (8H, m), 2.13 (6H, s), 2.14-2.18 (2H, m), 2.19 (3H, s), 2.45-2.56 (1H, m), 2.98 (1H, t, J=9.2 Hz), 3.22-3.46 (4H, m), 7.09-7.13 (1H, m), 7.22-7.26 (2H, m), 7.31-7.43 (3H, m).

IR (ATR): 2952, 2867, 2208, 1604, 1558, 1468, 1363, 1299, 1191, 704 cm$^{-1}$.

Anal. Calcd for C$_{26}$H$_{30}$N$_4$O·0.25H$_2$O: C, 74.52; H, 7.34; N, 13.37. Found: C, 74.57; H, 7.31; N, 13.31.

Reference Example 276

Methyl 1-(4-cyano-7-fluoro-5-methyl-6-phenyl-1,3-benzoxazol-2-yl)cyclopropanecarboxylate (I-276)

With cooling with ice, thionyl chloride (148 μl, 2.05 mmol) was added to a dichloromethane (10 ml) solution of 1-(methoxycarbonyl)cyclopropanecarboxylic acid (250 mg, 1.73 mmol), followed by stirring at room temperature for 1 hour. The reaction liquid was concentrated under reduced pressure, the residue was dissolved in acetonitrile (10 ml), and 4-amino-6-fluoro-5-hydroxy-2-methylbiphenyl-3-carbonitrile (382 mg, 1.58 mmol) was added, and with cooling with ice, triethylamine (396 μl, 2.84 mmol) was added, followed by stirring a room temperature for 16 hours. Further, an acid chloride formed from 1-(methoxycarbonyl)cyclopropanecarboxylic acid (500 mg, 3.47 mmol) and thionyl chloride (296 μl, 4.11 mmol), and triethylamine (1.00 ml, 7.17 mmol) were added to the reaction liquid, followed by stirring at room temperature for 2 hours. The reaction liquid was concentrated under reduced pressure, then dissolved in ethyl acetate, washed with saturated brine. After drying over anhydrous sodium sulfate, the insoluble matter was separated by filtration, and the residue obtained by concentration was dissolved in xylene (15 ml), and pyridinium p-toluenesulfonate (95 mg) was added, followed by heating under reflux in an oil bath at 160° C. for 5 hours. The reaction liquid was concentrated under reduced pressure, then dissolved in ethyl acetate, washed with saturated brine. After drying over anhydrous sodium sulfate, the insoluble matter was separated by filtration, and the residue obtained by concentration was purified by silica gel column chromatography (eluent, n-hexane:ethyl acetate=2:1, v/v) to obtain the entitled compound (40.0 mg, 7%) as a colorless oily substance.

MS (ESI) m/z: 351 (M+1)$^+$.

$^1$H-NMR (CDCl$_3$) δ: 1.73-1.90 (4H, m), 2.42 (3H, s), 3.78 (3H, s), 7.23-7.27 (2H, m), 7.45-7.54 (3H, m).

Example 125

Methyl 1-{4-cyano-7-[(3S)-(dimethylamino)pyrrolidin-1-yl]-5-methyl-6-phenyl-1,3-benzoxazol-2-yl}cyclopropanecarboxylate (#125)

(3S)-3-(Dimethylamino)pyrrolidine (22 μl, 0.171 mmol) and triethylamine (24 μl, 0.171 mmol) were added to a dimethyl sulfoxide (1 ml) solution of methyl 1-(4-cyano-7-fluoro-5-methyl-6-phenyl-1,3-benzoxazol-2-yl)cyclopropanecarboxylate (I-276) (40 mg, 0.114 mmol), followed by stirring in an oil bath at 100° C. for 4 hours. The reaction liquid was concentrated under reduced pressure, then the residue was dissolved in chloroform, and washed with saturated brine. After drying over anhydrous sodium sulfate, the insoluble matter was separated by filtration, and the residue obtained by concentration was purified by silica gel column chromatography (eluent, chloroform:methanol=10:1, v/v) to obtain the entitled compound (10.0 mg, 20%) as an orange solid.

MS (ESI) m/z: 445 (M+1)$^+$.

HRMS (ESI) m/z: 445.2198 (Calcd for C$_{26}$H$_{29}$N$_4$O$_3$ 445.2240).

$^1$H-NMR (CDCl$_3$) δ: 1.58-1.82 (5H, m), 1.91-2.00 (1H, m), 2.13 (6H, s), 2.19 (3H, s), 2.48-2.59 (1H, m), 2.91-3.00 (1H, m), 3.29-3.38 (2H, m), 3.41-3.47 (1H, m), 3.76 (3H, s), 7.10-7.13 (1H, m), 7.22-7.27 (1H, m), 7.33-7.43 (3H, m).

IR (ATR): 3016, 2952, 2870, 2821, 2775, 2212, 1736, 1697, 1606, 1585, 1469, 1439, 1400, 1365, 1308, 1201, 1157, 1124, 1061, 989, 960, 916, 862 cm$^{-1}$.

Example 126

N-(1-{4-Cyano-7-[(3S)-dimethylamino)pyrrolidin-1-yl]-5-methyl-6-phenyl-1,3-benzoxazol-2-yl}azetidin-3-yl)acetamide (#126)

With cooling with ice, trifluoroacetic acid (1 ml) was added to a dichloromethane (1 ml) solution of tert-butyl (1-{4-cyano-7-[(3S)-3-(dimethylamino)pyrrolidin-yl]-5-methyl-6-phenyl-1,3-benzoxazol-2-yl}azetidin-3-yl)carbamate (I-195) (150 mg, 0.290 mmol), followed by stirring at room temperature for 1 hour. The reaction liquid was concentrated under reduced pressure, dissolved in pyridine (3 ml), and with cooling with ice, acetic anhydride (41 μl, 0.436 mmol) was added, followed by stirring at room temperature for 1 hour. The reaction liquid was concentrated under reduced pressure, the residue was dissolved in chloroform, and washed with water and saturated brine. After drying over anhydrous sodium sulfate, the insoluble matter was separated by filtration, and the residue obtained by concentration was purified by silica gel column chromatography (eluent, chloroform:methanol=10:1, v/v), the eluate was purified in slurry with diethyl ether to obtain the entitled compound (55 mg, 39%) as a pale yellow solid.

mp: 124-126° C.

MS (ESI) m/z: 459 (M+1)$^+$.

$^1$H-NMR (CDCl$_3$) δ: 1.47-1.64 (1H, m), 1.85-1.95 (1H, m), 2.05 (3H, s), 2.12 (6H, s), 2.14 (3H, s), 2.46-2.58 (1H, m), 2.84-2.95 (1H, m), 3.14 (1H, td, J=10.1, 6.7 Hz), 3.20-3.27 (2H, m), 4.14-4.19 (2H, m), 4.57-4.63 (2H, m), 4.85-4.93 (1H, m), 6.18 (1H, d, J=7.3 Hz), 7.08-7.11 (1H, m), 7.03-7.46 (4H, m).

IR (ATR): 3282, 3055, 2949, 2875, 2821, 2775, 2206, 1635, 1595, 1558, 1468, 1439, 1408, 1367, 1288, 1194, 1153, 1070, 1039, 982, 943, 918, 885, 831, 781, 727 cm$^{-1}$.

Anal. Calcd for C$_{26}$H$_{30}$N$_6$O$_2$.1.75H$_2$O: C, 63.72; H, 6.89; N, 17.15. Found: C, 63.91; H, 6.61; N, 17.39.

Reference Example 277 tert-Butyl [1-(4-cyano-7-fluoro-5-methyl-6-phenyl-1,3-benzoxazol-2-yl)azetidin-3-yl]methylcarbamate (I-277)

With cooling with ice, methyl iodide (70 μl, 1.13 mmol) and sodium hydride (55%, w/w) (45 mg, 1.04 mmol) were added to a tetrahydrofuran (8 ml)/dimethyl formamide (2 ml) mixture solution of tert-butyl [1-(4-cyano-7-fluoro-5-methyl-5-phenyl-1,3-benzoxazol-2-yl)azetidin-3-yl]carbamate (I-194) (398 mg, 0.942 mmol), followed by stirring for 2 hours with cooling with ice. With cooling with ice, aqueous 10% citric acid was added to the reaction liquid, followed by concentration under reduced pressure. The residue was dissolved in ethyl acetate, washed with water and saturated brine. After drying over anhydrous sodium sulfate, the insoluble matter was separated by filtration, and the residue obtained by concentration was purified by silica gel column chromatography (eluent, chloroform:ethyl acetate=20:1→4:1, v/v) to obtain the entitled compound (375 mg, 91%) as a colorless foamy substance.

MS (FAB) m/z: 437 (M+1)$^+$.

HRMS (FAB) m/z: 437.1978 (Calcd for C$_{24}$H$_{26}$FN$_4$O$_3$ 437.1989).

$^1$H-NMR (CDCl$_3$) δ: 1.48 (9H, s), 2.35 (3H, s), 2.98 (3H, s), 4.39-4.59 (4H, m), 7.22-7.26 (2H, m), 7.41-7.52 (3H, m).

IR (ATR): 2976, 2927, 2889, 2222, 1693, 1639, 1574, 1479, 1444, 1421, 1367, 1331, 1288, 1246, 1149, 1115, 1059, 957, 916 cm$^{-1}$.

Example 127

N-(1-{4-Cyano-7-[(3S)-(dimethylamino)pyrrolidin-1-yl]-5-methyl-6-phenyl-1,3-benzoxazol-2-yl}azetidin-3-yl)-N-methylacetamide (#127)

(3S)-3-(Dimethylamino)pyrrolidine (87 μl, 0.687 mmol) and triethylamine (96 μl, 0.687 mmol) were added to a dimethyl sulfoxide (5 ml) solution of tert-butyl [1-(4-cyano-7-fluoro-5-methyl-6-phenyl-1,3-benzoxazol-2-yl)azetidin-3-yl]methylcarbamate (I-277) (200 mg, 0.458 mmol), followed by stirring in an oil bath at 150° C. for 2 hours. The reaction liquid was concentrated under reduced pressure, then the residue was dissolved in ethyl acetate, and washed with water and saturated brine. After drying over anhydrous sodium sulfate, the insoluble matter was separated by filtration, and the residue obtained by concentration was purified by silica gel column chromatography (eluent, chloroform:methanol=10:1, v/v). Trifluoroacetic acid (2 ml) was added to a dichloromethane (2 ml) solution of the obtained eluate, followed by stirring at room temperature for 15 hours. The reaction liquid was concentrated under reduced pressure, then the residue was dissolved in pyridine (1 ml), and acetic anhydride (34 μl, 0.362 mmol) was added, followed by stirring at room temperature for 2 hours. The reaction liquid was concentrated under reduced pressure, then the residue was dissolved in chloroform, washed with saturated brine, and dried over anhydrous sodium sulfate. The insoluble matter was separated by filtration, concentrated under reduced pressure, and the resulting residue was purified by preparative TLC (eluent, chloroform:methanol=10:1, v/v) to obtain the entitled compound (30 mg, 13%) as a pale brown foamy substance.

MS (ESI) m/z: 473 (M+1)$^+$.

$^1$H-NMR (CDCl$_3$) δ: 1.49-1.64 (1H, m), 1.84-1.95 (1H, m), 2.11 (6H, s), 2.15 (3H, s), 2.15 (3H, s), 2.43-2.54 (1H, m), 2.85-2.95 (1H, m), 3.10-3.19 (1H, m), 3.15 (3H, s), 3.22-3.29 (2H, m), 4.25-4.32 (2H, m), 4.48-4.57 (2H, m), 5.45-5.54 (1H, m), 7.10 (1H, d, J=7.3 Hz), 7.22 (1H, dd, J=7.1, 2.2 Hz), 7.30-7.42 (3H, m).

IR (ATR): 2949, 2873, 2823, 2775, 2208, 1635, 1601, 1562, 1468, 1408, 1365, 1327, 1294, 1246, 1217, 1198, 1157, 1043, 984, 941, 916, 829 cm$^{-1}$.

Anal. Calcd for C$_{27}$H$_{32}$N$_6$O$_2$·1.5H$_2$O: C, 64.91; H, 7.06; N, 16.82. Found: C, 65.25; H, 6.84; N, 16.59.

Reference Example 278 tert-Butyl N-(4-cyano-7-fluoro-5-methyl-6-phenyl-1,3-benzoxazol-2-yl)-β-alaninate (I-278)

With cooling with ice, tert-butyl 3-aminopropionate hydrochloride (230 mg, 1.26 mmol) and diisopropylethylamine (430 μl, 2.53 mmol) were added to a dichloromethane (10 ml) solution of 2-chloro-7-fluoro-5-methyl-6-phenyl-1,3-benzoxazole-4-cabonitrile (I-130) (302 mg, 1.05 mmol), followed by stirring at room temperature for 1 hour. The reaction liquid was cooled to room temperature, then ethyl acetate was added, and followed by washing with saturated brine. After drying over anhydrous sodium sulfate, the insoluble matter was separated by filtration, and the residue obtained by concentration was purified by silica gel column chromatography (eluent, n-hexane:ethyl acetate=4:1→1:1, v/v) to obtain the entitled compound (402 mg, 97%) as a white solid.

MS (FAB) m/z: 396 (M+1)$^+$.

HRMS (FAB) m/z: 396.1701 (Calcd for C$_{22}$H$_{23}$FN$_3$O$_3$ 396.1723).

$^1$H-NMR (CDCl$_3$) δ: 1.48 (9H, s), 2.35 (3H, s), 2.65 (2H, t, J=5.6 Hz), 3.81 (2H, dt, J=6.1, 5.6 Hz), 5.98 (1H, t, J=6.1 Hz), 7.20-7.55 (5H, m).

IR (ATR): 3170, 3089, 2978, 2937, 2222, 1730, 1684, 1643, 1585, 1489, 1448, 1425, 1379, 1323, 1290, 1213, 1169, 1119, 1057, 1036, 957, 926, 849, 804, 7.81 cm$^{-1}$.

Reference Example 279 tert-Butyl N-{4-cyano-7-[(3S)-3-(dimethylamino)pyrrolidin-1-yl]-5-methyl-6-phenyl-1,3-benzoxazol-2-yl)-β-alaninate (I-279)

(3S)-3-(dimethylamino)pyrrolidine (161 μl, 1.27 mmol) and triethylamine (177 μl, 1.27 mmol) were added to a dimethyl sulfoxide (9 ml) solution of tert-butyl N-(4-cyano-7-fluoro-5-methyl-6-phenyl-1,3-benzoxazol-2-yl)-β-alaninate (I-278) (335 mg, 0.847 mmol), followed by stirring in an oil bath at 150° C. for 5 hours. The reaction liquid was concentrated under reduced pressure, the residue was dissolved in ethyl acetate and washed with water and saturated brine. After drying over anhydrous sodium sulfate, the insoluble matter was separated by filtration, the residue obtained by concentration was purified by silica gel column chromatography (eluent, chloroform:methanol=20:1, v/v) to obtain the entitled compound (120 mg, 29%) as a brown oily substance.

MS (FAB) m/z: 490 (M+1)$^+$.

HRMS (FAB) m/z: 490.2847 (Calcd for C$_{28}$H$_{36}$N$_5$O$_3$ 490.2818).

$^1$H-NMR (CDCl$_3$) δ: 1.48 (9H, s), 1.51-1.61 ($^1$H, m), 1.83-1.93 (1H, m), 2.11 (6H, s), 2.15 (3H, s), 2.18-2.36 (2H, m), 2.42-2.52 (1H, m), 2.76-2.89 (1H, m), 3.13-3.32 (3H, m), 3.72-3.79 (2H, m), 5.69-5.75 (1H, m), 7.05-7.50 (5H, m).

IR (ATR): 3452, 3209, 2976, 2925, 2870, 2823, 2777, 2208, 1726, 1645, 1603, 1572, 1466, 1414, 1367, 1321, 1292, 1248, 1215, 1155, 1117, 1059, 1041, 985, 955, 916, 845, 754 cm$^{-1}$.

Example 128

Methyl N-{4-cyano-7-[(3S)-3-(dimethylamino)pyrrolidin-1-yl]-5-methyl-6-phenyl-1,3-benzoxazol-2-yl)-β-alaninate (#128)

Trifluoroacetic acid (1 ml) was added to a dichloromethane (2 ml) solution of tert-butyl N-{4-cyano-7-[(3S)-3-(dimethylamino)pyrrolidin-1-yl]-5-methyl-6-phenyl-1,3-benzoxazol-2-yl)-β-alaninate (I-279) (51 mg, 0.104 mmol), followed by stirring at room temperature for 2 hours. The reaction liquid was concentrated under reduced pressure, the residue was dissolved in dichloromethane (1 ml), and at room temperature, thionyl chloride (10 μl, 0.138 mmol) was added, followed by stirring at room temperature for 1 hour. The reaction liquid was concentrated under reduced pressure, the then dissolved in chloroform, and washed with an aqueous saturated sodium hydrogencarbonate solution and saturated brine. After drying over anhydrous sodium sulfate and concentration, the insoluble matter was separated by filtration, the solvent was evaporated away, and the resulting residue was purified by preparative TLC (eluent, chloroform:methanol=20:1, v/v), the eluate was purified in slurry with diethyl ether to obtain the entitled compound (8.00 mg, 17%) as a pale yellow solid.

MS (ESI) m/z: 448 (M+1)$^+$.

$^1$H-NMR (CDCl$_3$) δ: 1.50-1.70 (1H, m), 1.85-1.93 (1H, m), 2.12 (6H, s), 2.15 (3H, s), 2.44-2.55 (1H, m), 2.72-2.77 (2H, m), 2.83-2.92 (1H, m), 3.12-3.31 (3H, m), 3.74 (3H, s), 3.77-3.85 (2H, m), 5.70-5.85 (1H, m), 7.09-7.41 (5H, m).

IR (ATR): 3355, 2949, 2866, 2819, 2773, 2206, 1720, 1643, 1603, 1572, 1442, 1412, 1367, 1333, 1300, 1246, 1198, 1173, 1041, 1011, 980, 955, 918, 852, 789, 760, 704 cm$^{-1}$.

Anal. Calcd for C$_{25}$H$_{29}$N$_5$O$_3$.0.75H$_2$O: C, 65.13; H, 6.67; N, 15.19. Found: C, 65.41; H, 6.44; N, 15.09.

Reference Example 280

Ethyl 4-[(4-cyano-7-fluoro-5-methyl-6-phenyl-1,3-benzoxazol-2-yl)amino]butanoate (I-280)

With cooling with ice, ethyl 4-aminobutanoate hydrochloride (149 mg, 0.892 mmol) and diisopropylethylamine (303 μl, 1.78 mmol) were added to a dichloromethane (7 ml) solution of 2-chloro-7-fluoro-5-methyl-6-phenyl-1,3-benzoxazole-4-cabonitrile (I-130) (213 mg, 0.743 mmol), followed by stirring at room temperature for 15 hours. The reaction liquid was concentrated under reduced pressure, ethyl acetate was added, followed by washing with saturated brine. After drying over anhydrous sodium sulfate, the insoluble matter was separated by filtration, and the residue obtained by concentration was purified by silica gel column chromatography (eluent, n-hexane:ethyl acetate=2:1→1:1, v/v) to obtain the entitled compound (279 mg, 99%) as a white solid.

MS (ESI) m/z: 382 (M+1)$^+$.

$^1$H-NMR (CDCl$_3$) δ: 1.27 (3H, t, J=7.1 Hz), 2.01-2.10 (2H, m), 2.35 (3H, s), 2.48 (2H, t, J=7.0 Hz), 3.65 (2H, q, J=6.4 Hz), 4.17 (2H, q, J=7.2 Hz), 5.96 (1-H, br s), 7.21-7.26 (2H, m), 7.39-7.50 (3H, m).

Reference Example 281

Ethyl 4-({4-cyano-7-[(3S)-3-(dimethylamino)pyrrolidin-1-yl]-5-methyl-6-phenyl-1,3-benzoxazol-2-yl}amino)butanoate (I-281)

(3S)-3-(Dimethylamino)pyrrolidine (139 μl, 1.10 mmol) and triethylamine (153 μl, 1.10 mmol) were added to a dimethyl sulfoxide (5 ml) solution of ethyl 4-[(4-cyano-7-fluoro-5-methyl-6-phenyl-1,3-benzoxazol-2-yl)amino]butanoate (I-280) (279 mg, 0.732 mmol), followed by stirring in an oil bath at 150° C. for 5 hours. The reaction liquid was concentrated under reduced pressure, the residue was dissolved in chloroform and washed with saturated brine. After drying over anhydrous sodium sulfate, the insoluble matter was separated by filtration, the residue obtained by concentration was purified by silica gel column chromatography (eluent, chloroform:methanol=10:1, v/v) to obtain the entitled compound (170 mg, 49%) as a brown oily substance.

MS (ESI) m/z: 476 (M+1)$^+$.

$^1$H-NMR (CDCl$_3$) δ: 1.26 (3H, t, J=7.1 Hz), 1.49-1.61 (1H, m), 1.86-1.95 (1H, m), 1.98-2.07 (2H, m), 2.13 (6H, s), 2.15 (3H, s), 2.43-2.49 (2H, m), 2.49-2.58 (1H, m), 2.87-2.96 (1H, m), 3.14-3.29 (3H, m), 3.60 (2H, q, J=6.5 Hz), 4.15 (2H, q, J=7.2 Hz), 5.72 (1H, br s), 7.09-7.13 (1H, m), 7.21-7.41 (4H, m).

Reference Example 282

4-({4-Cyano-7-[(3S)-3-(dimethylamino)pyrrolidin-1-yl]-5-methyl-6-phenyl-1,3-benzoxazol-2-yl}amino)butanoic acid (I-282)

With cooling with ice, aqueous 1 N sodium hydroxide solution (536 μl, 0.536 mmol) was added to an ethanol (3.5 ml) solution of ethyl 4-({4-cyano-7-[(3S)-3-(dimethylamino)pyrrolidin-1-yl]-5-methyl-6-phenyl-1,3-benzoxazol-2-yl}amino)butanoate (I-281) (170 mg, 0.357 mmol), followed by stirring at room temperature for 15 hours. With cooling with ice, aqueous 1 N hydrochloric acid solution (536 μl, 0.536 mmol) was added to the reaction liquid, followed by concentration under reduced pressure. The resulting residue was purified by preparative TLC (eluent, chloroform:methanol=5:1, v/v) to obtain the entitled compound (110 mg, 69%) as a pale brown foamy substance.

MS (ESI) m/z: 448 (M+1)$^+$.

$^1$H-NMR (CDCl$_3$) δ: 1.74-1.84 (1H, m), 1.85-1.95 (1H, m), 1.96-2.13 (2H, m), 2.17-2.26 (1H, m), 2.19 (3H, s), 2.38 (6H, s), 2.39-2.43 (1H, m), 2.47-2.87 (3H, m), 3.13 (1H, dd, J=10.0, 6.6 Hz), 3.26-3.34 (1H, m), 3.65 (2H, q, J=7.2 Hz), 3.79 (1H, dd, J=9.9, 6.0 Hz), 7.14-7.41 (5H, m).

Example 129

7-[(3S)-3-(Dimethylamino)pyrrolidin-1-yl]-5-methyl-2-(2-oxopyrolidin-1-yl-6-phenyl-1,3-benzoxazole-4-carbonitrile (#129)

At room temperature, thionyl chloride (43.5 μl, 0.603 mmol) was added to a dichloromethane (2 ml) solution of 4-({4-cyano-7-[(3S)-3-(dimethylamino)pyrrolidin-1-yl]-5-methyl-6-phenyl-1,3-benzoxazol-2-yl}amino)butanoic acid (I-282) (90.0 mg, 0.201 mmol), followed by stirring at room temperature for 1 hour. The reaction liquid was concentrated under reduced pressure, pyridine (2 ml) was added to the residue, followed by stirring in an oil bath at 70° C. for 1 hour. The reaction liquid was concentrated under reduced pressure, the residue was dissolved in chloroform, washed with saturated brine. After drying over anhydrous sodium sulfate, the insoluble matter was separated by filtration, and the residue obtained by concentration was purified by preparative TLC (eluent, chloroform:methanol=10:1, v/v) to obtain the entitled compound (54.0 ml, 62%) as a white solid.

mp: 196-198° C.

MS (ESI) m/z: 430 (M+1)$^+$.

$^1$H-NMR (CDCl$_3$) δ: 1.51-1.66 (1H, m), 1.91-2.01 (1H, m), 2.13 (6H, s), 2.18 (3H, s), 2.22-2.32 (2H, m), 2.45-2.55 (1H, m), 2.67 (2H, t, J=8.1 Hz), 2.94 (1H, t, J=9.4 Hz), 3.31-3.44 (3H, m), 4.19 (2H, t, J=7.2 Hz), 7.12 (1H, d, J=7.1 Hz), 7.23-7.28 (1H, m), 7.31-7.43 (3H, m).

IR (ATR): 2974, 2952, 2871, 2821, 2773, 2210, 1743, 1593, 1552, 1468, 1441, 1408, 1389, 1363, 1304, 1248, 1186, 1155, 1063, 1005, 935, 918, 837 cm$^{-1}$.

Anal. Calcd for C$_{25}$H$_{27}$N$_5$O$_2$.0.25H$_2$O: C, 69.18; H, 6.39; N, 16.14. Found: C, 69.14; H, 6.24; N, 16.04.

Reference Example 283

7-Fluoro-5-methyl-2-morpholine-4-yl-6-phenyl-1,3-benzoxazole-4-carbonitrile (I-283)

With cooling with ice, morpholine (36 µl, 0.413 mmol) and diisopropylethylamine (140 µl, 0.825 mmol) were added to a dichloromethane (3 ml) solution of 2-chloro-7-fluoro-5-methyl-6-phenylbenzoxazole-4-carbonitrile (I-130) (99 mg, 0.344 mmol), followed by stirring at room temperature for 2 hours. The reaction liquid was concentrated under reduced pressure, then the resulting residue was purified by silica gel column chromatography (eluent, n-hexane:ethyl acetate=2:1, v/v) to obtain the entitled compound (115 mg, 99%) as a white solid.

MS (ESI) m/z: 338 (M+1)$^+$.
$^1$H-NMR (CDCl$_3$) δ: 2.35 (3H, s), 3.77-3.87 (8H, m), 7.20-7.28 (2H, m), 7.40-7.52 (3H, m).

Example 130

7-[(3S)-3-(Dimethylamino)pyrrolidin-1-yl]-5-methyl-2-morpholin-4-yl-6-phenyl-1,3-benzoxazole-4-carbonitrile (#130)

(3S)-3-(Dimethylamino)pyrrolidine (55 µl, 0.435 mmol) and triethylamine (70 µl, 0.502 mmol) were added to a dimethyl sulfoxide (3 ml) solution of 7-fluoro-5-methyl-2-morpholin-4-yl-6-phenyl-1,3-benzoxazole-4-carbonitrile (I-283) (113 mg, 0.335 mmol), followed by stirring in an oil bath at 150° C. for 2 hours. The reaction liquid was concentrated under reduced pressure, the residue was dissolved in chloroform and washed with saturated brine. After drying over anhydrous sodium sulfate, the insoluble matter was separated by filtration, the residue obtained by concentration was preparative TLC (eluent, chloroform:methanol=10:1, v/v), and the obtained eluate was recrystallized from hot ethanol to obtain the entitled compound (33.0 mg, 22%) as a white solid.

mp: 215-217° C.
MS (ESI) m/z: 432 (M+1)$^+$.
$^1$H-NMR (CDCl$_3$) δ: 1.65-1.50 (1H, m), 1.96-1.84 (1H, m), 2.12 (6H, s), 2.15 (3H, s), 2.54-2.42 (1H, m), 2.91 (1H, t, J=9.03 Hz), 3.15 (1H, d, J=10.13, 6.59 Hz), 3.31-3.22 (2H, m), 3.74-3.67 (4H, m), 3.85-3.79 (4H, m), 7.08-7.14 (1H, m), 7.20-7.24 (1H, m), 7.30-7.42 (3H, m).
IR (ATR): 3651, 3057, 2958, 2860, 2773, 2202, 1631, 1603, 1566, 1467, 1444, 1404, 1365, 1333, 1277, 1255, 1159, 1115, 1051, 980, 897, 837, 783 cm$^{-1}$.
Anal. Calcd for C$_{25}$H$_{29}$N$_5$O$_2$.0.75H$_2$O: C, 67.47; H, 6.91; N, 15.74. Found: C, 67.74; H, 6.83; N, 15.73.

Reference Example 284

4-Cyano-7-fluoro-N,5-dimethyl-6-phenyl-N-propyl-1,3-benzoxazole-2-carboxamide (I-284)

Under nitrogen atmosphere, trimethylaluminium (1.03 M n-hexane solution) (2.40 ml, 2.47 mmol) was dropwise added at room temperature to a toluene (6 ml) solution of N-methylpropylamine (127 µl, 1.23 mmol), followed by stirring for 40 minutes. Subsequently, a dichloromethane (2 ml) solution of ethyl 4-cyano-7-fluoro-5-methyl-6-phenyl-1,3-benzoxazole-2-carboxylate (I-111) (200 mg, 617 µmol) was dropwise added, followed by stirring for 48.5 hours. After the reaction, aqueous 1 N hydrochloric acid solution was added to the reaction liquid with cooling with ice, followed by stirring at room temperature, then the reaction liquid was extracted with chloroform. Next, the combined organic layer was dried over anhydrous magnesium sulfate, filtered, and the filtrate was concentrated under reduced pressure. The resulting residue was purified by middle-pressure liquid chromatography (eluent, n-hexane:ethyl acetate=2:1, v/v) to obtain the entitled compound (120 mg, 55%) as a pale yellow solid.

MS (ESI) m/z: 352 (M+1)$^+$.
$^1$H-NMR (CDCl$_3$) δ: 0.94-1.04 (3H, m), 1.69-1.85 (2H, m), 2.47 (3H, s), 3.20 (1.59H, s), 3.48 (1.41H, s), 3.56-3.62 (0.94H, m), 3.80-3.86 (1.06H, m), 7.24-7.28 (2H, m), 7.46-7.55 (3H, m).
IR (ATR): 2227, 1651, 1469, 1396, 1248, 1115 cm$^{-1}$.

Example 131

4-Cyano-7-[(3S)-3-(dimethylamino)pyrrolidin-1-yl]-N,5-dimethyl-6-phenyl-N-propyl-1,3-benzoxazole-2-carboxamide (#131)

Under nitrogen atmosphere, a dimethyl sulfoxide (1 ml) solution of (3S)-3-(dimethylamino)pyrrolidine (49 µl, 383 µmol) was added at 140 to 150° C. to a dimethyl sulfoxide (5 ml) solution of 4-cyano-7-fluoro-N,5-dimethyl-6-phenyl-N-propyl-1,3-benzoxazole-2-carboxamide (I-284) (112 mg, 319 µmol) and triethylamine (58 µl, 415 µmol), followed by stirring at the same temperature for 140 minutes. After cooling, saturated brine was added to the reaction liquid, and the reaction liquid was extracted with ethyl acetate. Next, the combined organic layer was washed with saturated brine, then dried over anhydrous magnesium sulfate, filtered, and the filtrate was concentrated under the reduced pressure. The resulting residue was purified by middle-pressure liquid chromatography (eluent, dichloromethane:methanol=10:1, v/v) to obtain the entitled compound (62 mg, 44%) as an amorphous substance.

MS (ESI) m/z: 446 (M+1)$^+$.
$^1$H-NMR (CDCl$_3$) δ: 0.93-1.03 (3H, m), 1.56-1.82 (3H, m), 1.93-2.02 (1H, m), 2.09 (6H, s), 2.22 (3H, s), 2.45-2.56 (1H, m), 2.78 (1H, t, J=9.3 Hz), 3.17 (1.62H, s), 3.20-3.26 (1H, m), 3.52 (1.38H, s), 3.53-3.65 (3H, m), 3.89 (1H, t, J=7.4 Hz), 7.13 (1H, d, J=7.1 Hz), 7.24-7.28 (1H, m), 7.34-7.45 (3H, m).
IR (ATR): 2212, 1651, 1604, 1577, 1469, 1439, 1396, 1365, 1304, 1119 cm$^{-1}$.
Anal. Calcd for C$_{26}$H$_{31}$N$_5$O$_2$.0.25H$_2$O: C, 69.39; H, 7.05; N, 15.56. Found: C, 69.51; H, 7.07; N, 15.23.

Reference Example 285

4-Cyano-N-ethyl-7-fluoro-N,5-dimethyl-6-phenyl-1,3-benzoxazole-2-carboxamide (I-285)

Under nitrogen atmosphere, trimethylaluminium (1.03 M n-hexane solution) (2.40 ml, 2.47 mmol) was dropwise added at room temperature to a dichloromethane (8 ml) solution of N-ethylmethylamine (146 mg, 2.47 mmol), followed by stirring for 80 minutes. Subsequently, a dichloromethane (4 ml) solution of ethyl 4-cyano-7-fluoro-5-methyl-6-phenyl-1,3-benzoxazole-2-carboxylate (I-111) (400 mg, 1.23 mmol) was dropwise added, followed by stirring for 19 hours. After the reaction, aqueous 1 N hydrochloric acid solution was added to the reaction liquid with cooling with ice, followed by stirring at room temperature, then the reaction liquid was extracted with chloroform. Next, the combined organic layer was dried over anhydrous magnesium sulfate, filtered, and the filtrate was concentrated under reduced pressure. The resulting residue was purified by middle-pressure liquid chromatography (eluent, n-hexane:ethyl acetate=2:1, v/v) to obtain the entitled compound (362 mg, 87%) as a white solid.

MS (ESI) m/z: 338 (M+1)⁺.

¹H-NMR (CDCl₃) δ: 1.30 (1.44H, t, J=7.3 Hz), 1.38 (1.56H, t, J=7.1 Hz), 2.47 (3H, s), 3.19 (1.56H, s), 3.49 (1.44H, s), 3.68 (0.96H, q, J=7.3 Hz), 3.89 (1.04H, q, J=7.1 Hz), 7.25-7.28 (2H, m), 7.46-7.55 (3H, m).

IR (ATR): 2227, 1655, 1475, 1400, 1128, 1107 cm⁻¹.

Example 132

4-Cyano-7-[(3S)-3-(dimethylamino)pyrrolidin-1-yl]-N-ethyl-N,5-dimethyl-6-phenyl-1,3-benzoxazole-2-carboxamide (#132)

Under nitrogen atmosphere, a dimethyl sulfoxide (1 ml) solution of (3S)-3-(dimethylamino)pyrrolidine (80 μl, 633 μmol) was added at 140 to 150° C. to a dimethyl sulfoxide (10 ml) solution of 4-cyano-N-ethyl-7-fluoro-N,5-dimethyl-6-phenyl-1,3-benzoxazole-2-carboxamide (I-285) (178 mg, 528 μmol) and triethylamine (96 μl, 686 μmol), followed by stirring at the same temperature for 165 minutes. After cooling, saturated brine was added to the reaction liquid, and the reaction liquid was extracted with ethyl acetate. Next, the combined organic layer was washed with saturated brine, then dried over anhydrous magnesium sulfate, filtered, and the filtrate was concentrated under the reduced pressure. The resulting residue was purified by preparative TLC (eluent, dichloromethane:methanol=10:1, v/v) to obtain the entitled compound (119 mg, 52%) as an amorphous substance.

MS (ESI) m/z: 432 (M+1)⁺.

¹H-NMR (CDCl₃) δ: 1.28 (1.5H, t, J=7.1 Hz), 1.36 (1.5H, t, J=7.1 Hz), 1.55-1.72 (1H, m), 1.93-2.01 (1H, m), 2.08 (6H, s), 2.22 (3H, s), 2.43, 2.53 (1H, m), 2.71-2.78 (1H, m), 3.16 (1.5H, s), 3.19-3.25 (1H, m), 3.51 (1.5H, s), 3.56-3.70 (3H, m), 3.94 (1H, q, J=7.2 Hz), 7.10-7.14 (1H, m), 7.24-7.28 (1H, m), 7.34-7.45 (3H, m).

IR (ATR): 2212, 1651, 1604, 1471, 1439, 1396, 1365, 1304, 1115 cm⁻¹.

Anal. Calcd for C₂₅H₂₉N₅O₂ 0.25H₂O: C, 68.86; H, 6.82; N, 16.06. Found: C, 68.71; H, 6.68; N, 15.80.

Example 133

4-Cyano-N-ethyl-N,5-dimethyl-7-[(3S)-3-(methylamino)pyrrolidin-1-yl]-6-phenyl-1,3-benzoxazole-2-carboxamide (#133)

Under nitrogen atmosphere, a dimethyl sulfoxide (1 ml) solution of (3S)-3-(methylamino)pyrrolidine (67 μl, 633 μmol) was added at 140 to 150° C. to a dimethyl sulfoxide (10 ml) solution of 4-cyano-N-ethyl-7-fluoro-N,5-dimethyl-6-phenyl-1,3-benzoxazole-2-carboxamide (I-285) (178 mg, 528 μmol) and triethylamine (96 μl, 686 μmol), followed by stirring at the same temperature for 160 minutes. After cooling, saturated brine was added to the reaction liquid, and the reaction liquid was extracted with ethyl acetate. Next, the combined organic layer was washed with saturated brine, then dried over anhydrous magnesium sulfate, filtered, and the filtrate was concentrated under the reduced pressure. The resulting residue was purified by preparative TLC (eluent, dichloromethane:methanol=10:1, v/v) to obtain the entitled compound (71 mg, 32%) as an amorphous substance.

MS (ESI) m/z: 418 (M+1)⁺.

¹H-NMR (CDCl₃) δ: 1.28 (1.5H, t, J=7.2 Hz), 1.37 (1.5H, t, J=7.1 Hz), 1.55-1.65 (1H, m), 1.86-1.95 (1H, m), 2.22 (3H, s), 2.30 (3H, s), 2.90-2.96 (1H, m), 3.03-3.10 (1H, m), 3.16 (1.5H, s), 3.26-3.33 (1H, m), 3.37-3.54 (2H, m), 3.52 (1.5H, s), 3.65 (1H, q, J=7.2 Hz), 3.95 (1H, q, J=7.1 Hz), 7.18-7.21 (2H, m), 7.34-7.44 (3H, m).

IR (ATR): 2210, 1649, 1604, 1468, 1439, 1394, 1365, 1304, 1115 cm⁻¹.

Anal. Calcd for C₂₄H₂₇N₅O₂.0.5H₂O: C, 67.59; H, 6.62; N, 16.42. Found: C, 67.50; H, 6.46; N, 16.10.

Reference Example 286 tert-Butyl (2-fluoroethyl)carbamate (I-286)

2-Fluoroethylamine (2 g, 20.1 mmol) was dissolved in dichloromethane (100 ml), then triethylamine (4.3 ml, 30.2 mmol) and di-t-dibutyl carbonate (5.36 g, 24.12 mmol) was added, followed by stirring at room temperature for 20 minutes. The reaction liquid was washed with an aqueous saturated sodium hydrogencarbonate solution and saturate brine. The organic layer was dried over anhydrous magnesium sulfate, then the solvent was evaporated away under reduced pressure. The resulting residue was purified by silica gel column chromatography (eluent, ethyl acetate:n-hexane=1:1, v/v) to obtain the entitled compound (3.26 g, 100%) as a colorless oil.

¹H-NMR (CDCl₃) δ: 1.45 (9H, s), 1.53 (3H, s), 3.36-3.49 (2H, m), 4.41 (1H, t, J=4.8 Hz), 4.53 (1H, t, J=4.8 Hz), 4.95 (1H, s).

Reference Example 287 tert-Butyl (2-fluoroethyl)methylcarbamate (I-287)

Under nitrogen atmosphere, tert-butyl (2-fluoroethyl)carbamate (I-286) (2 g, 20.1 mmol) was dissolved in N,N-dimethylformamide (50 ml), then sodium hydride (55%, w/w) (803 mg, 18.4 mmol) was added to the solution at 0° C., followed by stirring at 0° C. for 30 minutes. After 30 minutes, iodomethane (1.2 ml, 19.7 mmol) was added, followed by stirring at room temperature for 19 hours. Ethyl acetate was added to the reaction liquid, followed by washing with saturated brine. The organic layer was dried over anhydrous magnesium sulfate, then the solvent was evaporated away under reduced pressure. The resulting residue was purified by silica gel column chromatography (eluent, n-hexane:ethyl acetate=3:1, v/V) to obtain the entitled compound (970 mg, 45%) as a white crystal.

¹H-NMR (CDCl₃) δ: 1.46 (9H, s), 2.95 (3H, s), 3.43-3.58 (2H, m), 4.43-4.63 (2H, m).

Reference Example 288

2-Fluoro-N-methylethanamine hydrochloride (I-288)

4 N Hydrochloric acid/1,4-dioxane (20 ml) was added to tert-butyl (2-fluoroethyl)methylcarbamate (I-287) (950 mg, 5.36 mmol), followed by stirring at room temperature for 4 hours. After the reaction, the solvent was evaporated away under reduced pressure to obtain the entitled compound (325 mg, 53%) as a white crystal.

Reference Example 289

4-Cyano-7-fluoro-N-(2-fluoroethyl)-N,5-dimethyl-6-phenyl-1,3-benzoxazole-2-carboxyamide (I-289)

2-Fluoro-N-methylethanamine hydrochloride (I-288) (143 mg, 1.86 mmol) was dissolved in dichloromethane (20 ml), then trimethylaluminium (1.03 M n-hexane solution) (1.8 ml, 1.86 mmol) was dropwise added, followed by stirring at room temperature for 30 minutes. Ethyl 4-cyano-fluoro-5-methyl-6-phenyl-benzoxazole-2-carboxylate (I-111) (200 mg, 0.62 mmol) dissolved in dichloromethane (10 ml) was dropwise added to the solution, followed by stirring at room temperature for 20 hours. Aqueous 1 N hydrochloric acid solution was added to the reaction liquid, followed by stirring at room temperature for 10 minutes. This was diluted with chloroform, and washed with saturated brine. The obtained organic layer was dried over anhydrous magnesium sulfate, the solvent was evaporated away under reduced pressure. The resulting residue was purified by silica gel column chromatography (eluent, ethyl acetate:n-hexane=1:2, v/v) to obtain the entitled compound (50 mg, 22%) as a white crystal.

$^1$H-NMR (CDCl$_3$) δ: 2.48 (6H, s), 3.82-3.98 (2H, m), 4.35-4.39 (1H, m), 4.71-4.74 (1H, m), 4.81-4.86 (1H, m), 7.25-7.28 (2H, m), 7.49-7.55 (3H, m).

Example 134

4-Cyano-N-(2-fluoroethyl)-N,5-dimethyl-7-[(3S)-3-(methylamino)pyrrolidin-1-yl]-6-phenyl-1,3-benzoxazole-2-carboxamide (#134)

4-Cyano-7-fluoro-N-(2-fluoroethyl)-N,5-dimethyl-6-phenyl-1,3-benzoxazole-2-carboxyamide (I-289) (50 mg, 0.14 mmol) and triethylamine (26 μl, 0.18 mmol) were dissolved in dimethyl sulfoxide (3 ml), and at 150° C., (3S)-3-(methylamino)pyrrolidine (16 μl, 0.15 mmol) was added at 150° C., followed by stirring under nitrogen atmosphere at 150° C. for 1 hour. After cooled, this was concentrated under reduced pressure, diluted with chloroform, and washed with saturated brine. The organic layer was dried over anhydrous magnesium sulfate, then the solvent was evaporated away under reduced pressure. The resulting residue was purified by preparative TLC (eluent, chloroform:methanol 4:1, v/v) to obtain the entitled compound (5 mg, 9%) as a brown oil.

MS (ESI) m/z: 436 (M+1)$^+$.

$^1$H-NMR (CDCl$_3$) δ: 1.62-1.68 (1H, m), 1.87-1.97 (1H, m), 2.22 (3H, s), 2.32 (3H, s), 2.62 (3H, s), 2.95-3.14 (2H, m), 3.30-3.53 (3H, m), 3.84-3.96 (1H, m), 4.29-4.41 (1H, m), 4.66-4.90 (1H, m), 7.17-7.21 (2H, m), 7.34-7.45 (3H, m).

IR (ATR): 2208, 1646, 1600, 1465, 1363, 1211, 1007, 704 cm$^{-1}$.

Reference Example 290

(1R*,2R*)-2-(4-Cyano-fluoro-5-methyl-6-phenyl-benzoxazol-2-yl)-cyclopropanecarbonyldimethylamide (I-290)

Dimethylamine hydrochloride (228 mg, 2.8 mmol) was dissolved in dichloromethane (30 ml), then trimethylaluminium (1.03 M n-hexane solution) (2.7 ml, 2.8 mmol) was dropwise added, followed by stirring at room temperature for 30 minutes. Ethyl (1R*,2R*)-2-(4-cyano-fluoro-5-methyl-6-phenyl-benzoxazol-2-yl)-cyclopropanecarboxylate (I-216) (340 mg, 0.93 mmol) dissolved in dichloromethane (10 ml) was dropwise added to the solution, followed by stirring at room temperature for 19 hours. Aqueous 1 N hydrochloric acid solution was added to the reaction liquid, followed by stirring at room temperature for 10 minutes. This was diluted with chloroform, and washed with saturated brine. The obtained organic layer was dried over anhydrous magnesium sulfate, and the solvent was evaporated away under reduced pressure. The resulting residue was purified by silica gel column chromatography (eluent, ethyl acetate:n-hexane=1:2, v/v) to obtain the entitled compound (277 mg, 82%) as a white amorphous substance.

$^1$H-NMR (CDCl$_3$) δ: 1.71-1.86 (2H, m), 2.41 (1.6H, s), 2.63 (1.4H, s), 2.68-2.75 (1H, m), 2.81-2.90 (1H, m), 3.02 (3H, s), 3.22 (3H, s), 6.97-7.01 (1H, m), 7.22-7.26 (2H, m), 7.43-7.54 (3H, m).

Example 135

(1R*,2R*)-2-[4-Cyano-7-((S)-3-dimethylamino-pyrrolidinyl)-5-methyl-6-phenyl-benzoxazol-2-yl]-cyclopropanecarbonyldimethylamide (#135)

A dimethyl sulfoxide (1 ml) solution of (3S)-3-(methylamino)pyrrolidine (115 μl, 0.91 mmol) was added to a dimethyl sulfoxide (15 ml) solution of (1R*,2R*)-2-(4-cyano-fluoro-5-methyl-6-phenyl-benzoxazol (I-290) (275 mg, 0.76 mmol) and methylamine (137 μl, 0.98 mmol) at 150° C., followed by stirring at the same temperature for 1 hour. After cooling, the reaction liquid was concentrated under reduced pressure, then saturated brine was added to the residue, and the reaction liquid was extracted with chloroform. After drying over anhydrous magnesium sulfate and filtration, the filtrate was concentrated under reduced pressure. The resulting residue was purified by preparative TLC (eluent, chloroform:methanol=10:1, v/v) to obtain the entitled compound (89 mg, 26%) as a white solid.

mp: 105-108° C.

MS (ESI) m/z: 458 (M+1)$^+$.

$^1$H-NMR (CDCl$_3$) δ: 1.57-1.66 (5H, m), 1.68-1.76 (2H, m), 1.90-2.00 (1H, m), 2.12 (6H, s), 2.18 (3H, s), 2.45-2.56 (1H, m), 2.62-2.80 (2H, m), 2.86-2.94 (1H, m), 3.01 (3H, s), 3.22 (3H, s), 3.25-3.45 (3H, m), 7.08-7.13 (1H, m), 7.21-7.25 (1H, m), 7.32-7.43 (3H, m).

IR (ATR): 2210, 1639, 1587, 1467, 1398, 1363, 1139, 702 cm$^{-1}$.

Anal. Calcd for $C_{27}H_{31}N_5O_2 \cdot 0.75H_2O$: C, 68.84; H, 6.95; N, 14.87. Found: C, 69.08; H, 6.99; N, 14.97.

Reference Example 291

(1S*,2S*)-2-(4-Cyano-7-fluoro-5-methyl-6-phenyl-1,3-benzoxazol-2-yl)cyclopropanecarboxyamide (I-291)

Ammonium chloride (881 mg, 16.5 mmol) was dissolved in toluene (20 ml), then trimethylaluminium (1.03 M n-hexane solution) (16 ml, 16.5 mmol) was dropwise added, followed by stirring at room temperature for 30 minutes. Ethyl (1S*,2S*)-4-cyano-fluoro-5-methyl-6-phenyl-benzoxazole-2-carboxylate (I-216) (2 g, 5.49 mmol) dissolved in toluene (10 ml) was dropwise added to the solution, followed by stirring at 100° C. for 3 hours. Aqueous 1 N hydrochloric acid solution was added to the reaction liquid, followed by stirring at 0° C. for 1 hour. Ethyl acetate was added to the reaction liquid, followed by washing with saturated brine. The organic layer was dried over anhydrous magnesium sulfate, then the solvent was evaporated away under reduced pressure. A mixture liquid of ethyl acetate:hexane (1:1, v/v) was added to the resulting residue to be in suspension. The suspension was filtered to obtain the entitled compound (800 mg, 44%) as a white crystal.

$^1$H-NMR (CDCl$_3$) δ: 1.72-1.80 (1H, m), 1.82-1.89 (1H, m), 2.41 (3H, s), 2.40-2.45 (1H, m), 2.82-2.88 (1H, m), 7.22-7.26 (1H, m), 7.44-7.53 (1H, m).

Example 136

(1S*,2S*)-2-{4-Cyano-7-[(3S)-3-dimethylamino) pyrrolidin-1-yl]-5-methyl-6-phenyl-1,3-benzoxazol-2-yl}cyclopropanecarboxyamide (#136)

(3S)-3-(Dimethylamino)pyrrolidine (41 μl, 0.36 mmol) was added at 150° C. to a dimethyl sulfoxide (5 ml) solution of (1S*,2S*)-2-(4-cyano-7-fluoro-5-methyl-6-phenyl-1,3-benzoxazol-2-yl)cyclopropanecarboxyamide (I-291) (100 mg, 0.30 mmol) and triethylamine (54 μl, 0.39 mmol), followed by stirring at the same temperature for 30 minutes. After cooled, this was concentrated under reduced pressure, diluted with ethyl acetate, washed with saturated brine. The organic layer was dried over anhydrous magnesium sulfate, then the solvent was evaporated away under reduced pressure. The resulting residue was purified by preparative TLC (eluent, chloroform:methanol=5:1, y/v) to obtain the entitled compound (24 mg, 19%) as a white crystal.

MS (ESI) m/z: 430 (M+1)$^+$.

$^1$H-NMR (CDCl$_3$) δ: 1.53-1.70 (2H, m), 1.73-1.80 (1H, m), 1.90-2.00 (1H, m), 2.11 (3H, s), 2.13 (3H, s), 2.15 (3H, s), 2.43-2.55 (2H, m), 2.69-2.77 (1H, m), 2.83-2.97 (1H, m), 3.22-3.47 (2H, m), 5.88 (1H, brs), 6.39 (1H, brs), 7.07-7.11 (1H, m), 7.20-7.25 (1H, m), 7.31-7.44 (1H, m).

IR (ATR): 1952, 2208, 1668, 1585, 1467, 1363, 1299, 1155, 908, 702 cm$^{-1}$.

Anal. Calcd for C$_{25}$H$_{27}$N$_5$O$_2$.0.5H$_2$O: C, 68.57; H, 6.44; N, 15.97. Found: C, 68.98; H, 6.52; N, 15.57.

Example 137

2-Cyclopropyl-5-methyl-7-[(3S)-3-(methylamino) pyrrolidin-1-yl]-6-phenyl-1,3-benzoxazole-4-carbonitrile (#137)

2-Cyclopropyl-7-fluoro-5-methyl-6-phenylbenzoxazole-4-carbonitrile (I-173) (250 mg, 0.86 mmol) was dissolved in dimethyl sulfoxide (5 ml), then at room temperature, triethylamine (155 μl, 1.11 mmol) and (3S)-3-(methylamino)pyrrolidine (119 μl, 1.11 mmol) were added. After stirred under nitrogen atmosphere at 90° C. for 13 hours, this was cooled to room temperature. The reaction liquid was fractionated with ethyl acetate and an aqueous saturated sodium hydrogencarbonate solution. The aqueous layer was further extracted twice with ethyl acetate. The organic layers were combined, washed with saturated brine, and dried over anhydrous sodium sulfate. The insoluble matter was separated by filtration, then the solvent was evaporated away, and the resulting residue was purified by preparative TLC (eluent, chloroform:methanol=93:7, v/v) to obtain the entitled compound (201 mg, 63%) as a white solid.

MS (ESI) m/z: 373 (M+1)$^+$.

HRMS (EI) m/z: 372.1944 (Calcd for C$_{23}$H$_{24}$N$_4$O 372.1950).

$^1$H-NMR (CDCl$_3$) δ: 1.17-1.30 (4H, m), 1.59 (1H, dq, J=6.6, 6.6 Hz), 1.87-1.96 (1H, m), 2.17 (3H, s), 2.20-2.27 (1H, m), 2.32 (3H, s), 2.92 (1H, dd, J=5.1, 10.0 Hz), 3.07 (1H, dq, J=5.1, 5.1 Hz), 3.20-3.27 (2H, m), 3.32-3.38 (1H, m), 7.16-7.20 (2H, m), 7.32-7.42 (3H, m).

IR (ATR): 3346, 2200, 1608, 1587, 1562, 1465, 1438, 1365, 1340, 1302 cm$^{-1}$.

Anal. Calcd for C$_{23}$H$_{24}$N$_4$O.0.25H$_2$O: C, 73.28; H, 6.55; N, 14.86. Found: C, 73.46; H, 6.43; N, 14.68.

Example 138

2-Cyclopropyl-7-[(3S)-3-(ethylamino)pyrrolidin-1-yl]-5-methyl-6-phenyl-1,3-benzoxazole-4-carbonitrile (#138)

(3S)-3-(Ethylamino)pyrrolidine (85 μl, 0.684 mmol) and triethylamine (95 μl, 0.684 mmol) were added to a dimethyl sulfoxide (2 ml) solution of 2-cyclopropyl-7-fluoro-5-methyl-6-phenyl-1,3-benzoxazole-4-carbonitrile (I-173) (100 mg, 0.342 mmol), followed by stirring in an oil bath at 95° C. for 3 hours. The reaction liquid was concentrated under reduced pressure, then the residue was dissolved in ethyl acetate, and washed with water and saturated brine. After drying over anhydrous sodium sulfate, the insoluble matter was separated by filtration, and the residue obtained by concentration was purified by preparative TLC (eluent, chloroform:methanol=10:1, v/v), and the obtained eluate was purified in slurry with isopropyl ether to obtain the entitled compound (31.0 mg, 23%) as a white solid.

mp: 209-211° C.

MS (ESI) m/z: 387 (M+1)$^+$.

$^1$H-NMR (CDCl$_3$) δ: 1.14-1.38 (7H, m), 2.02-2.17 (2H, m), 2.19 (3H, s), 2.21-2.29 (1H, m), 2.64-2.81 (2H, m), 3.09-3.19 (1H, m), 3.35-3.53 (4H, m), 7.15-7.22 (2H, m), 7.33-7.48 (3H, m).

IR (ATR): 3055, 3018, 2966, 2871, 2821, 2210, 1606, 1587, 1562, 1468, 1441, 1400, 1365, 1302, 1267, 1227, 1142, 1065, 1030, 957, 874, 818, 783 cm$^{-1}$.

Anal. Calcd for C$_{24}$H$_{26}$N$_4$O.0.5H$_2$O: C, 72.89; H, 6.88; N, 14.17. Found: C, 72.66; H, 6.84; N, 13.75.

Example 139

2-Cyclopropyl-7-{[2-(dimethylamino)ethyl](methyl) amino)}-5-methyl-6-phenyl-1,3-benzoxazole-4-carbonitrile (#139)

N,N,N'-Trimethylethylenediamine (177 μl, 1.37 mmol) and triethylamine (191 μl, 1.37 mmol) were added to a dimethyl sulfoxide (5 ml) solution of 2-cyclopropyl-7-fluoro-5-methyl-6-phenyl-1,3-benzoxazole-4-carbonitrile (I-173) (200 mg, 0.684 mmol), followed by stirring in an oil bath at 100° C. for 2 hours. Water was added to the reaction liquid, followed by extraction with ethyl acetate, and the obtained organic layer was washed with water and saturated brine. After drying over anhydrous sodium sulfate, the insoluble matter was separated by filtration, and the residue obtained by concentration was purified by preparative TLC (eluent, chloroform:methanol=10:1, v/v), and the obtained eluate was recrystallized with isopropyl ether/n-hexane to obtain the entitled compound (6.00 mg, 2%) as a white solid.

MS (FAB) m/z: 375 (M+1)$^+$.

HRMS (FAB) m/z: 375.2190 (Calcd for C$_{23}$H$_{27}$N$_4$O 375.2185).

$^1$H-NMR (CDCl$_3$) δ: 1.18-1.35 (4H, m) 2.10 (6H, s), 2.03-2.14 (2H, m), 2.26 (3H, s), 2.23-2.31 (1H, m), 2.70 (3H, s), 3.07 (2H, t, J=7.07 Hz), 7.17-7.20 (2H, m), 7.32-7.39 (1H, m), 7.40-7.47 (2H, m).

IR (ATR): 2968, 2941, 2858, 2817, 2767, 2214, 1606, 1591, 1562, 1485, 1456, 1396, 1365, 1298, 1269, 1174, 1138, 1084, 1028, 982, 951, 879 cm$^{-1}$.

Reference Example 292

5-Bromomethyl-2-cyclopropyl-7-fluoro-6-phenyl-1,3-benzoxazole-4-carbonitrile (I-292)

Under nitrogen atmosphere, a carbon tetrachloride (12 ml) solution of 2-cyclopropyl-7-fluoro-5-methyl-6-phenyl-1,3-benzoxazole-4-carbonitrile (I-173) (1.00 g, 3.42 mmol), N-bromosuccinimide (913 mg, 5.13 mmol) and 2,2'-azobis(isobutyronitrile) (56 mg, 342 μmol) was stirred at 80° C. for 13 hours. After cooling, the solvent was evaporated away under reduced pressure, and the resulting residue was purified by middle-pressure liquid chromatography (eluent, n-hexane:ethyl acetate=5:1, v/v) to obtain the entitled compound (1.04 g, 82%) as a white solid.

MS (ESI) m/z: 371, 373 (M+1)$^+$.

$^1$H-NMR (CDCl$_3$) δ: 1.29-1.35 (2H, m), 1.39-1.45 (2H, m), 2.28-2.36 (1H, m), 4.50 (2H, s), 7.36-7.42 (2H, m), 7.50-7.55 (3H, m).

IR (ATR): 2227, 1566, 1469, 1415, 1325, 1265, 1219, 1122, 1036 cm$^{-1}$.

Reference Example 293

2-Cyclopropyl-7-fluoro-5-fluoromethyl-6-phenyl-1,3-benzoxazole-4-carbonitrile (I-293)

Under nitrogen atmosphere at 0° C., tetra(n-butyl)ammonium fluoride (1.0 M tetrahydrofuran solution) (1.50 ml, 1.50 mmol) was added to a tetrahydrofuran (12 ml) solution of 5-bromomethyl-2-cyclopropyl-7-fluoro-6-phenyl-1,3-benzoxazole-4-carbonitrile (I-292) (426 mg, 1.15 mmol), followed by stirring with cooling with water for 1.5 hours. The solvent was evaporated away under reduced pressure, then the resulting residue was purified by middle-pressure liquid chromatography (eluent, n-hexane:ethyl acetate=4:1, v/v) to obtain the entitled compound (212 mg, 59%) as a colorless oil.

MS (ESI) m/z: 311 (M+1)$^+$.

$^1$H-NMR (CDCl$_3$) δ: 1.30-1.37 (2H, m), 1.41-1.47 (2H, m), 2.29-2.38 (1H, m), 5.37 (2H, d, J=47.6 Hz), 7.30-7.37 (2H, m), 7.47-7.53 (3H, m).

Example 140

2-Cyclopropyl-5-fluoromethyl-7-[(3S)-3-(methylamino)pyrrolidin-1-yl]-6-phenyl-1,3-benzoxazole-4-carbonitrile (#140)

Under nitrogen atmosphere at 130° C., (3S)-3-(methylamino)pyrrolidine (85 μl, 801 μmol) was added to a dimethyl sulfoxide (7 ml) solution of 2-cyclopropyl-7-fluoro-5-fluoromethyl-6-phenyl-1,3-benzoxazole-4-carbonitrile (I-293) (207 mg, 667 μmol) and triethylamine (121 μl, 867 μmol), followed by stirring at the same temperature for 30 minutes. After cooling, saturated brine was added to the reaction liquid, and the mixture liquid was extracted with ethyl acetate. Next, the combined organic layer was washed with saturated brine, then dried over anhydrous magnesium sulfate, filtered, and the filtrate was concentrated under reduced pressure. The resulting residue was purified by middle-pressure liquid chromatography (eluent, dichloromethane:methanol=5:1, v/v) to obtain a crude product of the entitled compound. The crude product of the entitled compound was dissolved in ethyl acetate, washed with an aqueous saturated sodium hydrogencarbonate solution, then the aqueous layer was extracted with ethyl acetate. The combined organic layer was dried over anhydrous magnesium sulfate, filtered, and the filtrate was concentrated under reduced pressure to obtain the entitled compound (62 mg, 24%) as an amorphous substance.

MS (ESI) m/z: 391 (M+1)$^+$.

$^1$H-NMR (CDCl$_3$) δ: 1.18-1.34 (4H, m), 1.48-1.65 (1H, m), 1.86-1.97 (1H, m), 2.21-2.29 (1H, m), 2.32 (3H, s), 2.92 (1H, dd, J=10.0, 4.9 Hz), 3.03-3.11 (1H, m), 3.21-3.30 (2H, m), 3.35-3.43 (1H, m), 5.17 (2H, d, J=47.6 Hz), 7.23-7.29 (2H, m), 7.36-7.42 (3H, m).

IR (ATR): 2210, 1604, 1587, 1560, 1466, 1441, 1385, 1360 cm$^{-1}$.

Anal. Calcd for C$_{23}$H$_{23}$FN$_4$O.0.25H$_2$O: C, 69.94; H, 6.00; N, 14.19; F, 4.81. Found: C, 70.25; H, 5.94; N, 13.75; F, 4.44.

Reference Example 294

Dimethyl 2-(4-cyano-2-cyclopropyl-5-methyl-6-phenyl-1,3-benzoxazol-7-yl)malonate (I-294)

2-Cyclopropyl-7-fluoro-5-methyl-6-phenyl-1,3-benzoxazole-4-carbonitrile (I-173) (2.69 g, 9.20 mmol) was dissolved in dimethyl sulfoxide (50 ml), then at room temperature, potassium carbonate (3.82 g, 27.61 mmol) and dimethyl malonate (2.1 ml, 18.41 mmol) were added. The solution was stirred under nitrogen atmosphere at 90° C. for 14 hours. The reaction liquid was cooled to room temperature, then ethyl acetate and water were added to the reaction liquid, followed by vigorously stirring for 10 minutes. The aqueous layer was separated, extracted twice with ethyl acetate. The organic layers were combined, washed with saturated brine, then dried over anhydrous sodium sulfate. The insoluble matter was separated by filtration, the solvent was evaporated away, and the resulting residue was purified by middle-pressure liquid chromatography (eluent, n-hexane:ethyl acetate=3:1, v/v) to obtain the entitled compound (2.878 g, 77%) as a colorless gel MS (ESI) m/z: 405 (M+1)$^+$.

HRMS (EI) m/z: 404.1337 (Calcd for C$_{23}$H$_{20}$N$_2$O$_5$ 404.1373).

$^1$H-NMR (CDCl$_3$) δ: 1.22-1.33 (4H, m), 2.23-2.31 (1H, m), 2.29 (3H, s), 3.70 (6H, s), 4.56 (1H, s), 7.07-7.11 (2H, m), 7.42-7.51 (3H, m).

IR (ATR): 2227, 1739, 1566, 1435, 1404, 1296, 1254, 1194, 1151, 1120, 1028, 750, 712 cm$^{-1}$.

Reference Example 295

Methyl (4-cyano-2-cyclopropyl-5-methyl-6-phenyl-1,3-benzoxazol-7-yl)acetate (I-295)

Dimethyl 2-(4-cyano-2-cyclopropyl-5-methyl-6-phenyl-1,3-benzoxazol-7-yl)malonate (I-294) (2.887 g, 7.11 mmol) was dissolved in dimethyl sulfoxide (50 ml) and water (5 ml), then at room temperature, magnesium chloride (2.03 g, 21.34 mmol) was added. The solution was stirred at 90° C. for 23 hours, then cooled to room temperature. The solvent was evaporated away under reduced pressure, the residue was fractionated with ethyl acetate and saturated brine. The aqueous layer was separated, extracted twice with ethyl acetate. The organic layers were combined, washed with saturated brine, and dried over anhydrous sodium sulfate. The insoluble matter was separated by filtration, the solvent was evaporated away, and the resulting residue was purified by middle-pressure liquid chromatography (eluent, n-hexane:ethyl acetate=3:1, v/v) to obtain the entitled compound (2.216 g, 90%) as a pale yellow solid.

MS (ESI) m/z: 347 (M+1)$^+$.

HRMS (EI) m/z: 346.1295 (Calcd for $C_{21}H_{18}N_2O_3$ 346.1318).

$^1$H-NMR (CDCl$_3$) δ: 1.21-1.38 (4H, m), 2.23-2.32 (1H, m), 2.30 (3H, s), 3.60 (3H, s), 3.62 (2H, s), 7.08-7.12 (2H, m), 7.39-7.48 (3H, m).

IR (ATR): 2222, 1740, 1556, 1398, 1342, 1294, 1234, 1161, 1151, 1101, 885, 710 cm$^{-1}$.

Reference Example 296

Methyl 2-(4-cyano-2-cyclopropyl-5-methyl-6-phenyl-1,3-benzoxazol-7-yl)pent-4-enate (I-296)

Methyl (4-cyano-2-cyclopropyl-5-methyl-6-phenyl-1,3-benzoxazol-7-yl)acetate (I-295) (2.215 g, 6.40 mmol) was dissolved in tetrahydrofuran (45 ml), and under nitrogen atmosphere at −78° C., potassium hexamethyldisilazide (0.5 M toluene solution) (19.2 ml, 9.59 mmol) was dropwise added, taking 10 minutes. After stirring at the same temperature for 1 hour, allyl bromide (847 μl, 9.59 mmol) was gradually added. The solution was gradually warmed up to 0° C., taking 1.5 hours, followed by stirring at the same temperature for 2 hours. At 0° C., aqueous saturated ammonium chloride solution was added to the solution, followed by stirring for 15 minutes. Under reduced pressure, THF was evaporated away, and the residue was extracted three times with ethyl acetate. The organic layers were combined, washed with saturated brine, and dried over anhydrous sodium sulfate. The insoluble matter was separated by filtration, the solvent was evaporated away, and the resulting residue was purified by middle-pressure liquid chromatography (eluent, n-hexane:ethyl acetate=4:1, v/v) to obtain the entitled compound (1.709 g, 69%) as a colorless gel. 410 mg (18.5%) of unreacted methyl (4-cyano-2-cyclopropyl-5-methyl-6-phenyl-1,3-benzoxazol-7-yl)acetate was recovered.

MS (ESI) m/z: 387 (M+1)$^+$.

HRMS (EI) m/z: 386, 1614 (Calcd for $C_{24}H_{22}N_2O_3$ 386.1631).

$^1$H-NMR (CDCl$_3$) δ: 1.22-1.37 (4H, m), 2.27 (3H, s), 2.27-2.34 (1H, m), 2.62-2.70 (1H, m), 2.77-2.87 (1H, m), 3.63 (3H, s), 3.66 (1H, dd, J=6.6, 9.0 Hz), 4.80 (1H, dd, J=1.2, 17.1 Hz), 4.84 (1H, dd, J=1.2, 10.0 Hz), 5.42-5.53 (1H, m), 7.08-7.12 (1H, m), 7.15-7.20 (1H, m), 7.40-7.50 (3H, m).

IR (ATR): 2225, 1736, 1562, 1402, 1194, 1173, 781, 754, 708 cm$^{-1}$.

Reference Example 297

2-Cyclopropyl-7-(1-hydroxymethylbut-3-enyl)-5-methyl-6-phenyl-1,3-benzoxazole-4-carbonitrile (I-297)

Methyl 2-(4-cyano-2-cyclopropyl-5-methyl-6-phenyl-1,3-benzoxazol-7-yl)pent-4-enate (I-296) (100 mg, 0.26 mmol) was dissolved in tetrahydrofuran (2 ml), then under nitrogen atmosphere at −78° C., Super Hydride (1.0 M tetrahydrofuran solution) (570 μl, 0.52 mmol) was dropwise added. After stirring at the same temperature for 2 hours, aqueous saturated ammonium chloride solution was added, followed by further stirring at room, temperature for 10 minutes. The solution was extracted three times with ethyl acetate. The organic layers were combined, washed with saturated brine, dried over anhydrous sodium sulfate. The insoluble matter was separated by filtration, the solvent was evaporated away, and the resulting residue was purified by middle-pressure liquid chromatography (eluent, n-hexane:ethyl acetate=2:1, v/v) to obtain the entitled compound (88 mg, 95%) as a colorless gel.

MS (ESI) m/z: 359 (M+1)$^+$.

$^1$H-NMR (CDCl$_3$) δ: 1.22-1.37 (4H, m), 1.78-1.83 (1H, br), 2.21 (3H, s), 2.23-2.31 (1H, m), 2.41-2.59 (2H, m), 2.96 (1H, ddd, J=6.6, 8.5, 14.9 Hz), 3.78-3.87 (1H, m), 3.90-4.00 (1H, m), 4.78-4.88 (2H, m), 5.42-5.53 (1H, m), 7.06-7.10 (1H, m), 7.16-7.20 (1H, m), 7.37-7.48 (3H, m).

Reference Example 298

2-Cyclopropyl-7-(1-iodomethylbut-3-enyl)-5-methyl-6-phenyl-1,3-benzoxazole-4-carbonitrile (I-298)

Imidazole (321 mg, 4.71 mmol), triphenyl phosphine (1.235 g, 4.71 mmol) and then iodine (956 mg, 3.77 mmol) were added to a solution of 2-cyclopropyl-7-(1-hydroxymethylbut-3-enyl)-5-methyl-6-phenyl-1,3-benzoxazole-4-carbonitrile (I-297) (675 mg, 1.88 mmol) dissolved in benzene (20 ml). The solution was stirred under nitrogen atmosphere at room temperature for 20 hours, then aqueous saturated sodium thiosulfate solution was added, followed by stirring at the same temperature for 10 minutes. The aqueous layer was separated, this was extracted three times with ethyl acetate. The organic layers were combined, washed with saturated brine, then dried over anhydrous sodium sulfate. The insoluble matter was separated by filtration, the solvent was evaporated away, and the resulting residue was purified by middle-pressure liquid chromatography (eluent, n-hexane: ethyl acetate=19:1, v/v) to obtain the entitled compound (707 mg, 80%).

MS (ESI) m/z: 469 (M+1)$^+$.

$^1$H-NMR (CDCl$_3$) δ: 1.25-1.37 (4H, m), 2.23 (3H, s), 2.25-2.38 (1H, m), 2.45-2.57 (2H, m), 3.03 (1H, dq, J=6.3, 10.0 Hz), 3.42 (1H, dd, J=6.3, 10.0 Hz), 3.60 (1H, t, J=10.0 Hz), 4.82-4.92 (2H, m), 5.38-5.50 (1H, m), 7.04-7.08 (1H, m), 7.26-7.30 (1H, m), 7.40-7.50 (3H, m).

Reference Example 299

7-(1-Allylbut-3-enyl)-2-cyclopropyl-5-methyl-6-phenyl-1,3-benzoxazole-4-carbonitrile (I-299)

Copper (I) iodide (52 mg, 0.27 mmol) was suspended in tetrahydrofuran (3 ml), and under nitrogen atmosphere at −30° C., vinylmagnesium bromide (1 M tetrahydrofuran solution) (2.72 ml, 2.72 mmol) was dropwise added. The solution was stirred at the same temperature for 30 minutes, then a solution of 2-cyclopropyl-7-(1 iodomethylbut-3-enyl)-5-methyl-6-phenyl-1,3-benzoxazole-4-carbonitrile (I-298) (425 mg, 0.91 mmol) dissolved in tetrahydrofuran (6 ml) was gradually added. After stirring at the same temperature for 1 hour and 20 minutes and heating up to 0° C., aqueous saturated ammonium chloride solution was added, followed by further stirring for 30 minutes. This was extracted three times with ethyl acetate. The organic layers were combined, washed with saturated brine, and dried over anhydrous sodium sulfate. The insoluble matter was separated by filtration, the solvent was evaporated away, and the resulting residue was purified by middle-pressure liquid chromatography (eluent, n-hexane:ethyl acetate=9:1, v/v) to obtain the entitled compound (243 mg, 73%) as a colorless gel.

MS (ESI) m/z: 369 (M+1)$^+$.

$^1$H-NMR (CDCl$_3$) δ: 1.22-1.38 (4H, m), 2.22 (3H, s), 2.29-2.43 (3H, m), 2.48-2.58 (2H, m), 2.68-2.78 (1H, m), 4.77-4.88 (4H, m), 5.40-5.52 (2H, m), 7.05-7.10 (2H, m), 7.40-7.48 (3H, m).

Reference Example 300

7-(Cyclopent-3-enyl)-2-cyclopropyl-5-methyl-6-phenyl-1,3-benzoxazole-4-carbonitrile (I-300)

At room temperature, Grubbs catalyst second generation (92 mg, 0.11 mol) was added to a solution of 7-(1-allylbut-3-enyl)-2-cyclopropyl-5-methyl-6-phenyl-1,3-benzoxazole-4-carbonitrile (I-299) (400 mg, 1.09 mmol) dissolved in dichloromethane; (108 ml). Under nitrogen atmosphere, the solution was stirred at 50° C. for 3.5 hours. After cooling to room temperature, the solvent was evaporated away under reduced pressure. The residue was purified by middle-pressure liquid chromatography (eluent, n-hexane:ethyl acetate=9:1, v/v) to obtain the entitled compound (282 mg, 76%) as a white solid.

MS (ESI) m/z: 341 (M+1)$^+$.

$^1$H-NMR (CDCl$_3$) δ: 1.19-1.30 (4H, m), 2.20-2.31 (1H, m), 2.26 (3H, s), 2.48-2.59 (2H, m), 2.60-2.70 (2H, m), 3.20 (1H, ddd, J=8.1, 9.5, 17.8 Hz), 5.72 (2H, s), 7.20-7.23 (2H, m), 7.38-7.48 (3H, m).

Reference Example 301

2-Cyclopropyl-7-[(1R*,3S*,4S*)-3-hydroxy-4-iodocyclopentyl]-5-methyl-6-phenyl-1,3-benzoxazole-4-carbonitrile (I-301)

7-Cyclopent-3-enyl-2-cyclopropyl-5-methyl-6-phenyl-1,3-benzoxazole-4-carbonitrile (I-300) (240 mg, 0.71 mmol) was dissolved in tetrahydrofuran (4.8 ml) and aqueous 0.25 M potassium dihydrogenphosphate solution (2.4 ml), and at 0° C., N-iodosuccinimide (476 mg, 2.12 mmol) was added. The solution was warmed from 0° C. up to room temperature, then stirred for 8.5 hours, and at 0° C., aqueous saturated sodium thiosulfate solution was added. The solution was extracted three times with ethyl acetate. The organic layers were combined, washed with saturated brine, and dried over anhydrous sodium sulfate. The insoluble matter was separated by filtration, the solvent was evaporated away, and the resulting residue was purified by middle-pressure liquid chromatography (eluent, n-hexane:ethyl acetate=2:1, v/v) to obtain the entitled compound (241 mg, 71%) as a white solid.

MS (ESI) m/z: 485 (M+1)$^+$

HRMS (EI) m/z: 484.0669 (Calcd for $C_{23}H_{21}IN_2O_2$ 484.0648).

$^1$H-NMR (CDCl$_3$) δ: 1.25-1.40 (4H, m), 1.88-1.97 (1H, m), 2.17-2.32 (3H, m), 2.25 (3H, s), 2.40 (1H, d, J=3.9 Hz), 2.61 (1H, ddd, J=6.8, 8.3, 14.6 Hz), 3.27 (1H, dq, J=8.3, 9.3 Hz), 4.32-4.41 (2H, m), 7.06-7.12 (2H, m), 7.41-7.51 (3H, m).

IR (ATR): 3502, 2225, 1560, 1066, 1045, 1026, 982, 945, 879, 754, 704 cm$^{-1}$.

Reference Example 302

2-Cyclopropyl-7-[(1S*,3R*)-3-hydroxycyclopentyl]-5-methyl-6-phenyl-1,3-benzoxazole-4-carbonitrile (I-302)

2-Cyclopropyl-7-[(1R*,3S*,4S*)-3-hydroxy-4-iodocyclopentyl]-5-methyl-6-phenyl-1,3-benzoxazole-4-carbonitrile (I-301) (240 mg, 0.50 mol) was dissolved in toluene (4.8 ml), then at room temperature, 2,2'-azobisisobutyronitrile (8 mg, 0.05 mmol) and tri-n-butyltin hydride (180 µl, 0.64 mmol) were added. The solution was heated under reflux under nitrogen atmosphere for 3 hours. Monitoring the reaction by TLC showed the remaining starting material, and the solution was cooled to room temperature and tri-n-butyltin hydride (89 µl, 0.32 mmol) was again added. After further heated under reflux for 1 hour, this was cooled to room temperature. The solvent was evaporated away under reduced pressure, and the resulting residue was combined with the entitled compound (I-302) separately synthesized according to a different method, and purified by middle-pressure liquid chromatography (eluent, n-hexane:ethyl acetate=1:1, v/v) to obtain the entitled compound (113 mg, 60%) as a colorless gel.

MS (ESI) m/z: 359 (M+1)$^+$

HRMS (EI) m/z: 358.1652 (Calcd for $C_{23}H_{22}N_2O_2$ 358.1681).

$^1$H-NMR (CDCl$_3$) δ: 1.23-1.39 (4H, m), 1.70-1.98 (5H, m), 2.16-2.23 (2H, m), 2.23 (3H, s), 2.26-2.33 (1H, m), 2.74-2.85 (1H, m), 4.26 (1H, q, J=5.1 Hz), 7.07-7.11 (2H, m), 7.39-7.49 (3H, m).

IR (ATR): 3420, 2225, 1562, 1404, 1294, 1030, 732, 712 cm$^{-1}$.

Reference Example 303

2-Cyclopropyl-5-methyl-7-(3-oxocyclopentyl)-6-phenyl-1,3-benzoxazole-4-carbonitrile (I-303)

2-Cyclopropyl-7-[(1S*,3R*)-3-hydroxycyclopentyl]-5-methyl-6-phenyl-1,3-benzoxazole-4-carbonitrile (I-302) (50 mg, 0.14 mmol) was dissolved in dichloromethane (1 ml), and at 0° C., Dess-Martin reagent (118 mg, 0.28 mmol) was added. The solution was stirred at room temperature for 3 hours, then again cooled at 0° C., and aqueous saturated sodium thiosulfate solution and an aqueous saturated sodium hydrogencarbonate solution were added, followed by further stirring for 10 minutes. The solution was extracted three times with dichloromethane. The organic layers were combined, washed with saturated brine, and dried over anhydrous sodium sulfate. The insoluble matter was separated by filtration, the solvent was evaporated away and the resulting residue was purified by middle-pressure liquid chromatography (eluent, n-hexane:ethyl acetate=3:1, v/v) to obtain the entitled compound (44 mg, 89%) as a white solid.

MS (ESI) m/z: 357 (M+1)$^+$

HRMS (EI) m/z: 356.1542 (Calcd for $C_{23}H_{20}N_2O_2$ 356.1524).

$^1$H-NMR (CDCl$_3$) δ: 1.23-1.35 (4H, m), 2.07-2.20 (2H, m), 2.23-2.51 (4H, m), 2.25 (3H, s), 2.74 (1H, ddd, J=1.5, 11.0, 18.3 Hz), 3.15-3.26 (1H, m), 7.08-7.17 (2H, m), 7.42-7.52 (3H, m).

IR (ATR): 2222, 1736, 1560, 1288, 1244, 1155, 1105, 1036, 949, 874, 781, 706 cm$^{-1}$.

Examples 141 and 142

2-Cyclopropyl-7-[(1R*,3R*)-3-(dimethylamino) cyclopentyl]-5-methyl-6-phenyl-1,3-benzoxazole-4-carbonitrile (#141) and 2-Cyclopropyl-7-[(1R*,3S*)-3-(dimethylamino)cyclopentyl]-5-methyl-6-phenyl-1,3-benzoxazole-4-carbonitrile (#142)

2-Cyclopropyl-5-methyl-7-(3-oxocyclopentyl)-6-phenyl-1,3-benzoxazole-4-carbonitrile (I-303) (44 mg, 0.12 mmol) was dissolved in chloroform (1 ml) and methanol (1 ml), and at 0° C., dimethylamine (2 M tetrahydrofuran solution) (247 µl, 0.49 mmol), acetic acid (29 µl, 0.49 mmol) and sodium cyanoborohydride (33 mg, 0.49 mmol) were added. The solution was gradually warmed up to room temperature, then stirred for 21 hours, and fractionated with chloroform and an aqueous saturated sodium hydrogencarbonate solution. The aqueous layer was extracted twice with chloroform. The organic layers were combined, washed with saturated brine, and dried over anhydrous sodium sulfate. The insoluble matter was separated by filtration, the solvent was evaporated away and the resulting residue was purified by preparative TLC (eluent, chloroform:7 N ammonia/methanol solution=97:3, v/v) to obtain 2-cyclopropyl-7-[(1R*,3R*)-3-(dimethylamino)cyclopentyl]-5-methyl-6-phenyl-1,3-benzoxazole-4-carbonitrile (#141) (9.6 mg, 20%) as a white solid. Next, 2-cyclopropyl-7-[(1R*,3S*)-3-(dimethylamino) cyclopentyl]-5-methyl-6-phenyl-1,3-benzoxazole-4-carbonitrile (#142) (26 mg, 55%) was obtained as a white solid.

MS (ESI) m/z: 386 (M+1)$^+$

HRMS (EI) m/z: 385.2134 (Calcd for $C_{25}H_{27}N_3O$ 385.2154).

$^1$H-NMR (CDCl$_3$) δ: 1.24-1.46 (5H, m), 1.77-2.13 (5H, m), 2.23 (9H, s), 2.28-2.35 (1H, m), 2.83-2.94 (1H, m), 2.95-3.05 (1H, m), 7.06-7.10 (2H, m), 7.38-7.48 (3H, m).

IR (ATR): 2956, 2929, 2224, 1726, 1564, 1458, 1288, 1271, 1120, 1072, 710 cm$^{-1}$. #142:

MS (ESI) m/z: 386 (M+1)$^+$

HRMS (EI) m/z: 385.2159 (Calcd for $C_{25}H_{27}N_3O$ 385.2155).

$^1$H-NMR (CDCl$_3$) δ: 1.23-1.41 (4H, m), 1.79-2.16 (6H, m), 2.22 (3H, s), 2.27-2.35 (1H, m), 2.30 (6H, s), 2.42-2.53 (1H, m), 2.80-2.90 (1H, m), 7.07-7.12 (2H, m), 7.40-7.50 (3H, m).

IR (ATR): 2951, 2226, 1562, 1404, 754, 712 cm$^{-1}$.

Reference Example 304

6-[3-tert-Butyldimethylsiloxy)cyclopent-1-enyl]-2-cyclopropyl-7-fluoro-5-methyl-1,3-benzoxazole-4-carbonitrile (I-304)

6-Bromo-2-cyclopropyl-7-fluoro-5-methyl-1,3-benzoxazole-4-carbonitrile (I-77) (200 mg, 0.68 mmol), tert-butyldimethylsilyl-(3-n-tributylstannylcyclopent-2-enyloxy) silane (429 mg, 0.88 mmol) and 2,6-di-tert-butyl-β-cresol (2 grains) were dissolved in 1,4-dioxane (6 ml), and at room temperature, bis(triphenylphosphine)palladium(II) dichloride (48 mg, 0.07 mmol) was added. The solution was stirred under nitrogen atmosphere at 100° C. for 15 hours. After cooling to room temperature, the insoluble matter was separated by filtration with washing with ethyl acetate. The filtrate was washed with saturated brine, and dried over anhydrous sodium sulfate. The insoluble matter was separated by filtration, the solvent was evaporated away, and the resulting residue was purified by middle-pressure liquid chromatography (eluent, n-hexane:ethyl acetate=9:1, v/v) to obtain the entitled compound (246 mg, 88%) as a colorless gel.

MS (ESI) m/z: 413 (M+1)$^+$.

HRMS (EI) m/z: 412.2000 (Calcd for $C_{23}H_{29}FN_2O_2Si$ 412.1982).

$^1$H-NMR (CDCl$_3$) δ: 0.10 (3H, s), 0.92 (9H, s), 1.24-1.40 (4H, m), 1.86-1.95 (1H, m), 2.24-2.31 (1H, m), 2.35-2.54 (2H, m), 2.55 (3H, s), 2.64-2.71 (1H, m), 5.05-5.10 (1H, m), 5.75 (1H, q, J=2.0 Hz).

IR (ATR): 2927, 2229, 1568, 1252, 1115 1065, 835, 773 cm$^{-1}$.

Reference Example 305

2-Cyclopropyl-7-fluoro-6-(3-hydroxycyclopent-1-enyl)-5-methyl-1,3-benzoxazole-4-carbonitrile (I-305)

6-[3-(tert-Butyldimethylsiloxy)cyclopent-1-enyl]-2-cyclopropyl-7-fluoro-5-methyl-1,3-benzoxazole-4-carbonitrile (I-304) (275 mg, 0.67 mmol) was dissolved in tetrahydrofuran (6 ml), and at 0° C., tetra-n-butylammonium fluoride (1.0 M tetrahydrofuran solution, 1.0 ml, 1.0 mmol) was added. After stirring at room temperature under nitrogen atmosphere for 16 hours, aqueous saturated ammonium chloride solution was added to the solution at 0° C., followed by stirring at the same temperature for 5 minutes. This was extracted three times with ethyl acetate. The organic layers were combined, washed with saturated brine, and dried over anhydrous sodium sulfate. The insoluble matter was separated by filtration, the solvent was evaporated away, and the resulting residue was purified by middle-pressure liquid chromatography (eluent, n-hexane:ethyl acetate=1:1, v/v) to obtain the entitled compound (91 mg, 46%) as a white solid.

MS (ESI) m/z: 299 (M+1)$^+$.

HRMS (EI) m/z: 298.1135 (Calcd for $C_{17}H_{15}FN_2O_2$ 198.1118).

$^1$H-NMR (CDCl$_3$) δ: 1.24-1.40 (4H, m), 1.67-1.77 (1H, br), 1.90-2.00 (1H, m), 2.25-2.31 (1H, m), 2.47-2.60 (5H, m), 2.70-2.80 (1H, m), 5.05-5.12 (1H, br), 5.88 (1H, dd, J=1.7, 3.9 Hz).

IR (ATR): 3462, 2231, 1564, 1412, 1317, 1117, 1061, 1032, 930, 868 cm$^{-1}$.

Reference Example 306

2-Cyclopropyl-7-[(3S)-3-(dimethylamino)pyrrolidin-1-yl]-6-(3-hydroxycyclopent-1-enyl)-5-methyl-1,3-benzoxazole-4-carbonitrile (I-306)

2-Cyclopropyl-7-fluoro-6-(3-hydroxycyclopent-1-enyl)-5-methyl-1,3-benzoxazole-4-carbonitrile (I-305) (50 mg, 0.17 mmol) was dissolved in dimethyl sulfoxide (1.5 ml), then at room temperature, triethylamine (28 µl, 0.20 mmol) and (3S)-3-(dimethylamino)pyrrolidine (26 µl, 0.20 mmol) were added. The reaction liquid was stirred under nitrogen atmosphere at 90° C. for 12.5 hours. After cooling to room temperature, the reaction liquid was fractionated with ethyl acetate and an aqueous saturated sodium hydrogencarbonate solution. The aqueous layer was further extracted twice with ethyl acetate. The organic layers were combined, washed with saturated brine, and dried over anhydrous sodium sulfate. The insoluble matter was separated by filtration, the solvent was evaporated away, and the resulting residue was purified by preparative TLC (eluent, chloroform:7 N ammo-

Example 143

6-Cyclopentadienyl-2-cyclopropyl-7-[(3S)-3-(dimethylamino)pyrrolidin-1-yl]-5-methyl-1,3-benzoxazole-4-carbonitrile (#143)

2-Cyclopropyl-7-[(3S)-3-(dimethylamino)pyrrolidin-1-yl]-6-(3-hydroxycyclopent-1-enyl)-5-methyl-1,3-benzoxazole-4-carbonitrile (I-306) (83 mg, 0.21 mmol) was dissolved in ethanol (0.85 ml) and diethyl ether (1.7 ml), and at room temperature, 1 M hydrochloric acid/ethanol solution (222 μl, 0.22 mmol) was added. After stirring at the same temperature for 4 hours, the solvent was evaporated away under reduced pressure. Ether was added to the residue, and this was concentrated under reduced pressure. This operation was repeated once again. Ether was added to the residue, followed by sonication, and the solvent was removed with a pipette. The residue was dried at 60° C. under reduced pressure for 2 hours to obtain the entitled compound (62 g, 65%) as a brown solid.

MS (ESI) m/z: 375 (M+1)$^+$.

$^1$H-NMR (CDCl$_3$) δ: 0.92-1.06 (0.5H, m), 1.24-1.35 (3.5H, m), 1.90-2.12 (1H, m), 2.23-2.46 (2H, m), 2.32 (2.6H, s), 2.34 (0.4H, s), 2.78-2.90 (6H, br), 2.85-3.00 (1H, m), 3.20-3.32 (1H, m), 3.45-3.93 (5H, m), 6.27-6.81 (3H, m).

IR (ATR): 2210, 1606, 1585, 560, 1468, 1400, 1363, 1163, 1093, 1028, 901 cm$^{-1}$.

Anal. Calcd for C$_{23}$H$_{26}$N$_4$O.1.0HCl.2.5H$_2$O: C, 60.58; H, 7.07; N, 12.29. Found: C, 60.82; H, 6.88; N, 12.18.

Reference Example 307

2-Cyclopropyl-7-fluoro-5-methyl-6-(thiophen-2-yl)-1,3-benzoxazole-4-carbonitrile (I-307)

6-Bromo-2-cyclopropyl-7-fluoro-5-methyl-1,3-benzoxazole-4-carbonitrile (I-77) (200 mg, 0.68 mmol), 2-(tri-n-butylstannyl)thiophene (280 μl, 0.88 mmol) and 2,6-di-tert-butyl-p-cresol (2 grains) were dissolved in 1,4-dioxane (6 ml), and at room temperature, bis(triphenylphosphine)palladium(II) dichloride (48 mg, 0.07 mmol) was added. The solution was stirred under nitrogen atmosphere at 100° C. for 15 hours. After cooling to room temperature, the insoluble matter was separated by filtration with washing with ethyl acetate. The filtrate was washed with saturated brine, and dried over anhydrous sodium sulfate. The insoluble matter was separated by filtration, the solvent was evaporated away, and the resulting residue was purified by middle-pressure liquid chromatography (eluent, n-hexane:ethyl acetate=19:1, v/v) to obtain the entitled compound (194 mg, 96%) as a white solid.

MS (ESI) m/z: 299 (M+1)$^+$.

HRMS (EI) m/z: 298.0593 (Calcd for C$_{16}$H$_{11}$FN$_2$OS 298.0576).

$^1$H-NMR (CDCl$_3$) δ: 1.27-1.43 (4H, m), 2.28-2.35 (1H, m), 2.51 (3H, s), 7.03 (1H, dd, J=1.0, 3.4 Hz), 71.8 (1H, dd, J=3.4, 5.1 Hz), 7.51-7.53 (1H, m).

IR (AIR); 2229, 1560, 1402, 1329, 1309, 1167, 1111, 1093, 1036, 879, 715 cm$^{-1}$.

Reference Example 307-1

2-Cyclopropyl-7-fluoro-5-methyl-6-(thiophen-3-yl)-1,3-benzoxazole-4-carbonitrile (I-307-1)

6-Bromo-2-cyclopropyl-7-fluoro-5-methylbenzoxazole-4-carbonitrile (I-77) (200 mg, 0.68 mmol), 3-thiopheneboronic acid (347 mg, 2.71 mmol) and tripotassium phosphate (288 mg, 1.36 mmol) were suspended in 1,4-dioxane (8 ml), and at room temperature, tetrakis(triphenylphosphine)palladium(0) (157 mg, 0.14 mmol) was added. The mixture liquid was stirred under nitrogen atmosphere at 95° C. for 61 hours, then cooled to room temperature. The insoluble matter was separated by filtration with washing with ethyl acetate, and the filtrate was washed with saturated brine. The organic layer was dried over anhydrous sodium sulfate. The insoluble matter was separated by filtration, the solvent was evaporated away, and the resulting residue was purified by middle-pressure liquid chromatography (eluent, n-hexane:ethyl acetate=19:1, v/v) to obtain the entitled compound (99 mg, 49%) as a white solid.

MS (ESI) m/z: 299 (M+1)$^+$.

HRMS (EI) m/z: 298.0574 (Calcd for C$_{16}$H$_{11}$FN$_2$OS 298.0576).

$^1$H-NMR (CDCl$_3$) δ: 1.25-1.42 (4H, m), 2.47 (3H, s), 7.05 (1H, dt, J=1.2, 4.9 Hz), 7.28 (1H, dd, J=1.2, 2.9 Hz), 7.48 (1H, dd, J=2.9, 4.9 Hz).

IR (ATR): 2227, 1560, 1419, 1333, 1311, 1171, 1119, 1097, 1036, 941, 881, 833, 802, 750, 731 cm$^{-1}$.

Reference Example 307-2

6-(5-Chlorothiophen-2-yl)-2-cyclopropyl-7-fluoro-5-methyl-1,3-benzoxazole-4-carbonitrile (I-307-2)

According to the synthetic method of Reference Example 307-1 and using 5-chlorothiophene-2-boronic acid, the entitled compound was obtained from I-77 as a white solid (yield, 21%).

MS (ESI) m/z: 333, 335 (M+1)$^+$.

$^1$H-NMR (CDCl$_3$) δ: 1.28-1.43 (4H, m), 2.28-2.35 (1H, m), 2.54 (3H, s), 6.81 (1H, d, J=3.7 Hz), 7.00 (1H, d, J=3.7 Hz).

Reference Example 307-3

6-(3-Chlorophenyl)-2-cyclopropyl-7-fluoro-5-methylbenzoxazole-4-carbonitrile (I-307-3)

According to the synthetic method of Reference Example 307-1 and using 3-chlorophenylboronic acid, the entitled compound was obtained from I-77 as a white solid (yield, 90%).

HRMS (EI) m/z: 326.0599 (Calcd for C$_{18}$H$_{12}$ClN$_2$O 326.0622).

$^1$H-NMR (CDCl$_3$) δ: 1.27-1.43 (4H, m), 2.28-2.35 (1H, m), 2.41 (3H, s), 7.12-7.15 (1H, m), 7.25-7.27 (1H, m), 7.43-7.45 (2H, m).

IR (ATR): 2227, 1567, 1404, 1323, 1124, 1022, 931, 864, 791, 748, 716 cm$^{-1}$.

Reference Example 307-4

2-Cyclopropyl-7-fluoro-5-methyl-6-(4-methylthiophen-3-benzoxazole-4-carbonitrile (I-307-4)

According to the synthetic method of Reference Example 307-1 and using 4-methyl-3-thiopheneboronic acid, the entitled compound was obtained from I-77 as a white solid (yield, 93%).

HRMS (EI) m/z: 312.0715 (calcd for $C_{17}H_{13}FN_2OS$ 312.0732).

$^1$H-NMR (CDCl$_3$) δ: 1.26-1.43 (4H, m), 1.99 (3H, s), 2.27-2.35 (1H, m), 2.36 (3H, s), 7.12-7.14 (1H, m), 7.15 (1H, d, J=3.2 Hz).

IR (ATR): 2227, 1568, 1404, 1321, 1142, 1109, 1026, 930, 862, 804, 756 cm$^{-1}$.

Reference Example 307-5

2-Cyclopropyl-6-(2,5-difluorophenyl)-7-fluoro-5-methyl-1,3-benzoxazole-4-carbonitrile (I-307-5)

According to the synthetic method of Reference Example 307-1 and using 2,5-difluorophenylboronic acid, the entitled compound was obtained from I-77 as a white solid (yield, 28%).

HRMS (EI) m/z: 328.0834 (Calcd for $C_{18}H_{11}F_3N_2O$ 328.0824).

$^1$H-NMR (CDCl$_3$) δ: 1.27-1.43 (4H, m), 2.28-2.36 (1H, m), 2.43 (3H, s), 6.93-7.00 (1H, m), 7.13-7.23 (2H, m).

IR (ATR): 2227, 1570, 1498, 1473, 1425, 1404, 1325, 1248, 1196, 1122, 1032, 887, 877, 823, 816, 775, 748, 727 cm$^{-1}$.

Reference Example 307-6

2-Cyclopropyl-7-fluoro-6-(3-furyl)-5-methyl-1,3-benzoxazole-4-carbonitrile (I-307-6)

According to the synthetic method of Reference Example 307-1 and using 3-furanphenylboronic acid, the entitled compound was obtained from I-77 as a white solid (yield, 63%).

MS (ESL) m/z: 283 (M+1)$^+$.

$^1$H-NMR (CDCl$_3$) δ: 1.26-1.42 (4H, m), 2.26-2.32 (1H, m), 2.56 (3H, s), 6.49 (1H, s), 7.53 (1H, s), 7.59 (1H, s).

Reference Example 307-7

2-Cyclopropyl-7-fluoro-6-(3-trifluoromethylphenyl)-5-methyl-1,3-benzoxazole-4-carbonitrile (I-307-7)

According to the synthetic method of Reference Example 307-1 and using 3-(trifluoromethyl)phenylboronic acid, the entitled compound was obtained from I-77 as a white solid (yield, 82%).

MS (ESI) m/z: 361 (M+1)$^+$.

$^1$H-NMR (CDCl$_3$) δ: 1.27-1.44 (4H, m), 2.27-2.35 (1H, m), 2.40 (3H, s), 7.42-7.84 (5H, m).

Reference Example 307-8

2-Cyclopropyl-7-fluoro-5-methyl-6-(3-methylphenyl)-1,3-benzoxazole-4-carbonitrile (I-307-8)

According to the synthetic method of Reference Example 307-1 and using 3-methylphenylboronic acid, the entitled compound was obtained from I-77 as a white solid (yield, 68%).

MS (ESI) m/z: 307 (M+1)$^+$.

$^1$H-NMR (CDCl$_3$) δ: 1.26-1.40 (4H, m), 2.11-2.15 (1H, m), 2.34 (3H, s), 2.75 (3H, s), 6.71-6.79 (2H, m), 6.99-7.08 (1H, m), 7.19-7.28 (1H, m).

Reference Example 307-9

2-Cyclopropyl-7-fluoro-6-(3-hydroxymethylphenyl)-5-methyl-1,3-benzoxazole-4-carbonitrile (I-307-9)

According to the synthetic method of Reference Example 307-1 and using 3-(hydroxymethyl)phenylboronic acid, the entitled compound was obtained from I-77 as a white solid (yield, 93%).

HRMS (EI) m/z: 322.1116 (Calcd for $C_{19}H_{15}FN_2O_2$ 322.1117).

$^1$H-NMR (CDCl$_3$) δ: 1.26-1.42 (4H, m), 2.00-2.08 (1H, br), 2.28-2.34 (1H, m), 2.39 (3H, s), 4.78 (2H, d, J=4.6 Hz), 7.16 (1H, dt, J=1.5 Hz), 7.26 (1H, br s), 7.44-7.51 (2H, m).

IR (ATR): 3265, 2225, 1570, 412, 1325, 1124, 1007, 933, 877, 812, 758, 737 cm$^{-1}$.

Reference Example 307-10

2-Cyclopropyl-7-fluoro-6-[3-(fluoromethyl)phenyl]-5-methyl-1,3-benzoxazole-4-carbonitrile (I-307-9) carbonitrile (I-307-10)

Under nitrogen atmosphere, diethylaminosulfur trifluoride (668 μl, 5.10 mmol) was dropwise added at 0° C. to a dichloromethane (10 ml) solution of 2-cyclopropyl-7-fluoro-6-[3-(hydroxymethyl)phenyl]-5-methyl-1,3-benzoxazole-4-carbonitrile (I-307-9) (331 mg, 1.02 mmol), followed by stirring at room temperature for 17.5 hours. At 0° C., an aqueous saturated sodium hydrogencarbonate solution was added to the reaction liquid, followed by stirring at room temperature, and the mixture liquid was extracted with chloroform. Next, the combined organic layer was dried over anhydrous magnesium sulfate, filtered, and the filtrate was concentrated under reduced pressure. The resulting residue was purified by middle-pressure liquid chromatography (eluent, n-hexane: ethyl acetate=4:1, v/v) to obtain the entitled compound (209 mg, 63%) as a pale dark brown solid.

MS (ESI) m/z: 325 (M+1)$^+$.

$^1$H-NMR (CDCl$_3$) δ: 1.25-1.32 (2H, m), 1.37-1.43 (2H, m), 2.27-2.35 (1H, m), 2.40 (3H, s), 5.45 (2H, d, J=47.8 Hz), 7.22-7.28 (2H, m), 7.46 (1H, d, J=7.6 Hz), 7.53 (1H, d, J=7.6 Hz).

IR (ATR): 2225, 1570, 1412, 1323, 1265, 1122 cm$^{-1}$.

Reference Example 307-11

2-Cyclopropyl-7-fluoro-6-(3-methoxyphenyl)-5-methyl-1,3-benzoxazole-4-carbonitrile (I-307-11)

According to the synthetic method of Reference Example 307-1 and using 3-methoxyphenylboronic acid, the entitled compound was obtained from I-77 as a white solid (yield, 101% with inseparable impurities).

MS (ESI) m/z: 323 (M+1)$^+$.

$^1$H-NMR (CDCl$_3$) δ: 1.26-1.42 (4H, m), 2.28-2.35 (1H, m), 2.41 (3H, s), 3.84 (3H, s), 6.77 (1H, t, J=2.2 Hz), 6.82 (1H, d, J=7.6 Hz), 6.99 (1H, ddd, J=0.7, 2.2 Hz), 7.41 (1H, t, J=7.6 Hz).

Reference Example 307-12

6-(3-Cyanophenyl-2-cyclopropyl-7-fluoro-5-methyl-1,3-benzoxazole-4-carbonitrile (I-307-12)

According to the synthetic method of Reference Example 307-1 and using 3-cyanophenylboronic acid, the entitled compound was obtained from I-77 as a white solid (yield, 30%).

MS (ESI) m/z: 318 (M+1)$^+$.

HRMS (EI) m/z: 317.0977 (Calcd for C$_{19}$H$_{12}$FN$_3$O 317.0964).

$^1$H-NMR (CDCl$_3$) δ: 1.30-1.45 (4H, m), 2.29-2.36 (1H, m), 2.40 (3H, s), 7.54 (1H, d, J=7.8 Hz), 7.60 (1H, br s), 7.66 (1H, t, J=7.8 Hz), 7.78 (1H, dt, J=1.2, 7.8 Hz).

IR (ATR): 2229, 1570, 1408, 1323, 1259, 1122, 1030, 931, 877, 806, 758, 735 cm$^{-1}$.

Reference Example 307-13

6-(2-Aminophenyl)-2-cyclopropyl-7-fluoro-5-methyl-1,3-benzoxazole-4-carbonitrile (I-307-13)

According to the synthetic method of Reference Example 307-1 and using 3-aminophenylboronic acid, the entitled compound was obtained from I-77 as a brown solid (yield, 55%).

MS (ESI) m/z: 308 (M+1)$^+$.

$^1$H-NMR (CDCl$_3$) δ: 1.25-1.32 (2H, m), 1.37-1.43 (2H, m), 2.27-2.35 (1H, m), 2.40 (3H, s), 6.81-6.90 (2H, m), 6.94-6.99 (1H, m), 7.24-7.30 (1H, m).

IR (ATR): 2222, 1622, 1568, 1454, 1321, 1309, 1254, 1120 cm$^{-1}$.

Example 144

2-Cyclopropyl-7-[(3S)-3-(dimethylamino)pyrrolidin-1-yl]-5-methyl-6-(thiophen-2-yl)-1,3-benzoxazole-4-carbonitrile (#144)

2-Cyclopropyl-7-fluoro-5-methyl-6-(thiophen-2-yl)-1,3-benzoxazole-4-carbonitrile (I-307) (192 mg, 0.64 mmol) was dissolved in dimethyl sulfoxide (4 ml), and at room temperature, triethylamine (117 µl, 0.84 mmol) and (3S)-3-(dimethylamino)pyrrolidine (106 µl, 0.84 mmol) was added. After stirred under nitrogen atmosphere at 90° C. for 12.5 hours, this was cooled to room temperature. The reaction liquid was fractionated with ethyl acetate and saturated brine. The aqueous layer was further extracted twice with ethyl acetate. The organic layers were combined, washed with saturated brine, then dried over anhydrous sodium sulfate. The insoluble matter was separated by filtration, then the solvent was evaporated away, and the resulting residue was purified by preparative TLC (eluent, chloroform:methanol=93:7, v/v) to obtain the entitled compound (208 mg, 83%) as a pale brown solid.

MS (ESI) m/z: 393 (M+1)$^+$.

HRMS (EI) m/z: 392.1659 (Calcd for C$_{22}$H$_{24}$N$_4$OS 392.1689).

$^1$H-NMR (CDCl$_3$) δ: 1.17-1.30 (4H, m), 1.60-1.71 (1H, m), 1.96-2.03 (1H, m), 2.18 (6H, s), 2.19-2.28 (1H, m), 2.29 (3H, s), 2.51-2.60 (1H, m), 3.08 (1H, t, J=9.5 Hz), 3.39 (1H, dt, J=6.6, 10.5 Hz), 3.44-3.73 (2H, m), 6.88 (1H, dd, J=1.2, 3.4 Hz), 7.07 (1H, dd, J=3.4, 5.1 Hz), 7.40 (1H, dd, J=1.2, 5.1 Hz).

IR (ATR): 2206, 1604, 1585, 1556, 1468, 1437, 1392, 1362, 1176, 1151, 852, 706 cm$^{-1}$.

Anal. Calcd for C$_{22}$H$_{24}$N$_4$OS.0.25H$_2$O: C, 66.55; H, 6.22; N, 14.11; S, 8.08. Found: C, 66.66; H, 6.08; N, 14.18; S, 8.25.

Example 144-1

2-Cyclopropyl-7-[(3S)-3-(dimethylamino)pyrrolidin-1-yl]-5-methyl-6-(thiophen-3-yl)-1,3-benzoxazole-4-carbonitrile (#144-1)

According to the synthetic method of Example 144, the entitled compound (112 mg, 87%) was obtained from I-307-1 (97 mg, 0.33 mmol) as a pale brown solid.

MS (ESI) m/z: 393 (M+1)$^+$.

HRMS (EI) m/z: 392.1659 (Calcd for C$_{22}$H$_{24}$N$_4$OS 392.1671).

$^1$H-NMR (CDCl$_3$) δ: 1.17-1.30 (4H, m), 1.58-1.69 (1H, m), 1.95-2.02 (1H, m), 2.17 (6H, s), 2.20-2.27 (1H, m), 2.22 (3H, s), 2.49-2.57 (1H, m), 2.99 (1H, dd, J=7.8, 8.5 Hz), 3.30-3.39 (2H, m), 3.42 (1H, dt, J=3.0, 8.5 Hz), 6.96 (1H, d, J=4.8 Hz), 7.05 (1H, br s), 7.38 (1H, dd, J=2.9, 4.8 Hz).

IR (ATR): 2206, 1604, 1585, 1560, 1469, 1442, 1365, 1174, 11.51 cm$^{-1}$.

Anal. Calcd for C$_{22}$H$_{24}$N$_4$OS.0.25H$_2$O: C, 66.55; H, 6.22; N, 14.11; S, 8.08. Found: C, 66.55; H, 6.07; N, 14.17; S, 8.11.

Example 144-2

6-(5-Chlorothiophen-2-yl)-2-cyclopropyl-7-[(3S)-3-(dimethylamino)pyrrolidin-1-yl]-5-methyl-1,3-benzoxazole-4-carbonitrile (#144-2)

According to the synthetic method of Example 144, the entitled compound (50 mg, 83%) was obtained from I-307-2 (47 mg, 0.14 mmol) as a pale brown solid.

MS (ESI) m/z: 427, 429 (M+1)$^+$.

HRMS (EI) m/z: 426.1278 (Calcd for C$_{22}$H$_{23}$ClN$_4$OS 426.1281).

$^1$H-NMR (CDCl$_3$) δ: 1.17-1.31 (4H, m), 1.66-1.77 (1H, m), 2.00-2.09 (1H, m), 2.16-2.28 (1H, m), 2.23 (6H, s), 2.33 (3H, s), 2.57-2.68 (1H, m), 3.25 (1H, t, J=9.4 Hz), 3.42-3.60 (3H, m), 6.67 (1H, d, J=3.4 Hz), 6.90 (1H, dd, J=0.5, 3.4 Hz).

IR (ATR): 2210, 1604, 1585, 1556, 1466, 1444, 1390, 1362, 1194, 1173, 1151, 1059, 806 cm$^{-1}$.

Anal. Calcd for C$_{22}$H$_{23}$ClN$_4$OS.0.5H$_2$O: C, 60.61; H, 5.55; N, 12.85; Cl, 8.13; S, 7.17. Found: C, 60.66; H, 5.32; N, 12.48; Cl, 8.17; S, 7.17.

Example 144-3

6-(3-Chlorophenyl)-2-cyclopropyl-7-[(3S)-3-(dimethylamino)pyrrolidin-1-yl]-5-methyl-1,3-benzoxazole-4-carbonitrile (#144-3)

According to the synthetic method of Example 144, the entitled compound (344 mg, 91%) was obtained from I-307-3 (295 mg, 0.90 mmol) as a cream-colored solid.

MS (ESI) m/z: 421 (M+1)$^+$.

HRMS (EI) m/z: 420.1706 (Calcd for C$_{24}$H$_{25}$ClN$_4$O 420.1717).

¹H-NMR (CDCl₃) δ: 1.18-1.31 (4H, m), 1.59-1.70 (1H, m), 1.93-2.03 (1H, m), 2.18 (6H, s), 2.19 (3H, s), 2.20-2.28 (1H, m), 2.45-2.65 (1H, m), 2.93-3.13 (1H, m), 3.17-3.41 (3H, m), 7.00-7.03 (0.5H, m), 7.11-7.13 (0.5H, m), 7.13-7.17 (0.5H, m), 7.26-7.29 (0.5H, m), 7.31-7.39 (2H, m).

IR (ATR): 2202, 1606, 1560, 1468, 1446, 1363, 1200, 1155, 798, 750, 712, 692 cm⁻¹.

Anal. Calcd for $C_{24}H_{25}ClN_4O \cdot 0.25H_2O$: C, 67.76; H, 6.04; N, 13.17; Cl, 8.33. Found: C, 67.71; H, 5.95; N, 13.11; Cl, 8.80.

Example 144-4

2-Cyclopropyl-7-[(3S)-3-(dimethylamino)pyrrolidin-1-yl]-5-methyl-6-(4-methylthiophen-3-yl)-1,3-benzoxazole-4-carbonitrile (#144-4)

According to the synthetic method of Example 144, the entitled compound (218 mg, 88%) was obtained from I-307-4 (190 mg, 0.61 mmol) as a cream-colored solid.

MS (ESI) m/z: 407 (M+1)⁺.

HRMS (EI) m/z: 406.1836 (Calcd for $C_{23}H_{26}N_4OS$ 406.1827).

¹H-NMR (CDCl₃) δ: 1.17-1.30 (4H, m), 1.59-1.70 (1H, m), 1.88 (1.5H, d, J=1.0 Hz) 1.95-2.05 (1H, m), 2.01 (1.5H, d, J=1.0 Hz), 2.13 (1.5H, s), 2.17 (3H, s), 2.17 (3H, s), 2.18 (1.5H, s), 2.20-2.28 (1H, m), 2.47-2.57 (1H, m), 2.91 (0.5H, t, J=9.5 Hz), 3.04 (0.5H, t, J=9.5 Hz), 3.26 (0.5H, dd, J=7.1, 9.5 Hz), 3.32-3.41 (2H, m), 3.44-3.50 (0.5H, m), 6.94 (0.5H, d, J=3.2 Hz), 6.98-7.00 (0.5H, m), 7.03 (0.5H, d, J=3.2 Hz), 7.03-7.05 (0.5H, m).

IR (ATR): 2208, 1606, 1587, 1560, 1473, 1442, 1392, 1363, 1194, 1153, 858, 754 cm⁻¹.

Anal. Calcd for $C_{23}H_{26}N_4OS \cdot 0.75H_2O$: C, 65.76; H, 6.60; N, 13.34; S, 7.63. Found: C, 66.06; H, 6.28; N, 13.37; S, 7.91.

Example 144-5

2-Cyclopropyl-6-(2,5-difluorophenyl)-7-[(3S)-3-(dimethylamino)pyrrolidin-1-yl]-5-methyl-1,3-benzoxazole-4-carbonitrile (#144-5)

According to the synthetic method of Example 144, the entitled compound (74 mg, 95%) was obtained from I-307-5 (60 mg, 0.18 mmol) as a white amorphous substance.

MS (ESI) m/z: 423 (M+1)⁺.

HRMS (EI) m/z: 422.1933 (Calcd for $C_{24}H_{24}F_2N_4O$ 422.1918).

¹H-NMR (CDCl₃) δ: 1.18-1.32 (4H, m), 1.59-1.76 (1H, m), 1.83-2.07 (1H, m), 2.17 (6H, s), 2.20 (1.5H, s), 2.22 (1.5H, s), 2.20-2.28 (1H, m), 2.51-2.64 (1H, m), 3.00 (0.5H, t, J=9.5 Hz), 3.09 (0.5H, dd, J=6.1, 9.5 Hz), 3.27-3.43 (3H, m), 6.76-6.81 (0.5H, m), 6.92-6.97 (0.5H, m), 7.04-7.15 (2H, m).

IR (ATR): 2210, 1606, 1589, 1560, 1469, 1427, 1365, 1182, 818, 773, 748 cm⁻¹.

Anal. Calcd for $C_{24}H_{24}F_2N_4O \cdot 0.5H_2O$: C, 66.81; H, 5.84; N, 12.98; F, 8.81. Found: C, 67.33; H, 5.83; N, 12.65; F, 8.36.

Example 144-6

2-Cyclopropyl-7-[(3S)-3-(dimethylamino)pyrrolidin-1-yl]-6-(3-furyl)-5-methyl-1,3-benzoxazole-4-carbonitrile (#144-6)

According to the synthetic method of Example 144, the entitled compound (35 mg, 31%) was obtained from I-307-6 (85 mg, 0.30 mmol) as a white crystal.

MS (ESI) m/z: 377 (M+1)⁺.

¹H-NMR (CDCl₃) δ: 1.16-1.30 (4H, m), 1.63-1.74 (1H, m), 1.99-2.07 (1H, m), 2.21 (6H, s), 2.19-2.26 (1H, m), 2.30 (3H, s), 2.54-2.63 (1H, m), 3.23 (1H, t, J=9.2 Hz), 3.41-3.51 (3H, m), 6.35-6.37 (1H, m), 7.27-7.29 (0.5H, m), 7.51-7.53 (1H, m).

IR (ATR): 2777, 2208, 1583, 1465, 1363, 1153, 1037, 871 cm⁻¹.

Anal. Calcd for $C_{22}H_{24}N_4O_2 \cdot 0.5H_2O$: C, 68.55; H, 6.54; N, 14.53. Found: C, 68.70; H, 6.35; N, 14.38.

Example 144-7

2-Cyclopropyl-7-[(3S)-3-(dimethylamino)pyrrolidin-1-yl]-6-(3-trifluoromethylphenyl)-5-methyl-1,3-benzoxazole-4-carbonitrile (#144-7)

According to the synthetic method of Example 144, the entitled compound (78 mg, 41%) was obtained from I-307-7 (150 mg, 0.42 mmol) as a white crystal.

MS (ESI) m/z: 455 (M+1)⁺.

¹H-NMR (CDCl₃) δ: 1.18-1.32 (4H, m), 1.54-1.69 (1H, m), 1.87-2.02 (1H, m), 2.11 (6H, s), 2.15 (1.5H, s), 2.17 (1.5H, s), 2.20-2.28 (1H, m), 2.43-2.59 (1H, m), 3.01-3.11 (1H, m), 3.19-3.38 (3H, m), 7.30-7.66 (4H, m).

IR (ATR): 2206, 1589, 1467, 1334, 1162, 1128, 1076, 815, 704 cm⁻¹.

Anal. Calcd for $C_{25}H_{23}F_3N_4O \cdot 0.25H_2O$: C, 65.42; H, 5.60; N, 12.21; F, 12.42. Found: C, 65.55; H, 5.47; N, 11.92; F, 12.61.

Example 144-8

2-Cyclopropyl-7-[(3S)-3-(dimethylamino)pyrrolidin-1-yl]-5-methyl-6-(3-methylphenyl)-1,3-benzoxazole-4-carbonitrile (#144-8)

According to the synthetic method of Example 144, the entitled compound (19 mg, 13%) was obtained from I-307-8 (110 mg, 0.36 mmol) as a pale yellow amorphous substance.

MS (ESI) m/z: 401 (M+1)⁺.

¹H-NMR (CDCl₃) δ: 1.16-1.30 (4H, m), 1.54-1.66 (1H, m), 1.89-1.99 (1H, m), 2.14 (6H, s), 2.16 (1.5H, s), 2.17 (1.5H, s), 2.20-2.27 (1H, m), 2.36 (1.5H, s), 2.37 (1.5H, s), 2.46-2.56 (1H, m), 2.97 (1H, q, J=8.9 Hz), 3.18-3.38 (3H, m), 6.87-6.92 (1H, m), 7.00-7.05 (1H, m), 7.12-7.17 (1H, m), 7.23-7.30 (1H, m).

IR (ATR): 2206, 1589, 1467, 1334, 1162, 1128, 1076, 815, 704 cm⁻¹.

Anal. Calcd for $C_{25}H_{28}N_4O \cdot 0.5H_2O$: C, 73.32; H, 7.14; N, 3.48. Found: C, 73.66; H, 7.15; N, 12.86.

Example 144-9

2-Cyclopropyl-7-[(3S)-3-(dimethylamino)pyrrolidin-1-yl]-6-(3-hydroxymethylphenyl)-5-methyl-1,3-benzoxazole-4-carbonitrile (#144-9)

According to the synthetic method of Example 144, the entitled compound (233 mg, 89%) was obtained from I-307-9 (202 mg, 0.63 mmol) as a pale brown amorphous substance.

MS (ESI) m/z: 417 (M+1)$^+$

HRMS (EI) m/z: 416.2231 (Calcd for $C_{25}H_{28}N_4O_2$ 416.2212).

$^1$H-NMR (CDCl$_3$) δ: 1.17-1.33 (4H, m), 1.54-1.67 (1H, m), 1.85-2.05 (2H, m), 2.03 (3H, s), 2.18 (1.5H, s), 2.20-2.28 (1H, m), 2.24 (1.5H, s), 2.30-2.90 (1H, br), 2.40-2.60 (2H, m), 2.94-3.03 (1H, m), 3.14-3.26 (0.5H, m), 3.36 (0.5H, dd, J=6.8, 9.8 Hz), 3.47-3.57 (1.5H, m), 4.62 (0.5H, d, J=12.7 Hz), 4.66 (0.5H, d, J=12.7 Hz), 4.71 (1H, s), 7.04 (0.5H, d, J=7.1 Hz), 7.16 (0.5H, d, J=7.1 Hz), 7.24 (0.5H, s), 7.26 (0.5H, s), 7.33-7.43 (2H, m).

IR (ATR): 3340, 2210, 1606, 1587, 1560, 1468, 1398, 1363, 1155, 1030 cm$^{-1}$.

Anal. Calcd for $C_{25}H_{28}N_4O_2 \cdot 0.5H_2O$: C, 70.56; H, 6.87; N, 13.17. Found: C, 70.25; H, 6.77; N, 12.91.

Example 144-10

2-Cyclopropyl-7-[(3S)-3-(dimethylamino)pyrrolidin-1-yl]-6-[3-(fluoromethyl)phenyl]-5-methyl-1,3-benzoxazole-4-carbonitrile (#144-10)

According to the synthetic method of Example 144, the entitled compound (74 mg, 28%) was obtained from I-307-10 (206 mg, 635 μmol) as a pale dark brown solid.

mp: 104-107° C.

MS (ESI) m/z: 419 (M+1)$^+$.

$^1$H-NMR (CDCl$_3$) δ: 1.16-1.23 (2H, m), 1.24-1.30 (2H, m), 1.52-1.65 (1H, m), 1.88-1.98 (1H, m), 2.12 (3H, s), 2.13 (3H, s), 2.16-2.18 (3H, m), 2.20-2.29 (1H, m), 2.44-2.56 (1H, m), 2.84-3.02 (1H, m), 3.14-3.38 (3H, m), 5.40 (2H, dd, J=47.7, 1.6 Hz), 7.09-7.14 (1H, m), 7.23-7.29 (1H, m), 7.36 (1H, d, J=7.8 Hz), 7.39-7.47 (1H, m).

IR (ATR): 2206, 1608, 1589, 1564, 1469, 1398, 1365, 1309, 1215, 1157 cm$^{-1}$.

Anal. Calcd for $C_{23}H_{27}FN_4O \cdot 0.25H_2O$: C, 70.98; H, 6.55; N, 13.24; F, 4.49. Found: C, 71.45; H, 6.48; N, 12.90; F, 4.62.

Example 144-11

2-Cyclopropyl-7-[(3S)-3-(dimethylamino)pyrrolidin-1-yl]-6-(3-methoxyphenyl)-5-methyl-1,3-benzoxazole-4-carbonitrile (#144-11)

According to the synthetic method of Example 144, the entitled compound (79 mg, 47%) was obtained from I-307-11 (131 mg, 0.41 mmol) as a white needle.

MS (ESI) m/z: 417 (M+1)$^+$

HRMS (EI) m/z: 416.2231 (Calcd for $C_{25}H_{28}N_4O_2$ 416.2212).

$^1$H-NMR (CDCl$_3$) δ: 1.16-1.30 (4H, m), 1.57-1.69 (1H, m), 1.91-2.00 (1H, m), 2.16 (3H, s), 2.17 (3H, s), 2.18 (1.5H, s), 2.20 (1.5H, s), 2.20-2.28 (1H, m), 2.50-2.60 (1H, m), 3.04 (0.5H, t, J=9.0 Hz), 3.07 (0.5H, t, J=9.0 Hz), 3.21-3.42 (3H, m), 3.80 (1.5H, s), 3.82 (1.5H, s), 6.65 (0.5H, t, J=2.0 Hz), 6.71 (0.5H, d, J=7.6 Hz), 6.79 (0.5H, t, J=2.0 Hz), 6.84 (0.5H, d, J=7.6 Hz), 6.87-6.91 (1H, m), 7.29 (0.5H, d, J=8.5 Hz), 7.33 (0.5H, d, J=8.5 Hz).

IR (ATR): 2204, 1608, 1585, 1562, 1466, 1363, 1309, 1240, 1198, 1159, 1041, 800, 777, 746, 700 cm$^{-1}$.

Anal. Calcd for $C_{25}H_{28}N_4O_2 \cdot 0.25H_2O$: C, 71.32; H, 6.82; N, 13.31. Found: C, 71.28; H, 6.77; N, 13.11.

Example 144-12

6-(3-Cyanophenyl)-2-cyclopropyl-7-[(3S)-3-(dimethylamino)pyrrolidin-1-yl]-5-methyl-1,3-benzoxazole-4-carbonitrile (#144-12)

According to the synthetic method of Example 144, the entitled compound (59 mg) was obtained from I-307-12 (46 mg, 0.14 mmol) as a white solid. This was washed in slurry with diisopropyl ether to obtain a white solid (45 mg, 75%).

MS (ESI) m/z: 412 (M+1)$^+$

HRMS (EI) m/z: 411.2064 (Calcd for $C_{25}H_{25}N_5O$ 411.2052).

$^1$H-NMR (CDCl$_3$) δ: 1.20-1.33 (4H, m), 1.58-1.69 (1H, m), 1.92-2.02 (1H, m), 2.14 (1.5H, s), 2.14 (1.5H, s), 2.15 (3H, s), 2.16 (3H, s), 2.21-2.28 (1H, m), 2.50-2.61 (1H, m), 2.92 (0.5H, t, J=9.0 Hz), 3.01 (0.5H, t, J=9.0 Hz), 3.15 (0.5H, dt, J=6.6, 10.0 Hz), 3.21-3.39 (2.5H, m), 7.42 (0.5H, dt, J=1.2, 7.8 Hz), 7.45 (0.5H, s), 7.53-7.62 (2H, m), 7.68 (0.5H, d, J=9.0 Hz), 7.68 (0.5H, d, J=9.0 Hz).

IR (ATR): 2210, 1606, 1587, 1560, 1470, 1415, 1365, 1273, 1157, 1047, 1028, 874, 818, 756 cm$^{-1}$.

Anal. Calcd for $C_{25}H_{25}N_5O \cdot 0.5H_2O$: C, 71.41; H, 6.23; N, 16.65. Found: C, 71.43; H, 6.03; N, 16.36.

Example 144-13

6-(2-Aminophenyl)-2-cyclopropyl-7-[(3S)-3-(dimethylamino)pyrrolidin-1-yl]-5-methyl-1,3-benzoxazole-4-carbonitrile (#144-13)

According to the synthetic method of Example 144, the entitled compound (29 mg, 12%) was obtained from I-307-13 (189 mg, 615 μmol) as a pale dark brown solid.

mp: 191-194° C.

MS (ESI) m/z: 402 (M+1)$^+$.

$^1$H-NMR (CDCl$_3$) δ: 1.14-1.30 (4H, m), 1.91-2.02 (1H, m), 2.08-2.29 (10H, m), 2.54 (1H, brs), 3.01-3.18 (1H, m), 3.29-3.63 (5H, m), 6.67-6.83 (2.48H, m), 6.95 (0.52H, d, J=7.6 Hz), 7.16 (1H, t, J=7.2 Hz).

IR (ATR): 3413, 3386, 3313, 3195, 2208, 1603, 1583, 1558, 1469, 1452, 1363, 1298, 1155 cm$^{-1}$.

Anal. Calcd for $C_{24}H_{27}N_5O \cdot 0.25H_2O$: C, 71.00; H, 6.83; N, 17.25. Found: C, 70.70; H, 6.72; N, 16.92.

Reference Example 308

4-Cyano-7-fluoro-N,N,5-trimethyl-6-(thiophen-2-yl)-1,3-benzoxazole-2-carboxamide (I-308)

6-Bromo-4-cyano-7-fluoro-N,N,5-trimethyl-1,3-benzoxazole-2-carboxamide (I-127) (200 mg, 0.61 mmol), 2-(n-tributylstannyl)thiophene (253 μl, 0.80 mmol) and 2,6-di-tert-butyl-p-cresol (2 grains) were dissolved in 1,4-dioxane (6 ml), and at room temperature, bis(triphenylphosphine)palladium(II) dichloride (43 mg, 0.06 mmol) was added. The solution was stirred under nitrogen atmosphere at 100° C. for 18 hours. After cooling to room temperature, the insoluble matter was separated by filtration with washing with ethyl acetate. The filtrate was washed with saturated brine, and dried over anhydrous sodium sulfate. The insoluble matter was separated by filtration, the solvent was evaporated away, and the resulting residue was purified by middle-pressure liquid chromatography (eluent, n-hexane:ethyl acetate=2:1, v/v) to obtain the entitled compound (161 mg, 80%) as a white solid.

MS (ESI) m/z: 330 (M+1)$^+$.

HRMS (EI) m/z: 329.0623 (Calcd for $C_{16}H_{12}FN_3O_2S$ 329.0634).

$^1$H-NMR (CDCl$_3$) δ: 2.59 (3H, s), 3.2 (3H, s), 3.53 (3H, s), 7.08 (1H, dd, J=1.0, 3.7 Hz), 7.21 (1H, dd, J=3., 5.1 Hz), 7.56 (1H, dd, J=1.0, 5.1 Hz).

IR (ATR): 2226, 1651, 1537, 1398, 1325, 1254, 1126, 1099, 949, 702 cm$^{-1}$.

Example 145

4-Cyano-N,N,5-trimethyl-7-[(3S)-3-(methylamino)pyrrolidin-1-yl]-6-(thiophen-2-yl)-1,3-benzoxazole-2-carboxamide (#145)

4-Cyano-7-fluoro-N,N,5-trimethyl-6-(thiophen-2-yl)-1,3-benzoxazole-2-carboxamide (I-308) (160 mg, 0.49 mmol) was dissolved in dimethyl sulfoxide (8.7 ml), and at room temperature, triethylamine (81 µl, 0.58 mmol) was added. The solution was gradually heated from room temperature up to 150° C., and a solution of (3S)-3-(methylamino)pyrrolidine (62 µl, 0.58 mmol) dissolved in dimethyl sulfoxide (1 ml) was added all at a time. After stirred at the same temperature for 50 minutes, this was cooled to room temperature. The solvent was evaporated away under reduced pressure, and the resulting residue was fractionated with chloroform and saturated brine. The aqueous layer was further fractionated twice with chloroform. The organic layers were combined, washed with saturated brine, and dried over anhydrous sodium sulfate. The insoluble matter was separated by filtration, the solvent was evaporated away, and the resulting residue was roughly purified by preparative TLC (eluent, chloroform:7 N ammonia/methanol solution=95:5, v/v), and the roughly-purified product was again purified by preparative TLC (eluent, chloroform:methanol=9:1, v/v) to obtain the entitled compound (119 mg, 60%) as a yellow amorphous substance.

MS (ESI) m/z; 410 (M+1)$^+$.

HRMS (EI) m/z; 409.1549 (Calcd for $C_{21}H_{23}N_5O_2S$ 409.1573).

$^1$H-NMR (CDCl$_3$) δ: 1.65-1.73 (1H, m), 1.92-2.01 (1H, m), 2.34 (3H, s), 2.36 (3H, s), 3.12-3.19 (2H, m), 3.20 (3H, s), 3.48-3.65 (3H, s), 3.54 (3H, s), 6.92 (1H, dd, J=1.2, 3.4 Hz), 7.09 (1H, dd, J=3.4, 5.1 Hz), 7.43 (1H, dd, J=1.2, 5.1 Hz).

IR (ATR): 3319, 2210, 1651, 1603, 1468, 1435, 1390, 1369, 1286, 1107, 700 cm$^{-1}$.

Anal. Calcd for $C_{21}H_{23}N_5O_2S \cdot 0.75H_2O$: C, 59.63; H, 5.84; N, 16.56; S, 7.58. Found: C, 60.02; H, 5.75; N, 16.05; S, 7.56.

Reference Example 309

4-Amino-3'-chloro-6-fluoro-5-hydroxy-3-methylbiphenyl-3-carbonitrile (I-309)

2-Amino-5-bromo-4-fluoro-3-hydroxy-6-methylbenzonitrile (I-75) (2.0 g, 8.16 mmol), 3-chlorophenylboronic acid (2.63 g, 16.3 mmol) and cesium carbonate (5.32 g, 16.3 mmol) were dissolved in 1,4-dioxane (90 ml)/water (10 ml), and at room temperature, (tetrakistriphenylphosphine)palladium(0) (943 mg, 0.82 mmol) was added. The solution was stirred in a nitrogen steam at 100° C. for 12 hours. After cooling to room temperature, the insoluble matter was separated by filtration with washing with ethyl acetate. The filtrate was concentrated under reduced pressure, and the residue was fractionated with ethyl acetate and saturated brine. The aqueous layer was separated, this was further extracted twice with ethyl acetate. The organic layers were combined, washed with saturated brine, and dried over anhydrous sodium sulfate. The insoluble matter was separated by filtration, the solvent was evaporated away, and the resulting residue was purified by middle-pressure liquid chromatography (eluent, chloroform:ethyl acetate=95:5, v/v) to obtain the entitled compound (1.76 g, 78%) as a pale brown solid.

MS (ESI) m/z: 277 (M+1)$^+$.

$^1$H-NMR (DMSO-d$_6$) δ: 2.08 (3H, s), 5.77 (2H, s), 7.21 (1H, dt, J=2.0, 6.3 Hz), 7.32 (1H, brs), 7.42-7.48 (2H, m).

Reference Example 309-1

4-Amino-6-fluoro-5-hydroxy-2-methylbiphenyl-3,3'-dicarbonitrile (I-309-1)

According to the synthetic method of Reference Example 309 and using 3-cyanophenylboronic acid, the entitled compound was obtained from I-75 as a white solid (yield, 40%).

HRMS (EI) m/z: 267.0784 (Calcd for $C_{15}H_{10}FN_3O$ 267.0808).

$^1$H-NMR (DMSO-d$_6$) δ: 2.10 (3H, s), 5.85 (2H, s), 7.63 (1H, br d, J=7.8 Hz), 7.68 (1H, t, J=7.8 Hz), 7.80 (1H, s), 7.88 (1H, dt, J=7.8 Hz), 9.80 (1H, s).

IR (ATR): 3489, 3398, 3286, 2224, 1645, 1510, 1416, 1261, 1205, 1151, 1059 cm$^{-1}$.

Reference Example 309-2

4-Amino-6-fluoro-5-hydroxy-2,3'-dimethylbiphenyl-3-carbonitrile (I-309-2)

According to the synthetic method of Reference Example 309 and using 3-methylphenylboronic acid, the entitled compound was obtained from I-75 as a white solid (yield, 68%).

$^1$H-NMR (CDCl$_3$) δ: 2.21 (3H, s), 2.40 (3H, s), 6.98-7.05 (2H, m), 7.18-7.21 (1H, m), 7.30-7.34 (1H, m).

Reference Example 310

Ethyl 6-(3-chlorophenyl)-4-cyano-7-fluoro-5-methyl-1,3-benzoxazole-2-carboxylate (I-310)

A mixture of 4-amino-3'-chloro-6-fluoro-5-hydroxy-3-methylbiphenyl-3-carbonitrile (I-309) (1.75 g, 6.32 mmol) and ethyl triethoxyacetate (95% purity, 4.40 g, 18.97 mol) was stirred at 100° C. for 15.5 hours. After cooling to room temperature, the liquid component was evaporated under reduced pressure. Hexane was added to the residue, followed by sonication, and a brown solid was precipitated. This was collected by filtration with washing with n-hexane, and dried at 60° C. Under reduced pressure to obtain the entitled compound (2.072 g, 91%) as a brown solid.

MS (ESI) m/z: 3.59 (M+1)$^+$.

HRMS (EI) m/z: 358.0490 (Calcd for $C_{18}H_{12}ClFN_2O_3$ 358.0520).

$^1$H-NMR (CDCl$_3$) δ: 1.52 (3H, t, J=7.1 Hz), 2.49 (3H, s), 4.60 (2H, q, J=7.1 Hz), 7.15-7.18 (1H, m), 7.27 (1H, s), 7.46-7.51 (2H, m).

IR (ATR): 2225, 1734, 1549, 1470, 1400, 1331, 1284, 1190, 1161, 1126 cm$^{-1}$.

Reference Example 310-1

Ethyl 4-cyano-6-(3-cyanophenyl)-7-fluoro-5-methyl-1,3-benzoxazole-2-carboxylate (I-310-1)

According to the synthetic method of Reference Example 310, the entitled compound was obtained from I-309-1 as a white solid (yield, 55%).

MS (ESI) m/z: 350 (M+1)$^+$.

HRMS (EI) m/z: 349.0855 (Calcd for $C_{19}H_{12}FN_3O_3$ 349.0862).

$^1$H-NMR (CDCl$_3$) δ: 1.52 (3H, t, J=7.1 Hz), 2.48 (3H, s), 4.61 (2H, q, J=7.1 Hz), 7.55 (1H, d, J=7.8 Hz), 7.61 (1H, s), 7.69 (1H, t, J=7.8 Hz), 7.82 (1H, d, J=7.8 Hz).

IR (ATR): 2231, 1743, 1277, 1213, 1155, 1124, 958, 808, 756 cm$^{-1}$.

Reference Example 310-2

Ethyl 4-cyano-7-fluoro-5-methyl-6-(3-methylphenyl)-1,3-benzoxazole-2-carboxylate (I-310-2)

According to the synthetic method of Reference Example 310, the entitled compound was obtained from I-310-2 as a white crystal (yield, 47%).

MS (ESI) m/z: 339 (M+1)$^+$.

Reference Example 311

6-(3-Chlorophenyl)-4-cyano-7-fluoro-N,N,5-trimethyl-1,3-benzoxazole-2-carboxamide (I-311)

Dimethylamine hydrochloride (1.406 g, 17.27 mmol) was suspended in dichloromethane (20 ml), and under nitrogen atmosphere at 0° C., trimethylaluminium (1.03 M n-hexane solution) (16.8 ml, 17.27 mmol) was gradually dropwise added. After stirring at room temperature for 30 minutes, a dichloromethane (20 ml) solution of ethyl 6-(3-chlorophenyl)-4-cyano-7-fluoro-5-methyl-1,3-benzoxazole-2-carboxylate (I-310) (2.065 g, 5.75 mmol) was dropwise added at 0° C. The solution was stirred for 21 hours with gradually heating up to room temperature, then at 0° C., aqueous 1 N hydrochloric acid solution (50 ml) was dropwise added, taking 15 minutes. After stirring at the same temperature for 30 minutes, the reaction liquid was extracted three times with dichloromethane. The organic layers were combined, washed with saturated brine, then dried over anhydrous sodium sulfate. The insoluble matter was separated by filtration, the solvent was evaporated away, and the resulting residue was purified by middle-pressure liquid chromatography (eluent, chloroform:acetone=99:1, v/v) to obtain the entitled compound (1.641 g, 80%) as a pale yellow solid.

HRMS (EI) m/z: 357.0688 (Calcd for $C_{18}H_{13}ClFN_3O_2$ 357.0680).

$^1$H-NMR (CDCl$_3$) δ: 2.48 (3H, s), 3.24 (3H, s), 3.54 (3H, s), 7.14-7.19 (1H, m), 7.28 (1H, s), 7.46-7.49 (2H, m).

IR (ATR): 2229, 1660, 1470, 1327, 1257, 1128, 1101, 1080, 949, 796, 746, 717, 694 cm$^{-1}$.

Reference Example 311-1

4-Cyano-6-(3-cyanophenyl)-7-fluoro-N,N,5-trimethyl-1,3-benzoxazole-2-carboxamide (I-311-1)

According to the synthetic method of Reference Example 311, the entitled compound was obtained from I-310-1 as a pale yellow solid (yield, 85%).

MS (ESI) m/z: 349 (M+1)$^+$.

HRMS (EI) m/z: 348.1002 (Calcd for $C_{19}H_{13}FN_4O_2$ 348.1022).

$^1$H-NMR (CDCl$_3$) δ: 2.47 (3H, s), 3.24 (3H, s), 3.54 (3H, s), 7.54 (1H, dt, J=1.5, 7.8 Hz), 7.60 (1H, t, J=1.5 Hz), 7.68 (1H, dt, J=0.5, 7.8 Hz), 7.81 (1H, dt, J=1.5, 7.8 Hz).

IR (ATR): 2229, 1662, 1402, 1130, 1101, 951, 822, 760, 735 cm$^{-1}$.

Reference Example 311-2

4-Cyano-7-fluoro-N,N,5-trimethyl-6-(3-m (I-311-2)

According to the synthetic method of Reference Example 311, the entitled compound was obtained from I-310-2 as a white amorphous substance (yield, 30%).

MS (EST) m/z: 338 (M+1)$^+$.

$^1$H-NMR (CDCl$_3$) δ: 2.43 (3H, s), 2.46 (3H, s), 3.23 (3H, s), 3.54 (3H, s), 7.03-7.06 (2H, m), 7.26-7.31 (1H, m), 7.38-7.42 (1H, m).

Example 146

6-(3-Chlorophenyl)-4-cyano-N,N,5-trimethyl-7-[(3S)-3-(methylamino)pyrrolidin-1-yl]-1,3-benzoxazole-2-carboxamide (#146)

6-(3-Chlorophenyl)-4-cyano-7-fluoro-N,N,5-trimethyl-1,3-benzoxazole-2-carboxamide (I-311) (500 mg, 1.40 mmol) was dissolved in dimethyl sulfoxide (20 ml), and at room temperature, triethylamine (215 μl, 1.54 mmol) was added. The solution was gradually heated from room temperature up to 150° C., and a solution of (3S)-3-(methylamino)pyrrolidine (164 μl, 1.54 mmol) dissolved in dimethyl sulfoxide (3 ml) was added all at a time. After stirred at the same temperature for 30 minutes, this was cooled to room temperature. The solvent was evaporated away under reduced pressure, and the resulting residue was fractionated with chloroform and an aqueous saturated sodium hydrogencarbonate solution. The aqueous layer was further extracted twice with chloroform. The organic layers were combined, washed with saturated brine, and dried over anhydrous sodium sulfate. The insoluble matter was separated by filtration, the solvent was evaporated away, and the resulting residue was first roughly purified by middle-pressure liquid chromatography using an eluent of chloroform:methanol=95:5 (v/v), and then the roughly-purified product was purified by preparative TLC (eluent, chloroform:7 N ammonia/methanol solution=95:5, v/v), and further the obtained solid was purified in slurry with diisopropyl ether to obtain the entitled compound (250 mg, 41%) as a pale yellow solid.

MS (ESI) m/z: 438 (M+1)$^+$.

HRMS (EI) m/z: 437.1604 (Calcd for $C_{23}H_{24}ClN_5O_2$ 437.1619).

$^1$H-NMR (CDCl$_3$) δ: 1.45-1.58 (1H, br), 1.61-1.71 (1H, m), 1.89-1.99 (1H, m), 2.22 (1.5H, s), 2.23 (1.5H, s), 2.33 (1.5H, s), 2.34 (1.5H, s), 2.99 (0.5H, dd, J=4.4, 10.2 Hz), 3.02

(0.5H, dd, J=4.4, 10.2 Hz), 3.08-3.16 (1H, m), 3.20 (3H, s), 3.30-3.55 (3H, m), 3.55 (3H, s), 7.08-7.14 (1H, m), 7.21-7.23 (1H, m), 7.35-7.39 (2H, m).

IR (ATR): 2212, 1655, 1606, 1468, 1394, 1367, 1113, 793, 714 cm$^{-1}$.

Anal. Calcd for $C_{23}H_{24}ClN_5O_2 \cdot 0.25H_2O$: C, 62.44; H, 5.58; N, 15.83; Cl, 8.01. Found: C, 62.22; H, 5.36; N, 15.65; Cl, 8.86.

Example 146-1

4-Cyano-6-(3-cyanophenyl)-N,N,5-trimethyl-7-[(3S)-3-(methylamino)pyrrolidin-1-yl]1,3-benzoxazole-2-carboxamide (#146-1)

According to the synthetic method of Example 146, the entitled compound (230 mg, 48%) was obtained from I-3.11-1 (390 mg, 1.12 mmol) as a pale brown solid.

MS (ESI): 429 (M+1)$^+$.

HRMS (EI) m/z: 428.1932 (Calcd for $C_{24}H_{24}N_6O_2$ 428.1960).

$^1$H-NMR (CDCl$_3$) δ: 1.60-1.85 (2H, m), 1.90-1.99 (1H, m), 2.20 (3H, s), 2.34 (1.5H, s), 2.95-3.05 (1H, m), 3.14 (1H, q, J=5.4 Hz), 3.21 (3H, s), 3.26-3.55 (3H, m), 3.56 (3H, s), 7.47-7.51 (1H, m), 7.54 (1H, s), 7.57 (1H, t, J=7.6 Hz), 7.70 (1H, dt, J=1.5, 7.6 Hz).

IR (ATR): 2212, 1655, 1606, 1579, 1470, 1394, 1369, 1309, 1113, 1309, 1113, 822, 698 cm$^{-1}$.

Anal. Calcd for $C_{24}H_{24}N_6O_2 \cdot 0.75H_2O$: C, 65.22; H, 5.81; N, 19.01. Found: C, 65.08; H, 5.50; N, 18.64.

Example 146-2

4-Cyano-N,N,5-trimethyl-7-[(3S)-3-(methylamino)pyrrolidin-1-yl]-6-(3-methylphenyl)-1,3-benzoxazole-2-carboxamide (#146-2)

According to the synthetic method of Example 146, the entitled compound (208 mg, 31%) was obtained from I-311-2 (540 mg, 1.60 mmol) as a pale yellow crystal.

MS (ESI) m/z: 41.8 (M+1)$^+$.

$^1$H-NMR (CDCl$_3$) δ: 1.57-1.66 (1H, m), 1.86-1.99 (1H, m), 2.22 (3H, s), 2.31 (3H, s), 2.38 (3H, s), 2.94-3.00 (1H, m), 3.04-3.11 (1H, m), 3.20 (3H, s), 3.34-3.44 (1H, m), 3.56 (3H, s), 6.96-7.01 (2H, m), 7.16-7.19 (1H, m), 7.27-7.32 (1H, m).

IR (ATR): 2210, 1654, 1602, 1467, 1392, 1365, 1259, 1106, 750 cm$^{-1}$.

Anal. Calcd for $C_{24}H_{27}N_5O_2 \cdot 0.25H_2O$: C, 68.31; H, 6.57; N, 16.40. Found: C, 68.34; H, 6.59; N, 16.00.

Example 147

4-Cyano-N-(2-methoxyethyl)-N,5-dimethyl-7-[(3S)-3-(methylamino)pyrrolidin-1-yl]-6-phenyl-1,3-benzoxazole-2-carboxamide (#147)

Under nitrogen atmosphere, a dimethyl sulfoxide (1 ml) solution of (3S)-3-(methylamino)pyrrolidine (109 µl, 1.03 mmol) was added at 140 to 150° C. to a dimethyl sulfoxide (8 ml) solution of 4-cyano-7-fluoro-N-(2-methoxyethyl)-N,5-dimethyl-6-phenyl-1,3-benzoxazole-2-carboxamide (I-122) (314 mg, 855 µmol) and triethylamine (155 µl, 1.11 mmol), followed by stirring at the same temperature for 50 minutes. After cooling, saturated brine was added to the reaction liquid, and the mixture liquid was extracted with ethyl acetate. Next, the combined organic layer was washed with saturated brine, then dried over anhydrous magnesium sulfate, filtered, and the filtrate was concentrated under reduced pressure. The resulting residue was purified by middle-pressure liquid chromatography (eluent, dichloromethane:methanol=10:1, v/v) to obtain a rough product of the entitled compound. The rough product of the entitled compound was dissolved in chloroform, washed with an aqueous saturated sodium hydrogencarbonate solution, then the aqueous layer was extracted with chloroform. The combined organic layer was dried over anhydrous magnesium sulfate, filtered, and the filtrate was concentrated under reduced pressure to obtain the entitled compound (117 mg, 31%) as an amorphous substance.

MS (ESI) m/z: 448 (M+1)$^+$.

$^1$H-NMR (CDCl$_3$) δ: 1.55-1.65 (1H, m), 1.86-1.95 (1H, m), 2.21 (1.65H, s), 2.22 (1.35H, s), 2.30 (3H, s), 2.94 (1H, dd, J=10.6, 4.5 Hz), 3.03-3.10 (1H, m), 3.23 (1.65H, s), 3.27-3.33 (1H, m), 3.34 (1.65H, s), 3.38-3.53 (2H, m), 3.39 (1.35H, s), 3.61 (1.35H, s), 3.67-3.72 (2H, m), 3.76-3.81 (0.90H, m), 4.14-4.18 (1.10H, m), 7.17-7.21 (2H, m), 7.34-7.44 (3H, m).

IR (ATR): 2210, 1651, 1603, 1576, 1468, 1439, 1394, 1365, 1304, 1099 cm$^{-1}$.

Anal. Calcd for $C_{25}H_{29}N_5O_3 \cdot 0.25H_2O$: C, 66.43; H, 6.58; N, 15.49. Found: C, 66.85; H, 6.54; N, 15.25.

Reference Example 312

7-Fluoro-2-(1-fluoro-1-methylethyl)-5-methyl-6-phenyl-1,3-benzoxazole-4-carbonitrile (I-312)

Under nitrogen atmosphere, diethylaminosulfur trifluoride (293 µl, 2.24 mmol) was dropwise added at 0° C. to a dichloromethane (5 ml) solution of 7-fluoro-2-(1-hydroxy-1-methylethyl)-5-methyl-6-phenyl-1,3-benzoxazole-4-carbonitrile (I-112) (139 mg, 448 µmol), followed by stirring at room temperature for 14 hours. At 0° C., an aqueous saturated sodium hydrogencarbonate solution was added to the reaction liquid, then the mixture liquid was extracted with chloroform. Next, the combined organic layer was dried over anhydrous magnesium sulfate, filtered, and the filtrate was concentrated under reduced pressure. The resulting residue was purified by middle-pressure liquid chromatography (eluent, n-hexane:ethyl acetate=5:1, v/v) to obtain the entitled compound (134 mg, 96%) as a pale yellow solid.

MS (ESI) m/z: 313 (M+1)$^+$.

$^1$H-NMR (CDCl$_3$) δ: 1.96 (6H, d, J=2.10 Hz), 2.44 (3H, s), 7.23-7.27 (2H, m), 7.44-7.55 (3H, m).

IR (ATR): 2231, 1568, 1475, 1390, 1375, 1346, 1327, 1279, 1163, 1122 cm$^{-1}$.

Example 148

7-[(3S)-3-(Dimethylamino)pyrrolidin-1-yl]-2-(1-fluoro-1-methylethyl)-5-methyl-6-phenyl-1,3-benzoxazole-4-carbonitrile (#148)

Under nitrogen atmosphere, a dimethyl sulfoxide (4 ml) solution of 7-fluoro-2-(1-fluoro-1-methylethyl)-5-methyl-6-phenyl-1,3-benzoxazole-4-carbonitrile (I-312) (128 mg, 410 µmol), triethylamine (74 µl, 533 µmol) and (3S)-3-(dimethylamino)pyrrolidine (62 µl, 492 µmol) was stirred at 90° C. for 2.5 hours. After cooling, saturated-brine was added to the reaction liquid, and the mixture liquid was extracted with ethyl acetate. Next, the combined organic layer was dried over anhydrous magnesium sulfate, filtered, and the filtrate was concentrated under reduced pressure. The resulting residue was purified by middle-pressure liquid chromatography (eluent, dichloromethane:methanol=10:1, v/v) to obtain a rough product of the entitled compound, followed by suspension washing with diethyl ether to obtain the entitled compound as a pale yellow solid. The filtrate was concentrated, and the obtained solid was washed by suspension with isopropyl ether to obtain the entitled compound as a pale yellow solid (total 54 mg, 38%).

mp: 130-132° C.

MS (ESI) m/z: 407 (M+1)$^+$.

$^1$H-NMR (CDCl$_3$) δ: 1.57-1.67 (1H, m), 1.91 (6H, dd, J=21.2, 2.4 Hz), 1.92-2.01 (1H, m), 2.12 (6H, s), 2.20 (3H, s), 2.45-2.55 (1H, m), 2.92 (1H, t, J=9.2 Hz), 3.28-3.50 (3H, m), 7.08-7.14 (1H, m), 7.22-7.28 (1H, m), 7.32-7.44 (3H, m).

IR (ATR): 2204, 1604, 1579, 1466, 1452, 1441, 1363, 1304, 1157, 1136 cm$^{-1}$.

Anal. Calcd for C$_{24}$H$_{27}$FN$_4$O: C, 70.91; H, 6.69; N, 13.78; F, 4.67. Found: C, 70.54; H, 6.70; N, 13.65; F, 4.56.

Reference Example 313

2-(4-Cyano-2-cyclopropyl-5-methyl-6-phenyl-1,3-benzoxazol-7-yl)-N,N-dimethylacetamide (I-313)

At room temperature, trimethylaluminium/n-hexane solution (1.03 mol/l) (547 μl, 0.563 mmol) was added to a toluene (2 ml) suspension of dimethylamine hydrochloride (38.3 mg, 0.469 mmol), followed by stirring at room temperature for 30 minutes. Methyl (4-cyano-2-cyclopropyl-5-methyl-6-phenyl-1,3-benzoxazol-7-yl)acetate (I-295) (65.0 mg, 0.188 mmol) was added to the reaction liquid, followed by heating under reflux in an oil bath at 120° C. for 15 hours. With cooling with ice, 1 N hydrochloric acid was added to the reaction liquid. After extraction with ethyl acetate, the obtained organic layer was washed with saturated brine, dried over anhydrous sodium sulfate, then the insoluble matter was separated by filtration, and the residue obtained by concentration was purified by preparative TLC (eluent, chloroform:methanol=10:1, v/v) to obtain the entitled compound (56.0 mg, 83%) as a white solid.

MS (FAB) m/z: 360 (M+1)$^+$.

HRMS (FAB) m/z: 360.1706 (Calcd for C$_{22}$H$_{22}$N$_3$O$_2$ 360.1712).

$^1$H-NMR (CDCl$_3$) δ: 1.17-1.37 (4H, m), 2.20-2.27 (1H, m), 2.28 (3H, s), 2.70 (3H, s), 2.86 (3H, s), 3.58 (2H, s), 7.11-7.15 (2H, m), 7.37-7.47 (3H, m).

IR (ATR): 3057, 3005, 2927, 2864, 2224, 1647, 1603, 1560, 1493, 1444, 1396, 1319, 1296, 1261, 1174, 1140, 1099, 1063, 1030, 966, 945, 885, 837 cm$^{-1}$.

Reference Example 314

2-(4-Cyano-2-cyclopropyl-5-methyl-6-phenyl-1,3-benzoxazol-7-yl)-N,N-dimethylethanethioamide (I-314)

2,4-Bis(4-methoxyphenyl)-1,3-dithia-2,4-diphosphetan-2,4-disulfide (24.8 mg, 0.061 mmol) was added to a toluene (1 ml) solution of 2-(4-cyano-2-cyclopropyl-5-methyl-6-phenyl-1,3-benzoxazol-7-yl)-N,N-dimethylacetamide (I-313) (20.0 mg, 0.056 mmol), followed by stirring in ah oil bath at 125° C. for 5 hours. The reaction liquid was concentrated, and the resulting residue was purified by silica gel column chromatography (eluent, n-hexane:ethyl acetate=1:1, v/v) to obtain the entitled compound (14.0 mg, 67%) as a yellow solid.

MS (FAB) m/z: 376 (M+1)$^+$.

HRMS (FAB) m/z: 376.1466 (Calcd for C$_{22}$H$_{22}$N$_3$OS 376.1484).

$^1$H-NMR (CDCl$_3$) δ: 1.18-1.36 (4H, m), 2.22-2.30 (1H, m), 2.27 (3H, s), 2.95 (3H, s), 3.39 (3H, s), 3.92 (2H, s), 7.17-7.20 (2H, m), 7.39-7.46 (3H, m).

IR (ATR): 3057, 3018, 2927, 2854, 2224, 1601, 1562, 1516, 1446, 1398, 1296, 1273, 1151, 1103, 1028, 947, 881, 814, 781, 756 cm$^{-1}$.

Example 149

2-Cyclopropyl-7-[2-(dimethylamino)ethyl]-5-methyl-6-phenyl-1,3-benzoxazole-4-carbonitrile (#149)

Raney nickel (corresponding to 0.2 ml) was added to an ethanol (1 ml)/tetrahydrofuran (1 ml) solution of 2-(4-cyano-2-cyclopropyl-5-methyl-6-phenyl-1,3-benzoxazol-7-yl)-N,N-dimethylethanethioamide (I-314) (14.0 mg, 0.037 mmol), followed by stirring in an oil bath at 50° C. for 5 hours. The reaction liquid was filtered, the filtrate was concentrated, and the resulting residue was purified by preparative TLC (eluent, chloroform:methanol=10:1, v/v) to obtain the entitled compound (6.00 mg, 47%) as a white solid.

MS (FAB) m/z: 346 (M+1)$^+$.

HRMS (FAB) m/z: 346.1902 (Calcd for C$_{22}$H$_{24}$N$_3$O 346.1919).

$^1$H-NMR (CDCl$_3$) δ: 1.19-1.36 (4H, m), 2.08 (6H, s), 2.25-2.32 (1H, m), 2.27 (3H, s), 2.33-2.40 (2H, m), 2.72-2.79 (2H, m), 7.10-7.15 (2H, m), 7.38-7.49 (3H, m).

IR (ATR): 2970, 2929, 2856, 2819, 2769, 2224, 1622, 1601, 1562, 1462, 1400, 1298, 1196, 1147, 1099, 1043, 1005, 943, 885, 818, 783, 764 cm$^{-1}$.

Reference Example 315

2-Cyclopropyl-7-fluoro-6-isopropenyl-5-methyl-1,3-benzoxazole-4-carbonitrile (I-315)

Under nitrogen atmosphere, zinc (520 mg, 0.79 mmol) was suspended in tetrahydrofuran (8 ml), then diiodomethyl (320 μl, 3.97 mmol) was added to the suspension, followed by stirring at room temperature for 30 minutes. The reaction liquid was cooled to 0° C. then titanium tetrachloride (794 μl 0794 mmol) was dropwise added, followed by stirring at room temperature for 30 minutes. After 30 minutes, 6-acetyl-2-cyclopropyl-7-fluoro-5-methyl-1,3-benzoxazole-4-carbonitrile (I-82) (205 mg, 0-794 mmol) dissolved in tetrahydrofuran (2 ml) was dropwise added to the reaction liquid, followed by stirring at room temperature for 30 minutes. Ethyl acetate was added to the reaction liquid, followed by washing with 1 N hydrochloric acid and saturated brine. The organic layer was dried over anhydrous magnesium sulfate, then the solvent was evaporated away under reduced pressure. The resulting residue was purified by silica gel column chromatography (eluent, ethyl acetate:n-hexane=4:1, v/v) to obtain the entitled compound (35 mg, 17%) as a white crystal.

MS (ESI) m/z: 257 (M+1)$^+$.

$^1$H-NMR (CDCl$_3$) δ: 1.23-1.39 (4H, m), 2.01-2.04 (3H, m), 2.24-2.32 (1H, m), 2.55 (3H, s), 4.94-4.96 (1H, m), 5.46-5.49 (1H, m).

Example 150

2-Cyclopropyl-7-[(3S)-3-(dimethylamino)pyrrolidin-1-yl]-6-isopropenyl-5-methyl-1,3-benzoxazole-4-carbonitrile (#150)

2-Cyclopropyl-7-fluoro-6-isopropenyl-5-methyl-1,3-benzoxazole-4-carbonitrile (I-315) (34 mg, 0.13 mmol) was dissolved in dimethyl sulfide (2 ml), then triethylamine (38 μl, 0.27 mmol) and (3S)-3-(dimethylamino)pyrrolidine (36 μl, 0.28 mmol) were added, followed by stirring under nitrogen atmosphere at 90° C. for 4 hours. After cooled, this was concentrated under reduced pressure, diluted with chloroform and washed with saturated brine. The organic layer was dried over anhydrous magnesium sulfate, then the solvent was evaporated away under reduced pressure. The resulting residue was purified by preparative TLC (eluent, chloroform:methanol=10:1, v/v) to obtain the entitled compound (21 mg, 25%) as a brown crystal.

MS (ESI) m/z: 351 (M+1)$^+$.

$^1$H-NMR (CDCl$_3$) δ: 1.14-1.29 (4H, m), 1.73-1.88 (1H, m), 1.90 (2H, s), 2.03 (1H, s), 2.10-2.26 (2H, m), 2.31 (6H, s), 2.46 (3H, s), 2.65-2.82 (1H, m), 3.57-3.73 (3H, m), 3.77-3.98 (1H, m), 4.87 (0.4H, brs), 4.98 (0.6H, brs), 5.39 (0.4H, brs), 5.44 (0.6H, brs).

IR (ATR): 2771, 2208, 1585, 1560, 1471, 1358, 1153, 1052, 920 cm$^{-1}$.

Anal. Calcd for C$_{21}$H$_{26}$N$_4$O.0.5H$_2$O: C, 70.17; H, 7.57; N, 15.59. Found: C, 70.61; H, 7.42; N, 15.39.

Reference Example 316

4-Cyano-2-cyclopropyl-7-fluoro-5-methyl-1,3-benzoxazole-6-carboxylic acid (I-316)

2-Cyclopropyl-7-fluoro-6-formyl-5-methyl-1,3-benzoxazole-4-carbonitrile (I-182) (160 mg, 0.66 mmol) was dissolved in tert-butanol (4.5 ml)-water (3 ml)-tetrahydrofuran (3 ml), then at 0° C., sodium dihydrogenphosphate dihydrate (153 mg, 0.98 mmol), 2-methyl-2-butene (292 μl, 2.62 mmol), sodium chlorite (purity 80%, 222 mg, 1.97 mmol) were added. This was stirred for 15 hours with gradually warming up to room temperature. At 0° C., aqueous 1 N hydrochloric acid solution and ethyl acetate were added to the reaction liquid, followed by stirring at the same temperature for 10 minutes. The aqueous layer was separated, and extracted twice with ethyl acetate. The organic layers were combined, washed with saturated brine, and dried over anhydrous sodium sulfate. The insoluble matter was separated by filtration, the solvent was evaporated away to obtain the entitled compound. This was used in the next reaction as such.

Reference Example 317

4-Cyano-2-cyclopropyl-7-fluoro-5-methyl-1,3-benzoxazole-6-carboxamide (I-317)

4-Cyano-2-cyclopropyl-7-fluoro-5-methyl-1,3-benzoxazole-6-carboxylic acid (I-316) obtained in the above reaction was dissolved in N,N-dimethylformamide (4 ml), then at 0° C., 1-(3-dimethylaminopropyl)-3-ethylcarbodiimide hydrochloride (251 mg, 1.31 mmol), 1-hydroxybenzotriazole (177 mg, 1.31 mmol), aqueous 28% ammonia solution (120 μl, 1.97 mmol) were added. The solution was stirred at room temperature for 4 days, then the reaction liquid was fractionated with ethyl acetate and saturated brine. The aqueous layer was further extracted twice with ethyl acetate. The organic layers were combined, washed with saturated brine, and dried over anhydrous sodium sulfate. The insoluble matter was separated by filtration, the solvent was evaporated away, and the resulting residue was purified by middle-pressure liquid chromatography (eluent, n-hexane:ethyl acetate=2:3, v/v) to obtain the entitled compound (126 mg, 74%) as a white solid.

MS (ESI) m/z: 260 (M+1)$^+$ $^1$H-NMR (CDCl$_3$) δ: 1.24-1.34 (4H, m), 1.38-1.46 (1H, m), 1.52 (3H, x), 8.00 (1H, br s), 8.13 (1H, brs).

Reference Example 318 tert-Butyl (4-cyano-2-cyclopropyl-7-fluoro-5-methyl-1,3-benzoxazol-6-carboxamide (I-318)

4-Cyano-2-cyclopropyl-7-fluoro-5-methyl-1,3-benzoxazole-6-carboxamide (I-317) (80 mg, 0.31 mmol) was dissolved in tert-butanol (3 ml)-1,4-dioxane (1 ml), then at room temperature, lead tetraacetate (purity 95%, 288 mg, 0.62 mmol) was added. The suspension was stirred at 90° C. for 28 hours. After cooling to room temperature, the insoluble matter was separated by filtration with washing with ethyl acetate. The filtrate was washed with an aqueous saturated sodium hydrogencarbonate solution and then with saturated brine, and dried over anhydrous sodium sulfate. The insoluble matter was separated by filtration, the solvent was evaporated away, and the resulting residue was purified by middle-pressure liquid chromatography (eluent, n-hexane:ethyl acetate=4:1, v/v) to obtain the entitled compound (40 mg, 39%) as a pale yellow gel.

MS (ESI) m/z: 332 (M+1)$^+$ $^1$H-NMR (CDCl$_3$) δ: 1.26-1.41 (4H, m), 1.49 (9H, s), 2.25-2.32 (1H, m), 2.55 (3H, s), 6.24 (1H, br s).

Reference Example 319

6-Amino-2-cyclopropyl-7-fluoro-5-methyl-1,3-benzoxazole-4-carbonitrile (I-319)

tert-Butyl (4-cyano-2-cyclopropyl-7-fluoro-5-methyl-1,3-benzoxazol-6-yl)carbamate (I-319) (40 mg, 0.12 mmol) was dissolved in dichloromethane (1 ml), then at room temperature, trifluoroacetic acid (1 ml) was added. The solution was stirred at the same temperature for 6 hours, then the solvent was evaporated away under reduced pressure, and the residue was fractionated with dichloromethane and an aqueous saturated sodium hydrogencarbonate solution. The aqueous layer was further extracted twice with dichloromethane. The organic layers were combined, washed with saturated brine, and dried over anhydrous sodium sulfate. The insoluble matter was separated by filtration, then the solvent was evaporated away, and the resulting residue was purified by middle-pressure liquid chromatography (eluent, n-hexane:ethyl acetate=2:1, v/v) to obtain the entitled compound (27 mg, 97%) as a pale brown solid.

MS (ESI) m/z: 232 (M+1)$^+$ $^1$H-NMR (CDCl$_3$) δ: 1.18-1.34 (4H, m), 2.20-2.27 (1H, m), 2.45 (3H, s), 3.84 (2H, br s).

Reference Example 320

2-Cyclopropyl-7-fluoro-5-methyl-6-(pyrrol-1-yl)-1,3-benzoxazole-4-carbonitrile (I-320)

6-Amino-2-cyclopropyl-7-fluoro-5-methyl-1,3-benzoxazole-4-carbonitrile (I-319) (29 mg, 0.13 mmol) was dissolved in acetic acid (2 ml), then at room temperature, 2,5-dimethoxytetrahydrofuran (49 μl, 0.38 mml) was added. The solution was stirred at 100° C. for 3 hours, then cooled to room temperature. The solvent was evaporated away under reduced pressure, the resulting residue was fractionated with ethyl acetate and an aqueous saturated sodium hydrogencarbonate solution. The aqueous layer was further extracted twice with ethyl acetate. The organic layers were combined, washed with saturated brine, and dried over anhydrous sodium sulfate. The insoluble matter was separated by filtration, the solvent was evaporated away, and the resulting residue was purified by middle-pressure liquid chromatography (eluent, n-hexane:ethyl acetate=9:1, v/v) to obtain the entitled compound (28.5 mg, 81%) as a white solid.

MS (ESI) m/z: 282 (M+1)$^+$ $^1$H-NMR (CDCl$_3$) δ: 1.29-1.44 (4H, m), 2.28-2.36 (1H, m), 2.36 (3H, s), 6.41 (2H, t, J=2.2 Hz), 6.69 (2H, dt, J=0.7, 2.2 Hz).

Example 151

2-Cyclopropyl-7-[(3S)-3-(dimethylamino)pyrrolidin-1-yl]-5-methyl-6-(pyrrol-1-yl)-1,3-benzoxazole-4-carbonitrile (#151)

2-Cyclopropyl-7-fluoro-5-methyl-6-(pyrrol-1-yl)-1,3-benzoxazole-4-carbonitrile (I-320) (28 mg, 0.10 mmol) was dissolved in dimethyl sulfoxide (2 ml), then at room temperature, triethylamine (18 μl, 0.13 mmol) and (3S)-3-(dimethylamino)pyrrolidine (17 μl, 0.13 mmol) were added, followed by stirring under nitrogen atmosphere at 100° C. for 5.5 hours. The reaction liquid was cooled to room temperature, then fractionated with ethyl acetate and an aqueous saturated sodium hydrogencarbonate solution. The aqueous layer was further extracted twice with ethyl acetate. The organic layers were combined, washed with saturated brine, and dried over anhydrous sodium sulfate. The insoluble matter was separated by filtration, the solvent was evaporated away, and the resulting residue was roughly purified by preparative TLC (eluent, chloroform:methanol=92:8, v/v), and the obtained solid was further purified in slurry with diisopropyl ether. This was dried at 60° C. under reduced pressure for 12 hours to obtain the entitled compound (26.5 mg, 71%) as a white solid.

MS (ESI) m/z: 376 (M+1)$^+$

HRMS (EI) m/z: 375.2036 (Calcd for C$_{22}$H$_{25}$N$_5$O 375.2059).

$^1$H-NMR (CDCl$_3$) δ: 1.18-1.30 (4H, m), 1.62-1.73 (1H, m), 1.97-2.06 (1H, m), 2.09 (3H, s), 2.19 (6H, s), 2.20-2.27 (1H, m), 2.51-2.61 (1H, m), 3.01 (1H, dd, J=8.8, 10.0 Hz), 3.35 (1H, dt, J=6.6, 10.5 Hz), 3.42 (1H, dd, J=7.1, 10.0 Hz), 3.52-3.60 (1H, m), 6.24-6.30 (2H, m), 6.56-6.62 (2H, m).

IR (ATR): 2208, 1606, 1587, 1556, 1497, 1373, 1325, 1169, 735 cm$^{-1}$.

Anal. Calcd for C$_{22}$H$_{25}$N$_5$O.0.5H$_2$O: C, 68.73; H, 6.82; N, 18.22. Found: C, 68.89; H, 6.59; N, 18.22.

Reference Example 321

6-Dimethylamino-2-cyclopropyl-7-fluoro-5-methyl-1,3-benzoxazole-4-carbonitrile (I-321)

Trifluoroacetic acid (5 ml) was added to tert-butyl (4-cyano-2-cyclopropyl-7-fluoro-5-methyl-1,3-benzoxazol-6-yl) carbamate (I-318) (70 mg, 0.211 mmol), followed by stirring at room temperature for 1 hour. The reaction liquid was evaporated under reduced pressure, and the resulting residue was dissolved in acetic acid (2 ml). 38% formaldehyde (153 μl, 2.11 mmol) was added to the solution, then sodium cyanoborohydride (70 mg, 2.11 mmol) was added, followed by stirring at room temperature for 1 hour. Ethyl acetate was added to the reaction liquid, followed by washing with saturated brine. The organic layer was dried over anhydrous magnesium sulfate, then the solvent was evaporated away under reduced pressure. The resulting residue was purified by preparative TLC (eluent, ethyl acetate:n-hexane=3:1, v/v) to obtain the entitled compound (23 mg, 42%) as a white crystal.

MS (ESI) m/z: 260 (M+1)$^+$.

$^1$H-NMR (CDCl$_3$) δ: 1.21-1.37 (4H, m), 2.22-2.29 (1H, m), 2.58 (3H, s), 2.82 (6H, s).

Example 152

2-Cyclopropyl-6-dimethylamino-7-[(3S)-3-(dimethylamino)pyrrolidin-1-yl]-5-methyl-1,3-benzoxazole-4-carbonitrile (#152)

6-Dimethylamino-2-Cyclopropyl-7-fluoro-5-methyl-1,3-benzoxazole-4-carbonitrile (I-321) (34 mg, 0.10 mmol) was dissolved in dimethyl sulfide (4 ml), then triethylamine (29 μl, 0.20 mmol) and (3S)-3-(dimethylamino)pyrrolidine (27 μl, 0.21 mmol) were added, followed by stirring under nitrogen atmosphere at 100° C. for 24 hours. After cooled, this was concentrated under reduced pressure, diluted with chloroform, and washed with saturated brine. The organic layer was dried over anhydrous magnesium sulfate, then the solvent was evaporated away under reduced pressure. The resulting residue was purified by preparative TLC (eluent, chloroform:methanol=10:1, v/v) to obtain the entitled compound (20 mg, 64%) as a white crystal.

MS (ESI) m/z: 354 (M+1)$^+$.

$^1$H-NMR (CDCl$_3$) δ: 1.13-1.29 (4H, m), 1.75-1.85 (1H, m), 2.16-2.22 (2H, m), 2.45 (6H, s), 2.65-2.76 (6H, m), 3.68-3.72 (3H, m), 3.88-3.93 (1H, m).

IR (ATR): 2771, 2202, 1581, 1465, 1454, 1033, 954, 767 cm$^{-1}$.

Anal. Calcd for C$_{20}$H$_{27}$N$_5$O.0.25H$_2$O: C, 67.11; H, 7.74; N, 19.56. Found: C, 67.25; H, 7.74; N, 19.36.

Reference Example 322

2-Cyclopropyl-7-methoxy-5-methyl-6-phenyl-1,3-benzoxazole-4-carbonitrile (I-322)

Under argon atmosphere, bis(triphenylphosphine)palladium(II) dichloride (777 mg, 1.11 mmol) was added to a 1,4-dioxane (110 ml) solution of 6-bromo-2-cyclopropyl-7-methoxy-5-methyl-1,3-benzoxazole-4-carbonitrile (I-83) (3.40 g, 11.1 mmol), tributylphenyltin (5.28 g, 14.4 mmol) and 2,6-di-tert-butylcresol (488 mg, 2.21 mmol), followed by stirring in an oil bath at 100° C. for 15 hours. The reaction liquid was concentrated under reduced pressure, the residue was dissolved in ethyl acetate, and washed with water and saturated brine. After drying over anhydrous sodium sulfate, the insoluble matter was separated by filtration, and the residue obtained by concentration was washed with diethyl ether to obtain the entitled compound (3.30 g, 98%) as a pale gray solid.

MS (ESI) m/z: 305 (M+1)$^+$.

$^1$H-NMR (CDCl$_3$) δ: 1.21-1.37 (4H, m), 2.23-2.31 (1H, m), 2.28 (3H, s), 4.10 (3H, s), 7.10-7.61 (5H, m).

Reference Example 323

4-Cyano-2-cyclopropyl-5-methyl-6-phenyl-1,3-benzoxazol-7-yl trifluoromethanesulfonate (I-323)

2-Cyclopropyl-7-methoxy-5-methyl-6-phenyl-1,3-benzoxazole-4-carbonitrile (I-322) (3.30 g, 10.8 mmol) was dissolved in dimethylacetamide (67 ml), then sodium acetate (2.67 g, 32.5 mmol) was added, followed by stirring in an oil bath at 130° C. for 15 hours. The reaction liquid was concentrated under reduced pressure, then water was added, followed by extraction with a mixed solvent of chloroform/methanol (19:1), then the obtained organic layer was dried over anhydrous sodium sulfate, the insoluble matter was separated by filtration, the residue obtained by concentration was dissolved in pyridine (67 ml), then 4-dimethylaminopyridine (265 mg, 2.17 mmol) and trifluoromethanesulfonic anhydride (5.34 ml, 32.5 mmol) was added, followed by stirring at room temperature for 23 hours. The reaction liquid was concentrated under reduced pressure, the residue was dissolved in ethyl acetate, and washed with aqueous 1N hydrochloric acid, water and saturated brine. After drying over anhydrous sodium sulfate, the insoluble matter was separated by filtration, and the residue obtained by concentration was purified by silica gel column chromatography (eluent, n-hexane:ethyl acetate=4:1, v/v) to obtain the entitled compound (1.98 g, 43%) as a pale yellow solid.

MS (EI) m/z: 422 (M)$^+$.

HRMS (EI) m/z: 422.0542 (Calcd for $C_{19}H_{13}F_3N_2O_4S$ 422.0548).

$^1$H-NMR (CDCl$_3$) δ: 1.28-1.43 (4H, m), 2.27-2.38 (1H, m), 2.41 (3H, s), 7.21-7.25 (2H, m), 7.46-7.54 (3H, m).

IR (ATR): 3062, 3022, 2929, 2229, 1610, 1570, 1500, 1425, 1352, 1290, 1213, 1134, 1086, 1028, 957, 931, 883, 814 cm$^{-1}$.

Reference Example 324

2-Cyclopropyl-7-(1-hydroxymethylvinyl)-5-methyl-6-phenyl-1,3-benzoxazole-4-carbonitrile (I-324)

4-Cyano-2-cyclopropyl-5-methyl-6-phenyl-1,3-benzoxazol-7-yl trifluoromethanesulfonate (I-323) (760 mg, 1.80 mmol) was dissolved in dimethylformamide (10 ml), then triethylamine (276 μl, 1.98 mmol), allyl alcohol (209 mg, 3.60 mmol), 1,1'-bis(diphenylphosphino)ferrocene (79.8 mg, 0.144 mmol) and palladium(II) acetate (24.2 mg, 0.108 mmol) were added, followed by stirring in an oil bath at 100° C. under argon atmosphere for 16 hours. The reaction liquid was concentrated under reduced pressure, the residue was dissolved in ethyl acetate, washed with water and saturated brine. After drying over anhydrous sodium sulfate, the insoluble matter was separated by filtration, and the residue obtained by concentration was purified by silica gel column chromatography (eluent, n-hexane:ethyl acetate=1:1, v/v) to obtain the entitled compound (193 mg, 32%) as a colorless oily substance.

MS (ESI) m/z: 33.1 (M+1)$^+$.

$^1$H-NMR (CDCl$_3$) δ: 1.20-1.37 (4H, m), 2.22-2.29 (1H, m), 2.33 (3H, s), 3.96 (2H, d, J=6.59 Hz), 5.14 (1H, d, J=1.22 Hz), 5.51 (1H, d, J=1.22 Hz), 7.14 (2H, dd, J=7.68, 1.83 Hz), 7.35-7.44 (3H, m).

Reference Example 325 tert-Butyl [2-(4-cyano-2-cyclopropyl-5-methyl-6-phenyl-1,3-benzoxazol-7-yl)prop-2-en-1-yl]carbamate (I-325)

With cooling with ice, triphenyl phosphine (230 mg, 0.876 mmol), diethyl azodicarboxylate (40% toluene solution) (382 mg, 0.876 mmol) and diphenylphosphorylazide (188 μl, 0.876 mmol) were added to a tetrahydrofuran (6 ml) solution of 2-cyclopropyl-7-(1-hydroxymethylvinyl)-5-methyl-6-phenyl-1,3-benzoxazole-4-carbonitrile (I-324) (193 mg, 0.584 mmol), followed by stirring at room temperature for 19 hours. The reaction liquid was concentrated under reduced pressure, then water was added, followed by extraction with ethyl acetate, and the obtained organic layer was washed with water and saturated brine. After drying over anhydrous sodium sulfate, the insoluble matter was separated by filtration, and the residue obtained by concentration was purified by silica gel column chromatography (eluent, n-hexane:ethyl acetate=2:1, v/v), the obtained eluate was dissolved in a mixed solvent of tetrahydrofuran (5 ml) and water (1 ml), then triphenyl phosphine (230 mg, 0.876 mmol) was added, followed by stirring at room temperature for 3 hours. The reaction liquid was concentrated under reduced pressure, dissolved in chloroform, washed with an aqueous saturated sodium hydrogencarbonate solution and saturated brine. After drying over anhydrous sodium sulfate, the insoluble matter was separated by filtration, and the residue obtained by concentration was purified by silica gel column chromatography (eluent, chloroform:methanol=10:1, v/v), the obtained eluate was dissolved in dichloromethane (6 ml), then di-tert-butyl dicarbonate (191 mg, 0.876 mmol) was added, followed by stirring at room temperature for 15 hours. The reaction liquid was concentrated, and the resulting residue was purified by silica gel column chromatography (eluent, n-hexane:ethyl acetate=2:1, v/v) to obtain, the entitled compound (98.0 mg, 39%) as a white solid.

MS (ESI) m/z: 430 (M+1)$^+$.

3H-NMR (CDCl$_3$) δ: 11.20-1.38 (4H, m), 1.33 (9H, s), 2.21-2.30 (1H, m), 2.32 (3H, s), 3.59-3.68 (2H, m), 4.34 (1H, s), 5.05 (1H, s), 5.37 (1H, d, J=0.98 Hz), 7.10-7.16 (2H, m), 7.35-7.43 (3H, m).

IR (ATR): 3375, 3057, 3010, 2978, 2931, 2227, 1701, 1616, 1597, 1558, 1504, 1454, 1390, 1365, 1323, 1277, 1248, 1167, 1099, 1051, 1028, 945, 918, 877, 839 cm$^{-1}$.

Reference Example 326 tert-Butyl allyl[2-(4-cyano-2-cyclopropyl-5-methyl-6-phenyl-1,3-benzoxazol-7-yl)prop-2-en-1-yl]carbamate (I-326)

tert-Butyl [2-(4-cyano-2-cyclopropyl-5-methyl-6-phenyl-1,3-benzoxazol-7-yl)prop-2-en-1-yl]carbamate (I-325) (97.0 mg, 0.226 mmol) and allyl bromide (28.7 μl, 0.339 mmol) were dissolved in dimethylformamide (2 ml), then with cooling with ice, sodium hydride (55% w/w) (11.8 mg, 0.271 mmol) was added, followed by stirring for 2 hours with cooling with ice. With cooling with ice, aqueous 10% citric acid solution was added to the reaction liquid, followed by concentration under reduced pressure. The resulting residue was dissolved in ethyl acetate, washed with water and saturated brine. After drying over anhydrous sodium sulfate, the insoluble matter was separated by filtration, and the residue obtained by concentration was purified by silica gel column chromatography (eluent, n-hexane:ethyl acetate=2:1, v/v) to obtain the entitled compound (105 mg, 99%) as a colorless oily substance.

MS (ESI) m/z: 470 (M+1)$^+$.

$^1$H-NMR (CDCl$_3$) δ: 1.19-1.37 (4H, m), 1.22 (9H, s), 2.20-2.29 (1H, m), 2.31 (3H, s), 3.42-3.54 (2H, m), 3.72, 3.78 (2H, m), 4.94 (1H, dd, J=17.09, 1.46 Hz), 5.00-5.07 (2H, m), 5.16-5.26 (1H, m), 5.51-5.67 (1H, m), 7.04-7.18 (2H, m), 7.34-7.44 (3H, m).

IR (ATR): 3080, 3010, 2978, 2929, 2225, 1691, 1645, 1616, 1597, 1560, 1456, 1402, 1390, 1365, 1290, 1248, 1167, 1097, 1047, 1030, 941, 922, 874, 839 cm$^{-1}$.

Reference Example 327 tert-Butyl 3-(4-cyano-2-cyclopropyl-5-methyl-6-phenyl-1,3-benzoxazol-7-yl)-2,5-dihydro-1H-pyrrole-1-carboxamide (I-327)

1,3-Bis(2,4,6-trimethylphenyl)-2-imidazolidinylidene) dichloro(phenylmethylene)-tricyclohexylphosphine)ruthenium (8.80 mg, 0.010 mmol) was added to a benzene (20 ml) solution of tert-butyl allyl[2-(4-cyano-2-cyclopropyl-5-methyl-6-phenyl-1,3-benzoxazol-7-yl)prop-2-en-1-yl]carbamate (I-326) (97.0 mg, 0.207 mmol), followed by stirring in an oil bath at 65° C. for 8 hours. The reaction liquid was concentrated under reduced pressure, and the resulting residue was purified by silica gel column chromatography (eluent, n-hexane:ethyl acetate=1:1, v/v) to obtain the entitled compound (52.0 mg, 57%) as a white solid.

MS (ESI) m/z: 442 (M+1)$^+$.

$^1$H-NMR (CDCl$_3$) δ: 1.20-1.39 (4H, m), 1.41 (5H, s), 1.44 (4H, s), 2.22-2.33 (4H, m), 3.72-3.79 (1H, m), 4.01-4.16 (3H, m), 5.57 (0.5H, s), 5.86 (0.5H, s), 7.08-7.15 (2H, m), 7.35-7.47 (3H, m).

Example 153

2-Cyclopropyl-7-(2,5-dihydro-1H-pyrrol-3-yl)-5-methyl-6-phenyl-1,3-benzoxazole-4-carbonitrile (#153)

tert-Butyl 3-(4-cyano-2-cyclopropyl-5-methyl-6-phenyl-1,3-benzoxazol-7-yl)-2,5-dihydro-1H-pyrrole-1-carboxamide (I-327) (52.0 mg, 0.118 mmol) was dissolved in dichloromethane (4 ml), and with cooling with ice, trifluoroacetic acid (2 ml) was added, followed by stirring at room temperature for 2 hours. The reaction liquid was concentrated under reduced pressure, dissolved in chloroform, washed with an aqueous saturated sodium hydrogencarbonate solution and saturated brine, and dried over anhydrous sodium sulfate. The insoluble matter was separated by filtration, and the residue obtained by concentration under reduced pressure was purified by preparative TLC (eluent, chloroform:methanol=10:1, v/v) and purified in slurry with isopropyl ether to obtain the entitled compound (26.0 mg, 62%) as a white solid.

mp: 172-174° C.

MS (ESI) m/z: 342 (M+1)$^+$.

$^1$H-NMR (CDCl$_3$) δ: 1.20-1.39 (4H, m), 1.84 (1H, br s), 2.24-2.30 (1H, m), 2.31 (3H, s), 3.43-3.49 (2H, m), 3.72-3.79 (2H, m), 5.89-5.93 (1H, m), 7.08-7.14 (2H, m), 7.38-7.45 (3H, m).

IR (ATR): 3375, 2914, 2871, 2833, 2783, 2220, 1610, 1593, 1556, 1442, 1389, 1333, 1292, 1196, 1144, 1092, 1045, 997, 951, 868, 820 cm$^{-1}$.

Anal. Calcd for C$_{22}$H$_{19}$N$_3$O.0.75H$_2$O: C, 74.45; H, 5.82; N, 11.84. Found: C, 74.24; H, 5.40; N, 11.68.

Reference Example 328 tert-Butyl (2S)-2-[(dimethylamino)methyl]pyrrolidine-1-carboxylate (I-328)

With cooling with ice, methanesulfonyl chloride (923 μl, 11.9 mmol) and triethylamine (1.94 ml, 13.9 mmol) were added to a dichloromethane (100 ml) solution of tert-butyl (2S)-2-(hydroxymethyl)pyrrolidine-1-carboxylate (2.00 g, 9.94 mmol), followed by stirring for 30 minutes with cooling with ice. The reaction liquid was concentrated under reduced pressure, dissolved in ethyl acetate, and washed with saturated brine. After drying over anhydrous sodium sulfate, the insoluble matter was separated by filtration, and the residue obtained by concentration was dissolved in acetone (50 ml), then sodium iodide (1.49 g, 9.94 mmol) was added, followed by heating under reflux in an oil bath at 85° C. for 5 hours. The reaction liquid was concentrated under reduced pressure, the residue was suspended in ethyl acetate, washed with water and saturated brine. After drying over anhydrous sodium sulfate, the insoluble matter was separated by filtration, the residue obtained by concentration was dissolved in dimethylformamide (30 ml), then dimethylamine hydrochloride (2.43 g, 29.8 mmol) and potassium carbonate (2.75 g, 19.9 mmol) were added, followed by stirring at room temperature for 24 hours. The reaction liquid was concentrated under reduced pressure, the residue was suspended in ethyl acetate, and washed with water and saturated brine. After drying over anhydrous sodium sulfate and concentration, the resulting residue was purified by silica gel column chromatography (eluent, chloroform:methanol=10:1, v/v) to obtain the entitled compound (92.0 mg, 4%) as a colorless oily substance.

MS (ESI) m/z: 229 (M+1)$^+$.

$^1$H-NMR (CDCl$_3$) δ: 1.47 (9H, s), 1.75-2.00 (4H, m), 2.06-2.56 (8H, m), 3.33 (2H, s), 3.70-4.05 (1H, m).

IR (ATR): 2974, 2929, 2875, 2362, 2222, 2114, 2048, 1815, 1799, 1685, 1581, 1475, 1392, 1367, 1288, 1252, 1165, 1119, 1039, 964, 906, 854, 775 cm$^{-1}$.

Example 154

2-Cyclopropyl-7-{(2S)-2-[(dimethylamino)methyl]pyrrolidin-1-yl}-5-methyl-6-phenyl-1,3-benzoxazole-4-carbonitrile (#154)

tert-Butyl (2S)-2-[(dimethylamino)methyl]pyrrolidine-1-carboxylate (I-328) (92.0 mg, 0.403 mmol) was dissolved in dichloromethane (1 ml), and at room temperature, trifluoroacetic acid (1 ml) was added, followed by stirring at room temperature for 1 hour. The reaction liquid was concentrated under reduced pressure, the residue was dissolved in dimethyl sulfoxide (2 ml), then triethylamine (84.2 μl, 0.604 mmol) and 2-cyclopropyl-7-fluoro-5-methyl-6-phenyl-1,3-benzoxazole-4-carbonitrile (I-173) (118 mg, 0.403 mmol) was added, followed by stirring in an oil bath at 100° C. for 5 hours. The reaction liquid was concentrated under reduced pressure, the residue was dissolved in ethyl acetate, and washed with water and saturated brine. After drying over anhydrous sodium sulfate, the insoluble matter was separated by filtration, the residue obtained by concentration was purified by preparative TLC (eluent, chloroform:methanol=10:1, v/v) to obtain the entitled compound (32.0 mg, 20%) as a colorless oily substance.

MS (FAB) m/z: 401 (M+1)$^+$.

HRMS (FAB) m/z: 401.2358 (Calcd for C$_{25}$H$_{29}$N$_4$O 401.2341).

$^1$H-NMR (CDCl$_3$) δ: 1.12-1.36 (4H, m), 1.45-1.72 (4H, m), 2.03-2.15 (2H, m), 2.15-2.26 (10H, m), 2.52-2.63 (1H, m), 2.78-2.89 (1H, m), 4.16-4.27 (1H, m), 7.06 (1H, d, J=7.56 Hz), 7.24-7.46 (4H, m).

IR (ATR): 2968, 2939, 2870, 2817, 2769, 2357, 2332, 2212, 1606, 1589, 1564, 1458, 1400, 1363, 1302, 1267, 1221, 1155, 1101, 1036, 987, 955, 889, 845 cm$^{-1}$.

Reference Example 329 tert-Butyl {1[(1S),(2R)-1-phenyl-ethyl]azetidin-2-ylmethyl}carbamate (I-329)

Wife cooling with ice, lithiumaluminium hydride (750 mg) was added to a tetrahydrofuran (20 ml) solution of [1[(1S),(2R)]-1-(1-phenylethyl)azetidine-2-carbonitrile (1.01 g, 5.42 mmol) synthesized according to the method described in J. Org. Chem., 70, 9028-9031 (2005), followed by stirring at room temperature for 10 minutes. With cooling with ice, water (750 μl) and aqueous 1 N sodium hydroxide solution (3 ml) were added, followed by stirring at room temperature for 20 minutes. The insoluble matter was removed by filtration, the solvent of the filtrate was evaporated away, and the resulting residue was dissolved in dichloromethane (20 ml). Triethylamine (800 μl) and di-tert-butyl dicarbonate (1.77 g, 8.12 mmol) were added, followed by stirring at room temperature for 1 hour. After the solvent was evaporated away, the resisting residue was purified by column chromatography (eluent, chloroform:methanol=99:1, v/v) to obtain the entitled compound (1.499 g, 95%) as a pale yellow oily substance.

$^1$H-NMR (CDCl$_3$) δ: 1.21 (3H, d, J=6.4 Hz), 1.41 (9H, s), 1.82-1.95 (2H, m), 2.15-2.22 (1H, m), 2.70-2.80 (1H, m), 2.85-2.93 (1H, m), 3.15-3.30 (1H, m), 3.41 (1H, dt, J=3.2, 6.8 Hz), 4.47 (1H, brs), 7.20-7.31 (5H, m).

Reference Example 330 tert-Butyl methyl-{[(1S),(2R)-1-phenyl-ethyl]azetidin-2-ylmethyl}carbamate (I-330)

Iodomethane (600 μl) was added to an N,N-dimethylformamide (20 ml) solution of tert-butyl {1[(1S),(2R)-1-phenyl-ethyl]azetidin-2-ylmethyl}carbamate (I-329) (1.49 g, 5.13 mmol), then with cooling with ice, sodium hydride (55%, w/w) (300 mg) was added, followed by stirring at room temperature for 2 hours. Water was poured into the reaction liquid, followed by extraction with ethyl acetate. The organic layer was washed with water and saturated brine, then dried over anhydrous sodium sulfate, and the solvent was evaporated away. The resulting residue was purified by column chromatography (eluent, chloroform:methanol=98:2, v/v) to obtain the entitled compound (1.193 g, 76%) as a pale yellow oily substance. This was used in the next reaction as such.

Reference Example 331 tert-Butyl (2R)-azetidin-2-ylmethyl-methylcarbamate (I-331)

10% Palladium-carbon catalyst (500 mg) was added to an ethanol (50 ml) solution of tert-butyl methyl-{1-[(1S),(2R)-1-phenyl-ethyl]azetidin-2-ylmethyl}carbamate (I-330) (470 mg, 1.546 mmol), followed by stirring under hydrogen atmosphere at 40 to 50° C. for 4 hours. The catalyst was removed by filtration, the solvent was evaporated to obtain a crude product of the entitled compound. This was used in the next reaction as such.

Example 155

4-Cyano-7-{(2R)-2-[methylamino)methyl]azetidin-1-yl}-N,N,5-trimethyl-6-phenyl-1,3-benzoxazole-2-carboxamide (#155)

4-Cyano-7-fluoro-N,N,5-trimethyl-6-phenyl-1,3-benzoxazole-2-carboxamide (I-184) (427 mg, 1.25 mmol) was dissolved in dimethyl sulfoxide (15 ml), then at room temperature, triethylamine (350 μl, 2.52 mmol) was added. Under nitrogen atmosphere, the solution was heated at 150° C., then a dimethyl sulfoxide (10 ml) solution of the above-mentioned tert-butyl (2R)-azetidin-2-ylmethyl-methylcarbamate (I-331) was added to it all at a time. The solution was stirred under nitrogen atmosphere at the same temperature for 20 minutes. After cooling, water was added to the reaction liquid, followed by extraction with ethyl acetate. The organic layer was washed with water and saturated brine, then dried over anhydrous sodium sulfate, and the solvent was evaporated away. With cooling with ice, 4 N hydrochloric acid/dioxane solution (10 ml) was added to the resulting residue, followed by stirring at the same temperature for 20 minutes. The solvent was evaporated away, and the resulting residue was dissolved in chloroform, washed with saturated sodium bicarbonate water and saturated brine, dried over anhydrous sodium sulfate, and the solvent was evaporated away. The resulting residue was purified by column chromatography (eluent, chloroform:methanol=95:5, v/v), and further separated and purified by preparative TLC (eluent, chloroform:methanol=95:5, v/v) to obtain the entitled compound (85 mg, 16%). This was recrystallized from ethanol/isopropyl ether to obtain a colorless solid (32 mg).

mp: 215-218° C.

MS (EI) m/z: 421 (M$^+$).

$^1$H-NMR (CDCl$_3$) δ: 1.47-1.55 (1H, m), 2.23 (3H, s), 2.27 (3H, s), 2.30-2.41 (1H, m), 2.55-2.64 (2H, m), 2.73-2.80 (1H, m), 3.21 (3H, s), 3.57 (3H, s), 4.13-4.20 (1H, m), 4.74 (1H, brs), 6.88-7.02 (2H, m), 7.17 (1H, dt, J=2.4, 8.4 Hz), 7.49-7.55 (1H, m).

IR (ATR): 2210, 1653, 1618, 1579, 1512, 1398, 1109 cm$^{-1}$.

Anal. Calcd for C$_{23}$H$_{24}$FN$_5$O$_2$: C, 65.54; H, 5.74; N, 16.62. Found: C, 65.22; H, 5.72; N, 16.39.

Example 155-1

4-Cyano-6-(3-fluorophenyl-7-{(2R)-2-[(methylamino)methyl]azetidin-1-yl}-N,N,5-trimethyl-6-phenyl-1,3-benzoxazole-2-carboxamide (#155-1)

Similarly to the synthetic method of Example 155 and from 4-cyano-7-fluoro-6-(3-fluorophenyl)-N,N,5-trimethyl-1,3-benzoxazole-2-carboxamide (I-114) (756 mg, 2.34 mmol) and tert-butyl (2R)-azetidin-2-ylmethyl-methylcarbamate (I-331) (515 mg, 2.57 mmol), the entitled compound (45 mg, 5%) was obtained as a pale brown solid.

mp: 214-223° C.

MS (EI) m/z: 403 (M$^+$).

$^1$H-NMR (CDCl$_3$) δ: 1.46-1.54 (1H, m), 2.22 (3H, s), 2.27 (3H, s), 2.30-2.47 (1H, m), 2.56-2.74 (3H, m), 3.21 (3H, s), 3.57 (3H, s), 4-17 (1H, d, J=8.8 Hz), 4.75 (1H, brs), 7.15-7.20 (2H, m), 7.45-7.55 (3H, m).

IR (ATR): 2208, 1652, 1616, 1508, 1402, 1111, 708, 513 cm$^{-1}$.

Anal. Calcd for C$_{23}$H$_{26}$N$_5$O$_2$.0.5H$_2$O: C, 66.97; H, 6.35; N, 16.98. Found: C, 67.11; H, 6.13; N, 16.58.

Reference Example 332 tert-Butyl methyl-(3-tri-n-butylstannylcyclopent-2-enyl)carbamate (I-332)

Tert-butyl (3-tri-n-butylstannylcyclopent-2-enyl)carbamate (2.0 g, 4.24 mmol) was dissolved in N,N-dimethylformamide (40 ml), and at 0° C., methyl iodide (527 µl, 8.47 mmol) and then sodium hydride (55%, w/w), (277 mg, 6.35 mmol) were added. With gradually warming from 0° C. up to room temperature, this was stirred for 24 hours. At 0° C., aqueous saturated ammonium chloride solution was added to the solution, followed by stirring at the same temperature for 30 minutes. The solution was extracted three times with ethyl acetate. The organic layers were combined, washed with saturated brine, and dried over anhydrous sodium sulfate. The insoluble matter was separated by filtration, the solvent was evaporated away, and the resulting residue was purified by middle-pressure liquid chromatography (eluent, n-hexane:ethyl acetate=99:1, v/v) to obtain a colorless oil (1.982 g, 96%).

$^1$H-NMR (CDCl$_3$) δ: 0.87-0.94 (15H, m), 1.31 (6H, dq, J=7.3 Hz), 1.47 (9H, s), 1.45-1.58 (7H, m), 2.07-2.20 (1H, m), 2.36-2.47 (1H, m), 2.48-2.56 (1H, m), 2.59 (3H, brs), 5.08-5.53 (1H, br), 5.60-5.70 (1H, m).

Reference Example 333

7-Benzylamino-4-cyano-6-(3-fluorophenyl)-N,N-5-trimethyl-1,3-benzoxazole-2-carboxamide (I-333)

4-Cyano-7-fluoro-6-(3-fluorophenyl)-N,N,5-trimethyl-1,3-benzoxazole-2-carboxamide (I-184) (5.0 g, 14.65 mmol) was dissolved in dimethyl sulfoxide (292 ml), then at room temperature, triethylamine (2.45 ml, 17.58 mmol) was added, followed by heating at 150° C., Benzylamine (1.92 ml, 17.58 mmol) was added to the solution all at a time, followed by stirring for 45 minutes. The reaction liquid was cooled to room temperature, the solvent was evaporated away under reduced pressure. The residue was fractionated with chloroform and saturated brine, and the organic layer was dried over anhydrous sodium sulfate. The insoluble matter was separated by filtration, the solvent was evaporated away, and the resulting residue was purified by silica gel column chromatography (eluent, chloroform:acetone=98:2, v/v) to obtain the entitled compound (3.961 g, 63%) as a yellow solid.

MS (ESI) m/z: 429 (M+1)$^+$
HRMS (EI) m/z: 428.1679 (Calcd for C$_{25}$H$_{21}$FN$_4$O$_2$ 428.1648).
$^1$H-NMR (CDCl$_3$) δ: 2.23 (3H, s), 3.20 (3H, s), 3.49 (3H, s), 4.28 (1H, t, J=6.6 Hz), 5.83 (2H, d, J=6.6 Hz), 6.91 (1H, ddd, J=1.5, 2.4, 9.0 Hz), 6.98 (1H, d, J=7.9 Hz), 7.13-7.30 (6H, m), 7.52 (1H, dt, J=6.0, 7.9 Hz).
IR (ATR): 3356, 2214, 1655, 1616, 1581, 1398, 1109, 752 cm$^{-1}$.

Reference Example 334

7-Amino-4-cyano-6-(3-fluorophenyl)-N,N,5-trimethyl-1,3-benzoxazole-2-carboxamide (I-334)

7-Benzylamino-4-cyano-6-(3-fluorophenyl)-N,N,5-trimethyl-1,3-benzoxazole-2-carboxamide 2-carboxamide (I-333) (3.46 g, 8.08 mmol) was suspended in acetic acid, then at room temperature, palladium hydroxide (20 wt. % on carbon, 3.46 g) was added. The suspension was stirred under atmospheric pressure of hydrogen at 100° C. for 15 hours. The suspension was cooled to room temperature, then the catalyst was separated by filtration with washing with ethyl acetate. The filtrate was evaporated under reduced pressure, the resulting residue was fractionated with ethyl acetate and aqueous 0.5 M sodium hydroxide solution. The organic layer was separated, washed with saturated brine, and dried over anhydrous sodium sulfate. The insoluble matter was separated by filtration, the solvent was evaporated away, and the resulting residue was purified by middle-pressure liquid chromatography (eluent, n-hexane:ethyl acetate=2:3, v/v) to obtain the entitled compound (711 mg, 26%) as a pale yellow solid.

MS (ESI) m/z: 339 (M+1)$^+$
HRMS (EI) m/z: 338.1204 (Calcd for C$_{18}$H$_{15}$FN$_4$O$_2$ 338.1179).
$^1$H-NMR (CDCl$_3$) δ: 2.31 (3H, s), 3.22 (3H, s), 3.60 (3H, s), 4.23 (2H, brs), 6.97 (1H, ddd, J=1.5, 2.7, 9.0 Hz), 7.03 (1H, dt, J=1.5, 7.6 Hz), 7.17 (1H, ddt, J=1.5, 2.7, 9.0 Hz), 7.53 (1H, dt, J=6.1, 8.1 Hz).
IR (ATR): 3371, 2218, 1633, 1579, 1105, 800, 760, 737 cm$^{-1}$.

Reference Example 335

7-Bromo-4-cyano-6-(3-fluorophenyl)-N,N,5-trimethyl-1,3-benzoxazole-2-carboxamide (I-335)

7-Amino-4-cyano-6-(3-fluorophenyl)-N,N,5-trimethyl-1,3-benzoxazole-2-carboxamide (I-334) (710 mg, 2.10 mmol), copper(II) bromide (1.03 g, 4.62 mmol) was suspended in acetonitrile (25 ml), and at room temperature, tert-butyl nitrite (purity 90%), (615 µl, 4.62 mmol) was added. The suspension was stirred under nitrogen atmosphere at 60° C. for 1 hour. With the reaction going on, generation of nitrogen was observed. The reaction liquid was cooled to room temperature, then fractionated with ethyl acetate and aqueous 1 M hydrochloric acid solution. The aqueous layer was further extracted twice with ethyl acetate. The organic layers were combined, washed with saturated brine, then dried over anhydrous sodium sulfate. The insoluble matter was separated by filtration, the solvent was evaporated away, and the resulting residue was purified by middle-pressure liquid chromatography (eluent, n-hexane:ethyl acetate=3:1, v/v) to obtain the entitled compound (614 mg, 73%) as a white solid.

MS (ESI) m/z: 402, 404 (M+1)$^+$
$^1$H-NMR (CDCl$_3$) δ: 2.43 (3H, s), 3.23 (3H, s), 3.50 (3H, s), 6.90 (1H, ddd, J=1.7, 2.4, 8.6 Hz), 6.95 (1H, ddd, J=1.0, 1.7, 7.8 Hz), 7.19 (1H, ddt, J=1.0, 2.4, 8.6 Hz), 7.51 (1H, dt, J=5.9, 7.8 Hz).

Reference Example 336 tert-Butyl {3-[4-cyano-2-dimethylcarbamoyl-6-(3-fluorophenyl)-5-methyl-1,3-benzoxazol-7-yl]cyclopent-2-enyl}methylcarbamate (I-336)

7-Bromo-4-cyano-6-(3-fluorophenyl)-N,N,5-trimethyl-1,3-benzoxazole-2-carboxamide (I-335) (260 mg, 0.65 mmol) and tert-butyl methyl-(3-tri-n-butylstannylcyclopent-2-enyl)carbamate (I-33) (472 mg, 0.97 mol) were dissolved in 1,4-dioxane (8 ml), and at room temperature, 2,6-di-tert-butyl-paracresol (3 mg, 0.01 mmol) and then bis(triphenylphosphine)palladium(II) dichloride (46 mg, 0.07 mmol) were added. The solution was stirred under nitrogen atmosphere at 100° C. for 11 hours, then cooled to room temperature. The insoluble matter was separated by filtration with washing with ethyl acetate. The filtrate was concentrated under reduced pressure. The residue was combined with a crude product of the entitled compound that had been separately produced according to the same method, and then purified by middle-pressure liquid chromatography (eluent, n-hexane:ethyl acetate=3:2, v/v) to obtain the entitled compound (544 mg, 92%) as a pale yellow solid.

MS (ESI) m/z: 463 (M+1)$^+$ $^1$H-NMR (CDCl$_3$) δ: 1.45 and 1.45 (each 4.5H, each s), 1.47-1.61 (1H, m), 2.10-2.35 (3H, m), 2.39 (3H, s), 2.40 (3H, s), 3.22 (3H, s), 3.53 (3H, s), 5.17-5.45 (1H, br), 5.61-5.64 (0.5H, m), 5.64-5.75 (0.5H, br), 6.80-7.00 (2H, m), 7.09-7.17 (1H, m), 7.39-7.48 (1H, m).

IR (ATR): 2359, 2227, 1685, 1662, 1392, 1333, 1149, 1107 cm$^{-1}$.

Example 156

4-Cyano-6-(3-fluorophenyl)-N,N,5-trimethyl-7-[3-(methylamino)cyclopent-1-enyl]-1,3-benzoxazole-2-carboxamide (#156)

tert-Butyl {3-[4-cyano-2-dimethylcarbamoyl-6-(3-fluorophenyl)-5-methyl-1,3-benzoxazol-7-yl]cyclopent-2-enyl}methylcarbamate (I-366) (544 mg, 1.05 mmol) was dissolved in 4 N hydrochloric acid/1,4-dioxane solution (11 ml), and stirred at room temperature for 50 minutes. The solvent was evaporated away under reduced pressure, then ethanol was added to the resulting residue, followed by concentration under reduced pressure. This operation was repeated once again. The residue was dissolved in chloroform/an aqueous saturated sodium hydrogencarbonate solution (1:1, v/v), and vigorously stirred for 5 minutes. The aqueous layer was separated, and extracted twice with 10% methanol-containing chloroform solution. The organic layers were combined, washed with saturated brine, and dried over anhydrous sodium sulfate. The insoluble matter was separated by filtration, the solvent was evaporated away, and the resulting residue was purified by preparative TLC (eluent, chloroform:7N ammonia-containing methanol solution=93:7, v/v) to obtain a crude product (350 mg). This was washed in slurry with diisopropyl ether to collect a pale brown solid by filtration. The solid was dried at 60° C. under reduced pressure for 15 hours to obtain the entitled compound (330 mg, 75%).

MS (ESI) m/z: 419 (M+1)$^+$

HRMS (FAB) m/z: 419.1904 (Calcd for C$_{24}$H$_{24}$FN$_4$O$_2$ 419.1883).

$^1$H-NMR (CDCl$_3$) δ: 1.45-1.60 (2H, m), 2.11-2.20 (1H, m), 2.25-2.31 (2H, m), 2.31 (3H, s), 2.40 (3H, d, J=1.0 Hz), 3.21 (3H, s), 3.51 (3H, s), 3.74-3.80 (1H, m), 5.88-5.91 (1H, m), 6.83-6.98 (2H, m), 7.12 (1H, ddt, J=1.2, 2.4, 8.3 Hz), 7.39-7.46 (1H, m).

IR (ATR): 2224, 1653, 1579, 1444, 1400, 1336, 1261, 1207, 1107, 770 cm$^{-1}$.

Anal. Calcd for C$_{24}$H$_{23}$FN$_4$O$_2$ 0.5H$_2$O: C, 67.43; H, 5.66; N, 13.11; F, 4.44. Found: C, 67.30; H, 5.45; N, 12.93; F, 4.41.

Reference Example 337

4-Cyano-7-(4-methoxybenzylamino)-N,N,5-trimethyl-6-phenyl-1,3-benzoxazole-2-carboxamide (I-337)

4-Cyano-7-fluoro-N,N,5-trimethyl-6-phenyl-1,3-benzoxazole-2-carboxamide (I-114) (1.0 g, 3-09 mmol) was dissolved in dimethyl sulfoxide (60 ml), then at room temperature, triethylamine (560 μl, 4.02 mmol) was added, followed by heating at 150° C. 4-Methoxybenzylamine (525 μl, 4.02 mmol) was added to the solution all at a time, followed by stirring for 1.5 hours. The reaction liquid was cooled to room temperature, and the solvent was evaporated away under reduced pressure. The residue was fractionated with chloroform and saturated brine, and the organic layer was dried over anhydrous sodium sulfate. The insoluble matter was separated by filtration, the solvent was evaporated away, and the resulting residue was purified by middle-pressure liquid chromatography (eluent, chloroform:acetone=98:2, v/v) to obtain the entitled compound (665 mg, 49%) as a yellow solid.

MS (ESI) m/z: 441 (M+1)$^+$

HRMS (EI) m/z: 440.1867 (Calcd for C$_{26}$H$_{24}$N$_4$O$_3$ 440.1849).

$^1$H-NMR (CDCl$_3$) δ: 2.21 (3H, s), 3.52 (3H, s), 3.75 (3H, s), 4.26 (1H, t, J=6.6 Hz), 4.74 (1H, t, J=6.6 Hz), 6.77-6.82 (2H, m), 7.10-7.19 (4H, m), 7.41-7.47 (1H, m), 7.49-7.55 (1H, m).

IR (ATR): 3332, 2212, 1641, 1610, 1527, 1510, 1404, 1308, 1244, 1176, 1107, 1032, 700 cm$^{-1}$.

Reference Example 338

7-Amino-4-cyano-N,N,5-trimethyl-6-phenyl-1,3-benzoxazole-2-carboxamide (I-338)

4-Cyano-7-(4-methoxybenzylamino)-N,N,5-trimethyl-6-phenyl-1,3-benzoxazole-2-carboxamide (I-337) (2.10 g, 4.77 mmol) was dissolved in trifluoroacetic acid (22 ml), and stirred at room temperature for 13 hours. The solvent was evaporated away under reduced pressure, and the resulting residue was added to chloroform (25 ml) and an aqueous saturated sodium hydrogencarbonate solution (25 ml), followed by vigorously stirring for 15 minutes. The organic layer was separated, the aqueous layer was further extracted twice with chloroform. The organic layers were combined, washed with saturated brine, and dried over anhydrous sodium sulfate. The insoluble matter was separated by filtration, the solvent was evaporated away, and the resulting residue was purified by middle-pressure liquid chromatography (eluent, chloroform:acetone=98:2, v/v) to obtain the entitled compound (1.456 g, 95%) as a brown solid.

MS (ESI) m/z: 321 (M+1)$^+$

HRMS (EI) m/z: 320.1276 (Calcd for C$_{18}$H$_{16}$N$_4$O$_2$ 320.1273).

$^1$H-NMR (CDCl$_3$) δ: 2.30 (3H, s), 3.22 (3H, s), 3.61 (3H, s), 4.42 (2H, br s), 7.21-7.25 (2H, m), 7.43-7.49 (1H, m), 751-7.57 (2H, m).

IR (ATR): 3338, 2212, 1635, 1404, 1105, 712 cm$^{-1}$.

Reference Example 339

7-Bromo-4-cyano-N,N,5-trimethyl-6-phenyl-1,3-benzoxazole-2-carboxamide (I-339)

7-Amino-4-cyano-N,N,5-trimethyl-6-phenyl-1,3-benzoxazole-2-carboxamide (I-338) (300 mg, 0.94 mmol) was dissolved in acetonitrile (10 ml), then at room temperature, copper(II) bromide (460 mg, 2.06 mmol) and tert-butyl nitrite (purity 90%), (275 μl, 2.06 mmol) were added. The suspension was stirred under nitrogen atmosphere at 60° C. for 1 hour and 40 minutes. With the reaction going on, generation of nitrogen was observed. The reaction liquid was cooled to room temperature, then fractionated with ethyl acetate and aqueous 1 M hydrochloric acid solution. The aqueous layer was further extracted twice with ethyl acetate. The organic layers were combined, washed with saturated brine, then dried over anhydrous sodium sulfate. The insoluble matter was separated by filtration, the solvent was evaporated away, and the resulting residue was purified by middle-pressure liquid chromatography (eluent, n-hexane:ethyl acetate=3:1, v/v) to obtain the entitled compound (279 mg, 78%) as a white solid.

MS (ESI) m/z: 384, 386 (M+1)$^+$

HRMS (FAB) m/z: 383.0270 (Calcd for $C_{18}H_{14}BrN_3O_2$ 383.0270).

$^1$H-NMR (CDCl$_3$) δ: 2.42 (3H, s), 3.23 (3H, s), 3.50 (3H, s), 7.13-7.18 (2H, m), 7.46-7.55 (3H, m).

IR (ATR): 2229, 1659, 1535, 1394, 1255, 1099, 1020, 951, 854, 773, 696 cm$^{-1}$.

Reference Example 340 tert-Butyl {3-[4-cyano-2-dimethylcarbamoyl-5-methyl-6-phenyl-1,3-benzoxazol-7-yl]cyclopent-2-enyl}methylcarbamate (I-340)

7-Bromo-4-cyano-N,N,5-trimethyl-6-phenyl-1,3-benzoxazole-2-carboxamide (I-339) (275 mg, 0.72 mmol) and tert-butyl methyl-(3-tri-n-butylstannylcyclopent-2-enyl)carbamate (I-332) (453 mg, 0.93 mol) were dissolved in 1,4-dioxane (8 ml), and at room temperature, 2,6-di-tert-butyl-paracresol (3 mg, 0.01 mmol) and then bis(triphenylphosphine)palladium(II) dichloride (50 mg, 0.07 mmol) were added. The solution was stirred under nitrogen atmosphere at 100° C. for 24 hours, then cooled to room temperature. The insoluble matter was separated by filtration with washing with ethyl acetate. The filtrate was concentrated under reduced pressure. The solvent was evaporated away, and the resulting residue was purified by middle-pressure liquid chromatography (eluent, n-hexane:ethyl acetate=2:1, v/v) to obtain the entitled compound (316 mg, 88%) as a colorless gel.

MS (ESI) m/z: 445 (M−55)$^+$, 523 (M+1)$^+$ $^1$H-NMR (CDCl$_3$) δ: 1.44 (9H, s), 1.44-1.56 (1H, m), 2.10-2.50 (6H, m), 2.38 (3H, s), 3.22 (3H, s), 3.53 (3H, s), 5.10-5.45 (1H, br), 5.58-5.71 (1H, br), 7.09-7.19 (2H, m), 7.37-7.46 (3H, m).

IR (ATR): 2225, 1686, 1657, 1389, 1329, 1155, 1103, 752, 704 cm$^{-1}$.

Reference Examples 340-1 and 340-2

Optical resolution (I-340-1, I-340-2) of tert-butyl {3-[4-cyano-2-dimethylcarbamoyl-5-methyl-6-phenyl-1,3-benzoxazol-7-yl]cyclopent-2-enyl}methylcarbamate (I-340)

tert-Butyl {3-[4-cyano-2-dimethylcarbamoyl-5-methyl-6-phenyl-1,3-benzoxazol-7-yl]cyclopent-2-enyl}methylcarbamate (I-340) was subjected to optical resolution under the following condition, using partitioning CHIRALPAK IA (Daicel Chemical, 2 cmϕ×25 cm).

Mobile phase: chloroform/n-hexane=1:3, v/v

Sample injection: 20 g/ml

Flow rate: 10 ml/min

The first eluate, I-340-1 (135 mg) was obtained. The second eluate, I-340-2 (155 mg) was obtained. The optical purity of I-340-1 and I-340-2 was confirmed under the following condition, using assaying CHIRALPAK IA (Daicel Chemical)

Mobile phase: chloroform/n-hexane=1:3, v/v

Sample injection: 10 μl (1 mg of sample dissolved in 1 ml of mobile phase)

Flow rate: 1 ml/min

I-340-1:99% ee; I-340-2:93% ee.

Example 156-1

4-Cyano-N,N,5-trimethyl-7-[3-(methylamino)cyclopent-2-enyl]-6-phenyl-1,3-benzoxazole-2-carboxamide (#156-1)

tert-Butyl {3-[4-cyano-2-dimethylcarbamoyl-5-methyl-6-phenyl-1,3-benzoxazol-7-yl]cyclopent-2-enyl}methylcarbamate (I-340-1) (134 mg, 0.27 mmol) was dissolved in 4 N hydrochloric acid/1,4-dioxane solution (3 ml), and stirred at room temperature for 2 hours. The solvent was evaporated away under reduced pressure, then ethanol was added to the resulting residue, followed by concentration under reduced pressure. This operation was repeated once again. The residue was dissolved in chloroform (15 ml) and an aqueous saturated sodium hydrogencarbonate solution (15 ml), and vigorously stirred for 10 minutes. The aqueous layer was separated, extracted twice with chloroform. The organic layers were combined, washed with saturated brine, and dried over anhydrous sodium sulfate. The insoluble matter was separated by filtration, the solvent was evaporated away, and the resulting residue was purified by preparative TLC (eluent, chloroform:7 N ammonia-containing methanol solution=93:7, v/v) to obtain a roughly-purified product (60 mg). This was further purified by preparative TLC (eluent, chloroform:methanol=9:1, v/v) to obtain a brown solid (50 mg). The solid was washed in slurry with diisopropyl ether, and a pale brown solid was collected by filtration. The solid was dried at 60° C. under reduced pressure for 48 hours to obtain the entitled compound (42 mg, 39%).

MS (ESI) m/z: 401 (M+1)$^+$.

HRMS (FAB) m/z: 401.2008 (Calcd for $C_{24}H_{25}FN_4O_2$ 401.1977).

$^1$H-NMR (CDCl$_3$) δ: 1.43-1.52 (1H, m), 2.08-2.17 (1H, m), 2.20-2.26 (2H, m), 2.28 (3H, s), 2.39 (3H, s), 3.21 (3H, s), 3.52 (3H, s), 3.70-3.77 (1H, m), 5.88 (1H, dd, J=1.7, 3.9 Hz), 7.09-7.12 (1H, m), 7.13-7.19 (1H, m), 7.38-7.46 (3H, m).

IR (ATR): 2935, 2222, 1653, 1541, 1442, 1398, 1109, 775, 716, 704 cm$^{-1}$.

Anal. Calcd for $C_{24}H_{24}N_4O_2$·0.75$H_2O$: C, 69.63; H, 6.21; N, 13.53. Found: C, 69.88; H, 5.96; N, 13.49.

Example 156-2

4-Cyano-N,N,5-trimethyl-7-[3-(methylamino)cyclopent-2-enyl]-6-phenyl-1,3-benzoxazole-2-carboxamide (#156-2)

tert-Butyl {3-[4-cyano-2-dimethylcarbamoyl-5-methyl-6-phenyl-1,3-benzoxazol-7-yl]cyclopent-2-enyl}methylcarbamate (I-340-2) (154 mg, 0.31 mmol) was dissolved in 4 N hydrochloric acid/1,4-dioxane solution (3 ml), and stirred at room temperature for 1 hour. The solvent was evaporated away under reduced pressure, then ethanol was added to the resulting residue, followed by concentration under reduced pressure. This operation was repeated once again. The residue was dissolved in chloroform (15 ml) and an aqueous saturated sodium hydrogencarbonate solution (15 ml), and vigorously stirred for 10 minutes. The aqueous layer was separated, extracted twice with chloroform. The organic layers were combined, washed with saturated brine, and dried over anhydrous sodium sulfate. The insoluble matter was separated by filtration, the solvent was evaporated away, and the resulting residue was purified by preparative TLC (eluent, chloroform:methanol=9:1, v/v), and this was further purified by preparative TLC (eluent, chloroform:7 N ammonia-containing methanol solution=93:7, v/v) to obtain a brown solid (74 mg). The solid was washed in slurry with diisopropyl ether, and a pale brown solid was collected by filtration. The solid was dried at 60° C. under reduced pressure for 48 hours to obtain the entitled compound (57 mg, 46%).

MS (ESI) m/z: 401 (M+1)$^+$

HRMS (FAB) m/z: 401.1959 (Calcd for $C_{24}H_{25}FN_4O_2$ 401.1978).

$^1$H-NMR (CDCl$_3$) δ: 1.43-1.52 (1H, m), 2.08-2.17 (1H, m), 2.20-2.26 (2H, m), 2.28 (3H, s), 2.39 (3H, s), 3.21 (3H, s), 3.52 (3H, s), 3.70-3.77 (1H, m), 5.88 (1H, dd, J=1.7, 3.9 Hz), 7.09-7.12 (1H, m), 7.13-7.19 (1H, m), 7.38-7.46 (3H, m).

IR (ATR): 2933, 2222, 1653, 1543, 1443, 1398, 1107, 775, 717, 704 cm$^{-1}$.

Anal. Calcd for $C_{24}H_{24}N_4O_2 \cdot 0.5H_2O$: C, 70.40; H, 6.15; N, 13.68. Found: C, 70.69; H, 6.02; N, 13.63.

Reference Example 341 tert-Butyl 5-oxo-1-[(1R)-1-phenylethyl]pyrrolidine-3-carboxylate (I-341)

With cooling with ice, oxalyl chloride (15.7 ml, 0.18 mol) was dropwise added to a dichloromethane (200 ml) solution of 5-oxo-1-[(1R)-1-phenylethyl]pyrrolidine-3-carboxylic acid (35 g, 0.15 mol) synthesized according to the method described in J. Med. Chem., 30, 1711-1715 (1987), then a catalytic amount of N,N-dimethylformamide was added, followed by stirring as such for 1 hour, then warming up to room temperature and further stirring for 1 hour. The reaction liquid was dried to solidness under reduced pressure (toluene azeotropy three times). This was dissolved in dichloromethane (100 ml), and the solution was dropwise added to a dichloromethane (150 ml) solution containing tert-butanol (43 ml, 0.45 mol) with cooling with ice. Triethylamine (31.4 ml, 0.225 mol) was further dropwise added at the same temperature, followed by stirring at room temperature for 16 hours. Water was added to the reaction liquid, and the dichloromethane layer was collected, and this was washed with water and saturated brine. After drying over anhydrous sodium sulfate and concentration under reduced pressure, the resulting residue was purified by silica gel column chromatography (eluent, n-hexane:ethyl acetate=3:1→1:1→1:2→1:3, v/v) to obtain the entitled compound (including mixture of optical isomers) (34.227 g in total, 79%). This was used in the next, reaction as such.

Reference Example 342 tert-Butyl(3S)-3-methyl-5-oxo-1-[(1R)-1-phenylethyl]pyrrolidine-3-carboxylate (I-342)

Methyl iodide (21.8 ml, 0.35 mol) was added to an N,N-dimethylformamide (150 ml) solution of tert-butyl 5-oxo-1-[(1R)-1-phenylethyl]pyrrolidine-3-carboxylate (I-341) (20.28 g, 70.1 mmol), then at room temperature, sodium hydride (55%, w/w) (1 g) was added, followed by stirring as such. Afterwards, sodium hydride (1.9 g, 2.7 g, 2.79 g, 1.97 g) was successively added, followed by stirring at room temperature for 13 hours. With cooling with ice, aqueous 10% citric acid solution was added to the reaction liquid, followed by extraction with ethyl acetate. The organic layer was washed with saturated brine, dried over anhydrous sodium sulfate, and the solvent was evaporated away. The resulting residue was separated and purified by silica gel column chromatography (eluent, n-hexane:ethyl acetate=3:1, v/v) to obtain the entitled compound (7.65 g, 36%).

$^1$H-NMR (CDCl$_3$) δ: 1.34 (9H, s), 1.35 (3H, s), 1.52 (3H, d, J=7.08 Hz), 2.26 (1H, d, J=16.9 Hz), 2.92 (1H, d, J=16.9 Hz), 3.05 (1H, d, J=10.0 Hz), 3.32 (1H, d, J=10.0 Hz), 5.50 (1H, q, J=7.08 Hz), 7.24-7.36 (5H, m).

Reference Example 343 tert-Butyl {(3S)-3-methyl-5-oxo-1-[(1R)-1-phenylethyl]pyrrolidin-3-yl}carbamate (I-343)

With cooling with ice, trifluoroacetic acid (7 ml) was added to a dichloromethane (14 ml) solution of tert-butyl (3S)-3-methyl-5-oxo-1-[(1R)-1-phenylethyl]pyrrolidine-3-carboxylate (I-342) (800 mg, 2.64 mmol), followed by stirring at room temperature for 13 hours. The reaction liquid was concentrated under reduced pressure, dissolved in chloroform, washed with saturated brine (60 ml). After drying over anhydrous sodium sulfate and concentration under reduced pressure, the resulting residue was dissolved in toluene (20 ml), then triethylamine (735 μl, 5.27 mmol) and diphenylphosphorylazide (739 μl, 3.43 mmol) were added, followed by stirring at room temperature for 30 minutes, then by stirring in an oil bath at 125° C. for 3 hours. tert-Butanol (20 ml) was added to the reaction liquid, followed by stirring in an oil bath at 100° C. for 11 hours. The reaction liquid was concentrated under reduced pressure, the residue was dissolved in ethyl acetate, washed with saturated brine. After drying over anhydrous sodium sulfate and concentration, the resulting residue was purified by silica gel column chromatography (eluent, n-hexane:ethyl acetate=2:1→1:4, v/v) to obtain the entitled compound (500 mg, 60%) as a colorless oily substance.

MS (ESI) m/z: 319 (M+1)$^+$.

$^1$H-NMR (CDCl$_3$) δ: 1.35 (9H, s), 1.47 (3H, s), 1.51 (3H, d, J=7.08 Hz), 2.43 (1H, d, J=16.60 Hz), 2.66 (1H, d, J=16.60 Hz), 3.20-3.33 (2H, m), 4.54 (1H, s), 5.51 (1H, q, J=7.08 Hz), 7.24-7.35 (5H, m).

IR (ATR): 3319, 2976, 2935, 2881, 1672, 1603, 1522, 1496, 1448, 1425, 1366, 1313, 1277, 1252, 1167, 1066, 1032, 1016, 931, 874, 785 cm$^{-1}$.

Reference Example 344 tert-Butyl {(3S)-3-methyl-1-[(1R)-1-phenylethyl]pyrrolidin-3-yl}carbamate (I-344)

tert-Butyl {(3S)-3-methyl-5-oxo-1-[(1R)-1-phenylethyl]pyrrolidin-3-yl}carbamate (I-343) (500 mg, 1.57 mmol) was dissolved in tetrahydrofuran (15 ml), and with cooling with ice, borane/tetrahydrofuran complex (1.2 mol/l tetrahydrofuran solution) (3.93 ml, 4.71 mmol) was added, followed by stirring at room temperature for 17 hours. Ethanol (12 ml), triethylamine (4 ml) and water (4 ml) were added to the reaction liquid, followed by stirring in an oil bath at 90° C. for 3 hours. The reaction liquid was concentrated under reduced pressure, dissolved in ethyl acetate, and washed with an aqueous saturated sodium hydrogencarbonate solution and saturated brine. After drying over anhydrous sodium sulfate, the insoluble matter was separated by filtration, and the residue obtained by concentration was purified by silica gel column chromatography (eluent, n-hexane:ethyl acetate=2:1→1:2, v/v) to obtain the entitled compound (406 mg, 85%) as a colorless oily substance.

MS (ESI) m/z: 305 (M+1)$^+$.

$^1$H-NMR (CDCl$_3$) δ: 1.33 (3H, d, J=6.59 Hz), 1.43 (3H, s), 1.43 (9H, s), 1.75-1.86 (1H, m), 1.95-2.06 (1H, m), 2.41 (1H, d, J=9.52 Hz), 2.51-2.67 (2H, m), 2.67-2.77 (1H, m), 3.25 (1H, q, J=6.59 Hz), 4.68 (1H, s), 7.19-7.33 (5H, m).

IR (ATR): 3356, 2972, 2931, 2871, 2787, 1697, 1604, 1493, 1452, 1390, 1365, 1277, 1250, 1165, 1068, 1032, 964, 872 cm$^{-1}$.

Reference Example 345 tert-Butyl [(3S)-3-methylpyrrolidin-3-yl]carbamate (I-345)

tert-Butyl {(3S)-3-methyl-1-[(1R)-1-phenylethyl]pyrrolidin-3-yl}carbamate (I-344) (406 mg, 1.33 mmol) was dissolved in 1,4-dioxane (13 ml), then palladium hydroxide catalyst (20 wt. % on carbon) (100 mg) was added, followed by stirring in an oil bath at 50° C. Under hydrogen atmosphere for 5 hours. The reaction liquid was filtered, and the filtrate was concentrated under reduced pressure to obtain the entitled compound (266 mg, 100%) as a colorless oily substance.

MS (ESI) m/z: 201 (M+1)$^+$.

$^1$H-NMR (CDCl$_3$) δ: 1.41 (3H, s), 1.44 (9H, s), 1.69-1.78 (1H, m), 1.89-2.07 (2H, m), 2.72 (1H, d, J=11.47 Hz), 2.88-2.99 (1H, m), 3.04-3.21 (2H, m), 4.59 (1H, brs).

IR (ATR): 3340, 3195, 2974, 2931, 2871, 1693, 1523, 1446, 1365, 1279, 1252, 1169, 1066, 985, 947, 874, 783 cm$^{-1}$.

Reference Example 346

Benzyl (3S)-3-[(tert-butoxycarbonyl)amino]-3-methylpyrrolidine-1-carboxylate (I-346)

tert-Butyl [(3S)-3-methylpyrrolidin-3-yl]carbamate (I-345) (240 mg, 1.20 mmol) was dissolved in diethyl ether (12 ml), then an aqueous saturated sodium hydrogencarbonate solution (12 ml) was added, and at room temperature, benzyloxycarbonyl chloride (222 µl, 1.56 mmol) was added, followed by stirring at room temperature for 16 hours. The reaction liquid was extracted with ethyl acetate, and the obtained organic layer was washed with saturated brine. After drying over anhydrous sodium sulfate, the insoluble matter was separated by filtration, and the residue obtained by concentration was purified by silica gel column chromatography (eluent, n-hexane:ethyl acetate=2:1, v/v) to obtain the entitled compound (400 mg, 100%) as a colorless oily substance.

MS (ESI) m/z: 357 (M+23)$^+$.

$^1$H-NMR (CDCl$_3$) δ: 1.41-1.46 (12H, m), 1.74-1.87 (1H, m), 2.18-2.47 (1H, m), 3.35 (1H, d, J=11.22 Hz), 3.44-3.71 (3H, m), 4.54 (1H, s), 5.10-5.15 (2H, m), 7.24-7.38 (5H, m).

IR (ATR): 3344, 2974, 2885, 1689, 1522, 1498, 1446, 1419, 1390, 1363, 1344, 1271, 1254, 1169, 1101, 1076, 1022, 953, 876, 768 cm$^{-1}$.

Reference Example 347

Benzyl (3S)-3-[(tert-butoxycarbonyl)(methyl) amino]-3-methylpyrrolidine-1-carboxylate (I-347)

Benzyl (3S)-3-[(tert-butoxycarbonyl)amino]-3-methylpyrrolidine-1-carboxylate (I-346) (400 mg, 1.20 mmol) and methyl iodide (112 µl, 1.79 mmol) were dissolved in dimethylformamide (12 ml), and with cooling with ice, sodium hydride (55% w/w) (62.6 mg, 1.44 mmol) was added, followed by stirring for 2 hours with cooling with ice. With cooling with ice, aqueous 10% citric acid solution was added to the reaction liquid, followed by extraction with ethyl acetate, and the obtained organic layer was washed with water and saturated brine. After drying over anhydrous sodium sulfate, the insoluble matter was separated by filtration, and the residue obtained by concentration was purified by silica gel column chromatography (eluent, n-hexane:ethyl acetate=2:1, v/v) to obtain the entitled compound (367 mg, 88%) as a colorless oily substance.

MS (ESI) m/z: 371 (M+23)$^+$.

$^1$H-NMR (CDCl$_3$) δ: 1.26-1.31 (3H, m), 1.43-1.49 (9H, m), 1.97-2.20 (2H, m), 2.82-2.87 (3H, m), 3.28-3.38 (1H, m), 3.41-3.48 (1H, m), 3.51-3.63 (1H, m), 3.83-3.95 (1H, m), 5.08-5.19 (2H, m), 7.22-7.39 (5H, m).

IR (ATR): 2974, 2885, 1689, 1454, 1417, 1363, 1342, 1232, 1169, 1144, 1099, 1003, 966, 883, 825 cm$^{-1}$.

Reference Example 348 tert-Butyl methyl[(3S)-3-methylpyrrolidin-3-yl]carbamate (I-348)

Benzyl (3S)-3-[(tert-butoxycarbonyl)(methyl)amino]-3-methylpyrrolidine-1-carboxylate (I-347) (367 mg, 1.05 mmol) was dissolved in 1,4-dioxane (10 ml), then palladium hydroxide catalyst (37 mg) was added, followed by stirring under hydrogen atmosphere at room temperature for 5 hours. The reaction liquid was filtered, and the filtrate was concentrated under reduced pressure to obtain a crude product of the entitled compound. This was used in the next reaction as such.

Reference Example 348

Alternative Synthetic Method

Tert-Butyl {(3S)-3-methyl-5-oxo-1-[(1R)-1-phenylethyl]pyrrolidin-3-yl}carbamate (I-343) (4.08 g, 12.8 mmol) and methyl iodide (1.20 ml, 19.2 mmol) were dissolved in N,N-dimethylformamide (120 ml), and with cooling with ice, sodium hydride (55% w/w) (671 mg, 15.4 mmol) was added, followed by stirring for 1 hour with cooling with ice. With cooling with ice, aqueous 10% citric acid solution was added to the reaction liquid, followed by concentration under reduced pressure. The resulting residue was dissolved in ethyl acetate, washed with saturated brine, and dried over anhydrous sodium sulfate, then the insoluble was separated by filtration, and the residue obtained by concentration was purified by silica gel column chromatography (eluent, n-hexane:ethyl acetate=2:1→1:4, v/v) to obtain tert-butyl methyl-{(3S)-3-methyl-5-oxo-1-[(1R)-1-phenylethyl]pyrrolidin-3-yl}carbamate (4.09 g, 96%) as a colorless oily substance.

MS (ESI) m/z: 333 (M+1)$^+$.

HRMS (ESI) m/z: 333.2168 (Calcd for C$_{19}$H$_{29}$N$_2$O$_3$ 333.2178).

$^1$H-NMR (CDCl$_3$) δ: 1.35 (3H, s), 1.40 (9H, s), 1.52 (3H, d, J=7.32 Hz), 2.42 (1H, d, J=15.87 Hz), 2.74 (1H, d, J=15.87 Hz), 2.75 (3H, s), 3.14 (1H, d, J=10.50 Hz), 3.44-3.60 (1H, m), 5.52 (1H, q, J=7.32 Hz), 7.23-7.37 (5H, m).

IR (ATR): 2974, 2931, 1685, 1483, 1450, 1427, 1365, 1308, 1252, 1223, 1169, 1145, 1122, 1012, 883, 777 cm$^{-1}$.

The above-mentioned tert-butyl methyl-{(3S)-3-methyl-5-oxo-1-[(1R)-1-phenylethyl]pyrrolidin-3-yl}carbamate (3.94 g, 11.9 mmol) was dissolved in tetrahydrofuran (120 ml), then with cooling with ice, borane/tetrahydrofuran complex (29.6 ml 35.6 mmol) was added, followed by stirring at room temperature for 17 hours. Ethanol (36 ml), triethylamine (12 ml) and water (12 ml) were added to the reaction liquid, followed by stirring in an oil bath at 80° C. for 2 hours. The reaction liquid was concentrated under reduced pressure, partitioned with ethyl acetate and water, and the aqueous layer was extracted with ethyl acetate. The organic layer was washed with saturated brine, dried over anhydrous sodium sulfate, the insoluble matter was separated by filtration, and the residue obtained by concentration was purified by silica gel column chromatography (eluent, n-hexane:ethyl acetate=1:1, v/v) to obtain tert-butyl methyl-{(3S)-3-methyl-1-[(1R)-1-phenylethyl]pyrrolidin-3-yl}carbamate (2.44 g, 65%) as a colorless oily substance.

MS (ESI) m/z: 319 (M+1)$^+$.

HRMS (ESI) m/z: 319.2373 (Calcd for $C_{19}H_{31}N_2O_2$ 319.2386).

$^1$H-NMR (CDCl$_3$) δ: 1.33 (3H, d, J=6.59 Hz), 1.33 (3H, s), 1.40 (9H, s), 1.97-1.87 (1H, m), 2.12-2.23 (1H, m), 2.33-2.43 (1H, m), 2.58 (1H, d, J=9.52 Hz), 2.65 (1H, d, J=9.52 Hz), 2.75 (3H, s), 2.81-2.90 (1H, m), 3.22 (1H, q, J=6.59 Hz), 7.18-7.34 (5H, m).

IR (ATR): 2972, 2929, 2787, 1689, 1493, 1477, 1452, 3421, 1365, 1281, 1247, 1167, 1115, 1009, 972, 874, 764 cm$^{-1}$.

The above-mentioned tert-butyl methyl-{(3S)-3-methyl-1-[(1R)-1-phenylethyl]pyrrolidin-3-yl}carbamate (2.43 g, 7.63 mmol) was dissolved in 1,4-dioxane (76 ml), then palladium hydroxide catalyst (20 wt. %) (500 mg) was added, followed by stirring in an oil bath at 70° C. for 5 hours. The reaction liquid was filtered, and the filtrate was concentrated under reduced pressure to obtain the entitled compound (1.64 g, 100%) as a colorless oily substance.

MS (ESI) m/z: 215 (M+1)$^+$.

HRMS (ESI) m/z: 215.1750 (Calcd for $C_{11}H_{23}N_2O_2$ 215.1760).

$^1$H-NMR (CDCl$_3$) δ: 1.28 (3H, s), 1.46 (9H, s), 1.77-1.94 (1H, m), 2.02-2.11 (1H, m), 2.87 (3H, s), 2.92-3.09 (3H, m), 3.16 (1H, d, J=11.47 Hz).

IR (ATR): 2974, 2931, 2873, 1687, 1541, 1477, 1419, 1363, 1252, 1171, 1130, 1039, 1011, 935, 879, 812, 775 cm$^{-1}$.

Example 157

4-Cyano-6-(3-fluorophenyl)-N,N,5-trimethyl-7-[(3S)-3-methyl-3-(methylamino)pyrrolidin-1-yl]-1,3-benzoxazole-2-carboxamide (#157)

A dimethyl sulfoxide (0.5 ml) solution of the above-mentioned tert-butyl methyl[(3S)-3-methylpyrrolidin-3-yl]carbamate (I-348) and triethylamine (172 µl, 1.23 mmol) was added to a dimethyl sulfoxide (4.5 ml) solution of 4-cyano-7-fluoro-6-(3-fluorophenyl)-N,N,5-trimethyl-1,3-benzoxazole-2-carboxamide (I-184) (300 mg, 0.878 mmol) stirred in an oil bath at 150° C., followed by stirring in an oil bath at 150° C. for 30 minutes. The reaction liquid was concentrated under reduced pressure, the residue was dissolved in ethyl acetate, and washed with water and saturated brine. After drying over anhydrous sodium sulfate, the insoluble matter was separated by filtration, and the residue obtained by concentration was purified by silica gel column chromatography (eluent, n-hexane:ethyl acetate=1:1→1:2, v/v). The obtained yellow foamy substance was dissolved in dichloromethane (3 ml), and with cooling with ice, trifluoroacetic acid (6 ml) was added, followed by stirring at room temperature for 8 hours. The reaction liquid was concentrated under reduced pressure, then an aqueous saturated sodium hydrogencarbonate solution was added, followed by extraction with chloroform. After drying over anhydrous sodium sulfate, the insoluble matter was separated by filtration, the residue obtained by concentration was purified by preparative TLC (eluent, chloroform:methanol=10:1, v/v), and the obtained eluate was purified in slurry with a mixed solvent of isopropyl ether and hexane to obtain the entitled compound (80.0 mg, 21%) as a pale yellow solid.

mp: 178-180° C.

MS (ESI) m/z: 436 (M+1)$^+$.

$^1$H-NMR (CDCl$_3$) δ: 1.14 (3H, s), 1.58-1.70 (1H, m), 1.76-1.88 (1H, m), 2.15-1.93 (1H, m), 2.23 (3H, s), 2.29 (3H, s), 3.09 (1H, t, J=9.40 Hz), 3.20 (3H, s), 3.45-3.22 (3H, m), 3.55 (3H, s), 6.93 (1H, d, J=9.03 Hz), 6.99 (1H, d, J=7.81 Hz), 7.05-7.15 (1H, m), 7.37-7.44 (1H, m).

IR (ATR): 3321, 3057, 2966, 2873, 2796, 2208, 1655, 1604, 1577, 1471, 1442, 1394, 1367, 1313, 1259, 1201, 1155, 1111, 1063, 970, 901, 798, 781 cm$^{-1}$.

Anal. Calcd for $C_{24}H_{26}FN_5O_2 \cdot 0.25H_2O$: C, 65.51; H, 6.07; N, 15.92; F, 4.32. Found: C, 65.56; H, 5.87; N, 15.57; F, 4.35.

Example 158

4-Cyano-N,N,5-trimethyl-7-[(3S)-3-(methylamino)pyrrolidin-1-yl]-6-(2-methyl-1,3-thiazol-4-yl)-1,3-benzoxazole-2-carboxamide (#158)

A dimethyl sulfoxide (1 ml) solution of tert-butyl methyl [(3S)-3-methylpyrrolidin-3-yl]carbamate (299 mg, 1.39 mmol) and triethylamine (227 µl, 1.63 mmol) was added to a dimethyl sulfoxide (6 ml) solution of 4-cyano-7-fluoro-N,N, 5-trimethyl-6-(2-methyl-1,3-thiazol-4-yl)-1,3-benzoxazole-2-carboxamide (I-129) (400 mg, 1.16 mmol) stirred in an oil bath at 150° C., followed by stirring in an oil bath at 150° C. for 30 minutes. The reaction liquid was concentrated under reduced pressure, the residue was dissolved in ethyl acetate, and washed with water and saturated brine. After drying over anhydrous sodium sulfate, the insoluble matter was separated by filtration, and the residue obtained by concentration was purified by silica gel column chromatography (eluent, n-hexane:ethyl acetate=1:1→0:1, v/v).

The obtained yellow foamy substance was dissolved in dichloromethane (6 ml), and with cooling with ice, trifluoroacetic acid (6 ml) was added, followed by stirring at room temperature for 1 hour. The reaction liquid was concentrated under reduced pressure, then an aqueous saturated sodium hydrogencarbonate solution was added, followed by extraction with chloroform. After drying over anhydrous sodium sulfate, the insoluble matter was separated by filtration, and the residue obtained by concentration was recrystallized with a mixed solvent of chloroform and isopropyl ether to obtain the entitled compound (320 mg, 60%) as a pale yellow solid.

mp: 138-140° C.

MS (ESI) m/z: 439 (M+1)$^+$.

$^1$H-NMR (CDCl$_3$) δ: 1.15 (3H, s), 1.60-1.70 (1H, m), 1.76-1.86 (1H, m), 2.25 (3H, s), 2.30 (3H, s), 2.79 (3H, s), 3.12 (1H, d, J=10.25 Hz), 3.20 (3H, s), 3.22 (1H, d, J=10.25 Hz), 3.42-3.53 (2H, m), 3.55 (3H, s), 6.98 (1H, s).

IR (ATR): 2964, 2875, 2212, 1655, 1606, 1579, 1471, 1446, 1390, 1371, 1306, 1252, 1178, 1111, 1065, 982, 903, 864, 752 cm$^{-1}$.

Anal. Calcd for $C_{22}H_{26}N_6O_2S.1H_2O$: C, 57.88; H, 6.18; N, 18.41; S, 7.02. Found: C, 57.60; H, 5.91; N, 18.26; S, 7.04.

Example 159

4-Cyano-N,N,5-trimethyl-7-[(3S)-3-methyl-3-(methylamino)pyrrolidin-1-yl]-6-phenyl-1,3-benzoxazole-2-carboxamide (#159)

A dimethyl sulfoxide (1 ml) solution of tert-butyl methyl [(3S)-3-methylpyrrolidin-3-yl]carbamate (I-348) (318 mg, 1.48 mmol) and triethylamine (241 μl, 1.73 mmol) was added to a dimethyl sulfoxide (6 ml) solution of 4-cyano-7-fluoro-N,N,5-trimethyl-6-phenyl-1,3-benzoxazole-2-carboxamide (I-114) (400 mg, 1.24 mmol) stirred in an oil bath at 150° C., followed by stirring in an oil bath at 150° C. for 30 minutes. The reaction liquid was concentrated under reduced pressure, the residue was dissolved in ethyl acetate, and washed with water and saturated brine. After drying over anhydrous sodium sulfate, the insoluble matter was separated by filtration, and the residue obtained by concentration was purified by silica gel column chromatography (eluent, hexane:ethyl acetate=1:1→1:2, v/v). The obtained yellow foamy substance was dissolved in dichloromethane (3 ml), and with cooling with ice, trifluoroacetic acid (6 ml) was added, followed by stirring at room temperature for 5 hours. The reaction liquid was concentrated under reduced pressure, then an aqueous saturated sodium hydrogencarbonate solution and water were added, followed by extraction with chloroform. After drying over anhydrous sodium sulfate, the insoluble matter was separated by filtration, the residue obtained by concentration was purified by preparative TLC (eluent, chloroform:methanol=10:1, v/v), and the obtained eluate was recrystallized from isopropyl ether to obtain the entitled compound (109 mg, 21%) as a pale yellow solid.

mp: 172-174° C.

MS (ESI) m/z: 418 (M+1)$^+$.

$^1$H-NMR (CDCl$_3$) δ: 1.13 (3H, s), 1.55-1.85 (2H, m), 2.23 (3H, s), 2.27 (3H, s), 3.07 (1H, d, J=10.50 Hz), 3.20 (3H, s), 3.18-3.40 (3H, m), 3.55 (3H, s), 7.16-7.46 (5H, m).

IR (ATR): 3319, 2962, 2929, 2856, 2798, 2212, 1655, 1604, 1577, 1471, 1442, 1396, 1367, 1308, 1259, 1201, 1153, 1111, 1070, 1016, 970, 916, 785 cm$^{-1}$.

Anal. Calcd for $C_{24}H_{27}N_5O_2.0.5H_2O$: C, 67.59; H, 6.62; N, 16.42. Found: C, 67.72; H, 6.46; N, 16.24.

Example 160

7-[(3S)-3-Amino-3-methylpyrrolidin-1-yl]-4-cyano-N,N,5-trimethyl-6-phenyl-1,3-benzoxazole-2-carboxamide (#160)

A dimethyl sulfoxide (1 ml) solution of tert-butyl [(3S)-3-methylpyrrolidin-3-yl]carbamate (I-345) (300 mg, 1.50 mmol) and triethylamine (244 μl, 1.75 mmol) was added to a dimethyl sulfoxide (6 ml) solution of 4-cyano-7-fluoro-N,N,5-trimethyl-6-phenyl-1,3-benzoxazole-2-carboxamide (I-114) (404 mg, 1.25 mmol) stirred in an oil bath at 150° C., followed by stirring in an oil bath at 150° C. for 30 minutes. The reaction liquid was concentrated under reduced pressure, the residue was dissolved in ethyl acetate, and washed with aqueous 10% citric acid solution, water and saturated brine. After drying over anhydrous sodium sulfate, the insoluble matter was separated by filtration, and the residue obtained by concentration was purified by silica gel column chromatography (eluent, n-hexane:ethyl acetate=1:1→1:2, v/v). The obtained yellow foamy substance was dissolved in dichloromethane (5 ml), and with cooling with ice, trifluoroacetic acid (10 ml) was added, followed by stirring at room temperature for 5 hours. The reaction liquid was concentrated under reduced pressure, then an aqueous saturated sodium hydrogencarbonate solution and water were added, followed by extraction with chloroform. After drying over anhydrous sodium sulfate, the insoluble matter was separated by filtration, the residue obtained by concentration was purified by preparative TLC (eluent, chloroform:methanol=10:1, v/v), and the obtained eluate was purified in slurry with isopropyl ether to obtain the entitled compound (210 mg, 41%) as a pale yellow solid.

mp: 202-204° C.

MS (ESI) m/z: 404 (M+1)$^+$.

$^1$H-NMR (CDCl$_3$) δ: 1.16 (3H, s), 1.51-1.71 (2H, m), 2.23 (3H, s), 3.20 (3H, s), 3.12-3.33 (4H, m), 3.56 (3H, s), 7.14-7.46 (5H, m).

IR (ATR): 2956, 2931, 2871, 2212, 1720, 1655, 1604, 1577, 1473, 1444, 1396, 1367, 1306, 1259, 1203, 1153, 1111, 1070, 1016, 970, 904, 866, 831 cm$^{-1}$.

Anal. Calcd for $C_{23}H_{25}N_5O_2.0.25H_2O$: C, 67.71; H, 6.30; N, 17.17. Found: C, 67.67; H, 6.14; N, 16.90.

Experimental Example 1

The antifungal activity of the compounds of the invention was determined according to the method mentioned below.

(1) Medium;

An YPD20 medium (1% yeast extract, 2% peptone, 20% glucose) was used, (2) Preparation of Cell Liquid for Inoculation:

Cells incubated overnight with Sabouraud dextrose agar at 30° C. were suspended in 0.1% Tween 80-added saline, and then added to a concentrated medium (1.33% yeast extract, 2.67% peptone, 13.33% glucose) so that the final cell concentration could be 5×10$^3$ cells/ml, thereby preparing a cell liquid for inoculation.

(3) Production of Chemical Dilution Plate:

A metered sample was dissolved in dimethyl sulfoxide, and a 2-fold dilution series was prepared using dimethyl sulfoxide. A chemical dilution of 2 μl each was added to a flat-bottom 96-well plate with 40% glucose (48 μl) put in each well, thereby producing a chemical dilution plate.

(4) Inoculation and Cultivation of Cell Liquid:

The cell liquid (150 μl) prepared in (2) was added to the chemical dilution plate produced in (3), followed by aerobic static cultivation at 37° C.

(5) Determination of Antifungal Activity (GI80 Value):

After cultivation for 28 to 24 hours, the plate was stirred, and its absorbance (600 nm) was measured. Based on the absorbance as the index, the minimum chemical concentration for at least 80% cell growth inhibition relative to the cell growth in the chemical-free well was computed as a GI80 value.

The results are shown in the following Tables.

TABLE 1

| | GI80 (μg/ml) | | |
| --- | --- | --- | --- |
| Example No. | C. albicans ATCC90028 | C. albicans ATCC MYA-573 | C. glabrata ATCC48435 |
| 1 | 0.063 | 0.063 | 0.032 |
| 2 | 0.5 | 0.25 | 0.125 |

TABLE 1-continued

| | GI80 (µg/ml) | | |
|---|---|---|---|
| Example No. | C. albicans ATCC90028 | C. albicans ATCC MYA-573 | C. glabrata ATCC48435 |
| 13 | 0.063 | 0.125 | 0.032 |
| 14 | 0.25 | 0.25 | 0.125 |
| 22 | 0.5 | 1 | 0.5 |
| 23 | 1 | 1 | 0.5 |
| 34 | 0.25 | 0.25 | 0.032 |
| 35 | 0.25 | 0.25 | 0.032 |
| 40 | 0.063 | 0.063 | 0.016 |
| 40-1 | 0.25 | 0.25 | 0.032 |
| 49 | 0.5 | 0.5 | 0.063 |
| 50 | 2 | 2 | 0.25 |
| 51 | 1 | 1 | 0.25 |
| 52 | 1 | 1 | 0.25 |
| 54 | 0.125 | 0.25 | 0.063 |
| 56 | 0.125 | 0.5 | 0.063 |
| 62 | 0.063 | 0.063 | 0.032 |
| 67 | >4 | >4 | 0.25 |
| 72 | 0.5 | 0.5 | 0.125 |
| 82 | 0.063 | 0.125 | 0.032 |
| 83 | 0.5 | 0.5 | 0.125 |
| 93 | 0.125 | 0.125 | 0.032 |
| 98 | 0.5 | 0.5 | 0.125 |
| 106 | 0.063 | 0.125 | <0.016 |
| 112 | 0.032 | 0.063 | 0.032 |

TABLE 2

| | GI80 (µg/ml) | | |
|---|---|---|---|
| Example No. | C. albicans ATCC90028 | C. albicans ATCC MYA-573 | C. glabrata ATCC48435 |
| 122 | 0.5 | 0.5 | 0.125 |
| 126 | 0.5 | 0.5 | 0.125 |
| 129 | 0.25 | 0.5 | 0.063 |
| 134 | 0.5 | 0.5 | 0.125 |
| 135 | 0.125 | 0.125 | 0.063 |
| 140 | 0.5 | 0.5 | 0.125 |
| 144-1 | 0.25 | 0.25 | 0.032 |
| 144-5 | 0.125 | 0.25 | 0.032 |
| 144-11 | 0.25 | 0.5 | 0.125 |
| 144-13 | 1 | 1 | 0.5 |
| 145 | 0.5 | 0.5 | 0.125 |
| 146 | 0.125 | 0.25 | 0.125 |
| 146-2 | 0.125 | 0.25 | 0.063 |
| 148 | 0.032 | 0.063 | <0.016 |
| 151 | 2 | 1 | 0.25 |
| 154 | 1 | 1 | 0.25 |
| 155 | 0.5 | 2 | 0.125 |
| 156-1 | 0.25 | 0.25 | 0.063 |
| 158 | 0.5 | 2 | 0.25 |
| 159 | 0.063 | 0.063 | <0.016 |
| FCZ * | 0.25 | >4 | >4 |
| ITZ ** | <0.016 | 0.125 | 0.25 |

* Fluconazole,
** Itraconazole

Preparation formulation examples are shown below.

Preparation Example 1

Capsules

| | |
|---|---|
| Compound of Example 159 | 100.0 mg |
| Corn starch | 23.0 mg |
| CMC calcium | 22.5 mg |
| Hydroxymethyl cellulose | 3.0 mg |
| Magnesium stearate | 1.5 mg |
| Total | 150.0 mg |

Preparation Example 2

Solution

| | |
|---|---|
| Compound of Example 159 | 1 to 10 g |
| Acetic acid, lactic acid or hydrochloric acid | 0.1 to 3 g |
| Ethyl parahydroxybenzoate | 0.1 g |
| Purified water | 86.9 to 98.8 g |
| Total | 100 g |

Preparation Example 3

Powder for Feed Admixture

| | |
|---|---|
| Compound of Example 159 | 1 to 10 g |
| Corn starch | 98.5 to 89.5 g |
| Light silicic anhydride | 0.5 g |
| Total | 100 g |

The invention claimed is:

1. A compound of the following formula (I) or a pharmaceutically acceptable salt thereof:

Formula 1

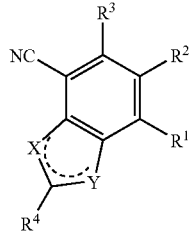

(I)

in the formula, $R^1$ means a group selected from the following structures:

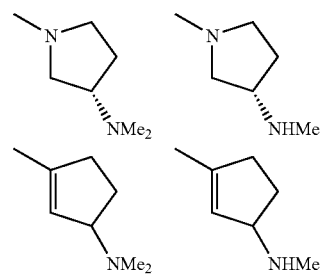

-continued

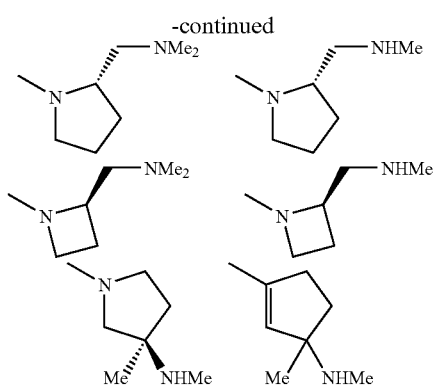

R² means a group selected from a halogen atom and the following structures:

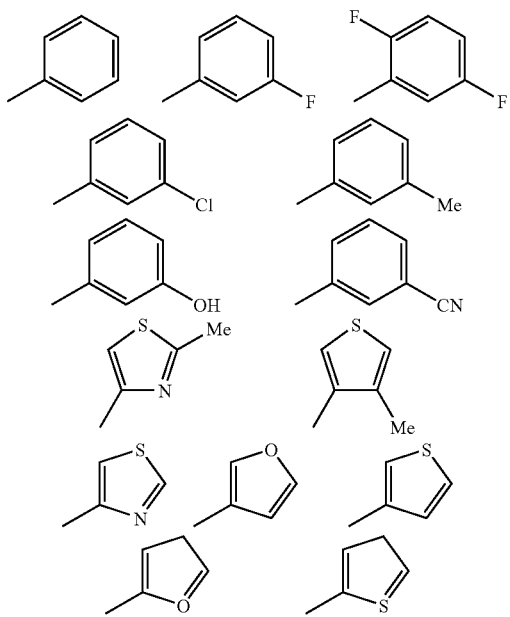

R³ means
a hydrogen atom,
a linear-chain or branched-chain alkyl group having from 1 to 4 carbon atoms,
a cyclic alkyl group having 3 or 4 carbon atoms,
an alkoxy group having from 1 to 4 carbon atoms,
a dialkylamino group having the same or different alkyl chains and having from 2 to 4 carbon atoms in total,
a halogenomethyl group, or
an alkoxymethyl group having an alkoxy group having from 1 to 3 carbon atoms;
R⁴ means a group selected from the following groups [i] to [vi]:
[i]:
a linear-chain or branched-chain alkyl group having from 1 to 6 carbon atoms, or a cycloalkyl group having from 3 to 6 carbon atoms,
these may have one or more groups selected, optionally duplicatively, from the following substituent group 4 wherein an alkyl group is excluded from the substituent group 4;

[ii]:
an aromatic hydrocarbon group, or
a 5-membered or 6-membered aromatic heterocyclic group containing from 1 to 4 hetero atoms selected, optionally duplicatively, from a nitrogen atom, an oxygen atom and a sulfur atom,
these may have one or more groups selected, optionally duplicatively, from the substituent group 4;
[iii]:
an aromatic hetero ring-substituted alkyl group composed of a 5-membered or 6-membered aromatic heterocyclic group containing from 1 to 4 hetero atoms selected, optionally duplicatively, from a nitrogen atom, an oxygen atom and a sulfur atom, and a divalent hydrocarbon group having from 1 to 3 carbon atoms, or
an aralkyl group composed of an aromatic hydrocarbon group and a divalent hydrocarbon group having from 1 to 3 carbon atoms,
these aromatic heterocyclic group and aromatic hydrocarbon group may have one or more groups selected, optionally duplicatively, from the substituent group 4;
[iv]:
an amino group,
an alkylamino group having an alkyl group having from 1 to 6 carbon atoms,
a dialkylamino group having alkyl groups having from 1 to 6 carbon atoms that may be the same or different,
a 4-membered to 6-membered, saturated, nitrogen-containing heterocyclic group having a bonding site at the nitrogen atom, or
a disubstituted amino group in which one substituent is a 4-membered to 6-membered, saturated, nitrogen-containing heterocyclic group having a bonding site at the carbon atom and the other is an alkyl group having from 1 to 6 carbon atoms,
these alkyl moieties may have one or more groups selected, optionally duplicatively, from the substituent group 4 wherein an alkyl group is excluded from the substituent group 4, and the nitrogen-containing heterocyclic group may have one or more groups selected, optionally duplicatively, from the substituent group 4;
[v]:
a group of the following formula:

—C(=O)—R⁴¹ wherein R⁴¹ on the carbon atom means
an alkylamino group having an alkyl group having from 1 to 6 carbon atoms,
a dialkylamino group having alkyl groups having from 1 to 6 carbon atoms that may be the same or different,
an alkoxy group having from 1 to 6 carbon atoms,
an alkyl(alkoxy)amino group having an alkyl group having from 1 to 6 carbon atoms and an alkoxy group having from 1 to 6 carbon atoms,
a 5-membered or 6-membered, saturated cyclic, nitrogen-containing heterocyclic group containing 1 or 2 hetero atoms selected, optionally duplicatively, from a group consisting of a nitrogen atom, an oxygen atom and a sulfur atom and bonding to the carbonyl at the nitrogen atom,
a disubstituted amino group having a 5-membered or 6-membered aromatic heterocyclic group containing from 1 to 4 hetero atoms selected, optionally duplicatively, from a group consisting of a nitrogen atom, an oxygen atom and a sulfur atom, and an alkyl group having from 1 to 6 carbon atoms, an aromatic hetero ring-substituted alkyl group composed of a 5-membered or 6-membered aromatic heterocyclic group containing from 1 to 4 hetero atoms selected, optionally duplicatively, from a group consisting of a nitrogen atom, an oxygen atom and a sulfur atom, and an alkylene group having from 1 to 3 carbon atoms, or a substituted dialkylamino group having alkyl groups having from 1 to 6 carbon atoms,

[vi]:

a group of the following formula:

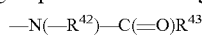

—N(—R$^{42}$)—C(=O)R$^{43}$ wherein R$^{42}$ and R$^{43}$ each independently mean a hydrogen atom or an alkyl group having from 1 to 6 carbon atoms, or they may combine together to be a polymethylene chain to form a lactam structure;

the alkyl moiety of the group in the above [v] and [vi] and the alkyl moiety of the alkoxy group therein may have one or more groups selected, optionally duplicatively, from the groups of the substituent group 4 wherein an alkyl group is excluded from the substituent group 4, and the aromatic or saturated heterocyclic group may have one or more groups selected, optionally duplicatively, from the substituent group 4;

the substituent of group 4 is selected from:

a halogen atom, an amino group, a hydroxyl group, a carboxy group, an alkoxy group having from 1 to 6 carbon atoms, an alkylthio group having from 1 to 6 carbon atoms, an acyl group having from 2 to 7 carbon atoms, an alkoxycarbonyl group having from 2 to 7 carbon atoms, an alkyl group having from 1 to 6 carbon atoms, a cycloalkyl group having from 3 to 6 carbon atoms, an aralkyloxy group having from 7 to 9 carbon atoms, an aralkyloxycarbonyl group having from 8 to 10 carbon atoms, and a group of the following formula:

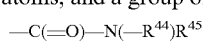

—C(=O)—N(—R$^{44}$)R$^{45}$ wherein R$^{44}$ and R$^{45}$ on the nitrogen atom each independently represent a hydrogen atom, an alkyl group having from 1 to 6 carbon atoms, or an aryl group having from 6 to 10 carbon atoms;

in this, the amino group in the substituent group 4 may have 1 or 2 substituents selected from a group consisting of an alkyl group having from 1 to 6 carbon atoms, an acyl group having from 2 to 7 carbon atoms, a cycloalkyl group having from 3 to 6 carbon atoms, an aryl group having from 6 to 10 carbon atoms, an aralkyl group having from 7 to 12 carbon atoms, an aromatic heterocyclic group, an alkylsulfonyl group having from 1 to 6 carbon atoms, and an arylsulfonyl group having from 6 to 10 carbon atoms;

X and Y each independently mean a nitrogen atom, an oxygen atom, a sulfur atom, N—R$^5$ or C—R$^6$, R$^5$ and R$^6$ each independently mean a hydrogen atom or an alkyl group having from 1 to 6 carbon atoms, and the ring containing X and Y may be a saturated ring or an aromatic ring; and Me is a methyl group.

2. The compound or the pharmaceutically acceptable salt thereof as described in claim 1, wherein the ring containing X and Y is an aromatic ring, and X and Y are any one of the following combinations:

(1) X is a nitrogen atom and Y is an oxygen atom,
(2) X is a nitrogen atom and Y is N—R$^5$,
(3) X is an oxygen atom and Y is a nitrogen atom,
(4) X is an oxygen atom and Y is C—R$^6$,
(5) X is N—R$^5$ and Y is C—R$^6$,
(6) X is a nitrogen atom and Y is a sulfur atom,
(7) X is a sulfur atom and Y is a nitrogen atom.

3. A drug comprising the compound or the pharmaceutically acceptable salt thereof as described in claim 1 or 2.

4. A remedy for fungal infections, comprising the compound or the pharmaceutically acceptable salt thereof as described in claim 1 or 2.

5. An antifungal comprising the compound or the pharmaceutically acceptable salt thereof as described in claim 1 or 2 for use in the treatment of fungal infections.

6. A method of treating a fungal infection, comprising administering the compound or the pharmaceutically acceptable salt thereof as described in claim 1 or 2 to a patient in need thereof.

* * * * *